US012071476B2

(12) United States Patent
Jacobson et al.

(10) Patent No.: US 12,071,476 B2
(45) Date of Patent: Aug. 27, 2024

(54) IL-6 ANTIBODIES AND FUSION CONSTRUCTS AND CONJUGATES THEREOF

(71) Applicant: KODIAK SCIENCES INC., Palo Alto, CA (US)

(72) Inventors: Rachel D. Jacobson, Belmont, CA (US); Fernando Corrêa, Hayward, CA (US); Hong Liang, Hillsborough, CA (US); Daniel Victor Perlroth, Palo Alto, CA (US)

(73) Assignee: KODIAK SCIENCES INC., Palo Alto, CA (US)

(*) Notice: Subject to any disclaimer, the term of this patent is extended or adjusted under 35 U.S.C. 154(b) by 0 days.

(21) Appl. No.: 16/290,128

(22) Filed: Mar. 1, 2019

(65) Prior Publication Data

US 2019/0270806 A1    Sep. 5, 2019

Related U.S. Application Data

(60) Provisional application No. 62/727,950, filed on Sep. 6, 2018, provisional application No. 62/637,575, filed on Mar. 2, 2018.

(51) Int. Cl.
| | | |
|---|---|---|
| *C07K 16/24* | (2006.01) | |
| *A61K 9/00* | (2006.01) | |
| *A61K 9/08* | (2006.01) | |
| *A61K 47/59* | (2017.01) | |
| *A61K 47/60* | (2017.01) | |
| *A61K 47/68* | (2017.01) | |
| *A61P 3/10* | (2006.01) | |
| *A61P 27/02* | (2006.01) | |
| *C07K 14/705* | (2006.01) | |

(52) U.S. Cl.
CPC .......... *C07K 16/248* (2013.01); *A61K 9/0048* (2013.01); *A61K 9/08* (2013.01); *A61K 47/59* (2017.08); *A61K 47/60* (2017.08); *A61K 47/6883* (2017.08); *A61P 3/10* (2018.01); *A61P 27/02* (2018.01); *C07K 14/705* (2013.01); *C07K 2317/31* (2013.01); *C07K 2317/52* (2013.01); *C07K 2317/73* (2013.01); *C07K 2317/76* (2013.01); *C07K 2317/92* (2013.01); *C07K 2319/00* (2013.01); *C07K 2319/30* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 4,485,045 A | 11/1984 | Regen |
| 4,544,545 A | 10/1985 | Ryan et al. |
| 4,609,707 A | 9/1986 | Nowinski et al. |
| 4,634,664 A | 1/1987 | Oestberg |
| 4,634,666 A | 1/1987 | Engleman et al. |
| 4,683,195 A | 7/1987 | Mullis et al. |
| 4,683,202 A | 7/1987 | Mullis |
| 4,754,065 A | 6/1988 | Levenson et al. |
| 4,777,127 A | 10/1988 | Jukka et al. |
| 4,800,159 A | 1/1989 | Mullis et al. |
| 4,816,567 A | 3/1989 | Cabilly et al. |
| 4,892,538 A | 1/1990 | Aebischer et al. |
| 5,013,556 A | 5/1991 | Woodle et al. |
| 5,047,335 A | 9/1991 | Paulson et al. |
| 5,219,740 A | 6/1993 | Dusty et al. |
| 5,225,539 A | 7/1993 | Winter |
| 5,252,713 A | 10/1993 | Morgan, Jr. et al. |
| 5,278,299 A | 1/1994 | Wong et al. |
| 5,283,187 A | 2/1994 | Aebischer et al. |
| 5,325,525 A | 6/1994 | Shan et al. |
| 5,336,603 A | 8/1994 | Capon et al. |
| 5,422,120 A | 6/1995 | Kim et al. |
| 5,510,261 A | 4/1996 | Goochee et al. |
| 5,530,101 A | 6/1996 | Queen et al. |
| 5,545,806 A | 8/1996 | Lonberg et al. |
| 5,565,332 A | 10/1996 | Hoogenboom et al. |
| 5,569,825 A | 10/1996 | Lonberg et al. |
| 5,580,859 A | 12/1996 | Felgner et al. |
| 5,585,089 A | 12/1996 | Queen et al. |
| 5,624,821 A | 4/1997 | Winter et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,663,425 A | 9/1997 | Detroit et al. |
| 5,681,746 A | 10/1997 | Bodner et al. |

(Continued)

FOREIGN PATENT DOCUMENTS

| | | |
|---|---|---|
| AU | 2010330727 | 12/2010 |
| AU | 2011239434 | 8/2015 |

(Continued)

OTHER PUBLICATIONS

Machine translation of WO 2015/109898 published Jul. 2015 (translation accessed May 15, 2020).*
International Search Report and Written Opinion in International Application No. PCT/US2019/020418, mailed Jun. 20, 2019.
U.S. Appl. No. 09/253,689, filed Feb. 20, 1999, Fung et al.
U.S. Appl. No. 16/795,450, filed Feb. 19, 2020, Perlroth et al.
Alconcel, S.N.S. et al., "FDA-approved poly(ethylene glycol)-protein conjugate drugs," www.rsc.org/polymers, Polymer Chemistry, vol. 2, Issue 7, pp. 1442, 2011.
Allen et al., "Combined antiangiogenic and anti-PD-L1 therapy stimulates tumor immunity through HEV formation", Science Translational Medicine, 9(385): dated Apr. 12, 2017.
Alley, S. et al., "Contribution of linker stability to the activities of anticancer immunoconjugates," Bioconjugate Chem., vol. 19, No. 3, pp. 759-765, 2008.

(Continued)

*Primary Examiner* — Marianne P Allen
(74) *Attorney, Agent, or Firm* — KNOBBE, MARTENS, OLSON & BEAR, LLP

(57) ABSTRACT

The present invention provides antagonizing antibodies that bind to IL-6, fusion proteins thereof with VEGF Trap, and conjugates of either thereof, and methods of using same. The anti-IL-6 antibodies can be used therapeutically alone or in combination with other therapeutics to diseases.

39 Claims, 68 Drawing Sheets

Specification includes a Sequence Listing.

(56) References Cited

U.S. PATENT DOCUMENTS

| | | |
|---|---|---|
| 5,733,743 A | 3/1998 | Johnson et al. |
| 5,741,923 A | 4/1998 | Driver et al. |
| 5,763,548 A | 6/1998 | Matyjaszewski et al. |
| 5,770,429 A | 6/1998 | Lonberg et al. |
| 5,789,487 A | 8/1998 | Matyjaszewski et al. |
| 5,789,650 A | 8/1998 | Lonberg et al. |
| 5,807,937 A | 9/1998 | Matyjaszewski et al. |
| 5,814,318 A | 9/1998 | Lonberg et al. |
| 5,814,482 A | 9/1998 | Dubensky, Jr. et al. |
| 5,834,597 A | 11/1998 | Tso et al. |
| 5,837,242 A | 11/1998 | Holliger et al. |
| 5,858,657 A | 1/1999 | Winter et al. |
| 5,859,205 A | 1/1999 | Adair et al. |
| 5,863,551 A | 1/1999 | Woerly |
| 5,871,907 A | 2/1999 | Winter et al. |
| 5,872,218 A | 2/1999 | Wolf et al. |
| 5,874,299 A | 2/1999 | Lonberg et al. |
| 5,877,218 A | 3/1999 | Herzig et al. |
| 5,877,397 A | 3/1999 | Lonberg et al. |
| 5,882,644 A | 3/1999 | Chang et al. |
| 5,945,491 A | 8/1999 | Matyjaszewski et al. |
| 5,981,786 A | 11/1999 | Kitano et al. |
| 6,111,022 A | 8/2000 | Matyjaszewski et al. |
| 6,121,371 A | 9/2000 | Matyjaszewski et al. |
| 6,124,411 A | 9/2000 | Matyjaszewski et al. |
| 6,162,882 A | 12/2000 | Matyjaszewski et al. |
| 6,270,993 B1 | 8/2001 | Shibuya et al. |
| 6,344,050 B1 | 2/2002 | Chen |
| 6,376,471 B1 | 4/2002 | Lawrence, III et al. |
| 6,383,486 B1 | 5/2002 | Davis-Smyth et al. |
| 6,407,187 B1 | 6/2002 | Matyjaszewski et al. |
| 6,407,213 B1 | 6/2002 | Carter et al. |
| 6,413,942 B1 | 7/2002 | Felgner et al. |
| 6,436,908 B1 | 8/2002 | Koch et al. |
| 6,512,060 B1 | 1/2003 | Matyjaszewski et al. |
| 6,538,091 B1 | 3/2003 | Matyjaszewski et al. |
| 6,541,580 B1 | 4/2003 | Matyjaszewski et al. |
| 6,554,853 B2 | 4/2003 | Chen |
| 6,555,593 B1 | 4/2003 | Hoyle et al. |
| 6,583,272 B1 | 6/2003 | Bailon |
| 6,624,262 B2 | 9/2003 | Matyjaszewski et al. |
| 6,624,821 B1 | 9/2003 | Shin et al. |
| 6,627,314 B2 | 9/2003 | Matyjaszewski et al. |
| 6,632,926 B1 | 10/2003 | Chen et al. |
| 6,759,491 B2 | 7/2004 | Matyjaszewski et al. |
| 6,790,919 B2 | 9/2004 | Matyjaszewski et al. |
| 6,833,349 B2 | 12/2004 | Xia et al. |
| 6,852,816 B2 | 2/2005 | Lewis et al. |
| 6,870,033 B1 | 3/2005 | Hsei et al. |
| 6,881,557 B2 | 4/2005 | Foote |
| 6,884,879 B1 | 4/2005 | Baca et al. |
| 6,887,962 B2 | 5/2005 | Matyjaszewski et al. |
| 6,956,107 B2 | 10/2005 | Fung et al. |
| 6,979,556 B2 | 12/2005 | Simmons et al. |
| 6,992,176 B2 | 1/2006 | Reiter et al. |
| 7,019,082 B2 | 3/2006 | Matyjaszewski et al. |
| 7,049,373 B2 | 5/2006 | Matyjaszewski et al. |
| 7,052,691 B2 | 5/2006 | Sleeman et al. |
| 7,056,455 B2 | 6/2006 | Matyjaszewski et al. |
| 7,056,509 B2 | 6/2006 | Thorpe et al. |
| 7,060,269 B1 | 6/2006 | Baca et al. |
| 7,060,271 B2 | 6/2006 | Ramakrishnan et al. |
| 7,064,166 B2 | 6/2006 | Matyjaszewski et al. |
| 7,070,959 B1 | 7/2006 | Papadopoulos et al. |
| 7,071,159 B2 | 7/2006 | Kendall et al. |
| 7,122,636 B1 | 10/2006 | Hsei et al. |
| 7,125,938 B2 | 10/2006 | Matyjaszewski et al. |
| 7,157,530 B2 | 1/2007 | Matyjaszewski et al. |
| 7,169,901 B2 | 1/2007 | Baca et al. |
| 7,297,334 B2 | 1/2007 | Baca et al. |
| 7,214,776 B2 | 5/2007 | Hsei et al. |
| 7,291,721 B2 | 11/2007 | Giles-Komar et al. |
| 7,300,653 B2 | 11/2007 | Wiegand et al. |
| 7,300,990 B2 | 11/2007 | Lewis et al. |
| 7,303,748 B2 | 12/2007 | Wiegand et al. |
| 7,306,799 B2 | 12/2007 | Wiegand et al. |
| 7,345,027 B2 | 3/2008 | Tolentino et al. |
| 7,348,424 B2 | 3/2008 | Miyazawa et al. |
| 7,351,411 B2 | 4/2008 | Holash et al. |
| 7,354,578 B2 | 4/2008 | Kandel et al. |
| 7,354,579 B2 | 4/2008 | Holash et al. |
| 7,354,580 B2 | 4/2008 | Cedarbaum |
| 7,354,581 B2 | 4/2008 | Cedarbaum et al. |
| 7,354,582 B2 | 4/2008 | Yung et al. |
| 7,365,166 B2 | 4/2008 | Baca et al. |
| 7,374,757 B2 | 5/2008 | Papadopoulos et al. |
| 7,375,193 B2 | 5/2008 | Baca et al. |
| 7,378,095 B2 | 5/2008 | Cao et al. |
| 7,507,405 B2 | 3/2009 | Hsei et al. |
| 7,521,541 B2 | 4/2009 | Eigenbrot et al. |
| 7,531,172 B2 | 5/2009 | Stahl et al. |
| 7,560,112 B2 | 7/2009 | Chen et al. |
| 7,569,655 B2 | 8/2009 | Pacetti et al. |
| 7,608,261 B2 | 10/2009 | Furfine et al. |
| 7,612,182 B2 | 11/2009 | Gilles-Komar et al. |
| 7,740,844 B2 | 6/2010 | Hong et al. |
| 7,740,850 B2 | 6/2010 | Zhu et al. |
| 7,750,138 B2 | 7/2010 | Fang et al. |
| 7,754,208 B2 | 7/2010 | Ledbetter et al. |
| 7,754,855 B1 | 7/2010 | Cox, III et al. |
| 7,758,859 B2 | 7/2010 | Fuh et al. |
| 7,759,472 B2 | 7/2010 | Shima et al. |
| 7,842,789 B2 | 11/2010 | Hsei et al. |
| 7,855,178 B2 | 12/2010 | Alitalo et al. |
| 7,893,173 B2 | 2/2011 | Matyjaszewski et al. |
| 7,919,099 B2 | 4/2011 | Tahara et al. |
| 7,928,072 B2 | 4/2011 | Scaria et al. |
| 7,955,597 B2 | 6/2011 | Giles-Komar et al. |
| 8,003,097 B2 | 8/2011 | Schroeter et al. |
| 8,007,798 B2 | 8/2011 | Ashkenazi et al. |
| 8,007,799 B2 | 8/2011 | Van Bruggen et al. |
| 8,008,453 B2 | 8/2011 | Gegg et al. |
| 8,034,905 B2 | 10/2011 | Kavlie et al. |
| 8,048,418 B2 | 11/2011 | Noguera-Troise et al. |
| 8,067,002 B2 | 11/2011 | An et al. |
| 8,092,797 B2 | 1/2012 | Fuh et al. |
| 8,092,803 B2 | 1/2012 | Furfine et al. |
| 8,101,177 B2 | 1/2012 | Fuh et al. |
| 8,110,546 B2 | 2/2012 | Dix et al. |
| 8,124,076 B2 | 2/2012 | Solomon et al. |
| 8,147,830 B2 | 4/2012 | Johnson et al. |
| 8,163,726 B2 | 4/2012 | Wen et al. |
| 8,187,597 B2 | 5/2012 | Shima et al. |
| 8,206,707 B2 | 6/2012 | Shima et al. |
| 8,211,864 B2 | 7/2012 | Ambati et al. |
| 8,216,571 B2 | 7/2012 | Ramachandra et al. |
| 8,216,575 B2 | 7/2012 | Yu |
| 8,231,907 B2 | 7/2012 | Lillard et al. |
| 8,236,312 B2 | 8/2012 | Park et al. |
| RE43,672 E | 9/2012 | Chan et al. |
| 8,268,314 B2 | 9/2012 | Baehner et al. |
| 8,273,352 B2 | 9/2012 | Huang et al. |
| 8,273,353 B2 | 9/2012 | Davis-Smyth et al. |
| 8,309,532 B2 | 11/2012 | Feinstein et al. |
| 8,318,169 B2 | 11/2012 | Trogden et al. |
| 8,324,169 B2 | 12/2012 | Quinn |
| 8,329,866 B2 | 12/2012 | Rosendahl et al. |
| 8,349,325 B2 | 1/2013 | Brophy et al. |
| 8,388,963 B2 | 3/2013 | Vrignaud et al. |
| 8,455,622 B2 | 6/2013 | McDonagh et al. |
| 8,486,397 B2 | 7/2013 | Bagri et al. |
| 8,492,527 B2 | 7/2013 | Fuh et al. |
| 8,506,962 B2 | 8/2013 | Trogden et al. |
| 8,512,699 B2 | 8/2013 | Fuh et al. |
| 8,546,345 B2 | 10/2013 | Tolentino et al. |
| 8,557,246 B2 | 10/2013 | Escribano et al. |
| 8,571,802 B2 | 10/2013 | Robinson et al. |
| 8,614,235 B2 | 12/2013 | Robinson et al. |
| 8,632,774 B2 | 1/2014 | Misher et al. |
| 8,658,633 B2 | 2/2014 | Poulaki et al. |
| 8,663,639 B2 | 3/2014 | Dor et al. |
| 8,685,397 B2 | 4/2014 | Shima et al. |
| 8,691,226 B2 | 4/2014 | Chiu et al. |
| 8,703,130 B2 | 4/2014 | Baehner et al. |

(56) References Cited

U.S. PATENT DOCUMENTS

| | | |
|---|---|---|
| 8,703,133 B2 | 4/2014 | Chen et al. |
| 8,753,625 B2 | 6/2014 | Fung et al. |
| 8,765,432 B2 | 7/2014 | Charles |
| 8,785,385 B2 | 7/2014 | Stout et al. |
| 8,790,647 B2 | 7/2014 | Greenwood et al. |
| 8,802,129 B2 | 8/2014 | Whitcup et al. |
| 8,815,236 B2 | 8/2014 | Burke et al. |
| 8,822,645 B2 | 9/2014 | Ghayur et al. |
| 8,834,884 B2 | 9/2014 | Trogden et al. |
| 8,846,021 B2 | 9/2014 | Charles |
| 8,864,869 B2 | 9/2014 | Pakola et al. |
| 8,883,157 B1 | 11/2014 | Clube |
| 8,883,519 B1 | 11/2014 | Perez et al. |
| 8,911,768 B2 | 12/2014 | Whitcup et al. |
| 8,926,972 B2 | 1/2015 | Zhou et al. |
| 8,945,552 B2 | 2/2015 | Baehner et al. |
| 8,962,804 B2 | 2/2015 | Williams |
| 8,986,692 B2 | 3/2015 | Li et al. |
| 9,029,508 B2 | 5/2015 | Ghayur et al. |
| 9,045,551 B2 | 6/2015 | Gu et al. |
| 9,079,953 B2 | 7/2015 | Harding et al. |
| 9,125,940 B2 | 9/2015 | Ma et al. |
| 9,149,427 B2 | 10/2015 | Ling et al. |
| 9,163,093 B2 | 10/2015 | Gu et al. |
| 9,214,906 B2 | 12/2015 | Marsan et al. |
| 9,217,039 B2 | 12/2015 | Pedersen et al. |
| 9,220,631 B2 | 12/2015 | Sigg et al. |
| 9,226,917 B2 | 1/2016 | Strong et al. |
| 9,241,906 B2 | 1/2016 | Freeman et al. |
| 9,254,338 B2 | 2/2016 | Yancopoulos |
| 9,265,827 B2 | 2/2016 | Wiegand et al. |
| 9,273,113 B2 | 3/2016 | Davis-Smyth et al. |
| 9,334,324 B2 | 5/2016 | Choo et al. |
| 9,353,177 B2 | 5/2016 | Fuh et al. |
| 9,388,239 B2 | 7/2016 | Baldi et al. |
| 9,388,180 B2 | 8/2016 | Clube |
| 9,409,990 B2 | 8/2016 | Zhang |
| 9,416,180 B1 | 8/2016 | Clube |
| 9,416,210 B2 | 8/2016 | Emrick et al. |
| 9,421,256 B2 | 8/2016 | Kavlie et al. |
| 9,428,575 B2 | 8/2016 | Lai et al. |
| 9,567,403 B2 | 2/2017 | Wu et al. |
| 9,575,067 B2 | 2/2017 | Kosmeder et al. |
| 9,650,443 B2 | 5/2017 | Song et al. |
| 9,650,444 B2 | 5/2017 | Wiegand et al. |
| 9,657,084 B2 | 5/2017 | Ke et al. |
| 9,669,069 B2 | 6/2017 | Yancopoulos |
| 9,682,144 B2 | 6/2017 | Thorin et al. |
| 9,695,233 B2 | 7/2017 | Duerr et al. |
| 9,708,390 B2 | 7/2017 | Sivakumar et al. |
| 9,708,396 B2 | 7/2017 | Baehner et al. |
| 9,708,397 B2 | 7/2017 | Greenwood et al. |
| 9,815,893 B2 | 11/2017 | Akamatsu |
| 9,822,174 B2 | 11/2017 | Doh et al. |
| 9,840,553 B2 | 12/2017 | Perlroth et al. |
| 9,850,514 B2 | 12/2017 | Laird et al. |
| 9,914,770 B2 | 3/2018 | Shandilya et al. |
| 9,931,330 B2 | 4/2018 | Zarnitsyn et al. |
| 9,937,129 B2 | 4/2018 | Freeman et al. |
| 9,943,573 B2 | 4/2018 | Constable et al. |
| 9,944,720 B2 | 4/2018 | Gu et al. |
| 9,962,333 B2 | 5/2018 | Gailard et al. |
| 10,004,788 B2 | 6/2018 | Constable et al. |
| 10,035,850 B2 | 7/2018 | Gekkieva et al. |
| 10,072,075 B2 | 9/2018 | Koenig et al. |
| 10,106,605 B2 | 10/2018 | Ghosh et al. |
| 10,130,681 B2 | 11/2018 | Yancopoulos |
| 10,184,010 B2 | 1/2019 | Lee et al. |
| 10,208,124 B2 | 2/2019 | Le Bouteiller et al. |
| 10,208,355 B2 | 2/2019 | Bais et al. |
| 10,240,207 B2 | 3/2019 | Yu et al. |
| 10,259,862 B2 | 4/2019 | Carter et al. |
| 10,363,290 B2 | 7/2019 | Perlroth et al. |
| 10,406,226 B2 | 9/2019 | Dix et al. |
| 10,421,984 B2 | 9/2019 | Laird et al. |
| 10,456,466 B2 | 10/2019 | Fang et al. |
| 10,456,470 B2 | 10/2019 | Bais et al. |
| 10,464,992 B2 | 11/2019 | Furfine et al. |
| 10,519,226 B2 | 12/2019 | Rau et al. |
| 10,526,382 B2 | 1/2020 | Bel Aiba et al. |
| 10,568,951 B2 | 2/2020 | Sigl |
| 10,548,998 B2 | 4/2020 | Bradbury et al. |
| 10,702,608 B2 | 7/2020 | Charles et al. |
| 10,828,345 B2 | 11/2020 | Yancopoulos |
| 10,857,205 B2 | 12/2020 | Yancopoulos |
| 10,857,231 B2 | 12/2020 | Yancopoulos |
| 10,888,601 B2 | 1/2021 | Yancopoulos |
| 11,066,465 B2 | 7/2021 | Perlroth et al. |
| 11,071,771 B2 | 7/2021 | Perlroth et al. |
| 11,155,610 B2 | 10/2021 | Perlroth et al. |
| 11,584,790 B2 | 2/2023 | Perlroth et al. |
| 11,590,235 B2 | 2/2023 | Charles et al. |
| 11,819,531 B2 | 11/2023 | Charles et al. |
| 2002/0044937 A1 | 4/2002 | Birnstiel et al. |
| 2002/0032315 A1 | 6/2002 | Baca et al. |
| 2002/0091082 A1 | 7/2002 | Aiello |
| 2003/0113335 A1 | 6/2003 | Li et al. |
| 2003/0118592 A1 | 6/2003 | Ledbetter et al. |
| 2003/0143596 A1 | 7/2003 | Bentley et al. |
| 2003/0171320 A1 | 9/2003 | Guyer |
| 2003/0235536 A1 | 12/2003 | Blumberg et al. |
| 2004/0010376 A1 | 1/2004 | Luo et al. |
| 2004/0063881 A1 | 4/2004 | Lewis et al. |
| 2004/0091490 A1 | 5/2004 | Johnson et al. |
| 2004/0247588 A1 | 12/2004 | Johnson et al. |
| 2004/0253596 A1 | 12/2004 | Pawlak et al. |
| 2004/0266688 A1 | 12/2004 | Nayak |
| 2005/0041080 A1 | 2/2005 | Hall et al. |
| 2005/0074497 A1 | 4/2005 | Schultz |
| 2005/0100500 A1 | 5/2005 | Kishita |
| 2005/0100550 A1* | 5/2005 | Trikha .............. C07K 16/2848 424/146.1 |
| 2005/0112061 A1 | 5/2005 | Holash et al. |
| 2005/0112088 A1 | 5/2005 | Zhao et al. |
| 2005/0118651 A1 | 6/2005 | Basi et al. |
| 2005/0123501 A1 | 6/2005 | Lews |
| 2005/0136049 A1 | 6/2005 | Ledbetter et al. |
| 2005/0159556 A1 | 7/2005 | Lewis et al. |
| 2005/0180945 A1 | 8/2005 | Chaikof et al. |
| 2005/0214286 A1 | 9/2005 | Epstein et al. |
| 2005/0220880 A1 | 10/2005 | Lewis et al. |
| 2005/0239088 A1 | 10/2005 | Shepard et al. |
| 2005/0276796 A1 | 12/2005 | Tomatsu et al. |
| 2005/0281822 A1 | 12/2005 | Cedarbaum et al. |
| 2005/0281861 A1 | 12/2005 | Hughes et al. |
| 2005/0282233 A1 | 12/2005 | Eriksson et al. |
| 2006/0058234 A1* | 3/2006 | Daly ................. C07K 14/71 514/8.1 |
| 2006/0067930 A1 | 3/2006 | Adams et al. |
| 2006/0135714 A1 | 6/2006 | Lewis et al. |
| 2006/0165804 A1 | 7/2006 | Lewis et al. |
| 2006/0167230 A1 | 7/2006 | Koga et al. |
| 2006/0182783 A1 | 8/2006 | Hughes et al. |
| 2006/0193830 A1 | 8/2006 | Hauswirth et al. |
| 2006/0217285 A1 | 9/2006 | Destarac |
| 2006/0231107 A1 | 10/2006 | Glickman et al. |
| 2006/0234347 A1 | 10/2006 | Harding et al. |
| 2007/0037183 A1 | 2/2007 | Edwards et al. |
| 2007/0037214 A1 | 2/2007 | Luo et al. |
| 2007/0037760 A1 | 2/2007 | Tolentino et al. |
| 2007/0041967 A1 | 2/2007 | Jung et al. |
| 2007/0059302 A1 | 3/2007 | Baca et al. |
| 2007/0059336 A1 | 3/2007 | Hughes et al. |
| 2007/0071756 A1 | 3/2007 | Peyman |
| 2007/0111279 A1 | 5/2007 | Rosenberg |
| 2007/0134244 A1 | 6/2007 | Slakter et al. |
| 2007/0141104 A1 | 6/2007 | Hauenstein |
| 2007/0167526 A1 | 7/2007 | Zhang et al. |
| 2007/0190058 A1 | 8/2007 | Shams |
| 2007/0196374 A1 | 8/2007 | Baca et al. |
| 2007/0258976 A1 | 11/2007 | Ward et al. |
| 2007/0264236 A1 | 11/2007 | Yang |
| 2007/0265203 A1 | 11/2007 | Eriksson et al. |
| 2008/0008736 A1 | 1/2008 | Glauser |

(56) References Cited

U.S. PATENT DOCUMENTS

| | | |
|---|---|---|
| 2008/0070855 A1 | 3/2008 | Gills |
| 2008/0096923 A1 | 4/2008 | Girach |
| 2008/0124450 A1 | 5/2008 | Pacetti |
| 2008/0147178 A1 | 6/2008 | Pacetti et al. |
| 2008/0152654 A1 | 6/2008 | Reich et al. |
| 2008/0167600 A1 | 7/2008 | Peyman |
| 2008/0187534 A1 | 8/2008 | Baca et al. |
| 2008/0187966 A1 | 8/2008 | Simmons |
| 2008/0199464 A1 | 8/2008 | Plowman et al. |
| 2008/0226629 A1 | 9/2008 | Baca et al. |
| 2008/0242587 A1 | 10/2008 | Kim et al. |
| 2008/0248030 A1 | 10/2008 | Folkman et al. |
| 2008/0268051 A1 | 10/2008 | Hughes et al. |
| 2008/0292628 A1 | 11/2008 | Hui |
| 2009/0053137 A1 | 2/2009 | Moore |
| 2009/0053217 A1 | 2/2009 | Blank et al. |
| 2009/0053786 A1 | 2/2009 | Kao et al. |
| 2009/0060906 A1 | 3/2009 | Barry et al. |
| 2009/0061533 A1 | 3/2009 | Minami |
| 2009/0092664 A1 | 4/2009 | Mumper et al. |
| 2009/0098139 A1 | 4/2009 | Katz et al. |
| 2009/0104259 A1 | 4/2009 | Tolentino et al. |
| 2009/0117103 A1 | 7/2009 | Devalaraja et al. |
| 2009/0220504 A1 | 9/2009 | Chuntharapai et al. |
| 2009/0226441 A1 | 9/2009 | Yan et al. |
| 2009/0249503 A1 | 10/2009 | Rosendahl |
| 2009/0285826 A1 | 11/2009 | Bonnel et al. |
| 2009/0324679 A1 | 12/2009 | Ippoliti et al. |
| 2010/0086551 A1 | 4/2010 | Olwill et al. |
| 2010/0098730 A1 | 4/2010 | Lowman et al. |
| 2010/0059541 A1 | 5/2010 | Downing et al. |
| 2010/0111942 A1 | 5/2010 | Shima et al. |
| 2010/0111963 A1 | 5/2010 | Shams |
| 2010/0129375 A1 | 5/2010 | Junge et al. |
| 2010/0150911 A1 | 6/2010 | Caiado De Castro et al. |
| 2010/0151566 A1 | 6/2010 | Lamdan et al. |
| 2010/0158850 A1 | 6/2010 | Baker, Jr. et al. |
| 2010/0166700 A1 | 7/2010 | Charles |
| 2010/0233079 A1 | 9/2010 | Jakob et al. |
| 2010/0247515 A1 | 9/2010 | Steward et al. |
| 2010/0254995 A1 | 10/2010 | Steward et al. |
| 2010/0260668 A1 | 10/2010 | Ghayur et al. |
| 2010/0260760 A1 | 10/2010 | Blank et al. |
| 2010/0278896 A1 | 11/2010 | Khaw et al. |
| 2010/0291065 A1 | 11/2010 | Kabanov et al. |
| 2011/0033378 A1 | 2/2011 | Dimasi et al. |
| 2011/0047103 A1 | 2/2011 | Swamy et al. |
| 2011/0052575 A1 | 3/2011 | Baca et al. |
| 2011/0054031 A1 | 3/2011 | McNamara et al. |
| 2011/0059080 A1 | 3/2011 | Cornfeld et al. |
| 2011/0064738 A1 | 3/2011 | Blank et al. |
| 2011/0076278 A1 | 3/2011 | Khodadoust |
| 2011/0076279 A1 | 3/2011 | Ramachandra et al. |
| 2011/0081342 A1 | 4/2011 | Baca et al. |
| 2011/0104069 A1 | 5/2011 | Xu et al. |
| 2011/0110932 A1 | 5/2011 | Patel |
| 2011/0117189 A1 | 5/2011 | Mazzone et al. |
| 2011/0159608 A1 | 6/2011 | Graham |
| 2011/0165648 A1 | 7/2011 | Campange et al. |
| 2011/0177074 A1 | 7/2011 | Sivakumar et al. |
| 2011/0189174 A1 | 8/2011 | Shafiee et al. |
| 2011/0200593 A1 | 8/2011 | Shima et al. |
| 2011/0262432 A1 | 10/2011 | Plouet et al. |
| 2011/0263827 A1 | 10/2011 | Ghayur et al. |
| 2011/0305689 A1 | 12/2011 | Kim |
| 2012/0003641 A1 | 1/2012 | Graham et al. |
| 2012/0006716 A1 | 1/2012 | Frey et al. |
| 2012/0009185 A1 | 1/2012 | Shams |
| 2012/0070428 A1 | 3/2012 | Chan et al. |
| 2012/0076787 A1 | 3/2012 | Adamson et al. |
| 2012/0100136 A1 | 4/2012 | Patel et al. |
| 2012/0100166 A1 | 4/2012 | Roschke et al. |
| 2012/0128626 A1 | 5/2012 | Smith |
| 2012/0134993 A1 | 5/2012 | Pan et al. |
| 2012/0135070 A1 | 5/2012 | Kros et al. |
| 2012/0141573 A1 | 6/2012 | Ling et al. |
| 2012/0156202 A1 | 6/2012 | Shantha et al. |
| 2012/0164079 A1 | 6/2012 | Sharma |
| 2012/0014957 A1 | 7/2012 | Ghayur et al. |
| 2012/0213705 A1 | 8/2012 | Dimasi et al. |
| 2012/0244147 A1 | 9/2012 | Theuer et al. |
| 2012/0258108 A1 | 10/2012 | Ghayur et al. |
| 2012/0263722 A1 | 10/2012 | Ghayur et al. |
| 2012/0276083 A1 | 11/2012 | Junge et al. |
| 2012/0282211 A1 | 11/2012 | Washburn et al. |
| 2012/0301478 A1 | 11/2012 | Ohura et al. |
| 2012/0322738 A1 | 12/2012 | Behrens et al. |
| 2013/0004486 A1 | 1/2013 | Chan et al. |
| 2013/0004511 A1 | 1/2013 | Thorin et al. |
| 2013/0034517 A1 | 2/2013 | Charles et al. |
| 2013/0040889 A1 | 2/2013 | Bolt et al. |
| 2013/0045522 A1 | 2/2013 | Charles et al. |
| 2013/0058927 A1 | 3/2013 | Baca et al. |
| 2013/0071394 A1 | 3/2013 | Troyer et al. |
| 2013/0122003 A1 | 5/2013 | Zhang |
| 2013/0129733 A1 | 5/2013 | Ye et al. |
| 2013/0129749 A1 | 5/2013 | Ye et al. |
| 2013/0129830 A1 | 5/2013 | Chen et al. |
| 2013/0142796 A1 | 6/2013 | Ray et al. |
| 2013/0195806 A1* | 8/2013 | Gay .................. A61K 9/0048 424/93.7 |
| 2013/0202613 A1 | 8/2013 | Pakola et al. |
| 2013/0259881 A1 | 10/2013 | Fandl et al. |
| 2013/0323242 A1 | 12/2013 | Everett et al. |
| 2013/0323302 A1 | 12/2013 | Constable et al. |
| 2013/0330341 A1 | 12/2013 | Chiron et al. |
| 2013/0337534 A1 | 12/2013 | Charles |
| 2013/0344129 A1 | 12/2013 | Washburn et al. |
| 2014/0010823 A1 | 1/2014 | Robinson et al. |
| 2014/0024776 A1 | 1/2014 | Charles et al. |
| 2014/0051642 A1 | 2/2014 | Castan |
| 2014/0170140 A1 | 2/2014 | Bennett et al. |
| 2014/0065137 A1 | 3/2014 | Huang et al. |
| 2014/0065142 A1* | 3/2014 | Roschke .............. C07K 16/241 424/134.1 |
| 2014/0079694 A1 | 3/2014 | Robinson et al. |
| 2014/0081003 A1 | 3/2014 | Laird et al. |
| 2014/0086934 A1 | 3/2014 | Shams |
| 2014/0093499 A1 | 4/2014 | Gschwing et al. |
| 2014/0128575 A1 | 5/2014 | Kao et al. |
| 2014/0134169 A1 | 5/2014 | Kuhnert et al. |
| 2014/0154246 A1 | 6/2014 | Robinson et al. |
| 2014/0154255 A1 | 6/2014 | Akamatsu |
| 2014/0161817 A1 | 6/2014 | Siedler et al. |
| 2014/0186350 A1 | 7/2014 | Ghosh et al. |
| 2014/0193486 A1 | 7/2014 | Liu et al. |
| 2014/0213769 A1 | 7/2014 | Hong et al. |
| 2014/0242082 A1 | 8/2014 | Shima et al. |
| 2014/0287025 A1 | 9/2014 | Liu et al. |
| 2014/0294810 A1 | 10/2014 | Lowman et al. |
| 2014/0302009 A1 | 10/2014 | Ogura et al. |
| 2014/0339122 A1 | 11/2014 | Weeks et al. |
| 2014/0341893 A1 | 11/2014 | Andres et al. |
| 2014/0341977 A1 | 11/2014 | Constable et al. |
| 2015/0004128 A1 | 1/2015 | Charles et al. |
| 2015/0017095 A1 | 1/2015 | Ghayur et al. |
| 2015/0017163 A1 | 1/2015 | Patel et al. |
| 2015/0023951 A1 | 1/2015 | Baca et al. |
| 2015/0030598 A1 | 1/2015 | Croasdale et al. |
| 2015/0037422 A1 | 2/2015 | Kaplan et al. |
| 2015/0037627 A1 | 2/2015 | Armacanqui et al. |
| 2015/0044214 A1 | 2/2015 | Imhof-Jung et al. |
| 2015/0050714 A1 | 2/2015 | Charles |
| 2015/0056195 A1 | 2/2015 | Bertolotto-Ballotti |
| 2015/0065781 A1 | 3/2015 | Bais et al. |
| 2015/0071861 A1 | 3/2015 | Kondo et al. |
| 2015/0071924 A1 | 3/2015 | Swamy et al. |
| 2015/0071941 A1 | 3/2015 | Sodhi et al. |
| 2015/0073381 A1 | 3/2015 | Kauper et al. |
| 2015/0079084 A1 | 3/2015 | Her et al. |
| 2015/0079089 A1 | 3/2015 | Wadehra et al. |
| 2015/0093375 A1 | 4/2015 | Junge et al. |
| 2015/0093390 A1 | 4/2015 | Bansal |
| 2015/0098988 A1 | 4/2015 | Bollag et al. |

(56) References Cited

U.S. PATENT DOCUMENTS

| | | |
|---|---|---|
| 2015/0104452 A1 | 4/2015 | Ghayur et al. |
| 2015/0105734 A1 | 4/2015 | Bryant et al. |
| 2015/0110788 A1 | 4/2015 | Kim et al. |
| 2015/0125468 A1 | 5/2015 | Schmidt et al. |
| 2015/0147317 A1 | 5/2015 | Robblee et al. |
| 2015/0148585 A1 | 5/2015 | Das et al. |
| 2015/0158952 A1 | 6/2015 | Mao et al. |
| 2015/0175689 A1 | 6/2015 | Fuh et al. |
| 2015/0182623 A1 | 7/2015 | Everett et al. |
| 2015/0191535 A1 | 7/2015 | Baehner et al. |
| 2015/0202289 A1 | 7/2015 | Shima et al. |
| 2015/0203591 A1 | 7/2015 | Liang et al. |
| 2015/0210771 A1 | 7/2015 | Crystal et al. |
| 2015/0216795 A1 | 8/2015 | Assadourian et al. |
| 2015/0232548 A1 | 8/2015 | Klien et al. |
| 2015/0246124 A1 | 9/2015 | Fyfe et al. |
| 2015/0250874 A1 | 9/2015 | Yan et al. |
| 2015/0297675 A1 | 10/2015 | Osborne |
| 2015/0315283 A1 | 11/2015 | Ghayur et al. |
| 2015/0368329 A1 | 12/2015 | Hastings et al. |
| 2015/0376271 A1* | 12/2015 | Perlroth ............ A61K 38/1866 424/134.1 |
| 2015/0376272 A1 | 12/2015 | Chung et al. |
| 2016/0008485 A1 | 1/2016 | Marquette et al. |
| 2016/0015770 A1 | 1/2016 | Zacks et al. |
| 2016/0024483 A1 | 1/2016 | Kim et al. |
| 2016/0038589 A1 | 2/2016 | Pate |
| 2016/0046730 A1 | 2/2016 | Ghayur et al. |
| 2016/0068613 A1 | 3/2016 | Regula et al. |
| 2016/0129080 A1 | 5/2016 | Osborne |
| 2016/0130321 A1 | 5/2016 | Burian |
| 2016/0130336 A1 | 5/2016 | Lai et al. |
| 2016/0137717 A1 | 5/2016 | Burian |
| 2016/0144025 A1 | 5/2016 | Vitti et al. |
| 2016/0158320 A1 | 6/2016 | Schultz et al. |
| 2016/0159893 A1 | 6/2016 | Burian et al. |
| 2016/0159894 A1 | 6/2016 | Hartmann et al. |
| 2016/0168240 A1 | 6/2016 | Burian et al. |
| 2016/0184445 A1 | 6/2016 | Perlroth et al. |
| 2016/0194370 A1 | 7/2016 | Quian et al. |
| 2016/0194389 A1 | 7/2016 | Regula et al. |
| 2016/0199501 A1 | 7/2016 | Charles et al. |
| 2016/0243225 A1 | 8/2016 | Ioffe et al. |
| 2016/0243227 A1 | 8/2016 | Fyfe et al. |
| 2016/0257738 A1 | 9/2016 | Baca et al. |
| 2016/0279241 A1 | 9/2016 | Dupont et al. |
| 2016/0287715 A1 | 10/2016 | Charles et al. |
| 2016/0289317 A1 | 10/2016 | Bollag et al. |
| 2016/0296550 A1 | 10/2016 | Patel et al. |
| 2016/0297854 A1 | 10/2016 | Ghosh et al. |
| 2016/0340420 A1 | 11/2016 | Zhang et al. |
| 2016/0346400 A1 | 12/2016 | Emrick et al. |
| 2016/0347843 A1 | 12/2016 | Broering et al. |
| 2016/0369005 A1 | 12/2016 | Lippincott et al. |
| 2017/0002060 A1 | 1/2017 | Bolen et al. |
| 2017/0007581 A1 | 1/2017 | Robinson et al. |
| 2017/0007710 A1 | 1/2017 | Charles et al. |
| 2017/0015755 A1 | 1/2017 | Walsh et al. |
| 2017/0029494 A1 | 2/2017 | Ashman et al. |
| 2017/0035883 A1 | 2/2017 | Gragoudas et al. |
| 2017/0056469 A1 | 3/2017 | Lezzi |
| 2017/0065677 A1 | 3/2017 | Weston-Davies |
| 2017/0079955 A1 | 3/2017 | Boyd |
| 2017/0100478 A1 | 4/2017 | Fyfe et al. |
| 2017/0114127 A1 | 4/2017 | Trout et al. |
| 2017/0129962 A1 | 5/2017 | Regula |
| 2017/0143826 A1 | 5/2017 | Dupont et al. |
| 2017/0143841 A1 | 5/2017 | Charles et al. |
| 2017/0143848 A1 | 5/2017 | Calias et al. |
| 2017/0159114 A1 | 6/2017 | Graham et al. |
| 2017/0190766 A1 | 7/2017 | Perlroth et al. |
| 2017/0210796 A1 | 7/2017 | Siedler et al. |
| 2017/0224815 A1 | 8/2017 | Tirgan |
| 2017/0232199 A1 | 8/2017 | Fiedler |
| 2017/0233444 A1 | 8/2017 | Stout et al. |
| 2017/0240626 A1 | 8/2017 | Baehner et al. |
| 2017/0240629 A1 | 8/2017 | Bedoucha et al. |
| 2017/0253651 A1 | 9/2017 | Chen et al. |
| 2017/0283511 A1 | 10/2017 | Goldenberg et al. |
| 2017/0290876 A1 | 10/2017 | Ghosh et al. |
| 2017/0275353 A1 | 11/2017 | Sheng et al. |
| 2017/0313780 A1 | 11/2017 | Kao et al. |
| 2017/0327569 A1 | 11/2017 | Lu et al. |
| 2017/0349669 A1 | 12/2017 | Imhof-Jung et al. |
| 2017/0362317 A1 | 12/2017 | Lee et al. |
| 2017/0369564 A1 | 12/2017 | Baca et al. |
| 2017/0369566 A1 | 12/2017 | Baehner et al. |
| 2018/0000779 A1 | 1/2018 | Sakamoto et al. |
| 2018/0000933 A1 | 1/2018 | Ingram et al. |
| 2018/0042765 A1 | 2/2018 | Noronha et al. |
| 2018/0057602 A1 | 3/2018 | Theuer et al. |
| 2018/0092897 A1 | 4/2018 | Zarnitsyn et al. |
| 2018/0133288 A1 | 5/2018 | Kim et al. |
| 2018/0134780 A1 | 5/2018 | Klein et al. |
| 2018/0334499 A1 | 5/2018 | Olwill et al. |
| 2018/0155431 A1 | 6/2018 | Herting et al. |
| 2018/0161407 A1 | 6/2018 | Borodic |
| 2018/0186866 A1 | 7/2018 | Falkenstein et al. |
| 2018/0207292 A1 | 7/2018 | Burian et al. |
| 2018/0208642 A1 | 7/2018 | Lim et al. |
| 2018/0221339 A1 | 8/2018 | Boyd et al. |
| 2018/0221483 A1 | 8/2018 | Gaillard et al. |
| 2018/0230540 A1 | 8/2018 | Gosh et al. |
| 2018/0236066 A1 | 8/2018 | Maecher et al. |
| 2018/0237484 A1 | 8/2018 | Kwon et al. |
| 2018/0244762 A1 | 8/2018 | Perlroth et al. |
| 2018/0251545 A1 | 9/2018 | Cao et al. |
| 2018/0276336 A1 | 9/2018 | Perlee et al. |
| 2018/0326126 A1 | 11/2018 | Fiedler |
| 2018/0334496 A1 | 11/2018 | Perlroth et al. |
| 2018/0344847 A1 | 12/2018 | Dupont et al. |
| 2018/0355030 A1 | 12/2018 | Greene et al. |
| 2018/0369380 A1 | 12/2018 | Gragoudas et al. |
| 2018/0371072 A1 | 12/2018 | Theuer et al. |
| 2019/0000919 A1 | 1/2019 | Brockmeyer et al. |
| 2019/0011455 A1 | 1/2019 | Lebert et al. |
| 2019/0016817 A1 | 1/2019 | Taddei et al. |
| 2019/0031783 A1 | 1/2019 | Gu et al. |
| 2019/0062444 A1 | 2/2019 | Walsh et al. |
| 2019/0085056 A1 | 3/2019 | Lebert et al. |
| 2019/0091331 A1 | 3/2019 | Yang et al. |
| 2019/0100581 A1 | 4/2019 | Koenig et al. |
| 2019/0100582 A1 | 4/2019 | Blumenkran et al. |
| 2019/0127454 A1 | 5/2019 | Yang et al. |
| 2019/0127455 A1 | 5/2019 | Simpson et al. |
| 2019/0142975 A1 | 5/2019 | Keravala et al. |
| 2019/0153119 A1 | 5/2019 | Migone et al. |
| 2019/0153471 A1 | 5/2019 | Paul et al. |
| 2019/0161549 A1 | 5/2019 | Choong |
| 2019/0185555 A1 | 6/2019 | Swamy et al. |
| 2019/0194713 A1 | 6/2019 | Mandell et al. |
| 2019/0202904 A1 | 7/2019 | Fellouse et al. |
| 2019/0211091 A1 | 7/2019 | Simpson et al. |
| 2019/0216945 A1 | 7/2019 | Yang et al. |
| 2019/0218263 A1 | 7/2019 | Trese et al. |
| 2019/0224046 A1 | 7/2019 | Heitzmann et al. |
| 2019/0231986 A1 | 8/2019 | Devaraneni |
| 2019/0233517 A1 | 8/2019 | Wu |
| 2019/0255074 A1 | 8/2019 | Song et al. |
| 2019/0255155 A1 | 8/2019 | Perlroth et al. |
| 2019/0256556 A1 | 8/2019 | Giese et al. |
| 2019/0262476 A1 | 8/2019 | Lorenz et al. |
| 2019/0231799 A1 | 9/2019 | Peters et al. |
| 2019/0270806 A1 | 9/2019 | Jacobson et al. |
| 2019/0292239 A1 | 9/2019 | Carter et al. |
| 2019/0300607 A1 | 10/2019 | Isumi |
| 2019/0307691 A1 | 10/2019 | Gaillard et al. |
| 2019/0321467 A1 | 10/2019 | Santos et al. |
| 2019/0322732 A1 | 10/2019 | Murakami et al. |
| 2019/0330335 A1 | 10/2019 | Schwabe et al. |
| 2019/0336482 A1 | 11/2019 | Boyd |
| 2019/0343918 A1 | 11/2019 | Graham et al. |
| 2019/0358335 A1 | 11/2019 | Russell et al. |
| 2019/0360027 A1 | 11/2019 | Perlee et al. |

(56) References Cited

U.S. PATENT DOCUMENTS

| | | |
|---|---|---|
| 2019/0381008 A1 | 12/2019 | Zeitz et al. |
| 2019/0381194 A1 | 12/2019 | Tretiakova et al. |
| 2019/0388522 A1 | 12/2019 | Burian et al. |
| 2020/0000930 A1 | 1/2020 | Charles |
| 2020/0002411 A1 | 1/2020 | Famili et al. |
| 2020/0002426 A1 | 1/2020 | Sheng et al. |
| 2020/0048341 A1 | 2/2020 | Ghosh et al. |
| 2020/0055923 A1 | 2/2020 | Torella et al. |
| 2020/0055933 A1 | 2/2020 | Hailman et al. |
| 2020/0055958 A1 | 2/2020 | Chen et al. |
| 2020/0057058 A1 | 2/2020 | Olsen et al. |
| 2020/0086139 A1 | 3/2020 | Das et al. |
| 2020/0087389 A1 | 3/2020 | Theuer et al. |
| 2020/0095309 A1 | 3/2020 | Peters |
| 2020/0095310 A1 | 3/2020 | Regula et al. |
| 2020/0171179 A1 | 6/2020 | Charles et al. |
| 2020/0261590 A1 | 8/2020 | Charles et al. |
| 2020/0262905 A1 | 8/2020 | Perlroth et al. |
| 2021/0107999 A1 | 4/2021 | Ehrlich et al. |
| 2021/0324063 A1 | 10/2021 | Perlroth et al. |
| 2021/0402015 A1 | 12/2021 | Charles et al. |
| 2022/0096643 A1 | 3/2022 | Charles |
| 2023/0173081 A1 | 6/2023 | Charles et al. |
| 2023/0250133 A1 | 8/2023 | Zurbriggen et al. |

FOREIGN PATENT DOCUMENTS

| | | |
|---|---|---|
| AU | 2015207898 | 8/2015 |
| AU | 2017201930 | 4/2017 |
| BR | 11 2012 014556 | 3/2017 |
| BR | 11 2012 0261185 | 8/2017 |
| CA | 2783615 | 6/2011 |
| CA | 2795667 | 10/2011 |
| CL | 02881/2012 | 7/2013 |
| CN | 101389690 | 3/2009 |
| CN | 102250246 A | 11/2011 |
| CN | 102311502 | 11/2012 |
| CN | 102811713 | 12/2012 |
| CN | 103134874 | 6/2013 |
| CN | 103193819 | 7/2013 |
| CN | 103421039 | 12/2013 |
| CN | 103492489 | 1/2014 |
| CN | 103898101 | 7/2014 |
| CN | 106075466 | 11/2016 |
| CN | 106432557 | 2/2017 |
| CN | 107208076 | 9/2017 |
| CN | 107428824 | 12/2017 |
| CN | 108712911 A | 10/2018 |
| CO | 12119310 | 12/2012 |
| CO | 12203725 | 2/2013 |
| EP | 0345242 | 12/1989 |
| EP | 0863908 | 9/1998 |
| EP | 0874857 | 11/1998 |
| EP | 0577648 | 6/2001 |
| EP | 0968291 | 1/2004 |
| EP | 1179541 | 6/2004 |
| EP | 0929323 | 12/2004 |
| EP | 1325932 | 4/2005 |
| EP | 0971959 | 12/2005 |
| EP | 0973804 | 12/2006 |
| EP | 1465933 | 8/2007 |
| EP | 1135498 | 1/2008 |
| EP | 1592719 | 3/2008 |
| EP | 1988910 | 11/2008 |
| EP | 1605847 | 9/2009 |
| EP | 1732621 | 12/2009 |
| EP | 1968594 | 9/2010 |
| EP | 2260873 | 12/2010 |
| EP | 1802373 | 7/2011 |
| EP | 2301580 | 1/2012 |
| EP | 1660057 | 5/2012 |
| EP | 2029746 | 7/2012 |
| EP | 1802334 | 8/2012 |
| EP | 2329821 | 8/2012 |
| EP | 2512462 | 10/2012 |
| EP | 2203180 | 11/2012 |
| EP | 2558538 | 2/2013 |
| EP | 2199306 | 6/2013 |
| EP | 2604279 | 6/2013 |
| EP | 2155783 | 7/2013 |
| EP | 2446890 | 9/2013 |
| EP | 2344537 | 1/2014 |
| EP | 2274008 | 2/2014 |
| EP | 2042597 | 5/2014 |
| EP | 2524693 | 5/2014 |
| EP | 2540843 | 7/2014 |
| EP | 1991275 | 11/2014 |
| EP | 2443150 | 1/2015 |
| EP | 1802325 | 2/2015 |
| EP | 1989231 | 5/2015 |
| EP | 2217261 | 10/2015 |
| EP | 2596807 | 12/2015 |
| EP | 2200700 | 1/2016 |
| EP | 2307055 | 1/2016 |
| EP | 2259795 | 4/2016 |
| EP | 2516465 | 5/2016 |
| EP | 3041513 | 7/2016 |
| EP | 2411411 | 8/2016 |
| EP | 2575881 | 9/2016 |
| EP | 2473526 | 8/2017 |
| EP | 2491134 | 8/2017 |
| EP | 3222142 | 9/2017 |
| EP | 2327415 | 10/2017 |
| EP | 2785744 | 10/2017 |
| EP | 2188302 | 11/2017 |
| EP | 2467156 | 11/2017 |
| EP | 2894167 | 11/2017 |
| EP | 2925778 | 11/2017 |
| EP | 2784092 | 12/2017 |
| EP | 3254678 | 12/2017 |
| EP | 2792687 | 5/2018 |
| EP | 2319925 | 7/2018 |
| EP | 2662388 | 8/2018 |
| EP | 2872534 | 8/2018 |
| EP | 3122878 | 10/2018 |
| EP | 3401331 | 11/2018 |
| EP | 1861096 | 12/2018 |
| EP | 2726612 | 3/2019 |
| EP | 3038647 | 3/2019 |
| EP | 3020731 | 6/2019 |
| EP | 2924052 | 7/2019 |
| EP | 2846836 | 8/2019 |
| EP | 3327026 | 8/2019 |
| EP | 2951307 | 12/2019 |
| EP | 3450553 | 12/2019 |
| EP | 3600441 | 2/2020 |
| EP | 3610010 | 2/2020 |
| EP | 3038646 | 3/2020 |
| EP | 3104880 | 3/2020 |
| EP | 3216803 | 3/2020 |
| EP | 3268386 | 3/2021 |
| GB | 2200651 | 8/1988 |
| GB | 9621522 | 12/1995 |
| IL | 260323 | 8/2018 |
| IN | 6116/CHENP/2012 | 12/2015 |
| IN | 9473/CHENP/2012 | 12/2015 |
| IN | 201817026516 | 11/2018 |
| JP | S58-154591 | 9/1983 |
| JP | H04-502850 | 5/1992 |
| JP | H10 139832 | 5/1998 |
| JP | H11 217588 | 8/1999 |
| JP | 2003-064132 | 3/2003 |
| JP | 2003-508023 | 3/2003 |
| JP | 2003-508606 | 3/2003 |
| JP | 2004-510851 | 4/2004 |
| JP | 2005-239989 | 9/2005 |
| JP | 2005-255969 | 9/2005 |
| JP | 2006-503549 | 2/2006 |
| JP | 2007-263935 | 10/2007 |
| JP | 2007-531513 | 11/2007 |
| JP | 2008-133434 | 6/2008 |
| JP | 2008-524247 | 7/2008 |
| JP | 2008-536498 | 9/2008 |
| JP | 2009-042617 | 2/2009 |

(56) References Cited

FOREIGN PATENT DOCUMENTS

| | | |
|---|---|---|
| JP | 2009-532330 | 9/2009 |
| JP | 2009-533519 | 9/2009 |
| JP | 2009-542862 | 12/2009 |
| JP | 2009-543895 | 12/2009 |
| JP | 2010-117189 | 5/2010 |
| JP | 2010-279389 | 12/2010 |
| JP | 2011-50073 | 1/2011 |
| JP | 2011-518546 | 5/2011 |
| JP | 2012-025820 | 2/2012 |
| JP | 2012-521768 | 9/2012 |
| JP | 2013-515099 | 5/2013 |
| JP | 2013-519699 | 5/2013 |
| JP | 2013-534931 | 9/2013 |
| JP | 2014-043456 | 3/2014 |
| JP | 5528710 | 6/2014 |
| JP | 5760007 | 6/2015 |
| JP | 5745009 | 7/2015 |
| JP | 2016-14015 | 1/2016 |
| JP | 5846044 | 1/2016 |
| JP | 2016-040371 | 3/2016 |
| JP | 5990629 | 8/2016 |
| JP | 2016-530302 | 9/2016 |
| JP | 2017-31410 | 2/2017 |
| JP | 2018-87330 | 6/2018 |
| JP | 6416832 | 10/2018 |
| KR | 10-0808116 | 3/2008 |
| KR | 20120123340 | 11/2012 |
| KR | 2013-0097636 | 9/2013 |
| KR | 10-1852044 | 4/2018 |
| MX | 2012006970 | 10/2012 |
| MX | 2012011876 | 11/2012 |
| MX | 346423 | 3/2017 |
| MX | 2016017290 | 8/2017 |
| RU | 2376373 C2 | 12/2009 |
| WO | WO 1987/04462 | 7/1987 |
| WO | WO 1990/07936 | 7/1990 |
| WO | WO 1990/11092 | 10/1990 |
| WO | WO 1991/02805 | 3/1991 |
| WO | WO 1991/10741 | 7/1991 |
| WO | WO 1991/14445 | 10/1991 |
| WO | WO 1991/17271 | 11/1991 |
| WO | WO 1992/01047 | 1/1992 |
| WO | WO 1993/03769 | 3/1993 |
| WO | WO 1993/10218 | 5/1993 |
| WO | WO 1993/11230 | 6/1993 |
| WO | WO 1993/12227 | 6/1993 |
| WO | WO 1993/19191 | 9/1993 |
| WO | WO 1993/25234 | 12/1993 |
| WO | WO 1993/25673 | 12/1993 |
| WO | WO 1993/25698 | 12/1993 |
| WO | WO 1994/03622 | 2/1994 |
| WO | WO 1994/016748 | 8/1994 |
| WO | WO 1994/23697 | 10/1994 |
| WO | WO 1994/12649 | 11/1994 |
| WO | WO 1994/28938 | 12/1994 |
| WO | WO 1995/00655 | 1/1995 |
| WO | WO 1995/07994 | 3/1995 |
| WO | WO 1995/13796 | 5/1995 |
| WO | WO 1995/11984 | 7/1995 |
| WO | WO 1995/30763 | 11/1995 |
| WO | WO 1996/17072 | 6/1996 |
| WO | WO 1997/14702 | 4/1997 |
| WO | WO 1997/14703 | 4/1997 |
| WO | WO 1997/37029 | 10/1997 |
| WO | WO 1997/42338 | 11/1997 |
| WO | WO 98/16535 | 4/1998 |
| WO | WO 1998/45331 | 10/1998 |
| WO | WO 1999/064065 | 12/1999 |
| WO | WO 2000/09560 | 5/2000 |
| WO | WO 00/37502 | 6/2000 |
| WO | WO 2000/034337 | 6/2000 |
| WO | WO 2000/059968 | 10/2000 |
| WO | WO 00/75319 | 12/2000 |
| WO | WO 01/00854 | 1/2001 |
| WO | WO 2001/41827 | 6/2001 |
| WO | WO 2002/028929 | 4/2002 |
| WO | WO 03/020906 | 3/2003 |
| WO | WO 2003/062290 | 7/2003 |
| WO | WO 2003/074026 | 9/2003 |
| WO | WO 2003/074090 | 9/2003 |
| WO | WO 2004/003144 | 1/2004 |
| WO | WO 2004/020405 | 3/2004 |
| WO | WO 2004/063237 | 7/2004 |
| WO | WO 2004/065417 | 8/2004 |
| WO | WO 2004/091494 | 10/2004 |
| WO | WO 2004/113394 | 12/2004 |
| WO | WO 2005/028539 | 3/2005 |
| WO | WO 2005/058367 | 6/2005 |
| WO | WO 2005/120166 | 12/2005 |
| WO | WO 2006/063055 | 6/2006 |
| WO | WO 2006/113277 | 10/2006 |
| WO | WO 2006/118547 | 11/2006 |
| WO | WO 2007/005253 | 1/2007 |
| WO | WO 2007/011873 | 1/2007 |
| WO | WO 2007/075534 | 7/2007 |
| WO | WO 2007/100902 | 9/2007 |
| WO | WO 2007/1112675 | 10/2007 |
| WO | WO 2008/020827 | 2/2008 |
| WO | WO 2008/025856 | 3/2008 |
| WO | WO 2008/098930 | 8/2008 |
| WO | WO 2008/112257 | 9/2008 |
| WO | WO 2008/112289 | 9/2008 |
| WO | WO 2008/119565 | 10/2008 |
| WO | WO 2008/119567 | 10/2008 |
| WO | WO 2008/144248 | 11/2008 |
| WO | WO 2008/155134 | 12/2008 |
| WO | WO 2009/052249 | 4/2009 |
| WO | WO 2005/047334 | 5/2009 |
| WO | WO 2009/052439 | 6/2009 |
| WO | WO 2009/105669 | 8/2009 |
| WO | WO 2009/120922 | 10/2009 |
| WO | WO 2009/138473 | 11/2009 |
| WO | WO 2009/149205 | 12/2009 |
| WO | WO 2010/040508 | 4/2010 |
| WO | WO 2010/068862 | 6/2010 |
| WO | WO 2010/068864 | 6/2010 |
| WO | WO 2010/085542 | 7/2010 |
| WO | WO 2010/111625 | 9/2010 |
| WO | WO 2010/136492 | 12/2010 |
| WO | WO 2001/18080 | 3/2011 |
| WO | WO 2011/075185 | 6/2011 |
| WO | WO 2011/075736 | 6/2011 |
| WO | WO 2011/116387 | 9/2011 |
| WO | WO 2011/119656 | 9/2011 |
| WO | WO 2011/130694 | 10/2011 |
| WO | WO 2011/153243 | 12/2011 |
| WO | WO 2012/146610 | 11/2012 |
| WO | WO 2012/163520 | 12/2012 |
| WO | WO 2013/059137 | 4/2013 |
| WO | WO 2013/071016 | 5/2013 |
| WO | WO 2013/082563 | 6/2013 |
| WO | WO 2013/093809 | 6/2013 |
| WO | WO 2013/173129 | 11/2013 |
| WO | WO 2014/006113 | 1/2014 |
| WO | WO 2014/033184 | 3/2014 |
| WO | WO 2014/060401 | 4/2014 |
| WO | WO 2014/068443 A1 | 5/2014 |
| WO | WO 2014/072888 A1 | 5/2014 |
| WO | WO 2014/101287 | 7/2014 |
| WO | WO 2014/160507 | 10/2014 |
| WO | WO 2014/177460 | 11/2014 |
| WO | WO 2015/004616 | 1/2015 |
| WO | WO 2015/035342 | 3/2015 |
| WO | WO 2015/058048 | 4/2015 |
| WO | WO 2015/058369 | 4/2015 |
| WO | WO 2015/059220 | 4/2015 |
| WO | WO 2015/109898 * | 7/2015 |
| WO | WO 2015/110067 | 7/2015 |
| WO | WO 2015/135583 | 9/2015 |
| WO | WO 2015/168321 | 11/2015 |
| WO | WO 2015/198240 | 12/2015 |
| WO | WO 2015/198243 | 12/2015 |
| WO | WO 2015/200905 | 12/2015 |
| WO | WO 2016/008975 | 1/2016 |

(56) References Cited

FOREIGN PATENT DOCUMENTS

| | | |
|---|---|---|
| WO | WO 2016/044041 | 3/2016 |
| WO | WO 2016/045626 | 3/2016 |
| WO | WO 2016/061562 | 4/2016 |
| WO | WO 2016/073157 | 5/2016 |
| WO | WO 2016/073894 | 5/2016 |
| WO | WO 2016/085750 | 6/2016 |
| WO | WO 2016/145189 | 9/2016 |
| WO | WO 2016/160923 | 10/2016 |
| WO | WO 2016/170039 | 10/2016 |
| WO | WO 2017/046140 | 3/2017 |
| WO | WO 2017/117464 | 7/2017 |
| WO | WO 2017/120600 | 7/2017 |
| WO | WO 2017/120601 | 7/2017 |
| WO | WO 2017/204298 | 11/2017 |
| WO | WO 2017/205559 | 11/2017 |
| WO | WO 2018/114728 | 6/2018 |
| WO | WO 2018/122053 | 7/2018 |
| WO | WO 2018/139991 | 8/2018 |
| WO | WO 2018/175319 | 9/2018 |
| WO | WO 2018/182527 | 10/2018 |
| WO | WO 2018/185110 | 10/2018 |
| WO | WO 2018/191548 | 10/2018 |
| WO | WO 2018/217995 | 11/2018 |
| WO | WO 2018/218215 | 11/2018 |
| WO | WO 2019/020777 | 1/2019 |
| WO | WO 2019/038552 | 2/2019 |
| WO | WO 2019/040397 | 2/2019 |
| WO | WO 2019/043649 | 3/2019 |
| WO | WO 2019/057946 | 3/2019 |
| WO | WO 2019/067540 | 4/2019 |
| WO | WO 2019/091384 | 5/2019 |
| WO | WO 2019/099786 | 5/2019 |
| WO | WO 2019/104279 | 5/2019 |
| WO | WO 2019/113225 | 6/2019 |
| WO | WO 2009/092011 | 7/2019 |
| WO | WO 2019/134686 | 7/2019 |
| WO | WO 2019/147944 | 8/2019 |
| WO | WO 2019/154349 | 8/2019 |
| WO | WO 2019/154776 | 8/2019 |
| WO | WO 2019/164219 | 8/2019 |
| WO | WO 2019/169341 | 9/2019 |
| WO | WO 2019/173482 | 9/2019 |
| WO | WO 2019/175727 | 9/2019 |
| WO | WO 2019/178438 | 9/2019 |
| WO | WO 2019/184909 | 10/2019 |
| WO | WO 2019/195313 | 10/2019 |
| WO | WO 2019/200181 | 10/2019 |
| WO | WO 2019/201866 | 10/2019 |
| WO | WO 2019/204380 | 10/2019 |
| WO | WO 2019/229116 | 12/2019 |
| WO | WO 2020/006486 | 1/2020 |
| WO | WO 2020/043184 | 3/2020 |
| WO | WO 2021/226404 | 11/2021 |
| WO | WO 2021/226404 A9 | 11/2021 |

OTHER PUBLICATIONS

Altamirano, C.V. et al., "Association of tetramers of human butyrylcholinesterase is mediated by conserved aromatic residues of the carboxy terminus," Chemico-Biological Interactions, vols. 119-120, pp. 53-60, May 14, 1999.

Ambati et al., "Mechanisms of age-related macular degeneration," Neuron, vol. 75, No. 1, pp. 26-39, 2012.

Anderson, W.F., "Human gene therapy," Science, vol. 256, No. 5058, pp. 808-813, May 8, 1992.

Andrae et al., "Role of platelet-derived growth factors in physiology and medicine," Genes & Development, vol. 22, pp. 1276-1312, 2008.

Armulik, A. et al., "Endothelial/Pericyte Interactions," Circulation Research, vol. 97, Issue 6, pp. 512-523, Sep. 16, 2005.

Dayhoff, M. O., 1978, A model of evolutionary change in proteins-Matrices for detecting distant relationships. In Atlas of Protein Sequence and Structure, National Biomedical Research Foundation, Washington DC vol. 5, Suppl. 3, pp. 345-358.

Baldwin, A. et al., "Reversible maleimide-thiol adducts yield glutathione-sensitive poly(ethylene glycol)-heparin hydrogels," Polymer Chemistry, vol. 4, Issue 1, pp. 133-143, Jan. 7, 2013.

Baldwin, A. et al., "Tunable degradation of maleimide-thiol adducts in reducing environments," Bioconjug Chem, vol. 22, No. 10, pp. 1946-1953, Oct. 19, 2011.

Baluk, P. et al., "Cellular abnormalities of blood vessels as targets in cancer," Current Opinion in Genetics & Development, vol. 15, Issue 1, pp. 102-111, Feb. 2005.

Bates, D.O. et al., "Vascular endothelial growth factor increases microvascular permeability via a Ca(2+)-dependent pathway," American Journal of Physiology, vol. 273, No. 2, pp. H687-H694, Aug. 1, 1997.

Beranger et al., IMGT Scientifite Chart, http://www.imgt.org/IMGTScientificChart/Numbering/Hu_IGHGnber.html, created May 5, 2001.

Berthold, W. et al., "Protein Purification: Aspects of Processes for Pharmaceutical Products," Biologicals, vol. 22, Issue 2, pp. 135-150, Jun. 1994.

Blong, M. Renee et al., "Tetramerization domain of human butyrylcholinesterase is at the C-terminus," Biochemical Journal, vol. 327, No. 3, pp. 747-757, Nov. 1, 1997.

Bock, F. et al. Safety Profile of Topical VEGF Neutralization at the Cornea, Investigative Opthalmology & Visual Science, vol. 50, No. 5, pp. 2095-2012, (2009).

Bowen-Pope et al., "History of Discovery: Platelet-derived Growth Factor," Arterioscler Thromb Vasc Biol., vol. 31, No. 11, pp. 2397-2401, Nov. 2011.

Bontempo, et al., "Cysteine-Reactive Polymers Synthesized by Atom Transfer Radical Polymerization for Conjugation to Proteins," J. Am. Chem. Soc. (2004), 126, pp. 15372-15373.

Boyd et al., "The effect of the removal of sialic acid, galactose and total carbohydrate on the functional activity of Campath-1H", Molecular Immunology, vol. 32: dated Dec. 1995, pp. 1311-1318.

Brown, D. et al., "Ranibizumab versus Verteporfin for Neovascular Age-Related Macular Degeneration," The New England Journal of Medicine, vol. 355, No. 14, pp. 1432-1444, Oct. 5, 2006.

Cannard, K., "The acute treatment of nerve agent exposure," Journal of the Neurological Sciences, vol. 249, Issue 1, pp. 86-94.

Capel et al., "Heterogeneity of human IgG Fc receptors", Immunomethods, 4(1): dated Feb. 1994 pp. 25-34.

Capon, D. et al., "Designing CD4 immunoadhesins for AIDS therapy," Nature, vol. 337, pp. 525-531, 1989.

Carmeliet, P., "Angiogenesis in healt and disease," Nature Medicine, vol. 9, pp. 653-660, (2003).

Carmeliet, P., "Synergism between vascular endothelial growth factor and placental growth factor contributes to angiogenesis and plasma extravasation in pathological conditions," Nature Medicine, vol. 7, No. 5, pp. 575-583, May 2001.

Carmeliet, "Mechanisms of angiogenesis and arteriogenesis," Nature Medicine, vol. 6, No. 3, pp. 389-395, 2000.

Cascio, C. et al., "Use of serum cholinesterases in severe organophosphorus poisoning," Minerva Anestesiologica, vol. 54, in 6 pages, 1988.

Casset, F. et al. A Peptide Mimetic of an Anti0CD4 Monoclonal Antibody by Rational Design, Biochemical and Biophysical Research Communications, vol. 307, pp. 198-205, (2003).

Chames, Patrick et al., "Therapeutic antibodies: successes, limitations and hopes for the future," British Journal of Pharmacology, Wiley-Blackwell, UK; Biosciences Information Service, vol. 157, No. 2, May 1, 2009, pp. 220-233.

Chen et al., "Factors affecting endotoxin removal from recombinant therapeutic proteins by anion exchange chromatography," Protein Expression and Purification, vol. 64, pp. 76-81, 2009.

Chen, et al., "Lubrication at Physiological Pressures by Polyzwitterionic Brushes," Science, (2009), 323, pp. 1698-1701.

Chen, et al., "Polymeric Phosphorylcholine-Camptothecin Conjugates Prepared by Controlled Free Radical Polymerizationand Click Chemistry," Bioconjugate Chem., (2009), 20:12, pp. 2331-2341.

(56) References Cited

OTHER PUBLICATIONS

Chen, Y et al. Selection and Analyisi an Optimized Anti-VEGF Antibody: Crystal Structure of an Affinity-Matured Complex with Antigen, J. Mol. Biol., vol. 293, pp. 865-881 , (1999).
Chothia, C. et al., "Canonical structures for the hypervariable regions of immunoglobulins," Journal of Molecular Biology, vol. 196, Issue 4, pp. 901-917, Aug. 20, 1989.
Chothia, C. et al., "Conformations of immunoglobulin hypervariable regions," Nature, vol. 342, pp. 877-883, Dec. 1989.
Christy, N.E. et al., "Antibiotic prophylaxis of postoperative endophthalmitis," Annals of Ophthalmology, vol. 11, No. 8, pp. 1261-1265, Aug. 1, 1979.
Cohen, S.Y. et al., "Causes of unsuccessful ranibizumab treatment in exudative age-related macular degeneration in clinical settings," Retina, vol. 32, Issue 8, pp. 1480-1485, Sep. 2012.
Crowe, et al., "Recombinant human respiratory syncytial virus (RSV) monoclonal antibody Fab is effective therapeutically when introduced directly into the lungs of RSV-infected mice," Proc. Natl. Acad. Sci. USA, (1994) 91 pp. 1386-1390.
Database WPI Week 200833 Thomson Scientific, London, GB; AN 2008-E72441 XP002795732, & CN 101 053 681 A (Univ Tianjin), Oct. 17, 2007.
Da Pieve, et al., "Conjugation of PolyPEG®, Linear PEG and Branched PEG to a Thiol-Modified Aptamer," Poster, Warwick Effect Polymers Ltd, retrieved from <http:www.wep-ltd.co.uk> (2010).
Da Pieve, et al., "Modification of Thiol Functionalized Aptamers by Conjugation of Synthetic Polymers," Bioconjugate Chem., (2010), 21:1, pp. 169-174.
Daneshian, M. et al., "In vitro pyrogen test for toxic or immunomodulatory drugs," Journal of Immunological Methods, vol. 313, Issues 1-2, pp. 169-175, Jun. 30, 2006.
De Pascalis, R. et al., "Grafting of "abbreviated" complementarity-determining regions containing specificity-determining residues essential for ligand contact to engineer a less immunogenic humanized monoclonal antibody," J. Immunol., vol. 169, No. 6, pp. 3076-3084, Sep. 15, 2002.
Declaration of Harvey N. Masonson, M.D., under 37 C.F.R., for U.S. Appl. No. 12/465,051, filed May 13, 2009, including Exhibits A, B, and C, signed Jul. 6, 2011, in 50 pages.
Dillon et al., "Structural and functional characterization of disulfide isoforms of the human IgG2 subclass," The Journal of Biological Chemistry, vol. 283, No. 23, pp. 16206-16215, 2008.
Ding, J.L. et al., "A new era of pyrogen testing," Trends in Biotechnology, vol. 19, Issue 8, pp. 277-281, Aug. 1, 2001.
Dong, et al., "ARGET ATRP of 2-(Dimethylamino)ethyl Methacrylate as an Intrinsic Reducing Agent," Macromolecules, (2008), 41:19 pp. 6868-6870.
Dong, et al., "Well-Defined High-Molecular-Weight Polyacrylonitrile via Activators Regenerated by Electron Transfer ATRP," Macromolecules, (2007), 40:9, pp. 2974-2977.
Du et al. "pH-Sensitive Vesicles based on a Biocompatible Zwitterionic Diblock Copolymer" J. Am. Chem. Soc., Dec. 1, 2005, 127, 17982-17983.
Edelman et al., "The covalent structure of an entire yG immunoglobulin molecule," Proceedings of the National Academy of Sciences, vol. 63, pp. 78-85, May 1, 1969.
Edwards et al., "The Remarkable Flexibility of the Human Antibody Repertoire; Isolation of Over One Thousand Different Antibodies to a Single Protein, BLyS", J. Mol. Biol., vol. 334, pp. 103-118, 2003.
Ellman, G. et al., "A new and rapid colorimetric determination of acetylcholinesterase activity," Biochemical Pharmacology, vol. 7, Issue 2, pp. 88-95, Jul. 1961.
Engelgau, M et al. Evolving Diabetes Burden in the United States. Ann of Int Med. 140 (11): 945-951, 2004.
Eppstein et al., "Biological activity of liposome-encapsulated murine interferon gamma is mediated by a cell membrane receptor", Proc. Natl. Acad. Sci. USA, vol. 82: dated Jun. 1985 pp. 3688-3692.
Facts About Diabetic Eye Disease, National Eye Institute, https://nei.nih.gov/health/diabetic/retinopathy, publication reviewed Sep. 2015, accessed Mar. 27, 2018, in 7 pages. The reference is a webpage, aApplicants note that the webpage was printed on Mar. 27, 2018, and has a copyright date of 2015 ; however, the webpage may have been available, in some form, prior to this date.
Fares, F.A. et al., "Design of a long-acting follitropin agonist by fusing the C-terminal sequence of the chorionic gonadotropin beta subunit to the follitropin beta subunit," Proc Natl Acad Sci USA, vol. 89, No. 10, pp. 4304-4308, May 15, 1992.
Ferrara, N. et al., "Discovery and development of bevacizumab, an anti-VEGF antibody for treating cancer," Nature Reviews Drug Discovery, vol. 3, pp. 391-400, May 2004.
Ferrara, N. et al., "The Biology of Vascular Endothelial Growth Factor," Endocrine Reviews, vol. 18, No. 1, pp. 4-25, (1997).
Ferrara, et al. Development of Ranibizumab, An Anti-Vascular Endothelial Growth, as Therapy for Neovascular Age-Related Macular Degeneration, Retina, The Journal of Retinal and Vitreous Diseas, vol. 26, Issue No. 8, pp. 859-870, (2006).
Ferrara, et al., "The Biology of VEGF and its Receptors", Nature Medicine, vol. 9 No. 6, pp. 669-676, (2003).
Fiske, M. et al., "Method for reducing endotoxin in Moraxella catarrhalis UspA2 protein preparations," Journal of Chromatography B: Biomedical Sciences and Applications, vol. 753, Issue 2, pp. 269-278, Apr. 5, 2001.
Folkman, J., "Angiogenesis: an organizing principle for drug discover?" Nature Reviews, Drug Discovery, vol. 6, pp. 273-286, Apr. 2007.
Fontaine et al., "Long-Term Stabilization of Maleimide-Thiol Conjugates," Bioconjugate Chem., vol. 26, pp. 145-152, 2015.
Foster, Graham R., "Pegylated interferons for the treatment of chronic Hepatitis C," Drugs, vol. 70, Issue 2, pp. 147-165, Jan. 2010.
Friedman, D.S. et al., "Prevalence of age-related macular degeneration in the United States," Arch. Ophthalmol., vol. 122, No. 4, pp. 564-572, Apr. 2004.
Greene et al., "Protective Groups in Organic Synthesis," 3rd Edition, John Wiley and Sons, Inc., New York, (1999). In 52 pages which includes only the Title Page and Table of Contents.
Gillies, et al., "Dendrimers and Dedritic Polymers in Drug Delivery," Drug Delivery today, Jan. 2005, vol. 10, No. 1, pp. 35-43.
Goodson, R.J. et al., "Site-directed pegylation of recombinant interleukin-2 at its glycosylation site," Nature Biotechnology, vol. 8, pp. 343-346, 1990.
Goel, N. et al., "Certolizumab pegol," mAbs, vol. 2, No. 2, pp. 137-147, Mar. /Apr. 2010.
Gordon, M. et al., "Determinatino of the normality of cholinesterase solutions," Analytical Biochemistry, vol. 85, Issue 2, pp. 519-527, Apr. 1978.
Gorun, V. et al., "Modified Ellman procedure for assay of cholinesterases in crude enzymatic preparations," Analytical Biochemistry, vol. 86, Issue 1, pp. 324-326, May 1978.
Gualberto, Antonio, "Brentuximab Vedotin (SGN-35), an antibody-drug conjugate for the treatment of CD30-positive malignancies," Expert Opinion on Investigational Drugs, vol. 21, Issue 2, pp. 205-216, 2012.
Guyer et al., "Immunoglobulin Binding by Mouse Intestinal Epithelial Cell Receptors", The Journal of Immunology, 117(2): dated Aug. 1, 1976, pp. 587-893.
Haddleton, et al., "Phenolic Ester-Based Initiators for Transition Metal Mediated Living Polymerization," Macromolecules, (1999), 32, pp. 8732-8739.
Haishima, Y et al. Estimation of uncertainty in kinetic-colorimetric assay of bacterial endotoxins, J Pharm Biomed Analysis, 32: 1, pp. 495-503, (2003).
Haupt, H. et al., "Isolierung und physikalisch-chemische Charakterisierung der Cholinesterase aus Humanserum," Blut, vol. 14, Issue 2, pp. 65-75, Nov. 1966.
Hein J., 1990, Unified Approach to Alignment and Phylogenies pp. 626-645 Methods in Enzymology vol. 183, Academic Press, Inc., San Diego, CA.
Heise et al., "Starlike Polymeric Architectures by Atom Transfer Radical Polymerization: Templates for the Production of Low Dielectric Constant Thin Films," Macromolecules, Jan. 17, 2000, 33:2346-2354.

(56) References Cited

OTHER PUBLICATIONS

Heise, et al., "Investigation of the Initiation Behavior of a Dendritic 12-Arm Initiator in Atom Transfer Radical Polymerization," Macromolecules, (2001), 34:11, pp. 3798-3801.
Higgins, D.G. and Sharp, P.M., "Fast and sensitive multiple sequence alignments on a microcomputer" CABIOS 5: dated 1989, pp. 151-153.
Heredia, et al., "In Situ Preparation of Protein-'Smart' Polymer Conjugates with Retention of Bioactivity," J. Am. Chem. Soc., (2005), 127, pp. 16955-16960.
Hinton et al., "Engineered human IgG antibodies with longer serum half-lives in primates", Journal of Biological Chemistry, 279(8): dated Feb. 20, 2004 in 5 pages.
Hirayama, C. et al., "Chromatographic removal of endotoxin from protein solutions by polymer particles," Journal of Chromatography B, vol. 781, Issues 1-2, pp. 419-432, Dec. 5, 2002.
Hoffmann, S. et al., "International validation of novel pyrogen tests based on human monocytoid cells," Journal of Immunological Methods, vol. 298, Issues 1-2, pp. 161-173, Mar. 2005.
Holash, J et al. VEGF-Trap: A VEGF Blocker with Potent Antitumor Effects, PNAS, vol. 9, No. 17, pp. 11393-11398, (2002).
Holliger, P. et al., "'Diabodies': small bivalent and bispecific antibody fragments," Proc. Natl. Acad. Sci. USA, vol. 90, No. 14, pp. 6444-6448, Jul. 15, 1993.
Hong, et al., "Preparation of Segmented Copolymers in the Presence of an Immobilized/Soluble Hybrid ATRP Catalyst System," Macromolecules, (2003), 36:1, pp. 27-35.
Hsu et al., "Differential N-Glycan Patterns of Secreted and Intracellular IgG Produced in Trichoplusia ni Cells" Journey of Biol. Chem. vol. 272: dated 1997, pp. 9062-9070.
Huang, Y.J. et al., "Recombinant human butyrylcholinesterase from milk of transgenic animals to protect against organophosphate poisoning," PNAS, vol. 104, No. 34, pp. 13603-13608, Aug. 21, 2007.
Huang, Y-S. et al., "Engineering a pharmacologically superior form of granulocyte-colony-stimulating factor by fusion with gelatin-like-protein polymer," European Journal of Pharmaceutics and Biopharmaceutics, vol. 74, Issue 3, pp. 435-441, Mar. 2010.
Humphreys et al., "Alternative antibody FAB' fragment PEGylation strategies: combination of strong reducing agents, disruption of the interchain disulphide bond and disulphide engineering," Protein Engineering, Design & Selection, vol. 20, No. 5, pp. 227-234, 2007.
Huston, James S., "Protein engineering of single-chain Fv analogs and fusion proteins," Methods of Enzymology, vol. 203, pp. 46-96, 1991.
Hwang et al., "Hepatic uptake and degradation of unilamellar sphingomyelin/cholesterol liposomes: a kinetic study", Proceedings of the National Academy of Sciences of the United States of America, 77(7): dated Jul. 1980, pp. 4030-4034.
Ishikawa, K. et al., "Molecular mechanisms of subretinal fibrosis in age-related macular degeneration," Experimental Eye Research, vol. 142, pp. 19-25, Jan. 2016.
IUPAC Gold Book, Random Copolymerization, available at https://goldbook.iupac.org/html/R/R05126.html, Feb. 24, 2014 The reference is a webpage, aApplicants note that the webpage was printed on Nov. 21, 2017, and has a copyright date of 2014 ; however, the webpage may have been available, in some form, prior to this date.
Iwasaki, et al., "Platelet compatible blood filtration fabrics using a phosphorylcholine polymer having high surface mobility," Biomaterials, (2003), 24 pp. 3599-3604.
Iwasaki, Yasuhiko et al., "Synthesis and Characterization of Amphiphilic Polyphosphates with hydrophilic graft chains and Cholesteryl Groups as Nanocarriers", Biomacromolecules, 2006, 7, 1433-1438.
Jakubowski, et al., "Activators Regenerated by Electron Transfer for Atom Transfer Radical Polymerization of Styrene," Macromolecules, (2006), 39:1, pp. 39-45.
Jankova, et al., "Star Polymers by ATRP of Styrene and Acrylates Employing Multifunctional Initiators," Journal of Polymer Science Part A: Polymer Chemistry, Mar. 30, 2005, vol. 43, pp. 3748-3759.
Janssen, Alzheimer Immunotherapy Research & Development, LLC, AAB-001 in Patients With Mild to Moderate Alzheimer's Disease, Clinical Trials, gov, NIH, 2005, [retrieved on Jun. 19, 2012]. Retrieved from the Internet: <http://clinicaltrials.gov/ct2/show/NCT00112073?term=aab-001&rank=3>.
Jefferis et al., "Glycosylation of Antibody Molecules: Structural and Functional Significance", Antibody Engineering, vol. 65: dated 1997, pp. 111-128.
Wyss and Wagner, "The structural role of sugars in glycoproteins" Current Opin. Biotech. vol. 7: dated 1996, pp. 409-416.
Jeon, et al., "Synthesis of High Molecular Weight 3-Arm Star PMMA by ARGET ATRP," Macromolecular, 17:4 pp. 240-244, (2009).
Jo, N. et al., "Inhibition of platelet-derived growth factor B signaling enhances the efficacy of anti-vascular endothelial growth factor therapy in multiple models of ocular neovascularization," American Journal of Pathology, vol. 168, No. 6, pp. 2036-2053, Jun. 2006.
Johnson et al., "Kabat Database and its applications: 30 years after the first variability plot", Nucleic Acids Research, 28(1): Jan. 1, 2000, pp. 214-218.
Jones, A., Analysis of Polypeptides and Proteins, Adv. Drug Delivery Rev. 10:, pp. 29-90, (1993).
Jorg T. Regula, et al., "Targeting key angiogenic pathways with a bispecific CrossMab, optimized for neovascular eye diseases, " EMBO Molecular Medicine (online), vol. 8, No. 11, Oct. 14, 2016, pp. 1265-1288.
Junghans, R.P., "Anti-Tac-H, a humanized antibody to the interleukin 2 receptor with new features for immunotherapyin malignant and immune disorders," Cancer Research, vol. 50, pp. 1495-1502, Mar. 1, 1990.
Kabat, E.A. et al., "Sequences of proteins of immunological interest," in 10 pages, 1991 (includes title page and table of contents only).
Kallis, G.B. et al., "Differential reactivity of the functional sulfhydryl groups of cysteine-32 and cysteine-35 present in the reduced form of thioredoxin from *Escherichia coli*.," The Journal of Biological Chemistry, vol. 255, No. 21, pp. 10261-10266, Nov. 10, 1980.
Katschke et al., "Inhibiting Alternative Pathway Complement Activation by Targeting the Factor D Exosite", The Journal of Biological Chemistry, vol. 287, No. 16, pp. 12886-12892, Apr. 13, 2012.
Kempen, J, et al. The Prevalence of Diabetic Retinopathy Among Adults in the United States, Arch Opthalmol., vol. 122, pp. 532-563, (2004).
Kim et al., "Identifying amino acid residues that influence plasma clearance of murine IgG1 fragments by site-directed mutagenesis", European Journal of Immunology, 24(3): dated Mar. 1994.
Kizhakkedathu, et al., "Synthesis of Well-Defined Environmentally Responsive Polymer Brushes by Aqueous ATRP," Macromolecules, (2004), 37:3, pp. 734-743.
Kohler et al., "Continuous cultures of fused cells secreting antibody of predefined specificity", Nature, vol. 256: dated 1975, pp. 495-497.
Kostelny, S.A. et al., "Formation of a bispecific antibody by the use of leucine zippers," J. Immunol., vol. 148, No. 5, pp. 1547-1553, Mar. 1, 1992.
Kuhnert, F. et al. "Soluble receptor-mediated selective inhibition of VEGFR and PDGFR_signaling during physiologic and tumor angiogenesis", PNAS, vol. 105, No. 29, pp. 10185-10190, (2008).
Kumar et al., "PDGF-DD targeting arrests pathological angiogenesis by modulating GSK3β phosphorylation," JBC Papers in Press, published on Mar. 15, 2010 as Manuscript M110.113787, retrieved on Jun. 18, 2015 from http://www.jbc.org; However, as this item is accessible on the world wide web, it may have been available in some form at an earlier point in time.
Kumar, A. et al., "Platelet-derived growth factor-DD targeting arrests pathological angiogenesis by modulating glycogen synthase kinase-3β phosphorylation," The Journal of Biological Chemistry, vol. 285, No. 20, pp. 15500-15510, May 14, 2010.
Kunik et al., "Paratome: an online tool for systematic indentification of antigen-binding regions in antibodies based on sequence or structure", Nucleic Acids Research, vol. 40: Jun. 6, 2012, W521-524.

(56) References Cited

OTHER PUBLICATIONS

Kwiatdowski, et al., "High Molecular Weight Polymethacrylates by AGET ATRP under High Pressure," Macromolecules, (2008), 41:4, pp. 1067-1069.
Lacciardi, et al., "Synthesis of Novel Folic Acid-Functionalized Biocompatible Block Copolymers by Atom Transfer Radical Polymerization for Gene Delivery and Encapsulation of Hydrophobic Drugs," Biomacromolecules, (2005), 6:2, pp. 1085-1096.
Lafaut et al., "Clinicopathological correlation in exudative age related macular degeneration: histological differentiation between classic and occult choroidal neovascularisation," Br J Ophthalmol, vol. 84, pp. 239-243, 2000.
Lazar et al., "Engineered antibody Fc variants with enhanced effector function", Proc Natl Acad Sci U S A, 103(11): dated Mar. 14, 2006 in 6 pages.
Lee, Ernes C., "Clinical manifestations of sarin nerve gas exposure," J. Am. Med. Assoc., vol. 290, No. 5, pp. 659-662, Aug. 6, 2003.
Lee, Vincent H.L., "Peptide and Protein Drug Delivery," CRC Press, 1990.
Lefranc et al., "IMGT unique numbering for immunoglobulin and T cell receptor variable domains and Ig superfamily V-like domains", Developmental and Comparative Immunology, vol. 27: dated 2003, pp. 55-77.
Lena, et al., "Investigation of metal ligand affinities of atom transfer radical polymerization catalysts with a quadrupole ion trap," Dalton Transactions, (2009), 41, pp. 8884-8889.
Lewis, et al., "Crosslinkable coatings from phosphorylcholine-based polymers," Biomaterials, (2001), 22, pp. 99-111.
Lewis, et al., "Poly(2-methacryloyloxyethyl phosphorylcholine) for Protein Conjugation," Bioconjugate Chem., (2008), 19:11, pp. 2144-2155.
Lin, Weifeng et al., "A novel zwitterionic copolymer with a short poly(methyl acrylic acid) block for improving both conjugation and separation efficiency of a protein without losing its bioactivity". Journal of Materialos Chemistry B. May 21, 2013, vol. 1, No. 19, pp. 2482-2488. See abstract; and p. 2487.
Lindley, H., "A study of the kinetics of the reaction between thiol compounds and chloroacetamide," Biochem J., vol. 74, pp. 577-584, Mar. 1960.
Liu, et al., "Syntheses and Micellar Properties of Well-Defined Amphiphilic AB2 and A2B Y-Shaped Miltoarm Star Copolymers of ε-Caprolactone and 2-(Dimethylamino) ethyl Methacrylate," Journal of Polymer Science: Part A: Polymer Chemistry, DOI 10.1002/pola, published online in Wiley InterSciences (www.intersience.wiley.com), 22 Sep. 2006; accepted Nov. 23, 2006.
Lloyd et al., "Modelling the human immune response: performance of a 1011 human antibody repertoire against a broad panel of therapeutically relevant antigens", Protein Engineering Design & Selection, vol. 22, No. 3, pp. 159-168, 2009.
Lockridge, O. et al., "Complete amino acid sequence of human serum cholinesterase," The Journal of Biological Chemistry, vol. 262, pp. 549-557, Jan. 15, 1987.
Lockridge, O. et al., "Large scale purification of butyrylcholinesterase from human plasma suitable for injection into monkeys; A potential new therapeutic for protection against cocaine and nerve agent toxicity," The Journal of Medical, Chemical, Biological, and Radiological Defense, 3:nihms5095, doi:10.1901/jaba.2005.3-nihms5095, 2005.
Lucentis ramibizumab (reb) Name of the Medicine, Active ingredient Ranibizumab, Product Information Sheet, in 30 pages, based on CDS dated Aug. 30, 2013.
Lutz, et al., "Preparation of Ideal PEG Analogues with a Tunable Thermosensitivity by Controlled Radical Copolymerization of 2-(2-Methoxyethoxy)ethyl Methacrylate and Oligo(ethylene glycol) Methacrylate," Macromolecules, (2006), 39:2, pp. 893-896.
Luxon, B. et al., "Pegylated interferons for the treatment of chronic hepatitis C infection," Clinical Therapeutics, vol. 24, Issue 9, pp. 1363-1383, Sep. 2002.
Ma, et al., "Synthesis of Biocompatible Polymers. 1. Homopolymerization of 2-Methacryloyloxyethyl Phosphorylcholine via ATRP in Protic Solvents: An Optimization Study," Macromolecules, (2002), 35:25, pp. 9306-9314.
Ma, et al., "Well-Defined Biocompatible Block Copolymers via Atom Transfer Radical Polymerization of 2-Methacryloyloxyethyl Phosphorylcholine in Protic Media," Macromolecules, (2003), 36:10, pp. 3475-3484.
Mabry, R. et al., "A dual-targeting PDGFRβ/VEGF-A molecule assembled from stable antibody fragments demonstrates anti-angiogenic activity in vitro and in vivo", Landes Bioscience, vol. 2, Issue 2, pp. 20-34 (2010).
MacCallum, R. et al., Antibody-Antigen Interactions: Contact Analysis and Binding Site Toopgraphy, J/. Mol Biol., vol. 262, pp. 732-745, (1996).
Magalhaes et al., "Methods of Endotoxin Removal from Biological Preparations: a Review," J. Pharm Pharmaceut Sci., vol. 10, No. 3, pp. 388-404, 2007.
Makabe et al., "Thermodynamic Consequences of Mutations in Vernier Zone Residues of a Humanized Anti-human Epidermal Growth Factor Receptor Murine Antibody, 528", Journal of Biological Chemistry, vol. 283: dated Jan. 11, 2008, pp. 1156-1166.
Mantovani, et al., "Design and Synthesis of N-Maleimido-Functionalized Hydrophilic Polymers via Copper-Mediated Living Radical Polymerization: A Suitable Alternative to PEGylation," J. Am. Chem. Soc., (2005), 127, pp. 2966-2973.
Marticorena, J. et al., "Sterile endophthalmitis after intravitreal injections," Mediators of Inflammation, vol. 2012, 6 pages, (2012).
Martin et al., "Modeling antibody hypervariable loops: A combined algorithm", Proc. Natl. Acad. Sci. USA, vol. 86: dated Dec. 1989, pp. 9268-9272.
Masson, P. et al., "Expression and Refolding of Functional Human butyrylcholinesterase from *E. coli*", Multidisciplinary Approaches to Cholinesterase Functions, New York, pp. 49-52, 1992.
Matyjaszewski, et al., "Diminishing catalyst concentration in atom transfer radical polymerization with reducing agents," PNAS, (Oct. 17, 2006), 103:42, pp. 15309-15314.
Mayadunne, R. et al. Living Free Radical Polymerization with Reversible Addition-Fragmentation Chain Transfer (RAFT Polymerization): Approaches to Star Polymers, Macromolecules, vol. 36, pp. 1505-1513, (2003).
McCafferty et al., "Phage antibodies: filamentous phage displaying antibody variable domains", Nature, vol. 348: dated 1990, pp. 552-554.
McPherson, D. et al., "Production and Purification of a Recombinant Elastomeric Polypeptide, G-(VPGVG)19-VPGV, from *Escherichia coli*," Biotechnology Process, vol. 8, Issue 4, pp. 347-352, Jul./Aug. 1992.
McRae, et al. "Pentafluorophenyl Ester-Functionalized Phosphorylcholine Polymers: Preparation of Linear, Two-Arm, and Grafted Polymer-Protein Conjugates," Biomacromolecules, 13, 2099-2109 (2012).
Meng, X. et al. New Generation Recombinant hBuChe-FC Fusion with In-Vivo Performance Equivilanet to Gold Standard Plasma-Derive hbuChe-A First-in-Class Broad Spectrum Bioscanvenger that is Sustainable, Scalable, and Highly Cost-Effective on a Troop-Equivalent-Dose (TED) Basis.
Millard, C.B. et al., "Design and expression of organophosphorus acid anhydride hydrolase activity in human butyrylcholinesterase," Biochemistry, vol. 34, No. 49, p. 15925-15933, 1995.
Min, et al., "Use of Ascorbic Acid as Reducing Agent for Synthesis of Well-Defined Polymers by ARGET ATRP," Macromolecules, (2007), 40:6, pp. 1789-1791.
Miyamoto, et al., "Effect of water-soluble Phospholipid polymers conjugated with papain on the enzymatic stability," Biomaterials, (2004), 25, pp. 71-76.
Mones, Jordi, Inhibiting VEGF and PDGF to Treat AMD, http://www.reviewofophthalmology.com/content/d/retinal_insider/c/29979/#stash.fJePfjQ4.dpuf, Spain, Sep. 9, 2011.
Morris, G.E., "Epitope mapping protocols in methods in molecular biology," vol. 66, 1996.
Myers, E.W. and Muller W., "Optimal alignments in linear space" CABIOS 4: dated 1988, pp. 11-17.

(56) References Cited

OTHER PUBLICATIONS

Neuberger. "Generating high-avidity human Mabs in mice" Nature Biotechnology 14, 826 (1996).
Ng, et al., "Successful Cu-Mediated Atom Transfer Radical Polymerization in the Absence of Conventional Chelating Nitrogen Ligans," Macromolecules, (2010), 43:2, pp. 592-594.
Ogikubo, Y. et al., "Evaluation of the bacterial endotoxin test for quantification of endotoxin contamination of porcine vaccines," Biologicals, vol. 32, Issue 2, pp. 88-93, Jun. 2004.
Oh, et al., "Preparation of Poly(oligo(ethylene glycol) monomethyl ether methacrylate) by Homogeneous Aqueous AGET ATRP," Macromolecules, (2006), 39:9, pp. 3161-3167.
Ong, K. et al., "A rapid highly-sensitive endotoxin detection system," Biosensors and Bioelectronics, vol. 21, Issue 12, pp. 2270-2274, Jun. 15, 2006.
Oestberg, L. et al., "Human X (mouse X human) hybridomas stably producing human antibodies," Hybridoma, vol. 2, No. 4, pp. 361-367, 1983.
Padlan, Eduardo A., "A possible procedure for reducing the immunogenicity of antibody variable domains while preserving their ligand-binding properties," Molecular Immunology, vol. 28, Issues 4-5, pp. 489-498, Apr.-May 1991.
Palma, et al., "A new bispphosphonate-containing 99mTc(I) tricarbonyl complex potentially useful as bone-seeking agent: synthesis and biological evaluation," J Biol Inorg Chem, 12:667-679, (2007).
Pan, C. et al. Comparison of Long-Acting Bevacizumab Formulations in the Treatment of Choroidal Neovascularization in a Rat Model, Journal of Ocular Pharmacology and Therapeutics., vol. 27, No. 3, pp. 219-224, (2011).
Papadopoulos et al., "Binding and neutralization of vascular endothelial growth factor (VEGF) and related ligands by VEGF Trap, ranibizumab and bevacizumab," Angiogenesis, vol. 15, pp. 171-185, 2012.
Pasut, et al., "Protein peptide and non-peptide drug PEGylation for therapeutic application," Expert Opin. Ther. Patents, 14(6) 859-894 (2004).
Paul, W., Fundamental Immunology, 2nd ed. Raven Press, N.Y., (1989). table of contents.
Petsch, D. et al., "Endotoxin removal from protein solutions," Journal of Biotechnology, vol. 76, Issues 2-3, pp. 97-119, Jan. 21, 2000.
Pennock, S. et al. Vascular Endothelial Growth Factor a Competitively Inhibits Platelet-Derived Growth Factor (PDGF)-Dependent Activation of PDGF Receptor and Subsequent Signaling Events and Cellar Responses, Molecular and Cell Biology, vol. 32, No. 2, pp. 1955-1966, (2012).
Piedmonte, D. et al., "Formulation of Neulasta® (pegfilgrastim)," Advanced Drug Delivery Reviews, vol. 60, Issue 3, pp. 50-58, Jan. 3, 2008.
Pietrasik, et al., "Synthesis of High Molecular Weight Poly(styrene-co-acrylonitrile) Copolymers with Controlled Architecture," Macromolecules, (2006), 39:19, pp. 6384-6390.
Poljak, R. "Production and structure of diabodies," Structure, vol. 2, Issue 12, pp. 1121-1123, Dec. 1994.
Pratt, et al. End-Functionalized Phosphorycholine Methacrylate and Their Use in Protein Conjugation, Biomacromlecules, vol. 9, pp. 2891-2897, (2008).
Presta et al., "Humanization of an Anti-Vascular Endothelial Growth Factor Monoclonal Antibody for the Therapy of Solid Tumors and Other Disorders," Cancer Research, vol. 57, pp. 4593-4599, 1997.
Raetz, C.R. et al., "Gram-negative endotoxin: an extraordinary lipid with profound effects on eukaryotic signal transduction," The FASEB Journal, vol. 5, No. 12, pp. 2652-2660, Sep. 1991.
Raica, M. et al., "Platelet-derived growth factor (PDGF)/PDGF receptors (PDGFR) axis as target for antitumor and antiangiogenic therapy," Pharmaceuticals, vol. 3, No. 3, pp. 572-599, (2010).
Ranganathan, et al., "Synthesis of Thermoresponsive Mixed Arm Star Polymers by Combination of RAFT and ATRP from a Multifunctional Core and Its Self-Assembly in Water," Macromolecules, (2008), 41:12, pp. 4226-4234.

*Regeneron Pharmaceuticals Inc.* vs. *Bayer Pharma AG* Approved Judgment dated Feb. 21, 2013.
Ravetch et al., "Fc receptors", Annual Review of Immunology, vol. 9: dated Apr. 1991, pp. 457-492.
Regillo, C. et al., "Randomized, double-masked, sham-controlled trial of ranibizumab for neovascular age-related macular degeneration: PIER Study Year 1," American Journal of Ophthalmology, vol. 145, Issue 2, pp. 239-248, Feb. 2008.
Roitt, I.M., "Immunology—Second Edition", Gower Medical Publishing, 1989, pp. 5.8, 5.9.
Roberts et al., "Chemistry for Peptide and Protein PEGylation," Advanced Drug Delivery Reviews 2002 54:459-476.
Roberts, W.G. et al., "Increased microvascular permeability and endothelial fenestration induced by vascular endothelial growth factor," Journal of Cell Science, vol. 108, pp. 2369-2379, (1995).
Robinson, E.D., "Comparison of labeled trees with valency three" Comb. Theor. vol. 11: dated 1971, pp. 105.
Robinson, K. et al. Controlled Polymerization of 2-Hydroxyethyl Methacrylate by ATRP at Ambient Temperature, Macromolecules, vol. 34, pp. 3155-3158, (2001).
Rosenfeld, P. et al., "Ranibizumab for neovascular age-related macular degeneration," The New England Journal of Medicine, vol. 355, No. 14, pp. 1419-1431, Oct. 5, 2006.
Rudikoff, S. et al., Single Amino Acid Substituon Altering Antigen-Bidning Specificity, Proc Natl. Acad. Sci. USA, vol. 79, pp. 1979-1983, (1982).
Ruiz, et al., "Synthesis structure and surface dynamics of phosphorylcholine functional biomimicking polymers," Biomaterials, (1998), 19, pp. 987-998.
Ryan, et al., "Conjugation of salmon calcitonin to a combed-shaped end functionalized poly(poly(ethylene glycol) methyl ether methacrylate) yields a bioactive stable conjugate," Journal of Controlled Release, (2009), 135 pp. 51-59.
Rycroft, B.W., "Penicillin and the control of deep intra-ocular infection," British J. Ophthalmol, vol. 29, No. 2, pp. 57-87, Feb. 1945.
Sakaki, et al., "Stabilization of an antibody conjugated with enzyme by 2-methacryloyloxyethyl phosphorylcholine copolymer in enzyme-linked immunosorbent assay," J Biomed Mater Res, (1999), 47, pp. 523-528.
Samanta, et al., "End-Functionalized Phosphorylcholine Methacrylates and their Use in Protein Conjugation," Biomacromolecules, (2008), 9:(10), pp. 2891-2897.
Samudrala et al., "Ab initio protein structure prediction using a combined hierarchical approach", Proteins, Structure, Function, Bioinformatics, 37(S3): dated 1999, pp. 194-198.
Saitou, N., Nei, M., "The neighbor-joining method: a new method for reconstructing phylogenetic trees." Mol. Biol. Evol. vol. 4: dated 1987, pp. 406-425.
Sayers, et al., "The Reduced Viscosity of PolyPEG® Compared with Linear PEG," WEP designer polymers, www.wep-ltd.co.uk, in 1 page, Feb. 11, 2009.
Schellenberger, V. et al., "A recombinant polypeptide extends the in vivo half-life of peptides and proteins in a tunable manner," Nature Biotechnology, vol. 27, pp. 1186-1190, 2009.
Schlapschy, M. et al., "Fusion of a recombinant antibody fragment with a homo-amino-acid polymer: effects on biophysical properties and prolonged plasma half-life," Protein Eng Des Sel, vol. 20, Issue 6, pp. 273-284, Jun. 1, 2007.
Seo et al., "Conformational Recovery and Preservation of Protein Nature from Heat -Induced Debaturation by Water-Soluble Phospholipid Plymer Conjugation," Biomaterials, vol. 30, 2009, pp. 4859-4867.
Shen, B.Q. et al., "Conjugation site modulates the in vivo stability and therapeutic activity of antibody-drug conjugates," Nature Biotechnology, vol. 30, pp. 184-189, 2012.
Shim et al., "Structures of a platelet-derived growth factor/propeptide complex and a platelet-derived growth factor/receptor complex," PNAS, vol. 107, No. 25, pp. 11307-11312, 2010.
Songsivilai, S. et al., "Bispecific antibody: a tool for diagnosis and treatment of disease," Clin Exp. Immunol., vol. 79, No. 3, pp. 315-321, Mar. 1990.

(56) References Cited

OTHER PUBLICATIONS

Stenzel, Martina H., "Bioconjugation using thiols: Old chemistry rediscovered to connect polymers with nature's building blocks," ACS Macro letters, vol. 2, No. 1, pp. 14-18, 2013.
Stuttfeld et al., "Structure and function of VEGF receptors," Life, vol. 61, No. 9, pp. 915-922, 2009.
Tamura, M. et al., "Structural correlates of an anticarcinoma antibody: Identification of specificity-determining residues (SDRs) and development of a minimally immunogenic antibody variant by retention of SDRs only," The Journal of Immunology, vol. 164, No. 3, pp. 1432-1441, Feb. 1, 2000.
Tao, et al., "α-Aldehyde Terminally Functional Methacrylic Polymers from Living Radical Polymerization: Application in Protein Conjugation 'Pegylation'," J. Am. Chem. Soc., (2004), 126:41, pp. 13220-13221.
Tao, Lei et al., "Branched polymer-protein conjugates made from mid-chain-functional P (HPMA)", Biomacromolecules, 2009, vol. 10, No. 10, pp. 2487-2851. See abstract; pp. 2847 and 2850; and scheme 2.
Tonkinson, J. et al., "New Drugs: Antisense Oligodeoxynucleotides as Clinical Therapeutic Agents," Cancer Investigation, vol. 14, No. 1, pp. 54-65, 1996.
Tsukamoto et al., "Combined Blockade of IL6 and PD-1/PD-L1 Signaling Abrogates Mutual Regulation of Their Immunosuppressive Effects in the Tumor Microenvironment", Cancer Research, 78(17): dated Sep. 2018 in 12 pages.
Ueda, et al., "Preparation of 2-Methacryloyloxyethyl Phosphocrycholine Copolymers with Alkyl Methacrylates and their Blood Campatability," Polymer Journal, vol. 24, No. 11, pp. 1259-1269 (1992).
UniProtKB-G3R0B5, retrieved on Mar. 19, 2016.
Uutela et al., "PDFG-D induces macrophage recruitment, increased intersitial pressure, and blood vessel maturation during angiogenesis," Blood, vol. 104, No. 10, pp. 3198-3204, Nov. 15, 2004.
Vajdos, F. et al., "Comprehensive functional maps of the antigen-binding site of an anti-ErbB2 antibody obtained with shotgun scanning mutagenesis," Journal of Molecular Biology, vol. 320, Issue 2, pp. 415-428, Jul. 5, 2002.
Vafa, O. et al. An Engineered FC Variant of an IG Eliminates All Immune Effecotr Functions via Structural Perturbations, Methods, vol. 65, pp. 114-126, (2014).
Venditto, et al., "Cancer Therapies Utilizing the Camtothecins: A Review of the Vivo Literature," Molecular Pharmaceutics, vol. 7, No. 2, pp. 307-349 (2010).
Veronese, Francesco M., "Peptide and protein PEGylation: a review of problems and solutions," Biomaterials, vol. 22, Issue 5, pp. 405-417, Mar. 1, 2001.
Voynov et al., "Design and application of antibody cysteine variants," Bioconjugate Chemistry, vol. 21, pp. 385-392, Jan. 21, 2010.
Wagner, E. et al., "Transferrin-polycation conjugates as carriers for DNA uptake into cells," Proc. Natl. Acad. Sci. USA, vol. 87, No. 9, pp. 3410-3414, May 1, 1990.
Wang, X. et al., "Disulfide scrambling in IgG2 monoclonal antibodies: Insights from molecular dynamics simulations," Pharmaceutical Research, vol. 28, Issue 12, pp. 3128-3144, Dec. 2011.
Wang, et al., "Controlled/'Living' Radical Polymerization. Atom Transfer Radical Polymerization in the Presence of Transition-Metal Complexes," J. Am. Chem. Soc., (1995), 117:20, pp. 5614-5615.
Wang, et al., "Synthesis and Evaluation of Water-Soluble Polymers Bone-Targeted Drug Delivery Systems," Bioconjugate Chem., 14, 853-859 (2003).
Warwick Effect Polymers, PowerPoint presentation, "Polymers for the Healthcare and Specialty Materials Industries," Jan. 2009, pp. 1-29.
Wilbur, W.J. and Lipman, D.J., "Rapid similarity searches of nucleic acid and protein data banks" 1983, Proc. Natl. Acad. Sci. USA 80: pp. 726-730.
Wittwer et al., "Glycosylation at Asn-184 inhibits the conversion of single-chain to two-chain tissue-type plasminogen activator by plasmin", Biochemistry, 29(17): dated May 1, 1990, pp. 4175-4180.
Wright et al., "Effect of glycosylation on antibody function: implications for genetic engineering", Trends Biotechnol, 15(1): dated Jan. 1997, pp. 26-32.
Wolfe, A. et al., "Use of cholinesterases as pretreatment drugs for the protection of rhesus monkeys against soman toxicity," Toxicology and Applied Pharmacology, vol. 117, Issue 2, pp. 189-193, Dec. 1992.
Wu, G.Y. et al., "Receptor-mediated in vitro gene transformation by a soluble DNA carrier system," Journal of Biological Chemistry, vol. 262, pp. 4429-4432, Apr. 5, 1987.
Wu, H et al., Humanization of a Murine Monoclonal Antibody by Simultaneous Optimization of Frameork and CDR Resiudes, J. Mol. Biol., vol. 294, pp. 151-162, (1999).
Xiaoying, S. et al. Synthesis and Characterization of a Multiarm Star Polymer, Journal of Polymer Science, vol. 42, pp. 2356-2364, (2004).
Yaseen, et al., "The Structure of Zwitterionic Phosphoacholine Surfactant Monolayers," Langmuir, (2006), 22:13, pp. 5825-5832.
Yeh, P. et al., "Design of yeast-secreted albumin derivatives for human therapy: biological and antiviral properties of a serum albumin-CD4 genetic conjugate," Proc Natl Acad Sci USA, vol. 89, No. 5, pp. 1904-1908, Mar. 1, 1992.
Yu, L et al. Internaction Between Bevacizumab and Murie VEGF-A: A Reassessment, Investigative Opthalmology & Visual Science, vol. 49, No. 2, pp. 522-527, (2008).
Yusa, et al., "Synthesis of Well-Defined Amphiphilic Block Copolymers Having Phospholipid Polymer Sequences as a Novel biocompatible Polymer Micelle Reagents," Biomacromolecules, 6, 663-670 (2005).
Zebrowski, B. et al., "Vascular endothelial growth factor levels and induction of permeability in malignant pleural effusions," Clinical Cancer Research, vol. 5, pp. 3364-3368, Nov. 1999.
Zetter, "Angiogenesis and Tumor Metastasis," Annu. Rev. Med., vol. 49, pp. 407-424, 1998.
Zhang, X et al. Synthesis of Functional Polystyrenes by Atom Transfer Radical Polymerization Using Protected and Unprotected Carboxylic Acid Initiators, Macromolecules, vol. 32, pp. 7349-7353, (1999).
Zhang, X et al., Prevalence of Diabetic Retinopathy in the United States, 2005-2008, JAMA. vol. 304, No. 6, pp. 649-656, (2010).
Advisory Action Dated Apr. 18, 2019 in U.S. Appl. No. 15/394,500.
Advisory Action Jun. 12, 2014 in U.S. Appl. No. 13/959,563.
Advisory Action Dated Nov. 29. 2018 in U.S. Appl. No. 14/916,180 in 3 pages.
Advisory Action Dated Dec. 11, 2018 in U.S. Appl. No. 14/916,180.
Extended European Search Report received in European Patent Application No. 17165316.5 dated Aug. 2, 2017.
Extended European Search Report received in European Patent Application No. 17181272.0 dated Feb. 23, 2018 in.
Extended European Search Report mailed Mar. 21, 2016 in EP Application No. 11769715.1, dated Jul. 18, 2016.
Extended Search Report received in European Patent Application No. 14841835.3 dated Mar. 14, 2017.
Extended Search Report received in European Patent Application No. 15851363.0 dated Jan. 30, 2 2018.
First Examination Report in NZ Application No. 6009449, dated Mar. 14, 2013.
First Examination Report in NZ Application No. 603048, dated Jun. 13, 2013 in 2 pages.
International Preliminary Report on Patentability dated Feb. 11, 2014 in PCT Application No. PCT/US2011/32768.
International Preliminary Report on Patentability (IPRP) issued Jun. 24, 2014, in International Application No. PCT/IB2012/057491, 10 pages.
International Preliminary Report on Patentability (IPRP) mailed Jul. 5, 2016, in International Application No. PCT/US2015/038203.
International Preliminary Report on Patentability mailed Apr. 18, 2017 in International Application No. PCT/US2015/056112.
International Preliminary Report on Patentability on dated Jul. 3, 2018 for International Patent Application No. PCT/US2016/069336 filed Dec. 29, 2016.
International Search Report and Written Opinion Dated Feb. 27, 2013 In International Application No. PCT/US2012/060301.

(56) References Cited

OTHER PUBLICATIONS

International Search Report and Written Opinion for PCT/US2018/027378 mailed Sep. 27, 2018.
International Search Report and Written Opinion mailed Mar. 30, 2017 for International Patent Application No. PCT/US2016/069336 filed Dec. 29, 2016.
International Search Report in PCT Application No. PCT/US2007/005372, dated Aug. 8, 2008.
International Search Report and Written Opinion mailed Sep. 9, 2010 in PCT Application No. PCT/US2010/034252.
International Search Report and Written Opinion mailed May 9, 2011 in PCT Application No. PCT/US2010/61358.
International Search Report and Written Opinion dated Dec. 16, 2011 in PCT Application Np. PCT/US2011/327681.
International Search Report in PCT Application No. PCT/US2014/054622, dated Feb. 27, 2015.
International Search Report and Written Opinion for PCT/US2015/038203, mailed Dec. 8, 2015.
International Search Report and Written Opinion Dated Apr. 1, 2016 in International Application No. PCT/US2015/056112.
International Search Report mailed Jun. 4, 2013, in International Application No. PCT/IB2012/057491.
Notice of Allowance Dated Jul. 31, 2014 in U.S. Appl. No. 13/959,563.
Notice of Allowance dated Sep. 26, 2018 in Canadian Patent Application No. 2,783,615.
Notice of Allowance Dated Jan. 28, 2014 in U.S. Appl. No. 13/515,913.
Notice of Allowance Dated Aug. 9, 2017 in U.S. Appl. No. 14/753,824.
Notice of Allowance Dated Sep. 11, 2018 in U.S. Appl. No. 14/932,913.
Notice of Allowance Dated Jan. 30, 2019 in U.S. Appl. No. 14/932,913.
Notice of Final Rejection received in Korean Patent Application No. 10-2012-7029878 dated Aug. 28, 2017.
Notice of Final Rejection received in Korean Patent Application No. 10-2012-7029878 dated Oct. 27, 2017.
Notice of Rejection received in Japanese Patent Application No. 2016-159104 dated Jun. 27, 2017.
Notice of Rejection received in Japanese Patent Application No. 2016-159104 dated Feb. 26, 2018.
Notice to File a Response received in Korean Patent Application No. 10-2012-7018788 dated Sep. 13, 2017.
Office Action Dated Jun. 21, 2018 in U.S. Appl. No. 15/394,500.
Office Action Dated Jan. 7, 2019 in U.S. Appl. No. 15/394,500.
Office Action Dated Aug. 7, 2019 in U.S. Appl. No. 15/394,500.
Office Action in U.S. Appl. No. 13/959,563, dated Oct. 10, 2013.
Office Action in U.S. Appl. No. 13/959,563, dated Feb. 20, 2014.
Office Action in U.S. Appl. No. 14/456,875, dated Jun. 9, 2015.
Office Action in U.S. Appl. No. 14/456,875, dated Oct. 5, 2016 in 10 pages.
Office Action in U.S. Appl. No. 14/456,875, dated Apr. 20, 2017.
Office Action in U.S. Appl. No. 14/456,875, dated Dec. 14, 2017.
Office Action in U.S. Appl. No. 14/456,875, dated Aug. 28, 2018.
Office Action in U.S. Appl. No. 14/456,875, dated Mar. 8, 2019.
Office Action dated Feb. 7, 2012 in U.S. Appl. No. 12/281,071.
Office Action in JP Patent Application No. 2008-557399, dated May 25, 2013.
Office Action in CA Application No. 2783615, dated Sep. 16, 2016.
Office Action in CA Application No. 2783615, dated Jan. 9, 2018.
Office Action Dated Dec. 14, 2015 in U.S. Appl. No. 14/265,174.
Office Action Received in Chinese Patent Application No. 201080062252.7 dated Apr. 20, 2017.
Office Action received in Chinese Patent Application No. 2015800564492 dated Apr. 22, 2020.
Office Action Received in Chinese Patent Application No. 201610439969.8 dated Jul. 24, 2018.
Office Action in EP Application No. 10838353.0, dated Oct. 4, 2016.
Office Action in European Patent Application No. 17181272.0 dated Oct. 31, 2018.
Office Action in European Patent Application No. 17181272.0 dated Mar. 22, 2019.
Office Action In JP Application No. 2012-544945 dated Jul. 9, 2014.
Office Action Dated Feb. 8, 2018 In Indian Patent Application No. 6116/CHENP/2012.
Office Action dated Jul. 15, 2020 in Mexican patent Application No. MX/a/2016/017290.
Office Action in KR Application No. 10-2012-7018788, dated Mar. 10, 2017.
Office Action Dated Dec. 31, 2013 in U.S. Appl. No. 13/516,173.
Office Action Dated Jul. 2, 2014 in U.S. Appl. No. 13/516,173.
Office Action Dated Dec. 16, 2014 in U.S. Appl. No. 13/516,173.
Office Action Dated May 30, 2017 U.S. Appl. No. 15/099,234.
Office Action Dated Oct. 19, 2018 U.S. Appl. No. 15/099,234.
Office Action Dated May 14, 2019 U.S. Appl. No. 15/099,234.
Office Action Dated Apr. 12, 2018 In Australian Patent Application Np. 2017201930.
Office Action Dated Mar. 27, 2019 In Australian Patent Application Np. 2017201930.
Office Action Dated Jun. 2, 2016 U.S. Appl. No. 13/901,483.
Office Action Dated Feb. 9, 2018 in U.S. Appl. No. 15/368,376.
Office Action Dated Sep. 10, 2018 in U.S. Appl. No. 15/368,376.
Office Action Dated Mar. 11, 2019 in U.S. Appl. No. 15/368,376.
Office Action Dated Apr. 6, 2017 Canadian Patent Application No. 2,795,667.
Office Action Dated Dec. 29, 2017 Canadian Patent Application No. 2,795,667.
Office Action in CN Application No. 201180028682.1, dated Aug. 21, 2014.
Office Action in CN Application No. 201180028682.1, dated Jan. 26, 2015.
Office Action in CN Application No. 20118002868.1, dated Aug. 11, 2015.
Office Action received in Chinese Patent Application No. 201610446624.5 dated Mar. 12, 2018 in 12 pages.
Office Action received in Chinese Patent Application No. 201610446624.5 dated Nov. 26, 2018.
Office Action received in Chinese Patent Application No. 201580046779.3 mailed Apr. 3, 2020.
Office Action received in European Patent Application No. 11769715.1 dated Nov. 9, 2017.
Office Action Dated Jun. 27, 2018 in Indian Patent Application No. 9476/CHENP/2012 in 5 pages.
Office Action in JP Application No. 2013-505799, dated Feb. 19, 2015.
Office Action in JP Application No. 2015-165282, dated Aug. 15, 2016.
Office Action in JP Application No. 2015-165282, dated Aug. 1, 2017.
Office Action in JP Application No. 2015-165282, dated Sep. 27, 2018.
Office Action Dated Nov. 27, 2018 in Japanese Patent Application No. JP 2017-231724.
Office Action in KR Application No. 10-2012-7029878, dated Mar. 8, 2017.
Office Action Dated Mar. 9, 2018 in KR Application No. 10-2017-703456.
Office Action Dated Aug. 28, 2018 in KR Application No. 10-2017-703456.
Office Action Dated Oct. 26, 2018 in KR Application No. 10-2017-703456.
Office Action received in Mexican Patent Application No. MX/a/2012/011876 dated Jul. 13, 2017.
Office Action Dated Jan. 16, 2018 in MX Application No. MX/a/2012/011876.
Office Action dated Jun. 6, 2018 in Mexican patent Application No. MX/a/2012/011876.
Office Action dated Dec. 17, 2018 in Mexican patent Application No. MX/a/2012/011876.
Office Action Dated Jan. 23, 2019 in European Patent Application No. EP 14841835.3.

(56) References Cited

OTHER PUBLICATIONS

Office Action Dated Jul. 13, 2018 in Japanese Patent Application No. 2016-540916.
Office Action Dated Jan. 24. 2018 in U.S. Appl. No. 14/916,180.
Office Action Dated Aug. 10. 2018 in U.S. Appl. No. 14/916,180.
Office Action Dated Mar. 8, 2019 in U.S. Appl. No. 14/916,180.
Office Action Dated Feb. 27, 2017 in U.S. Appl. No. 14/753,824.
Office Action Dated Jan. 9, 2019 in U.S. Appl. No. 15/820,325.
Office Action Dated Jul. 29, 2019 in U.S. Appl. No. 15/820,325.
Office Action Dated Jan. 20, 2020 in Japanese Patent Application No. JP 2016-575823.
Office Action Dated Jun. 4, 2019 in Japanese Patent Application No. JP 2016-575823.
Office Action Dated May 8, 2017 in U.S. Appl. No. 14/932,913.
Office Action Dated Aug. 16, 2017 in U.S. Appl. No. 14/932,913.
Office Action Dated Dec. 15, 2017 in U.S. Appl. No. 14/932,913.
Office Action Dated May 4, 2018 in U.S. Appl. No. 14/932,913.
Office Action Dated Feb. 21, 2019 in European Patent Application No. 15851363.0.
Office Action Dated May 8, 2018 in Japanese Patent Application No. 2017-520515.
Office Action Dated Dec. 18, 2018 in Japanese Patent Application No. 2017-520515.
Office Action Dated Apr. 23, 2019 in Korean Patent Application No. KR 10-2017-7013268.
Patent Examination Report No. 1 in AU Application No. 2010330727, dated Nov. 19, 2014.
Patent Examination Report in AU Application No. 2011239434, dated Mar. 19, 2014.
Patent Examination Report in AU Application No. 2015207898, dated Mar. 23, 2016.
Patent Examination Report in AU Application No. 2015207898, dated May 27, 2017.
PCT Invitation to Pay Additional Fees Mailed Feb. 3, 2016 in International Application No. PCT/US2015/056112.
Restriction Requirement Dated Mar. 7, 2018 in U.S. Appl. No. 15/394,500.
Restriction Requirement Dated Jun. 20, 2011 in U.S. Application No. 12/28107.
Restriction Requirement Dated Jul. 15, 2015 in U.S. Appl. No. 14/265,174.
Restriction Requirement Dated Aug. 14, 2013 in U.S. Appl. No. 13/515,913.
Restriction Requirement mailed Sep. 3, 2013 in U.S. Appl. No. 13/516,173.
Restriction Requirement Dated Feb. 9, 2017 U.S. Appl. No. 15/099,234.
Restriction Requirement Dated November 3. 2015 U.S. Appl. No. 13/901,483.
Restriction Requirement Dated Aug. 21, 2017 in U.S. Appl. No. 15/368,376.
Restriction Requirement Dated Jan. 30, 2017 in U.S. Appl. No. 14/916,180.
Restriction Requirement Dated Aug. 16. 2017in U.S. Appl. No. 14/916,180.
Restriction Requirement Dated Jan. 13, 2017in U.S. Appl. No. 14/932,913.
Supplemental European Search Report received in European Patent Application No. EP 07752096.3 mailed Feb. 19, 2013.
Supplemental European Search Report mailed Feb. 2, 2015 in European Patent Application No. EP 10838353.0 mailed Feb. 3, 2015.
File History of U.S. Appl. No. 15/952,092 , filed Apr. 12, 2018.
File History of U.S. Appl. No. 15/394,500, filed Dec. 29, 2016.
File History of U.S. Appl. No. 13/959,563, filed Aug. 5, 2013.
File History of U.S. Appl. No. 14/456,875, filed Aug. 11, 2014.
File History of U.S. Appl. No. 12/281,071, filed Aug. 28. 2008.
File History of U.S. Appl. No. 14/265,174, filed Apr. 29, 2014.
File History of U.S. Appl. No. 15/182,278, filed Jun. 14, 2016.
File History of U.S. Appl. No. 13/515,913, filed Aug. 27, 2012.
File History of U.S. Appl. No. 13/516,173, filed Aug. 27, 2012.
File History of U.S. Appl. No. 15/099,234, filed Apr. 14, 2016.
File History of U.S. Appl. No. 13/901,483, filed May 23, 2013.
File History of U.S. Appl. No. 15/368,376, filed Dec. 2, 2016.
File History of U.S. Appl. No. 14/916,180 filed Mar. 2, 2016.
File History of U.S. Appl. No. 14/753,824, filed Jun. 29, 2015.
File History of U.S. Appl. No. 15/820,325, filed Nov. 21, 2017.
File History of U.S. Appl. No. 14/932,913, filed Nov. 4, 2015.
Written Opinion, Singapore Patent Application No. 11201805420S mailed Dec. 22, 2019.
Search Report, Singapore Patent Application No. 11201805420S filed mailed Dec. 22, 2019.
Rejection Decision Received in Chinese Patent Application No. 201610439969.8 dated Sep. 20, 2019.
Japanese Office Action, JP 2018-189049, mailed Dec. 3, 2019.
Office Action, BR112012026110408.5, mailed Aug. 23, 2019.
Office Action dated Dec. 24, 2019 in Japanese Patent Application No. JP 2017-231724.
Office Action, JP2019-000261, mailed Feb. 12, 2020.
Office Action mailed Jul. 29, 2019, U.S. Appl. No. 15/820,325.
Office Action dated Oct. 18, 2019, European Patent Application No. 15851363.0.
OA Japanese Patent Application No. 2017-520515, mailed Feb. 17, 2020.
Office Action dated Nov. 14, 2019 in Korean Patent Application 10-2017-7013268.
Office Action dated Feb. 17, 2020 in Korean Patent Application 10-2017-7013268.
Final Office Action, U.S. Appl. No. 15/394,500, dated Dec. 30, 2019.
Office Action, U.S. Appl. No. 15/394,500, dated Aug. 7, 2019.
Final Office Action, U.S. Appl. No. 15/394,500 dated Jan. 7, 2019.
Notice of Allowance Dated Nov. 15, 2019 in U.S. Appl. No. 15/820,325.
Corrected Notice of Allowability Dated Feb. 27, 2020 in U.S. Appl. No. 15/820,325.
Notice of Allowance Dated Apr. 2, 2020 in U.S. Appl. No. 15/820,325.
Corrected Notice of Allowability Dated Apr. 29, 2020 in U.S. Appl. No. 15/820,325.
Supplementary Partial European Search Report Dated Dec. 21, 2017 in European Patent Application No. 15812238.2.
Extended European Search Report Dated Mar. 29, 2018 in European Patent Application No. 15812238.2.
Office Action dated Mar. 18, 2020 in Australian Application No. 2015279560.
Notice of Allowance Dated Jun. 10, 2020 in U.S. Appl. No. 15/820,325.
Office Action, U.S. Appl. No. 15/394,500, dated Jun. 23, 2020.
Office Action, Russian Patent Application No. 2018126519, dated Apr. 28, 2020.
Office Action, U.S. Appl. No. 15/952,092, dated Jun. 30, 2020.
Kimura, "Retroviral Delivery of DNA into the Livers of Transgenic Mice Bearing Premalignant and Malignant Hepatocellular Carcinomas" Human Gene Therapy, 1994, 5:845.
Connelly, "In Vivo Gene Delivery and Expression of Physiological Levels of Functional Human Factor VIII in Mice" Human Gene Therapy, 1995, 1:185.
Kaplitt, "Long-term gene expression and phenotypic correction using adeno-associated virus vectors in the mammalian brain" Nature Genetics, 1994, 8:148.
Curiel, "High-Efficiency Gene Transfer Mediated by Adenovirus Coupled to DNA-Polylysine Complexes" Hum. Gene Ther., 1992, 3:147.
Findeis et al., "Targeted delivery of DNA for gene therapy via receptors" Trends Biotechnol., 1993, 11:202.
Philip, "Efficient and sustained gene expression in primary T lymphocytes and primary and cultured tumor cells mediated by adeno-associated virus plasmid DNA complexed to cationic liposomes." Mol. Cell Biol., 1994, 14:2411.
Umana et al., "Engineered glycoforms of an antineuroblastoma IgG1 with optimized antibody-dependent cellular cytotoxic activity." 1999, Nature Biotech. 17:176-180.

(56) References Cited

OTHER PUBLICATIONS

Woffendin, "Nonviral and viral delivery of a human immunodeficiency virus protective gene into primary human T cells" Proc. Natl. Acad. Sci., 1994, 91:1581.

Zenke et al., "Receptor-mediated endocytosis of transferrin-polycation conjugates: an efficient way to introduce DNA into hematopoietic cells." Proc. Natl. Acad. Sci. USA, 1990, 87:3655.

Wu et al., "Receptor-mediated Gene Delivery and Expression in Viuo" J. Biol. Chem., 1988, 263.

Wu et al., "Receptor-mediated Gene Delivery in Vivo" J. Biol. Chem., 1991, 266.

Wu, "Targeting Genes: Delivery and Persistent Expression of a Foreign Gene Driven by Mammalian Regulatory Elements in Vivo" J. Biol. Chem., 1989, 264:16985.

Wu et al., "Incorporation of Adenovirus into a Ligand-based DNA Carrier System Results in Retention of Original Receptor Specificity and Enhances Targeted Gene Expression" J. Biol. Chem., 1994, 269.

De Haas et al., "Fc gamma receptors of phagocytes", Journal of Laboratory and Clinical Medicine, 126(4): dated Oct. 1995, pp. 330-341.

Jaffe, G. et al., "Intraocular drug delivery," CRC Press, Mar. 2006. Takahara, et al., Int. Symp, Nano-bio-Interfaces Rel. Mol. Molecular Mobility, Program and Abstracts Book, p. 25-26, https://www.nof.co.jp/business/life/product01.html (2009).

The OpenSAFELY Collaborative et al., "OpenSAFELY: factors associated with COVID-19-related hospital death in the linked electronic health records of 17 million adult NHS patients", medRxiv, May 7, 2020, in 22 pages (pre-print article not yet peer-reviewed). URL: https://www.medrxiv.org/content/10.1101/2020.05.06.20092999v1.

Office Action Received in Chinese Patent Application No. 201610439969.8 dated Mar. 19, 2019.

File History of U.S. Appl. No. 13/641,342, filed Dec. 2, 2016.

Notice of Acceptance for Patent Application, Australian Application No. 2015279560, dated Sep. 2, 2020, in 3 pages.

Restriction Requirement dated Jul. 20, 2016 in U.S. Appl. No. 14/753,824.

Corrected Notice of Allowability dated Sep. 29, 2017 in U.S. Appl. No. 14/753,824.

Restriction Requirement dated Mar. 24, 2021 in U.S. Appl. No. 16/795,450 in 5 pages.

Office Action dated Mar. 26, 2021 in Canadian Patent Application No. 2953698 in 4 pages.

Office Action with English translation dated Feb. 26, 2021 in Chinese Patent Application No. 201580046779.3 in 29 pages.

Office Action with English translation dated Jun. 2, 2021 in Chinese Patent Application No. 201580046779.3 in 27 pages.

Notice of Allowance Dated Sep. 4, 2020 in U.S. Appl. No. 15/820,325.

Notice of Allowance Dated Apr. 15, 2021 in U.S. Appl. No. 15/820,325.

Notice of Allowance Dated Dec. 22, 2020 in U.S. Appl. No. 15/820,325.

Corrected Notice of Allowability dated Oct. 16, 2020 in U.S. Appl. No. 15/820,325.

Office Action dated Jul. 9, 2020 in European Patent Application No. 15812238.2.

Decision of Refusal in JP Application No. 2016-575823 dated Oct. 27, 2020.

Pre-Appeal Report dated Apr. 27, 2021 in Japanese Patent Application No. JP 2016-575823 (Appeal No. 2021-002485) in 4 pages.

Office Action dated Feb. 15, 2021 in Russian Application No. 2020128737.

International Preliminary Report on Patentability dated Sep. 17, 2020 in International Application No. PCT/US2019/020418.

"Bevacizumab in Severe or Critical Patients With COVID-19 Pneumonia", ClinicalTrials.gov (study sponsored by Qilu Hospital of Shandong University) first posted Feb. 19, 2020 (last updated Sep. 14, 2020), in 4 pages. URL: https://clinicaltrials.gov/ct2/show/NCT04275414.

Beranger et al., IMGT Scientific Chart created May 17, 2001, in 4 pages. URL: http://www.imgt.org/IMGTScientificChart/Numbering/Hu_IGHGnber.html.

Chiou, H. et al., "In Vivo Gene Therapy via Receptor-Mediated DNA Delivery", in Gene Therapeutics: Methods and Applications of Direct Gene Transfer, J.A. Wolff, ed., 1994, in 14 pages.

Conti, P. "Induction of pro-inflammatory cytokines (IL-1 and IL-6) and lung inflammation by Coronavirus-19 (COVI-19 or SARS-CoV-2): anti-inflammatory strategies", Journal of Biological Regulators and Homeostatic Agents, Mar.-Apr. 2020, vol. 34(2), in 6 pages.

Gawlak, G. et al., "Chronic high-magnitude cyclic stretch stimulates EC inflammatory response via VEGF receptor 2-dependent mechanism", AJP Lung Cellular and Molecular Physiology, Mar. 2016, vol. 310(11), pp. L1062-L1070.

Herold, T. et al., "Level of IL-6 predicts respiratory failure in hospitalized symptomatic COVID-19 patients", medRxiv, Apr. 2020, in 7 pages. URL: https://www.medrxiv.org/content/10.1101/2020.04.01.20047381v2.

Huang, T. et al., "Cyclooxygenase-2 Activity Regulates Recruitment of VEGF-Secreting Ly6Chigh Monocytes in Ventilator-Induced Lung Injury", Internal Journal of Molecular Sciences, Apr. 2019, vol. 20(7), in 15 pages.

Iwahashi, M. et al., "CDR substitutions of a humanized monoclonal antibody (CC49): contributions of individual CDRs to antigen binding and immunogenicity," Mol. Immunol. 36: Issue 15-16, 1079-1091, 1999.

Kaner, R. J. et al., "Lung overexpression of the vascular endothelial growth factor gene induces pulmonary edema", American Journal of Respiratory Cell and Molecular Biology, Jun. 2000, vol. 22(6), pp. 657-664.

Karmpaliotis, D. et al., "Angiogenic growth factors in the pathophysiology of a murine model of acute lung injury", American Journal of Physiology—Lung Cellular and Molecular Physiology, Sep. 2002, vol. 283(3), pp. L585-L595.

Kim, J.K. et al., "Localization of the site of the murine IgG1 molecule that is involved in binding to the murine intestinal Fc receptor", European Journal of Immunology, Oct. 1994, vol. 24(10), pp. 2429-2434.

Le Cras, T. et al., "VEGF causes pulmonary hemorrhage, hemosiderosis, and air space enlargement in neonatal mice", American Journal of Physiology—Lung Cellular and Molecular Physiology, Jul. 2004, vol. 287(1), pp. L134-L142.

Medford, A. R. L. et al., "Vascular endothelial growth factor (VEGF) in acute lung injury (ALI) and acute respiratory distress syndrome (ARDS): paradox or paradigm?", Thorax, Jul. 2006, vol. 61(7), pp. 621-626.

Meng, X. et al., "Efficacy and safety of bevacizumab treatment for refractory brain edema: Case report", Medicine (Baltimore), Nov. 2017, vol. 96(44), in 4 pages.

Shen, G. et al., "Relief Effect of Bevacizumab on Severe Edema Induced by Re-irradiation in Brain Tumor Patients", Chinese Medical Journal (Engl.), Aug. 2015, vol. 128(15), pp. 2126-2129.

Shi, C. et al., "VEGF Production by Ly6C+high Monocytes Contributes to Ventilator-Induced Lung Injury", PLoS One, Oct. 2016, vol. 11(10), in 19 pages.

Thickett, D. et al., "Vascular Endothelial Growth Factor May Contribute to Increased Vascular Permeability in Acute Respiratory Distress Syndrome", American Journal of Respiratory and Critical Care Medicine, Nov. 2001, vol. 164(9), pp. 1601-1605.

Watanabe, M. et al., "Genetic Delivery of Bevacizumab to Suppress Vascular Endothelial Growth Factor-Induced High-Permeability Pulmonary Edema", Human Gene Therapy, Jun. 2009, vol. 20(6), pp. 598-610.

Zhang, Z. et al., "Vascular endothelial growth factor increased the permeability of respiratory barrier in acute respiratory distress syndrome model in mice", Biomedicine Pharmacotherapy, Jan. 2019, vol. 109, pp. 2434-2440.

International Search Report and Written Opinion for Application No. PCT/US2021/031194 in 18 pages, mailed Sep. 16, 2021.

Office Action for U.S. Appl. No. 16/795,450 in 117 pages, dated Jun. 25, 2021.

(56) References Cited

OTHER PUBLICATIONS

Corrected Notice of Allowability for U.S. Appl. No. 15/820,325 in 6 pages, dated Jun. 23, 2021.
Corrected Notice of Allowability for U.S. Appl. No. 15/820,325 in 5 pages, dated Jul. 21, 2021.
Corrected Notice of Allowability for U.S. Appl. No. 15/820,325 in 5 pages, dated Sep. 22, 2021.
Adler, A. P. et al., "Evasive resistance to VEGF blockade mediated by autocrine IL-6/STAT3 signaling in xenograft models of human cancer", Cancer Res, Aug. 2015, vol. 75, Supplement 15, p. 1378 (the reference document includes the abstract only).
Correa, F. et al., "Development of Novel Bispecific Anti-Inflammatory and Anti-Angiogenic Therapy for the Treatment of both Retinal Vascular and Inflammatory Diseases", Investigative Ophthalmology & Visual Science, Jul. 2019, vol. 60, p. 5396 (the reference document includes the abstract only).
Mesquida, M. et al., "Interleukin-6 blockade in ocular inflammatory diseases", Clinical and Experimental Immunology, Apr. 2014, vol. 176, No. 3, pp. 301-309.
Office Action for Canadian Application No. CA 2953698 in 4 pages, dated Mar. 16, 2022.
Office Action for Japanese Application No. JP 2016-575823 with English translation in 4 pages, dated Jan. 18, 2022.
Office Action for Japanese Application No. JP 2021-029145 with English translation in 22 pages, dated Mar. 1, 2022.
Office Action for Singapore Application No. SG 11202008242X in 16 pages, dated Apr. 5, 2022.
Final Office Action for U.S. Appl. No. 16/795,450 in 14 pages, dated Jan. 6, 2022.
Office Action for U.S. Appl. No. 16/795,450 in 15 pages, dated Apr. 28, 2022.
Fusion Importance of Order, Experimental Data provided by Applicant in Proceedings of European Application No. EP 16713194.5 filed Dec. 10, 2018, in 2 pages.
Hlavacek, W.S. et al., "Steric Effects on Multivalent Ligand Receptor Binding: Exclusion of Ligand Sites by Bound Cell Surface Receptors", Biophysical Journal, Jun. 1999, vol. 76(6), pp. 3031-3043.
Kadioglu, O. et al., "28—Targeting Angiogenesis by Therapeutic Antibodies", *Handbook of Therapeutic Antibodies*, Stefan Dubel and Janice M. Reichert (Eds.), 2nd Edition, Aug. 2014, pp. 823-850.
Saidi, A. et al., "Combined targeting of interleukin-6 and vascular endothelial growth factor potently inhibits glioma growth and invasiveness", International Journal of Cancer, Sep. 2009, vol. 125, No. 5, pp. 1054-1064.
Wiesmann, C. et al., "Crystal structure at 1.7 A resolution of VEGF in complex with domain 2 of the Flt-1 receptor", Cell, Nov. 1997, vol. 91(5), pp. 695-704.
Office Action for European Application No. EP 15812238.2 dated Dec. 12, 2022, in 7 pages.
Office Action for European Application No. EP 19761694.9 in 18 pages, dated Sep. 9, 2022.
Trial Decision to Grant for Japanese Application No. JP 2016-575823 with English translation in 3 pages, dated Jun. 14, 2022.
Office Action for Japanese Application No. JP 2021-029145 with English translation in 8 pages, dated Sep. 20, 2022.
Office Action for Russian Application No. RU 2020128737 with English translation in 11 pages, dated Aug. 17, 2022.
Office Action for Russian Application No. RU 2020128737 with English translation in 20 pages, dated Jan. 13, 2023.
International Preliminary Report on Patentability for Application No. PCT/US2021/031194 in 10 pages, mailed Nov. 17, 2022.
Office Action for U.S. Appl. No. 16/795,450 in 16 pages, dated Nov. 10, 2022.
Finkelstein A.V. et al., *Protein Physics: a course of lectures with color and stereoscopic illustrations and training problems*, 4th ed., 2012, Moscow, p. 23.
Office Action for Japanese Application No. JP 2020-545729 with English translation in 9 pages, dated Jan. 31, 2023.
Roitt, I. M. et al., *Immunology*, Fifth Ed., 2000, Publishing House "Mir", p. 150.
Serruys, P. et al., "Effect of an anti-PDGF-beta-receptor-blocking antibody on restenosis in patients undergoing elective stent placement", International Journal of Cardiovascular Interventions, 2003, vol. 5, No. 4, pp. 214-222 (abstract only).
Office Action for Canadian Application No. CA 2953698 in 3 pages, dated Feb. 21, 2023.
Office Action for Japanese Application No. JP 2021-029145 with English translation in 10 pages, dated Mar. 22, 2023.
Office Action for Russian Application No. RU 2020128737 with English translation in 13 pages, dated Apr. 13, 2023.
Office Action for U.S. Appl. No. 16/795,450 in 18 pages, dated May 23, 2023.
U.S. Appl. No. 17/997,866, filed Nov. 3, 2022, Perlroth et al.
Katschke, K. et al., "Inhibiting Alternative Pathway Complement Activation by Targeting the Factor D Exosite—Supplementary Material", The Journal of Biological Chemistry, Apr. 2012, vol. 287, No. 16, in 11 pages.
Office Action for Australian Application No. AU 2020286251 in 4 pages, dated May 22, 2023.
Office Action for Australian Application No. AU 2020286251 in 4 pages, dated Nov. 23, 2023.
Decision to Grant for Japanese Application No. JP 2021-029145 with English translation in 6 pages, dated Oct. 10, 2023.
Office Action for Japanese Application No. JP 2020-545729 with English translation in 13 pages, dated Jul. 25, 2023.
Office Action for New Zealand Application No. NZ 767586 in 6 pages, dated Sep. 19, 2023.
Decision to Grant for Russian Application No. RU 2020128737 with English translation in 38 pages, dated Nov. 10, 2023.
Reconsideration Report by Examiner before Appeal for Japanese Application No. JP 2020-545729 with English translation in 2 pages, dated Mar. 15, 2024.
Notice of Termination of Reconsideration by Examiners before Appeal Proceedings for Japanese Application No. JP 2020-545729 with English translation in 2 pages, dated Mar. 22, 2024.
Office Action for New Zealand Application No. NZ 767586 in 4 pages, dated Feb. 7, 2024.
Office Action for Singapore Application No. SG 11202008242X in 16 pages, dated Apr. 3, 2024.
Office Action for European Application No. 19761694.9 in 8 pages, dated May 8, 2024.

\* cited by examiner

FIG. 1

VPPGEDSKDVAAPHRQPLTSSERIDKQIRYILDGISALRKETCNKSNMCESSKEALAENNLNLPKMAEKDG
CFQSGFNEETCLVKIITGLLEFEVYLEYLQNRFESSEEQARAVQMSTKVLIQFLQKKAKNLDAITTPDPTTN
ASLLTKLQAQNQWLQDMTTHLILRSFKEFLQSSLRALRQM (SEQ ID NO: 1)

COMPOUND L

COMPOUND K

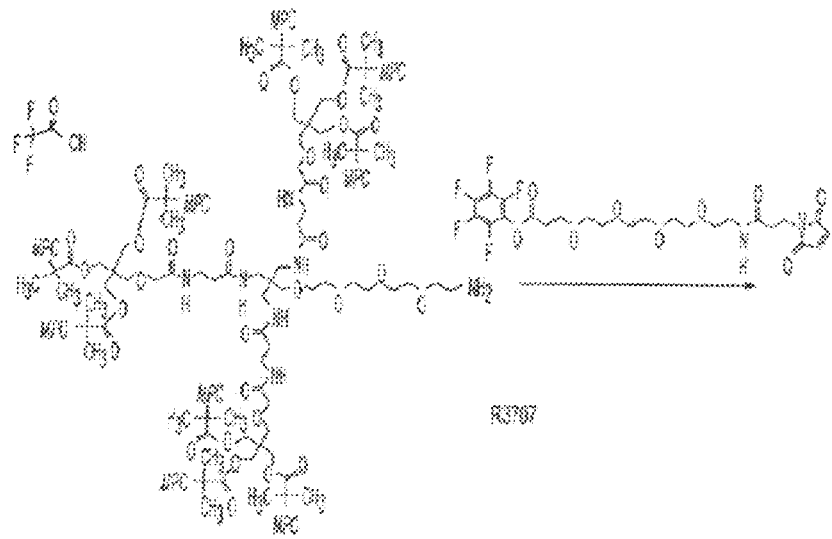
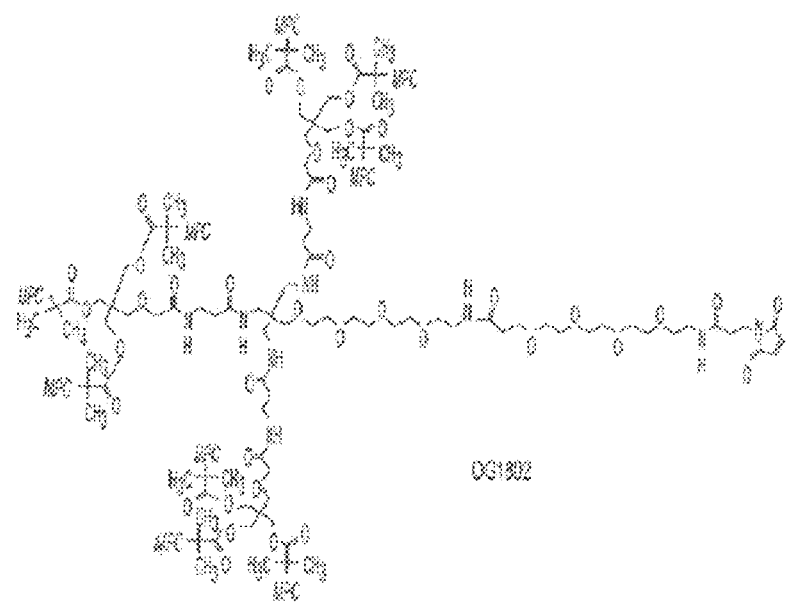
FIG. 2C

OG1801    FIG. 2J
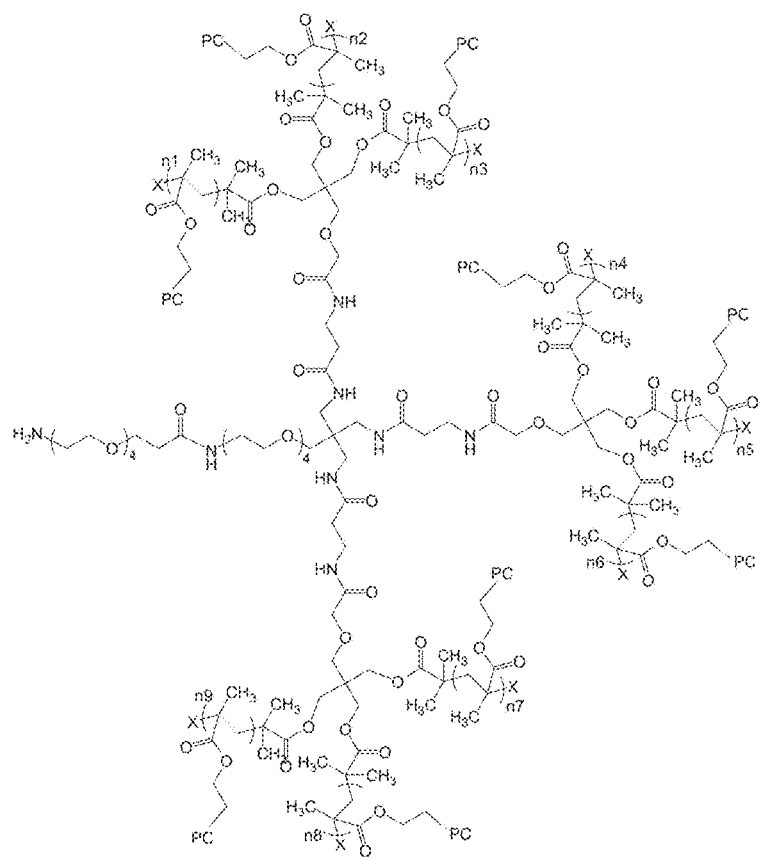
PC =
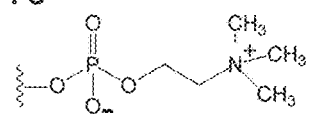
X=a) OR where R=H, methyl, ethyl, propyl, isopropyl, b) H, or c) any halide, including Br
n1, n2, n3, n4, n5, n6, n7, n8 and n9 are the same or different such that the sum of n1, n2, n3, n4, n5, n6, n6, n7, n8 and n9 is 2500 plus or minus 15%.

FIG. 2K
OG1802
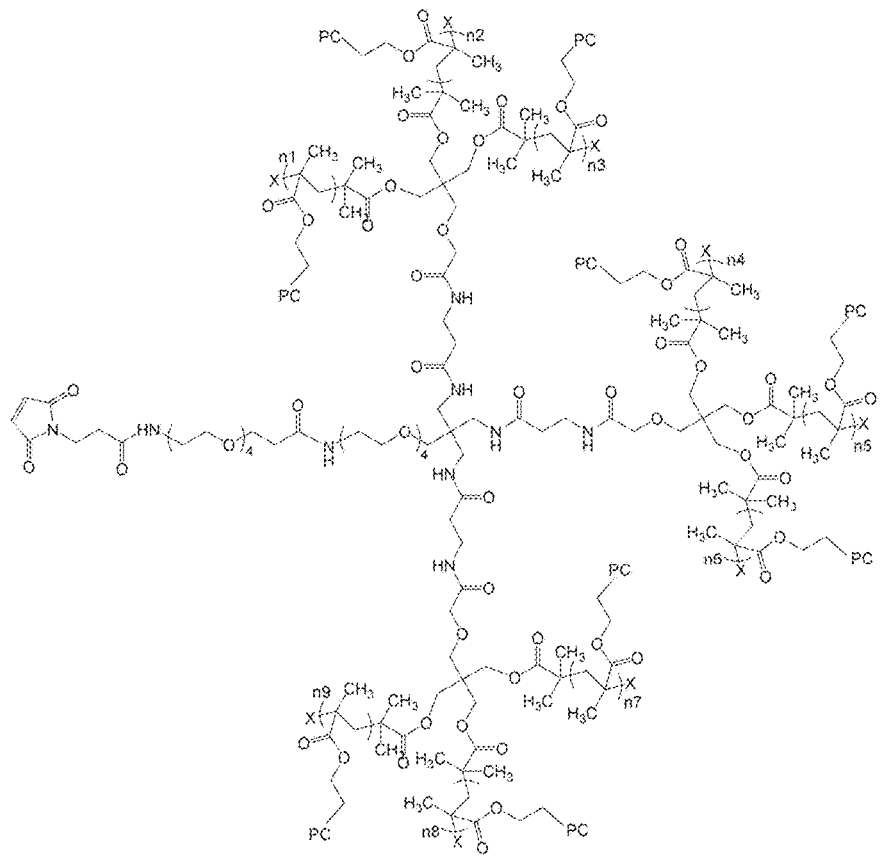
Definitions:
PC =
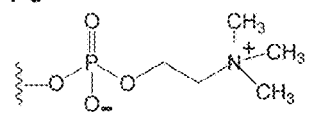
X=a) OR where R=H, methyl, ethyl, propyl, isopropyl. b) H, or c) any halide, including Br
n1, n2, n3, n4, n5, n6, n7, n8 and n9 are the same or different such that the sum of n1, n2, n3, n4, n5, n6, n6, n7, n8 and n9 is 2500 plus or minus 15%.

COMPOUND E

Generate library of randomized single-point mutations (except Met, Cys, and Asn) for putative CDR positions (total of 71).

↓

Select single point mutations that display similar or improved koff in comparison to the wild-type and introduce into mammalian system.

↓

Validate IL-6 binding and antibody expression/stability.

↓

Combine selected mutations into final construct.

FIG. 3

IL6/IL6R complex formation is inhibited by anti-IL6 mAb
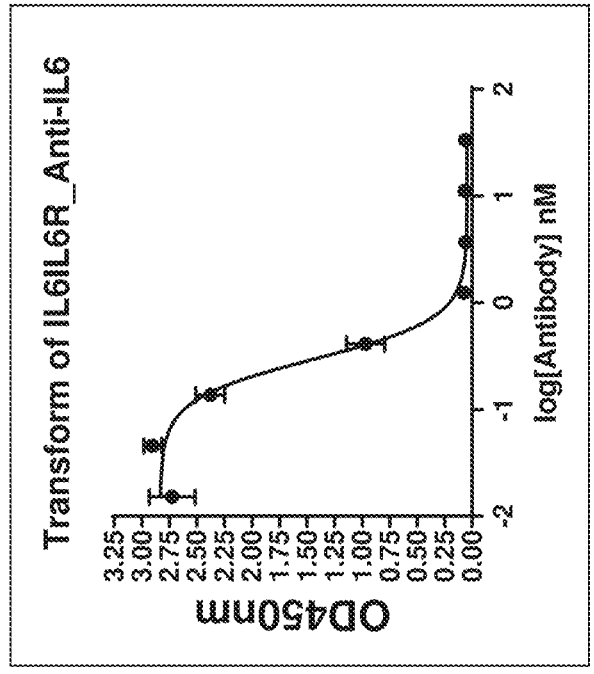
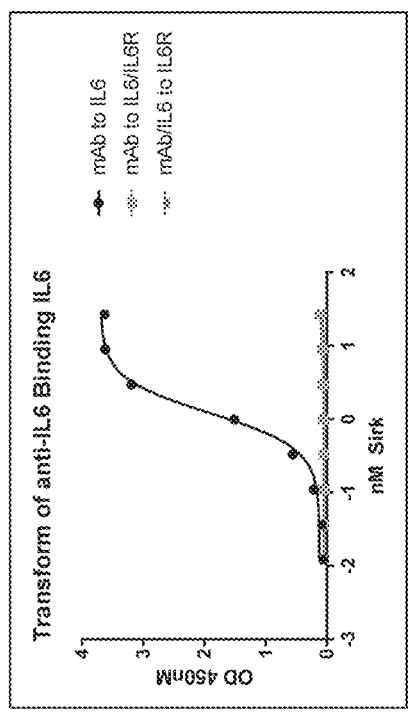
FIG. 4

Heavy Chain

EVQLVESGGGLVQPGGSLRLSCAAS GFTFSPFAIS WVRQAPGKGLEW VAKISPGGSWTYYSDTVTD RFTFSLDTSKSTAYLQMNSLRAEDTAVYYC ARQLWGYYALDV WQQGTLVTVSS (SEQ ID NO: 2)

Light Chain

DIQLTQSPSSLSASVGDRVTITC SASISVSYLY WYQQKPGKAPK LLIYDDSSLAS GVPSRFSGSGSGTD FTLTISSLQPEDFATYYC QQWSGYPYT FGQGTKVEIK (SEQ ID NO: 3)

FIG. 5

| Lane # | Variant |
|---|---|
| L | SeeBlue®Plus2 standard |
| 1 | AntiIL6 |
| 2 | AntiIL6-VEGFR |
| 3 | VEGFR-AntiIL6 |

Protein-A purified VEGFR-AntiIL6 and AntiIL6-VEGFR products derived from ExpiCHO-S cells show the presence of unexpected bands (highlighted in the gel) with sizes dependent on construct orientations.

FIG. 11B

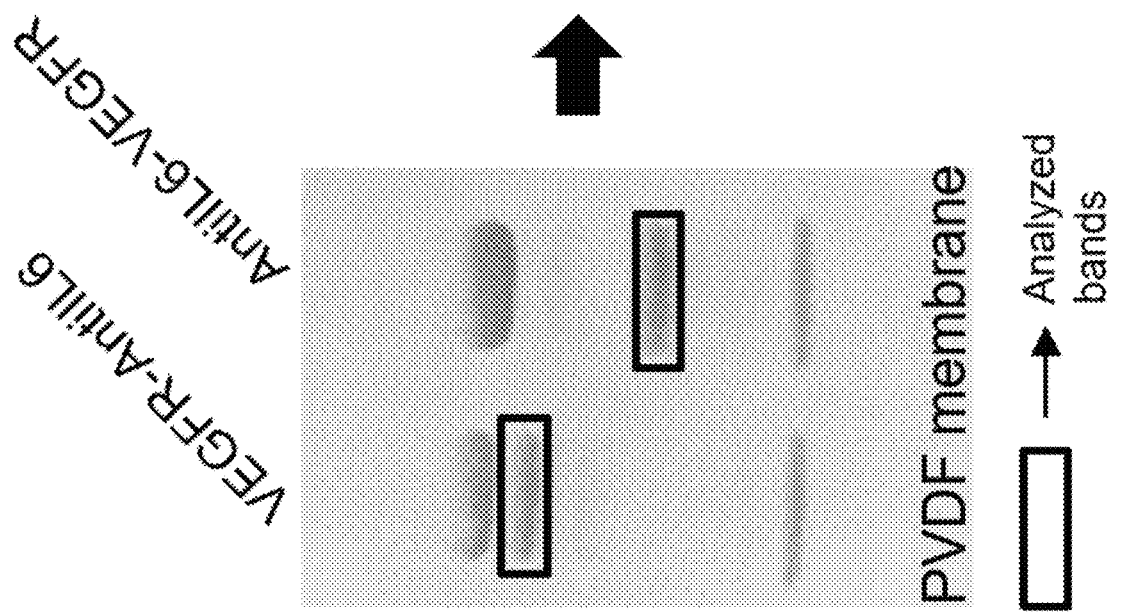
FIG. 12 (1 of 3)

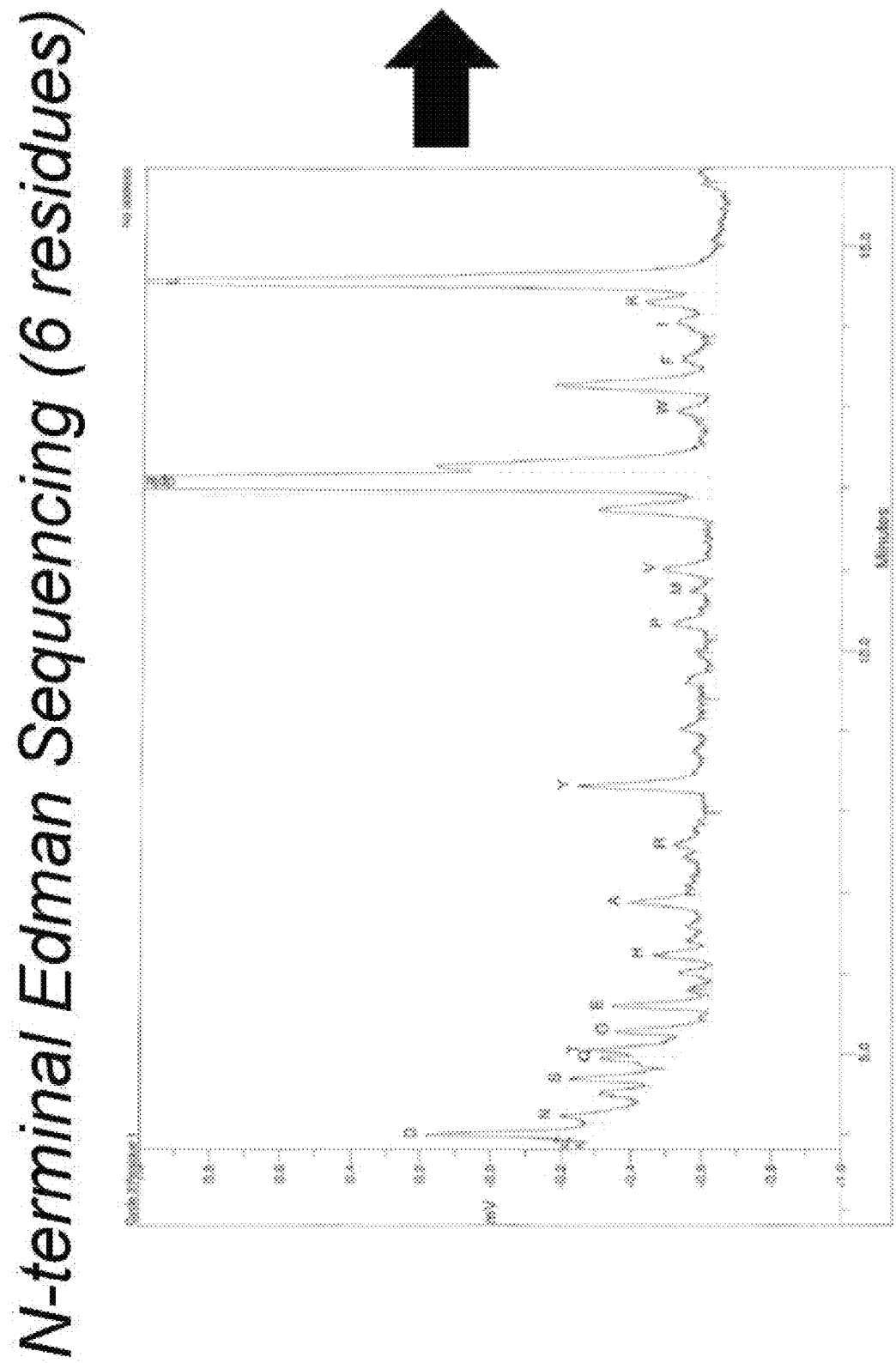
FIG. 12 (2 of 3)

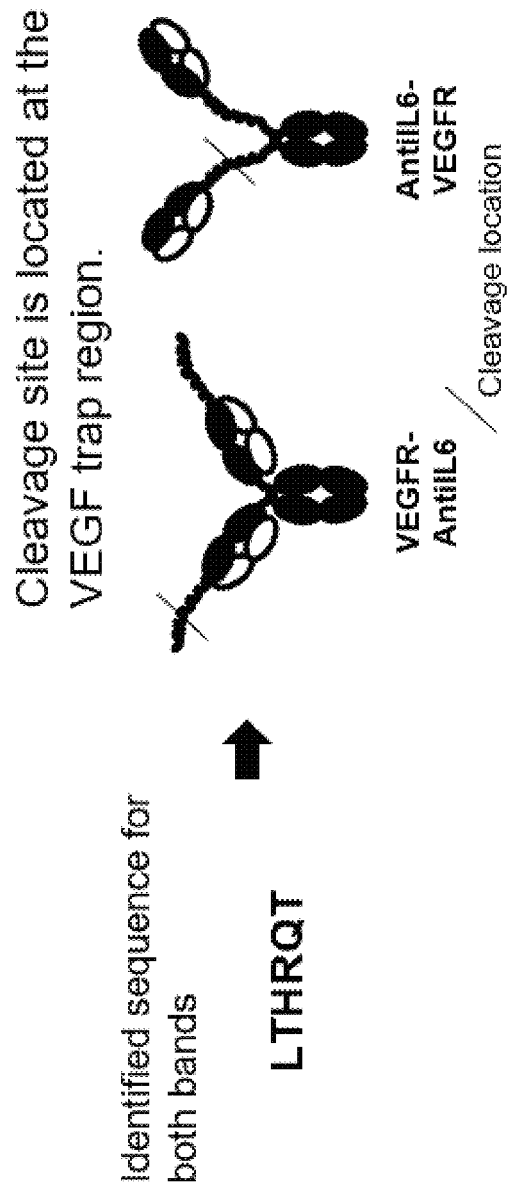
FIG. 12 (3 of 3)
*VEGFR-AntiIL6 and AntiIL6-VEGFR undergo cleavage at same site. N-terminal Edman sequencing analysis show that both bands contain the same N-terminal sequence, LTHRQT, which is located at the VEGF trap region.*

| Lane # | Variant |
|---|---|
| L | SeeBlue®Plus2 standard |
| 1 | VEGFR AntiIL6 |
| 2 | VEGFR AntiIL6 choOptim* |
| 3 | AntiIL6 VEGFR |
| 4 | AntiIL6 VEGFR K89Q |
| 5 | AntiIL6 VEGFR K89R |
| 6 | AntiIL6 VEGFR K89S |
| 7 | AntiIL6 VEGFR T90S |
| 8 | AntiIL6 VEGFR T90L |
| 9 | AntiIL6 VEGFR N91R |
| 10 | AntiIL6 VEGFR N91S |
| 11 | AntiIL6 VEGFR N91H |
| 12 | AntiIL6 VEGFR L93Y |
| 13 | AntiIL6 VEGFR T94I |
| 14 | AntiIL6 VEGFR T94L |
| 15 | AntiIL6 VEGFR H95Y |
| 16 | AntiIL6 VEGFR H95L |
| 17 | AntiIL6 VEGFR H95I |
| 18 | AntiIL6 VEGFR H95F |
| 19 | AntiIL6 VEGFR R96Q |

(*) VEGFR variant has codon sequence optimized for expression in CHO cells

> VEGF_trap_Variant_1

(SEQ ID NO: 4)
SDTGRPFVEMYSEIPEIIHMTEGRELVIPCRVTSPNITVTLKKFPLDTLIPDGKRIIWDSRKGFIISNATYKEIGLLTCEATVN
GHLYKTNYLIHRQTNTIIDVVLSPSHGIELSVGEKLVLNCTARTELNVGIDFNWEYPSSKHQHKKLVNRDLKTQSGSEMK
KFLSTLTIDGVTRSDQGLYTCAASSGLMTKKNSTFVRVHEK

FIG. 13D

> VEGF_trap_Variant_2

(SEQ ID NO: 5)
SDTGRPFVEMYSEIPEIIHMTEGRELVIPCRVTSPNITVTLKKFPLDTLIPDGKRIIWDSRKGFIISNATYKEIGLLTCEATVN
GHLYKTNYLTIRQTNTIIDVVLSPSHGIELSVGEKLVLNCTARTELNVGIDFNWEYPSSKHQHKKLVNRDLKTQSGSEMK
KFLSTLTIDGVTRSDQGLYTCAASSGLMTKKNSTFVRVHEK

FIG. 13E

> VEGF_trap_Variant_3

(SEQ ID NO: 6)
SDTGRPFVEMYSEIPEIIHMTEGRELVIPCRVTSPNITVTLKKFPLDTLIPDGKRIIWDSRKGFIISNATYKEIGLLTCEATVN
GHLYKTNYLTIRQTNTIIDVVLSPSHGIELSVGEKLVLNCTARTELNVGIDFNWEYPSSKHQHKKLVNRDLKTQSGSEMK
KFLSTLTIDGVTRSDQGLYTCAASSGLMTKKNSTFVRVHEK

| Lane # | Variant |
|---|---|
| L | SeeBlue®Plus2 standard |
| 1 | VEGFR_AntiIL6 |
| 2 | VEGFR_variant_3_AntiIL6_T94I/H95I |
| 3 | VEGFR_variant_1_AntiIL6_T94I |
| 4 | VEGFR_variant_2_AntiIL6_H95I |

*Effect of single point mutations on VEGF trap c

| Ligand | ka(1/Ms) | kd(1/s) | KD(M) | Rmax(RU) |
|---|---|---|---|---|
| VEGFR-AntiIL6 | 7.55E+07 | 6.03E-04 | 7.98E-12 | 296.2 |
| VEGFR_variant_1-AntiIL6 | 1.08E+08 | 1.99E-03 | 1.85E-11 | 345.6 |
| VEGFR_variant_2-AntiIL6 | 1.15E+08 | 1.64E-03 | 1.43E-11 | 302.9 |
| VEGFR_variant_3-AntiIL6 | 1.42E+08 | 2.66E-03 | 1.87E-11 | 317.2 |
| Eylea | 4.88E+07 | 2.61E-04 | 5.35E-12 | 477.4 |

|  | VEGFR-AntiIL6 Sig. | | | ttest control vs eylea | ttest control vs antiIL6 |
|---|---|---|---|---|---|
|  | ttest control | ttest eylea | ttest antiIL6 | | |
| Branching interval | 0.0004 | 0.0081 | 0.1337 | 0.3801 | 0.0748 |
| Mean Mesh Size | 0.0003 | 0.0017 | 0.0235 | 0.1049 | 0.9995 |
| Mesh index | 0.3851 | 0.0537 | 0.3528 | 0.0929 | 0.7572 |
| Nb branches | 0.0026 | 0.0151 | 0.0318 | 0.3175 | 0.2076 |
| Nb extrem. | 0.0074 | 0.4043 | 0.1769 | 0.1249 | 0.2009 |
| Nb isol. seg. | 0.8357 | 0.8243 | 0.9231 | 0.9400 | 0.9410 |
| Nb junctions | 0.0012 | 0.0204 | 0.0259 | 0.0773 | 0.0740 |
| Nb master junction | 0.0026 | 0.3645 | 0.4601 | 0.0271 | 0.0257 |
| Nb master segments | 0.0009 | 0.0105 | 0.0021 | 0.0358 | 0.0567 |
| Nb meshes | 0.0008 | 0.0076 | 0.0284 | 0.0140 | 0.0130 |
| Nb nodes | 0.0015 | 0.0232 | 0.0231 | 0.0682 | 0.0734 |
| Nb peaces | 0.0001 | 0.1038 | 0.0379 | 0.0047 | 0.0039 |
| Nb segments | 0.0021 | 0.0334 | 0.0298 | 0.0682 | 0.0812 |
| tot branches length | 0.0105 | 0.0066 | 0.0542 | 0.9644 | 0.4039 |
| Tot branching length | 0.0009 | 0.0050 | 0.0356 | 0.2349 | 0.0854 |
| tot isol. branches length | 0.9600 | 0.7893 | 0.8757 | 0.6795 | 0.7912 |
| tot length | 0.0003 | 0.0013 | 0.0143 | 0.2020 | 0.0324 |
| tot master segments length | 0.0006 | 0.0172 | 0.0150 | 0.0774 | 0.0524 |
| tot meshes area | 0.0029 | 0.0057 | 0.0560 | 0.1282 | 0.0877 |
| tot segments length | 0.0003 | 0.0081 | 0.0281 | 0.0757 | 0.0339 |

*gray squares are statistically significant; $P<0.05$

FIG. 16C

| ID | Sequence |
|---|---|
| VI (SEQ ID NO: 7) | EVQLVESGGGLVQPGGSLRLSCAASGFTFSPFAMHWVRQAPGKGLEWVAKISPGGSWTYYSDTVEDRFTFSLDTSKSTAYLQMNSLRAEDTAVYYCARQAWGYYALDIWGQGTLVTVSS |
| VII (SEQ ID NO: 8) | EVQLVESGGGLVQPGGSLRLSCAASGFTFSPFAMHWVRQAPGKGLEWVAKISPGGSWTYYSDTVEDRFTFSLDTSKSTAYLQMNSLRAEDTAVYYCARQSWGYYALDIWGQGTLVTVSS |
| VIII (SEQ ID NO: 9) | EVQLVESGGGLVQPGGSLRLSCAASGFTFSPFAMHWVRQAPGKGLEWVAKISPGGSWTYYSDTVEDRFTFSLDTSKSTAYLQMNSLRAEDTAVYYCARQGWGYYALDIWGQGTLVTVSS |
| IX (SEQ ID NO: 10) | EVQLVESGGGLVQPGGSLRLSCAASGFTFSPFAMHWVRQAPGKGLEWVAKISPGGSWTYYSDTVEDRFTFSLDTSKSTAYLQMNSLRAEDTAVYYCARQTWGYYALDIWGQGTLVTVSS |
| X (SEQ ID NO: 11) | EVQLVESGGGLVQPGGSLRLSCAASGFTFSPFAMHWVRQAPGKGLEWVAKISPGGSWTYYSDTVEDRFTFSLDTSKSTAYLQMNSLRAEDTAVYYCARQVWGYYALDIWGQGTLVTVSS |
| XI (SEQ ID NO: 12) | EVQLVESGGGLVQPGGSLRLSCAASGFTFSPFAMHWVRQAPGKGLEWVAKISPGGSWTYYSDTVEDRFTFSLDTSKSTAYLQMNSLRAEDTAVYYCARQQWGYYALDIWGQGTLVTVSS |
| XII (SEQ ID NO: 13) | EVQLVESGGGLVQPGGSLRLSCAASGFTFSPFAMHWVRQAPGKGLEWVAKISPGGSWTYYSDTVEDRFTFSLDTSKSTAYLQMNSLRAEDTAVYYCARQKWGYYALDIWGQGTLVTVSS |

FIG. 18

| ID | VEGF Trap Sequence |
|---|---|
| 1A | SDTGRPFVEMYSEIPEIIHMTEGRELVIPCRVTSPNITVTLKKFPLDTLIPDGKRIIWDSRKGFIISNATYKEIGL LTCEATVNGHLYKTNYLTHRQTNTIIDVVLSPSHGIELSVGEKLVLNCTARTELNVGIDFNWEYPSSKHQH KKLVNRDLKTQSGSEMKKFLSTLTIDGVTRSDQGLYTCAASSGLMTKKNSTFVRVHEK |
| 1B | SDTGRPFVEMYSEIPEIIHMTEGRELVIPCRVTSPNITVTLKKFPLDTLIPDGKRIIWDSRKGFIISNATYKEIGL LTCEATVNGHLYKTNYLIHRQTNTIIDVVLSPSHGIELSVGEKLVLNCTARTELNVGIDFNWEYPSSKHQHK KLVNRDLKTQSGSEMKKFLSTLTIDGVTRSDQGLYTCAASSGLMTKKNSTFVRVHEK |
| 1C | SDTGRPFVEMYSEIPEIIHMTEGRELVIPCRVTSPNITVTLKKFPLDTLIPDGKRIIWDSRKGFIISNATYKEIGL LTCEATVNGHLYKTNYLIRQTNTIIDVVLSPSHGIELSVGEKLVLNCTARTELNVGIDFNWEYPSSKHQHK KLVNRDLKTQSGSEMKKFLSTLTIDGVTRSDQGLYTCAASSGLMTKKNSTFVRVHEK |
| 1D | SDTGRPFVEMYSEIPEIIHMTEGRELVIPCRVTSPNITVTLKKFPLDTLIPDGKRIIWDSRKGFIISNATYKEIGL LTCEATVNGHLYKTNYLIIRQTNTIIDVVLSPSHGIELSVGEKLVLNCTARTELNVGIDFNWEYPSSKHQHK KLVNRDLKTQSGSEMKKFLSTLTIDGVTRSDQGLYTCAASSGLMTKKNSTFVRVHEK |

(SEQ ID NO: 14)
(SEQ ID NO: 15)
(SEQ ID NO: 16)
(SEQ ID NO: 17)

FIG. 19

| ID | Linker Sequence |
|---|---|
| 2A | GGGGSGGGS |

(SEQ ID NO: 18)

| ID | Heavy chain Sequence |
|---|---|
| 3A | EVQLVESGGGLVQPGGSLRLSCAASGFTFSPFAMHWVRQAPGKGLEWVAKISPGGSWTYYSDTVTDRFTFSLDTSKSTAYLQMNSLRAEDTAVYYCARQAWGYYALDIWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSCSPGK (SEQ ID NO: 19) |
| 3B | EVQLVESGGGLVQPGGSLRLSCAASGFTFSPFAMHWVRQAPGKGLEWVAKISPGGSWTYYSDTVTDRFTFSLDTSKSTAYLQMNSLRAEDTAVYYCARQSWGYYALDIWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSCSPGK (SEQ ID NO: 20) |
| 3C | EVQLVESGGGLVQPGGSLRLSCAASGFTFSPFAMHWVRQAPGKGLEWVAKISPGGSWTYYSDTVTDRFTFSLDTSKSTAYLQMNSLRAEDTAVYYCARQGWGYYALDIWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSCSPGK (SEQ ID NO: 21) |
| 3D | EVQLVESGGGLVQPGGSLRLSCAASGFTFSPFAMHWVRQAPGKGLEWVAKISPGGSWTYYSDTVTDRFTFSLDTSKSTAYLQMNSLRAEDTAVYYCARQTWGYYALDIWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSCSPGK (SEQ ID NO: 22) |
| 3E | EVQLVESGGGLVQPGGSLRLSCAASGFTFSPFAMHWVRQAPGKGLEWVAKISPGGSWTYYSDTVTDRFTFSLDTSKSTAYLQMNSLRAEDTAVYYCARQVWGYYALDIWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSCSPGK (SEQ ID NO: 23) |
| 3F | EVQLVESGGGLVQPGGSLRLSCAASGFTFSPFAMHWVRQAPGKGLEWVAKISPGGSWTYYSDTVTDRFTFSLDTSKSTAYLQMNSLRAEDTAVYYCARQQWGYYALDIWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTK |

| | |
|---|---|
| 3G | VDKKVEPKSCDKTHTCPPCPAPEAAGAPSVFLFPPKPKDTLMISRTPEVTCVVVDVSHEDPEVKFNWYVDG VEVHNAKTKPREEQYNSTYRVVSVLTVLHQDWLNGKEYKCKVSNKALPAPIEKTISKAKGQPREPQVYTL PPSREEMTKNQVSLTCLVKGFYPSDIAVEWESNGQPENNYKTTPPVLDSDGSFFLYSKLTVDKSRWQQGN VFSCSVMHEALHNHYTQKSLSLSCSPGK (SEQ ID NO: 24) |
| | EVQLVESGGGLVQPGGSLRLSCAASGFTFSPFAMHWVRQAPGKGLEWVAKISPGGSWTYYSDTVTDRFTF SLDTSKSTAYLQMNSLRAEDTAVYYCAROKWGYYALDIWGQGTLVTVSSASTKGPSVFPLAPSSKSTSGG TAALGCLVKDYFPEPVTVSWNSGALTSGVHTFPAVLQSSGLYSLSSVVTVPSSSLGTQTYICNVNHKPSNTK VDKKVEPKSCDKTHTCPPCPAPEAAGAPSVFLFPPKPKDTLMISRTPEVTCVVVDVSHEDPEVKFNWYVDG VEVHNAKTKPREEQYNSTYRVVSVLTVLHQDWLNGKEYKCKVSNKALPAPIEKTISKAKGQPREPQVYTL PPSREEMTKNQVSLTCLVKGFYPSDIAVEWESNGQPENNYKTTPPVLDSDGSFFLYSKLTVDKSRWQQGN VFSCSVMHEALHNHYTQKSLSLSCSPGK (SEQ ID NO: 25) |
| 3H | EVQLVESGGGLVQPGGSLRLSCAASGFTFSPFAISWVRQAPGKGLEWVAKISPGGSWTYYSDTVTDRFTFS LDTSKSTAYLQMNSLRAEDTAVYYCAROLWGYYALDVWGQGTLVTVSSASTKGPSVFPLAPSSKSTSGGT AALGCLVKDYFPEPVTVSWNSGALTSGVHTFPAVLQSSGLYSLSSVVTVPSSSLGTQTYICNVNHKPSNTK VDKKVEPKSCDKTHTCPPCPAPEAAGAPSVFLFPPKPKDTLMISRTPEVTCVVVDVSHEDPEVKFNWYVDG VEVHNAKTKPREEQYNSTYRVVSVLTVLHQDWLNGKEYKCKVSNKALPAPIEKTISKAKGQPREPQVYTL PPSREEMTKNQVSLTCLVKGFYPSDIAVEWESNGQPENNYKTTPPVLDSDGSFFLYSKLTVDKSRWQQGN VFSCSVMHEALHNHYTQKSLSLSCSPGK (SEQ ID NO: 26) |
| 3I | EVQLVESGGGLVQPGGSLRLSCAASGFTFSPFAWSWVRQAPGKGLEWVAKISPGGSWTYYSDTVTDRFTF SLDTSKSTAYLQMNSLRAEDTAVYYCAROLWGYYALDVWGQGTLVTVSSASTKGPSVFPLAPSSKSTSGG TAALGCLVKDYFPEPVTVSWNSGALTSGVHTFPAVLQSSGLYSLSSVVTVPSSSLGTQTYICNVNHKPSNTK VDKKVEPKSCDKTHTCPPCPAPEAAGAPSVFLFPPKPKDTLMISRTPEVTCVVVDVSHEDPEVKFNWYVDG VEVHNAKTKPREEQYNSTYRVVSVLTVLHQDWLNGKEYKCKVSNKALPAPIEKTISKAKGQPREPQVYTL PPSREEMTKNQVSLTCLVKGFYPSDIAVEWESNGQPENNYKTTPPVLDSDGSFFLYSKLTVDKSRWQQGN VFSCSVMHEALHNHYTQKSLSLSCSPGK (SEQ ID NO: 27) |

FIG. 21B

| ID | Light chain | |
|---|---|---|
| 4A | DIQLTQSPSSLSASVGDRVTITCSASISVSLIYWYQQKPGKAPKLLIYDDSSLASGVPSRFSGSGSGTDFTLTI SSLQPEDFATYYCQQWSGYPLTFGQGTKVEIKRTVAAPSVFIFPPSDEQLKSGTASVVCLLNNFYPREAKVQ WKVDNALQSGNSQESVTEQDSKDSTYSLSSTLTLSKADYEKHKVYACEVTHQGLSSPVTKSFNRGEC | (SEQ ID NO: 28) |
| 4B | DIQLTQSPSSLSASVGDRVTITCSASISVSLIYWYQQKPGKAPKLLIYDAESLASGVPSRFSGSGSGTDFTLTI SSLQPEDFATYYCQQWSGYPLTFGQGTKVEIKRTVAAPSVFIFPPSDEQLKSGTASVVCLLNNFYPREAKVQ WKVDNALQSGNSQESVTEQDSKDSTYSLSSTLTLSKADYEKHKVYACEVTHQGLSSPVTKSFNRGEC | (SEQ ID NO: 29) |
| 4C | DIQLTQSPSSLSASVGDRVTITCSASISVSLIYWYQQKPGKAPKLLIYDDSNLASGVPSRFGSGSGTDFTLTI SSLQPEDFATYYCQQWSGYPLTFGQGTKVEIKRTVAAPSVFIFPPSDEQLKSGTASVVCLLNNFYPREAKVQ WKVDNALQSGNSQESVTEQDSKDSTYSLSSTLTLSKADYEKHKVYACEVTHQGLSSPVTKSFNRGEC | (SEQ ID NO: 30) |

| ID | Light chain |
|---|---|
| 4A | DIQLTQSPSSLSASVGDRVTITCSASISVSYLYWYQQKPGKAPKLLIYDDSSLASGVPSRFSGSGSGTDFTLTI SSLQPEDFATYYCQQWSGYPYTFGQGTKVEIKRTVAAPSVFIFPPSDEQLKSGTASVVCLLNNFYPREAKVQ WKVDNALQSGNSQESVTEQDSKDSTYSLSSTLTLSKADYEKHKVYACEVTHQGLSSPVTKSFNRGEC (SEQ ID NO: 28) |
| 4B | DIQLTQSPSSLSASVGDRVTITCSASISVSYLYWYQQKPGKAPKLLIYDASSLASGVPSRFSGSGSGTDFTLTI SSLQPEDFATYYCQQWSGYPYTFGQGTKVEIKRTVAAPSVFIFPPSDEQLKSGTASVVCLLNNFYPREAKVQ WKVDNALQSGNSQESVTEQDSKDSTYSLSSTLTLSKADYEKHKVYACEVTHQGLSSPVTKSFNRGEC (SEQ ID NO: 29) |
| 4C | DIQLTQSPSSLSASVGDRVTITCSASISVSYLYWYQQKPGKAPKLLIYDDSNLASGVPSRFSGSGSGTDFTLTI SSLQPEDFATYYCQQWSGYPYTFGQGTKVEIKRTVAAPSVFIFPPSDEQLKSGTASVVCLLNNFYPREAKVQ WKVDNALQSGNSQESVTEQDSKDSTYSLSSTLTLSKADYEKHKVYACEVTHQGLSSPVTKSFNRGEC (SEQ ID NO: 30) |

| ID | Heavy chain - Fab | Heavy chain - Fc |
|----|-------------------|------------------|
| 5A | EVQLVESGGGLVQPGGSLRLSCAASGFTFSPFAM HWVRQAPGKGLEWVAKISPGGSWTYYSDTVTDR FTFSLDTSKSTAYLQMNSLRAEDTAVYYCARQA WGYYALDIWGQGTLVTVSSASTKGPSVFPLAPSS KSTSGGTAALGCLVKDYFPEPVTVSWNSGALTSG VHTFPAVLQSSGLYSLSSVVTVPSSSLGTQTYICN VNHKPSNTKVDKKVEPKSC (SEQ ID NO: 31) | DKTHTCPPCPAPEAAGAPSVFLFPPKPKDTLMISR TPEVTCVVVDVSHEDPEVKFNWYVDGVEVHNAK TKPREEQYNSTYRVVSVLTVLHQDWLNGKEYKC KVSNKALPAPIEKTISKAKGQPREPQVYTLPPSREE MTKNQVSLTCLVKGFYPSDIAVEWESNGQPENNY KTTPPVLDSDGSFFLYSKLTVDKSRWQQGNVFSC SVMHEALHNHYTQKSLSCSPGK (SEQ ID NO: 40) |
| 5B | EVQLVESGGGLVQPGGSLRLSCAASGFTFSPFAM HWVRQAPGKGLEWVAKISPGGSWTYYSDTVTDR FTFSLDTSKSTAYLQMNSLRAEDTAVYYCARQSW GYYALDIWGQGTLVTVSSASTKGPSVFPLAPSSKS TSGGTAALGCLVKDYFPEPVTVSWNSGALTSGVH TFPAVLQSSGLYSLSSVVTVPSSSLGTQTYICNVN HKPSNTKVDKKVEPKSC (SEQ ID NO: 32) | DKTHTCPPCPAPEAAGAPSVFLFPPKPKDTLMISR TPEVTCVVVDVSHEDPEVKFNWYVDGVEVHNAK TKPREEQYNSTYRVVSVLTVLHQDWLNGKEYKC KVSNKALPAPIEKTISKAKGQPREPQVYTLPPSREE MTKNQVSLTCLVKGFYPSDIAVEWESNGQPENNY KTTPPVLDSDGSFFLYSKLTVDKSRWQQGNVFSC SVMHEALHNHYTQKSLSCSPGK (SEQ ID NO: 41) |
| 5C | EVQLVESGGGLVQPGGSLRLSCAASGFTFSPFAM HWVRQAPGKGLEWVAKISPGGSWTYYSDTVTDR FTFSLDTSKSTAYLQMNSLRAEDTAVYYCARQG WGYYALDIWGQGTLVTVSSASTKGPSVFPLAPSS KSTSGGTAALGCLVKDYFPEPVTVSWNSGALTSG VHTFPAVLQSSGLYSLSSVVTVPSSSLGTQTYICN VNHKPSNTKVDKKVEPKSC (SEQ ID NO: 33) | DKTHTCPPCPAPEAAGAPSVFLFPPKPKDTLMISR TPEVTCVVVDVSHEDPEVKFNWYVDGVEVHNAK TKPREEQYNSTYRVVSVLTVLHQDWLNGKEYKC KVSNKALPAPIEKTISKAKGQPREPQVYTLPPSREE MTKNQVSLTCLVKGFYPSDIAVEWESNGQPENNY KTTPPVLDSDGSFFLYSKLTVDKSRWQQGNVFSC SVMHEALHNHYTQKSLSCSPGK (SEQ ID NO: 42) |
| 5D | EVQLVESGGGLVQPGGSLRLSCAASGFTFSPFAM HWVRQAPGKGLEWVAKISPGGSWTYYSDTVTDR FTFSLDTSKSTAYLQMNSLRAEDTAVYYCARQTW GYYALDIWGQGTLVTVSSASTKGPSVFPLAPSSKS TSGGTAALGCLVKDYFPEPVTVSWNSGALTSGVH TFPAVLQSSGLYSLSSVVTVPSSSLGTQTYICNVN HKPSNTKVDKKVEPKSC (SEQ ID NO: 34) | DKTHTCPPCPAPEAAGAPSVFLFPPKPKDTLMISR TPEVTCVVVDVSHEDPEVKFNWYVDGVEVHNAK TKPREEQYNSTYRVVSVLTVLHQDWLNGKEYKC KVSNKALPAPIEKTISKAKGQPREPQVYTLPPSREE MTKNQVSLTCLVKGFYPSDIAVEWESNGQPENNY KTTPPVLDSDGSFFLYSKLTVDKSRWQQGNVFSC SVMHEALHNHYTQKSLSCSPGK (SEQ ID NO: 43) |
| 5E | EVQLVESGGGLVQPGGSLRLSCAASGFTFSPFAM HWVRQAPGKGLEWVAKISPGGSWTYYSDTVTDR FTFSLDTSKSTAYLQMNSLRAEDTAVYYCARQV WGYYALDIWGQGTLVTVSSASTKGPSVFPLAPSS KSTSGGTAALGCLVKDYFPEPVTVSWNSGALTSG VHTFPAVLQSSGLYSLSSVVTVPSSSLGTQTYICN VNHKPSNTKVDKKVEPKSC (SEQ ID NO: 35) | DKTHTCPPCPAPEAAGAPSVFLFPPKPKDTLMISR TPEVTCVVVDVSHEDPEVKFNWYVDGVEVHNAK TKPREEQYNSTYRVVSVLTVLHQDWLNGKEYKC KVSNKALPAPIEKTISKAKGQPREPQVYTLPPSREE MTKNQVSLTCLVKGFYPSDIAVEWESNGQPENNY KTTPPVLDSDGSFFLYSKLTVDKSRWQQGNVFSC SVMHEALHNHYTQKSLSCSPGK (SEQ ID NO: 44) |

| | | |
|---|---|---|
| 5F | EVQLVESGGGLVQPGGSLRLSCAASGFTFSPFAM HWVRQAPGKGLEWVAKISPGGSWTYYSDTVTDR FTFSLDTSKSTAYLQMNSLRAEDTAVYYCARQQ WGYYALDIWGQGTLVTVSSASTKGPSVFPLAPSS KSTSGGTAALGCLVKDYFPEPVTVSWNSGALTSG VHTFPAVLQSSGLYSLSSVVTVPSSSLGTQTYICN VNHKPSNTKVDKKVEPKSC (SEQ ID NO: 36) | DKTHTCPPCPAPEAAGAPSVFLFPPKPKDTLMISR TPEVTCVVVDVSHEDPEVKFNWYVDGVEVHNAK TKPREEQYNSTYRVVSVLTVLHQDWLNGKEYKC KVSNKALPAPIEKTISKAKGQPREPQVYTLPPSREE MTKNQVSLTCLVKGFYPSDIAVEWESNGQPENNY KTTPPVLDSDGSFFLYSKLTVDKSRWQQGNVFSC SVMHEALHNHYTQKSLSLSCSPGK (SEQ ID NO: 45) |
| 5G | EVQLVESGGGLVQPGGSLRLSCAASGFTFSPFAM HWVRQAPGKGLEWVAKISPGGSWTYYSDTVTDR FTFSLDTSKSTAYLQMNSLRAEDTAVYYCARQK WGYYALDIWGQGTLVTVSSASTKGPSVFPLAPSS KSTSGGTAALGCLVKDYFPEPVTVSWNSGALTSG VHTFPAVLQSSGLYSLSSVVTVPSSSLGTQTYICN VNHKPSNTKVDKKVEPKSC (SEQ ID NO: 37) | DKTHTCPPCPAPEAAGAPSVFLFPPKPKDTLMISR TPEVTCVVVDVSHEDPEVKFNWYVDGVEVHNAK TKPREEQYNSTYRVVSVLTVLHQDWLNGKEYKC KVSNKALPAPIEKTISKAKGQPREPQVYTLPPSREE MTKNQVSLTCLVKGFYPSDIAVEWESNGQPENNY KTTPPVLDSDGSFFLYSKLTVDKSRWQQGNVFSC SVMHEALHNHYTQKSLSLSCSPGK (SEQ ID NO: 46) |
| 5H | EVQLVESGGGLVQPGGSLRLSCAASGFTFSPFAIS WVRQAPGKGLEWVAKISPGGSWTYYSDTVTDRF TFSLDTSKSTAYLQMNSLRAEDTAVYYCARQLW GYYALDVWGQGTLVTVSSASTKGPSVFPLAPSSK STSGGTAALGCLVKDYFPEPVTVSWNSGALTSGV HTFPAVLQSSGLYSLSSVVTVPSSSLGTQTYICNV NHKPSNTKVDKKVEPKSC (SEQ ID NO: 38) | DKTHTCPPCPAPEAAGAPSVFLFPPKPKDTLMISR TPEVTCVVVDVSHEDPEVKFNWYVDGVEVHNAK TKPREEQYNSTYRVVSVLTVLHQDWLNGKEYKC KVSNKALPAPIEKTISKAKGQPREPQVYTLPPSREE MTKNQVSLTCLVKGFYPSDIAVEWESNGQPENNY KTTPPVLDSDGSFFLYSKLTVDKSRWQQGNVFSC SVMHEALHNHYTQKSLSLSCSPGK (SEQ ID NO: 47) |
| 5I | EVQLVESGGGLVQPGGSLRLSCAASGFTFSPFAWS WVRQAPGKGLEWVAKISPGGSWTYYSDTVTDRF TFSLDTSKSTAYLQMNSLRAEDTAVYYCARQLW GYYALDVWGQGTLVTVSSASTKGPSVFPLAPSSK STSGGTAALGCLVKDYFPEPVTVSWNSGALTSGV HTFPAVLQSSGLYSLSSVVTVPSSSLGTQTYICNV NHKPSNTKVDKKVEPKSC (SEQ ID NO: 39) | DKTHTCPPCPAPEAAGAPSVFLFPPKPKDTLMISR TPEVTCVVVDVSHEDPEVKFNWYVDGVEVHNAK TKPREEQYNSTYRVVSVLTVLHQDWLNGKEYKC KVSNKALPAPIEKTISKAKGQPREPQVYTLPPSREE MTKNQVSLTCLVKGFYPSDIAVEWESNGQPENNY KTTPPVLDSDGSFFLYSKLTVDKSRWQQGNVFSC SVMHEALHNHYTQKSLSLSCSPGK (SEQ ID NO: 48) |

FIG. 23B

| ID | (SEQ ID NO:) | CDR1 | (SEQ ID NO:) | CDR2 | (SEQ ID NO:) | CDR3 |
|---|---|---|---|---|---|---|
| 3A / 5A | (49) | GFTFSPFAMH | 50 | AKISPGGSWTYYSDTVTD | 51 | ARQAWGYYALDI |
| 3B / 5B | 52 | GFTFSPFAMH | 53 | AKISPGGSWTYYSDTVTD | 54 | ARQSWGYYALDI |
| 3C / 5C | 55 | GFTFSPFAMH | 56 | AKISPGGSWTYYSDTVTD | 57 | ARQTWGYYALDI |
| 3D / 5D | 58 | GFTFSPFAMH | 59 | AKISPGGSWTYYSDTVTD | 60 | ARQIWGYYALDI |
| 3E / 5E | 61 | GFTFSPFAMH | 62 | AKISPGGSWTYYSDTVTD | 63 | ARQQWGYYALDI |
| 3F / 5F | 64 | GFTFSPFAMH | 65 | AKISPGGSWTYYSDTVTD | 66 | ARQMWGYYALDI |
| 3G / 5G | 67 | GFTFSPFAMH | 68 | AKISPGGSWTYYSDTVTD | 69 | ARQLWGYYALDI |
| 3H / 5H | 70 | GFTFSPFAIS | 71 | AKISPGGSWTYYSDTVTD | 72 | ARQLWGYYALDV |
| 3I / 5I | 73 | GFTFSPFAWS | 74 | AKISPGGSWTYYSDTVTD | 75 | ARQIWGYYALDV |

FIG. 24A

| ID | (SEQ ID NO:) | CDR1 | (SEQ ID NO:) | CDR2 | (SEQ ID NO:) | CDR3 |
|---|---|---|---|---|---|---|
| 4A | 76 | SASSSVSYLY | 77 | LLIYDDSSLAS | 78 | QQWSGYPYT |
| 4B | 79 | SASSSVSYLY | 80 | LLIYDASSLAS | 81 | QQWSGYPYT |
| 4C | 82 | SASSSVSYLY | 83 | LLIYDDSNLAS | 84 | QQWSGYPYT |

(SEQ ID NO: 85)
(SEQ ID NO: 86)
(SEQ ID NO: 87)
(SEQ ID NO: 88)

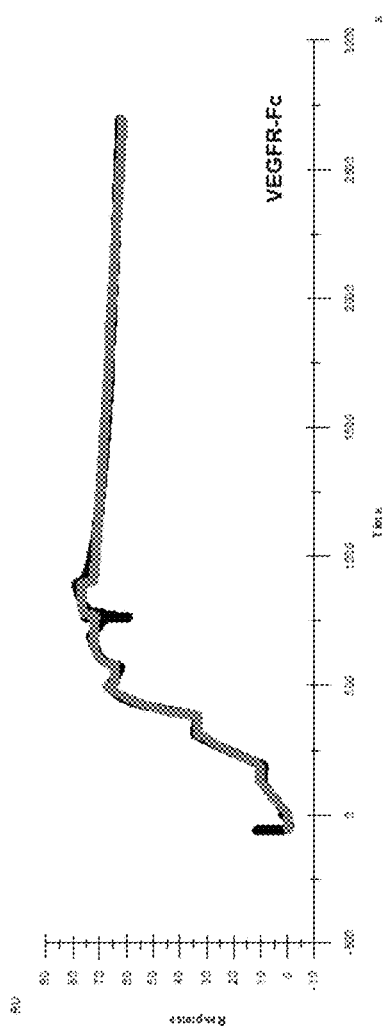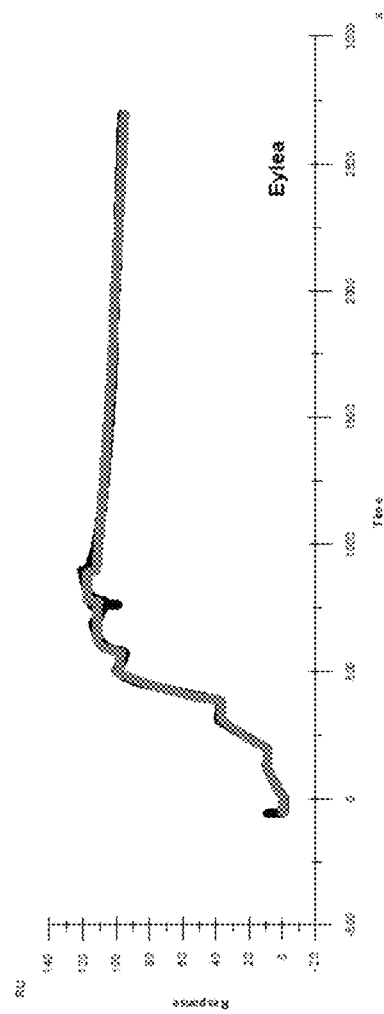
FIG. 26A
FIG. 26B
FIG. 26C

Light chain sequence
DIQLTQSPSSLSASVGDRVTITCSASISVSYLYWYQQKPGKAPKLLIYDDSSLASGVPSRFSGSGSGTDFTLTISSLQPEDFATYYCQQWSGYPYTFGQGTKVEIKRTVAAPSVFIFPPS
DEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 169)

*VL*
*CDR (Kabat numbering)*

Heavy chain sequence with notations
SDTGRPFVEMYSEIPEIIHMTEGRELVIPCRVTSPNITVTLKKFPLDTLIPDGKRIIWDSRKGFIISNATYKEIGLLTCEATVNGHLYKTNYLTHRQTNTIIDVVLSPSHGIELSV
GEKLVLNCTARTELNVGIDFNNWEYPSSKHQHKKLVNRDLKTQSGSEMKKFLSTLTIDGVTRSDQGLYTCAASSGLMTKKNSTFVRVHEKGGGGSGGGGSGGGGSEVQLVESG
GGLVQPGGSLRLSCAASGFTFSPEAMHWVRQAPGKGLEWVAKISPGGSWTYSDTVTDRFTFSLDTSKSTAYLQMNSLRAEDTAVYYCARQAWGYYALDIWGQGTLVTVSSASTK
GPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAP
EAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAK
GQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSCSPGK
(SEQ ID NO: 170)

*VEGFR*

*Linker*
*VH*
*CDR (Kabat numbering)*

FIG. 27

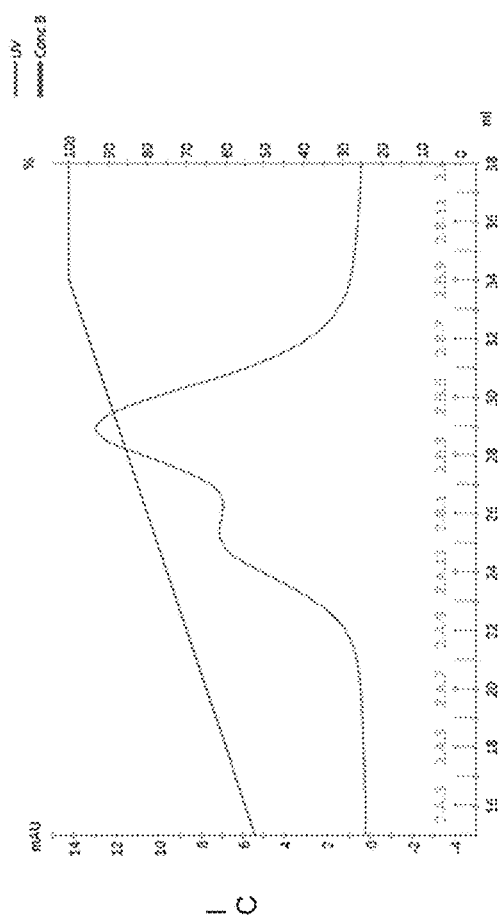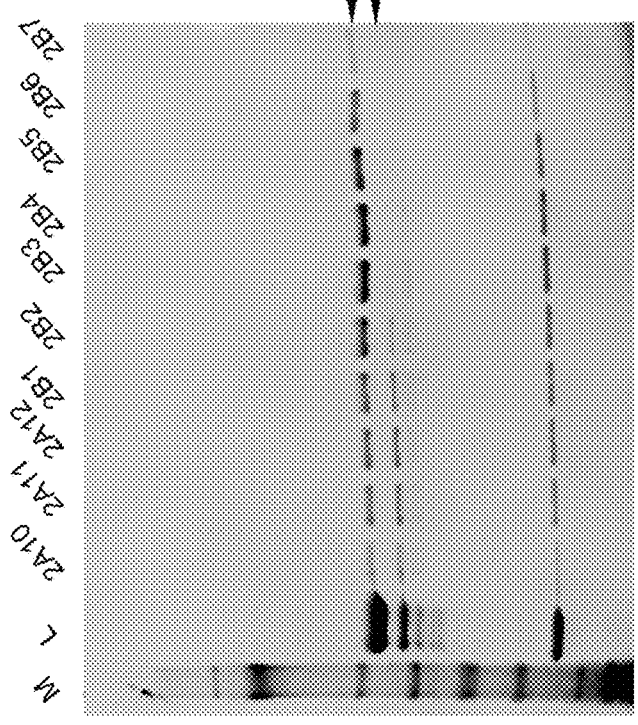
FIG. 33

Lipopolysaccharide stimulated tubule formation in HUVECs

| | ttest control | ttest eylea | ttest sirk | ttest control vs eylea | ttest control vs antiIL6 |
|---|---|---|---|---|---|
| Branching interval | 0.1392 | 0.6240 | 0.9181 | 0.2131 | 0.1689 |
| Mean Mesh Size | 0.0025 | 0.0164 | 0.0724 | 0.0733 | 0.8074 |
| Mesh index | 0.0005 | 0.0245 | 0.0102 | 0.0447 | 0.9311 |
| Nb branches | 0.0048 | 0.0147 | 0.0082 | 0.0719 | 0.4840 |
| Nb extrem. | 0.0000 | 0.0599 | 0.0000 | 0.0041 | 0.9205 |
| Nb isol. seg. | 0.0001 | 0.1210 | 0.0003 | 0.0203 | 0.9159 |
| Nb Junctions | 0.0029 | 0.0306 | 0.0027 | 0.0701 | 0.2399 |
| Nb master junction | 0.0007 | 0.1723 | 0.0115 | 0.3979 | 0.2245 |
| Nb master segments | 0.0779 | 0.0376 | 0.6322 | 0.2705 | 0.1356 |
| Nb meshes | 0.0080 | 0.0383 | 0.1343 | 0.0792 | 0.0537 |
| Nb nodes | 0.0199 | 0.0243 | 0.1411 | 0.2684 | 0.1625 |
| Nb peaces | 0.2964 | 0.3322 | 0.0627 | 0.9589 | 0.0146 |
| Nb segments | 0.0639 | 0.1129 | 0.9692 | 0.2413 | 0.0952 |
| tot branches length | 0.0023 | 0.1139 | 0.0167 | 0.0754 | 0.4362 |
| Tot branching length | 0.0009 | 0.1307 | 0.0062 | 0.0215 | 0.1494 |
| tot isol. branches length | 0.0087 | 0.1475 | 0.0202 | 0.4444 | 0.9355 |
| tot length | 0.4559 | 0.5253 | 0.0843 | 0.8983 | 0.0904 |
| tot master segments length | 0.0074 | 0.2439 | 0.0943 | 0.0344 | 0.0469 |
| tot meshes area | 0.0654 | 0.2517 | 0.6446 | 0.2118 | 0.1869 |
| tot segments length | 0.0014 | 0.1900 | 0.0287 | 0.6551 | 0.0317 |
| VEGFR-AntiIL6 Significance | | | | | |

FIG. 38

Statistical significance of HUVEC tubule inhibition shown in grey ($p<0.05$ by Student's t-test; n=3 independent experiments).
- First three columns are VEGFR-AntiIL6 compared to control, Eylea, or Anti-IL6.
- Next two columns are Eylea or Anti-IL6 compared to control

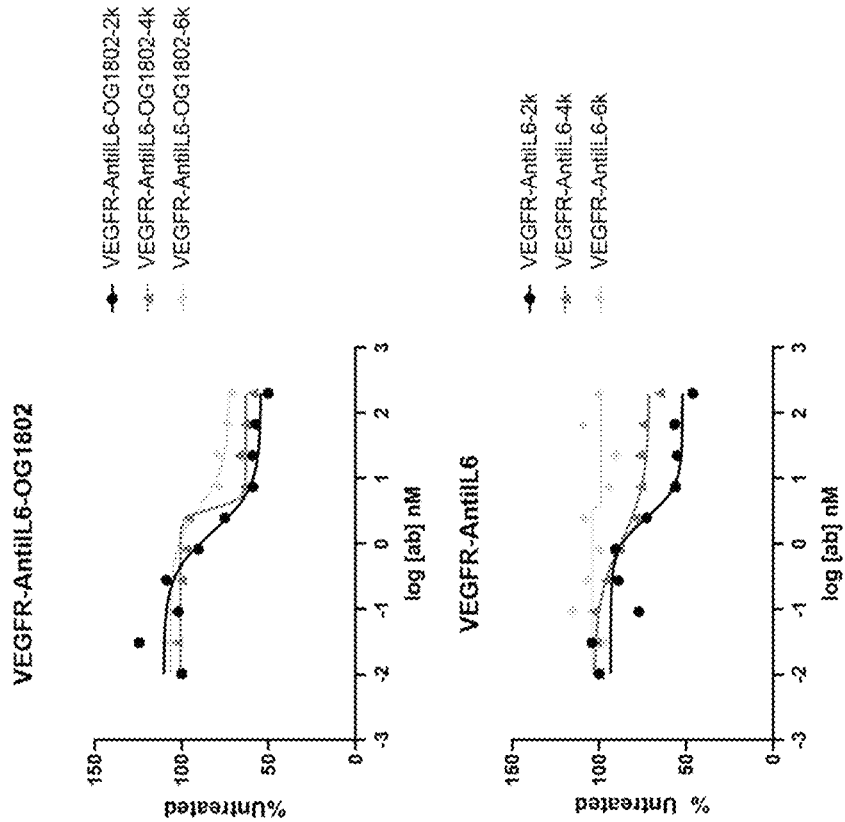
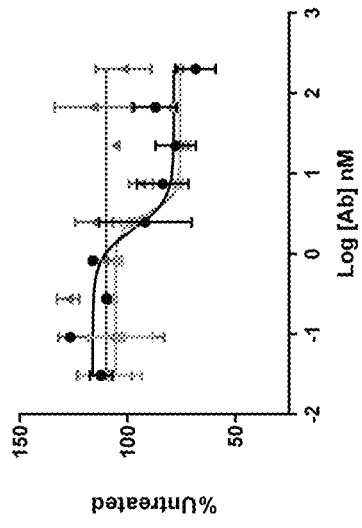
FIG. 40A
FIG. 40B

IL-6 ANTIBODIES AND FUSION CONSTRUCTS AND CONJUGATES THEREOF

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR § 1.57.

SEQUENCE LISTING

The present application is being filed along with a Sequence Listing in electronic format. The Sequence Listing is provided as a file entitled KDIAK044A_REPLACEMENT_SEQLIST2.txt, created Jul. 14, 2023, which is 395,613 bytes in size. The information in the electronic format of the Sequence Listing is incorporated herein by reference in its entirety.

FIELD

The present invention relates generally to fusion constructs that bind to IL-6 and/or VEGF.

BACKGROUND

Vascular endothelial growth factor A (VEGF-A) is a signal protein that mediates pro-angiogenic functions such as endothelial cell survival, proliferation, migration, and cell-cell permeability. Its activity has been shown to promote progression of retinal diseases such as choroidal neovascularization (CNV) in Age Related Macular Degeneration (AMD) and Diabetic Macular Edema (DME). Inhibition of VEGF-A signaling has been proven to be an effective means to stop progression of neovascular retinal diseases (Ferrara et al, Retina, 2006). Various therapeutic molecules have been developed to inhibit VEGF function. Among these, anti-VEGF monoclonal antibodies such as Ranibizumab and Bevacizumab have been shown to be safe and effective treatments against pathological angiogenesis. More recently, recombinantly made VEGFR fusion proteins such as Aflibercept (Eylea) and Conbercept (China), which act as VEGF "traps," are proving to be more effective and longer lasting than their antibody competitors.

Inflammation has been implicated in the pathogenesis of retinal diseases, and anti-inflammatory therapies such as steroids have been effective in treating uveitis and diabetic macular edema (DME). Detailed studies looking at inflammation and infection in the eye have shown that the pro-inflammatory cytokine, interleukin-6 (IL-6) is significantly elevated in the ocular fluids of refractory/chronic uveitis patients, and inhibition of IL-6 in animal models inhibits the onset of uveitis. High ocular fluid levels of IL-6 are also found in patients with DME and retinal vein occlusion. Additionally, chronic inflammatory cells have been seen on the surface of the Bruch's membrane in eyes with neovascular AMD, and patients with AMD have been reported to have increased serum levels of IL-6. Interestingly, IL-6 has also been observed to stimulate defective angiogenesis. In addition to autoimmune disorders such as rheumatoid arthritis, anti-IL-6 treatment has been shown to effectively treat uveitis and uveitic macular edema.

SUMMARY

In some aspects, an isolated antagonist antibody that specifically binds to IL-6 that is conjugated to a polymer is provided.

In some aspects, an isolated antagonistic antibody is provided. The antibody comprises a heavy chain amino acid variable region that comprises a heavy chain in Table 1; and a light chain amino acid variable region that comprises the light chain in Table 2.

In some aspects, an isolated antagonist antibody is provided. The antibody comprises: a heavy chain variable region (VH) comprising a VH complementarity determining region one (CDR1), VH CDR2, and VH CDR3 of the VH having an amino acid sequence selected from the group consisting of the CDRs in Table 1; and a light chain variable region (VL) comprising a VL CDR1, VL CDR2, and VL CDR3 of the VL having an amino acid sequence selected from the group consisting of the CDRs in Table 2.

In some aspects, an isolated antagonist antibody that binds to IL-6 is provided. The antibody comprises at least one of the following mutations based on EU numbering: L234A, L235A, and G237A.

In some aspects, an isolated antagonistic antibody that binds to IL-6 is provided. The antibody comprises a $CDR_H1$ that is the $CDR_H1$ in Table 1; a $CDR_H2$ that is the $CDR_H2$ in Table 1; a $CDR_H3$ that is the $CDR_H3$ in Table 1: a $CDR_L1$ that is the $CDR_L1$ in Table 2; a $CDR_L2$ that is the $CDR_L2$ in Table 2; a $CDR_L3$ that is the $CDR_L3$ in Table 2; at least one of the following mutations (EU numbering): L234A, L235A, and G237A; and at least one of the following mutations (EU numbering): Q347C or L443C.

In some aspects, a fusion protein is provided that comprises the isolated antagonist antibody; and a fragment of a VEGF binding protein.

In some aspects, a conjugate comprising any of the isolated antagonistic antibodies herein and a polymer is provided. The polymer is covalently attached to the antibody.

In some aspects, a conjugate is provided. The conjugate comprises the fusion protein as provided herein and a polymer, wherein the polymer is covalently attached to the fusion protein.

In some aspects, an isolated cell line that produces the isolated antagonistic antibody or the fusion protein is provided.

In some aspects, an isolated nucleic acid encoding an isolated antagonistic antibody or the fusion protein is provided.

In some aspects, a recombinant expression vector is provided. The vector comprises a nucleic acid encoding any of these constructs provided herein.

In some aspects, a host cell comprising an expression vector as provided herein is provided.

In some aspects, a method of producing an IL-6 antagonist antibody or fusion protein thereof is provided. The method comprises: culturing a cell line that recombinantly produces an isolated antagonistic antibody or the fusion protein under conditions wherein the antibody is produced; and recovering the antibody.

In some aspects, a pharmaceutical composition is provided. It comprises an isolated antagonistic antibody or the fusion protein and/or a conjugate as provided herein, and a pharmaceutically acceptable carrier.

In some aspects, a method for the treatment or prophylaxis of a disease in a patient in need thereof is provided. The method comprises administering to the patient an isolated antagonist antibody or the fusion protein and/or a conjugate as provided herein.

In some aspects, a method for the treatment or prophylaxis of a disease in a patient in need thereof is provided. The method comprises identifying a patient having hyperactive IL-6 and/or VEGF activity; and administering to the patient an isolated antagonist antibody or the fusion protein and/or a conjugate as provided herein.

In some aspects, a fusion protein is provided that comprises an IL-6 VH, an IL-6 VL, an IL-6 Fc, and a VEGF Trap, wherein the VEGF Trap is fused to IL-6 in one of the following manners: 1) to an N-terminal end of a heavy chain comprising IL-6 VH; or 2) between a hinge region and after a CH1 domain of a heavy chain comprising IL-6 VH.

In some aspects, an isolated antagonistic IL-6 antibody is provided that comprises a heavy chain amino acid variable region that comprises a heavy chain that has a sequence of at least one of SEQ ID NOs: 7-13,19-27, 89, 90, 256-262; and a light chain amino acid variable region that comprises the light chain that has a sequences of at least one of SEQ ID NOs: 91-93, 28-30.

In some aspects, an isolated antagonist IL-6 antibody is provided that comprises: a heavy chain variable region (VH) comprising 3 complementarity determining regions: VH (CDR1), VH CDR2, and VH CDR3 having an amino acid sequence from the CDRs listed in SEQ ID NO: 256; and a light chain variable region (VL) comprising a VL CDR1, VL CDR2, and VL CDR3 having an amino acid sequence selected from the group of CDRs listed in SEQ ID NO: 91-93.

In some aspects, an isolated antagonist antibody that binds to IL-6 is provided. The antibody comprises at least one of the following mutations based on EU numbering: L234A, L235A, and G237A.

In some embodiments, an isolated antagonistic antibody that binds to IL-6 is provided and comprises: a $CDR_H1$ that is a $CDR_H1$ in SEQ ID NO: 172; a $CDR_H2$ that is a $CDR_H2$ in SEQ ID NO: 173; a $CDR_H3$ that is a $CDR_H3$ in SEQ ID NO: 174: a $CDR_L1$ that is a $CDR_L1$ in SEQ ID NO: 199; a $CDR_L2$ that is a $CDR_L2$ in SEQ ID NO: 200; a $CDR_L3$ that is a $CDR_L3$ in SEQ ID NO: 201; at least one of the following mutations (EU numbering): L234A, L235A, and G237A; and at least one of the following mutations (EU numbering): Q347C or L443C.

In some aspects, a fusion protein comprising: the isolated antagonist antibody of any one provided herein (including fragments thereof)) and VEGF Trap is provided.

In some aspects, a conjugate comprising: any of the isolated antagonistic antibodies (including fragments) provided herein; and a polymer is provided, wherein the polymer is covalently attached to the antibody.

In some aspects, a conjugate comprising the fusion protein as provided herein; and a polymer, wherein the polymer is covalently attached to the fusion protein is provided.

In some aspects, a VEGFR-Anti-IL-6 dual inhibitor is provided. The VEGFR-Anti-IL-6 dual inhibitor comprises a trap antibody fusion of an anti-IL 6 antibody and an anti-VEGF trap (VEGFR1/2), wherein the dual inhibitor includes at least one point mutation within a VEGFR sequence to reduce cleavage of the VEGFR protein.

In some aspects, a protein construct comprising: at least 3 heavy chain CDRs; at least 3 light chain CDRs; a VEGF trap sequence; and a linker sequence, wherein each of the sequences is selected from a corresponding sequence within FIGS. 18-25 or from corresponding sequences from the tables herein (including, for example, 1, 2, 6, 7, 8, and 9).

In some aspects, a fusion protein comprising an IL-6 VH; an IL-6 VL; an IL-6 Fc; and a VEGF Trap is provided, wherein the fusion protein alters HUVEC proliferation. In some embodiments, altering HUVEC proliferation is inhibiting VEGF/IL6 mediated proliferation.

In some aspects, a fusion protein comprising a sequence that is at least 80% identical to SEQ ID NO: 263 and at least 80% identical to SEQ ID NO: 117 is provided, wherein the fusion protein is further conjugated to a polymer.

In some aspects, an isolated antagonist antibody that binds to IL-6 is provided. The antibody comprises at least one of the following mutations based on EU numbering: L234A, L235A, and G237A.

In some aspects, an isolated antagonistic antibody that binds to IL-6, the antibody comprising: a $CDR_H1$ that is a $CDR_H1$ in SEQ ID NO: 172; a $CDR_H2$ that is a $CDR_H2$ in SEQ ID NO: 173; a $CDR_H3$ that is a $CDR_H3$ in SEQ ID NO: 174: a $CDR_L1$ that is a $CDR_L1$ in SEQ ID NO: 199; a $CDR_L2$ that is a $CDR_L2$ in SEQ ID NO: 200; a $CDR_L3$ that is a $CDR_L3$ in SEQ ID NO: 201; at least one of the following mutations (EU numbering): L234A, L235A, and G237A; and at least one of the following mutations (EU numbering): Q347C or L443C is provided.

In some aspects, the VEGFR-Anti-IL-6 dual inhibitor comprises an anti-IL-6 heavy chain variable region sequences selected from SEQ ID NO: 7-13, 89, 90, and/or 256-262.

In some aspects, the VEGFR-Anti-IL-6 dual inhibitor has a VEGF trap sequences selected from at least one of SEQ ID Nos: 145, 15, 16, or 17.

In some aspects, the linker sequence is SEQ ID NO: 18.

In some aspects, a heavy chain sequence for the Anti-IL-6 molecule is provided that is selected from at least one of SEQ ID NOs 19-27 or includes at least the sequence in one of SEQ ID NOs: 89, 90, 256-262.

In some aspects, a light chain sequence for the anti-IL-6 molecule is provided that comprises at least 1, 2, or 3 light chain CDRs from at least one of SEQ ID NOs 76-84.

In some aspects, a heavy chain sequence for the Anti-IL-6 molecule is provided that comprises at least 1, 2, or 3 heavy chain CDRs from at least one of SEQ ID NOs 49-75.

In some aspects, a VEGFR-Anti-IL-6 dual inhibitor is provided that comprises a VEGFR-Fc sequence from at least one of SEQ ID NOs 85-88.

In some aspects, a VEGFR-Anti-IL-6 dual inhibitor is provided that comprises one or more of the sequences in any one or more of SEQ ID Nos 7-13, 145, 15-17, 18-84.

In aspects embodiments, a VEGFR-Anti-IL-6 dual inhibitor is provided that comprises an IL-6 VH; an IL-6 VL; an IL-6 Fc; a VEGF Trap; and a linker. In some embodiments, the IL-6 VH comprises a sequence from an IL6 VH sequence in any one of SEQ ID NOs: 19-27, 31-39, 89, 90, or 256-262. In some embodiments, the IL-6 VL comprises a sequence from an IL6 VL sequence in any one of SEQ ID Nos 28-30 or 91-93. In some embodiments, the Fc comprises a sequence from a Fc sequence in any one of SEQ ID NOs 40-48. In some embodiments, the VEGF Trap comprises a sequence from a VEGF trap sequence in any one of SEQ ID NOs: 145, 15, 16, or 17.

In some aspects, a fusion protein is provided that comprises an IL-6 VH; an IL-6 VL; an IL-6 Fc; and a VEGF Trap, wherein the fusion protein alters HUVEC proliferation. In some embodiments, altering HUVEC proliferation is inhibiting VEGF/IL6 mediated proliferation.

In some aspects, a fusion protein is provided that comprises a sequence that is at least 80% identical to SEQ ID NO: 263 and at least 80% identical to SEQ ID NO: 117 is provided. The fusion protein is further conjugated to a polymer. In some embodiments, the fusion protein is at least 95% identical to SEQ ID NO: 263 and at least 95% identical to SEQ ID NO: 117. In some embodiments, the protein comprises at least a) SEQ ID NO: 172, 173, 174, 199, 200, and 201, or b) a substitutions of 1, 2, or 3 amino acids within SEQ ID NO: 172, 173, 174, 199, 200, and/or 201, wherein the substitution is a conservative substitution.

In some aspects, an antibody of any one of provided herein comprises a) an amino acid sequence of SEQ ID NO: 169 and 170 or b) an amino acid sequence that is at least 80% identical to SEQ ID NO: 169 and at least 80% identical to SEQ ID NO: 170.

In some aspects, a fusion protein of any one provided herein comprises a) an amino acid sequence of SEQ ID NO: 169 and 170 or b) an amino acid sequence that is at least 80% identical to SEQ ID NO: 169 and at least 80% identical to SEQ ID NO: 170.

In some aspects, a conjugate of any one provided herein comprises a) an amino acid sequence of SEQ ID NO: 169 and 170 or b) an amino acid sequence that is at least 80% identical to SEQ ID NO: 169 and at least 80% identical to SEQ ID NO: 170.

In some aspects, a VEGFR-Anti-IL-6 dual inhibitor of any one provided herein comprises a) an amino acid sequence of SEQ ID NO: 169 and 170 or b) an amino acid sequence that is at least 80% identical to SEQ ID NO: 169 and at least 80% identical to SEQ ID NO: 170.

In some aspects, a protein of any one provided herein comprises a) an amino acid sequence of SEQ ID NO: 169 and 170 or b) an amino acid sequence that is at least 80% identical to SEQ ID NO: 169 and at least 80% identical to SEQ ID NO: 170.

BRIEF DESCRIPTION OF THE DRAWINGS

FIG. 1 depicts a sequence of IL-6.
FIG. 2C shows the synthesis of OG1802 from R3707.
FIG. 2I shows the synthesis of OG1786 from OG1785.
FIG. 2J shows OG1801.
FIG. 2K shows OG1802.
FIG. 3 depicts a flow chart for antibody selection and optimization.
FIG. 4 depicts ELISA data showing that anti-IL-6 mAb binds to IL-6, but not an IL-6/IL-6R complex, and that IL-6/IL-6R complex formation is inhibited by anti-IL-6 mAb.
FIG. 5 depicts some embodiments of the heavy and light chain variable regions of an IL-6-Ab. Embodiments of CDRs are shown in boxed regions. These sequences can also be employed in a IL-6 Ab-VEGF Trap fusion construct.

FIG. 9 also shows the results of an IL-6/IL-6R complex ELISA (middle). Dual inhibitors and antiIL-6 inhibited IL-6/IL-6R complex formation to the same degree. IC50 values: anti-IL-6=0.36 nM, VEGF Trap-antiIL-6=0.47 nM, and antiIL-6-VEGF Trap=0.32 nM. Eylea served as a negative control. FIG. 9 also shows the results of a VEGF/VEGFR competitive ELISA (bottom). Dual inhibitors, Eylea, and OG1950 inhibited VEGF binding to VEGFR to varying degrees. Eylea and the antiIL-6-VEGF Trap construct are comparable (4.24 nM vs. 4.53 nM), while the VEGF Trap-antiIL-6 construct was ~2 fold better (1.74 nM), and OG1950 showed superior maximal inhibition to other inhibitors (1.55 nM).

FIGS. 11A-11B depict SDS-PAGE bands of SeeBlue®Plus2 standard, Anti-IL-6, Anti-IL-6-VEGFR, and VEGFR-Anti-IL-6.

FIG. 12 depicts results of transfer to a PVDF membrane, N-terminal Edman Sequencing, which show that the cleaved products share the same N-Terminal sequence (LTHRQT), which shows that the cleavage site is located at the VEGF trap region.

FIGS. 13A-B depict SDS-PAGE bands of SeeBlue®Plus2 standard and 19 VEGF trap constructs.

FIGS. 13C-13E depict the sequence listings of VEGF_trap_variant_1, VEGF_trap_variant_2, and VEGF trap_variant_3.

FIGS. 13F-13G depict SDS-PAGE bands of SeeBlue®Plus2 standard and 4 VEGF trap variants, including VEGFR_variant_3, which has double point mutations T94I and H95I.

FIGS. 16B-16C depict statistics of the tubule formation assays with different parameters.

FIG. 18 illustrates embodiments of Anti-IL-6 heavy chain variable region sequences. CDRs are underlined.

FIG. 19 illustrates various embodiments of VEGF trap sequences. Section that varies between the sequences are in bold and underlined.

FIG. 20 illustrates some embodiments of linker (GS) sequence embodiments. It can be present as a double repeat Gly-Gly-Gly-Gly-Ser linker (GS).

FIG. 21 includes both FIG. 21A and FIG. 21B, which provide various embodiments of CDRs within the noted sequences.

FIG. 22 illustrates some embodiments of light chain sequences for Anti-IL-6 molecules. CDRs are underlined. FIG. 22 includes both FIG. 22A and FIG. 22B, which provide various embodiments of CDRs within the noted sequences.

FIG. 23 illustrates some embodiments of heavy chain sequences for Anti-IL-6 molecules. CDRs are underlined. FIG. 23 includes both FIG. 23A and FIG. 23B, which provide various embodiments of CDRs within the noted sequences.

FIGS. 24A-24B illustrate some embodiments of combinations of CDRs of FIGS. 21-23.

FIG. 25 illustrates some embodiments of VEGFR-Fc sequence variants. Section that varies between the sequences are in bold and underlined.

FIGS. 26A-26C illustrate affinity binding data.

FIG. 27 depicts the sequences of some embodiments of the VEGFR-AntiIL6-sequences. The CDRs (as defined by Kabat) are underlined. The greyed sections indicate the VEGFR constructs. The bolded text indicates the linker section. Mutations L234A, L235A, G237A and L443C (EU numbering) are double underlined. Each of these sections can be exchanged for other corresponding sections provided herein (e.g., alternative linkers or CDRs, etc.)

FIG. 33 depicts the results of a VEGFR-AntiIL6 HIC chromatography. Gel: is Novex 8-16% Tris-Glycine/reducing conditions, M=SeeBlue®Plus2 standard. L=VEGFR-AntiIL6 intact and cleaved mixture (load). Remaining lanes correspond to samples aliquoted at different buffer B concentrations as indicated on chromatogram. Intact (I) and cleaved (C) heavy chains are indicated. In Column Hi Trap Butly HP Buffer A is: 20 mM Sodium Phosphate pH 6, 1 M Ammonium sulfate. Buffer B is: 20 mM Sodium Phosphate pH 6.

FIG. 38 depicts the lipopolysaccharide stimulated tubule formation in HUVECs

FIG. 40A depicts the inhibition of VEGF/IL6 mediated proliferation of HUVECs.

FIG. 40B depicts the inhibition of HUVEC proliferation with increasing number of cells per well.

DETAILED DESCRIPTION

Figure 2A:
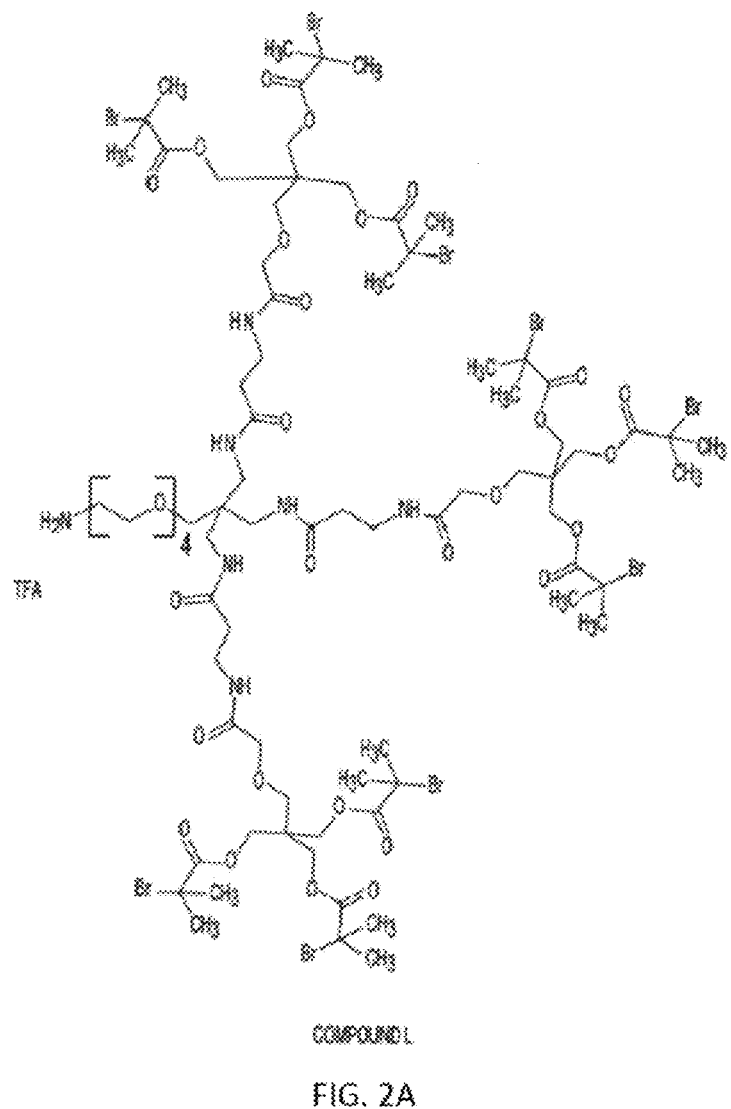
FIG. 2A shows Compound L.

To directly reduce the concurrent inflammation and defective angiogenesis that drive pathogenesis of neovascular retinal pathologies, presented herein are designed molecules that simultaneously block the functions of the pro-inflammatory cytokine IL-6 and the pro-angiogenic signal protein VEGF. These molecules are comprised of (1) an anti-IL-6 monoclonal antibody fused to (2) two VEGF binding domains of VEGF receptors (VEGFRs). The anti-IL-6 moiety specifically binds IL-6 and inhibits its interaction with the IL-6 receptor (IL-6R). The VEGF Trap moiety includes of a fusion of two VEGF binding domains (VEGFR1 domain 2, VEGFR2 domain 3) that work as a VEGF trap, preventing VEGF from binding to VEGF receptors. Additionally, in some embodiments, each of these dual inhibitor molecules is equipped with an unpaired cysteine at its C-terminus which can be conjugated with a half-life extending phosphorylcholine based biopolymer.

Various embodiments provided herein will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

The following terms, unless otherwise indicated, shall be understood to have the following meanings: the term "isolated molecule" as referring to a molecule (where the molecule is, for example, a polypeptide, a polynucleotide, or an antibody) that by virtue of its origin or source of derivation (1) is not associated with naturally associated components that accompany it in its native state, (2) is substantially free of other molecules from the same source, e.g., species, cell from which it is expressed, library, etc., (3) is expressed by a cell from a different species, or (4) does not occur in nature. Thus, a molecule that is chemically synthesized, or expressed in a cellular system different from the system from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

As used herein, unless designated otherwise, the term "IL-6" or "IL6" refers to human IL-6. In some embodiments, other forms of IL-6 are contemplated, and will be designated by specific reference to the other organisms, e.g., canine, feline, equine, and bovine. One exemplary human IL-6 is found as UniProt Accession NumberP05231.

Anti-IL-6 antibodies or other biologics described herein are typically provided in isolated form. This means that an antibody is typically at least 50% w/w pure of interfering proteins and other contaminants arising from its production or purification but does not exclude the possibility that the antibody is combined with a pharmaceutically acceptable excipient intended to facilitate its use. Sometimes antibodies are at least 60, 70, 80, 90, 95 or 99% w/w pure of interfering proteins and contaminants from production or purification. Often an antibody (or antibody conjugate) is the predominant macromolecular species remaining after its purification.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also, unless otherwise specified, any antigen binding portion thereof that competes with the intact antibody for specific binding, fusion proteins comprising an antigen binding portion, and any other modified configuration of the immunoglobulin molecule that comprises an antigen recognition site. Antigen binding portions include, for example, Fab, Fab', F(ab')$_2$, Fd, Fv, domain antibodies (dAbs, e.g., shark and camelid antibodies), fragments including complementarity determining regions (CDRs), single chain variable fragment antibodies (scFv), maxibodies, minibodies, intrabodies, diabodies, triabodies, tetrabodies, v-NAR and bis-scFv, and polypeptides that contain at least a portion of an immunoglobulin that is sufficient to confer specific antigen binding to the polypeptide. An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG$_1$, IgG$_2$, IgG$_3$, IgG$_4$, IgA$_1$ and IgA$_2$. The heavy-chain constant regions that correspond to the different classes of immunoglobulins are called alpha, delta, epsilon, gamma, and mu, respectively. The subunit structures and three-dimensional configurations of different classes of immunoglobulins are well known.

A "variable region" of an antibody refers to the variable region of the antibody light chain or the variable region of the antibody heavy chain, either alone or in combination. As known in the art, the variable regions of the heavy and light chains each consist of four framework regions (FRs) connected by three complementarity determining regions (CDRs) also known as hypervariable regions, and contribute to the formation of the antigen binding site of antibodies. If variants of a subject variable region are desired, particularly with substitution in amino acid residues outside of a CDR region (i.e., in the framework region), appropriate amino acid substitution, preferably, conservative amino acid substitution, can be identified by comparing the subject variable region to the variable regions of other antibodies which contain CDR1 and CDR2 sequences in the same canonincal class as the subject variable region (Chothia and Lesk, J Mol Biol 196(4): 901-917, 1987).

In certain embodiments, definitive delineation of a CDR and identification of residues comprising the binding site of an antibody is accomplished by solving the structure of the antibody and/or solving the structure of the antibody-ligand complex. In certain embodiments, that can be accomplished by any of a variety of techniques known to those skilled in the art, such as X-ray crystallography. In certain embodiments, various methods of analysis can be employed to identify or approximate the CDR regions. In certain embodiments, various methods of analysis can be employed to identify or approximate the CDR regions. Examples of such methods include, but are not limited to, the Kabat definition, the Chothia definition, the IMGT approach (Lefranc et al., 2003) Dev Comp Immunol. 27:55-77), computational programs such as Paratome (Kunik et al., 2012, Nucl Acids Res. W521-4), the AbM definition, and the conformational definition.

The Kabat definition is a standard for numbering the residues in an antibody and is typically used to identify CDR regions. See, e.g., Johnson & Wu, 2000, Nucleic Acids Res., 28: 214-8. The Chothia definition is similar to the Kabat definition, but the Chothia definition takes into account positions of certain structural loop regions. See, e.g., Chothia et al., 1986, J. Mol. Biol., 196: 901-17; Chothia et al., 1989, Nature, 342: 877-83. The AbM definition uses an integrated suite of computer programs produced by Oxford Molecular Group that model antibody structure. See, e.g., Martin et al., 1989, Proc Natl Acad Sci (USA), 86:9268-9272; "AbM™, A Computer Program for Modeling Variable Regions of Antibodies," Oxford, UK; Oxford Molecular, Ltd. The AbM definition models the tertiary structure of an antibody from primary sequence using a combination of knowledge databases and ab initio methods, such as those described by Samudrala et al., 1999, "Ab Initio Protein Structure Prediction Using a Combined Hierarchical Approach," in PROTEINS, Structure, Function and Genetics Suppl., 3:194-198. The contact definition is based on an analysis of the available complex crystal structures. See, e.g., MacCallum et al., 1996, J. Mol. Biol., 5:732-45. In another approach, referred to herein as the "conformational definition" of CDRs, the positions of the CDRs may be identified as the residues that make enthalpic contributions to antigen binding. See, e.g., Makabe et al., 2008, Journal of Biological Chemistry, 283:1156-1166. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, IMGT, Paratome, AbM, and/or conformational definitions, or a combination of any of the foregoing.

As known in the art, a "constant region" of an antibody refers to the constant region of the antibody light chain or the constant region of the antibody heavy chain, either alone or in combination.

As used herein, "monoclonal antibody" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, 1975, Nature 256:495, or may be made by recombinant DNA methods such as described in U.S. Pat. No. 4,816,567. The monoclonal antibodies may also be isolated from phage libraries generated using the techniques described in McCafferty et al., 1990, Nature 348:552-554, for example. As used herein, "humanized" antibody refers to forms of non-human (e.g. murine) antibodies that are chimeric immunoglobulins, immunoglobulin chains, or fragments thereof (such as Fv, Fab, Fab', F(ab')$_2$ or other antigen-binding subsequences of antibodies) that contain minimal sequence derived from non-human immunoglobulin. Preferably, humanized antibodies are human immunoglobulins (recipient antibody) in which residues from a CDR of the recipient are replaced by residues from a CDR of a non-human species (donor antibody) such as mouse, rat, or rabbit having the desired specificity, affinity, and capacity. The humanized antibody may comprise residues that are found neither in the recipient antibody nor in the imported CDR or framework sequences, but are included to further refine and optimize antibody performance.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen binding residues.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody. The term "epitope" refers to that portion of a molecule capable of being recognized by and bound by an antibody at one or more of the antibody's antigen-binding regions. Epitopes often consist of a surface grouping of molecules such as amino acids or sugar side chains and have specific three-dimensional structural characteristics as well as specific charge characteristics. In some embodiments, the epitope can be a protein epitope. Protein epitopes can be linear or conformational. In a linear epitope, all of the points of interaction between the protein and the interacting molecule (such as an antibody) occur linearly along the primary amino acid sequence of the protein. A "nonlinear epitope" or "conformational epitope" comprises noncontiguous polypeptides (or amino acids) within the antigenic protein to which an antibody specific to the epitope binds. The term "antigenic epitope" as used herein, is defined as a portion of an antigen to which an antibody can specifically bind as determined by any method well known in the art, for example, by conventional immunoassays. Once a desired epitope on an antigen is determined, it is possible to generate antibodies to that epitope, e.g., using the techniques described in the present specification. Alternatively, during the discovery process, the generation and characterization of antibodies may elucidate information about desirable epitopes. From this information, it is then possible to competitively screen antibodies for binding to the same epitope. An approach to achieve this is to conduct competition and cross-competition studies to find antibodies that compete or cross-compete with one another for binding to IL-6, e.g., the antibodies compete for binding to the antigen.

The term "compete," as used herein with regard to an antibody, means that a first antibody, or an antigen-binding portion thereof, binds to an epitope in a manner sufficiently similar to the binding of a second antibody, or an antigen-binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the present invention. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

As used herein, an antibody "interacts with" IL-6 when the equilibrium dissociation constant is equal to or less than 20 nM, preferably less than about 6 nM, more preferably less than about 1 nM, most preferably less than about 0.75 nM. In some embodiments, the affinity of the antibody is between 400 and 800 µM, e.g., 450-700, or 500-600 µM.

An IL-6 antagonist antibody encompasses antibodies that block, antagonize, suppress or reduce (to any degree including significantly) a IL-6 biological activity such as binding to IL-6R, IL-6/IL-6R complex binding to gp130, phosphorylation and activation of Stat3, cell proliferation, and stimulation of IL-6 mediated inflammatory or pro-angiogenic pathways. For purpose of the present disclosure, it will be explicitly understood that the term "IL-6 antagonist antibody" encompasses all the previously identified terms, titles, and functional states and characteristics whereby the IL-6 itself, an IL-6 biological activity, or the consequences of the biological activity, are substantially nullified, decreased, or neutralized in any meaningful degree. In some embodiments, an IL-6 antagonist antibody binds IL-6. Examples of IL-6 antagonist antibodies are provided herein.

An antibody that "preferentially binds" or "specifically binds" (used interchangeably herein) to an epitope is a term well understood in the art, and methods to determine such specific or preferential binding are also well known in the art. A molecule is said to exhibit "specific binding" or "preferential binding" if it reacts or associates more frequently, and/or more rapidly, and/or with greater duration and/or with greater affinity with a particular cell or substance than it does with alternative cells or substances. An antibody "specifically binds" or "preferentially binds" to a target if it binds with greater affinity, and/or avidity, and/or more readily, and/or with greater duration than it binds to other substances. For example, an antibody that specifically or preferentially binds to an IL-6 epitope is an antibody that binds this epitope with greater affinity, and/or avidity, and/or more readily, and/or with greater duration than it binds to other IL-6 epitopes or non-IL-6 epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

As used herein, "substantially pure" refers to material which is at least 50% pure (i.e., free from contaminants), more preferably, at least 90% pure, more preferably, at least 95% pure, yet more preferably, at least 98% pure, and most preferably, at least 99% pure.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As known in the art, the term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat. Kabat et al., Sequences of Proteins of Immunological Interest, 5th Ed. Public Health Service, National Institutes of Health, Bethesda, Md., 1991. The Fc region of an immunoglobulin generally comprises two constant domains, CH2 and CH3. As is known in the art, an Fc region can be present in dimer or monomeric form.

As used in the art, "Fc receptor" and "FcR" describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, 1991, Ann. Rev. Immunol., 9:457-92; Capel et al., 1994, Immunomethods, 4:25-34; and de Haas et al., 1995, J. Lab. Clin. Med., 126:330-41. "FcR" also includes the neonatal receptor, FcRn, which is responsible for the transfer of maternal IgGs to the fetus (Guyer et al., 1976, J. Immunol., 117:587; and Kim et al., 1994, J. Immunol., 24:249).

A "functional Fc region" possesses at least one effector function of a native sequence Fc region. Exemplary "effector functions" include C1q binding; complement dependent cytotoxicity; Fc receptor binding; antibody-dependent cell-mediated cytotoxicity; phagocytosis; down-regulation of cell surface receptors (e.g. B cell receptor), etc. Such effector functions generally require the Fe region to be combined with a binding domain (e.g. an antibody variable domain) and can be assessed using various assays known in the art for evaluating such antibody effector functions.

A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification, yet retains at least one effector function of the native sequence Fc region. Preferably, the variant Fe region has at least one amino acid substitution compared to a native sequence Fc region or to the Fc region of a parent polypeptide, e.g. from about one to about ten amino acid substitutions, and preferably, from about one to about five amino acid substitutions in a native sequence Fc region or in the Fe region of the parent polypeptide. The variant Fc region herein will preferably possess at least about 80% sequence identity with a native sequence Fc region and/or with an Fc region of a parent polypeptide, and most preferably, at least about 90% sequence identity therewith, more preferably, at least about 95%, at least about 96%, at least about 97%, at least about 98%, at least about 99% sequence identity therewith.

As used herein, "treatment" is an approach for obtaining beneficial or desired clinical results.

As used herein, "IL-6 and/or VEGF related disorders" include, for example, ocular disorders and systemic disorders. Ocular disorders include ocular disorders such as the ophthalmic inflammatory disease scleritis, non-proliferative diabetic retinopathy, proliferative diabetic retinopathy, diabetic macular edema, prevention of diabetic macular edema, prevention of proliferative diabetic retinopathy, wet age-related macular degeneration, prevention of wet age-related macular degeneration, dry age-related macular degeneration, venous, arterial or other blockage of the ocular and or retinal blood vessels with or without retinal edema, anterior and posterior uveitis, uveitic macular edema, and intraocular tumors. IL-6 related disorders also include disorders where there is an elevated level of IL-6 activity due to IL-6 interacting with IL-6R or soluble IL-6R (sIL-6R). In some embodiments, any one or more of the fusion proteins provided herein and/or any one or more of the conjugates provided herein can be used for treatment or prevention of any one or more of the IL-6 and/or VEGF related disorders. In some embodiments, the disorders include systemic diseases that affect the eye such as Grave's disease or neuromyelitis optica, or systemic diseases that do not affect the eye such as multiple sclerosis, rheumatoid arthritis. In some embodiments, the disorders include cytokine release syndrome following CAR-T or similar immune-oncology therapeutics.

Additionally, anti-IL6 molecules abrogate the induction of IL-6 expression observed following treatment with anti-PD-1/PD-L1 molecules (Tsukamoto et al, Cancer Res; 2018 78(17); 5011-22). It has also been shown that VEGF signaling blockade can improve anti-PD-L1 treatment (Allen et al, Sci Transl Med Apr. 12, 2017: 9(385)). Thus, these dual inhibitors can be used in combination with PD-1/PDL-1 modulators and/or other immune checkpoint inhibitors, to synergistically treat cancer. Other disorders can include cerebral edema in glioblastoma where anti-IL6 therapy may show additional benefits to anti-VEGF treatments. Other disorders include those with solid tumors.

As used herein, "Ameliorating" means a lessening or improvement of one or more symptoms as compared to not administering an IL-6 antibody, IL-6 antibody-VEGF Trap fusion, conjugate of IL-6 antibody, and/or conjugate of IL-6 antibody-VEGF Trap fusion. "Ameliorating" also includes shortening or reduction in duration of a symptom.

As used herein, "VEGF Trap" or similar term denotes the VEGF binding domains (VEGFR1 domain 2, VEGFR2 domain 3). This fragment allows for the protein to work as a VEGF trap, preventing VEGF from binding to cellularly expressed VEGF receptors. An example of this sequence can be found in Table 10. In some embodiments, the VEGF Trap only includes VEGFR1 domain 2, VEGFR2 domain 3. Various embodiments of Trap proteins are known in the art and can be found, for example in U.S. Pub. No. 20150376271, the entirety of which, with respect to various VEGF Trap embodiments (which are VEGFR proteins or fragments thereof) and fusions thereof, is incorporated herein by reference. In some embodiments, the term "VEGF Trap" or similar term refers to a full length extracellular region or any portion thereof, or combination of portions from different VEGF receptors that can antagonize signaling between at least one VEGF and VEGFR.

Figure 6:
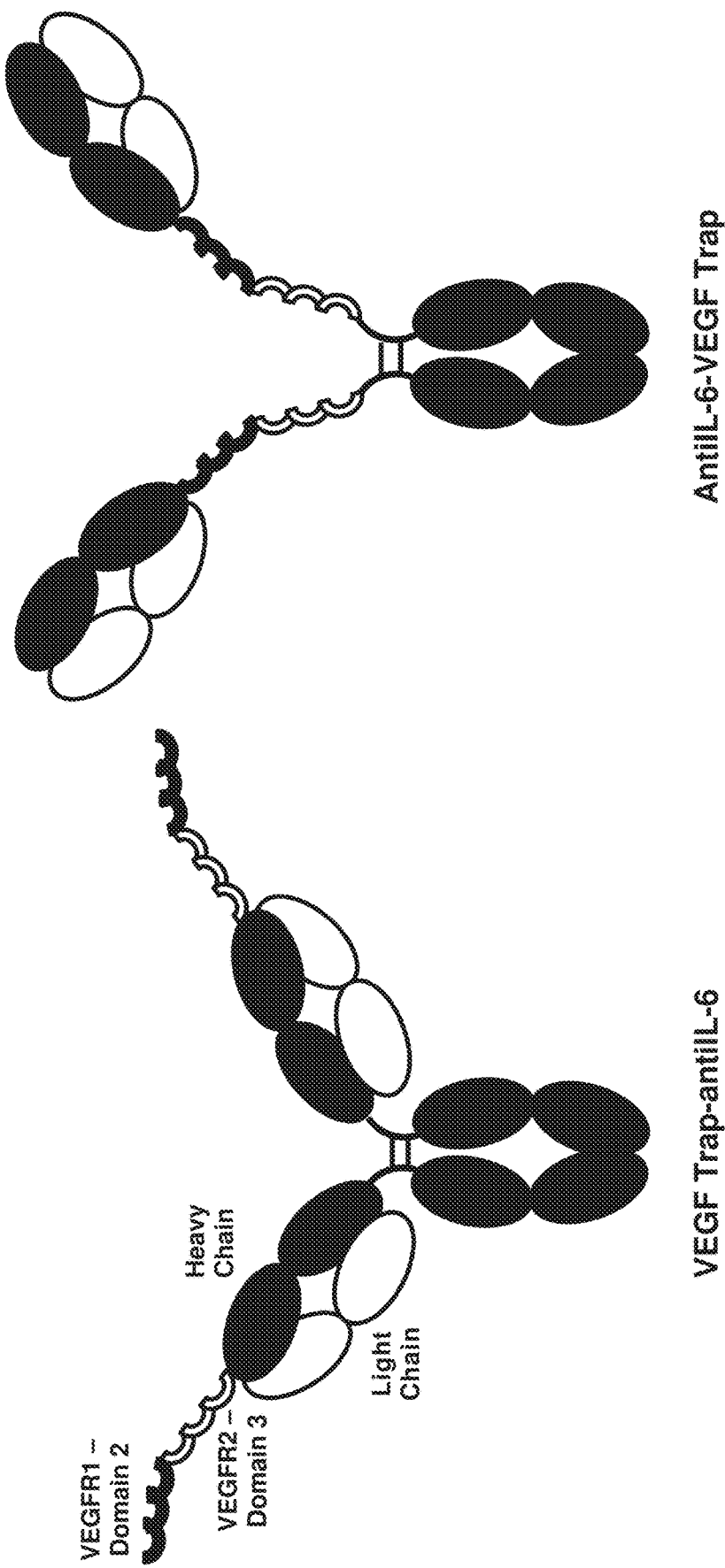
FIG. 6 depicts some embodiments of an IL-6-VEGF Trap fusion protein. The VEGF Trap domains are positioned at either at the N-terminus immediately preceding the variable domain (left) or positioned between the Fab region and the hinge region of the antibody (right).

As used herein, "IL-6 antibody-VEGF Trap fusion", "IL-6 antibody-VEGF Trap", "Ab IL-6-VEGF Trap", "AntiIL-6-VEGF Trap", "VEGFR-AntiIL6", "VEGFR-AntiIL-6", "VEGF Trap-anti-IL6 Antibody Fusion (TAF)", "VEGF Trap-IL6", "VEGFR IL-6", "IL6-VEGFR" or similar term or inverse terms (e.g. "VEGF Trap-IL-6 Ab," "VEGF Trap-IL-6 antibody fusion," etc.) denote the fusion between the IL-6 antibody and the VEGF Trap. Embodiments are depicted in FIG. 6. When used generically, the order of the two terms can be swapped. When used specifically, the order of the two terms denotes the relative position of the components in the construct. the term "Ab-Trap", "IL-6 Ab-VEGF Trap" "Ab IL-6 VEGF Trap" or "Ab IL-6-Trap" or "antiIL-6 VEGF Trap", "Trap-Ab", AntiIL-6-VEGFR, AntiIL6-VEGFR or other similar term or inverse terms (e.g. "VEGF Trap-IL-6 Ab," "VEGF Trap-IL-6 antibody fusion," etc.) denotes the arrangement of the Ab fused to the relevant domains of a VEGF binding protein so as to provide a VEGF trap. As noted above, this section of the VEGF binding protein is one that prevents VEGF from binding to VEGF receptors. As described herein, the arrangement (ordering) of the Trap and antibody sections can be varied. Thus, unless denoted otherwise explicitly or by context, the phrases used herein regarding Ab-Trap (or Il-6/VEGF Trap, etc.) fusions, denote all disclosed embodiments for the positioning of the antibody and the Trap. Thus, unless explained otherwise, the phrase Ab-Trap (or Il-6/VEGF Trap, etc.), denotes the left embodiment in FIG. 6, and the right embodiment in FIG. 6, and both embodiments in FIG. 6. Thus, the general language is denoted as disclosing all three options for convenience. If the orientation is specifically denoted, it can be denoted, for example, by stating that the "arrangement" can be one of: Trap-Ab, Trap IL-6 Ab, VEGF Trap Ab IL-6, VEGF Trap Ab IL6. Similarly, it will be appreciated that the context of some of the present Examples specific orientations or arrangements of the molecules, which are denoted by the context of the Example. Both arrangements (in the alternative and combined) are explicitly contemplated for all discussions of fusion proteins provided herein. In addition, due to the ordering, it is appreciated that the phrase IL-6 Ab, when used in the context of the fusion protein, includes both the option where the antibody is contiguous, FIG. 6, left-hand side, and where the TRAP is positioned "within" the Ab (FIG. 6 right-hand side). Again, the term "Ab" or "antibody", when used in the fusion protein context (or other similar term), encompasses all three options (left-hand side of FIG. 6, right-hand side of FIG. 6, and both options), unless otherwise noted. In some embodiments, the VEGF Trap is fused to IL-6 in one of the following manners: to an N-terminal end of a heavy chain comprising IL-6 VH; or between a hinge region and after a CH1 domain of a heavy chain comprising IL-6 VH. There is no difference between the designations of Ab, antibody, "anti" or other similar term when used in a name to designate and antibody or fragment thereof. There is no difference between the designations of "11-6" or "IL6" or "IL-6". As used herein, when referencing a fusion construct with IL-6, the terms "VEGF", "VEGFR", "VEGF Trap", "VEGFR Trap" are used interchangeably. The terms can have different meanings when used separately from the IL-6 fusion arrangement, which will depend upon the context of the term in question.

As used herein, the term "biopolymer" denotes that a polymer has been linked to the protein of interest. The term can also be described as the "conjugated" form of the protein. This can be done for all of the proteins described herein. Thus, IL-6 Ab biopolymers and IL-6 antibody-VEGF Trap biopolymers are contemplated for all such IL-6 Ab and IL-6 antibody-VEGF Trap provided herein. In addition, VEGF Trap biopolymers are also provided.

As used herein, "Antagonistic antibody" denotes an antibody that blocks one or more function or activity of the molecule that the antibody binds to.

As used herein, an "effective dosage" or "effective amount" of drug, compound, or pharmaceutical composition is an amount sufficient to effect any one or more beneficial or desired results. In more specific aspects, an effective amount prevents, alleviates or ameliorates symptoms of disease, and/or prolongs the survival of the subject being treated. For prophylactic use, beneficial or desired results include eliminating or reducing the risk, lessening the severity, or delaying the outset of the disease, including biochemical, histological and/or behavioral symptoms of the disease, its complications and intermediate pathological phenotypes presenting during development of the disease. For therapeutic use, beneficial or desired results include clinical results such as reducing one or more symptoms of a disease such as, for example, AMD including, for example without limitation, dry AMD and wet AMD, decreasing the dose of other medications required to treat the disease, enhancing the effect of another medication, and/or delaying the progression of AMD in patients. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

Anti-IL-6 antibodies are administered in an effective regime meaning a dosage, route of administration and frequency of administration that delays the onset, reduces the severity, inhibits further deterioration, and/or ameliorates at least one sign or symptom of a disorder. If a patient is already suffering from a disorder, the regime can be referred to as a therapeutically effective regime. If the patient is at elevated risk of the disorder relative to the general population but is not yet experiencing symptoms, the regime can be referred to as a prophylactically effective regime. In some instances, therapeutic or prophylactic efficacy can be observed in an individual patient relative to historical controls or past experience in the same patient. In other instances, therapeutic or prophylactic efficacy can be demonstrated in a preclinical or clinical trial in a population of treated patients relative to a control population of untreated patients.

Anti-IL-6-VEGF Traps are administered in an effective regime meaning a dosage, route of administration and frequency of administration that delays the onset, reduces the severity, inhibits further deterioration, and/or ameliorates at least one sign or symptom of a disorder. If a patient is already suffering from a disorder, the regime can be referred to as a therapeutically effective regime. If the patient is at elevated risk of the disorder relative to the general population but is not yet experiencing symptoms, the regime can be referred to as a prophylactically effective regime. In some instances, therapeutic or prophylactic efficacy can be observed in an individual patient relative to historical controls or past experience in the same patient. In other instances, therapeutic or prophylactic efficacy can be demonstrated in a preclinical or clinical trial in a population of treated patients relative to a control population of untreated patients.

The "biological half-life" of a substance is a pharmacokinetic parameter which specifies the time required for one half of the substance to be removed from an organism following introduction of the substance into the organism.

The term "preventing" or "prevent" refers to (a) keeping a disorder from occurring (b) delaying the onset of a disorder or onset of symptoms of a disorder, or (c) slowing the progression of an existing condition. Unless denoted otherwise, "preventing" does not require the absolute prohibition of the event from occurring.

An "individual" or a "subject" is a mammal or bird, more preferably, a human. Mammals also include, but are not limited to, farm animals (e.g., cows, pigs, horses, chickens, etc.), sport animals, pets, primates, horses, dogs, cats, mice and rats.

As used herein, "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, "pharmaceutically acceptable carrier" or "pharmaceutical acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, various types of wetting agents, detergents such as polysorbate 20 to prevent aggregation, and sugars such as sucrose as cryoprotectant. Preferred diluents for aerosol or parenteral administration are phosphate buffered saline (PBS) or normal (0.9%) saline.

Compositions comprising such carriers are formulated by well-known conventional methods (see, for example, Remington's Pharmaceutical Sciences, 18th edition, A. Gennaro, ed., Mack Publishing Co., Easton, PA, 1990; and Remington, The Science and Practice of Pharmacy 20th Ed. Mack Publishing, 2000).

The term "$k_{on}$", as used herein, refers to the rate constant for association of an antibody (or bioconjugate) to an antigen. Specifically, the rate constants ($k_{on}$ and $k_{off}$) and equilibrium dissociation constants are measured using full-length antibodies and/or Fab antibody fragments (i.e. univalent) and IL-6.

The term "$k_{off}$", as used herein, refers to the rate constant for dissociation of an antibody (or bioconjugate) from the antibody/antigen complex.

The term "$K_D$", as used herein, refers to the equilibrium dissociation constant of an antibody-antigen (or bioconjugate-antigen) interaction.

Reference to "about" a value or parameter herein includes (and describes) embodiments that are directed to that value or parameter per se. For example, description referring to "about X" includes description of "X." Numeric ranges are inclusive of the numbers defining the range.

The term "patient" includes human and other subjects (including mammals) that receive either prophylactic or therapeutic treatment.

For purposes of classifying amino acids substitutions as conservative or nonconservative, amino acids are grouped as follows: Group I (hydrophobic side chains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Percentage sequence identities are determined with antibody sequences maximally aligned by the Kabat numbering convention for a variable region or EU numbering for a constant region. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage. Sequence identities of other sequences can be determined by aligning sequences using algorithms, such as BESTFIT, FASTA, and TFASTA in the Wisconsin Genetics Software Package Release 7.0, Genetics Computer Group, 575 Science Dr., Madison, WI, using default gap parameters, or by inspection, and the best alignment (i.e., resulting in the highest percentage of sequence similarity over a comparison window). Percentage of sequence identity is calculated by comparing two optimally aligned sequences over a window of comparison, determining the number of positions at which the identical residues occurs in both sequences to yield the number of matched positions, dividing the number of matched positions by the total number of positions in the window of comparison (i.e., the window size), and multiplying the result by 100 to yield the percentage of sequence identity.

The term "antibody-dependent cellular cytotoxicity", or ADCC, is a mechanism for inducing cell death that depends upon the interaction of antibody-coated target cells (i.e., cells with bound antibody) with immune cells possessing lytic activity (also referred to as effector cells). Such effector cells include natural killer cells, monocytes/macrophages and neutrophils. ADCC is triggered by interactions between the Fc region of an antibody bound to a cell and Fcγ receptors, particularly FcγRI and FcγRIII, on immune effector cells such as neutrophils, macrophages and natural killer cells. The target cell is eliminated by phagocytosis or lysis, depending on the type of mediating effector cell. Death of the antibody-coated target cell occurs as a result of effector cell activity.

A humanized antibody is a genetically engineered antibody in which the CDRs from a non-human "donor" antibody are grafted into a human "acceptor" antibody sequences (see, e.g., Queen, U.S. Pat. Nos. 5,530,101 and 5,585,089; Winter, U.S. Pat. No. 5,225,539, Carter, U.S. Pat. No. 6,407,213, Adair, U.S. Pat. No. 5,859,205, 6,881,557, Foote, U.S. Pat. No. 6,881,557). The acceptor antibody sequences can be, for example, a mature human antibody sequence, a composite of such sequences, a consensus sequence of human antibody sequences, or a germline region sequence. Thus, a humanized antibody is an antibody having some or all CDRs entirely or substantially from a donor antibody and variable region framework sequences and constant regions, if present, entirely or substantially from human antibody sequences. Similarly a humanized heavy chain has at least one, two and usually all three CDRs entirely or substantially from a donor antibody heavy chain, and a heavy chain variable region framework sequence and heavy chain constant region, if present, substantially from human heavy chain variable region framework and constant region sequences. Similarly a humanized light chain has at least one, two and usually all three CDRs entirely or substantially from a donor antibody light chain, and a light chain variable region framework sequence and light chain constant region, if present, substantially from human light chain variable region framework and constant region sequences. Other than nanobodies and dAbs, a humanized antibody comprises a humanized heavy chain and a humanized light chain. A CDR in a humanized antibody is substantially from a corresponding CDR in a non-human antibody when at least 85%, 90%, 95% or 100% of corresponding residues (as defined by Kabat) are identical between the respective CDRs. The variable region framework sequences of an antibody chain or the constant region of an antibody chain are substantially from a human variable region framework sequence or human constant region respectively when at least 85, 90, 95 or 100% of corresponding residues defined by Kabat are identical.

Although humanized antibodies often incorporate all six CDRs (preferably as defined by Kabat) from a mouse antibody, they can also be made with less than all CDRs (e.g., at least 3, 4, or 5 CDRs from a mouse antibody) (e.g., Pascalis et al, J. Immunol. 169:3076, 2002; Vajdos et al., Journal of Molecular Biology, 320: 415-428, 2002; Iwahashi et al., Mol. Immunol. 36: 1079-1091, 1999; Tamura et al, Journal of Immunology, 164: 1432-1441, 2000).

A chimeric antibody is an antibody in which the mature variable regions of light and heavy chains of a non-human antibody (e.g., a mouse) are combined with human light and heavy chain constant regions. Such antibodies substantially or entirely retain the binding specificity of the mouse antibody and are about two-thirds human sequence.

A veneered antibody is a type of humanized antibody that retains some and usually all of the CDRs and some of the non-human variable region framework residues of a non-human antibody but replaces other variable region framework residues that may contribute to B- or T-cell epitopes, for example exposed residues (Padlan, Mol. Immunol. 28:489, 1991) with residues from the corresponding positions of a human antibody sequence. The result is an antibody in which the CDRs are entirely or substantially from a non-human antibody and the variable region frameworks of the non-human antibody are made more human-like by the substitutions. A human antibody can be isolated from a human, or otherwise result from expression of human immunoglobulin genes (e.g., in a transgenic mouse, in vitro or by phage display). Methods for producing human antibodies include the trioma method of Oestberg et al., Hybridoma 2:361-367 (1983); Oestberg, U.S. Pat. No. 4,634,664; and Engleman et al., U.S. Pat. No. 4,634,666, use of transgenic mice including human immunoglobulin genes (see, e.g., Lonberg et al., WO93/12227 (1993); U.S. Pat. Nos. 5,877,397, 5,874,299, 5,814,318, 5,789,650, 5,770,429, 5,661,016, 5,633,425, 5,625,126, 5,569,825, 5,545,806, Nature 148, 1547-1553 (1994), Nature Biotechnology 14, 826 (1996), Kucherlapati, WO 91/10741 (1991) and phage display methods (see, e.g. Dower et al., WO 91/17271 and McCafferty et al., WO 92/01047, U.S. Pat. Nos. 5,877,218, 5,871,907, 5,858,657, 5,837,242, 5,733,743 and 5,565,332.

A "polymer" is a molecule composed of many repeating subunits. The subunits, also sometimes referred to as "monomers" can be the same or different. There are both natural and synthetic polymers. DNA, protein and complex carbohydrates are examples of natural polymers. Poly-styrene and poly-acrylamide are examples of synthetic polymers. A polymer composed of repeating units of a single monomer is called a homopolymer. A polymer composed of two or more monomers is called a copolymer or sometimes a heteropolymer. A copolymer in which certain monomer types are clustered together are sometimes called block copolymers. Polymers can be linear or branched. When the polymer is branched, polymer chains having a common origin are sometimes referred to as a polymer arm(s).

An "initiator" is a compound capable of serving as a substrate on which one or more polymerizations can take place using monomers or comonomers as described herein. The polymerization can be a conventional free radical polymerization or preferably a controlled/"living" radical polymerization, such as Atom Transfer Radical Polymerization (ATRP), Reversible Addition-Fragmentation-Termination (RAFT) polymerization or nitroxide mediated polymerization (NMP). The polymerization can be a "pseudo" controlled polymerization, such as degenerative transfer. Initiators suitable for ATRP contain one or more labile bonds which can be homolytically cleaved to form an initiator fragment, I, being a radical capable of initiating a radical polymerization, and a radical scavenger, I', which reacts with the radical of the growing polymer chain to reversibly terminate the polymerization. The radical scavenger I' is typically a halogen, but can also be an organic moiety, such as a nitrile. In some embodiments of the present invention, the initiator contains one or more 2-bromoisobutyrate groups as sites for polymerization via ATRP.

A "chemical linker" refers to a chemical moiety that links two groups together, such as a half-life extending moiety and a protein. The linker can be cleavable or non-cleavable. Cleavable linkers can be hydrolysable, enzymatically cleavable, pH sensitive, photolabile, or disulfide linkers, among others. Other linkers include homobifunctional and hetero-bifunctional linkers. A "linking group" is a functional group capable of forming a covalent linkage consisting of one or more bonds to a bioactive agent. Non-limiting examples include those illustrated in Table 1 of WO2013059137 (incorporated by reference).

The term "reactive group" refers to a group that is capable of reacting with another chemical group to form a covalent bond, i.e. is covalently reactive under suitable reaction conditions, and generally represents a point of attachment for another substance. The reactive group is a moiety, such as maleimide or succinimidyl ester, is capable of chemically reacting with a functional group on a different moiety to form a covalent linkage. Reactive groups generally include nucleophiles, electrophiles and photoactivatable groups.

As used herein, "phosphorylcholine," also denoted as "PC," refers to the following:

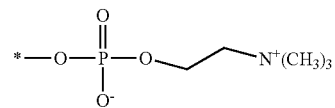

where * denotes the point of attachment. The phosphorylcholine is a zwitterionic group and includes salts (such as inner salts), and protonated and deprotonated forms thereof.

As used herein, "phosphorylcholine-based polymer" is a polymer that contains phosphorylcholine. "Zwitterion containing polymer" refers to a polymer that contains a zwitterion.

Poly(acryloyloxyethyl phosphorylcholine) containing polymer refers to a polymer containing 2-(acryloyloxy)ethyl-2-(trimethylammonium)ethyl phosphate as monomer.

Poly(methacryloyloxyethyl phosphorylcholine) containing polymer refers to a polymer containing 2-(methacryloyloxy)ethyl-2-(trimethylammonium)ethyl phosphate as monomer.

As used herein, "molecular weight" in the context of the polymer can be expressed as either a number average molecular weight, or a weight average molecular weight or a peak molecular weight. Unless otherwise indicated, all references to molecular weight herein refer to the peak molecular weight. These molecular weight determinations, number average (Mn), weight average (Mw) and peak (Mp), can be measured using size exclusion chromatography or other liquid chromatography techniques. Other methods for measuring molecular weight values can also be used, such as the use of end-group analysis or the measurement of colligative properties (e.g., freezing-point depression, boiling-point elevation, or osmotic pressure) to determine number average molecular weight, or the use of light scattering techniques, ultracentrifugation or viscometry to determine weight average molecular weight. In a preferred embodiment of the present invention, the molecular weight is measured by SEC-MALS (size exclusion chromatography—multi angle light scattering). The polymeric reagents of the invention are typically polydisperse (i.e., number average molecular weight and weight average molecular weight of the polymers are not equal). The Poly Dispersity Index (PDI) provides a measure for the dispersity of polymers in a mixture. PDI is given by the formula Mw/Mn. In this regard a homogenous protein will have a PDI of 1.0 (Mn is the same as Mw). Typically, the PDI for polymers will be above 1.0. Polymers in accordance with the present invention preferably have relatively low polydispersity (PDI) values of, for example, less than about 1.5, as judged, for example, by SEC-MALS. In other embodiments, the polydispersities (PDI) are more preferably in the range of about 1.4 to about 1.2, still more preferably less than about 1.15, and still more preferably less than about 1.10, yet still more preferably less than about 1.05, and most preferably less than about 1.03.

As used herein, "protected," "protected form," "protecting group" and "protective group" refer to the presence of a group (i.e., the protecting group) that prevents or blocks reaction of a particular chemically reactive functional group in a molecule under certain reaction conditions. Protecting groups vary depending upon the type of chemically reactive group being protected as well as the reaction conditions to be employed and the presence of additional reactive or protecting groups in the molecule, if any. Suitable protecting groups include those such as found in the treatise by Greene et al., "Protective Groups In Organic Synthesis," $3^{rd}$ Edition, John Wiley and Sons, Inc., New York, 1999.

As used herein, "alkyl" refers to a straight or branched, saturated, aliphatic radical having the number of carbon atoms indicated. For example, $C_1$-$C_6$ alkyl includes, but is not limited to, methyl, ethyl, propyl, isopropyl, butyl, isobutyl, see-butyl, tert-butyl, pentyl, isopentyl, hexyl, etc. Other alkyl groups include, but are not limited to heptyl, octyl, nonyl, decyl, etc. Alkyl can include any number of carbons, such as 1-2, 1-3, 1-4, 1-5, 1-6, 1-7, 1-8, 1-9, 1-10, 2-3, 2-4, 2-5, 2-6, 3-4, 3-5, 3-6, 4-5, 4-6 and 5-6 carbons.

The term "lower" referred to above and hereinafter in connection with organic radicals or compounds respectively defines a compound or radical which can be branched or unbranched with up to and including 7, preferably up to and including 4 and (as unbranched) one or two carbon atoms.

As used herein, "alkylene" refers to an alkyl group, as defined above, linking at least two other groups, i.e., a divalent hydrocarbon radical. The two moieties linked to the alkylene can be linked to the same atom or different atoms of the alkylene. For instance, a straight chain alkylene can be the bivalent radical of —(CH$_2$)$_n$—, where n is 1, 2, 3, 4, 5 or 6. Alkylene groups include, but are not limited to, methylene, ethylene, propylene, isopropylene, butylene, isobutylene, sec-butylene, pentylene and hexylene.

Substituents for the alkyl, alkenyl, alkylene, heteroalkyl, heteroalkylene, heteroalkenyl, alkynyl, cycloalkyl, heterocycloalkyl, cycloalkenyl, and heterocycloalkenyl radicals can be one or more of a variety of groups selected from, but not limited to: —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R', —NR"C(O)$_2$R', —NR—C(NR'R"R"')=NR"", —NR—C(NR'R")=NR', —S(O)R', —S(O)$_2$R', —S(O)$_2$NR'R", —NRSO$_2$R', —CN and —NO$_2$ in a number ranging from 1 to (2m'+1), where m' is the total number of carbon atoms in such radical. Each of R', R", R"' and R"" independently refers to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl.

As used herein, "alkoxy" refers to alkyl group attached to an oxygen atom and forms radical —O—R, wherein R is alkyl. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described herein. For example, the alkoxy groups can be substituted with halogens to form a "halo-alkoxy" group.

As used herein, "carboxyalkyl" means an alkyl group (as defined herein) substituted with a carboxy group. The term "carboxycycloalkyl" means an cycloalkyl group (as defined herein) substituted with a carboxy group. The term alkoxyalkyl means an alkyl group (as defined herein) substituted with an alkoxy group. The term "carboxy" employed herein refers to carboxylic acids and their esters.

As used herein, "haloalkyl" refers to alkyl as defined above where some or all of the hydrogen atoms are substituted with halogen atoms. Halogen (halo) preferably represents chloro or fluoro, but may also be bromo or iodo. For example, haloalkyl includes trifluoromethyl, fluoromethyl, 1,2,3,4,5-pentafluoro-phenyl, etc. The term "perfluoro" defines a compound or radical which has all available hydrogens that are replaced with fluorine. For example, perfluorophenyl refers to 1,2,3,4,5-pentafluorophenyl, perfluoromethyl refers to 1,1,1-trifluoromethyl, and perfluoromethoxy refers to 1,1,1-trifluoromethoxy. Haloalkyl can also be referred to as halo-substitute alkyl, such as fluoro-substituted alkyl.

As used herein, "cytokine" in the context of this invention is a member of a group of protein signaling molecules that may participate in cell-cell communication in immune and inflammatory responses. Cytokines are typically small, water-soluble glycoproteins that have a mass of about 8-35 kDa.

As used herein, "cycloalkyl" refers to a saturated mono- or multi-cyclic aliphatic ring system that contains from about 3 to 12, from 3 to 10, from 3 to 7, or from 3 to 6 carbon atoms. When cycloalkyl group is composed of two or more rings, the rings may be joined together with a fused ring or a spiro ring structure. When cycloalkyl group is composed of three or more rings, the rings may also join together forming a bridged ring structure. Monocyclic rings include, for example, cyclopropyl, cyclobutyl, cyclopentyl, cyclohexyl, and cyclooctyl. Bicyclic and polycyclic rings include, for example, bicyclo[1.1.1]pentane, bicylco[2.1.1]heptane, norbornane, decahydronaphthalene and adamantane. For example, $C_{3-8}$ cycloalkyl includes cyclopropyl, cyclobutyl, cyclopentyl, cyclohexyl, cyclooctyl, and norbornane.

As used herein, "endocyclic" refers to an atom or group of atoms which comprise part of a cyclic ring structure.

As used herein, "exocyclic" refers to an atom or group of atoms which are attached but do not define the cyclic ring structure.

As used herein, "cyclic alkyl ether" refers to a 4 or 5 member cyclic alkyl group having 3 or 4 endocyclic carbon atoms and 1 endocyclic oxygen or sulfur atom (e.g., oxetane, thietane, tetrahydrofuran, tetrahydrothiophene); or a 6 to 7 member cyclic alkyl group having 1 or 2 endocyclic oxygen or sulfur atoms (e.g., tetrahydropyran, 1,3-dioxane, 1,4-dioxane, tetrahydrothiopyran, 1,3-dithiane, 1,4-dithiane, 1,4-oxathiane).

As used herein, "alkenyl" refers to either a straight chain or branched hydrocarbon of 2 to 6 carbon atoms, having at least one double bond. Examples of alkenyl groups include, but are not limited to, vinyl, propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can also have from 2 to 3, 2 to 4, 2 to 5, 3 to 4, 3 to 5, 3 to 6, 4 to 5, 4 to 6 and 5 to 6 carbons.

As used herein, "alkenylene" refers to an alkenyl group, as defined above, linking at least two other groups, i.e., a divalent hydrocarbon radical. The two moieties linked to the alkenylene can be linked to the same atom or different atoms of the alkenylene. Alkenylene groups include, but are not limited to, ethenylene, propenylene, isopropenylene, butenylene, isobutenylene, sec-butenylene, pentenylene and hexenylene.

As used herein, "alkynyl" refers to either a straight chain or branched hydrocarbon of 2 to 6 carbon atoms, having at least one triple bond. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can also have from 2 to 3, 2 to 4, 2 to 5, 3 to 4, 3 to 5, 3 to 6, 4 to 5, 4 to 6 and 5 to 6 carbons.

As used herein, "alkynylene" refers to an alkynyl group, as defined above, linking at least two other groups, i.e., a divalent hydrocarbon radical. The two moieties linked to the alkynylene can be linked to the same atom or different atoms of the alkynylene. Alkynylene groups include, but are not limited to, ethynylene, propynylene, butynylene, sec-butynylene, pentynylene and hexynylene.

As used herein, "cycloalkylene" refers to a cycloalkyl group, as defined above, linking at least two other groups, i.e., a divalent hydrocarbon radical. The two moieties linked to the cycloalkylene can be linked to the same atom or different atoms of the cycloalkylene. Cycloalkylene groups include, but are not limited to, cyclopropylene, cyclobutylene, cyclopentylene, cyclohexylene, and cyclooctylene.

As used herein, "heterocycloalkyl" refers to a ring system having from 3 ring members to about 20 ring members and from 1 to about 5 heteroatoms such as N, O and S. Additional heteroatoms can also be useful, including, but not limited to, B, Al, Si and P. The heteroatoms can also be oxidized, such as, but not limited to, —S(O)— and —S(O)$_2$—. For example, heterocycle includes, but is not limited to, tetrahydrofuranyl, tetrahydrothiophenyl, morpholino, pyrrolidinyl, pyrrolinyl, imidazolidinyl, imidazolinyl, pyrazolidinyl, pyrazolinyl, piperazinyl, piperidinyl, indolinyl, quinuclidinyl and 1,4-dioxa-8-aza-spiro[4.5]dec-8-yl.

As used herein, "heterocycloalkylene" refers to a heterocyclalkyl group, as defined above, linking at least two other groups. The two moieties linked to the heterocycloalkylene can be linked to the same atom or different atoms of the heterocycloalkylene.

As used herein, "aryl" refers to a monocyclic or multicyclic (e.g., fused bicyclic, tricyclic or greater) aromatic ring assembly containing 6 to 16 carbon atoms. For example, aryl may be phenyl, benzyl or naphthyl, preferably phenyl. Aryl groups can be mono-, di- or tri-substituted by one, two or three radicals selected from alkyl, alkoxy, aryl, hydroxy, halogen, cyano, amino, amino-alkyl, trifluoromethyl, alkylenedioxy and oxy-$C_2$-$C_3$-alkylene; all of which are optionally further substituted, for instance as hereinbefore defined; or 1- or 2-naphthyl; or 1- or 2-phenanthrenyl. Alkylenedioxy is a divalent substitute attached to two adjacent carbon atoms of phenyl, e.g. methylenedioxy or ethylenedioxy. Oxy-$C_2$-$C_3$-alkylene is also a divalent substituent attached to two adjacent carbon atoms of phenyl, e.g. oxyethylene or oxypropylene. An example for oxy-$C_2$-$C_3$-alkylene-phenyl is 2,3-dihydrobenzofuran-5-yl.

Preferred as aryl is naphthyl, phenyl or phenyl mono- or disubstituted by alkoxy, phenyl, halogen, alkyl or trifluoromethyl, especially phenyl or phenyl-mono- or disubstituted by alkoxy, halogen or trifluoromethyl, and in particular phenyl.

Examples of substituted phenyl groups as R are, e.g. 4-chlorophen-1-yl, 3,4-dichlorophen-1-yl, 4-methoxyphen-1-yl, 4-methylphen-1-yl, 4-aminomethylphen-1-yl, 4-methoxyethylaminomethylphen-1-yl, 4-hydroxyethylaminomethylphen-1-yl, 4-hydroxyethyl-(methyl)-aminomethylphen-1-yl, 3-aminomethylphen-1-yl, 4-N-acetylaminomethylphen-1-yl, 4-aminophen-1-yl, 3-aminophen-1-yl, 2-aminophen-1-yl, 4-phenyl-phen-1-yl, 4-(imidazol-1-yl)-phenyl, 4-(imidazol-1-ylmethyl)-phen-1-yl, 4-(morpholin-1-yl)-phen-1-yl, 4-(morpholin-1-ylmethyl)-phen-1-yl, 4-(2-methoxyethylaminomethyl)-phen-1-yl and 4-(pyrrolidin-1-ylmethyl)-phen-1-yl, 4-(thiophenyl)-phen-1-yl, 4-(3-thiophenyl)-phen-1-yl, 4-(4-methylpiperazin-1-yl)-phen-1-yl, and 4-(piperidinyl)-phenyl and 4-(pyridinyl)-phenyl optionally substituted in the heterocyclic ring.

As used herein, "arylene" refers to an aryl group, as defined above, linking at least two other groups. The two moieties linked to the arylene are linked to different atoms of the arylene. Arylene groups include, but are not limited to, phenylene.

As used herein, "arylene-oxy" refers to an arylene group, as defined above, where one of the moieties linked to the arylene is linked through an oxygen atom. Arylene-oxy groups include, but are not limited to, phenylene-oxy.

Similarly, substituents for the aryl and heteroaryl groups are varied and are selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R''', —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro($C_1$-$C_4$)alkoxy, and perfluoro($C_1$-$C_4$)alkyl, in a number ranging from zero to the total number of open valences on the aromatic ring system; and where R', R" and R''' are independently selected from hydrogen, ($C_1$-$C_5$)alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted ($C_1$-$C_6$)alkyl.

As used herein, "heteroaryl" refers to a monocyclic or fused bicyclic or tricyclic aromatic ring assembly containing 5 to 16 ring atoms, where from 1 to 4 of the ring atoms are a heteroatom each N, O or S. For example, heteroaryl includes pyridyl, indolyl, indazolyl, quinoxalinyl, quinolinyl, isoquinolinyl, benzothienyl, benzofuranyl, furanyl, pyrrolyl, thiazolyl, benzothiazolyl, oxazolyl, isoxazolyl, triazolyl, tetrazolyl, pyrazolyl, imidazolyl, thienyl, or any other radicals substituted, especially mono- or di-substituted, by e.g. alkyl, nitro or halogen. Pyridyl represents 2-, 3- or 4-pyridyl, advantageously 2- or 3-pyridyl. Thienyl represents 2- or 3-thienyl. Quinolinyl represents preferably 2-, 3- or 4-quinolinyl. Isoquinolinyl represents preferably 1-, 3- or 4-isoquinolinyl. Benzopyranyl, benzothiopyranyl represents preferably 3-benzopyranyl or 3-benzothiopyranyl, respectively. Thiazolyl represents preferably 2- or 4-thiazolyl, and most preferred, 4-thiazolyl. Triazolyl is preferably 1-, 2- or 5-(1,2,4-triazolyl). Tetrazolyl is preferably 5-tetrazolyl.

Preferably, heteroaryl is pyridyl, indolyl, quinolinyl, pyrrolyl, thiazolyl, isoxazolyl, triazolyl, tetrazolyl, pyrazolyl, imidazolyl, thienyl, furanyl, benzothiazolyl, benzofuranyl, isoquinolinyl, benzothienyl, oxazolyl, indazolyl, or any of the radicals substituted, especially mono- or di-substituted.

The term "heteroalkyl" refers to an alkyl group having from 1 to 3 heteroatoms such as N, O and S. Additional heteroatoms can also be useful, including, but not limited to, B, Al, Si and P. The heteroatoms can also be oxidized, such as, but not limited to, —S(O)— and —S(O)$_2$—. For example, heteroalkyl can include ethers, thioethers, alkylamines and alkyl-thiols.

The term "heteroalkylene" refers to a heteroalkyl group, as defined above, linking at least two other groups. The two moieties linked to the heteroalkylene can be linked to the same atom or different atoms of the heteroalkylene.

As used herein, "electrophile" refers to an ion or atom or collection of atoms, which may be ionic, having an electrophilic center, i.e., a center that is electron seeking, capable of reacting with a nucleophile. An electrophile (or electrophilic reagent) is a reagent that forms a bond to its reaction partner (the nucleophile) by accepting both bonding electrons from that reaction partner.

As used herein, "nucleophile" refers to an ion or atom or collection of atoms, which may be ionic, having a nucleophilic center, i.e., a center that is seeking an electrophilic center or capable of reacting with an electrophile. A nucleophile (or nucleophilic reagent) is a reagent that forms a bond to its reaction partner (the electrophile) by donating both bonding electrons. A "nucleophilic group" refers to a nucleophile after it has reacted with a reactive group. Non limiting examples include amino, hydroxyl, alkoxy, haloalkoxy and the like.

As used herein, "maleimido" refers to a pyrrole-2,5-dione-1-yl group having the structure:

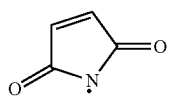

which upon reaction with a sulfhydryl (e.g., a thio alkyl) forms an —S-maleimido group having the structure

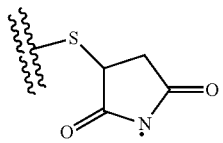

where "•" indicates the point of attachment for the maleimido group and "⚡" indicates the point of attachment of the sulfur atom the thiol to the remainder of the original sulfhydryl bearing group.

For the purpose of this disclosure, "naturally occurring amino acids" found in proteins and polypeptides are L-alanine, L-arginine, L-asparagine, L-aspartic acid, L-cysteine, L-glutamine, L-glutamic acid, L-glycine, L-histidine, L-isoleucine, L-leucine, L-lysine, L-methionine, L-phenylalanine, L-proline, L-serine, L-threonine, L-tryptophan, L-tyrosine, and or L-valine. "Non-naturally occurring amino acids" found in proteins are any amino acid other than those recited as naturally occurring amino acids. Non-naturally occurring amino acids include, without limitation, the D isomers of the naturally occurring amino acids, and mixtures of D and L isomers of the naturally occurring amino acids. Other amino acids, such as 4-hydroxyproline, desmosine, isodesmosine, 5-hydroxylysine, epsilon-N-methyllysine, 3-methylhistidine, although found in naturally occurring proteins, are considered to be non-naturally occurring amino acids found in proteins for the purpose of this disclosure as they are generally introduced by means other than ribosomal translation of mRNA.

As used herein, "linear" in reference to the geometry, architecture or overall structure of a polymer, refers to polymer having a single polymer arm.

As used herein, "branched," in reference to the geometry, architecture or overall structure of a polymer, refers to a polymer having 2 or more polymer "arms" extending from a core structure contained within an initiator. The initiator may be employed in an atom transfer radical polymerization (ATRP) reaction. A branched polymer may possess 2 polymer chains (arms), 3 polymer arms, 4 polymer arms, 5 polymer arms, 6 polymer arms, 7 polymer arms, 8 polymer arms, 9 polymer arms or more. Each polymer arm extends from a polymer initiation site. Each polymer initiation site is capable of being a site for the growth of a polymer chain by the addition of monomers. For example and not by way of limitation, using ATRP, the site of polymer initiation on an initiator is typically an organic halide undergoing a reversible redox process catalyzed by a transition metal compound such as cuprous halide. Preferably, the halide is a bromine.

As used herein, "pharmaceutically acceptable excipient" refer to an excipient that can be included in the compositions of the invention and that causes no significant adverse toxicological effect on the patient and is approved or approvable by the FDA for therapeutic use, particularly in humans. Non-limiting examples of pharmaceutically acceptable excipients include water, NaCl, normal saline solutions, lactated Ringer's, normal sucrose, normal glucose and the like.

Figure 2B:
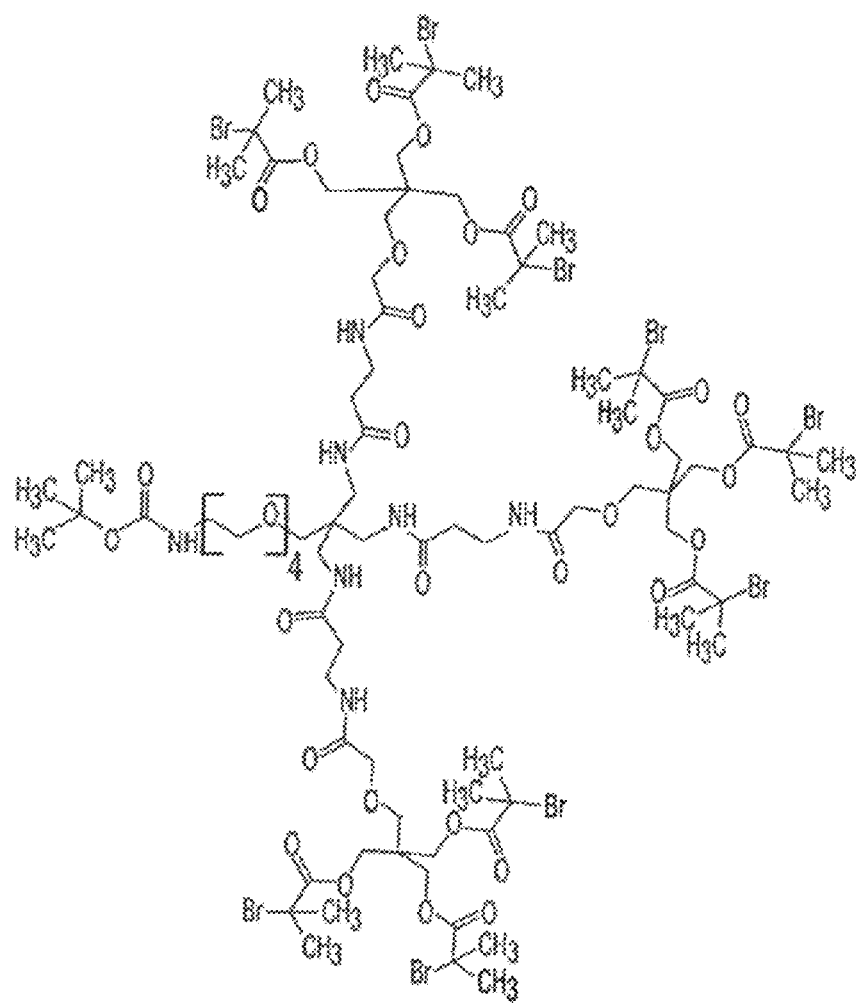
FIG. 2B shows Compound K.
Figure 2D:
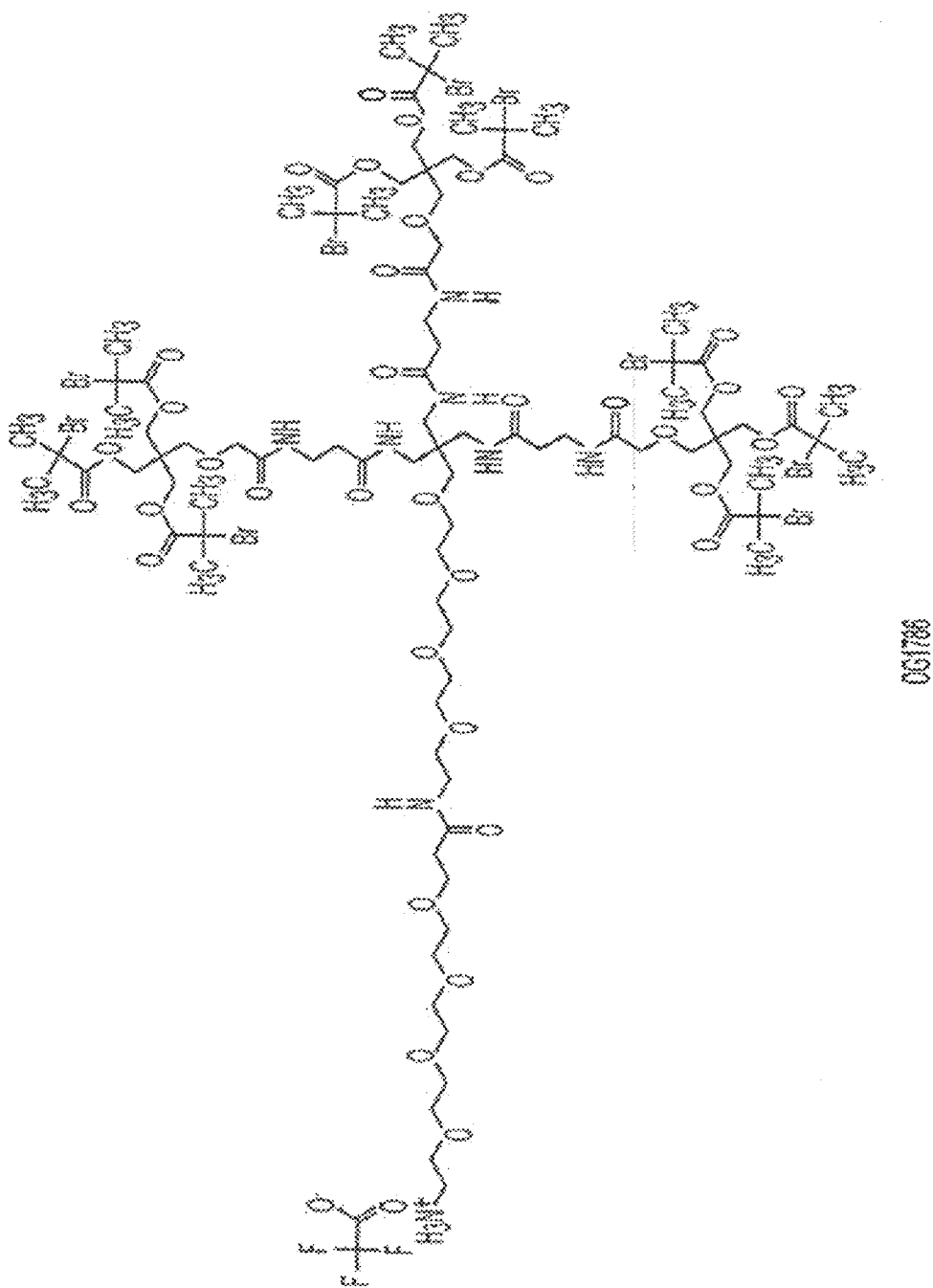
FIG. 2D shows OG1786.

As used herein, "OG1786" is a 9-arm initiator used for polymer synthesis with the structure shown in FIG. 2D, which depicts that salt form of OG1786 with trifluororacetic acid. OG1786 may be used in accordance with the present invention as other salts or as the free base.

As used herein, "OG1801" is an approximately (+/−15%) 750 kDa polymer (either by Mn or Mp) made using OG1786 as an initiator for ATRP synthesis using the monomer HEMA-PC. The structure of OG1801 is shown in FIG. 2J.

As used herein, "OG1802" is OG1801 with a maleimide functionality added, and it has the structure shown in FIG. 2K, wherein each of $n_1$, $n_2$, $n_3$, $n_4$, $n_5$, $n_6$, $n_7$, $n_8$ and $n_9$ is an integer (positive) (from 0 up to about 3000) such that the total molecular weight of the polymer is (Mw) 750,000±15% Daltons. When the term OG1802 is used to modify a protein term (such as VEGF trap or anti-IL-6 antibody), it designates that the protein is the conjugate protein.

Unless otherwise defined, all technical and scientific terms used herein have the same meaning as commonly understood by one of ordinary skill in the art to which this invention belongs. In case of conflict, the present specification, including definitions, will control. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular. Any example(s) following the term "e.g." or "for example" is not meant to be exhaustive or limiting.

The phrase "a" or "an" entity refers to one or more of that entity; for example, a compound refers to one or more compounds or at least one compound. As such, the terms "a" (or "an"), "one or more", and "at least one" can be used interchangeably herein.

As used herein, "about" means variation one might see in measurements taken among different instruments, samples, and sample preparations.

As used herein, CDR positions follow their order of appearance in variable domain when described. For example, heavy chain positions can be described as S35H or G66D. As used herein, Fc positions follow EU numbering when described or when noted to be in EU numbering. For example, mutations of antibodies can be described as L234A or L235A, which would be according to EU numbering. Positions may also be defined according to specified positions within a specific SEQ ID or sequence provided herein.

Multi-angle light scattering (MALS) is a technique of analyzing macromolecules where the laser light impinges on the molecule, the oscillating electric field of the light induces an oscillating dipole within it. This oscillating dipole will re-radiate light and can be measured using a MALS detector such as Wyatt miniDawn TREOS. The intensity of the radiated light depends on the magnitude of the dipole induced in the macromolecule which in turn is proportional to the polarizability of the macromolecule, the larger the induced dipole, and hence, the greater the intensity of the scattered light. Therefore, in order to analyze the scattering from a solution of such macromolecules, one should know their polarizability relative to the surrounding medium (e.g., the solvent). This may be determined from a measurement of the change, $\Delta n$, of the solution's refractive index n with the molecular concentration change, $\Delta c$, by measuring the dn/dc ($=\Delta n/\Delta c$) value using a Wyatt Optilab T-rEX differential refractometer. Two molar weight parameters that MALS determination employ are number average molecular weight (Mn) and weight average molecular weight (Mw) where the polydispersity index (PDI) equals Mw divided by Mn. SEC also allows another average molecular weight determination of the peak molecular weight Mp which is defined as the molecular weight of the highest peak at the SEC.

The PDI is used as a measure of the broadness of a molecular weight distribution of a polymer and bioconjugate which is derived from conjugation of a discrete protein to a polydisperse biopolymer (e.g., OG1802). For a protein sample, its polydispersity is close to 1.0 due to the fact that it is a product of translation where every protein molecule in a solution is expected to have almost the same length and molar mass. In contrast, due to the polydisperse nature of the biopolymer where the various length of polymer chains are synthesized during the polymerization process, it is very important to determine the PDI of the sample as one of its quality attribute for narrow distribution of molecular weight.

Size exclusion chromatography (SEC) is a chromatography technique in which molecules in solution are separated by their size. Typically an aqueous solution is applied to transport the sample through the column which is packed with resins of various pore sizes. The resin is expected to be inert to the analyte when passing through the column and the analytes separate from each other based on their unique size and the pore size characteristics of the selected column.

Coupling the SEC with MALS or SEC/MALS provides accurate distribution of molar mass and size (root mean square radius) as opposed to relying on a set of SEC calibration standards. This type of arrangement has many advantages over traditional column calibration methods. Since the light scattering and concentration are measured for each eluting fraction, the molar mass and size can be determined independently of the elution position. This is particularly relevant for species with non-globular shaped macromolecules such as the biopolymers (OG1802) or bioconjugates; such species typically do not elute in a manner that might be described by a set of column calibration standards.

In some embodiments, a SEC/MALS analysis includes a Waters HPLC system with Alliance 2695 solvent delivery module and Waters 2996 Photodiole Array Detector equipped with a Shodex SEC-HPLC column (7.8×300 mm). This is connected online with a Wyatt miniDawn TREOS and Wyatt Optilab T-rEX differential refractometer. The Empower software from Waters can be used to control the Waters HPLC system and the ASTRA V 6.1.7.16 software from Wyatt can be used to acquire the MALS data from the Wyatt miniDawn TREOS, dn/dc data from the T-rEX detector and the mass recovery data using the A280 absorbance signal from the Waters 2996 Photodiole Array detector. SEC can be carried out at 1 ml/min in 1×PBS pH 7.4, upon sample injection, the MALS and RI signals can be analyzed by the ASTRA software for determination of absolute molar mass (Mp, Mw, Mn) and polydisperse index (PDI). In addition, the calculation also involves the input dn/dc values for polymer and protein as 0.142 and 0.183, respectively. For bioconjugates dn/dc value, the dn/dc is calculated based on the weighted MW of the polymer and the protein to be about 0.148 using the formula below:

$$\text{Conjugate } dn/dc = 0.142 \times [\text{MWpolymer}/(\text{MWpolymer}+\text{MWprotein})] + 0.183 \times [\text{MWprotein}/(\text{MWpolymer}+\text{MWprotein})]$$

Where MWpolyme.r for OG1802 measured by SEC-MALS is about 800 kDa and the MWprotein for anti-IL-6 measured by SEC-MALS is about 145 kDa, the expected total molecular weight of the bioconjugate measured by SEC-MALS is about 1000 kDa. The MWprotein for the antiIL-6 VEGF Trap or VEGF Trap-antiIL-6 is about 192 kDa, and the expected total molecular weight of the bioconjugate is 1000-1100 kDa.

Exemplary methods and materials are described herein, although methods and materials similar or equivalent to those described herein can also be used in the practice or testing of the present invention. The materials, methods, and examples are illustrative only and not intended to be limiting.

I. IL-6 Antagonist Antibodies, IL-6 AB-VEGF Traps and/or Conjugates Thereof

Provided herein are anti-IL-6 antibodies that block, suppress or reduce (including significantly reduces) IL-6 biological activity, including downstream events mediated by IL-6. In some embodiments, the IL-6 antagonist antibody will have one or more of the CDR sequences provided herein.

In some embodiments, the isolated antagonist antibody specifically binds to IL-6.

In some embodiments, the antibody preferably reacts with IL-6 in a manner that inhibits IL-6 signaling function. In some embodiments, the IL-6 antagonist antibody specifically binds primate IL-6.

The antibodies useful in the present invention can encompass monoclonal antibodies, polyclonal antibodies, antibody fragments (e.g., Fab, Fab', F(ab')$_2$, Fv, Fc, etc.), chimeric antibodies, bispecific antibodies, heteroconjugate antibodies, single chain (ScFv), mutants thereof, fusion proteins comprising an antibody portion (e.g., a domain antibody), humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies may be murine, rat, human, or any other origin (including chimeric or humanized antibodies). In some embodiments, the IL-6 antagonist antibody is a monoclonal antibody. In some embodiments, the antibody is a human or humanized antibody.

In some embodiments, the antibody comprises a heavy chain amino acid variable region as shown in Tables 1, 2, 6, 7, 8 and/or 9 or FIG. 5. In some embodiments, an isolated antagonist antibody comprises a heavy chain variable region (VH) comprising a VH complementarity determining region one (CDR1), VH CDR2, and VH CDR3 of the VH having an amino acid sequence of that shown in Tables 1, 2, 6, 7, 8 and/or 9, and a light chain variable region (VL) comprising a VL CDR1, VL CDR2, and VL CDR3 of the VL having an amino acid sequence of that shown in the table.

In some embodiments, an isolated antagonist anti-IL-6 antibody is provided. The antibody comprises a heavy chain constant domain comprising one or more mutations to reduce effector function. In some embodiments, the one or more mutations reduce effector functions of the antibody related to the complement cascade, for example, a reduced activation of the complement cascade. In some embodiments, the reduction in effector function is at least about 50%.

In some embodiments, an isolated antagonist antibody that specifically binds to IL-6 comprising a heavy chain variable region (VH) and a light chain variable region (VL), wherein the antibody comprises the mutations L234A, L235A, and G237A (based on EU numbering) is provided. In some embodiments, the isolated antagonist antibody comprises the mutations L234A, L235A, and G237A. In some embodiments, the isolated antagonist antibody with mutations has minimized binding to FC gamma receptors or C1q. In some embodiments, the isolated antagonist antibody with mutations L234A, L235A, and G237A has minimized binding to FC gamma receptors or C1q. In some embodiments, an isolated antagonist anti-IL-6 antibody is provided, wherein the mutation(s) is located at one or more of the following amino acid positions (EU numbering): E233, L234, L235, G236, G237, A327, A330, and P331. In some embodiments, an isolated antagonist anti-IL-6 antibody is provided, wherein the mutation (s) is selected from the group consisting of E233P, L234V, L234A, L235A, G237A, A327G, A330S, and P331S.

In some embodiments, an isolated antagonist anti-IL-6 antibody is provided. The heavy chain constant domain further comprises a cysteine residue introduced by recombinant DNA technology. In some embodiments, the cysteine residue is selected from the group consisting of Q347C and L443C (EU numbering). In some embodiments, the cysteine residue is L443C (EU numbering).

In some embodiments, the antibody comprises all three of the following mutations (EU numbering) L234A, L235A, and G237A, and the antibody comprises L443C (EU numbering). In some embodiments, the antibody is a human IgG1, and a heavy chain constant domain of the antibody comprises one or more mutations that reduce an immune-mediated effector function.

In some embodiments, an isolated antagonist antibody is provided that binds an epitope on human IL-6 that is the same as or overlaps with the epitope recognized by an antibody comprising the amino acid sequences in any one or more of Tables: 1 and 2, and/or 6-9. In some embodiments, an IL-6 antibody with a cys and that is linked through that cysteine to a polymer is provided (as shown in Formula 17, herein).

In some embodiments, an isolated antagonist antibody that binds to IL-6 is provided. In some embodiments, the isolated antagonist antibody that binds to IL-6 comprises a heavy chain comprising the amino acid sequence shown in Tables 1, 2, 6, 7, 8 and/or 9, with or without the C-terminal lysine and a light chain comprising the amino acid sequence shown in Tables 1, 2, 6, 7, 8 and/or 9.

In some embodiments, an isolated antagonist antibody that binds to IL-6 is provided. The antibody comprises a VH comprising the amino acid sequence shown in Tables 1, 2, 6, 7, 8 and/or 9, or a sequence that is at least 90% identical thereto, having amino acid substitutions in residues that are not within a CDR. In some embodiments, the antibody comprises one or more of: HCDR1: in FIG. 5, HCDR2: in FIG. 5, HCDR3: in FIG. 5; LCDR1: in FIG. 5, LCDR2: in FIG. 5, LCDR3: in FIG. 5, for example, 1, 2, 3, 4, 5, or all 6 CDRs.

In some embodiments, an antibody that binds to IL-6 is provided, wherein the antibody comprises a CDRH1 that is the CDRH1 in Tables 1, 2, 6, 7, 8 and/or 9, a CDRH2 that is the CDRH2 in Tables 1, 2, 6, 7, 8 and/or 9, a CDRH3 that is the CDRH3 in Tables 1, 2, 6, 7, 8 and/or 9, a CDRL1 that is the CDRL1 in Tables 1, 2, 6, 7, 8 and/or 9, a CDRL2 that is the CDRL2 in Tables 1, 2, 6, 7, 8 and/or 9, a CDRL3 that is the CDRL3 in Tables 1, 2, 6, 7, 8 and/or 9, at least one of the following mutations: L234A, L235A, and G237A based on EU numbering, and at least one of the following mutations: Q347C or L443C based on EU numbering.

In some embodiments, an isolated antagonist anti-IL-6 antibody is provided. The heavy chain variable region of the antibody comprises three complementarity determining regions (CDRs) comprising the amino acid sequences shown in Table 1. In some embodiments, an isolated antagonist anti-IL-6 antibody is provided, wherein the light chain variable region of the antibody comprises three complementarity determining regions (CDRs) comprising the amino acid sequences shown in Table 2. In some embodiments, the antibody is one that contains one or more of the identified sequences in FIG. 5, e.g., one or more of the CDRS (including 2, 3, 4, 5 or 6 of the boxed CDRs) and/or the entire heavy and light chain variable regions.

In some embodiments, an isolated antagonist anti-IL-6 antibody comprises a heavy chain variable region (VH) that comprises three CDRs comprising the amino acid sequences shown in Table 1, and the light chain variable region (VL) of the antibody comprises three CDRs comprising the amino acid sequences shown in Table 2.

In some embodiments, an isolated antagonist anti-IL-6 antibody is provided. The VH comprises the amino acid sequences shown in Table 1 and the light chain variable region of the antibody comprises three CDRs comprising the amino acid sequences shown in Table 2.

In some embodiments, an isolated antagonist anti-IL-6 antibody is provided, wherein the antibody comprises a VL comprising the amino acid sequence shown in Table 2, or a variant thereof with one amino acid substitution in amino acids that are not within a CDR. In some embodiments, an isolated antagonist anti-IL-6 antibody is provided, wherein the antibody comprises a VH comprising the amino acid sequence shown in Table 1, or a variant thereof with several amino acid substitutions in amino acids that are not within a CDR.

In some embodiments, an isolated antagonist antibody is provided, wherein the antibody comprises a heavy chain comprising the amino acid sequence shown in Table 1, with a C-terminal lysine, and a light chain comprising the amino acid sequence shown in Table 2. In some embodiments, an isolated antagonist antibody is provided, wherein the antibody comprises a heavy chain comprising the amino acid sequence shown in Table 1, without a C-terminal lysine, and a light chain comprising the amino acid sequence shown in Table 2.

The IL-6 antagonist antibodies may be made by any method known in the art. General techniques for production of human and mouse antibodies are known in the art and/or are described herein.

IL-6 antagonist antibodies can be identified or characterized using methods known in the art, whereby reduction, amelioration, or neutralization of IL-6 biological activity is detected and/or measured. In some embodiments, an IL-6 antagonist antibody is identified by incubating a candidate antibody with IL-6 and monitoring binding to IL-6R or IL-6/IL-6R binding to gp130 and/or attendant reduction or neutralization of a biological activity of IL-6. The binding assay may be performed with, e.g., purified IL-6 polypeptide(s), or with cells naturally expressing (e.g., various strains), or transfected to express, IL-6 polypeptide(s). In one embodiment, the binding assay is a competitive binding assay, where the ability of a candidate antibody to compete with a known IL-6 antagonist antibody for IL-6 binding is evaluated. The assay may be performed in various formats, including the ELISA format.

Following initial identification, the activity of a candidate IL-6 antagonist antibody can be further confirmed and refined by bioassays, known to test the targeted biological activities. In some embodiments, an in vitro cell assay is used to further characterize a candidate IL-6 antagonist antibody.

IL-6 antagonist antibodies may be characterized using methods well known in the art. For example, one method is to identify the epitope to which it binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, New York, 1999. In an additional example, epitope mapping can be used to determine the sequence to which an IL-6 antagonist antibody binds. IL-6 antagonist antibody Epitope mapping is commercially available from various sources, for example, Pepscan Systems (Edelhertweg 15, 8219 PH Lelystad, The Netherlands). The epitope can be a linear epitope, i.e., contained in a single stretch of amino acids, or a conformational epitope formed by a three-dimensional interaction of amino acids that may not necessarily be contained in a single stretch. Peptides of varying lengths (e.g., at least 4-6 amino acids long) can be isolated or synthesized (e.g., recombinantly) and used for binding assays with an IL-6 antagonist antibody. In another example, the epitope to which the IL-6 antagonist antibody binds can be determined in a systematic screening by using overlapping peptides derived from the IL-6 sequence and determining binding by the IL-6 antagonist antibody. According to the gene fragment expression assays, the open reading frame encoding IL-6 is fragmented either randomly or by specific genetic constructions and the reactivity of the expressed fragments of IL-6 with the antibody to be tested is determined. The gene fragments may, for example, be produced by PCR and then transcribed and translated into protein in vitro, in the presence of radioactive amino acids. The binding of the antibody to the radioactively labeled IL-6 fragments is then determined by immunoprecipitation and gel electrophoresis. Certain epitopes can also be identified by using large libraries of random peptide sequences displayed on the surface of phage particles (phage libraries) or yeast (yeast display). Alternatively, a defined library of overlapping peptide fragments can be tested for binding to the test antibody in simple binding assays. In an additional example, mutagenesis of an antigen, domain swapping experiments and alanine scanning mutagenesis can be performed to identify residues required, sufficient, and/or necessary for epitope binding. For example, alanine scanning mutagenesis experiments can be performed using a mutant IL-6 in which various residues of the IL-6 polypeptide have been replaced with alanine. By assessing binding of the antibody to the mutant IL-6, the importance of the particular IL-6 residues to antibody binding can be assessed.

In some embodiments, an isolated antagonist anti-IL-6 antibody is provided, wherein the antibody binds human IL-6 with an affinity of between about 0.01 pM to about 10 nM. In some embodiments, an isolated antagonist anti-IL-6 antibody is provided, wherein the antibody binds human IL-6 with an affinity of between about 0.1 pM to about 2 nM. In some embodiments, an isolated antagonist anti-IL-6 antibody is provided, wherein the antibody binds human IL-6 with an affinity of about 0.01, 0.05, 0.1, 0.5, 1, 5, 10, 15, 20, 25, 30, 35, 40, 45, 50, 55, 60, 65, 70, 75, 80, 85, 90, 95 100, 200, 300, 400, 500, 600, 700, 800, 900, 1000 pM.

The binding affinity ($K_D$) of an IL-6 antagonist antibody to IL-6 can be about 0.001 to about 200 nM. In some embodiments, the binding affinity is any of about 200 nM, about 100 nM, about 50 nM, about 10 nM, about 1 nM, about 500 pM, about 100 pM, about 60 pM, about 50 pM, about 20 pM, about 15 pM, about 10 pM, about 5 pM, about 2 pM, or about 1 pM. In some embodiments, the binding affinity is less than any of about 250 nM, about 200 nM, about 100 nM, about 50 nM, about 10 nM, about 1 nM, about 500 pM, about 100 pM, about 50 pM, about 20 pM, about 10 pM, about 5 pM, about 2 pM, about 1 pM, about 0.5 pM, about 0.1 pM, about 0.05 pM, about 0.01 pM, about 0.005 pM, or about 0.001 pM.

In some embodiments, an isolated antagonist anti-IL-6 antibody is provided, wherein the antibody binds human IL-6 with a $k_{off}$ that is at least 5.0E-03 at 37 degrees. In some embodiments the $k_{off}$ is 5E-04. In some embodiments, an isolated antagonist anti-IL-6 antibody is provided, wherein the antibody binds human IL-6 with a $k_{off}$ that is better than 5.0E-04 at 37 degrees.

In some embodiments, binding affinity can be defined in terms of one or more of association constant ($k_a$), dissociation constant ($k_d$), and analyte concentration that achieves half-maximum binding capacity ($K_D$). In some embodiments, $k_a$ can range from about 0.50E+05 to about 5.00E+

08. In some embodiments, $k_d$ can range from about 0.50E-06 to about 5.00E-03. In some embodiments, $K_D$ can range from about 0.50E-12 to about 0.50E-07.

In some embodiments, a pharmaceutical composition comprising any of the antibodies disclosed herein is provided. In some embodiments, a pharmaceutical composition comprising any of the conjugates disclosed herein is provided. In some embodiments, the pharmaceutical composition comprises one or more pharmaceutically acceptable carriers. In some embodiments, the pharmaceutical composition is a liquid. In some embodiments, the pharmaceutical composition has an endotoxin level less than about 0.2 EU/ml. In some embodiments, the pharmaceutical composition is a liquid and has an endotoxin level less than about 0.2 EU/ml. In some embodiments, the pharmaceutical composition is a liquid and has an endotoxin level less than about 2.0, 1, 0.5, 0.2 EU/ml. In some embodiments, for example in intravitreal injection, the endotoxin limit is 0.01-0.02 EU/injection/eye.

Some embodiments provide any of the following, or compositions (including pharmaceutical compositions) comprising an antibody having a partial light chain sequence and a partial heavy chain sequence as found in Tables 1 and 2, or variants thereof. In Tables 1 and 2, the underlined sequences are some embodiments of CDR sequences as provided herein.

TABLE 1

Anti-IL-6 heavy chain variable region sequences. CDRs are underlined.

| ID | Sequence |
| --- | --- |
| I | EVQLVESGGGLVQPGGSLRLSCAASGFTFSPFAISWVRQAPGKGL EWVAKISPGGSWTYYSDTVTDRFTFSLDTSKSTAYLQMNSLRAED TAVYYCARQLWGYYALDVWGQGTLVTVSS (SEQ ID NO: 89) |
| II | EVQLVESGGGLVQPGGSLRLSCAASGFTFSPFAWSWVRQAPGKGL EWVAKISPGGSWTYYSDTVTDRFTFSLDTSKSTAYLQMNSLRAED TAVYYCARQLWGYYALDVWGQGTLVTVSS (SEQ ID NO: 90) |
| IIa | EVQLVESGGGLVQPGGSLRLSCAASGFTFSPFAMHWVRQAPGKGL EWVAKISPGGSWTYYSDTVTDRFTFSLDTSKSTAYLQMNSLRAED TAVYYCARQAWGYYALDIWGQGTLVTVSS (SEQ ID NO: 256) |
| IIb | EVQLVESGGGLVQPGGSLRLSCAASGFTFSPFAMHWVRQAPGKGL EWVAKISPGGSWTYYSDTVTDRFTFSLDTSKSTAYLQMNSLRAED TAVYYCARQSWGYYALDIWGQGTLVTVSS (SEQ ID NO: 257) |
| IIc | EVQLVESGGGLVQPGGSLRLSCAASGFTFSPFAMHWVRQAPGKGL EWVAKISPGGSWTYYSDTVTDRFTFSLDTSKSTAYLQMNSLRAED TAVYYCARQGWGYYALDIWGQGTLVTVSS (SEQ ID NO: 258) |
| IId | EVQLVESGGGLVQPGGSLRLSCAASGFTFSPFAMHWVRQAPGKGL EWVAKISPGGSWTYYSDTVTDRFTFSLDTSKSTAYLQMNSLRAED TAVYYCARQTWGYYALDIWGQGTLVTVSS (SEQ ID NO: 259) |
| IIe | EVQLVESGGGLVQPGGSLRLSCAASGFTFSPFAMHWVRQAPGKGL EWVAKISPGGSWTYYSDTVTDRFTFSLDTSKSTAYLQMNSLRAED TAVYYCARQVWGYYALDIWGQGTLVTVSS (SEQ ID NO: 260) |
| IIf | EVQLVESGGGLVQPGGSLRLSCAASGFTFSPFAMHWVRQAPGKGL EWVAKISPGGSWTYYSDTVTDRFTFSLDTSKSTAYLQMNSLRAED TAVYYCARQQWGYYALDIWGQGTLVTVSS (SEQ ID NO: 261) |

TABLE 1-continued

Anti-IL-6 heavy chain variable region sequences. CDRs are underlined.

| ID | Sequence |
| --- | --- |
| IIg | EVQLVESGGGLVQPGGSLRLSCAASGFTFSPFAMHWVRQAPGKGL EWVAKISPGGSWTYYSDTVTDRFTFSLDTSKSTAYLQMNSLRAED TAVYYCARQKWGYYALDIWGQGTLVTVSS (SEQ ID NO: 262) |

TABLE 2

Anti-IL-6 light chain variable region sequences. CDRs are underlined.

| ID | Sequence |
| --- | --- |
| III | DIQLTQSPSSLSASVGDRVTITCSASISVSYLYWYQQKPGKAPK LLIYDDSSLASGVPSRFSGSGSGTDFTLTISSLQPEDFATYYCQ QWSGYPYTFGQGTKVEIK (SEQ ID NO: 91) |
| IV | DIQLTQSPSSLSASVGDRVTITCSASISVSYLYWYQQKPGKAPK LLIYDASSLASGVPSRFSGSGSGTDFTLTISSLQPEDFATYYCQ QWSGYPYTFGQGTKVEIK (SEQ ID NO: 92) |
| V | DIQLTQSPSSLSASVGDRVTITCSASISVSYLYWYQQKPGKAPK LLIYDDSNLASGVPSRFSGSGSGTDFTLTISSLQPEDFATYYCQ QWSGYPYTFGQGTKVEIK (SEQ ID NO: 93) |

In some embodiments, the antibody does not have one or more (or any) of the following CDRs, Tables 3, 4, and/or 5.

TABLE 3

| Sequence | |
| --- | --- |
| Heavy chain | |
| CDR1 | GFTFSPFAMS (SEQ ID NO: 94) |
| CDR2 | KISPGGSWTYYSDTVTG (SEQ ID NO: 95) |
| CDR3 | QLWGYYALDI (SEQ ID NO: 171) |
| Light chain | |
| CDR1 | SASISVSYMY (SEQ ID NO: 96) |
| CDR2 | DMSNLAS (SEQ ID NO: 97) |
| CDR3 | MQWSGYPYT (SEQ ID NO: 98) |

TABLE 4

| Sequence | |
| --- | --- |
| Heavy chain | |
| CDR1 | PFAMS (SEQ ID NO: 244) |
| CDR2 | KISPGGSWTYYSDTVTG (SEQ ID NO: 245) |
| CDR3 | QLWGYYALDI (SEQ ID NO: 246) |
| Light chain | |
| CDR1 | SASISVSYMY (SEQ ID NO: 247) |
| CDR2 | DMSNLAS (SEQ ID NO: 248) |
| CDR3 | MQWSGYPYT (SEQ ID NO: 249) |

TABLE 5

| | Sequence |
|---|---|
| Heavy chain | |
| CDR1 | GFTFSPFAMS (SEQ ID NO: 250) |
| CDR2 | WVAKISPGGSWTYYSDTVTG (SEQ ID NO: 251) |
| CDR3 | ARQLWGYYALDI (SEQ ID NO: 252) |
| Light chain | |
| CDR1 | SASISVSYMY (SEQ ID NO: 253) |
| CDR2 | LLIYDMSNLAS (SEQ ID NO: 254) |
| CDR3 | MQWSGYPYT (SEQ ID NO: 255) |

In some embodiments, a composition as disclosed herein comprises an antibody having a partial or complete light chain sequence and a partial or complete heavy chain sequence from any of the options provided in Tables 1, 2, 6, 7, 8 and/or 9, or variants thereof. In some embodiments, the antibody (or binding fragment thereof) can include any one or more of the CDRs provided in Tables 1, 2, 6, 7, 8 and/or 9. In some embodiments, the antibody (or binding fragment thereof) can include any three or more of the CDRs provided in Tables 1, 2, 6, 7, 8 and/or 9. In some embodiments, the antibody (or binding fragment thereof) can include any all six of the CDRs provided in Tables 1, 2, 6, 7, 8 and/or 9. In some embodiments, the heavy and/or light chain can be any one or more of the other antibody constructs provided herein, including, for example, those provided in FIGS. 5, 18, and/or 21-24 and Tables 1, 3, 4, 5, 6, 7, 8 and/or 9.

In some embodiments, a composition as disclosed herein comprises an antibody having a partial or complete light chain CDR sequence and a partial or complete heavy chain CDR sequence from any of the options provided in Tables 1, 2, 6, 7, 8 and/or 9.

In some embodiments, CDR portions of IL-6 antagonist antibodies are also provided. Determination of CDR regions is well within the skill of the art. It is understood that in some embodiments, CDRs can be a combination of the IMGT and Paratome CDRs (also termed "combined CDRs" or "extended CDRs"). Determination of CDRs is well within the skill of the art. In some embodiments, the CDRs are the IMGT CDRs. In other embodiments, the CDRs are the Paratome CDRs. In other embodiments, the CDRs are the extended, AbM, conformational, Kabat, or Chothia CDRs. In embodiments with more than one CDR, the CDRs may be any of IMGT, Paratome, extended, Kabat, Chothia, AbM, conformational CDRs, or combinations thereof. In some embodiments, other CDR definitions may also be used. In some embodiments, only residues that are in common between 2, 3, 4, 5, 6, or 7 of the above definitions are used (resulting in a shorter sequence). In some embodiments, any residue in any of 2, 3, 4, 5, 6, or 7 of the above definitions can be used (resulting in a longer sequence).

In some embodiments, an IL-6 antagonist antibody comprises three CDRs of any one of the heavy chain variable regions shown in Tables 1, 2, 6, 7, 8 and/or 9. In some embodiments, the antibody comprises three CDRs of any one of the light chain variable regions shown in Tables 1, 2, 6, 7, 8 and/or 9. In some embodiments, the antibody comprises three CDRs of any one of the heavy chain variable regions shown in Table 1, and three CDRs of any one of the light chain variable regions shown in Table 2. In some embodiments, the CDRs are one or more of those designated in Tables 6 and/or 7, or 8 and/or 9 below:

TABLE 6

ANTI IL-6 HEAVY CHAIN CDR SEQUENCES.

| ID | CDR1 | CDR2 | CDR3 |
|---|---|---|---|
| I | GFTFSPFAIS (SEQ ID NO: 99) | VAKISPGGSWTYYSDTVTD (SEQ ID NO: 100) | ARQLWGYYALDV (SEQ ID NO: 101) |
| II | GFTFSPFAWS (SEQ ID NO: 102) | VAKISPGGSWTYYSDTVTD (SEQ ID NO: 103) | ARQLWGYYALDV (SEQ ID NO: 104) |
| IIa | GFTFSPFAMH (SEQ ID NO: 49) | VAKISPGGSWTYYSDTVTD (SEQ ID NO: 50) | ARQAWGYYALDI (SEQ ID NO: 51) |
| IIb | GFTFSPFAMH (SEQ ID NO: 52) | VAKISPGGSWTYYSDTVTD (SEQ ID NO: 53) | ARQSWGYYALDI (SEQ ID NO: 54) |
| IIc | GFTFSPFAMH (SEQ ID NO: 55) | VAKISPGGSWTYYSDTVTD (SEQ ID NO: 56) | ARQGWGYYALDI (SEQ ID NO: 57) |
| IId | GFTFSPFAMH (SEQ ID NO: 58) | VAKISPGGSWTYYSDTVTD (SEQ ID NO: 59) | ARQTWGYYALDI (SEQ ID NO: 60) |
| IIe | GFTFSPFAMH (SEQ ID NO: 61) | VAKISPGGSWTYYSDTVTD (SEQ ID NO: 62) | ARQVWGYYALDI (SEQ ID NO: 63) |
| IIf | GFTFSPFAMH (SEQ ID NO: 64) | VAKISPGGSWTYYSDTVTD (SEQ ID NO: 65) | ARQQWGYYALDI (SEQ ID NO: 66) |
| IIg | GFTFSPFAMH (SEQ ID NO: 67) | VAKISPGGSWTYYSDTVTD (SEQ ID NO: 68) | ARQKWGYYALDI (SEQ ID NO: 69) |

TABLE 7

ANTI IL-6 HEAVY CHAIN CDR SEQUENCES. Kabat

| CDR1 | CDR2 | CDR3 |
|---|---|---|
| PFAMH SEQ ID NO. 172) | KISPGGSWTYYSDTVTD SEQ ID NO. 173) | QAWGYYALDI SEQ ID NO. 174) |
| PFAMH SEQ ID NO. 175) | KISPGGSWTYYSDTVTD SEQ ID NO. 176) | QSWGYYALDI SEQ ID NO. 177) |
| PFAMH SEQ ID NO. 178) | KISPGGSWTYYSDTVTD SEQ ID NO. 179) | QGWGYYALDI SEQ ID NO. 180) |
| PFAMH SEQ ID NO. 181) | KISPGGSWTYYSDTVTD SEQ ID NO. 182) | QTWGYYALDI SEQ ID NO. 183) |
| PFAMH SEQ ID NO. 184) | KISPGGSWTYYSDTVTD SEQ ID NO. 185) | QVWGYYALDI SEQ ID NO. 186) |
| PFAMH SEQ ID NO. 187) | KISPGGSWTYYSDTVTD SEQ ID NO. 188) | QQWGYYALDI SEQ ID NO. 189) |
| PFAMH SEQ ID NO. 190) | KISPGGSWTYYSDTVTD SEQ ID NO. 191) | QKWGYYALDI SEQ ID NO. 192) |
| PFAIS SEQ ID NO. 193) | KISPGGSWTYYSDTVTD SEQ ID NO. 194) | QLWGYYALDV SEQ ID NO. 195) |
| PFAWS SEQ ID NO. 196) | KISPGGSWTYYSDTVTD SEQ ID NO. 197) | QLWGYYALDV SEQ ID NO. 198) |

TABLE 8

ANTI IL-6 LIGHT CHAIN CDR SEQUENCES.

| ID | CDR1 | CDR2 | CDR3 |
|---|---|---|---|
| III | SASISVSYLY (SEQ ID NO: 105) | LLIYDDSSLAS (SEQ ID NO: 106) | QQWSGYPYT (SEQ ID NO: 107) |
| IV | SASISVSYLY (SEQ ID NO: 108) | LLIYDASSLAS (SEQ ID NO: 109) | QQWSGYPYT (SEQ ID NO: 110) |
| V | SASISVSYLY (SEQ ID NO: 111) | LLIYDDSNLAS (SEQ ID NO: 112) | QQWSGYPYT (SEQ ID NO: 113) |

TABLE 9

ANTI IL-6 LIGHT CHAIN CDR SEQUENCES.

| CDR1 | CDR2 | CDR3 |
|---|---|---|
| SASISVSYLY SEQ ID NO. 199) | DDSSLAS SEQ ID NO. 200) | QQWSGYPYT SEQ ID NO. 201) |
| SASISVSYLY SEQ ID NO. 202) | DASSLAS SEQ ID NO. 203) | QQWSGYPYT SEQ ID NO. 204) |
| SASISVSYLY SEQ ID NO. 205) | DDSNLAS SEQ ID NO. 206) | QQWSGYPYT SEQ ID NO. 207) |

In some embodiments, the antibody used for binding to IL-6 can be one that includes one or more of the sequences in Tables 1, 2, 6, 7, 8 and/or 9. In some embodiments, the antibody used for binding to IL-6 can be one that includes three or more of the sequences in Tables 1, 2, 6, 7, 8 and/or 9. In some embodiments, the antibody used for binding to IL-6 can be one that includes six of the sequences in any one of Tables 1, 2, 6, 7, 8 and/or 9. In some embodiments, the antibody that binds to IL-6 can be one that competes for binding with an antibody that includes 6 of the specified CDRs in any one of Tables 1, 2, 6, 7, 8 and/or 9.

In some embodiments, the antibody can be linked or fused to a VEGF Trap sequence. In some embodiments, this Trap sequence can be as shown in Table 10. In some embodiments, the sequence is at least 80% identical to that shown in Table 10, e.g, at least 80, 85, 90, 95, 96, 97, 98, 99% identical to that shown in Table 10. In some embodiments, any of the VEGF Trap molecules in U.S. Pub. No. 20150376271 can be employed herein. In some embodiments, the VEGF Trap sequence is fused to IL-6 in one of the following manners: to an N-terminal end of a heavy chain comprising IL-6 VH (FIG. 6 left), or between a hinge region and after a CH1 domain of a heavy chain comprising IL-6 VH (FIG. 6 right). Unless designated otherwise, both options in the alternative and together are contemplated for the embodiments provided herein wherein any Ab-Trap fusion is discussed. In some embodiments, the term "Trap" refers to a full length extracellular region or any portion thereof, or combination of portions from different VEGF receptors that can antagonize signaling between at least one VEGF and VEGFR. Preferably, the extracellular trap segment includes at least one domain from one of VEGFR-1, -2 or -3, and more preferably at least two contiguous domains, such as D2 and D3. Optionally, an extracellular domain includes at least one domain from at least two different VEGFRs. A preferred extracellular domain comprises or consists essentially of D2 of VEGFR-1 and D3 of VEGFR-2.

TABLE 10

VEGFR1, DOMAIN 2 AND VEGFR2, DOMAIN 3 FUSION SEQUENCE

SDTGRPFVEMYSEIPEIIHMTEGRELVIPCRVTSPNITVTLKKFPLDT
LIPDGKRIIWDSRKGFIISNATYKEIGLLTCEATVNGHLYKTNYLTHR
QTNTIIDVVLSPSHGIELSVGEKLVLNCTARTELNVGIDFNWEYPSSK
HQHKKLVNRDLKTQSGSEMKKFLSTLTIDGVTRSDQGLYTCAASSGLM
TKKNSTFVRVHEK (SEQ ID NO: 114)

In some embodiments, the IL-6 Ab VEGF Trap construct can have any of the sequences provided in TABLE 11. In some embodiments, the construct can be at least identical to the sequences in Table 11, e.g., 80, 85, 90, 95, 96, 97, 98, 99 or higher. In some embodiments, the fusion protein can be in line with those percentages, with the exception that the antibody IL-6 domain does not contain one or more of the CDRs in Tables 3, 4, and/or 5. In some embodiments, the fusion protein is one that contains one or more of the identified sequences in FIG. 5, e.g., one of more of the CDRS (including 2, 3, 4, 5 or 6 of the boxed CDRs) and/or the entire heavy and light chain variable regions, along with a VEGF Trap sequence (e.g., Table 10). In some embodiments, the sequences can be directly fused to one another. In some embodiments, one or more flexible linking sequences or sections can be used. The linking sequence can be positioned between the Ab sequence and the VEGF Trap sequence. These sequences can be 5 to 30 amino acids in length. In some embodiments, the linking sequence can include G and S in a ratio of about 4:1. In some embodiments, the linker includes the following sequence: GGGGSGGGGS (SEQ ID NO: 115). In some embodiments, any flexible linker can be employed. In some embodiments, the Fc portion of the 11-6 Ab is IgG1.

TABLE 11

HEAVY AND LIGHT CHAIN SEQUENCES FOR DUAL INHIBITOR MOLECULES.
CDRS ARE UNDERLINED IN THE HEAVY AND LIGHT CHAINS, VEGF TRAP
SEQUENCE IS BOLDED IN BLACK, GLY-SER LINKER IS ITALICIZED.

| ID | Heavy chain | Light chain |
|---|---|---|
| A | SDTGRPFVEMYSEIPEIIHMTEGRELVIPCRVTSP NITVTLKKFPLDTLIPDGKRIIWDSRKGFIISNAT YKEIGLLTCEATVNGHLYKTNYLTHRQTNTIIDVV LSPSHGIELSVGEKLVLNCTARTELNVGIDFNWEY PSSKHQHKKLVNRDLKTQSGSEMKKFLSTLTIDGV TRSDQGLYTCAASSGLMTKKNSTFVRVHEK_GGGGS GGGGS_EVQLVESGGGLVQPGGSLRLSCAASGFTFS PFAISWVRQAPGKGLEWVAKISPGGSWTYYSDTVT DRFTFSLDTSKSTAYLQMNSLRAEDTAVYYCARQL WGYYALDVWGQGTLVTVSSASTKGPSVFPPLAPSSK | DIQLTQSPSSLSASVGDRVTITCSASISVSYLYWYQ QKPGKAPKLLIYDDSSLASGVPSRFSGSGSGTDFTL TISSLQPEDFATYYCQQWSGYPYTFGQGTKVEIKRT VAAPSVFIFPPSDEQLKSGTASVVCLLNNFYPREAK VQWKVDNALQSGNSQESVTEQDSKDSTYSLSSTLTL SKADYEKHKVYACEVTHQGLSSPVTKSFNRGEC (SEQ ID NO: 117) |

TABLE 11-continued

HEAVY AND LIGHT CHAIN SEQUENCES FOR DUAL INHIBITOR MOLECULES. CDRS ARE UNDERLINED IN THE HEAVY AND LIGHT CHAINS, VEGF TRAP SEQUENCE IS BOLDED IN BLACK, GLY-SER LINKER IS ITALICIZED.

| ID | Heavy chain | Light chain |
|---|---|---|
| | STSGGTAALGCLVKDYFPEPVTVSWNSGALTSGVH<br>TFPAVLQSSGLYSLSSVVTVPSSSLGTQTYICNVN<br>HKPSNTKVDKKVEPKSCDKTHTCPPCPAPEAAGAP<br>SVFLFPPKPKDTLMISRTPEVTCVVVDVSHEDPEV<br>KFNWYVDGVEVHNAKTKPREEQYNSTYRVVSVLTV<br>LHQDWLNGKEYKCKVSNKALPAPIEKTISKAKGQP<br>REPQVYTLPPSREEMTKNQVSLTCLVKGFYPSDIA<br>VEWESNGQPENNYKTTPPVLDSDGSFFLYSKLTVD<br>KSRWQQGNVFSCSVMHEALHNHYTQKSLSCSPGK<br>(SEQ ID NO: 116) | |
| B | SDTGRPFVEMYSEIPEIIHMTEGRELVIPCRVTSP<br>NITVTLKKFPLDTLIPDGKRIIWDSRKGFIISNAT<br>YKEIGLLTCEATVNGHLYKTNYLTHRQTNTIIDVV<br>LSPSHGIELSVGEKLVLNCTARTELNVGIDFNWEY<br>PSSKHQHKKLVNRDLKTQSGSEMKKFLSTLTIDGV<br>TRSDQGLYTCAASSGLMTKKNSTFVRVHEK_GGGGS_<br>_GGGGS_EVQLVESGGGLVQPGGSLRLSCAASGFTFS<br>PFAISWVRQAPGKGLEWVAKISPGGSWTYYSDTVT<br>DRFTFSLDTSKSTAYLQMNSLRAEDTAVYYCARQL<br>WGYYALDVWGQGTLVTVSSASTKGPSVFPLAPSSK<br>STSGGTAALGCLVKDYFPEPVTVSWNSGALTSGVH<br>TFPAVLQSSGLYSLSSVVTVPSSSLGTQTYICNVN<br>HKPSNTKVDKKVEPKSCDKTHTCPPCPAPEAAGAP<br>SVFLFPPKPKDTLMISRTPEVTCVVVDVSHEDPEV<br>KFNWYVDGVEVHNAKTKPREEQYNSTYRVVSVLTV<br>LHQDWLNGKEYKCKVSNKALPAPIEKTISKAKGQP<br>REPQVYTLPPSREEMTKNQVSLTCLVKGFYPSDIA<br>VEWESNGQPENNYKTTPPVLDSDGSFFLYSKLTVD<br>KSRWQQGNVFSCSVMHEALHNHYTQKSLSCSPGK<br>(SEQ ID NO: 118) | DIQLTQSPSSLSASVGDRVTITCSASISVSYLYWYQ<br>QKPGKAPKLLIYDASSLASGVPSRFSGSGSGTDFTL<br>TISSLQPEDFATYYCQQWSGYPYTFGQGTKVEIKRT<br>VAAPSVFIFPPSDEQLKSGTASVVCLLNNFYPREAK<br>VQWKVDNALQSGNSQESVTEQDSKDSTYSLSSTLTL<br>SKADYEKHKVYACEVTHQGLSSPVTKSFNRGEC<br>(SEQ ID NO: 119) |
| C | SDTGRPFVEMYSEIPEIIHMTEGRELVIPCRVTSP<br>NITVTLKKFPLDTLIPDGKRIIWDSRKGFIISNAT<br>YKEIGLLTCEATVNGHLYKTNYLTHRQTNTIIDVV<br>LSPSHGIELSVGEKLVLNCTARTELNVGIDFNWEY<br>PSSKHQHKKLVNRDLKTQSGSEMKKFLSTLTIDGV<br>TRSDQGLYTCAASSGLMTKKNSTFVRVHEK_GGGGS_<br>_GGGGS_EVQLVESGGGLVQPGGSLRLSCAASGFTFS<br>PFAISWVRQAPGKGLEWVAKISPGGSWTYYSDTVT<br>DRFTFSLDTSKSTAYLQMNSLRAEDTAVYYCARQL<br>WGYYALDVWGQGTLVTVSSASTKGPSVFPLAPSSK<br>STSGGTAALGCLVKDYFPEPVTVSWNSGALTSGVH<br>TFPAVLQSSGLYSLSSVVTVPSSSLGTQTYICNVN<br>HKPSNTKVDKKVEPKSCDKTHTCPPCPAPEAAGAP<br>SVFLFPPKPKDTLMISRTPEVTCVVVDVSHEDPEV<br>KFNWYVDGVEVHNAKTKPREEQYNSTYRVVSVLTV<br>LHQDWLNGKEYKCKVSNKALPAPIEKTISKAKGQP<br>REPQVYTLPPSREEMTKNQVSLTCLVKGFYPSDIA<br>VEWESNGQPENNYKTTPPVLDSDGSFFLYSKLTVD<br>KSRWQQGNVFSCSVMHEALHNHYTQKSLSCSPGK<br>(SEQ ID NO: 120) | DIQLTQSPSSLSASVGDRVTITCSASISVSYLYWYQ<br>QKPGKAPKLLIYDDSNLASGVPSRFSGSGSGTDFTL<br>TISSLQPEDFATYYCQQWSGYPYTFGQGTKVEIKRT<br>VAAPSVFIFPPSDEQLKSGTASVVCLLNNFYPREAK<br>VQWKVDNALQSGNSQESVTEQDSKDSTYSLSSTLTL<br>SKADYEKHKVYACEVTHQGLSSPVTKSFNRGEC<br>(SEQ ID NO: 121) |
| D | SDTGRPFVEMYSEIPEIIHMTEGRELVIPCRVTSP<br>NITVTLKKFPLDTLIPDGKRIIWDSRKGFIISNAT<br>YKEIGLLTCEATVNGHLYKTNYLTHRQTNTIIDVV<br>LSPSHGIELSVGEKLVLNCTARTELNVGIDFNWEY<br>PSSKHQHKKLVNRDLKTQSGSEMKKFLSTLTIDGV<br>TRSDQGLYTCAASSGLMTKKNSTFVRVHEK_GGGGS_<br>_GGGGS_EVQLVESGGGLVQPGGSLRLSCAASGFTFS<br>PFAWSWVRQAPGKGLEWVAKISPGGSWTYYSDTVT<br>DRFTFSLDTSKSTAYLQMNSLRAEDTAVYYCARQL<br>WGYYALDVWGQGTLVTVSSASTKGPSVFPLAPSSK<br>STSGGTAALGCLVKDYFPEPVTVSWNSGALTSGVH<br>TFPAVLQSSGLYSLSSVVTVPSSSLGTQTYICNVN<br>HKPSNTKVDKKVEPKSCDKTHTCPPCPAPEAAGAP<br>SVFLFPPKPKDTLMISRTPEVTCVVVDVSHEDPEV<br>KFNWYVDGVEVHNAKTKPREEQYNSTYRVVSVLTV<br>LHQDWLNGKEYKCKVSNKALPAPIEKTISKAKGQP<br>REPQVYTLPPSREEMTKNQVSLTCLVKGFYPSDIA<br>VEWESNGQPENNYKTTPPVLDSDGSFFLYSKLTVD<br>KSRWQQGNVFSCSVMHEALHNHYTQKSLSCSPGK<br>(SEQ ID NO: 122) | DIQLTQSPSSLSASVGDRVTITCSASISVSYLYWYQ<br>QKPGKAPKLLIYDDSSLASGVPSRFSGSGSGTDFTL<br>TISSLQPEDFATYYCQQWSGYPYTFGQGTKVEIKRT<br>VAAPSVFIFPPSDEQLKSGTASVVCLLNNFYPREAK<br>VQWKVDNALQSGNSQESVTEQDSKDSTYSLSSTLTL<br>SKADYEKHKVYACEVTHQGLSSPVTKSFNRGEC<br>(SEQ ID NO: 123) |

TABLE 11-continued

HEAVY AND LIGHT CHAIN SEQUENCES FOR DUAL INHIBITOR MOLECULES.
CDRS ARE UNDERLINED IN THE HEAVY AND LIGHT CHAINS, VEGF TRAP
SEQUENCE IS BOLDED IN BLACK, GLY-SER LINKER IS ITALICIZED.

| ID | Heavy chain | Light chain |
|---|---|---|
| E | SDTGRPFVEMYSEIPEIIHMTEGRELVIPCRVTSP NITVTLKKFPLDTLIPDGKRIIWDSRKGFIISNAT YKEIGLLTCEATVNGHLYKTNYLTHRQTNTIIDVV LSPSHGIELSVGEKLVLNCTARTELNVGIDFNWEY PSSKHQHKKLVNRDLKTQSGSEMKKFLSTLTIDGV TRSDQGLYTCAASSGLMTKKNSTFVRVHEK_GGGGS GGGGS_EVQLVESGGGLVQPGGSLRLSCAASGFTFS PFAWSWVRQAPGKGLEWVAKISPGGSWTYYSDTVT DRFTFSLDTSKSTAYLQMNSLRAEDTAVYYCARQL WGYYALDVWGQGTLVTVSSASTKGPSVFPLAPSSK STSGGTAALGCLVKDYFPEPVTVSWNSGALTSGVH TFPAVLQSSGLYSLSSVVTVPSSSLGTQTYICNVN HKPSNTKVDKKVEPKSCDKTHTCPPCPAPEAAGAP SVFLFPPKPKDTLMISRTPEVTCVVVDVSHEDPEV KFNWYVDGVEVHNAKTKPREEQYNSTYRVVSVLTV LHQDWLNGKEYKCKVSNKALPAPIEKTISKAKGQP REPQVYTLPPSREEMTKNQVSLTCLVKGFYPSDIA VEWESNGQPENNYKTTPPVLDSDGSFFLYSKLTVD KSRWQQGNVFSCSVMHEALHNHYTQKSLSCSPGK (SEQ ID NO: 124) | DIQLTQSPSSLSASVGDRVTITCSASISVSYLYWYQ QKPGKAPKLLIYDASSLASGVPSRFSGSGSGTDFTL TISSLQPEDFATYYCQQWSGYPYTFGQGTKVEIKRT VAAPSVFIFPPSDEQLKSGTASVVCLLNNFYPREAK VQWKVDNALQSGNSQESVTEQDSKDSTYSLSSTLTL SKADYEKHKVYACEVTHQGLSSPVTKSFNRGEC (SEQ ID NO: 125) |
| F | SDTGRPFVEMYSEIPEIIHMTEGRELVIPCRVTSP NITVTLKKFPLDTLIPDGKRIIWDSRKGFIISNAT YKEIGLLTCEATVNGHLYKTNYLTHRQTNTIIDVV LSPSHGIELSVGEKLVLNCTARTELNVGIDFNWEY PSSKHQHKKLVNRDLKTQSGSEMKKFLSTLTIDGV TRSDQGLYTCAASSGLMTKKNSTFVRVHEK_GGGGS GGGGS_EVQLVESGGGLVQPGGSLRLSCAASGFTFS PFAWSWVRQAPGKGLEWVAKISPGGSWTYYSDTVT DRFTFSLDTSKSTAYLQMNSLRAEDTAVYYCARQL WGYYALDVWGQGTLVTVSSASTKGPSVFPLAPSSK STSGGTAALGCLVKDYFPEPVTVSWNSGALTSGVH TFPAVLQSSGLYSLSSVVTVPSSSLGTQTYICNVN HKPSNTKVDKKVEPKSCDKTHTCPPCPAPEAAGAP SVFLFPPKPKDTLMISRTPEVTCVVVDVSHEDPEV KFNWYVDGVEVHNAKTKPREEQYNSTYRVVSVLTV LHQDWLNGKEYKCKVSNKALPAPIEKTISKAKGQP REPQVYTLPPSREEMTKNQVSLTCLVKGFYPSDIA VEWESNGQPENNYKTTPPVLDSDGSFFLYSKLTVD KSRWQQGNVFSCSVMHEALHNHYTQKSLSCSPGK (SEQ ID NO: 126) | DIQLTQSPSSLSASVGDRVTITCSASISVSYLYWYQ QKPGKAPKLLIYDDSNLASGVPSRFSGSGSGTDFTL TISSLQPEDFATYYCQQWSGYPYTFGQGTKVEIKRT VAAPSVFIFPPSDEQLKSGTASVVCLLNNFYPREAK VQWKVDNALQSGNSQESVTEQDSKDSTYSLSSTLTL SKADYEKHKVYACEVTHQGLSSPVTKSFNRGEC (SEQ ID NO: 127) |
| G | SDTGRPFVEMYSEIPEIIHMTEGRELVIPCRVTSP NITVTLKKFPLDTLIPDGKRIIWDSRKGFIISNAT YKEIGLLTCEATVNGHLYKTNYLTHRQTNTIIDVV LSPSHGIELSVGEKLVLNCTARTELNVGIDFNWEY PSSKHQHKKLVNRDLKTQSGSEMKKFLSTLTIDGV TRSDQGLYTCAASSGLMTKKNSTFVRVHEK_GGGGS GGGGS_EVQLVESGGGLVQPGGSLRLSCAASGFTFS PFAMHWVRQAPGKGLEWVAKISPGGSWTYYSDTVT DRFTFSLDTSKSTAYLQMNSLRAEDTAVYYCARQA WGYYALDIWGQGTLVTVSSASTKGPSVFPLAPSSK STSGGTAALGCLVKDYFPEPVTVSWNSGALTSGVH TFPAVLQSSGLYSLSSVVTVPSSSLGTQTYICNVN HKPSNTKVDKKVEPKSCDKTHTCPPCPAPEAAGAP SVFLFPPKPKDTLMISRTPEVTCVVVDVSHEDPEV KFNWYVDGVEVHNAKTKPREEQYNSTYRVVSVLTV LHQDWLNGKEYKCKVSNKALPAPIEKTISKAKGQP REPQVYTLPPSREEMTKNQVSLTCLVKGFYPSDIA VEWESNGQPENNYKTTPPVLDSDGSFFLYSKLTVD KSRWQQGNVFSCSVMHEALHNHYTQKSLSCSPGK (SEQ ID NO: 263) | DIQLTQSPSSLSASVGDRVTITCSASISVSYLYWYQ QKPGKAPKLLIYDDSSLASGVPSRFSGSGSGTDFTL TISSLQPEDFATYYCQQWSGYPYTFGQGTKVEIKRT VAAPSVFIFPPSDEQLKSGTASVVCLLNNFYPREAK VQWKVDNALQSGNSQESVTEQDSKDSTYSLSSTLTL SKADYEKHKVYACEVTHQGLSSPVTKSFNRGEC (SEQ ID NO: 117) |
| H | SDTGRPFVEMYSEIPEIIHMTEGRELVIPCRVTSP NITVTLKKFPLDTLIPDGKRIIWDSRKGFIISNAT YKEIGLLTCEATVNGHLYKTNYLTHRQTNTIIDVV LSPSHGIELSVGEKLVLNCTARTELNVGIDFNWEY PSSKHQHKKLVNRDLKTQSGSEMKKFLSTLTIDGV TRSDQGLYTCAASSGLMTKKNSTFVRVHEK_GGGGS GGGGS_EVQLVESGGGLVQPGGSLRLSCAASGFTFS PFAMHWVRQAPGKGLEWVAKISPGGSWTYYSDTVT DRFTFSLDTSKSTAYLQMNSLRAEDTAVYYCARQA WGYYALDIWGQGTLVTVSSASTKGPSVFPLAPSSK STSGGTAALGCLVKDYFPEPVTVSWNSGALTSGVH | DIQLTQSPSSLSASVGDRVTITCSASISVSYLYWYQ QKPGKAPKLLIYDASSLASGVPSRFSGSGSGTDFTL TISSLQPEDFATYYCQQWSGYPYTFGQGTKVEIKRT VAAPSVFIFPPSDEQLKSGTASVVCLLNNFYPREAK VQWKVDNALQSGNSQESVTEQDSKDSTYSLSSTLTL SKADYEKHKVYACEVTHQGLSSPVTKSFNRGEC (SEQ ID NO: 119) |

TABLE 11-continued

HEAVY AND LIGHT CHAIN SEQUENCES FOR DUAL INHIBITOR MOLECULES. CDRS ARE UNDERLINED IN THE HEAVY AND LIGHT CHAINS, VEGF TRAP SEQUENCE IS BOLDED IN BLACK, GLY-SER LINKER IS ITALICIZED.

| ID | Heavy chain | Light chain |
|---|---|---|
|  | TFPAVLQSSGLYSLSSVVTVPSSSLGTQTYICNVN<br>HKPSNTKVDKKVEPKSCDKTHTCPPCPAPEAAGAP<br>SVFLFPPKPKDTLMISRTPEVTCVVVDVSHEDPEV<br>KFNWYVDGVEVHNAKTKPREEQYNSTYRVVSVLTV<br>LHQDWLNGKEYKCKVSNKALPAPIEKTISKAKGQP<br>REPQVYTLPPSREEMTKNQVSLTCLVKGFYPSDIA<br>VEWESNGQPENNYKTTPPVLDSDGSFFLYSKLTVD<br>KSRWQQGNVFSCSVMHEALHNHYTQKSLSCSPGK<br>(SEQ ID NO: 263) |  |
| I | SDTGRPFVEMYSEIPEIIHMTEGRELVIPCRVTSP<br>NITVTLKKFPLDTLIPDGKRIIWDSRKGFIISNAT<br>YKEIGLLTCEATVNGHLYKTNYLTHRQTNTIIDVV<br>LSPSHGIELSVGEKLVLNCTARTELNVGIDFNWEY<br>PSSKHQHKKLVNRDLKTQSGSEMKKFLSTLTIDGV<br>TRSDQGLYTCAASSGLMTKKNSTFVRVHEK_GGGGS<br>GGGGS_EVQLVESGGGLVQPGGSLRLSCAASGFTFS<br>PFAMHWVRQAPGKGLEWVAKISPGGSWTYY<u>SDTVT<br>DRFTF</u>SLDTSKSTAYL<u>QMNSLRAEDTAVYYCARQA<br>W</u>GYYALDIWGQGTLVTVSSASTKGPSVFPLAPSSK<br>STSGGTAALGCLVKDYFPEPVTVSWNSGALTSGVH<br>TFPAVLQSSGLYSLSSVVTVPSSSLGTQTYICNVN<br>HKPSNTKVDKKVEPKSCDKTHTCPPCPAPEAAGAP<br>SVFLFPPKPKDTLMISRTPEVTCVVVDVSHEDPEV<br>KFNWYVDGVEVHNAKTKPREEQYNSTYRVVSVLTV<br>LHQDWLNGKEYKCKVSNKALPAPIEKTISKAKGQP<br>REPQVYTLPPSREEMTKNQVSLTCLVKGFYPSDIA<br>VEWESNGQPENNYKTTPPVLDSDGSFFLYSKLTVD<br>KSRWQQGNVFSCSVMHEALHNHYTQKSLSCSPGK<br>(SEQ ID NO: 263) | DIQLTQSPSSLSASVGDRVTITC<u>SASISVSYLY</u>WYQ<br>QKPGKAPKLLIY<u>DDSNLAS</u>GVPSRFSGSGSGTDFTL<br>TISSLQPEDFATYYC<u>QQWSGYPYT</u>FGQGTKVEIKRT<br>VAAPSVFIFPPSDEQLKSGTASVVCLLNNFYPREAK<br>VQWKVDNALQSGNSQESVTEQDSKDSTYSLSSTLTL<br>SKADYEKHKVYACEVTHQGLSSPVTKSFNRGEC<br>(SEQ ID NO: 121) |
| J | EVQLVESGGGLVQPGGSLRLSCAASGFTFSPFAIS<br>WVRQAPGKGLEWVAKISPGGSWTYY<u>SDTVTDRFTF</u><br>SLDTSKSTAYL<u>QMNSLRAEDTAVYYCARQLWGYYA<br>LDV</u>WGQGTLVTVSSASTKGPSVFPLAPSSKSTSGG<br>TAALGCLVKDYFPEPVTVSWNSGALTSGVHTFPAV<br>LQSSGLYSLSSVVTVPSSSLGTQTYICNVNHKPSN<br>TKVDKKVEPKSC_GGGGSGGGGS_SDTGRPFVEMYSE<br>IPEIIHMTEGRELVIPCRVTSPNITVTLKKFPLDT<br>LIPDGKRIIWDSRKGFIISNATYKEIGLLTCEATV<br>NGHLYKTNYLTHRQTNTIIDVVLSPSHGIELSVGE<br>KLVLNCTARTELNVGIDFNWEYPSSKHQHKKLVNR<br>DLKTQSGSEMKKFLSTLTIDGVTRSDQGLYTCAAS<br>SGLMTKKNSTFVRVHEKDKTHTCPPCPAPEAAGAP<br>SVFLFPPKPKDTLMISRTPEVTCVVVDVSHEDPEV<br>KFNWYVDGVEVHNAKTKPREEQYNSTYRVVSVLTV<br>LHQDWLNGKEYKCKVSNKALPAPIEKTISKAKGQP<br>REPQVYTLPPSREEMTKNQVSLTCLVKGFYPSDIA<br>VEWESNGQPENNYKTTPPVLDSDGSFFLYSKLTVD<br>KSRWQQGNVFSCSVMHEALHNHYTQKSLSCSPGK<br>(SEQ ID NO: 128) | DIQLTQSPSSLSASVGDRVTITC<u>SASISVSYLY</u>WYQ<br>QKPGKAPKLLIY<u>DDSSLAS</u>GVPSRFSGSGSGTDFTL<br>TISSLQPEDFATYYC<u>QQWSGYPYT</u>FGQGTKVEIKRT<br>VAAPSVFIFPPSDEQLKSGTASVVCLLNNFYPREAK<br>VQWKVDNALQSGNSQESVTEQDSKDSTYSLSSTLTL<br>SKADYEKHKVYACEVTHQGLSSPVTKSFNRGEC<br>(SEQ ID NO: 129) |
| K | EVQLVESGGGLVQPGGSLRLSCAASGFTFSPFAIS<br>WVRQAPGKGLEWVAKISPGGSWTYY<u>SDTVTDRFTF</u><br>SLDTSKSTAYL<u>QMNSLRAEDTAVYYCARQLWGYYA<br>LDV</u>WGQGTLVTVSSASTKGPSVFPLAPSSKSTSGG<br>TAALGCLVKDYFPEPVTVSWNSGALTSGVHTFPAV<br>LQSSGLYSLSSVVTVPSSSLGTQTYICNVNHKPSN<br>TKVDKKVEPKSC_GGGGSGGGGS_SDTGRPFVEMYSE<br>IPEIIHMTEGRELVIPCRVTSPNITVTLKKFPLDT<br>LIPDGKRIIWDSRKGFIISNATYKEIGLLTCEATV<br>NGHLYKTNYLTHRQTNTIIDVVLSPSHGIELSVGE<br>KLVLNCTARTELNVGIDFNWEYPSSKHQHKKLVNR<br>DLKTQSGSEMKKFLSTLTIDGVTRSDQGLYTCAAS<br>SGLMTKKNSTFVRVHEKDKTHTCPPCPAPEAAGAP<br>SVFLFPPKPKDTLMISRTPEVTCVVVDVSHEDPEV<br>KFNWYVDGVEVHNAKTKPREEQYNSTYRVVSVLTV<br>LHQDWLNGKEYKCKVSNKALPAPIEKTISKAKGQP<br>REPQVYTLPPSREEMTKNQVSLTCLVKGFYPSDIA<br>VEWESNGQPENNYKTTPPVLDSDGSFFLYSKLTVD<br>KSRWQQGNVFSCSVMHEALHNHYTQKSLSCSPGK<br>(SEQ ID NO: 130) | DIQLTQSPSSLSASVGDRVTITC<u>SASISVSYLY</u>WYQ<br>QKPGKAPKLLIY<u>DASSLAS</u>GVPSRFSGSGSGTDFTL<br>TISSLQPEDFATYYC<u>QQWSGYPYT</u>FGQGTKVEIKRT<br>VAAPSVFIFPPSDEQLKSGTASVVCLLNNFYPREAK<br>VQWKVDNALQSGNSQESVTEQDSKDSTYSLSSTLTL<br>SKADYEKHKVYACEVTHQGLSSPVTKSFNRGEC<br>(SEQ ID NO: 131) |

TABLE 11-continued

HEAVY AND LIGHT CHAIN SEQUENCES FOR DUAL INHIBITOR MOLECULES.
CDRS ARE UNDERLINED IN THE HEAVY AND LIGHT CHAINS, VEGF TRAP
SEQUENCE IS BOLDED IN BLACK, GLY-SER LINKER IS ITALICIZED.

| ID | Heavy chain | Light chain |
|---|---|---|
| L | EVQLVESGGGLVQPGGSLRLSCAASGFTFSPFAIS WVRQAPGKGLEWVAKISPGGSWTYYSDTVTDRFTF SLDTSKSTAYLQMNSLRAEDTAVYYCARQLWGYYA LDVWGQGTLVTVSSASTKGPSVFPLAPSSKSTSGG TAALGCLVKDYFPEPVTVSWNSGALTSGVHTFPAV LQSSGLYSLSSVVTVPSSSLGTQTYICNVNHKPSN TKVDKKVEPKSC*GGGGSGGGGS*SDTGRPFVEMYSE IPEIIHMTEGRELVIPCRVTSPNITVTLKKFPLDT LIPDGKRIIWDSRKGFIISNATYKEIGLLTCEATV NGHLYKTNYLTHRQTNTIIDVVLSPSHGIELSVGE KLVLNCTARTELNVGIDFNWEYPSSKHQHKKLVNR DLKTQSGSEMKKFLSTLTIDVTRSDQGLYTCAAS SGLMTKKNSTFVRVHEKDKTHTCPPCPAPEAAGAP SVFLFPPKPKDTLMISRTPEVTCVVVDVSHEDPEV KFNWYVDGVEVHNAKTKPREEQYNSTYRVVSVLTV LHQDWLNGKEYKCKVSNKALPAPIEKTISKAKGQP REPQVYTLPPSREEMTKNQVSLTCLVKGFYPSDIA VEWESNGQPENNYKTTPPVLDSDGSFFLYSKLTVD KSRWQQGNVFSCSVMHEALHNHYTQKSLSCSPGK (SEQ ID NO: 132) | DIQLTQSPSSLSASVGDRVTITCSASISVSYLYWYQ QKPGKAPKLLIYDDSNLASGVPSRFSGSGSGTDFTL TISSLQPEDFATYYCQQWSGYPYTFGQGTKVEIKRT VAAPSVFIFPPSDEQLKSGTASVVCLLNNFYPREAK VQWKVDNALQSGNSQESVTEQDSKDSTYSLSSTLTL SKADYEKHKVYACEVTHQGLSSPVTKSFNRGEC (SEQ ID NO: 133) |
| M | EVQLVESGGGLVQPGGSLRLSCAASGFTFSPFAWS WVRQAPGKGLEWVAKISPGGSWTYYSDTVTDRFTF SLDTSKSTAYLQMNSLRAEDTAVYYCARQLWGYYA LDVWGQGTLVTVSSASTKGPSVFPLAPSSKSTSGG TAALGCLVKDYFPEPVTVSWNSGALTSGVHTFPAV LQSSGLYSLSSVVTVPSSSLGTQTYICNVNHKPSN TKVDKKVEPKSC*GGGGSGGGGS*SDTGRPFVEMYSE IPEIIHMTEGRELVIPCRVTSPNITVTLKKFPLDT LIPDGKRIIWDSRKGFIISNATYKEIGLLTCEATV NGHLYKTNYLTHRQTNTIIDVVLSPSHGIELSVGE KLVLNCTARTELNVGIDFNWEYPSSKHQHKKLVNR DLKTQSGSEMKKFLSTLTIDVTRSDQGLYTCAAS SGLMTKKNSTFVRVHEKDKTHTCPPCPAPEAAGAP SVFLFPPKPKDTLMISRTPEVTCVVVDVSHEDPEV KFNWYVDGVEVHNAKTKPREEQYNSTYRVVSVLTV LHQDWLNGKEYKCKVSNKALPAPIEKTISKAKGQP REPQVYTLPPSREEMTKNQVSLTCLVKGFYPSDIA VEWESNGQPENNYKTTPPVLDSDGSFFLYSKLTVD KSRWQQGNVFSCSVMHEALHNHYTQKSLSCSPGK (SEQ ID NO: 134) | DIQLTQSPSSLSASVGDRVTITCSASISVSYLYWYQ QKPGKAPKLLIYDDSSLASGVPSRFSGSGSGTDFTL TISSLQPEDFATYYCQQWSGYPYTFGQGTKVEIKRT VAAPSVFIFPPSDEQLKSGTASVVCLLNNFYPREAK VQWKVDNALQSGNSQESVTEQDSKDSTYSLSSTLTL SKADYEKHKVYACEVTHQGLSSPVTKSFNRGEC (SEQ ID NO: 135) |
| N | EVQLVESGGGLVQPGGSLRLSCAASGFTFSPFAWS WVRQAPGKGLEWVAKISPGGSWTYYSDTVTDRFTF SLDTSKSTAYLQMNSLRAEDTAVYYCARQLWGYYA LDVWGQGTLVTVSSASTKGPSVFPLAPSSKSTSGG TAALGCLVKDYFPEPVTVSWNSGALTSGVHTFPAV LQSSGLYSLSSVVTVPSSSLGTQTYICNVNHKPSN TKVDKKVEPKSC*GGGGSGGGGS*SDTGRPFVEMYSE IPEIIHMTEGRELVIPCRVTSPNITVTLKKFPLDT LIPDGKRIIWDSRKGFIISNATYKEIGLLTCEATV NGHLYKTNYLTHRQTNTIIDVVLSPSHGIELSVGE KLVLNCTARTELNVGIDFNWEYPSSKHQHKKLVNR DLKTQSGSEMKKFLSTLTIDVTRSDQGLYTCAAS SGLMTKKNSTFVRVHEKDKTHTCPPCPAPEAAGAP SVFLFPPKPKDTLMISRTPEVTCVVVDVSHEDPEV KFNWYVDGVEVHNAKTKPREEQYNSTYRVVSVLTV LHQDWLNGKEYKCKVSNKALPAPIEKTISKAKGQP REPQVYTLPPSREEMTKNQVSLTCLVKGFYPSDIA VEWESNGQPENNYKTTPPVLDSDGSFFLYSKLTVD KSRWQQGNVFSCSVMHEALHNHYTQKSLSCSPGK (SEQ ID NO: 136) | DIQLTQSPSSLSASVGDRVTITCSASISVSYLYWYQ QKPGKAPKLLIYDASSLASGVPSRFSGSGSGTDFTL TISSLQPEDFATYYCQQWSGYPYTFGQGTKVEIKRT VAAPSVFIFPPSDEQLKSGTASVVCLLNNFYPREAK VQWKVDNALQSGNSQESVTEQDSKDSTYSLSSTLTL SKADYEKHKVYACEVTHQGLSSPVTKSFNRGEC (SEQ ID NO: 137) |
| O | EVQLVESGGGLVQPGGSLRLSCAASGFTFSPFAWS WVRQAPGKGLEWVAKISPGGSWTYYSDTVTDRFTF SLDTSKSTAYLQMNSLRAEDTAVYYCARQLWGYYA LDVWGQGTLVTVSSASTKGPSVFPLAPSSKSTSGG TAALGCLVKDYFPEPVTVSWNSGALTSGVHTFPAV LQSSGLYSLSSVVTVPSSSLGTQTYICNVNHKPSN TKVDKKVEPKSC*GGGGSGGGGS*SDTGRPFVEMYSE IPEIIHMTEGRELVIPCRVTSPNITVTLKKFPLDT LIPDGKRIIWDSRKGFIISNATYKEIGLLTCEATV NGHLYKTNYLTHRQTNTIIDVVLSPSHGIELSVGE | DIQLTQSPSSLSASVGDRVTITCSASISVSYLYWYQ QKPGKAPKLLIYDDSNLASGVPSRFSGSGSGTDFTL TISSLQPEDFATYYCQQWSGYPYTFGQGTKVEIKRT VAAPSVFIFPPSDEQLKSGTASVVCLLNNFYPREAK VQWKVDNALQSGNSQESVTEQDSKDSTYSLSSTLTL SKADYEKHKVYACEVTHQGLSSPVTKSFNRGEC (SEQ ID NO: 139) |

TABLE 11-continued

HEAVY AND LIGHT CHAIN SEQUENCES FOR DUAL INHIBITOR MOLECULES.
CDRS ARE UNDERLINED IN THE HEAVY AND LIGHT CHAINS, VEGF TRAP
SEQUENCE IS BOLDED IN BLACK, GLY-SER LINKER IS ITALICIZED.

| ID | Heavy chain | Light chain |
|---|---|---|
|  | KLVLNCTARTELNVGIDFNWEYPSSKHQHKKLVNRDLKTQSGSEMKKFLSTLTIDGVTRSDQGLYTCAASSGLMTKKNSTFVRVHEKDKTHTCPPCPAPEAAGAPSVFLEPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSCSPGK (SEQ ID NO: 138) |  |
| P | EVQLVESGGGLVQPGGSLRLSCAASGFTFSPFAMHWVRQAPGKGLEWVAKISPGGSWTYYSDTVTDRFTFSLDTSKSTAYLQMNSLRAEDTAVYYCARQAWGYYALDIWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC*GGGGSGGGGS*SDTGRPFVEMYSEIPEIIHMTEGRELVIPCRVTSPNITVTLKKFPLDTLIPDGKRIIWDSRKGFIISNATYKEIGLLTCEATVNGHLYKTNYLTHRQTNTIIDVVLSPSHGIELSVGEKLVLNCTARTELNVGIDFNWEYPSSKHQHKKLVNRDLKTQSGSEMKKFLSTLTIDGVTRSDQGLYTCAASSGLMTKKNSTFVRVHEKDKTHTCPPCPAPEAAGAPSVFLEPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSCSPGK (SEQ ID NO: 266) | DIQLTQSPSSLSASVGDRVTITCSASISVSYLYWYQQKPGKAPKLLIYDDSSLASGVPSRFSGSGSGTDFTLTISSLQPEDFATYYCQQWSGYPYTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 117) |
| Q | EVQLVESGGGLVQPGGSLRLSCAASGFTFSPFAMHWVRQAPGKGLEWVAKISPGGSWTYYSDTVTDRFTFSLDTSKSTAYLQMNSLRAEDTAVYYCARQAWGYYALDIWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC*GGGGSGGGGS*SDTGRPFVEMYSEIPEIIHMTEGRELVIPCRVTSPNITVTLKKFPLDTLIPDGKRIIWDSRKGFIISNATYKEIGLLTCEATVNGHLYKTNYLTHRQTNTIIDVVLSPSHGIELSVGEKLVLNCTARTELNVGIDFNWEYPSSKHQHKKLVNRDLKTQSGSEMKKFLSTLTIDGVTRSDQGLYTCAASSGLMTKKNSTFVRVHEKDKTHTCPPCPAPEAAGAPSVFLEPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSCSPGK (SEQ ID NO: 267) | DIQLTQSPSSLSASVGDRVTITCSASISVSYLYWYQQKPGKAPKLLIYDASSLASGVPSRFSGSGSGTDFTLTISSLQPEDFATYYCQQWSGYPYTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 119) |
| R | EVQLVESGGGLVQPGGSLRLSCAASGFTFSPFAMHWVRQAPGKGLEWVAKISPGGSWTYYSDTVTDRFTFSLDTSKSTAYLQMNSLRAEDTAVYYCARQAWGYYALDIWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC*GGGGSGGGGS*SDTGRPFVEMYSEIPEIIHMTEGRELVIPCRVTSPNITVTLKKFPLDTLIPDGKRIIWDSRKGFIISNATYKEIGLLTCEATVNGHLYKTNYLTHRQTNTIIDVVLSPSHGIELSVGEKLVLNCTARTELNVGIDFNWEYPSSKHQHKKLVNRDLKTQSGSEMKKFLSTLTIDGVTRSDQGLYTCAASSGLMTKKNSTFVRVHEKDKTHTCPPCPAPEAAGAPSVFLPPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSCSPGK (SEQ ID NO: 268) | DIQLTQSPSSLSASVGDRVTITCSASISVSYLYWYQQKPGKAPKLLIYDDSNLASGVPSRFSGSGSGTDFTLTISSLQPEDFATYYCQQWSGYPYTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 121) |

To express the anti-IL-6 antibodies and/or IL-6 VEGF Traps provided herein, DNA fragments encoding VH and VL regions described can first be obtained. Various modifications, e.g. mutations, deletions, and/or additions can also be introduced into the DNA sequences using standard methods known to those of skill in the art. For example, mutagenesis can be carried out using standard methods, such as PCR-mediated mutagenesis, in which the mutated nucleotides are incorporated into the PCR primers such that the PCR product contains the desired mutations or site-directed mutagenesis.

The invention encompasses modifications to the variable regions shown herein. For example, the invention includes antibodies comprising functionally equivalent variable regions and CDRs which do not significantly affect their properties as well as variants which have enhanced or decreased activity and/or affinity. For example, the amino acid sequence may be mutated to obtain an antibody with the desired binding affinity to IL-6. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or which mature (enhance) the affinity of the polypeptide for its ligand, or use of chemical analogs.

Amino acid sequence insertions include amino- and/or carboxyl-terminal fusions ranging in length from one residue to polypeptides containing a hundred or more residues, as well as intra-sequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the half-life of the antibody in the blood circulation.

Substitution variants have at least one amino acid residue in the antibody molecule removed and a different residue inserted in its place. The sites of greatest interest for substitutional mutagenesis include the hypervariable regions, but framework alterations are also contemplated. Conservative substitutions are shown in Table 12 under the heading of "conservative substitutions." If such substitutions result in a change in biological activity, then more substantial changes, denominated "exemplary substitutions" in Table 12, or as further described below in reference to amino acid classes, may be introduced and the products screened.

TABLE 12

Amino Acid Substitutions

| Original Residue | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |

TABLE 12-continued

Amino Acid Substitutions

| Original Residue | Conservative Substitutions | Exemplary Substitutions |
|---|---|---|
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a β-sheet or helical conformation, (b) the charge or hydrophobicity of the molecule at the target site, or (c) the bulk of the side chain. Naturally occurring residues are divided into groups based on common side-chain properties:

(1) Non-polar: Norleucine, Met, Ala, Val, Leu, Ile;
(2) Polar without charge: Cys, Ser, Thr, Asn, Gln;
(3) Acidic (negatively charged): Asp, Glu;
(4) Basic (positively charged): Lys, Arg;
(5) Residues that influence chain orientation: Gly, Pro; and
(6) Aromatic: Trp, Tyr, Phe, His.

Non-conservative substitutions are made by exchanging a member of one of these classes for another class.

One type of substitution, for example, that may be made is to change one or more cysteines in the antibody, which may be chemically reactive, to another residue, such as, without limitation, alanine or serine. For example, there can be a substitution of a non-canonical cysteine. The substitution can be made in a CDR or framework region of a variable domain or in the constant region of an antibody. In some embodiments, the cysteine is canonical. Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

The antibodies may also be modified, e.g. in the variable domains of the heavy and/or light chains, e.g., to alter a binding property of the antibody. Changes in the variable region can alter binding affinity and/or specificity. In some embodiments, no more than one to five conservative amino acid substitutions are made within a CDR domain. In other embodiments, no more than one to three conservative amino acid substitutions are made within a CDR domain. For example, a mutation may be made in one or more of the CDR regions to increase or decrease the $K_D$ of the antibody for IL-6, to increase or decrease $k_{off}$, or to alter the binding specificity of the antibody. Techniques in site-directed mutagenesis are well-known in the art. See, e.g., Sambrook et al. and Ausubel et al., supra.

According to an aspect, the IgG domain of an IL-6 antagonist antibody can be IgG1, IgG2, IgG3 or IgG4. According to another aspect, the IgG domain can be a composite in which a constant regions is formed from more than one of the above isotypes (e.g., $CH_1$ region from IgG2 or IgG4, hinge, CH$_2$ and CH$_3$ regions from IgG1). In choosing an isotype, it is known in the art that human isotopes IgG1 and IgG$_3$ have complement-mediated cytotoxicity whereas human isotypes IgG2 and IgG4 have poor or no complement-mediated cytotoxicity. In some embodiments the IL-6 antagonist antibody isotype is IgG1.

The light chain constant region can be either human lambda or kappa. In some embodiments, the IL-6 antagonist antibody has a human kappa light chain constant region.

Human constant regions show allotypic variation and isoallotypic variation between different individuals, that is, the constant regions can differ in different individuals at one or more polymorphic positions. Isoallotypes differ from allotypes in that sera recognizing an isoallotype binds to a non-polymorphic region of one or more other isotypes. Reference to a human constant region includes a constant region with any natural allotype or any permutation of residues occupying polymorphic positions in natural allotypes or up to 3, 5 or 10 substitutions for reducing or increasing effector function as described below.

One or several amino acids at the amino or carboxy terminus of the light and/or heavy chains such as the C-terminal lysine of the heavy chain, may be missing or derivatized in a proportion or all of the molecules.

Substitutions can be made in the constant regions to reduce or increase effector function such as complement-mediated cytotoxicity (CDC), antibody-dependent cell-mediated cytotoxicity (ADCC) (see, e.g., Winter et al., U.S. Pat. No. 5,624,821; Tso et al., U.S. Pat. No. 5,834,597; and Lazar et al., Proc. Natl. Acad. Sci. USA 103:4005, 2006), or to prolong half-life in humans (see, e.g., Hinton et al., J. Biol. Chem. 279:6213, 2004).

In some embodiments, the IL-6 antagonist antibodies provided herein include one more substitutions that reduce complement mediated cytotoxicity. Reduction in complement mediated cytotoxicity can be accomplished with or without reduction in Fc receptor binding depending on the nature of the mutation(s). Antibodies with reduced complement mediated cytotoxicity but little or no reduction in Fc receptor allow a desired effect of Fc-mediated phagocytosis of iC3b without activating complement, which may contribute to side effects. Exemplary mutations known to reduce complement-mediated cytotoxicity in human constant regions include mutations at positions 241, 264, 265, 270, 296, 297, 322, 329 and 331 by EU numbering. Mutations in positions 318, 320, and 322 have been reported to reduce complement activation in mouse antibodies. Alanine is a preferred residue to occupy these positions in a mutated constant region. Some exemplary human mutations that have been used include F241A, V264A, D265A, V296A, N297A, K322A, and P331S in human IgG3 and D270A or E, N297Q, K322A, P329A, and P331S in human IgG1 (EU numbering).

Here, as elsewhere, the EU numbering scheme is used for numbering amino acids in the constant region of an antibody. When a residue in a variable region is referenced herein (unless designated otherwise) the residue numbering is according to the variable domain (or, if designated, the SEQ ID NO). Substitution at any or all of positions 234, 235, 236 and/or 237 reduce affinity for Fcγ receptors, particularly FcγRI receptor and also reduces complement binding and activation (see, e.g., U.S. Pat. No. 6,624,821 WO/2009/052439). An alanine substitution at positions 234, 235 and 237 reduces effector functions, particularly in the context of human IgG1. Optionally, positions 234, 236 and/or 237 in human IgG2 are substituted with alanine and position 235 with glutamine. (See, e.g., U.S. Pat. No. 5,624,821) to reduce Fc receptor binding. Exemplary substitutions for increasing half-life include a Gln at position 250 and/or a Leu at position 428. In accordance with an aspect of the present invention, where the anti-IL-6 antibody presented has a human IgG1 isotype, it is preferred that the antibody has at least one mutation in the constant region. Preferably, the mutation reduces complement fixation or activation by the constant region. In particularly preferred aspects of the present invention, the antibody has one or more mutations at positions E233, L234, L235, G236, G237, A327, A330 and P331 by EU numbering. Still more preferably, the mutations constitute one or more of the following E233P, L234V, L234A, L235A, G237A, A327G, A330S and P331S by EU numbering. In the most preferred embodiments the human IgG1 has the following mutations L234A, L235A and G237A by EU numbering.

Conjugates

The half-life of IL-6 antagonist antibodies and/or IL-6 Ab VEGF Traps can be extended by attachment of a "half-life extending moieties" or "half-life extending groups," which terms are herein used interchangeably to refer to one or more chemical groups attached to one or more amino acid site chain functionalities such as —SH, —OH, —COOH, —CONH2, —NH2, or one or more N- and/or O-glycan structures and that can increase in vivo circulatory half-life of proteins/peptides when conjugated to these proteins/peptides. Examples of half-life extending moieties include polymers described herein, particularly those of zwitterionic monomers, such as HEMA-phosphorylcholine, PEG, biocompatible fatty acids and derivatives thereof, Hydroxy Alkyl Starch (HAS) e.g. Hydroxy Ethyl Starch (HES), Poly Ethylene Glycol (PEG), Poly (Glyr-Ser$_y$) (HAP), Hyaluronic acid (HA), Heparosan polymers (HEP), Fleximers, Dextran, Poly-sialic acids (PSA), Fc domains, Transferrin, 25 Albumin, Elastin like (ELP) peptides, XTEN polymers, PAS polymers, PA polymers, Albumin binding peptides, CTP peptides, FcRn binding peptides and any combination thereof.

In some embodiments, the antibody is conjugated with a phosphorylcholine containing polymer. In some embodiments, the antibody is conjugated with a poly(acryloyloxyethyl phosphorylcholine) containing polymer, such as a polymer of acrylic acid containing at least one acryloyloxyethyl phosphorylcholine monomer such as 2-methacryloyloxyethyl phosphorylcholine (i.e., 2-methacryloyl-2'-trimethylammonium ethyl phosphate).

In some embodiments, the antibody and/or antibody VEGF Trap fusion is conjugated with a water-soluble polymer, which refers to a polymer that is soluble in water. A solution of a water-soluble polymer may transmit at least about 75%, more preferably at least about 95% of light, transmitted by the same solution after filtering. On a weight basis, a water-soluble polymer or segment thereof may be at least about 35%, at least about 50%, about 70%, about 85%, about 95% or 100% (by weight of dry polymer) soluble in water.

In one embodiment a half-life extending moiety can be conjugated to an IL-6 antagonist antibodies and/or IL-6 Ab VEGF Trap via free amino groups of the protein using N-hydroxysuccinimide (NHS) esters. Reagents targeting conjugation to amine groups can randomly react to ε-amine group of lysines, α-amine group of N-terminal amino acids, and 6-amine group of histidines.

However, IL-6 antagonist antibodies of the present invention have many amine groups available for polymer conjugation. Conjugation of polymers to free amino groups, thus, might negatively impact the ability of the antibody to bind to the epitope.

In another embodiment, a half-life extending moiety is coupled to one or more free SH groups using any appropriate thiol-reactive chemistry including, without limitation, maleimide chemistry, or the coupling of polymer hydrazides or polymer amines to carbohydrate moieties of the IL-6 antagonist antibodies and/or IL-6 Ab VEGF Traps after prior oxidation. The use of maleimide coupling is a particularly preferred embodiment of the present invention. Coupling preferably occurs at cysteines naturally present or introduced via genetic engineering.

In some embodiments, polymers are covalently attached to cysteine residues introduced into IL-6 antagonist antibodies and/or IL-6 Ab VEGF Traps by site directed mutagenesis. In some embodiments, the cysteine residues in the Fc portion of the IL-6 antagonist antibody and/or IL-6 Ab VEGF Trap can be used. In some embodiments, sites to introduce cysteine residues into an Fc region are provided in WO 2013/093809, U.S. Pat. No. 7,521,541, WO 2008/020827, U.S. Pat. Nos. 8,008,453, 8,455,622 and US2012/0213705, incorporated herein by reference for all purposes. In some embodiments, cysteine mutations are Q347C and L443C referring to the human IgG heavy chain by the EU index of Kabat. In some embodiments, the cysteine added by directed mutagenesis for subsequent polymer attachment is L443C. In some embodiments, the stoichiometry of IL-6 antagonist antibody to polymer is 1:1; in other words, a conjugate consists essentially of molecules each comprising one molecule of IL-6 antagonist antibody and/or IL-6 Ab VEGF Trap conjugated to one molecule of polymer. In some embodiments, coupling can occur at one or more lysines.

In some embodiments, a conjugate comprises an isolated antagonist antibody that specifically binds to IL-6 or IL-6 Ab VEGF Trap is conjugated to a polymer. In some embodiments, the polymer comprises a zwitterionic monomer. In some embodiments, the zwitterionic monomer, without limitations, is HEMA-phosphorylcholine, PEG, biocompatible fatty acids and derivatives thereof, Hydroxy Alkyl Starch (HAS) e.g. Hydroxy Ethyl Starch (HES), Poly Ethylene Glycol (PEG), Poly (Glyx-Sery) (HAP), Hyaluronic acid (HA), Heparosan polymers (HEP), Fleximers, Dextran, Poly-sialic acids (PSA), Fc domains, Transferrin, 25 Albumin, Elastin like (ELP) peptides, XTEN polymers, PAS polymers, PA polymers, Albumin binding peptides, CTP peptides, or FcRn binding peptides. In some embodiments, the polymer comprising a zwitterionic monomer is a half-life extending moiety.

In some embodiments, the IL-6 antagonist antibody and/or IL-6 Ab VEGF Trap can have a half-life extending moiety attached. In some embodiments, the half-life extending moiety is a zwitterionic polymer but PEG or other half-life extenders discussed below can alternatively be used. In some embodiments, the zwitterionic polymer is formed of monomers having a phosphorylcholine group. In some embodiments, the monomer is 2-(acryloyloxyethyl)-2'-(trimethylammoniumethyl) phosphate. In some embodiments, the monomer is 2-(methacryloyloxyethyl)-2'-(trimethylammoniumethyl) phosphate (HEMA-PC).

In some embodiments, the polymer conjugated to the IL-6 antagonist antibody and/or IL-6 Ab VEGF Trap has at least 2 or 3 or more arms. Some polymers have 2, 3, 4, 5, 6, 7, 8, 9, 10, 11 or 12 arms. In some embodiments, the polymer has 3, 6 or 9 arms. In some embodiments, the polymer has 9 arms. In some embodiments, the polymer peak molecular weight is between 300,000 and 1,750,000 Da. In some embodiments, the polymer has a peak molecular weight between 500,000 and 1,000,000 Da. In some embodiments, the polymer has a peak molecular weight between 600,000 to 800,000 Da.

In some embodiments, a conjugate of antagonistic anti-IL-6 antibody and/or IL-6 Ab VEGF Trap and a polymer is provided. In some embodiments, the polymer has a peak molecular weight between 300,000 and 1,750,000 Daltons as measured by size exclusion chromatography—multi angle light scattering (hereinafter "SEC-MALS"). In some embodiments, the polymer has a peak molecular weight between 500,000 and 1,000,000 Daltons as measured by SEC-MALS. In some embodiments, the polymer has a peak molecular weight between 600,000 to 800,000 Daltons as measured by SEC-MALS.

In some embodiments, a half-life extending moiety may be conjugated to a naturally occurring cysteine residue of an IL-6 antagonist antibody and/or IL-6 Ab VEGF Trap provided herein. In some embodiments, the half-life extending moiety is conjugated added to a cysteine that is added via site directed mutagenesis. In some embodiments, the cysteine is added by using recombinant DNA technology to add the peptide SGGGC or CAA to the C-terminus of either the light or heavy chain. In some embodiments, the peptide is added to the heavy chain. In some embodiments, the cysteine residue introduced via recombinant DNA technology is selected from the group consisting of (EU numbering) Q347C and L443C.

In accordance with another aspect of the present invention, a pharmaceutical composition is presented having an IL-6 antagonist antibody and/or IL-6 Ab VEGF Trap and a pharmaceutically acceptable excipient.

IL-6 antagonist antibodies and/or IL-6 Ab VEGF Traps (or other constructs provided herein) can be produced by recombinant expression including (i) the production of recombinant DNA by genetic engineering, (ii) introducing recombinant DNA into prokaryotic or eukaryotic cells by, for example and without limitation, transfection, electroporation or microinjection, (iii) cultivating the transformed cells, (iv) expressing anti-IL-6 antibodies, e.g. constitutively or on induction, and (v) isolating the anti-IL-6 antibody, e.g. from the culture medium or by harvesting the transformed cells, in order to (vi) obtain purified anti-IL-6 antibody.

In some embodiments, a conjugate comprising an anti-IL-6 antibody and/or IL-6 Ab VEGF Trap and a polymer is provided (as well as the other constructs provided herein, such as a bioconjugate). The antibody and/or Ab-Trap is any one of the antibodies and/or Traps disclosed herein. In some embodiments, the antibody is an IgG. In some embodiments, the antibody is IgA, IgE, IgD or IgM. In some embodiments, the polymer is covalently bonded to a sulfhydryl group. In some embodiments, the polymer is covalently bonded to a sulfhydryl group from a cysteine residue. In some embodiments, the polymer is covalently bonded to a sulfhydryl group from a cysteine residue on the heavy chain. In some embodiments, the polymer is covalently bonded to a sulfhydryl group from a cysteine residue on the heavy chain of the IgG. In some embodiments, the antibody comprises a cysteine residue at position 347 or 443 (EU numbering). In some embodiments, the polymer is covalently bonded to a sulfhydryl group from a cysteine residue at position 347 or 443 (EU numbering).

IL-6 antagonist antibodies and/or IL-6 Ab VEGF Trap can be produced by expression in a suitable prokaryotic or eukaryotic host system characterized by producing a pharmacologically acceptable anti-IL-6 antibody molecule. Examples of eukaryotic cells are mammalian cells, such as CHO, COS, HEK 293, BHK, SK-Hip, and HepG2. Other suitable expression systems are prokaryotic (e.g., *E. coli* with pET/BL21 expression system), yeast (*Saccharomyces cerevisiae* and/or *Pichia pastoris* systems), and insect cells. In some embodiments, an isolated cell line that produces any of the antibodies and/or Ab-Traps disclosed herein is provided. In some embodiments, the isolated cell line is selected, without limitations, from one or more of CHO, k1SV, XCeed, CHOK1SV, GS-KO.

In some embodiments, an isolated nucleic acid encoding any of the antibodies and/or Ab-Traps disclosed herein is provided. In some embodiments, a recombinant expression vector comprising the isolated nucleic acid is provided. In some embodiments, a host cell comprises the expression vector.

A wide variety of vectors can be used for the preparation of the IL-6 antagonist antibodies and/or IL-6 Ab VEGF Traps and may be selected from eukaryotic and prokaryotic expression vectors. Examples of vectors for prokaryotic expression include plasmids such as, and without limitation, preset, pet, and pad, wherein the promoters used in prokaryotic expression vectors include one or more of, and without limitation, lac, trc, trp, recA, or araBAD. Examples of vectors for eukaryotic expression include, without limitation: (i) for expression in yeast, vectors such as, and without limitation, pAO, pPIC, pYES, or pMET, using promoters such as, and without limitation, AOX1, GAP, GAL1, or AUG1; (ii) for expression in insect cells, vectors such as and without limitation, pMT, pAc5, pIB, pMIB, or pBAC, using promoters such as and without limitation PH, p10, MT, Ac5, OpIE2, gp64, or polh, and (iii) for expression in mammalian cells, vectors such as, and without limitation, pSVL, pCMV, pRc/RSV, pcDNA3, or pBPV, and vectors derived from, in one aspect, viral systems such as and without limitation vaccinia virus, adeno-associated viruses, herpes viruses, or retroviruses, using promoters such as and without limitation CMV, SV40, EF-1, UbC, RSV, ADV, BPV, and beta-actin.

In some embodiments, a method of producing an IL-6 antagonist antibody and/or IL-6 Ab VEGF Trap is provided. In some embodiments, the method comprises culturing a cell line that recombinantly produces any of the antibodies and/or Ab-Traps disclosed herein under conditions wherein the antibody is produced and recovered. In some embodiments, a method of producing an IL-6 antagonist antibody and/or IL-6 Ab VEGF Trap is provided. In some embodiments, the method comprises culturing a cell line comprising nucleic acid encoding an antibody and/or Ab-Trap comprising a heavy chain comprising the amino acid sequence shown in Table 1 and a light chain comprising the amino acid sequence shown in Table 2 under conditions wherein the antibody and/or IL-6 Ab VEGF Trap is produced and recovered. In some embodiments, the heavy and light chains of the antibody and/or IL-6 Ab VEGF Trap are encoded on separate vectors. In some embodiments, the heavy and light chains of the antibody and/or IL-6 Ab VEGF Trap are encoded on the same vector.

In accordance with another aspect of the present invention, provided are methods for synthesizing a zwitterionic polymer-IL-6 antagonist antibody and/or IL-6 Ab VEGF Trap conjugates, the conjugate having one or more functional agents and one or more polymer arms wherein each of the polymer arms has one or more monomer units wherein at least one of the units has a zwitterion. For example, such a method can have the steps of:

a. providing an initiator having one or more sites for monomer polymerization and a first linker having an amine group wherein the initiator is a trifluoro acetic acid salt;
b. providing one or more monomers suitable for polymerization wherein at least one of the monomers is zwitterionic;
c. reacting the monomers with the initiator to form one or more polymer arms each corresponding to the sites for monomer polymerization to provide an initiator-polymer conjugate having the first linker with the amine group;
d. providing a second linker having at least second and third reactive groups;
e. coupling one of the second and third reactive groups of the second linker to the amine group of the first linker of the initiator-polymer conjugate to provide a linker-initiator-polymer conjugate having one or more reactive groups that were not used in the coupling step; and
f. coupling one or more functional agents to one or more of the unreacted reactive groups of the linker-initiator-polymer moiety to provide the polymer-functional agent conjugate.

In some embodiments, a conjugate comprising an isolated antagonist antibody and/or IL-6 Ab VEGF Trap that specifically binds to IL-6 and a phosphorylcholine-containing polymer is provided. In some embodiments, the polymer is covalently bonded to the antibody and/or Ab-Trap. In some embodiments, the polymer is non-covalently bonded to the antibody and/or Ab-Trap.

In some embodiments, a conjugate comprising an anti-IL-6 antibody and/or IL-6 Ab VEGF Trap and a phosphorylcholine containing polymer is provided. In some embodiments, the polymer is covalently bonded to the antibody outside a variable region of the antibody. In some embodiments, a conjugate comprising an anti-IL-6 antibody and/or IL-6 Ab VEGF Trap and a phosphorylcholine containing polymer is provided. The polymer is covalently bonded to the antibody at a cysteine outside a variable region of the antibody. In some embodiments, a conjugate comprising an anti-IL-6 antibody and/or IL-6 Ab VEGF Trap and a phosphorylcholine containing polymer is provided, wherein the polymer is covalently bonded to the antibody at a cysteine outside a variable region of the antibody wherein said cysteine has been added via recombinant DNA technology. In some embodiments of the conjugate, the polymer comprises 2(methacryloyloxy)ethyl (2-(trimethylammonio) ethyl) phosphate (MPC) monomers.

In accordance with another aspect of the present invention, a method is provided where the conjugation group (e.g. maleimide) is added after polymer synthesis. This is sometimes referred to as a "snap-on strategy" or "universal polymer strategy". See, e.g., U.S. patent application Ser. No. 14/916,180 (published as U.S. Patent Application Publication No. 20160199501), hereby incorporated by reference in its entirety. In some embodiments, a single initiator moiety can be used for large scale polymer synthesis. Thus, conditions can be developed for scaled up optimal polymer synthesis. Such polymers can then be adapted to various types of functional agents by "snapping-on" various types of linkers. For example, if it is desired to conjugate a larger functional agent to a polymer of the instant invention such as an antibody of even a Fab fragment, a longer linker sequence can be snapped on to the polymer. In contrast, smaller functional agents may call for relatively shorter linker sequences.

In some embodiments of the methods, the initiator has about 1, 2, 3, 4, 5, 6, 7, 8, 9, 10, 11, or 12 sites for polymer initiation. In some embodiments, the initiator has about 3, about 6, or about 9 sites for polymer initiation.

In accordance with another aspect of the present invention, a second linker has second, third, fourth, fifth, and sixth reactive groups. More preferably, a second linker has just second and third reactive groups.

In accordance with an aspect of the present invention, each polymer arm has from about 20 to about 2000 monomer units. Preferably, each arm has from about 100 to 500 monomer units or from about 500 to 1000 monomer units or from about 1000 to 1500 monomer units or from about 1500 to 2000 monomer units.

In accordance with an aspect of the present invention, the peak molecular weight of the polymer-functional agent conjugate is about 100,000 to 1,500,000 Da. Preferably, the peak molecular weight of the polymer-functional agent conjugate is about 200,000 to about 300,000 Da, about 400,000 to about 600,000 Da or about 650,000 to about 850,000 Da.

In accordance with another aspect of the present invention, the first linker is preferably alkyl, substituted alkyl, alkylene, alkoxy, carboxyalkyl, haloalkyl, cycloalkyl, cyclic alkyl ether, alkenyl, alkenylene, alkynyl, alkynylene, cycloalkylene, heterocycloalkyl, heterocycloalkylene, aryl, arylene, arylene-oxy, heteroaryl, amino, amido or any combination thereof. More preferably, the first linker has the formula:

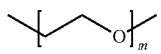

Formula (1)

wherein m is 1 to 10. In some embodiments, the first linker has the above formula (Formula (1)) and m is 4.

In some embodiments, the initiator preferably includes a structure selected from group consisting of

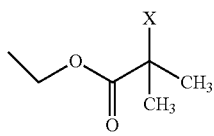

Formula (2)

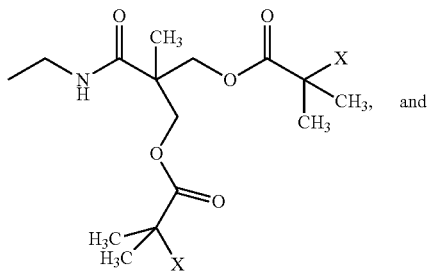 and

Formula (3)

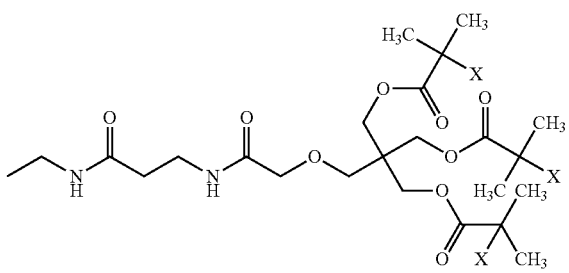

Formula (4)

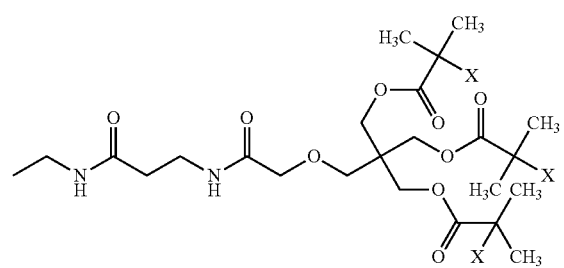

Formula (4)

wherein X is selected from the group consisting of NCS, F, Cl, Br and I. More preferably, X in Formula (2), Formula (3) and/or Formula (4) is Br.

In some embodiments, the monomer is selected from the group consisting of

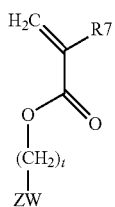

Formula (5)

-continued

Formula (6)
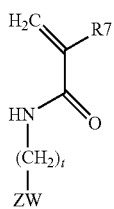

Formula (7)

Formula (8)

Formula (9)

wherein R7 is H or $C_1$-6 alkyl and t is 1 to 6.

More preferably, the monomer is selected from the group consisting of 2-(methacryloyloxyethyl)-2'-(trimethylammoniumethyl) phosphate (HEMA-PC) and 2-(acryloyloxyethyl)-2'-(trimethylammoniumethyl) phosphate.

Most preferably, the monomer is 2-(methacryloyloxyethyl)-2'-(trimethylammoniumethyl) phosphate.

The second linker moiety preferably comprises an activated ester having the

Formula (10)
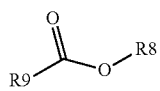

wherein R8 is selected from the group consisting of

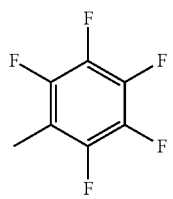 and 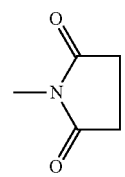

and R9 is

Formula (11)
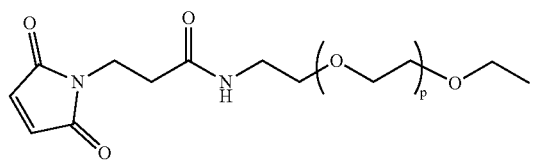

wherein p is 1 to 12.

In more preferred embodiments of the present invention, the polymer has 9 arms, m is 2-4, R9 is Formula (11)
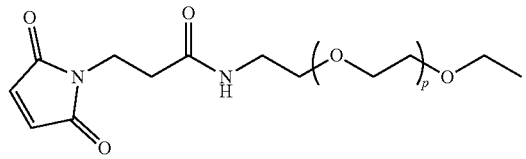

wherein p is 4 to 15. Still more preferably, m is 4 and p is 12.

In some embodiments, the radically polymerizable monomer is

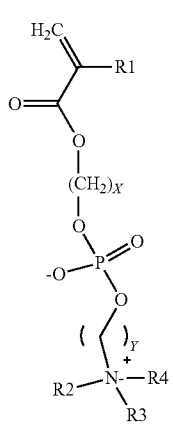

Formula (12)

wherein R1 is H or C1-6 alkyl, R2, R3, R4 are the same or different and are H or C1-4alkyl and X and Y are the same or different and are integers from 1-6. In some embodiments, R1, R2, R3 and R4 are each methyl and X and Y are each 2 in Formula (12).

In some embodiments, the radically polymerizable monomer is

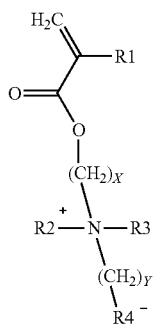

Formula (13)

wherein R1 is H or C1-6alkyl, R2 and R3 are the same or different and are H or C1-4alkyl, R4 is PO4-, SO3- or CO2- and X and Y are the same or different and are integers from 1-6. In some embodiments, R1, R2 and R3 are methyl, R4 is PO4- and X and Y are each 2 in Formula (13).

In some embodiments, the monomer is

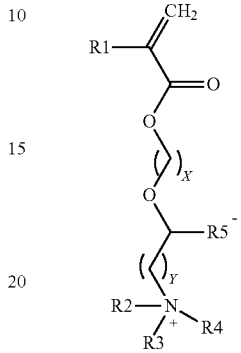

Formula (14)

wherein R1 is H or C1-6alkyl, R2, R3 and R4 are the same or different and are H or C1-4alkyl, R5 is PO4-, SO3- or CO2- and X and Y are the same or different and are integers from 1-6. In some embodiments, R1, R2, R3 and R4 are methyl, R5 is PO4- and X and Y are 2 in Formula (14).

When a polymer is the to be conjugated via a cysteine (or other specified residue), the polymer can be linked directly or indirectly to the residue (e.g., with an intervening initiator, and or spacer or the like).

In some embodiments, the phosphorylcholine containing polymer comprises 2-(methacryloyloxyethyl)-2'-(trimethyl-ammonium)ethyl phosphate (MPC) monomers as set forth below:

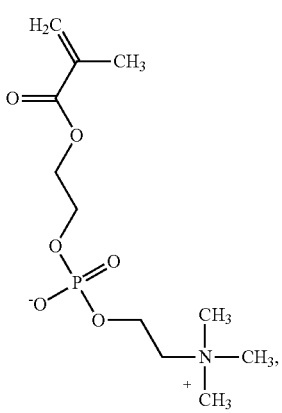

Formula (15)

such that the polymer comprises the following repeating units:

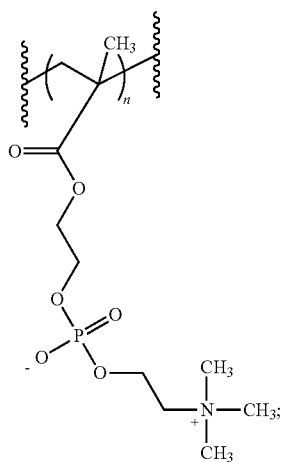

Formula (16)

where n is an integer from 1 to 3000 and the wavy lines indicate the points of attachment between monomer units in the polymer.

In some embodiments, the polymer has three or more arms, or is synthesized with an initiator comprising 3 or more polymer initiation sites. In some embodiments, the polymer has 2, 3, 4, 5, 6, 7, 8, 9, 10, 11 or 12 arms, or is synthesized with an initiator comprising 2, 3, 4, 5, 6, 7, 8, 9, 10, 11, or 12 polymer initiation sites. More preferably, the polymer has 3, 6, or 9 arms, or is synthesized with an initiator comprising 3, 6, or 9 polymer initiation sites. In some embodiments, the polymer has 9 arms, or is synthesized with an initiator comprising 9 polymer initiation sites.

In some embodiments, the polymer that is added has a molecular weight between about 300,000 and about 1,750,000 Da (SEC-MALs). In some embodiments, the polymer has a molecular weight between about 500,000 and about 1,000,000 Da. In some embodiments, the polymer has a molecular weight of between about 600,000 to about 900,000 Da. In some embodiments, the polymer has a molecular weight of between about 750,000 to about 850,000 Da. In some embodiments, the polymer has a molecular weight of between about 800,000 to about 850,000 Da. In some embodiments, the polymer has a molecular weight of between about 750,000 to about 800,000 Da.

In some embodiments, any of the antibodies and/or Ab-Traps described herein can be further conjugated to a polymer to form a bioconjugate. The molecular weight of the bioconjugate (in total, SEC-MALs) can be between about 350,000 and 2,000,000 Daltons, for example, between about 450,000 and 1,900,000 Daltons, between about 550,000 and 1,800,000 Daltons, between about 650,000 and 1,700,000 Daltons, between about 750,000 and 1,600,000 Daltons, between about 850,000 and 1,500,000 Daltons, between about 900,000 and 1,400,000 Daltons, between about 950,000 and 1,300,000 Daltons, between about 900,000 and 1,000,000 Daltons, between about 1,000,000 and 1,300,000 Daltons, between about 850,000 and 1,300,000 Daltons, between about 850,000 and 1,000,000 Daltons, and between about 1,000,000 and 1,200,000 Daltons. In some embodiments, the bioconjugate has a molecular weight between about 350,000 and 1,900,000 Daltons.

In some embodiments, the antibody and/or Ab-Trap conjugate is purified. In some embodiments, the polymer in aspect of the antibody and/or Ab-Trap conjugate is polydisperse, i.e. the polymer PDI is not 1.0. In some embodiments, the PDI is less than 1.5. In some embodiments, the PDI is less than 1.4. In some embodiments, the PDI is less than 1.3. In some embodiments the PDI is less than 1.2. In some embodiments the PDI is less than 1.1. In some embodiments, the conjugate PDI is equal to or less than 1.5.

In some embodiments, the antibody and/or Ab-Trap conjugate has an anti-IL-6 immunoglobulin G (IgG) bonded to a polymer, which polymer comprises MPC monomers, wherein the sequence of the anti-IL-6 heavy chain is in Table 1, and the sequence of the anti-IL-6 light chain is in Table 2, and wherein the antibody and/or Ab-Trap is bonded only at C442 to the polymer. In some embodiments, the polymer has 9 arms and has a molecular weight of between about 600,000 to about 1,000,000 Da.

In some embodiments, the antibody and/or Ab-Trap conjugate has an anti-IL-6 immunoglobulin G (IgG) bonded to a polymer, which polymer comprises MPC monomers, wherein the sequence of the anti-IL-6 heavy chain comprises in Table 1, and the sequence of the anti-IL-6 light chain comprises in Table 2, and wherein the antibody is bonded only at C443 (EU numbering to the polymer. In some embodiments, the polymer has 9 arms and has a molecular weight of between about 600,000 to about 1,000,000 Da. In some embodiments, the conjugate comprises a polymer that has 9 arms and the polymer has a molecular weight of between about 600,000 to about 900,000 Da.

In some embodiments, the antibody conjugate has the following structure:

Formula (17)

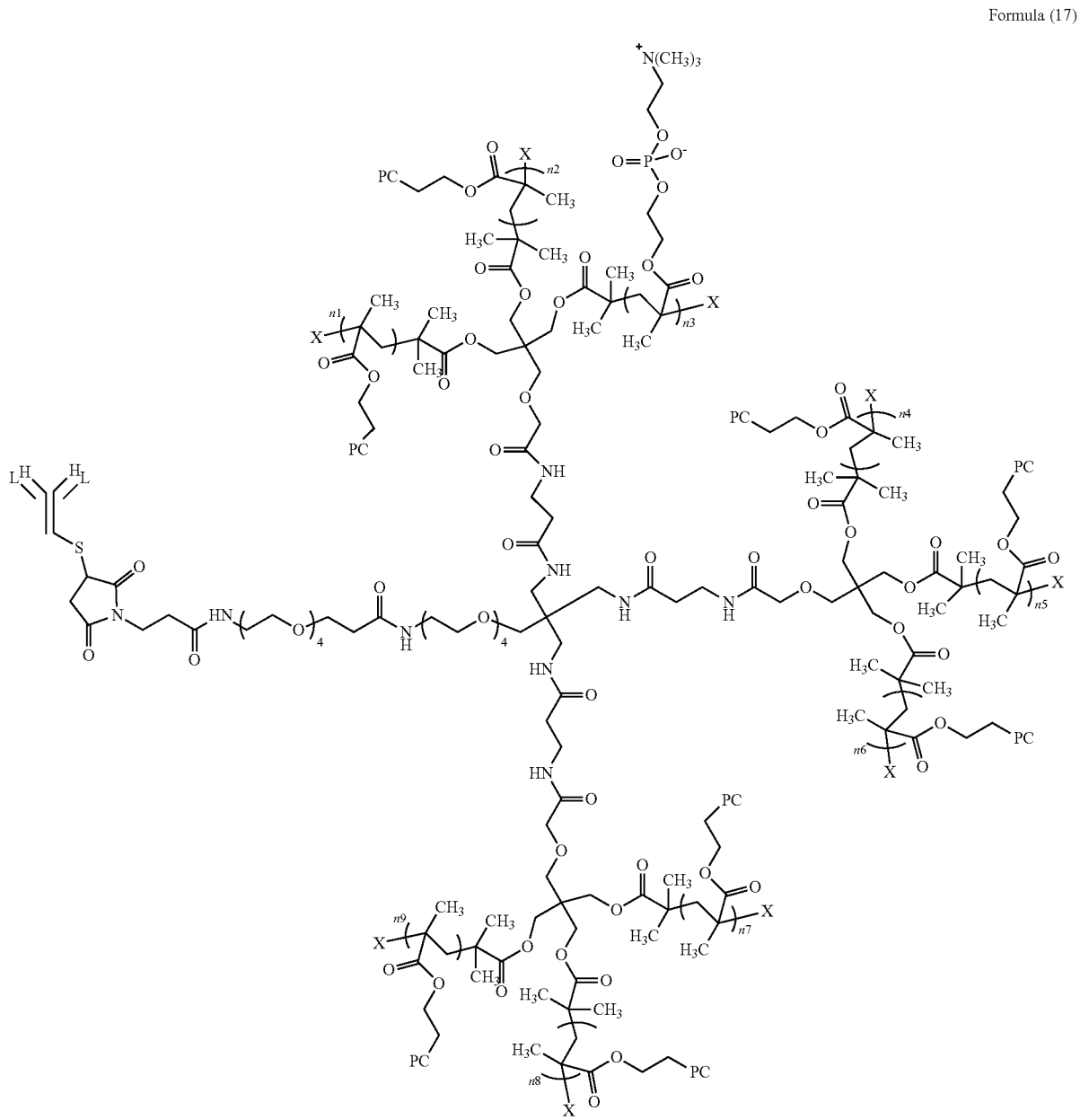

wherein: each heavy chain of the anti-IL-6 antibody is denoted by the letter H, and each light chain of the anti-IL-6 antibody is denoted by the letter L (which, in some embodiments, can further be linked to the Ab-Trap arrangement, as shown in FIG. 6);

the polymer is bonded to the anti-IL-6 antibody (and/or Ab-Trap) through the sulfhydryl of C443 (EU numbering), which bond is depicted on one of the heavy chains; PC is, where the curvy line indicates the point of attachment to the rest of the polymer; wherein X=a) OR where R=H, Methyl, ethyl, propyl, isopropyl, b) H, or c) any halide, including Br; and $n_1$, $n_2$, $n_3$, $n_4$, $n_5$, $n_6$, $n_7$, $n_8$ and $n_9$ are the same or different such that the sum of $n_1$, $n_2$, $n_3$, $n_4$, $n_5$, $n_6$, $n_7$, $n_8$ and $n_9$ is 2500 plus or minus 10%. In some embodiments, $n_1$, $n_2$, $n_3$, $n_4$, $n_5$, $n_6$, $n_7$, $n_8$ and $n_9$ are the same or different and are integers from 0 to 3000. In some embodiments, $n_1$, $n_2$, $n_3$, $n_4$, $n_5$, $n_6$, $n_7$, $n_8$ and $n_9$ are the same or different and are integers from 0 to 500. In some embodiments, X=OR, where R is a sugar, an aminoalkyl, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl, —CO—O—$R_7$, carbonyl —CCO—$R_7$, —CO—$NR_8R_9$, —$(CH_2)_n$—$COOR_7$, —CO—$(CH)_n$—$COOR_7$, —$(CH_2)_n$—$NR_8R_9$, ester, alkoxycarbonyl, aryloxycarbonyl, wherein n is an integer from 1 to 6, wherein each $R_7$, $R_8$ and $R_9$ is separately selected from the group consisting of a hydrogen atom, halogen atom, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl, a 5-membered ring, and a 6-membered ring. In some embodiments, Formula 17 can be part of a fusion protein, which would further include some or all of the sequence of Table 10, so as to make an IL-6 Ab VEGF Trap fusion protein. In some embodiments, the fusion in FIG. 27 can be used within formula 17, with the fusion replacing the depicted antibody.

In some embodiments, the antibody conjugate has the following structure:

Formula (17)

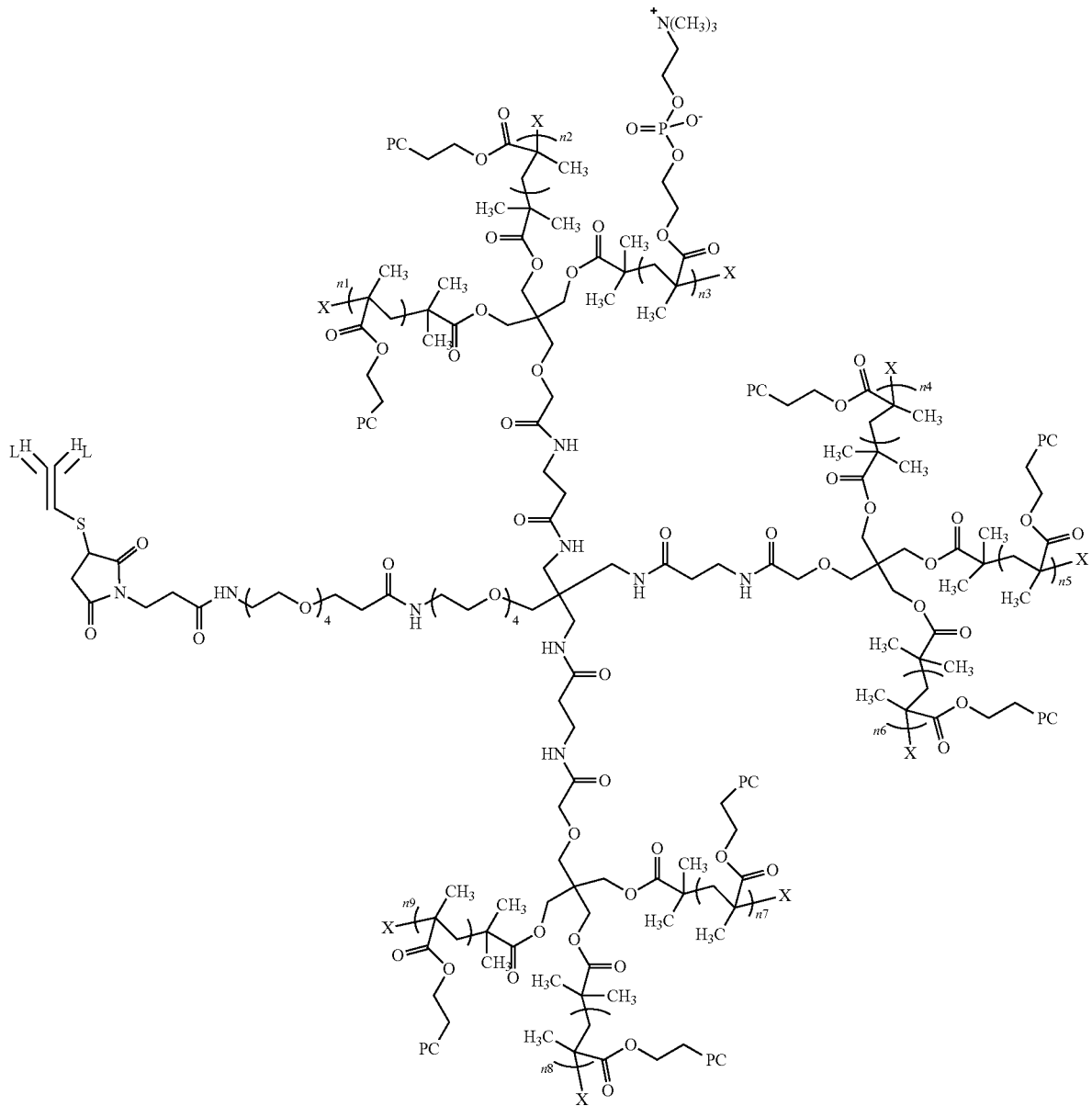

wherein:
each heavy chain of the antibody is denoted by the letter H, and each light chain of the anti-IL-6 antibody is denoted by the letter L (which, in some embodiments, can further be linked to the Ab-Trap arrangement, as shown in FIG. 6);
the polymer is bonded to the antibody through the sulfhydryl of C443 (EU numbering), which bond is depicted on one of the heavy chains;
PC is

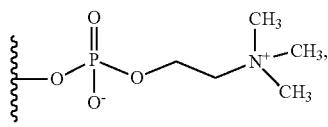 [SMILES: *OP(=O)([O-])OCC[N+](C)(C)C]

where the curvy line indicates the point of attachment to the rest of the polymer, where X=a) OR where R=H, methyl, ethyl, propyl, isopropyl, b) H, or c) any halide, including Br; and
n1, n2, n3, n4, n5, n6, n7, n8 and n9 are the same or different such that the sum of n1, n2, n3, n4, n5, n6, n7, n8 and n9 is 2500 plus or minus 15%. In some embodiments, the sum of n1, n2, n3, n4, n5, n6, n7, n8 and n9 is about 1500 to about 3500 plus or minus about 10% to about 20%. In some embodiments, the fusion in FIG. 27 can be used within formula 17, with the fusion replacing the depicted antibody.

In some embodiments, the antibody and/or Ab-Trap conjugate is present in a liquid formulation. In some embodiments, the antibody and/or Ab-Trap conjugate is combined with a pharmaceutically acceptable carrier.

In some embodiments, the isotype of the anti-IL-6 antibody (and/or IL-6 Ab-VEGF Trap) heavy chain, is IgG1 and has a $CH_1$, hinge, $CH_2$ and $CH_3$ domains. In some embodiments the light chain isotype is kappa.

In some embodiments, the IgG1 domain of the anti-IL-6 antibody (and/or IL-6 Ab-VEGF Trap) has one or more mutations to modulate effector function, such as ADCC, ADCP, and CDC. In some embodiments, the IgG1 mutations reduce effector function. In some embodiments the amino acids to use for effector function mutations include (EU numbering) E233X, L234X, L235X, G236X, G237X, G236X, D270X, K322X, A327X, P329X, A330X, A330X, P331X, and P331X, in which X is any natural or non-natural amino acid. In some embodiments, the mutations include one or more of the following: E233P, L234V, L234A, L235A, G237A, A327G, A330S and P331S (EU numbering). In some embodiments, the anti-IL-6 heavy chain has the following mutations (EU numbering): L234A, L235A and G237A. In some embodiments, the number of effector function mutations relative to a natural human IgG1 sequence is no more than 10. In some embodiments the number of effector function mutations relative to a natural human IgG1 sequence is no more than 5, 4, 3, 2 or 1. In some embodiments, the antibody (and/or IL-6 Ab-VEGF Trap) has decreased Fc gamma binding and/or complement C1q binding, such that the antibody's ability to result in an effector function is decreased. This can be especially advantageous for ophthalmic indications/disorders.

In some embodiments, the anti-IL-6 antibody (and/or IL-6 Ab-VEGF Trap) comprises one or more of the following amino acid mutations: L234A, L235A, G237A, and L443C (EU numbering, or 451A, 452A, and 454A, and 660C in SEQ ID NO: 170, as shown in double underlining in FIG. 27).

In some embodiments, the anti-IL-6 antibody (and/or IL-6 Ab VEGFTrap) is or is part of a human immunoglobulin G (IgG1).

In some embodiments, the IL-6 antibody (and/or IL-6 Ab-VEGF Trap) comprises a heavy chain constant domain that comprises one or more mutations that reduce an immune-mediated effector function.

In some embodiments, the anti-IL-6 heavy chain has a cysteine residue added as a mutation by recombinant DNA technology which can be used to conjugate a half-life extending moiety. In some embodiments, the mutation is Q347C (EU numbering) and/or L443C (EU numbering). In some embodiments, the mutation is L443C (EU numbering). In some embodiments, the stoichiometry of antibody to polymer is 1:1; in other words, a conjugate has one molecule of antibody conjugated to one molecule of polymer.

The half-life of the anti-IL-6 antibodies can be extended by attachment of a "half-life ("half life") extending moieties" or "half-life ("half life") extending groups". Half-life extending moieties include peptides and proteins which can be expressed in frame with the biological drug of issue (or conjugated chemically depending on the situation) and various polymers which can be attached or conjugated to one or more amino acid side chain or end functionalities such as —SH, —OH, —COOH, —CONH2, —NH2, or one or more N- and/or O-glycan structures. Half-life extending moieties generally act to increase the in vivo circulatory half-life of biologic drugs.

Examples of peptide/protein half-life extending moieties include Fc fusion (Capon D J, Chamow S M, Mordenti J, et al. Designing CD4 immunoadhesions for AIDS therapy. Nature. 1989. 337:525-31), human serum albumin (HAS) fusion (Yeh P, Landais D, Lemaitre M, et al. Design of yeast-secreted albumin derivatives for human therapy: biological and antiviral properties of a serum albumin-CD4 genetic conjugate. Proc Natl Acad Sci USA. 1992. 89:1904-08), carboxy terminal peptide (CTP) fusion (Fares F A, Suganuma N. Nishimori K, et al. Design of a long-acting follitropin agonist by fusing the C-terminal sequence of the chorionic gonadotropin beta subunit to the follitropin beta subunit. Proc Natl Acad Sci USA. 1992. 89:4304-08), genetic fusion of non-exact repeat peptide sequence (XTEN) fusion (Schellenberger V, Wang C W, Geething N C, et al. A recombinant polypeptide extends the in vivo half-life of peptides and proteins in a tunable manner. Nat Biotechnol. 2009. 27:1186-90), elastin like peptide (ELPylation) (MCpherson DT, Morrow C, Minehan D S, et al. Production and purification of a recombinant elastomeric polypeptide, G(VPGVG19-VPGV, from *Escherichia coli*. Biotechnol Prog. 1992. 8:347-52), human transferrin fusion (Prior C P, Lai C-H, Sadehghi H et al. Modified transferrin fusion proteins. Patent WO2004/020405. 2004), proline-alanine-serine (PASylation) (Skerra A, Theobald I, Schlapsky M. Biological active proteins having increased in vivo and/or vitro stability. Patent WO2008/155134 A1. 2008), homo-amino acid polymer (HAPylation) (Schlapschy M, Theobald I, Mack H, et al. Fusion of a recombinant antibody fragment with a homo-amino acid polymer: effects on biophysical properties and prolonged plasma half-life. Protein Eng Des Sel. 2007. 20:273-84) and gelatin like protein (GLK) fusion (Huang Y-S, Wen X-F, Zaro J L, et al. Engineering a pharmacologically superior form of granulocyte-colony-stimulating-factor by fusion with gelatin-like protein polymer. Eur J. Pharm Biopharm. 2010. 72:435-41).

Examples of polymer half-life extending moieties include polyethylene glycol (PEG), branched PEG, PolyPEG® (Warwick Effect Polymers; Coventry, UK), polysialic acid (PSA), starch, hydroxylethyl starch (HES), hydroxyalkyl starch (HAS), carbohydrate, polysaccharides, pullulane, chitosan, hyaluronic acid, chondroitin sulfate, dermatan sulfate, dextran, carboxymethyl-dextran, polyalkylene oxide (PAO), polyalkylene glycol (PAG), polypropylene glycol (PPG), polyoxazoline, polyacryloylmorpholine, polyvinyl alcohol (PVA), polycarboxylate, polyvinylpyrrolidone, polyphosphazene, polyoxazoline, polyethylene-co-maleic acid anyhydride, polystyrene-co-maleic acid anhydride, poly(1-hydroxymethyethylene hydroxymethylformal) (PHF), a zwitterionic polymer, a phosphorylcholine containing polymer and a polymer comprising MPC, Poly $(Gly_x\text{-}Ser_y)$, Hyaluronic acid (HA), Heparosan polymers (HEP), Fleximers, Dextran, and Poly-sialic acids (PSA).

In one embodiment a half-life extending moiety can be conjugated to an antibody via free amino groups of the protein using N-hydroxysuccinimide (NHS) esters. Reagents targeting conjugation to amine groups can randomly react to ε-amine group of lysines, α-amine group of N-terminal amino acids, and δ-amine group of histidines.

However, the anti-IL-6 antibodies (and/or IL-6 Ab-VEGF Trap) disclosed herein can have many amine groups available for polymer conjugation. Conjugation of polymers to free amino groups, thus, might negatively impact the ability of the antibody proteins to bind to IL-6 (and/or IL-6 Ab-VEGF Trap).

In some embodiments, a half-life extending moiety is coupled to one or more free SH groups using any appropriate thiol-reactive chemistry including, without limitation, maleimide chemistry, or the coupling of polymer hydrazides or polymer amines to carbohydrate moieties of the antibody after prior oxidation. In some embodiments maleimide coupling is used In some embodiments, coupling occurs at cysteines naturally present or introduced via genetic engineering.

In some embodiments, conjugates of antibody and high MW polymers serving as half-life extenders are provided. In some embodiments, a conjugate comprises an antibody (and/or IL-6 Ab-VEGF Trap) that is coupled to a zwitterionic polymer wherein the polymer is formed from one or more monomer units and wherein at least one monomer unit has a zwitterionic group is provided. In some embodiments, the zwitterionic group is phosphorylcholine.

In some embodiments, one of the monomer units is HEMA-PC. In some embodiments, a polymer is synthesized from a single monomer which is HEMA-PC.

In some embodiments, some antibody (and/or IL-6 Ab VEGFTrap) conjugates have 2, 3, or more polymer arms wherein the monomer is HEMA-PC. In some embodiments, the conjugates have 2, 3, 4, 5, 6, 7, 8, 9, 10, 11, or 12 polymer arms wherein the monomer is HEMA-PC. In some embodiments, the conjugates have 3, 6 or 9 arms. In some embodiments, the conjugate has 9 arms.

In some embodiments, polymer-antibody (and/or polymer-IL-6 Ab-VEGFTrap) conjugates have a polymer portion with a molecular weight of between 100,000 and 1,500,000 Da. In some embodiments, the conjugate has a polymer portion with a molecular weight between 500,000 and 1,000,000 Da. In some embodiments, the conjugate has a polymer portion with a molecular weight between 600,000 to 800,000 Da. In some embodiments, the conjugate has a polymer portion with a molecular weight between 600,000 and 850,000 Da and has 9 arms. When a molecular weight is given for an antibody conjugated to a polymer, the molecular weight will be the addition of the molecular weight of the protein, including any carbohydrate moieties associated therewith, and the molecular weight of the polymer.

In some embodiments, an anti-IL-6 antibody (and/or IL-6 Ab VEGF Trap) has a HEMA-PC polymer which has a molecular weight measured by Mw of between about 100 kDa and 1650 kDa is provided. In some embodiments, the molecular weight of the polymer as measured by Mw is between about 500 kDa and 1000 kDa. In some embodiments, the molecular weight of the polymer as measured by Mw is between about 600 kDa to about 900 kDa. In some embodiments, the polymer molecular weight as measured by Mw is 750 or 800 kDa plus or minus 15%.

In some embodiments, the polymer is made from an initiator suitable for ATRP having one or more polymer initiation sites. In some embodiments, the polymer initiation site has a 2-bromoisobutyrate site. In some embodiments, the initiator has 3 or more polymer initiation sites. In some embodiments, the initiator has 3, 4, 5, 6, 7, 8, 9, 10, 11 or 12 polymer initiation sites. In some embodiments, the initiator has 3, 6 or 9 polymer initiation sites. In some embodiments, the initiator has 9 polymer initiation sites. In some embodiments, the initiator is OG1786.

The anti-IL-6 antibodies (and/or IL-6 Ab-VEGFTrap) can be produced by recombinant expression including (i) the production of recombinant DNA by genetic engineering, (ii) introducing recombinant DNA into prokaryotic or eukaryotic cells by, for example and without limitation, transfection, electroporation or microinjection, (iii) cultivating the transformed cells, (iv) expressing antibody, e.g. constitutively or on induction, and (v) isolating the antibody, e.g. from the culture medium or by harvesting the transformed cells, in order to (vi) obtain purified antibody.

The anti-IL-6 antibodies (and/or IL-6 Ab-VEGF Trap) can be produced by expression in a suitable prokaryotic or eukaryotic host system characterized by producing a pharmacologically acceptable antibody molecule. Examples of eukaryotic cells are mammalian cells, such as CHO, COS, HEK 293, BHK, SK-Hip, and HepG2. Other suitable expression systems are prokaryotic (e.g., E. coli with pET/BL21 expression system), yeast (Saccharomyces cerevisiae and/or Pichia pastoris systems), and insect cells.

A wide variety of vectors can be used for the preparation of the antibodies (and/or IL-6 Ab-VEGF Trap) disclosed herein and are selected from eukaryotic and prokaryotic expression vectors. Examples of vectors for prokaryotic expression include plasmids such as, and without limitation, preset, pet, and pad, wherein the promoters used in prokaryotic expression vectors include one or more of, and without limitation, lac, trc, trp, recA, or araBAD. Examples of vectors for eukaryotic expression include: (i) for expression in yeast, vectors such as, and without limitation, pAO, pPIC, pYES, or pMET, using promoters such as, and without limitation, AOX1, GAP, GAL1, or AUG1; (ii) for expression in insect cells, vectors such as and without limitation, pMT, pAc5, pIB, pMIB, or pBAC, using promoters such as and without limitation PH, p10, MT, Ac5, OpIE2, gp64, or polh, and (iii) for expression in mammalian cells, vectors such as, and without limitation, pSVL, pCMV, pRc/RSV, pcDNA3, or pBPV, and vectors derived from, in one aspect, viral systems such as and without limitation vaccinia virus, adeno-associated viruses, herpes viruses, or retroviruses, using promoters such as and without limitation CMV, SV40, EF-1, UbC, RSV, ADV, BPV, and beta-actin.

In some embodiments, there is at least one polymer per protein. In some embodiments, the ratio of protein to polymer is 1:4 to 1:6. In some embodiments, the ratio of protein (Ab) to polymer is 1:5 molar ratio. In some embodiments, the amount of protein is 5, 4, 3, 2, or about 2.4 mg/ml.

In some embodiments, the purification following the combination of the polymer and the antibody further comprises a cation exchange column.

In some embodiments, the presence of the polymer attached to the IL-6 antagonist antibodies and/or IL-6 Ab VEGF Traps can provide a deeper potency due to the presence of the polymer itself. In some embodiments, the presence of the polymer, when used in combination with a heparin binding domain, (such as in VEGF) results in a conjugated molecule with deeper potency. In some embodiments, as shown in the HUVECs data provided in the examples below, the molecule is superior in angiogenesis. In some embodiments, this is a difference in nature of the conjugate molecule, not simply a difference in degree (e.g., comparing the conjugate to the unconjugated molecules). Furthermore, as shown in the HUVEC proliferation assays in the examples below, in some embodiments, the presence of the polymer provides for synergistic inhibition.

In addition, in some embodiments, as cell densities are increased (e.g., from 4,000 to 6,000), the potency of the conjugate may also improve.

In some embodiments, the amount (by weight of protein) of the conjugate used is more than 50 mg/ml. It can be, for example, 55, 60, 65, 70 or greater mg/ml (by weight of pre-conjugation protein).

Method of Conjugating Proteins to Polymers

In some embodiments, a method is presented of preparing a therapeutic protein-half life extending moiety conjugate having the step of conjugating a therapeutic protein which has a cysteine residue added via recombinant DNA technology to a half-life extending moiety having a sulfhydryl specific reacting group selected from the group consisting of maleimide, vinylsulfones, orthopyridyl-disulfides, and iodoacetamides to provide the therapeutic protein-half life extending moiety conjugate.

Figure 10:
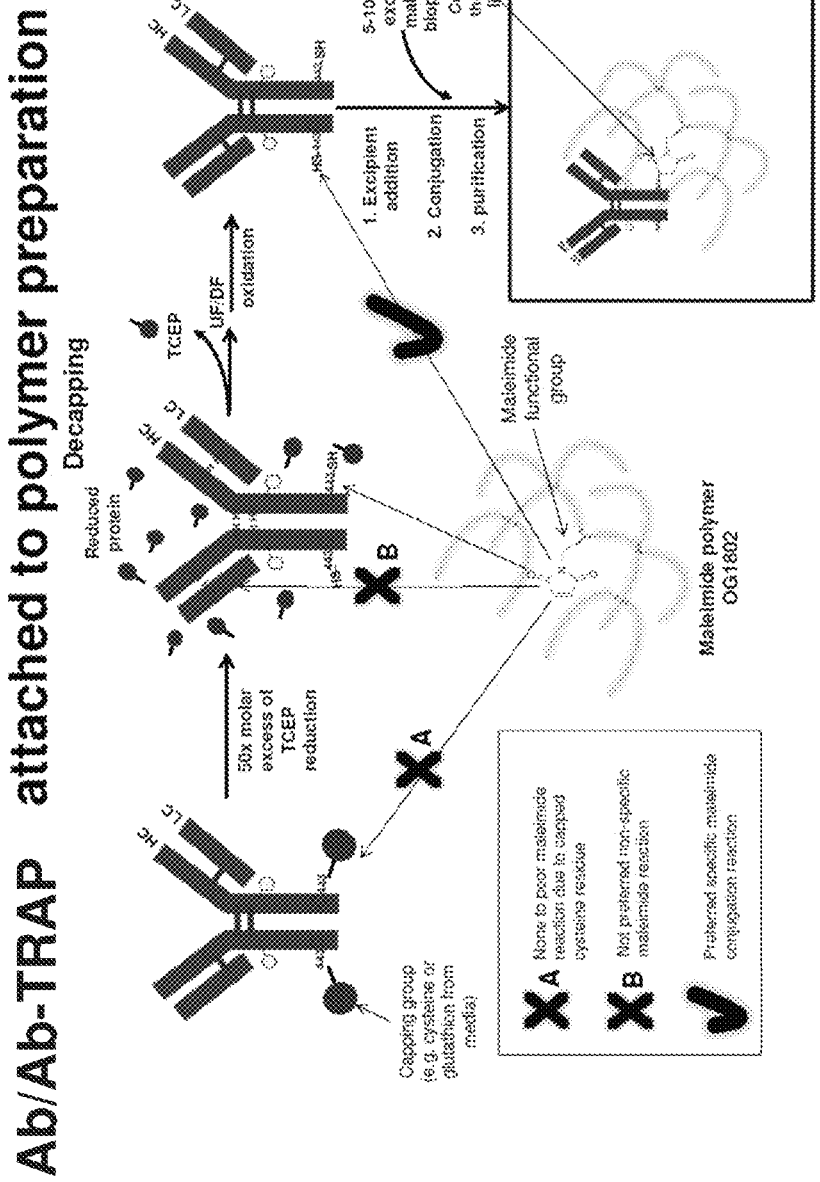
FIG. 10 depicts some embodiments of a method for preparing an antibody conjugate (which can also be applied for an Ab-Trap or Trap-Ab conjugate as well). While depicted as an antibody, one of skill in the art will appreciate, in the present context, that the Ab depiction within FIG. 10 can be swaped with a trap fusion (as shown in FIG. 6). For the sake of simplicity, the generic antibody depicted herein represents both options as an antibody and options as a fusion arrangement in the fusion trap context (unless, of course, it is already depicted as a fusion).

In some embodiments a method of preparing the antibody (and/or IL-6 Ab-VEGF Trap) conjugate is provided. As shown in FIG. 10, the method comprises reducing the protein with a 30× molar excess of the TCEP reducing agent (FIG. 10). After reduction, the antibody is oxidized to produce a decapped antibody where the inter- and intra-light and heavy chain disulfide bonds naturally occurring in the antibody are formed, but the engineered Cysteine on the heavy chain position L443C (EU numbering) remains to be decapped (FIG. 10). The antibody is then conjugated by adding an excipient and adding 2-10× molar excess of a maleimide biopolymer. (FIG. 10). The biopolymer links to the antibody through a covalent thioether linkage (FIG. 10). After conjugation, the antibody conjugate is purified with both unconjugated antibody and polymer removed (FIG. 10). In embodiments in which the protein is an Ab-Trap, the same position on the antibody can be used and the same approach employed.

The protein and process described above can be varied as well. Thus, in some embodiments, a process for preparing a conjugated protein (which need not be an antibody or an anti-IL-6 antibody) is provided. The process includes reducing one or more cysteines in a protein to form a decapped protein in a solution. After reducing the one or more cysteines the decapped protein is reoxidized to restore at least one disulfide linkage in the reduced protein while ensuring that an engineered cysteine residue in the protein remains in a free thiol form to form a reoxidized decapped protein in the solution. At least one excipient is then added to the solution. The excipient reduces a polymer induced protein precipitation. After the excipient is added, a polymer is added to the solution, which is conjugated to the reoxidized decapped protein at the engineered cysteine residue to form a conjugated protein.

In some embodiments, the molar excess of the reducing agent can be altered to any amount that functions. In some embodiments 10, 20, 30, 40, 50, 60, 70, 80, 90× molar excess of the reducing agent (which need not be TCEP in all embodiments) can be employed. In some embodiments, the reducing agent can be Trisodium 3,3',3"-phosphinetriyltris (benzene-1-sulphonate) (TPPTS). In some embodiments, any antibody (therapeutic or otherwise) can be employed. In some embodiments, 1, 2, 3, 4, 5, 6, 7, 8, 9, 10, 11, 12, 13, 14, 15× molar excess of a maleimide biopolymer can be employed. In some embodiments, there is an excess of decapped protein to polymer. In some embodiments, the amount of the reduced protein is less than the amount of the polymer. In some embodiments, the amount of the reduced protein is 90%, 80%, 70%, 60%, 50%, 40%, 30%, 20%, 10%, 5%, 4%, 3%, 2%, 1% of the amount of the polymer. In some embodiments, 10-15 times as much polymer is used as protein. In some embodiments the amount of the reduced antibody is greater than the amount of the polymer. In some embodiments the amount of the polymer is greater than the amount of the reduced antibody (and/or IL-6 Ab-VEGF Trap).

In some embodiments, the purification step is optional.

In some embodiments, the method of making an antibody conjugate (and/or Ab-Trap) comprises conjugating an anti-IL-6 antibody (and/or IL-6 Ab-VEGF Trap) to a phosphorylcholine containing polymer. In some embodiments the method comprises the steps of conjugating an anti-IL-6 antibody to a phosphorylcholine containing polymer. The anti-IL-6 antibody comprises an amino residue added via recombinant DNA technology. In some embodiments, the added amino acid residue is a cysteine residue. In some embodiments, the cysteine residue is added outside a variable region of the antibody. The cysteine residue can be added to either the heavy chain or light chain of the antibody.

In some embodiments, the polymer comprises or consists of a phosphorylcholine containing polymer. In some embodiments, the phosphorylcholine containing polymer comprises a sulfhydryl specific reacting group selected from the group consisting of a maleimide, a vinylsulfone, an orthopyridyl-disulfide, and an iodoacetamide. In some embodiments, the sulfhydryl specific reacting group on the phosphorylcholine containing polymer reacts with the cysteine residue on the anti-IL-6 antibody to make the antibody (and/or IL-6 Ab VEGF Trap) conjugate.

In some embodiments, the protein to be conjugated can be an antibody, an antibody protein fusion (e.g. IL-6 Ab-VEGF Trap), or a binding fragment thereof. In some embodiments, the protein is not an antibody but is an enzyme, a ligand, a receptor, or other protein or mutants or variants thereof. In some embodiments, the native protein contains at least one disulfide bond and at least one non-native cysteine.

In some embodiments, the excipient can be an acid or a base. In some embodiments, the excipient is a detergent, a sugar, or a charged amino acid. In some embodiments, the excipient assists in keeping the protein in solution during the conjugation to the polymer. In some embodiments, the excipient is added to the solution containing the protein, prior to the addition of the polymer to the solution that contains the protein.

In some embodiments, the reaction occurs under aqueous conditions between about pH 5 to about pH 9. In some embodiments, the reaction occurs between 6.0 and 8.5, between 6.5 and 8.0 or between 7.0 and 7.5.

In some embodiments, the polymer is conjugated to the protein at 2-37 degrees Celsius. In some embodiments, the conjugation occurs at 0-40 degrees Celsius, 5-35 degrees Celsius, 10-30 degrees Celsius, and 15-25 degrees Celsius.

In some embodiments, the conjugated proteins described herein can be contacted to an ion exchange medium or hydrophobic interaction chromatography or affinity chromatography medium for purification (to remove the conjugated from the unconjugated). In some embodiments, the ion exchange medium, hydrophobic interaction chromatography, and/or affinity chromatography medium separates the conjugated protein from the unconjugated free polymer and from the unconjugated reoxidized decapped protein.

In some embodiments, the processes described herein and outlined in FIG. 10 involves an excipient that is capable of facilitating and/or maintaining a solubility system. In some embodiments, the process allows the solution to maintain the solubility of the two components meant to interact. This can include the solubility of the protein and the polymer and then the end conjugate as well. In some embodiments, without the excipient approach, the issue can be that while the protein is soluble, when the biopolymer is added, the solubility of the solution (e.g., protein) drops and it crashes/precipitates out of solution. Of course, when the protein crashes out, it is not available to conjugate efficiently with the biopolymer. Thus, an excipient can be employed to maintain the solubility of the protein in the presence of the biopolymer so the two can couple to form the protein conjugate (or as depicted in FIG. 10, an antibody conjugate). This also allows for the solubility of the conjugate to be maintained.

In some embodiments, the polymers disclosed herein can comprise one or more of the following: a zwitterion, a phosphorylcholine, or a PEG linker bridging a center of a polymer branching point to the maleimide functional group. In some embodiments, any of the polymers provided herein can be added to a protein via the methods provided herein.

In some embodiments, any of the proteins provided herein can be conjugated to any of the polymers provided herein via one or more of the methods provided herein.

In some embodiments, the process(es) provided herein allow(s) for larger scale processing to make and purify protein and/or antibody conjugates. In some embodiments, the volume employed is at least 1 liter, for example 1, 10, 100, 1,000, 5,000, 10,000, liters or more. In some embodiments, the amount of the antibody conjugate produced and/or purified can be 0.1, 1, 10, 100, 1000, or more grams.

In some embodiments, the therapeutic protein may be any of the anti-IL-6 antibodies (and/or IL-6 Ab-VEGF Traps) described herein having a cysteine residue added via recombinant DNA technology. In some embodiments, the anti-IL-6 antibody heavy chain has the following CDRs: $CDR_H1$: in Table 1, $CDR_H2$: in Table 1, and $CDR_H3$: in Table 1. The heavy chain can also have arginine (R) at position 84 (via sequential numbering). In some embodiments, the anti-IL-6 light chain has the following CDRs: $CDR_L1$: in Table 2, $CDR_L2$: in Table 2, and CDRL3: in Table 2.

In some embodiments, the anti-IL-6 antibody (and/or IL-6 Ab-VEGF Trap) includes IgG1. In some embodiments, the heavy chain has one or more mutations to modulate effector function. In some embodiments, the mutations are to one or more of the following amino acid positions (EU numbering): E233, L234, L235, G236, G237, A327, A330, and P331. In some embodiments, the mutations are selected from the group consisting of: E233P, L234V, L234A, L235A, G237A, A327G, A330S and P331S (EU numbering). In some embodiments, the mutations are (EU numbering) L234A, L235A and G237A.

In some embodiments, the cysteine residue added to the therapeutic protein via recombinant DNA technology should not be involved in Cys-Cys disulfide bond pairing. In this regard, therapeutic proteins may be dimeric. So for example, an intact anti-IL-6 antibody (and/or IL-6 Ab-VEGF Trap) has two light chains and two heavy chains. If a Cys residue is introduced into the heavy chain for instance, the intact antibody will have two such introduced cysteines at identical positions and the possibility exists that these cysteine residues will form intra-chain disulfide bonds. If the introduced cysteine residues form Cys-Cys disulfide bonds or have a propensity to do so, that introduced Cys residue will not be useful for conjugation. It is known in the art how to avoid positions in the heavy and light chains that will give rise to intra-chain disulfide pairing. See, e.g., U.S. Patent Application No. 2015/0158952.

In some embodiments, the cysteine residue introduced via recombinant DNA technology is selected from the group consisting of (EU numbering) Q347C and L443C. In some embodiments, the cysteine residue is L443C (EU numbering). In some embodiments, the heavy chain the antibody has the amino acid sequence set forth in Table 1 and the light chain has the amino acid sequence of Table 2.

In some embodiments, the sulfhydral specific reacting group is maleimide.

In some embodiments, the half-life extending moiety is selected from the group consisting of polyethylene glycol (PEG), branched PEG, PolyPEG® (Warwick Effect Polymers; Coventry, UK), polysialic acid (PSA), starch, hydroxylethyl starch (HES), hydroxyalkyl starch (HAS), carbohydrate, polysaccharides, pullulane, chitosan, hyaluronic acid, chondroitin sulfate, dermatan sulfate, dextran, carboxymethyl-dextran, polyalkylene oxide (PAO), polyalkylene glycol (PAG), polypropylene glycol (PPG), polyoxazoline, polyacryloylmorpholine, polyvinyl alcohol (PVA), polycarboxylate, polyvinylpyrrolidone, polyphosphazene, polyoxazoline, polyethylene-co-maleic acid anyhydride, polystyrene-co-maleic acid anhydride, poly(1-hydroxymethyethylene hydroxymethylformal) (PHF), a zwitterionic polymer, a phosphorylcholine containing polymer and a polymer comprising 2-methacryloyloxy-2'-ethyl-trimethylammoniumphosphate (MPC).

In some embodiments, the half-life extending moiety is a zwitterionic polymer. In some embodiments, the zwitterion is phosphorylcholine, i.e. a phosphorylcholine containing polymer. In some embodiments, the polymer is composed of MPC units.

In some embodiments, the MPC polymer has three or more arms. In some embodiments, the MPC polymer has 2, 3, 4, 5, 6, 7, 8, 9, 10, 11 or 12 arms. In some embodiments, the MPC polymer has 3, 6, or 9 arms. In some embodiments, the MPC polymer has 9 arms. In some embodiments, the polymer is synthesized with an initiator comprising 2, 3, 4, 5, 6, 7, 8, 9, 10, 11, 12, or more polymer initiation sites In some embodiments, the MPC polymer has a molecular weight between about 300,000 and 1,750,000 Da. In some embodiments, the MPC polymer has a molecular weight between about 500,000 and 1,000,000 Da or between about 600,000 to 900,000 Da.

In some embodiments, the method of preparing a therapeutic protein-half life extending moiety conjugate has an additional step of contacting the therapeutic protein with a thiol reductant under conditions that produce a reduced cysteine sulfhydryl group. As discussed above, it is preferable that the cysteine residue added via recombinant DNA technology are unpaired, i.e. are not involved in Cys-Cys intra chain disulfide bonds or are not substantially involved in such bonding. However, Cys residues which are not involved in such Cys-Cys disulfide bonding and are free for conjugation are known to react with free cysteine in the culture media to form disulfide adducts. See, e.g., WO 2009/052249. A cysteine so derivatized will not be available for conjugation. To free the newly added cysteine from the disulfide adduct, the protein after purification is treated with a reducing agent, e.g., dithiothreitol. However, such treatment with a reducing agent will reduce all of the cysteine residues in the therapeutic protein, including native cysteines many of which are involved in inter and intra chain Cys-Cys disulfides bonds. The native Cys-Cys disulfides are generally crucial to protein stability and activity and they should be reformed. In some embodiments, all native (e.g., inter and intra) Cys-Cys disulfides are reformed.

To reform native inter and intra-chain disulfide residues, after reduction to remove the cysteine disulfide adducts, the therapeutic protein is exposed to oxidizing conditions and/or oxidizing agents for a prescribed period of time, e.g., overnight. In some embodiments, ambient air exposure overnight can be used to achieve reformation of the native disulfide bonds. In some embodiments, an oxidizing agent is employed to restore the native disulfides. In some embodiments, the oxidizing agent is selected from the group consisting of aqueous CuSO4 and dehydroascorbic acid (DHAA). In some embodiments, the oxidizing agent is DHAA. In some embodiments, the range of DHAA used is in the range of 5-30 equivalents. In some embodiments, the range is 10-30 equivalents. In some embodiments, the range is 15 equivalents.

In some embodiments, the thiol reductant is selected from the group consisting of: 3,3',3"-Phosphanetriyltripropanoic acid (TCEP), dithiothreitol (DTT), dithioerythritol (DTE), sodium borohydride (NaBH$_4$), sodium cyanoborohydride (NaCNBH3), β-mercaptoethanol (BME), cysteine hydrochloride, Trisodium 3,3',3"-phosphinetriyltris(benzene-1-sulphonate) (TPPTS). and cysteine. In some embodiments, the thiol reductant is TCEP.

In some embodiments, the thiol reductant concentration is between 1 and 100 fold molar excess relative to the therapeutic protein concentration. In some embodiments, the thiol reductant concentration is between 20 to 50 fold molar excess relative to the therapeutic protein concentration. In some embodiments, the thiol reductant is removed following incubation with the therapeutic protein prior to oxidation of the therapeutic protein.

In some embodiments, the method for conjugating a therapeutic protein to a half-life extending moiety has a further step of purifying the therapeutic protein conjugate after conjugation. In some embodiments, the therapeutic protein conjugate is purified using a technique selected from the group consisting of ion exchange chromatography, hydrophobic interaction chromatography, size exclusion chromatography, and affinity chromatography or combinations thereof.

In some embodiments, the therapeutic protein conjugate retains at least 20% biological activity relative to unconjugated therapeutic protein. In some embodiments, the therapeutic protein conjugate retains at least 50% biological activity relative to unconjugated therapeutic protein. In some embodiments, the therapeutic protein conjugate retains at least 90% biological activity relative to native therapeutic protein.

In some embodiments, the therapeutic protein conjugate has an increased half-life relative to unconjugated therapeutic protein. In some embodiments, the therapeutic protein conjugate has at least a 1.5 fold increase in half-life relative to unconjugated therapeutic protein. In some embodiments, the therapeutic protein conjugate has at least a 1.5, 2, 2.5, 3, 3.5, 4, 4.5 or 5 fold increase in half-life relative to unconjugated therapeutic protein.

In some embodiments, the zwitterionic polymer of the method of conjugating a therapeutic protein to a half-life extending moiety is a radically polymerizable monomer having a zwitterionc group and the method has a further step of polymerizing the free radically polymerizable zwitterionic monomer in a polymerization medium to provide a polymer, the medium comprising: the radically polymerizable zwitterionic monomer; a transition metal catalyst $M_t^{(q-1)+}$ wherein $M_t$ is a transition metal, q is a higher oxidation state of the metal and q−1 is a lower oxidation state of the metal, wherein the metal catalyst is supplied as a salt of the form $M_t^{(q-1)+}X'_{(q-1)}$ wherein X' is a counterion or group or the transition metal catalyst is supplied in situ by providing the inactive metal salt at its higher oxidation state $M_t^{q+}X'_q$ together with a reducing agent that is capable of reducing the transition metal from the oxidized inactive state to the reduced active state; a ligand; and an initiator.

To function as an ATRP transition metal catalyst, the transition metal should have at least two readily accessible oxidation states separated by one electron, a higher oxidation state and a lower oxidation state. In ATRP, a reversible redox reaction results in the transition metal catalyst cycling between the higher oxidation state and the lower oxidation state while the polymer chains cycle between having propagating chain ends and dormant chain ends. See, e.g., U.S. Pat. No. 7,893,173.

In some embodiments, the radically polymerizable zwitterionic monomer is selected from the group consisting of

Formula (18)

Formula (19)

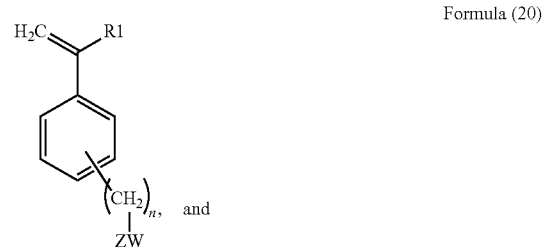

Formula (20)

and

-continued

Formula (21)

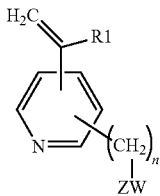

wherein R1 is H or C1-6 alkyl, ZW is a zwitterion and n is an integer from 1-6.

In some embodiments, the radically polymerizable monomer is

Formula (12)

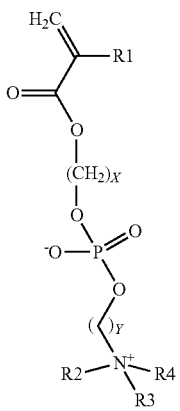

wherein R1 is H or C1-6 alkyl, R2, R3, R4 are the same or different and are H or C1-4alkyl and X and Y are the same or different and are integers from 1-6. In some embodiments, R1, R2, R3 and R4 are each methyl and X and Y are each 2 in Formula (12).

In some embodiments, the radically polymerizable monomer is

Formula (13)

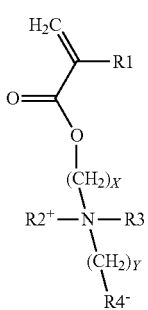

wherein R1 is H or C1-6alkyl, R2 and R3 are the same or different and are H or C1-4alkyl, R4 is PO4-, SO3- or CO2- and X and Y are the same or different and are integers from 1-6. In some embodiments, R1, R2 and R3 are methyl, R4 is PO4- and X and Y are each 2 in Formula (13).

In some embodiments, the monomer is

Formula (14)

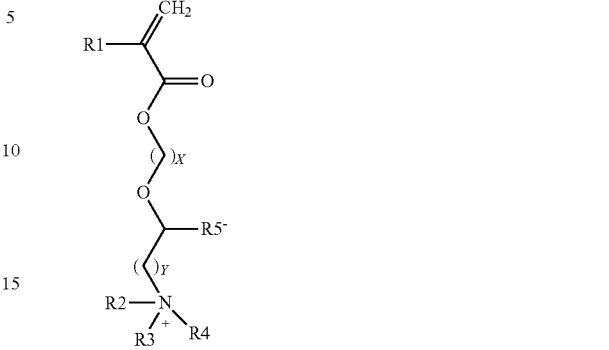

wherein R1 is H or C1-6alkyl, R2, R3 and R4 are the same or different and are H or C1-4alkyl, R5 is PO4-, SO3- or CO2- and X and Y are the same or different and are integers from 1-6. In some embodiments, R1, R2, R3 and R4 are methyl, R5 is PO4- and X and Y are 2 in Formula (14).

In some embodiments, the transition metal Mt is selected from the group consisting of Cu, Fe, Ru, Cr, Mo, W, Mn, Rh, Re, Co, V, Zn, Au, and Ag. In some embodiments, the metal catalyst is supplied as a salt of the form $M_t^{(q-1)+}X'_{(q-1)}$. $M_t^{(q-1)+}$ is selected from the group consisting of $Cu^{1+}$, $Fe^{2+}$, $Ru^{2+}$, $Cr^{2+}$, $Mo^{2+}$, $W^{2+}$, $Mn^{3+}$, $Rh^{3+}$, $Re^{2+}$, $Co^+$, $V^{2+}$, $Zn^+$, $Au^+$, and $Ag^+$ and X' is selected from the group consisting of halogen, $C_{1-6}$ alkoxy, $(SO_4)_{1/2}$, $(PO_4)_{1/3}$, $(R7PO_4)_{1/2}$, $(R7_2PO_4)$, triflate, hexaluorophosphate, methanesulfonate, arylsulfonate, CN and $R7CO_2$, where R7 is H or a straight or branched $C_{1-6}$ alkyl group which may be substituted from 1 to 5 times with a halogen. In some embodiments, $M_t^{(q-1)+}$ is $Cu^{1+}$ and X' is Br.

In some embodiments, $M_t^{(q-1)+}$ is supplied in situ. In some embodiments, $M_t^{q+}X_q$ is $CuBr_2$. In some embodiments, the reducing agent is an inorganic compound. In some embodiments, the reducing agent is selected from the group consisting of a sulfur compound of a low oxidation level, sodium hydrogen sulfite, an inorganic salt comprising a metal ion, a metal, hydrazine hydrate and derivatives of such compounds. In some embodiments, the reducing agent is a metal. In some embodiments, the reducing agent is $Cu^0$.

In some embodiments, the reducing agent is an organic compound. In some embodiments, the organic compound is selected from the group consisting of alkylthiols, mercaptoethanol, or carbonyl compounds that can be easily enolized, ascorbic acid, acetyl acetonate, camphosulfonic acid, hydroxy acetone, reducing sugars, monosaccharides, glucose, aldehydes, and derivatives of such organic compounds.

In some embodiments, the ligand is selected from the group consisting of 2,2'-bipyridine, 4,4'-Di-5-nonyl-2,2'-bipyridine, 4,4-dinonyl-2,2'-dipyridyl, 4,4',4"-tris(5-nonyl)-2,2':6',2"-terpyridine, N,N,N',N',N"-Pentamethyldiethylenetriamine, 1,1,4,7,10,10-Hexamethyltriethylenetetramine, Tris(2-dimethylaminoethyl)amine, N,N-bis(2-pyridylmethyl)octadecylamine, N,N,N',N'-tetra[(2-pyridal)methyl]ethylenediamine, tris[(2-pyridyl)methyl]amine, tris(2-aminoethyl)amine, tris(2-bis(3-butoxy-3-oxopropyl)aminoethyl)amine, tris(2-bis(3-(2-ethylhexoxy)-3-oxopropyl)aminoethyl)amine and Tris(2-bis(3-dodecoxy-3-oxopropyl)aminoethyl)amine. In some embodiments, the ligand is 2,2'-bipyridine.

In some embodiments the initiator has the structure:

$$R1-R2-(R3)_s$$ Formula (22)

wherein R1 is a nucleophilic reactive group, R2 comprises a linker, and R3 comprises a polymer synthesis initiator moiety having the structure

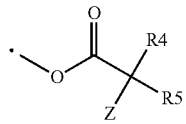

Formula (23)

wherein R4 and R5 and are the same or different and are selected from the group consisting of alkyl, substituted alkyl, alkylene, alkoxy, carboxyalkyl, haloalkyl, cycloalkyl, cyclic alkyl ether, alkenyl, alkenylene, alkynyl, alkynylene, cycloalkylene, heterocycloalkyl, heterocycloalkylene, aryl, arylene, arylene-oxy, heteroaryl, amino, amido or any combination thereof, Z is a halogen or CN; and s is an integer between 1 and 20.

In some embodiments, Z in Formula (23) is Br and R4 and R5 are each methyl. In some embodiments, R1 in Formula (22) is selected from the group consisting of NH2-, OH—, and SH—.

In some embodiments R2 in Formula (22) is alkyl, substituted alkyl, alkylene, alkoxy, carboxyalkyl, haloalkyl, cycloalkyl, cyclic alkyl ether, alkenyl, alkenylene, alkynyl, alkynylene, cycloalkylene, heterocycloalkyl, heterocycloalkylene, aryl, arylene, arylene-oxy, heteroaryl, amino, amido or any combination thereof. In some embodiments, R2 in Formula (22) is

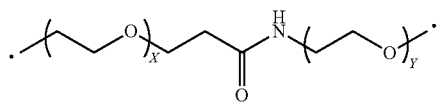

Formula (24)

wherein X and Y are the same or different and are integers from 1-20. In some embodiments, X and Y are each 4.

In some embodiments, R3 in Formula (22) is

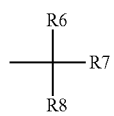

Formula (25)

wherein R6, R7 and R8 are the same or different and are selected from the group consisting of

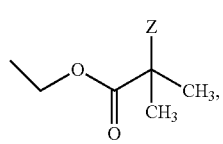

Formula (26)

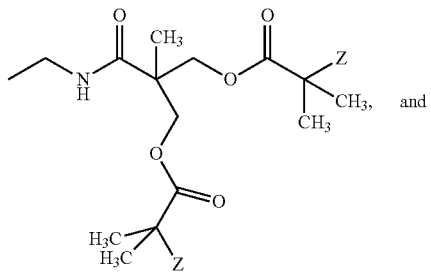

Formula (27)

and

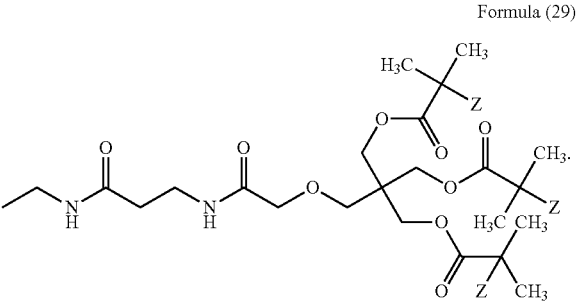

Formula (28)

wherein Z is NCS, F, Cl, Br or I. In some embodiments, Z in Formula (26), Formula (27) and/or Formula (28) is Br and R6, R7 and R8 in Formula (25) are each Formula (29)

In some embodiments, the initiator has the structure:

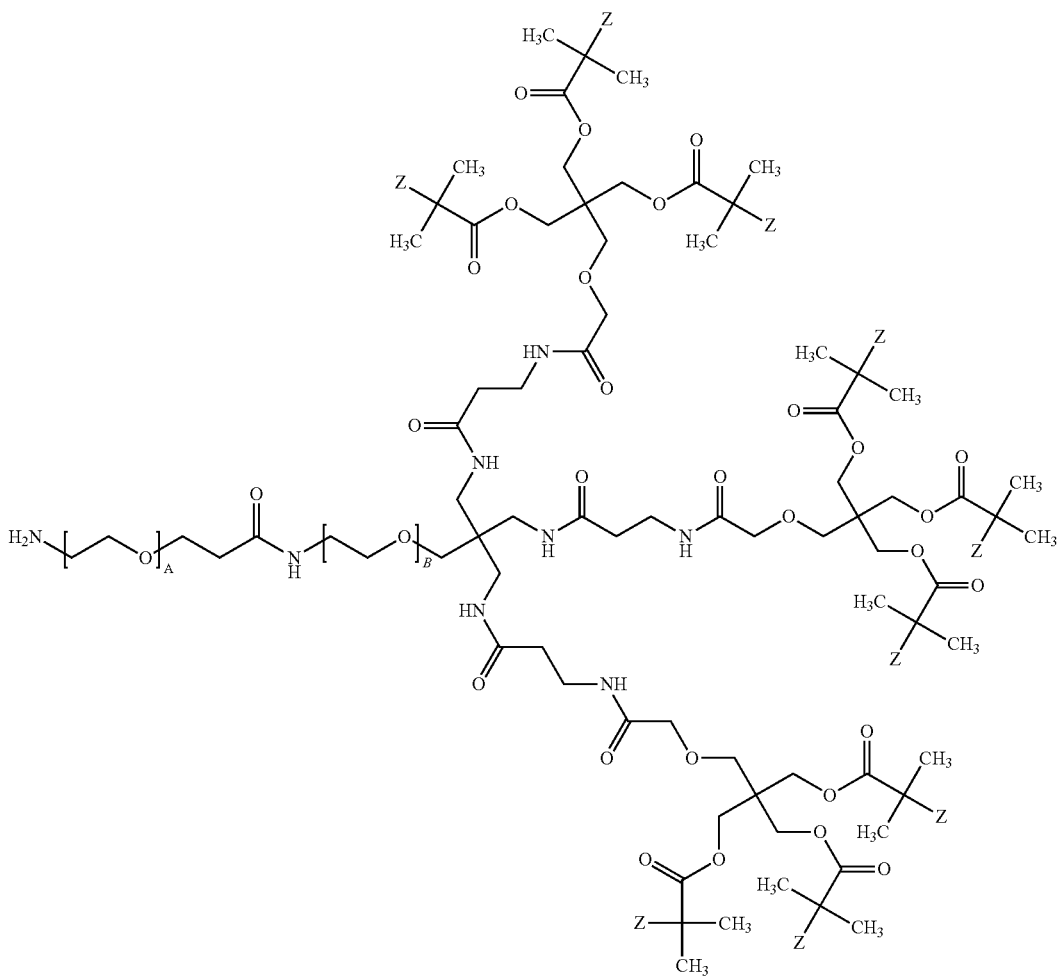

Formula (30)

wherein A and B are the same or different and are integers from 2 to 12 and Z is any halide, for example Br. In some embodiments, A and B are each 4 in Formula (30).

In some embodiments, the method further has the step of reacting the polymer with a maleimide reagent to provide a polymer having a terminal maleimide. In some embodiments, the maleimide compound is

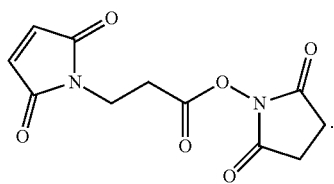

Formula (31)

A modification or mutation may also be made in a framework region or constant region to increase the half-life of an IL-6 antagonist antibody (and/or IL-6 Ab-VEGF Trap). See, e.g., PCT Publication No. WO 00/09560. A mutation in a framework region or constant region can also be made to alter the immunogenicity of the antibody, to provide a site for covalent or non-covalent binding to another molecule, or to alter such properties as complement fixation, FcR binding and antibody-dependent cell-mediated cytotoxicity. In some embodiments, no more than one to five conservative amino acid substitutions are made within the framework region or constant region. In other embodiments, no more than one to three conservative amino acid substitutions are made within the framework region or constant region. According to the invention, a single antibody may have mutations in any one or more of the CDRs or framework regions of the variable domain or in the constant region.

Modifications also include glycosylated and nonglycosylated polypeptides, as well as polypeptides with other post-translational modifications, such as, for example, glycosylation with different sugars, acetylation, and phosphorylation. Antibodies are glycosylated at conserved positions in their constant regions (Jefferis and Lund, 1997, Chem. Immunol. 65:111-128; Wright and Morrison, 1997, TibTECH 15:26-32). The oligosaccharide side chains of the immunoglobulins affect the protein's function (Boyd et al., 1996, Mol. Immunol. 32:1311-1318; Wittwe and Howard, 1990, Biochem. 29:4175-4180) and the intramolecular interaction between portions of the glycoprotein, which can affect the conformation and presented three-dimensional surface of the glycoprotein (Jefferis and Lund, supra; Wyss and Wagner, 1996, Current Opin. Biotech. 7:409-416). Oligosaccharides may also serve to target a given glycoprotein to certain molecules based upon specific recognition structures. Glycosylation of antibodies has also been reported to affect antibody-dependent cellular cytotoxicity (ADCC). In particular, antibodies produced by CHO cells with tetracycline-regulated expression of 0(1,4)-N-acetylglucosaminyltransferase III (GnTIII), a glycosyltransferase catalyzing formation of bisecting GlcNAc, was reported to have improved ADCC activity (Umana et al., 1999, Nature Biotech. 17:176-180).

[ ] Glycosylation of antibodies is typically either N-linked or O-linked. N-linked refers to the attachment of the carbohydrate moiety to the side chain of an asparagine residue. The tripeptide sequences asparagine-X-serine, asparagine-X-threonine, and asparagine-X-cysteine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody (and/or Ab-Trap) is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

The glycosylation pattern of antibodies (and/or Ab-Trap) may also be altered without altering the underlying nucleotide sequence. Glycosylation largely depends on the host cell used to express the antibody. Since the cell type used for expression of recombinant glycoproteins, e.g. antibodies, as potential therapeutics is rarely the native cell, variations in the glycosylation pattern of the antibodies can be expected (see, e.g. Hse et al., 1997, J. Biol. Chem. 272:9062-9070).

In addition to the choice of host cells, factors that affect glycosylation during recombinant production of antibodies (and/or Ab-Trap) include growth mode, media formulation, culture density, oxygenation, pH, purification schemes and the like. Various methods have been proposed to alter the glycosylation pattern achieved in a particular host organism including introducing or overexpressing certain enzymes involved in oligosaccharide production (U.S. Pat. Nos. 5,047,335; 5,510,261 and 5,278,299). Glycosylation, or certain types of glycosylation, can be enzymatically removed from the glycoprotein, for example, using endoglycosidase H (Endo H), N-glycosidase F, endoglycosidase F1, endoglycosidase F2, endoglycosidase F3. In addition, the recombinant host cell can be genetically engineered to be defective in processing certain types of polysaccharides. These and similar techniques are well known in the art.

Some embodiments provided herein can be employed as a therapeutic for inflammatory retinal diseases and/or retinal vesicular diseases with a component of inflammation. In addition to angiogenesis, inflammation has been implicated in the pathogenesis of these retinal diseases. Anti-inflammatory therapies such as steroids have been effective in treating both uveitis (a spectrum of diseases with intraocular inflammation as a defining characteristic) and diabetic macular edema (DME). Similarly, genetically inherited polymorphisms in IL-6 have been associated with higher PDR incidence in patients with type 2 diabetes. Moreover, disease progression in AMD, DR and RVO have been reported to be associated with increased serum and/or ocular levels of IL-6. Additionally, chronic inflammatory cells have been seen on the surface of the Bruch's membrane in eyes with neovascular AMD. IL-6 has been implicated in resistance to anti-VEGF treatments in DME patients. This in part is believed to be an indirect result of IL-6 mediated upregulation of VEGF expression [reference] as well as more direct VEGF-independent angiogenic functions mediated by IL-6 signaling that occur in the presence of VEGF inhibitors. In some embodiments, any one or more of these conditions can be treated and/or prevented by one or more of the compositions provided herein.

Figure 11A:
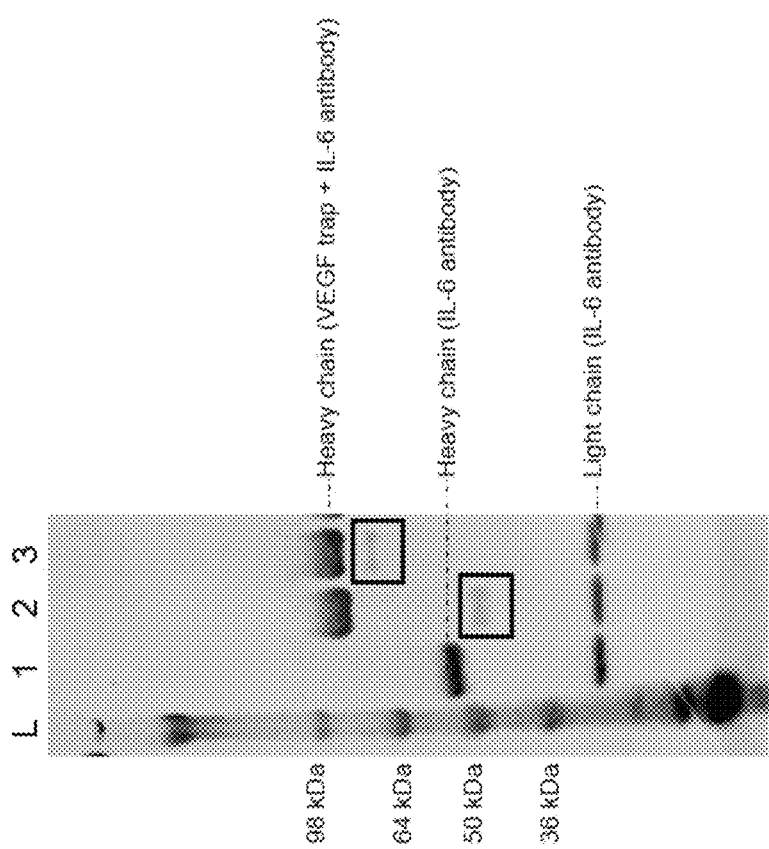
Figure 11C:
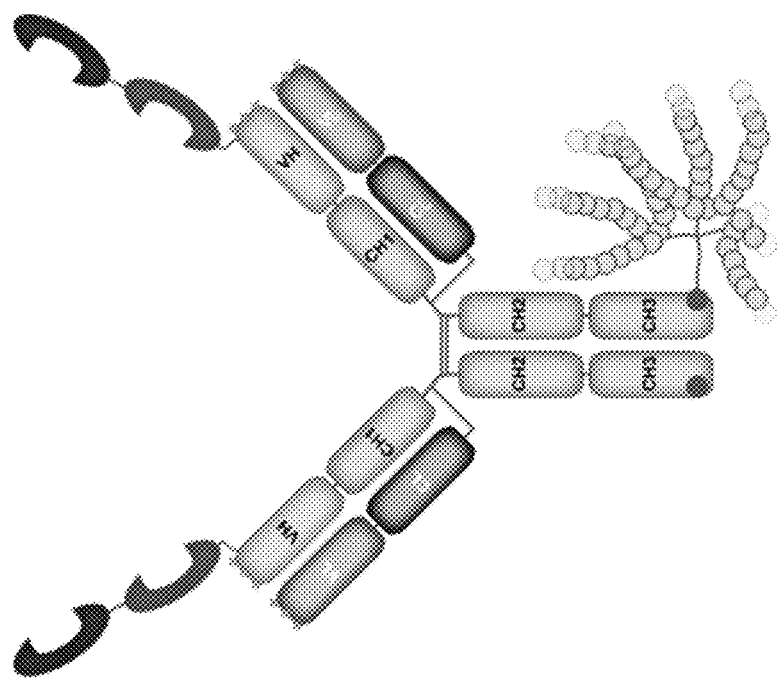
FIG. 11C depicts the conjugate construct of VEGFR-Anti-IL6, which is a fusion of Anti-VEGF (VEGFR1/2) and Anti-IL-6 conjugated with a phosphorylcholine-based polymer.

FIG. 11C illustrates some embodiments of a construct of a bioconjugate, which is a Trap-Antibody Fusion (TAF) of VEGF trap (VEGFR1/2) and Anti-IL-6 antibody conjugated with phosphorylcholine-based biopolymer. In some embodiments, Anti-VEGF/anti-IL-6 bioconjugate can have a molecular weight of 1.0 MDa, with a clinical dose of 6.0 mg, in some embodiments. The equivalent molar dose of anti-VEGF portion in bioconjugate can be 6 times that of clinical Ranibizumab dose, while the ocular half-life could be 3-5 times of that of Ranibizumab. CH represents constant heavy, CL represents constant light, Fab represents fragment antigen-binding, Fc represents fragment crystallizable, VEGFR represents vascular endothelial growth factor receptor, VH represents variable heavy, VL represents variable light, and * are CDR regions. Equivalent values are showed as fold changes relative to Ranibizumab.

Various sequence arrangements of the Anti-IL-6 antibody/VEGF trap (VEGFR1/2) can be employed or provided in different arrangements. FIG. 2I illustrates some embodiments of possible anti-IL-6 heavy chain variable region sequences. The CDRs are underlined.

Based on the results with the VEGF trap variants and improved Anti-IL-6 paratopes, 216 molecules in two different configurations were designed and prepared that comprised combinations of sequences as displayed in FIGS. 19, 20, 21, 22 and 23. For the first configuration (VEGFR-Anti-IL-6) the VEGF trap, as shown by sequences 1A-1D of FIG. 19 is positioned at the beginning of the protein, followed by a double repeat of a Gly-Gly-Gly-Gly-Ser linker (GS), as shown by sequence 2A of FIG. 20, which connects the trap to the N-terminus of the anti-IL-6 heavy chain, as shown by sequences 3A-3I of FIG. 21. These constructs can be paired with light chains listed as sequences 4A-4C of FIG. 22. In some embodiments, the VEGF trap (from FIG. 19) can be combined with any of the anti-IL-6 light chains and/or heavy chaings shown in any of the figures or tables provided herein.

In some embodiments, any of the VEGF trap variants provided herein can be paired with any of: the heavy and light chain sequences of IL-6 antibodies provided herein, and can be further modified by any of the polymers provided herein. In some embodiments, any of the VEGF trap variants provided herein can be paired with any of: the heavy and light chain variable sequences of IL-6 antibodies provided herein, and can be further modified by any of the polymers provided herein. In some embodiments, any of the VEGF trap variants provided herein can be paired with any of: the heavy and light chain 3 CDRs (HCDR1, HCDR2, HCDR3, LCDR1, LCDR2, and LCDR3) of IL-6 antibodies provided herein, and can be further modified by any of the polymers provided herein. In some embodiments, the IL-6-VEGF trap fusion comprises the components in FIG. 27.

In some embodiments, the sequence of the anti-IL-6-VEGF trap (or dual inhibitor, fusion protein, or conjugate thereof) includes SEQ ID NO: 169 as the light chain, SEQ ID NO: 170 as the heavy chain fused to the VEGFR trap, via a linker. In some embodiments, the sequence of the anti-IL-6-VEGF trap (or dual inhibitor, or fusion protein or conjugate thereof) is at least 80% identical to a molecule comprising SEQ ID NO: 169 and 170, including, for example, at least 85, 90, 95, 96, 97, 98, 99, or greater identity to the combination of SEQ ID NO: 170 and 169. In some embodiments, the sequence of the anti-IL-6-VEGF trap (or conjugate thereof) is at least 80% identical to a molecule comprising SEQ ID NO: 169 and at least 80% identical to the molecule comprising SEQ ID NO: 170, including, for example, at least 85, 90, 95, 96, 97, 98, 99%, or greater identity to SEQ ID NO: 170 and at least 85, 90, 95, 96, 97, 98, 99%, or greater identity to 169. In some embodiments, the CDRs remain as depicted in any of the CDRs provided herein for an anti-IL-6 antibody (including those in SEQ ID NO: 170 and 169), while the remainder of the sequences (heavy and light chain, heavy and light variable regions, and/or full fusion sequences (such as SEQ ID NO 169 and 170) are allowed to be vary such that the full sequence is at least 80, 85, 90, 95, 96, 97, 98, 99, or greater identity to the original sequence. In some embodiments, the CDRs can vary by 1, 2, or 3 conservative alterations, while the remainder of the sequences (heavy and light chain, heavy and light variable regions, and/or full fusion sequences (such as SEQ ID NO 169 and 170) are allowed to be vary such that the full sequence is at least 80, 85, 90, 95, 96, 97, 98, 99, or greater identity to the original sequence. In some embodiments, the trap sequence (that shown in gray in FIG. 27, or in FIG. 19) can retain at least 80, 85, 90, 95, 96, 97, 98, 99, or greater percent identity, and the CDRs can vary by 1, 2, or 3 conservative alterations, while the remainder of the sequences (heavy and light chain, heavy and light variable regions, and/or full fusion sequences (such as SEQ ID NO 169 and 170) are allowed to be vary such that the full sequence is at least 80, 85, 90, 95, 96, 97, 98, 99, or greater identity to the original sequence.

In some embodiments, the fusion protein (or dual inhibitor) or conjugate thereof comprises 1, 2, 3, 4, 5, or all 6 of the CDRs provided herein. In some embodiments, the fusion protein or conjugate thereof includes at least SEQ ID NOs: 49, 50, and 51 (or a variant with 1, 2, or 3 conservative substitutions). In some embodiments, the fusion protein (or dual inhibitor) or conjugate thereof includes at least SEQ ID NO:s 172, 173, and 174 (or a variant with 1, 2, or 3 conservative substitutions). In some embodiments, the fusion protein or conjugate thereof includes at least SEQ ID NO:s 49, 50, and 51 (or a variant with 1, 2, or 3 conservative substitutions) and at least SEQ ID NO:s 172, 173, and 174 (or a variant with 1, 2, or 3 conservative substitutions). In some embodiments, these 6 CDRs (or variants thereof) are contained within a human antibody framework region. In some embodiments, the CDRs are within the framework region of any of the antibodies provided herein, or variants thereof that are at least 80, 85, 90, 95, 96, 97, 98, 99, or greater percent identity to the heavy and/or light chain variable regions provided herein, including, without limitation, those in tables 1 for the heavy chain and 2 for the light chain. In some embodiments, the fusion protein (or dual inhibitor) or conjugate thereof includes at least SEQ ID NO:s 49, 50, and 51 (or a variant with 1, 2, or 3 conservative substitutions) and at least SEQ ID NO:s 172, 173, and 174 (or a variant with 1, 2, or 3 conservative substitutions) and these CDRs (including the variants) are substituted for the CDRs within one or more of the sequences in Table 11, or within a variant within table 11 (where, disregarding the CDRs in Table 11, the remaining sequence is at least 80, 85, 90, 91, 92, 93, 94, 95, 96, 97, 98, 99, 99.5 or greater percent identity to the heavy chain containing section and the light chain section in Table 11). Thus, in some embodiments, these 6 CDRs (and the variants thereof) can be substituted not only for the CDRs of the sequences noted in Tables 1 and 2, but also for variants thereof. In some embodiments, the CDRs provided in Tables 3, 4, 5 are excluded as options within the variants of possible CDRs. In some embodiment, the antibody (including fragments thereof) is one that is at least 80% identical to an antibody having the heavy and light chain variable regions depicted in FIG. 27, while maintaining the specific CDRs in FIG. 27 (so no variation within the CDR section in this embodiment).

In some embodiments, an isolated antagonistic IL-6 antibody is provided. It can comprise a heavy chain amino acid variable region that comprises a heavy chain that has a sequence of at least one of SEQ ID NOs: 7-13,19-27, 89, 90, 256-262; and a light chain amino acid variable region that comprises the light chain that has a sequences of at least one of SEQ ID NOs: 91-93, 28-30.

In some embodiments, an isolated antagonist IL-6 antibody is provided, that comprises a heavy chain variable region (VH) comprising 3 complementarity determining regions: VH (CDR1), VH CDR2, and VH CDR3 having an amino acid sequence from the CDRs listed in SEQ ID NO: 256; and a light chain variable region (VL) comprising a VL CDR1, VL CDR2, and VL CDR3 having an amino acid sequence selected from the group of CDRs listed in SEQ ID NO: 91-93.

In some embodiments, an isolated antagonist antibody that binds to IL-6 is provide. The antibody comprises at least one of the following mutations based on EU numbering: L234A, L235A, and G237A.

In some embodiments, an isolated antagonistic antibody that binds to IL-6, the antibody comprising: a $CDR_H1$ that is a $CDR_H1$ in SEQ ID NO: 172; a $CDR_H2$ that is a $CDR_H2$ in SEQ ID NO: 173; a $CDR_H3$ that is a $CDR_H3$ in SEQ ID NO: 174: a $CDR_L1$ that is a $CDR_L1$ in SEQ ID NO: 199; a $CDR_L2$ that is a $CDR_L2$ in SEQ ID NO: 200; a $CDR_L3$ that is a $CDR_L3$ in SEQ ID NO: 201; at least one of the following mutations (EU numbering): L234A, L235A, and G237A; and at least one of the following mutations (EU numbering): Q347C or L443C.

In some embodiments, the VEGFR-Anti-IL-6 dual inhibitor comprises an anti-IL-6 heavy chain variable region sequences selected from SEQ ID NO: 7-13, 89, 90, and/or 256-262.

In some embodiments, the VEGFR-Anti-IL-6 dual inhibitor has a VEGF trap sequences selected from at least one of SEQ ID Nos: 145, 15, 16, or 17.

In some embodiments, the linker sequence is SEQ ID NO: 18.

In some embodiments, the heavy chain sequence for the Anti-IL-6 molecules is selected from at least one of SEQ ID NOs 19-27 or includes at least the sequence in one of SEQ ID NOs: 89, 90, 256-262.

In some embodiments, the light chain sequence for the anti-IL-6 molecule comprises at least 1, 2, or 3 light chain CDRs from at least one of SEQ ID NOs 76-84.

In some embodiments, the heavy chain sequence for the Anti-IL-6 molecule comprises at least 1, 2, or 3 heavy chain CDRs from at least one of SEQ ID NOs 49-75.

In some embodiments, the VEGFR-Anti-IL-6 dual inhibitor comprises a VEGFR-Fc sequence from at least one of SEQ ID NOs 85-88.

In some embodiments, the VEGFR-Anti-IL-6 dual inhibitor comprises one or more of the sequences in any one or more of SEQ ID Nos 7-13, 145, 15-17, 18-84.

In some embodiments, the VEGFR-Anti-IL-6 dual inhibitor comprises an IL-6 VH; an IL-6 VL; an IL-6 Fc; a VEGF Trap; and a linker. In some embodiments, the IL-6 VH comprises a sequence from an IL6 VH sequence in any one of SEQ ID NOs 19-27, 31-39, 89, 90, or 256-262. In some embodiments, the IL-6 VL comprises a sequence from an IL6 VL sequence in any one of SEQ ID Nos 28-30 or 91-93. In some embodiments, the Fc comprises a sequence from a Fc sequence in any one of SEQ ID NOs 40-48. In some embodiments, the VEGF Trap comprises a sequence from a VEGF trap sequence in any one of SEQ ID NOs: 145, 15, 16, or 17.

In some embodiments, a fusion protein is provided that comprises an IL-6 VH; an IL-6 VL; an IL-6 Fc; and a VEGF Trap, wherein the fusion protein alters HUVEC proliferation. In some embodiments, altering HUVEC proliferation is inhibiting VEGF/IL6 mediated proliferation.

In some embodiments, a fusion protein comprising a sequence that is at least 80% identical to SEQ ID NO: 263 and at least 80% identical to SEQ ID NO: 117 is provided. The fusion protein is further conjugated to a polymer. In some embodiments, the fusion protein is at least 95% identical to SEQ ID NO: 263 and at least 95% identical to SEQ ID NO: 117. In some embodiments, the protein comprises at least a) SEQ ID NO: 172, 173, 174, 199, 200, and 201, or b) a substitutions of 1, 2, or 3 amino acids within SEQ ID NO: 172, 173, 174, 199, 200, and/or 201, wherein the substitution is a conservative substitution.

In some embodiments, any of the constructs provided herein can include one or more mutation at positions 94 and/or 95 of the VEGFR sequence. In some embodiments, the mutation(s) can be T94I and H95I. In some embodiments this reduces any cleavage of the VEGFR protein (as detailed in the examples below).

Figure 23A:
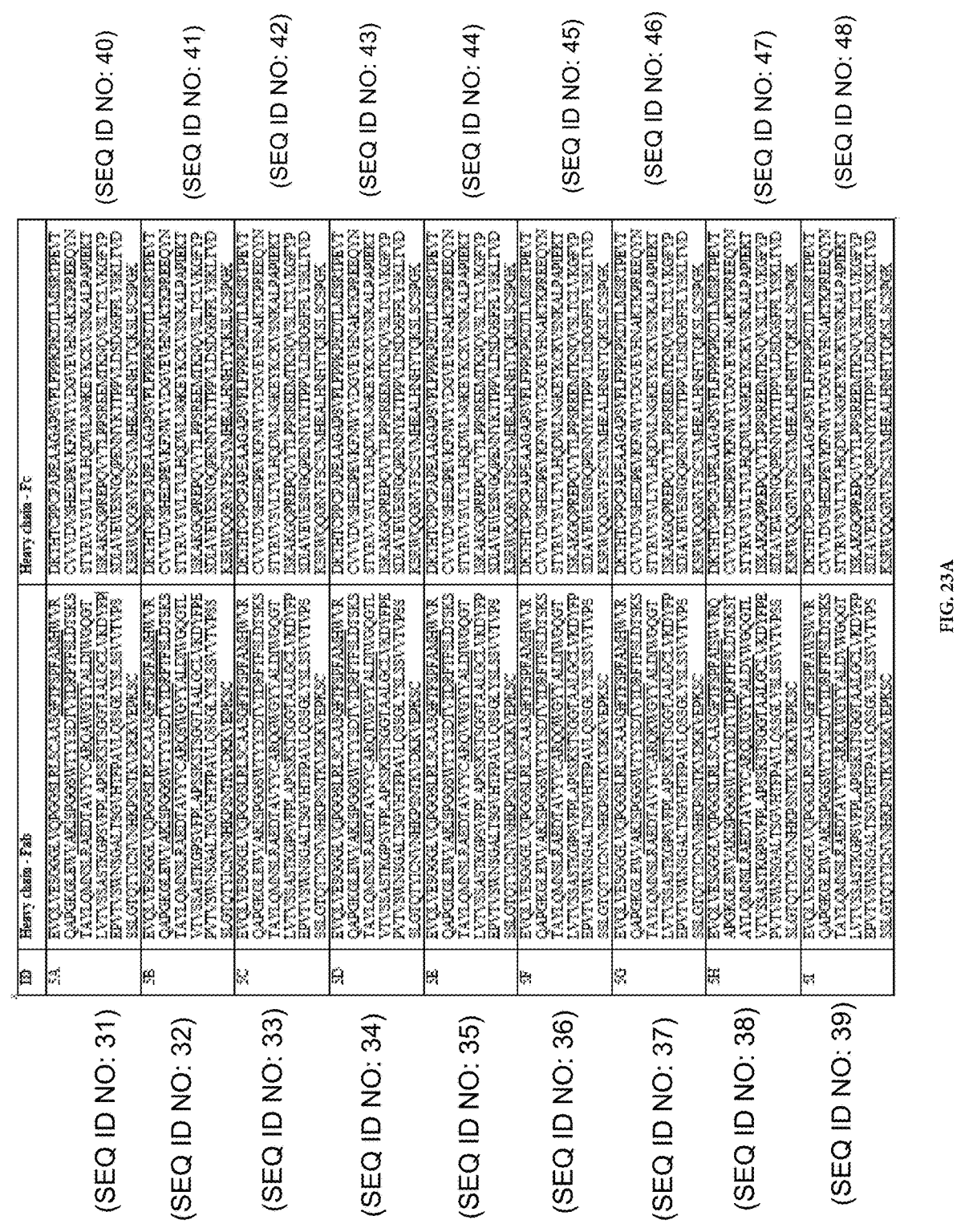

In some embodiments, (where Anti-IL-6-VEGFR is the orientation), the variable and constant domains of the heavy chain, illustrated by Heavy chain—Fab, sequences 5A-5I of FIG. 23, are connected to the VEGF trap, illustrated by sequences 1A-1D of FIG. 19, via the GS linker, illustrated by sequence 2A of FIG. 20, and then the Fc domain, illustrated by Heavy chain—Fc, sequences 5A-5I of FIG. 23, is fused to the C-terminal end of the VEGF trap. Thus, the VEGF trap is sandwiched between the antibody Fab and Fc regions. In some embodiments, these constructs can be paired with light chains listed on sequences 4A-4C of FIG. 22.

FIG. 19 illustrates some embodiments of VEGF trap sequences. Variation between the sequences is underlined and highlighted in bold. In some embodiments, any of the fusion constructs provided herein can include any of the highlighted and bolded variations provided in this, or any of the figures in the present specification.

FIG. 20 illustrates some embodiments of a double repeat Gly-Gly-Gly-Gly-Ser linker (GS) sequence. In some embodiments, more than one unit of sequence can be employed (for example, two, for a double repeat, three or more can be employed). In some embodiments, other linker sequences can be employed. In some embodiments, alternative linker sequences can be employed.

Figure 21:
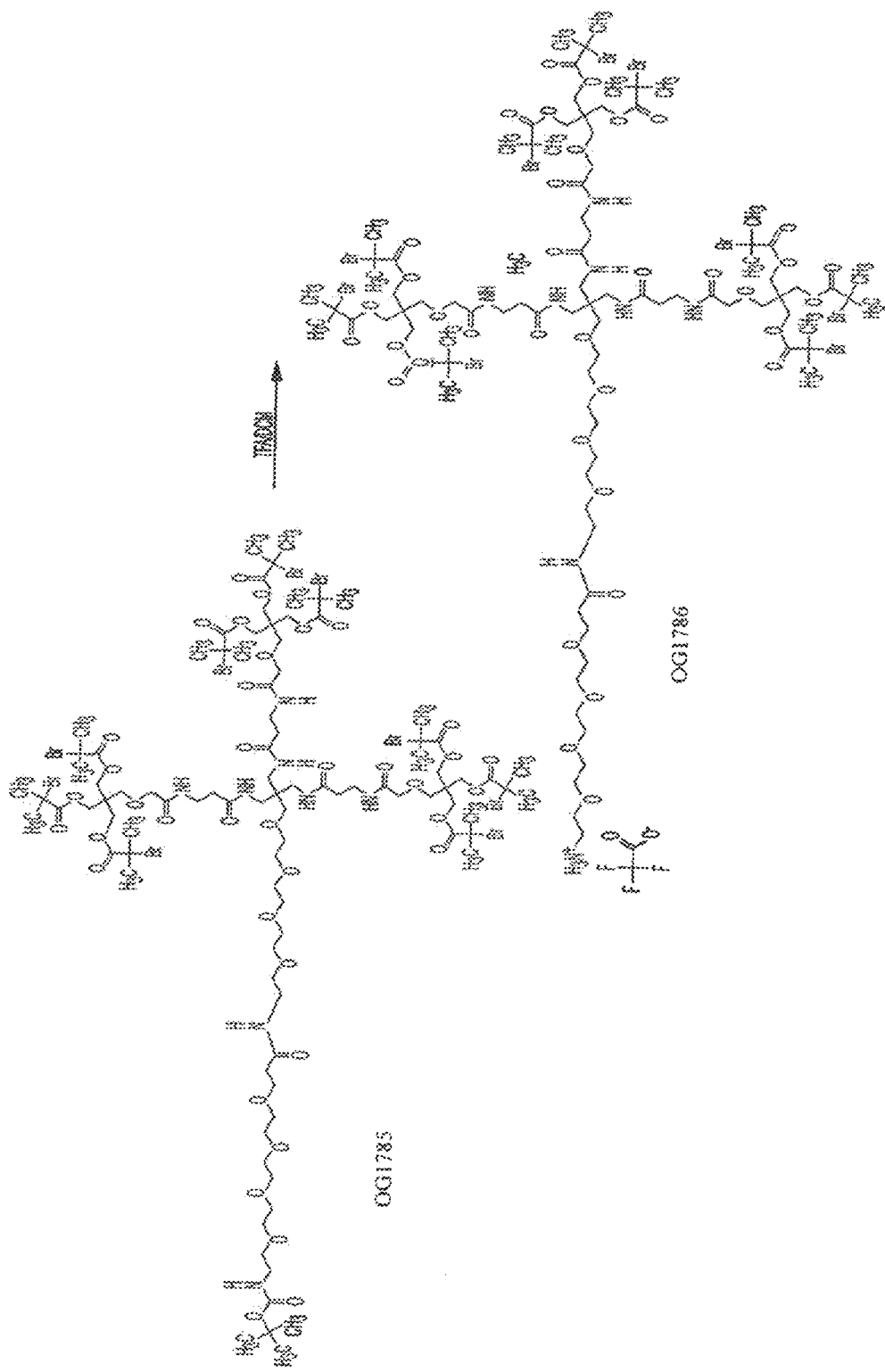
FIG. 21 illustrates some embodiments of heavy chain sequence for Anti-IL-6 molecules. CDRs are underlined.
Figure 21A:
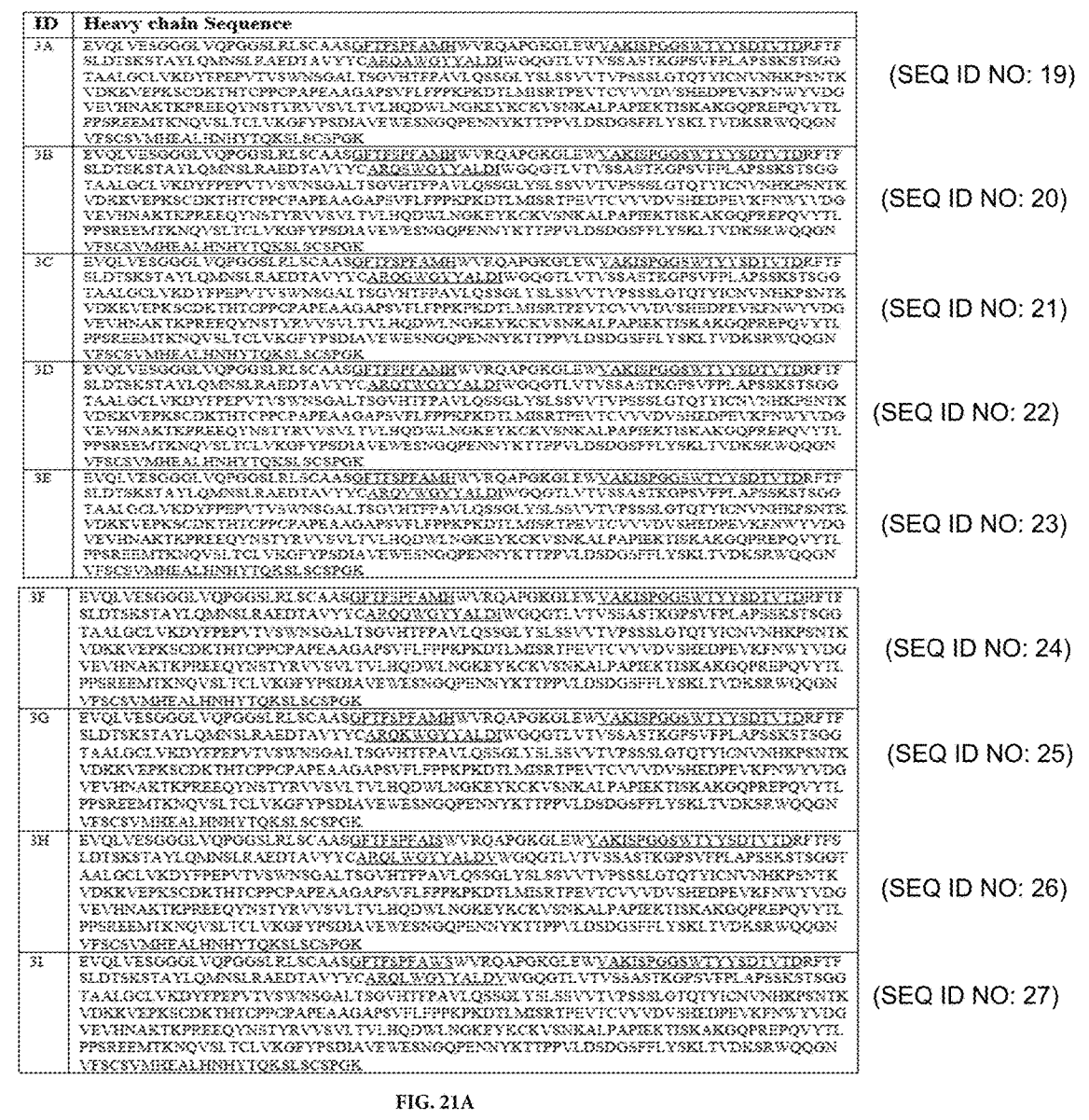

FIG. 21 illustrates heavy chain sequences for some embodiments of anti-IL-6 molecules. CDRs are underlined. In some embodiments, any of the sequences herein can be used in place of other heavy chain sequences that are part of fusion constructs in the present specification.

FIG. 22 illustrates some embodiments of light chain sequences for Anti-IL-6 molecules. CDRs are underlined. In some embodiments, any of the sequences herein can be used in place of other light chain sequences that are part of fusion constructs in the present specification.

FIG. 23 illustrates some embodiments of heavy chain (separated into Fab and Fc) sequences for Anti-IL-6 molecules. CDRs are underlined. In some embodiments, any of the sequences herein can be used in place of other heavy chain sequences that are part of fusion constructs in the present specification.

FIGS. 24A-24B illustrate the combinations of CDRs from FIGS. 21-23. FIG. 24A illustrates heavy chain CDR sequences as defined in FIGS. 21 and 23. FIG. 24B illustrates light chain CDR sequences as defined in FIG. 22. In some embodiments, rather than the entire heavy and/or light chain variable region being used in a construct, just the CDRs from one or more of the figures provided herein can be employed.

Figure 25:
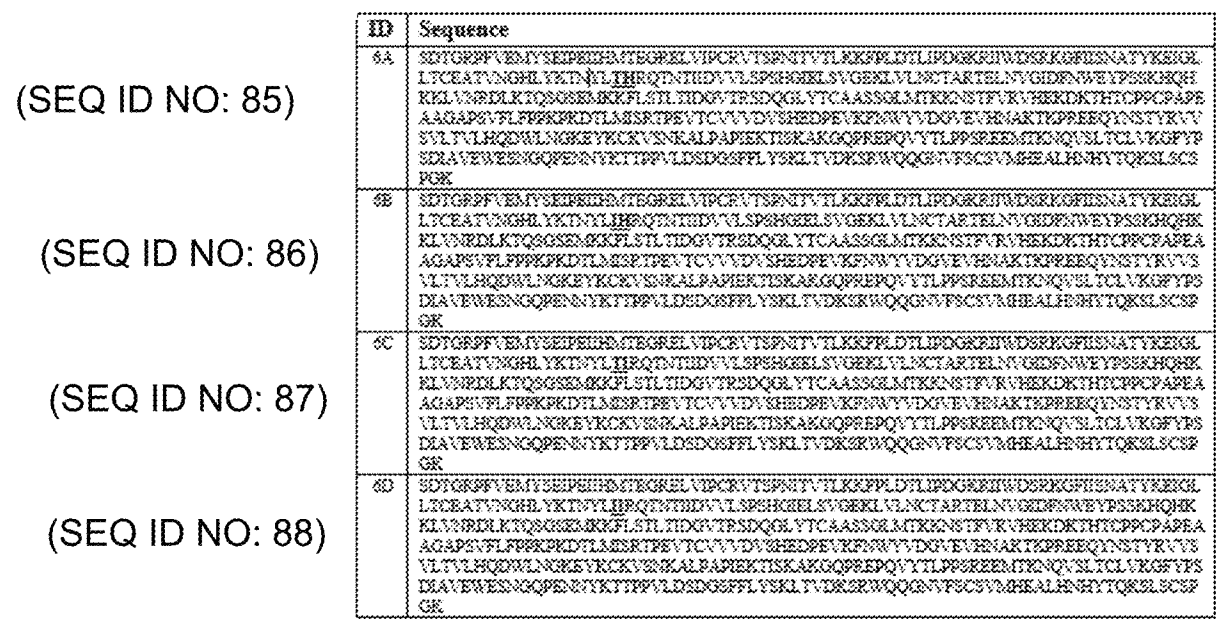

In some embodiments, the VEGFR-Fc trap fusion is part of an engineered IgG1 framework. In addition to the VEGFR-Anti-IL-6 and Anti-IL-6-VEGFR constructs, an anti-VEGF (VEGFR-Fc) molecule comprising the VEGF trap with cleavage resistant variants, as described above, and an engineered IgG1 Fc domain, as illustrated by sequences 6A-6D of FIG. 25, can be provided. The Fc domain for these molecules can contain L234A, L235A and G237A substitutions that minimize effector function, and L443C that allows site-specific conjugation with a half-life extending phosphorylcholine based biopolymer (residue positions follow EU numbering). FIG. 25 illustrates some embodiments of VEGFR-Fc sequence variants. Variation in the sequences is underlined and highlighted in bold. It is noted that these variations and/or combinations can provided a biotherapeutic that is further superior to and/or an alternative to other compounds currently used in therapy.

As shown in FIGS. 26A-26C, VEGFR-Fc and Eylea bind with similar affinity to VEGF. FIG. 26A illustrates the Biacore assays of VEGFR-Fc. FIG. 26B illustrates the Biacore assays of Eylea. FIG. 26C illustrates the experimental results (Ka, Kd, KD and Rmax) of VEGFR-Fc and Eylea.

In some embodiments, any one or more of the sequences for the specified amino acid sequence in any one or more of FIGS. 18-23, and 25 can be swapped into the corresponding structure of any of the other embodiments provided herein or exchanged with any of the other sequences provided herein. For example, any of the sequences within FIG. 13C-13E, 19, or 25 can be used with any of the IL-6 heavy chains from FIG. 18, 21, or 23, with any of the linkers provided herein (e.g., FIG. 20), with any of the light chains (FIG. 22). In some embodiments, the construct is a VEGFR-Anti-IL-6 configuration and it includes a combination of one of sequences 1A-1D (FIG. 19), linked to the linker (e.g., FIG. 20, sequence 2A), linked to a heavy chain IL-6 sequence (e.g., FIG. 21, sequence 3A or 3B), linked to a light chain sequence (e.g., FIG. 22, sequence 4A). In some embodiments, any one of sequences 1A-1D (FIG. 19), can be combined with a linker (FIG. 20), and with a heavy chain anti-IL-6 sequence (FIG. 21, sequences 3A-3I), and with a light chain anti-IL-6 sequence (FIG. 22, sequence 4A-4C). In some embodiments, any of the other corresponding sequences for any particular unit of construct provided herein can be swapped into or in place of any one of these units.

In some embodiments, the dual inhibitor provides one or more synergistic result. In some embodiments, the dual inhibitor is synergistically better than each section administered as a monotherapy (e.g. an IL-6 therapy and a VEGF therapy combined). In some embodiments, the combined VEGFR-IL-6 construct provides a synergistic result, as shown in the proliferation assay results (e.g., where the dual inhibitor has a clear effect on HUVEC proliferation, an important component of angiogenesis, while neither Eylea nor Anti-IL-6 achieve any change). Thus, in some embodiments, a method for controlling HUVEC proliferation is provided, whereby one employs a VEGFR-Anti-IL-6 construct as provided herein.

In other embodiments, the fusion construct simply provides an additive benefit by achieving both VEGF trap results and anti-IL-6 results.

In some embodiments, any one or more of the components in any one of more of tables provided herein can be combined together such that a VEGFR-anti-IL-6 construct is produced or such that an anti-IL-6-VEGFR construct is produced. In some embodiments, the construct will also include an Fc region. In some embodiments, the Fc region can be a human Fc region.

In some embodiments, the CDRs alone (with or without any particular framework section) can be employed as the antibody section. Thus, any one or more (e.g., 3 or 6) of the CDRs within each chain or pair of chains (heavy and light) can be used from any of the tables or figures provided herein, in combination with any of the other components (VEGFR and/or linkers). CDRs and/or 1, 2, or 3 heavy chain CDRs) from any of the IL-6 constructs provided herein can be combined with any one or more of the VEGFR sequences provided herein. In some embodiments, any heavy and/or light chain variable region from any of the IL-6 constructs provided herein can be combined with any one or more of the VEGFR sequences provided herein. In some embodiments, any of the linkers can be provided within the final construct as well.

In some embodiments, any nucleic acid sequence encoding any one of more of the amino acid sequences provided herein can be provided as well (e.g., in isolation, within a vector, or in a cell, etc.)

In some embodiments, any one or more of the polymers for conjugation to form the bioconjugate can be combined with any of the VEGFR-IL6 constructs provided herein.

In some embodiments, the VEGFR-anti-IL-6 combination is sequence 1A-1D (FIG. 19) for the VEGFR, linked to a linker (2A in FIG. 20), linked to a heavy chain (3A or 3B in FIG. 21), associated with light chain 4A from FIG. 22.

In some embodiments, the VEGFR-anti-IL-6 combination is sequence 1A (FIG. 19) for the VEGFR, linked to a linker (2A in FIG. 20), linked to a heavy chain (3A in FIG. 21), associated with light chain 4A from FIG. 22. In some embodiments, the VEGFR-anti-IL-6 combination is sequence 1B (FIG. 19) for the VEGFR, linked to a linker (2A in FIG. 20), linked to a heavy chain (3A in FIG. 21), associated with light chain 4A from FIG. 22. In some embodiments, the VEGFR-anti-IL-6 combination is sequence 1C (FIG. 19) for the VEGFR, linked to a linker (2A in FIG. 20), linked to a heavy chain (3A in FIG. 21), associated with light chain 4A from FIG. 22. In some embodiments, the VEGFR-anti-IL-6 combination is sequence 1D (FIG. 19) for the VEGFR, linked to a linker (2A in FIG. 20), linked to a heavy chain (3A in FIG. 21), associated with light chain 4A from FIG. 22.

In some embodiments, the VEGFR-anti-IL-6 combination is sequence 1A (FIG. 19) for the VEGFR, linked to a linker (2A in FIG. 20), linked to a heavy chain (3B in FIG. 21), associated with light chain 4A from FIG. 22. In some embodiments, the VEGFR-anti-IL-6 combination is sequence 1B (FIG. 19) for the VEGFR, linked to a linker (2A in FIG. 20), linked to a heavy chain (3B in FIG. 21), associated with light chain 4A from FIG. 22. In some embodiments, the VEGFR-anti-IL-6 combination is sequence 1C (FIG. 19) for the VEGFR, linked to a linker (2A in FIG. 20), linked to a heavy chain (3B in FIG. 21), associated with light chain 4A from FIG. 22. In some embodiments, the VEGFR-anti-IL-6 combination is sequence 1D (FIG. 19) for the VEGFR, linked to a linker (2A in FIG. 20), linked to a heavy chain (3B in FIG. 21), associated with light chain 4A from FIG. 22.

In some embodiments, any of the IL-6 antibody sequences can be employed with any of the VEGFR sequences provided herein. In some embodiments, any 1, 2, 3, 4, 5, or 6 CDRS (1, 2, or 3 light chain and 1, 2, or 3 heavy chain) anti-IL-6 sequences can be employed with any of the VEGFR arrangements.

In some embodiments, any anti-IL-6 antibody light and/or heavy chain can be employed, with any one or more of the point mutations provided in any one of more of Tables 30-33. In some embodiments, the fusion construct employs an anti-IL-6 construct that has a point mutation at any one or more of the positions identified in any one or more of Tables 30-33. In some embodiments, the positions altered are those underlined and bolded in the relevant figures as showing changed residues. In some embodiments, the construct is one that includes changes in heavy chain include one or more of S35H, G66D, L100A, or L100S and the changes in light chain include one or more of M32L, M50D, N52S or M88Q. CDR positions follow their order of appearance in the variable domain when described (e.g. S35H, G66D . . . ). Fc positions follow EU numbering when described (e.g. L234A, L235A . . ..) In some embodiments, the construct (e.g., antibody to Il-6, and/or IL-6 VEGF Trap, and/or IL-6 VEGF Trap bioconjugate (to one or more of the biopolymers provided herein)), includes 1, 2, 3, 4, 5, 6, 7, or 8 of the following in the heavy and light chains: S35H, G66D, L100A, and/or L100S in the heavy and M32L, M50D, N52S and/or M88Q in the light chain. In some embodiments, these point mutations can be used in any one of the Il-antibodies or constructs containing Il-6 antibodies provided herein.

As will be appreciated by one of skill in the art, there are a variety of constructs provided herein. Generally, these constructs can be grouped into: antibodies to Il-6, and/or Anti-IL-6 VEGF Trap (fusions of the antibody and VEGF Trap), and/or IL-6 VEGF Trap bioconjugate (the fusions with one or more of the biopolymers provided herein), and/or VEGF Trap constructs, and/or VEGF Trap biopolymers. Thus, any of the separate components provided herein (and variants thereof) can be used separately or in combination with one another. In some embodiments, the constructs of any of these groupings (antibodies to Il-6, and/or anti-IL-6 VEGF Trap (fusions of the antibody and VEGF Trap), and/or IL-6 VEGF Trap bioconjugate (the fusions with one or more of the biopolymers provided herein), and/or VEGF Trap constructs, and/or VEGF Trap biopolymers) can be used for any of the methods or other compositions provided herein. For example, any of these options can be used for any of the methods of treatment that are described in regard to IL-6 VEGF Trap therapies, and/or IL-6 therapies, and/or IL-6 VEGF Trap bioconjugates. As will be appreciated, the characteristics and properties of each of the construct can be different for each of the treatments, in line with the properties of the components detailed herein. Thus, the description provided herein with regard to, for example, cell lines, nucleic acids, therapies, and other embodiments, are not only specifically contemplated for anti-IL-6-VEGF Trap and/or bioconjugates thereof, but also for antibodies (and, for example, fragments thereof), antibody-bioconjugates, and VEGF Trap constructs separate from the anti-IL-VEGF Trap and/or bioconjugates. For example, in some embodiments, any of the point mutations (or combinations thereof) for IL-6 can be used in an antibody (or binding fragment thereof) for a treatment that is simply antibody based, instead of antibody and VEGF trap based arrangement. Thus, the point mutations for VEGF Trap and IL-6 antibodies is not limited to the context of fusion arrangements (although it does provide that), as it also describes such constructs (and uses thereof and method of making) separate from a fusion arrangement. Rather than repeat all such embodiments separately, it is noted that any such description for one of the arrangements (antibodies to Il-6, and/or Anti-IL-6 VEGF Trap (fusions of the antibody and VEGF Trap), and/or IL-6 VEGF Trap bioconjugate (the fusions with one or more of the biopolymers provided herein), and/or VEGF Trap constructs, and/or VEGF Trap biopolymers) applies and identifies the options for all of the other such arrangements (antibodies to Il-6, and/or Anti-IL-6 VEGF Trap (fusions of the antibody and VEGF Trap), and/or IL-6 VEGF Trap bioconjugate (the fusions with one or more of the biopolymers provided herein), and/or VEGF Trap constructs, and/or VEGF Trap biopolymers).

In some embodiments, any of the VEGF Trap constructs are contemplated for use as compositions, components, or therapies, including for example, those in FIGS. 13C-13E, 19, and 25 of the embodiments provided herein In some embodiments, any of the anti-IL-6 antibody constructs are contemplated for use as compositions, components, or therapies, including for example, those in tables 1 and 3, 4, 5, and FIGS. 5, 18, 21, 22, 23, and 24 of the embodiments provided herein.

In some embodiments, the fusion protein comprises a mutation at position 94 in the VEGF Trap sequence, at position 95 in the VEGF Trap sequence, or at T94I and H95I in the VEGF Trap sequence.

In some embodiments, a VEGFR-Anti-IL-6 dual inhibitor is provided. The VEGFR-Anti-IL-6 dual inhibitor comprises a trap antibody fusion of Anti-IL 6 antibody and a VEGF (VEGFR1/2) trap, wherein the dual inhibitor includes at least one point mutation within a VEGFR sequence to reduce cleavage of the VEGFR sequence. In some embodiments, the VEGFR-Anti-IL-6 dual inhibitor has a molecular weight of 1.0 MDa.

In some embodiments, the VEGR-Anti-IL-6 dual inhibitor provides therapy for inflammatory retinal diseases.

In some embodiments, the VEGFR-Anti-IL-6 dual inhibitor comprises a constant heavy, constant light, a fragment antigen binding, a fragment crystallizable (Fc), vascular endothelial growth factor receptor (VEGFR), a variable heavy, a variable light and CDR regions.

In some embodiments, the Anti-IL-6 heavy chain variable region sequences can be selected from options VI, VII, VIII, IX, X, XI, or XII of FIG. 18

In some embodiments, the VEGF trap sequence can be selected from at least one of options 1A, 1B, 1C or 1D of FIG. 19.

In some embodiments for the VEGR-anti-IL-6 dual inhibitor, the heavy chain sequence for anti-IL-6 molecules can be selected from at least one of options 3A, 3B, 3C, 3D, 3E, 3F, 3G, 3H, or 3I of FIG. 21.

In some embodiments for the VEGFR-anti-IL-6 dual inhibitor the light chain sequence for Anti-IL-6 molecules comprises at least 1, 2, or 3 light chain CDRs from at least one of option 4A, 4B, or 4C of FIG. 24B.

In some embodiments for the VEGFR-anti-IL-6 dual inhibitor the heavy chain sequence for the anti-IL-6 molecule comprises at least 1, 2, or 3 heavy chain CDRs from at least one of option 5A, 5B, 5C, 5D, 5E, 5F, 5G, 5H, or 5I of FIG. 24A.

In some embodiments, the VEGFR-Anti-IL-6 dual inhibitor comprises a VEGFR-Fc sequence from at least one of option 6A, 6B, 6C or 6D of FIG. 25.

In some embodiments, the VEGFR-anti-IL-6 dual inhibitor comprises one or more of the sequences in FIGS. 18-25.

In some embodiments, the VEGFR-Anti-IL-6 dual inhibitor comprises an IL-6 VH, an IL-6 VL, an IL-6 Fc, a VEGF Trap, and a linker. In some embodiments, the IL-6 VH comprises a sequence from an IL6 VH sequence in FIG. 21 or 23. In some embodiments, the IL-6 VL comprises a sequence from an IL6 VL sequence in FIG. 22. In some embodiments, the Fc comprises a sequence from a Fc sequence in FIG. 23. In some embodiments, the VEGF Trap comprises a sequence from a VEGF trap sequence.

In some embodiments, a protein construct is provided that comprises: at least 3 heavy chain CDRs; at least 3 light chain CDRs; a VEGF trap sequence; and a linker sequence, wherein each of the sequences is selected from a sequence within FIGS. 18-25.

In some embodiments, a fusion protein is provided that comprises: an IL-6 VH, an IL-6 VL, an IL-6 Fc, a VEGF Trap, and wherein the fusion protein alters HUVEC proliferation. In some embodiments, each sequence is selected from a sequence within FIGS. 18-25.

Polynucleotides, Vectors, and Host Cells

The invention also provides polynucleotides encoding any of the antibodies (and/or IL-6 Ab-VEGF Trap), including antibody fragments and modified antibodies described herein. In another aspect, the invention provides a method of making any of the polynucleotides described herein. Polynucleotides can be made and expressed by procedures known in the art. Accordingly, the invention provides polynucleotides or compositions, including pharmaceutical compositions, comprising polynucleotides, encoding any of the IL-6 antagonists antibodies (and/or IL-6 Ab-VEGF Traps) provided herein.

Polynucleotides complementary to any such sequences are also encompassed by the present invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes an antibody or a fragment thereof) or may comprise a variant of such a sequence. Polynucleotide variants contain one or more substitutions, additions, deletions and/or insertions such that the immunoreactivity of the encoded polypeptide is not diminished, relative to a native immunoreactive molecule. The effect on the immunoreactivity of the encoded polypeptide may generally be assessed as described herein. Variants preferably exhibit at least about 70% identity, more preferably, at least about 80% identity, yet more preferably, at least about 90% identity, and most preferably, at least about 95% identity to a polynucleotide sequence that encodes a native antibody or a fragment thereof.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned.

Optimal alignment of sequences for comparison may be conducted using the MegAlign® program in the Lasergene® suite of bioinformatics software (DNASTAR®, Inc., Madison, WI), using default parameters. This program embodies several alignment schemes described in the following references: Dayhoff, M. O., 1978, A model of evolutionary change in proteins—Matrices for detecting distant relationships. In Dayhoff, M.O. (ed.) Atlas of Protein Sequence and Structure, National Biomedical Research Foundation, Washington DC Vol. 5, Suppl. 3, pp. 345-358; Hein J., 1990, Unified Approach to Alignment and Phylogenes pp. 626-645 Methods in Enzymology vol. 183, Academic Press, Inc., San Diego, CA; Higgins, D. G. and Sharp, P. M., 1989, CABIOS 5:151-153; Myers, E. W. and Muller W., 1988, CABIOS 4:11-17; Robinson, E. D., 1971, Comb. Theor. 11:105; Santou, N., Nes, M., 1987, Mol. Biol. Evol. 4:406-425; Sneath, P. H. A. and Sokal, R. R., 1973, Numerical Taxonomy the Principles and Practice of Numerical Taxonomy, Freeman Press, San Francisco, CA; Wilbur, W. J. and Lipman, D. J., 1983, Proc. Natl. Acad. Sci. USA 80:726-730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native antibody (or a complementary sequence).

Suitable "moderately stringent conditions" include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2× SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/ 0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

The polynucleotides of this invention can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al., 1989.

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston, 1994.

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., 1989, supra, for example.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors are further provided. Expression vectors generally are replicable polynucleotide constructs that contain a polynucleotide according to the invention. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

The invention also provides host cells comprising any of the polynucleotides described herein. Any host cells capable of over-expressing heterologous DNAs can be used for the purpose of isolating the genes encoding the antibody, polypeptide or protein of interest. Non-limiting examples of mammalian host cells include but not limited to COS, HeLa, and CHO cells. See also PCT Publication No. WO 87/04462. Suitable non-mammalian host cells include prokaryotes (such as *E. coli* or *B. subtillis*) and yeast (such as *S. cerevisae, S. pombe*; or *K. lactis*). Preferably, the host cells express the cDNAs at a level of about 5 fold higher, more preferably, 10 fold higher, even more preferably, 20 fold higher than that of the corresponding endogenous antibody or protein of interest, if present, in the host cells. Screening the host cells for a specific binding to IL-6 is effected by an immunoassay or FACS. A cell overexpressing the antibody or protein of interest can be identified.

An expression vector can be used to direct expression of an IL-6 antagonist antibody (and/or IL-6 Ab-VEGF Trap). One skilled in the art is familiar with administration of expression vectors to obtain expression of an exogenous protein in vivo. See, e.g., U.S. Pat. Nos. 6,436,908; 6,413,942; and 6,376,471. Administration of expression vectors includes local or systemic administration, including injection, oral administration, particle gun or catheterized administration, and topical administration. In another embodiment, the expression vector is administered directly to the sympathetic trunk or ganglion, or into a coronary artery, atrium, ventricle, or pericardium.

Targeted delivery of therapeutic compositions containing an expression vector, or subgenomic polynucleotides can also be used. Receptor-mediated DNA delivery techniques are described in, for example, Findeis et al., Trends Biotechnol., 1993, 11:202; Chiou et al., Gene Therapeutics: Methods And Applications Of Direct Gene Transfer, J. A. Wolff, ed., 1994; Wu et al., J. Biol. Chem., 1988, 263:621; Wu et al., J. Biol. Chem., 1994, 269:542; Zenke et al., Proc. Natl. Acad. Sci. USA, 1990, 87:3655; Wu et al., J. Biol. Chem., 1991, 266:338. Therapeutic compositions containing a polynucleotide are administered in a range of about 100 ng to about 200 mg of DNA for local administration in a gene therapy protocol. Concentration ranges of about 500 ng to about 50 mg, about 1 µg to about 2 mg, about 5 µg to about 500 µg, and about 20 µg to about 100 µg of DNA can also be used during a gene therapy protocol. The therapeutic polynucleotides and polypeptides can be delivered using gene delivery vehicles. The gene delivery vehicle can be of viral or non-viral origin (see generally, Jolly, Cancer Gene Therapy, 1994, 1:51; Kimura, Human Gene Therapy, 1994, 5:845; Connelly, Human Gene Therapy, 1995, 1:185; and Kaplitt, Nature Genetics, 1994, 6:148). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther., 1992, 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther., 1992, 3:147); ligand-linked DNA (see, e.g., Wu, J. Biol. Chem., 1989, 264: 16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP 0524968. Additional approaches are described in Philip, Mol. Cell Biol., 1994, 14:2411, and in Woffendin, Proc. Natl. Acad. Sci., 1994, 91:1581.

Compositions

The invention also provides pharmaceutical compositions comprising an effective amount of an IL-6 antagonist antibody (and/or IL-6 Ab-VEGF Trap) conjugate described herein. Examples of such compositions, as well as how to formulate, are also described herein. In some embodiments, the composition comprises one or more IL-6 antagonist antibodies (and/or IL-6 Ab-VEGF Trap) and/or antibody (and/or Ab-Trap) conjugates. In other embodiments, the IL-6 antagonist antibody (and/or IL-6 Ab-VEGF Trap) recognizes human IL-6. In other embodiments, the IL-6 antagonist antibody is a human antibody. In other embodiments, the IL-6 antagonist antibody is a humanized antibody. In some embodiments, the IL-6 antagonist antibody comprises a constant region that does not trigger an unwanted or undesirable immune response, such as antibody-mediated lysis or ADCC. In other embodiments, the IL-6 antagonist (and/or IL-6 Ab-VEGF Trap) comprises one or more CDR(s) of the antibody (such as one, two, three, four, five, or, in some embodiments, all six CDRs).

It is understood that the compositions can comprise more than one IL-6 antagonist antibody (and/or IL-6 Ab-VEGF Trap) (e.g., a mixture of IL-6 antibodies that recognize different epitopes of IL-6). Other exemplary compositions comprise more than one IL-6 antagonist antibody (and/or IL-6 Ab-VEGF Trap) that recognize the same epitope(s), or different species of IL-6 antagonist antibodies (and/or IL-6 Ab-VEGF Trap) that bind to different epitopes of IL-6. In some embodiments, the compositions comprise a mixture of IL-6 antagonist antibodies (and/or IL-6 Ab-VEGF Trap) that recognize different variants of IL-6. In addition, in some embodiments, the composition can also, or instead, comprise more than one VEGF Trap. These alternative VEGF Trap sections can include different sequences for the VEGF Trap section, as long as the sections at least have the same or similar functionality as noted herein.

The composition used in the present invention can further comprise pharmaceutically acceptable carriers, excipients, or stabilizers (Remington: The Science and practice of Pharmacy 20th Ed., 2000, Lippincott Williams and Wilkins, Ed. K. E. Hoover), in the form of lyophilized formulations or aqueous solutions. Acceptable carriers, excipients, or stabilizers are nontoxic to recipients at the dosages and concentrations, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as Polysorbate, PLURONICS™ or polyethylene glycol (PEG). Pharmaceutically acceptable excipients are further described herein.

Pharmaceutical compositions adapted for parenteral administration include aqueous and non-aqueous sterile injection solution which may contain anti-oxidants, buffers, bacteriostats and solutes which render the formulation substantially isotonic with the blood of the intended recipient; and aqueous and non-aqueous sterile suspensions which may include suspending agents and thickening agents. Excipients which may be used for injectable solutions include water, alcohols, polyols, glycerin and vegetable oils, for example. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules and tablets. Pharmaceutical compositions can be substantially isotonic, implying an osmolality of about 250-350 mOsm/kg water.

The pharmaceutical compositions may contain preserving agents, solubilizing agents, stabilizing agents, wetting agents, emulsifiers, sweeteners, colorants, odorants, salts (substances of the present invention may themselves be provided in the form of a pharmaceutically acceptable salt), buffers, coating agents or antioxidants. They may also contain therapeutically active agents in addition to the substance of the present invention. The pharmaceutical compositions of the invention may be employed in combination with one or more pharmaceutically acceptable excipients. Such excipients may include, but are not limited to, saline, buffered saline (such as phosphate buffered saline), dextrose, liposomes, water, glycerol, ethanol and combinations thereof.

The IL-6 antagonist antibodies (and/or IL-6 Ab-VEGF Trap), IL-6 antagonist antibody (and/or IL-6 Ab-VEGF Trap) conjugates, and pharmaceutical compositions of the invention can be employed alone or in conjunction with other compounds, such as therapeutic compounds or molecules, e.g. anti-inflammatory drugs, analgesics or antibiotics. Such administration with other compounds may be simultaneous, separate or sequential. The components may be prepared in the form of a kit which may comprise instructions as appropriate.

Methods for Preventing or Treating Ophthalmic Disorders

In some embodiments, the antibodies (and/or IL-6 Ab-VEGF Trap) and the antibody (and/or IL-6 Ab-VEGF Trap) conjugates are useful in various applications including, but are not limited to, therapeutic treatment methods.

In some embodiments, a method for treating ocular disease, such as for example AMD is provided. In some embodiments, the method of treating AMD in a subject comprises administering to the subject in need thereof an effective amount of a composition (e.g., pharmaceutical composition) comprising any of the anti-IL-6 antibodies or IL6 Ab-VEGF Traps as described herein. As used herein, AMD includes dry AMD and wet AMD. In some embodiments, provided is a method of treating AMD in a subject, comprising administering to the subject in need thereof an effective amount of a composition comprising IL-6 antagonist antibodies or the IL-6 Ab-VEGF Traps or their conjugates as described herein. In some embodiments, the IL-6 antibody and/or IL-6 Ab VEGF Trap and/or conjugates thereof can be used to treat and/or prevent and/or reduce the risk of wet or neovascular macular degeneration, wet or neovascular age-related macular degeneration, dry age-related macular degeneration, venous, arterial or other blockage of the ocular and or retinal blood vessels with or without retinal edema, anterior and posterior uveitis, uveitic macular edema, diabetic retinopathy, proliferative diabetic retinopathy, diabetic macular edema, non-proliferative diabetic macular edema, and intraocular tumors. In some embodiments, the antibody, or IL-6 Ab-VEGFTrap can be used for: (i) VEGF therapy-resistant patients, (ii) patients who lose efficacy to anti-VEGF agents due to the progression of additional underlying pathologies such as fibrosis, wound-healing, and atrophy and/or (iii) undertreatment due to the requirement for frequent intravitreal injections.

In some embodiments, a method for treating an ocular disease, such as a systemic disease, is provided. In some embodiments, systemic diseases that affect the eye such as Grave's disease or neuromyelitis optica, or systemic diseases that do not affect the eye such as multiple sclerosis, rheumatoid arthritis can be treated via the methods and compositions provided herein.

In some embodiments, the compositions provided herein can be used in combination with immune modulators such as PD-1/PDL-1 for oncology indications.

In some embodiments, the methods described herein further comprise a step of treating a subject with one or more additional form(s) of therapy. In some embodiments, the additional form of therapy is an additional AMD therapy including, but not limited to, VISUDYNE©, laser photocoagulation or intravitreal injection of, e.g., LUCENTIS®, MACUGEN®, EYLEA®, OZURDEX®, ILUVIEN®, TRIESENCE®, or TRIVARIS®.

With respect to all methods described herein, reference to IL-6 antagonist antibodies (and/or IL-6 Ab-VEGF Trap) also includes compositions comprising one or more additional agents. These compositions may further comprise suitable excipients, such as pharmaceutically acceptable excipients including buffers, which are well known in the art. The present invention can be used alone or in combination with other methods of treatment.

In some embodiments, a method for the treatment or prophylaxis of a disease in a patient in need thereof is provided. In some embodiments, the method comprises administering to the patient any of the isolated antagonist antibodies (and/or IL-6 Ab-VEGF Trap) disclosed herein. In some embodiments, the method comprises administering to the patient any of the conjugates disclosed herein. In some embodiments, the method comprises administering to the patient any of the compositions disclosed herein. In some embodiments, the method comprises identifying a patient having hyperactive IL-6 activity and administering to the patient any of the isolated antagonist antibodies disclosed herein. In some embodiments, the method comprises identifying a patient having hyperactive IL-6 activity and administering to the patient any of the conjugates disclosed herein. In some embodiments, the method comprises identifying a patient having hyperactive IL-6 activity and administering to the patient any of the compositions disclosed herein. In some embodiments, the patient has elevated VEGF activity instead of, or in addition to, the elevated IL-6 activity.

In some embodiments, the disorder is selected from the group consisting of wet or neovascular macular degeneration, wet or neovascular age-related macular degeneration, dry age-related macular degeneration, venous, arterial or other blockage of the ocular and or retinal blood vessels with or without retinal edema, anterior and posterior uveitis, uveitic macular edema, diabetic retinopathy, proliferative diabetic retinopathy, diabetic macular edema, non-proliferative diabetic macular edema, and intraocular tumors.

In some embodiments, the isolated antibody (and/or IL-6 Ab-VEGF Trap), conjugate (and/or IL-6 Ab-VEGF Trap-conjugate), composition or a combination thereof is administered no more frequently than once a month. In some embodiments, the isolated antibody, conjugate, composition or a combination thereof is administered no more frequently than once every two months. In some embodiments, the isolated antibody (and/or IL-6 Ab-VEGF Trap), conjugate (and/or IL-6 Ab-VEGF Trap)-conjugate, composition or a combination thereof is administered no more frequently than once every three months. In some embodiments, the isolated construct (e.g., Ab or Ab-Trap, with or without the polymer) is administered with a frequency between once a year and once every two months. In some embodiments, the treatment can be a single application of the antibody. In some embodiments, the treatment can be as many applications of the antibody as needed or desired for an outcome.

The IL-6 antagonist antibody (and/or IL-6 Ab-VEGF Trap) or conjugate thereof can be administered to a subject via any suitable route. It should be apparent to a person skilled in the art that the examples described herein are not intended to be limiting but to be illustrative of the techniques available. Accordingly, in some embodiments, the IL-6 antagonist antibody (and/or IL-6 Ab-VEGF Trap) is administered to a subject in accord with known methods, such as intravenous administration, e.g., as a bolus or by continuous infusion over a period of time, by intramuscular, intraperitoneal, intracerebrospinal, transdermal, subcutaneous, intraarticular, sublingually, intrasynovial, via insufflation, intrathecal, oral, inhalation or topical routes. Administration can be systemic, e.g., intravenous administration, or localized. Commercially available nebulizers for liquid formulations, including jet nebulizers and ultrasonic nebulizers are useful for administration. Liquid formulations can be directly nebulized and lyophilized powder can be nebulized after reconstitution. Alternatively, IL-6 antagonist antibody (and/or IL-6 Ab-VEGF Trap) can be aerosolized using a fluorocarbon formulation and a metered dose inhaler, or inhaled as a lyophilized and milled powder.

In some embodiments, the IL-6 antagonist antibodies (and/or IL-6 Ab-VEGF Trap), IL-6 antagonist antibody (and/or IL-6 Ab-VEGF Trap) conjugates, and pharmaceutical compositions disclosed herein are used for prophylaxis or treatment of an ocular disease or condition. So used, the conjugates are typically formulated for and administered by ocular, intraocular, and/or intravitreal injection, and/or juxtascleral injection, and/or subtenon injection, and/or suprachoroidal injection and/or topical administration in the form of eye drops and/or ointment. Such IL-6 antagonist antibodies (and/or IL-6 Ab-VEGF Trap), IL-6 antagonist antibody (and/or IL-6 Ab-VEGF Trap) conjugates, and compositions can be delivered by a variety of methods, e.g. intravitreally as a device and/or a depot that allows for slow release of the compound into the vitreous, including those described in references such as Intraocular Drug Delivery, Jaffe, Jaffe, Ashton, and Pearson, editors, Taylor & Francis (March 2006). In one example, a device may be in the form of a minimum and/or a matrix and/or a passive diffusion system and/or encapsulated cells that release the compound for a prolonged period of time (Intraocular Drug Delivery, Jaffe, Jaffe, Ashton, and Pearson, editors, Taylor & Francis (March 2006). In therapy or as a prophylactic, the active agent may be administered to an individual as an injectable composition, for example as a sterile aqueous dispersion, preferably isotonic or substantially isotonic.

Formulations for ocular, intraocular or intravitreal administration can be prepared by methods and using ingredients known in the art. Proper penetration into the eye is desirable for efficient treatment. Unlike diseases of the front of the eye, where drugs can be delivered topically, retinal diseases merit a more site-specific approach. Eye drops and ointments rarely penetrate the back of the eye, and the blood-ocular barrier hinders penetration of systemically administered drugs into ocular tissue. In some embodiments, the method of choice for drug delivery to treat retinal disease, such as AMD and CNV, is direct intravitreal injection. In some embodiments, intravitreal injections are repeated at intervals which depend on the patient's condition, and the properties and half-life of the drug delivered.

For administration to mammals, and particularly humans, it is expected that the dosage of the active agent is from 0.01 mg/kg body weight, to typically around 1 mg/kg, for systemic administrations. For ocular diseases that require local administration (for example, intravitreal, supracoroidal, peri-ocular etc), dosage is typically 0.1 mg/eye/dose to 10 mg/eye/dose or more. In some embodiments, the dosage is 100 ul/dose/eye. In some embodiments, a needle can be used to administer the dosage. The needle can be, for example, a 30 gauge 2 inch needle or a ½ inch needle that is 27G or 29G. The physician can determine the actual dosage most suitable for an individual which depends on factors including the age, weight, sex and response of the individual, the disease or disorder being treated and the age and condition of the individual being treated. The above dosages are exemplary of the average case. There can, of course, be instances where higher or lower dosages are merited.

This dosage may be repeated as often as appropriate (e.g., weekly, fortnightly, monthly, quarterly). If side effects develop the amount and/or frequency of the dosage can be reduced, in accordance with normal clinical practice. In one embodiment, the pharmaceutical composition may be administered once every one to thirty days.

The IL-6 antagonist antibodies (and/or IL-6 Ab-VEGF Trap) of the present invention may be employed in accordance with the instant invention by expression of such polypeptides in vivo in a patient, i.e., gene therapy. There are two major approaches to getting the nucleic acid (optionally contained in a vector) into the patient's cells: in vivo and ex vivo. For in vivo delivery the nucleic acid is injected directly into the patient, usually at the sites where the therapeutic protein is required, i.e., where biological activity of the therapeutic protein is needed. For ex vivo treatment, the patient's cells are removed, the nucleic acid is introduced into these isolated cells, and the modified cells are administered to the patient either directly or, for example, encapsulated within porous membranes that are implanted into the patient (see, e.g., U.S. Pat. Nos. 4,892,538 and 5,283,187). There are a variety of techniques available for introducing nucleic acids into viable cells. The techniques vary depending upon whether the nucleic acid is transferred into cultured cells in vitro, or transferred in vivo in the cells of the intended host. Techniques suitable for the transfer of nucleic acid into mammalian cells in vitro include the use of liposomes, electroporation, microinjection, transduction, cell fusion, DEAE-dextran, the calcium phosphate precipitation method, etc. Transduction involves the association of a replication-defective, recombinant viral (preferably retroviral) particle with a cellular receptor, followed by introduction of the nucleic acids contained by the particle into the cell. A commonly used vector for ex vivo delivery of the gene is a retrovirus.

The currently preferred in vivo nucleic acid transfer techniques include transfection with viral or non-viral vectors (such as adenovirus, lentivirus, Herpes simplex I virus, or adeno-associated virus (AAV)) and lipid-based systems (useful lipids for lipid-mediated transfer of the gene are, for example, DOTMA, DOPE, and DC-Chol; see, e.g., Tonkinison et al., Cancer Investigation, 14(1): 54-65 (1996)). The most preferred vectors for use in gene therapy are viruses, most preferably adenoviruses, AAV, lentiviruses, or retroviruses. A viral vector such as a retroviral vector includes at least one transcriptional promoter/enhancer or locus-defining element(s), or other elements that control gene expression by other means such as alternate splicing, nuclear RNA export, or post-translational modification of messenger. In addition, a viral vector such as a retroviral vector includes a nucleic acid molecule that, when transcribed in the presence of a gene encoding the therapeutic protein, is operably linked thereto and acts as a translation initiation sequence. Such vector constructs also include a packaging signal, long terminal repeats (LTRs) or portions thereof, and positive and negative strand primer binding sites appropriate to the virus used (if these are not already present in the viral vector). In addition, such vector typically includes a signal sequence for secretion of the PRO polypeptide from a host cell in which it is placed. Preferably the signal sequence for this purpose is a mammalian signal sequence, most preferably the native signal sequence for the therapeutic protein. Optionally, the vector construct may also include a signal that directs polyadenylation, as well as one or more restriction sites and a translation termination sequence. By way of example, such vectors will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

In some situations, it is desirable to provide the nucleic acid source with an agent that targets the target cells, such as an antibody specific for a cell-surface membrane protein or the target cell, a ligand for a receptor on the target cell, etc. Where liposomes are employed, proteins that bind to a cell-surface membrane protein associated with endocytosis may be used for targeting and/or to facilitate uptake, e.g., capsid proteins or fragments thereof tropic for a particular cell type, antibodies for proteins that undergo internalization in cycling, and proteins that target intracellular localization and enhance intracellular half-life. The technique of receptor-mediated endocytosis is described, for example, by Wu et al., J. Biol. Chem., 262: 4429-4432 (1987); and Wagner et al., Proc. Natl. Acad. Sci. USA, 87: 3410-3414(1990). For a review of the currently known gene marking and gene therapy protocols, see, Anderson et al., Science, 256: 808-813 (1992). See also WO 93/25673 and the references cited therein.

Suitable gene therapy and methods for making retroviral particles and structural proteins can be found in, e.g., U.S. Pat. No. 5,681,746.

In accordance some aspects, a method for treatment or prophylaxis of an ocular disease in a mammal is presented in which a nucleic acid molecule that encodes an IL-6 antagonist antibody (and/or IL-6 Ab-VEGF Trap) is administered.

In some embodiments, these IL6/VEGF dual inhibitor molecules can be used to treat ocular disorders such as the ophthalmic inflammatory disease scleritis, non-proliferative diabetic retinopathy, proliferative diabetic retinopathy (PDR), diabetic macular edema, prevention of diabetic macular edema, prevention of proliferative diabetic retinopathy, wet age-related macular degeneration, prevention of wet age-related macular degeneration, uveitis, and uveitic macular edema.

The VEGFR-AntiIL6 therapeutics could also be used to treat systemic diseases that affect the eye such as Grave's disease or neuromyelitis optica, or systemic diseases that do not affect the eye such as multiple sclerosis, rheumatoid arthritis.

These molecules could also be used to treat cytokine release syndrome following CAR-T or similar immune-oncology therapeutics. Additionally, anti-IL6 molecules abrogate the induction of IL-6 expression observed following treatment with anti-PD-1/PD-L1 molecules (Tsukamoto et al, 2018). Additionally, VEGF signaling blockade can also improve anti-PD-L1 treatment (Allen et al, 2017). Thus, these dual inhibitors could be used in combination with immune checkpoint inhibitors (such as PD-1/PDL-1 modulators) to synergistically treat cancer. VEGF inhibition would provide additional benefit on top of this. Another application of this could be used to cerebral edema in glioblastoma where anti-IL6 therapy may show additional benefits to anti-VEGF treatments. The biopolymer may also allow for increased tissue distribution, which would be beneficial for penetrating solid tumors.

In some embodiments, the conjugate (or the various proteins) is useful for prevention of any one or more of the disorders provided herein.

Formulations

Therapeutic formulations of the IL-6 antagonist antibodies (and/or IL-6 Ab-VEGF Trap) and IL-6 antagonist antibody (and/or IL-6 Ab-VEGF Trap) conjugates used in accordance with the present invention are prepared for storage by mixing an antibody having the desired degree of purity with optional pharmaceutically acceptable carriers, excipients or stabilizers (Remington, The Science and Practice of Pharmacy 20th Ed. Mack Publishing, 2000), in the form of lyophilized formulations or aqueous solutions. Acceptable carriers, excipients, or stabilizers are nontoxic to recipients at the dosages and concentrations employed, and may comprise buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Liposomes containing the IL-6 antagonist antibody (and/or IL-6 Ab-VEGF Trap) and/or IL-6 antagonist antibody (and/or IL-6 Ab-VEGF Trap) conjugate are prepared by methods known in the art, such as described in Epstein, et al., Proc. Natl. Acad. Sci. USA 82:3688 (1985); Hwang, et al., Proc. Natl Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The active ingredients may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington, The Science and Practice of Pharmacy 20th Ed. Mack Publishing (2000).

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The formulations to be used for in vivo administration must be sterile. This is readily accomplished by, for example, filtration through sterile filtration membranes. Therapeutic IL-6 antagonist antibody (and/or IL-6 Ab-VEGF Trap) and/or antibody (and/or IL-6 Ab-VEGF Trap) conjugate compositions are generally placed into a container having a sterile access port, for example, an intravenous solution bag or vial having a stopper pierceable by a hypodermic injection needle. In some embodiments, the antibody and/or antibody conjugate compositions are placed into a syringe to provide a prefilled syringe.

In some embodiments, the composition is a pyrogen-free composition which is substantially free of endotoxins and/or related pyrogenic substances. Endotoxins include toxins that are confined inside a microorganism and are released only when the microorganisms are broken down or die. Pyrogenic substances also include fever-inducing, thermostable substances from the outer membrane of bacteria and other microorganisms. Both of these substances can cause fever, hypotension and shock if administered to humans. Due to the potential harmful effects, even low amounts of endotoxins must be removed from intravenously administered pharmaceutical drug solutions. For systemic injection such as IV or IP, the Food & Drug Administration ("FDA") has set an upper limit of 5 endotoxin units (EU) per dose per kilogram body weight in a single one hour period for intravenous drug applications (The United States Pharmacopeial Convention, Pharmacopeial Forum 26 (1):223 (2000)). When therapeutic proteins are administered in amounts of several hundred or thousand milligrams per kilogram body weight, as can be the case with proteins of interest (e.g., antibodies), even trace amounts of harmful and dangerous endotoxin must be removed. In some embodiments, the endotoxin and pyrogen levels in the composition are less than 10 EU/mg, or less than 5 EU/mg, or less than 1 EU/mg, or less than 0.1 EU/mg, or less than 0.01 EU/mg, or less than 0.001 EU/mg. In some embodiments, the compositions or methods provided herein allow for 0.1 EU/eye/injection. In some embodiments, the compositions or methods provided herein allow for 0.05 EU/eye/injection. In some embodiments, the compositions or methods provided herein allow for 0.02 EU/eye/injection. In some embodiments, the compositions or methods provided herein allow for 0.01 EU/eye/injection.

The compositions according to the present invention may be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from about 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as Polysorbate or polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.01%, and 5% surface-active agent, and can be between 0.01 and 0.02% or 0.1 and 2.5% (polysorbate 20 or 80). It will be appreciated that other ingredients may be added, for example mannitol or other pharmaceutically acceptable vehicles, if necessary.

Suitable emulsions may be prepared using commercially available fat emulsions, such as INTRALIPID™, LIPOSYN™, INFONUTROL™, LIPOFUNDIN™ and LIPIPHYSAN™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 µm, particularly 0.1 and 0.5 µm, and have a pH in the range of 5.5 to 8.0.

The emulsion compositions can be those prepared by mixing an IL-6 antagonist antibody (and/or IL-6 Ab-VEGF Trap) with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Kits

The invention also provides kits comprising any or all of the antibodies described herein. Kits of the invention include one or more containers comprising an IL-6 antagonist antibody (and/or IL-6 Ab-VEGF Trap) or conjugate described herein and instructions for use in accordance with any of the methods of the invention described herein. Generally, these instructions comprise a description of administration of the IL-6 antagonist antibody (and/or IL-6 Ab-VEGF Trap) or conjugate for the above described therapeutic treatments. In some embodiments, kits are provided for producing a single-dose administration unit. In certain embodiments, the kit can contain both a first container having a dried protein and a second container having an aqueous formulation. In certain embodiments, kits containing single and multi-chambered pre-filled syringes (e.g., liquid syringes and lyosyringes) are included.

In some embodiments, the antibody is a human antibody. In some embodiments, the antibody is a humanized antibody. In some embodiments, the antibody is a monoclonal antibody. The instructions relating to the use of an IL-6 antagonist antibody (and/or IL-6 Ab-VEGF Trap) or conjugate generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as prefilled syringe, an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an IL-6 antagonist antibody or conjugate. The container may further comprise a second pharmaceutically active agent.

Kits may optionally provide additional components such as buffers and interpretive information. In some embodiments, the kits can include an additional syringe and needle used for back fill of the dosing syringe. Normally, the kit comprises a container and a label or package insert(s) on or associated with the container.

The following examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

EXAMPLES

Despite the therapeutic success of anti-vascular endothelial growth factor (VEGF) biologic drugs for the treatment of neovascular retinal diseases, unmet need still exists due to (i) VEGF therapy-resistant patients, (ii) patients who lose efficacy to anti-VEGF agents due to the progression of additional underlying pathologies such as fibrosis, wound-healing, and atrophy (iii) undertreatment due to the requirement for frequent intravitreal injections. Below are results regarding novel bi-specific biologic agents designed to inhibit both VEGF and IL-6.

Methods Dual inhibitors were designed and characterized for their binding affinities to their respective targets by surface plasmon resonance (SPR). Functional aspects of the molecules were tested by (1) ELISA assays targeting the competitive blocking of each target to its respective receptor (2) VEGF and/or IL-6 stimulated primary human retinal microvascular endothelial cell (HRMVEC) proliferation assays can be performed, and (3) three-dimensional primary cell co-culture assays to assess the inhibition of angiogenic sprouting can be performed.

IL-6 Ab-VEGF Trap constructs bound with pM affinity to VEGF and IL-6. Binding kinetics of each target were independent of the presence of the other, indicating that both targets can bind simultaneously without interference. Binding of these molecules to each of their targets inhibits interactions with their respective cognate receptors.

When combined within a biopolymer conjugate platform, these dual inhibitor molecules provide a further therapeutic agent for the next generation of treatment and prevention of retinal diseases.

Example 1—Antibody Generation and Screening

Methods/Results

Anti-IL-6

The present examples outline the construction of an anti-IL-6 and anti-VEGF dual inhibitor molecule containing an IL-6 antibody in an engineered human IgG$_1$ framework and IgG$_1$ Fc domain fused to an anti-VEGF trap. The Fc domain for these molecules contains L234A, L235A and G237A substitutions that minimize effector function, and L443C that allows site specific conjugation with a half-life extending phosphorylcholine based biopolymer (residue positions follow EU numbering).

An anti-IL-6 paratope in the engineered human IgG$_1$ framework was affinity maturated using a combination of library scanning mutagenesis in E. coli followed by site-directed mutagenesis in a mammalian system. The construction of a dual expression plasmid system containing a heavy and light chain Fab with anti-IL-6 CDR sequences was achieved in E. coli. FIG. 3 depicts a flow chart of the process, which resulted in the antibody heavy and light chain variable regions in FIG. 5.

Fab libraries were constructed containing random single point mutations for all 71 CDR positions, excluding substitutions for Cys, Met and Asn due to the chemical liabilities associated with these amino acids. Small-scale expression in 96 well plates format was utilized for screening the Fab libraries. E. coli colonies (TG1 cells, Zymo Research) containing randomized single point mutations were picked into 96 well plates (1.5 mL) and grown overnight at 30° C. in LB Amp+2% glucose. A separate 96 well plate was created on the following day by removing 100 µL of culture and adding 100 µL of 30% glycerol, then stored at −80° C. The remaining culture was spun down for 20 min and later resuspended in 1.5 mL of LB Amp containing 1 mM IPTG for induction of protein expression at 30° C. After 5 hours, cells were spun down, resuspended in 500 µL of HBS-EP+ buffer and lysed by one freeze/thaw cycle. Lysates were centrifuged for 30 minutes and vacuum filtered (200 µL) into round bottom 96 well plates for Biacore analysis.

Affinities of anti-IL-6 Fabs were determined using a Biacore T200 (GE Healthcare) at 25° C. CM5 chips were activated with EDC and NHS, recombinant human IL-6 (R&D Systems) was diluted into 10 mM sodium acetate pH 5 to a concentration of 0.1 mg/mL and injected over the activated chip. Three ranges of antigen density (100-150 RU, 300-400 RU, 400-600 RU) were obtained by using variable flow times for each chip channel, later blocked with ethanolamine. Supernatants of the 96-well filtered culture lysates were injected at 50 µL/min for 120 seconds. Fitting of dissociation curves (300 seconds) to single exponential decay curve was used for the determination of dissociation rates ($k_{off}$). Chip surfaces were regenerated with 10 mM Glycine pH 1.7 solution injected at 50 µL/min during 60 seconds after every cycle of sample binding and dissociation. Clones that showed similar or improved $k_{off}$ values in comparison to the wild-type were submitted for DNA sequencing for mutation identification.

From the total of 71 CDR residue positions, screening data showed 15 residues were critical for IL-6 binding and could not be replaced by any other amino acid. Substitutions in tolerable positions resulted in similar $k_{off}$ values to the parent molecule (Table 13). Most of these single replacements were later introduced into the genes of the full heavy and light chains cloned in mammalian expression vectors, which were co-transfected into 3 ml cultures of Expi293 cells for protein production. On the fifth day, these cultures were centrifuged and the supernatants containing secreted antibodies were harvested and diluted in HBS-EP+ running buffer (1:20 ratio). Point mutants are in tables 13-18

TABLE 13

| | HEAVY CHAIN CDR1 | | | | | | | | |
|---|---|---|---|---|---|---|---|---|---|
| | G26 | F27 | T28 | F29 | S30 | P31 | F32 | A33 | M34 | S35 |
| F | | | | | | crit. | | crit. | | |
| L | | | | | | crit. | | crit. | | |
| I | | | | | | crit. | | crit. | | |
| V | | 4.05E−03 | | | | crit. | 5.41E−03 | crit. | | |
| S | 3.75E−03 | 3.93E−03 | | | | crit. | | crit. | | |
| P | | 4.18E−03 | | | | crit. | | crit. | | |
| T | | | | | | crit. | | crit. | | |
| A | | | 3.96E−03 | | | crit. | | crit. | | |
| Y | | | 3.90E−03 | 5.11E−03 | 3.52E−03 | crit. | | crit. | | |
| H | | | | 5.24E−03 | | crit. | | crit. | | 3.92E−03 |
| Q | | | | | | crit. | | crit. | | 3.54E−03 |
| K | | | 4.08E−03 | | | crit. | | crit. | | |
| D | | | | | | crit. | | crit. | | |

TABLE 13-continued

| | | | | HEAVY CHAIN CDR1 | | | | | |
|---|---|---|---|---|---|---|---|---|---|
| | G26 | F27 | T28 | F29 | S30 | P31 | F32 | A33 | M34 | S35 |
| E | | | 4.28E-03 | | | crit. | | crit. | | |
| W | | | | | 3.69E-03 | crit. | | crit. | 3.97E-03 | |
| R | 9.81E-03 | 9.94E-03 | | | | crit. | | crit. | | |
| G | | 4.01E-03 | | | 3.77E-03 | crit. | 5.29E-03 | crit. | | |

Table displays koff values (s–1) for every tolerable substitution within define CDR. In overall mutants present similar $k_{off}$ to parental molecule (4.94E-03±7.67E-04). Residues critical for IL-6 binding and did not tolerate replacements are indicated as 'crit'.

TABLE 14

| HEAVY CHAIN CDR2 | | | | | | | | | | |
|---|---|---|---|---|---|---|---|---|---|---|
| | V48 | A49 | K50 | I51 | S52 | P53 | G54 | G55 | S56 | W57 |
| F | | | crit. | | crit. | crit. | crit. | crit. | | 6.18E−03 |
| L | | | crit. | | crit. | crit. | crit. | crit. | | |
| I | 6.17E−03 | | crit. | | crit. | crit. | crit. | crit. | | |
| V | | | crit. | | crit. | crit. | crit. | crit. | | |
| S | | 5.42E−03 | crit. | | crit. | crit. | crit. | crit. | | |
| P | | | crit. | | crit. | crit. | crit. | crit. | | |
| T | | 5.71E−03 | crit. | | crit. | crit. | crit. | crit. | | |
| A | | | crit. | | crit. | crit. | crit. | crit. | | |
| Y | | | crit. | | crit | crit. | crit. | crit. | | |
| H | | | crit. | | crit. | crit. | crit. | crit. | 4.94E−03 | |
| Q | 5.40E−03 | | crit. | | crit. | crit. | crit. | crit. | | |
| K | | | crit. | | crit. | crit. | crit. | crit. | | |
| D | | | crit. | | crit. | crit. | crit. | crit. | | |
| E | | | crit. | | crit. | crit. | crit. | crit. | | |
| W | | | crit. | | crit. | crit. | crit. | crit. | | |
| R | | | crit. | 3.15E−03 | crit. | crit. | crit. | crit. | 5.09E−03 | |
| G | | | crit. | | crit. | crit. | crit. | crit. | | |

| | T58 | Y59 | Y60 | S61 | D62 | T63 | V64 | T65 | G66 |
|---|---|---|---|---|---|---|---|---|---|
| F | | crit. | crit. | | | | 6.04E−03 | | |
| L | | crit. | crit. | | | | | 5.92E−03 | |
| I | | crit. | crit. | | | | | 6.16E−03 | |
| V | 5.62E−03 | crit. | crit. | | | | | | |
| S | | crit. | crit. | | | | | | |
| P | | crit. | crit. | | | | | | |
| T | | crit. | crit. | | | | | | |
| A | | crit. | crit. | 6.04E−03 | | | 6.43E−03 | 6.15E−03 | |
| Y | | crit. | crit. | | | | | 5.74E−03 | |
| H | | crit. | crit. | | | | | | |
| Q | | crit. | crit. | | 4.34E−03 | 5.70E−03 | | | |
| K | 4.92E−03 | crit. | crit. | 5.69E−03 | | 6.11E−03 | | | |
| D | | crit. | crit. | | | 6.03E−03 | | 6.14E−03 | 6.07E−03 |
| E | | crit. | crit. | | | 5.53E−03 | | | 5.82E−03 |
| W | | crit. | crit. | | | | | | |
| R | 4.25E−03 | crit. | crit. | 5.85E−03 | | | | | |
| G | | crit. | crit. | | | 5.59E−03 | | 5.70E−03 | |

Table displays $k_{off}$ values (s−1) for every tolerable substitution within define CDR. In overall mutants present similar $k_{off}$ to parental molecule (4.94E-03±7.67E-04). Residues critical for IL-6 binding and did not tolerate replacements are indicated as 'crit'.

TABLE 15

| HEAVY CHAIN CDR3 | | | | | | | | | | | | |
|---|---|---|---|---|---|---|---|---|---|---|---|---|
| | A97 | R98 | Q99 | L100 | W101 | G102 | Y103 | Y104 | A105 | L106 | D107 | I108 |
| F | | | | | crit. | | | | | 6.01E−03 | | 3.40E−03 |
| L | | | | | crit. | | | | | | | |
| I | | | | | crit. | | | | | | | |

TABLE 15-continued

HEAVY CHAIN CDR3

| | A97 | R98 | Q99 | L100 | W101 | G102 | Y103 | Y104 | A105 | L106 | D107 | I108 |
|---|---|---|---|---|---|---|---|---|---|---|---|---|
| V | 4.12E-09 | | | | crit. | | | 0.00381 | | | | |
| S | | | | | crit. | | 0.00502 | | | | | 3.52E-03 |
| P | | | | | crit. | | | | | | | |
| T | | | | | crit. | | | | | | | |
| A | | | 3.88E-03 | | crit. | | | | | | | |
| Y | | | | | crit. | | | | | | | |
| H | | | 4.41E-03 | | crit. | | | | 0.00378 | | | |
| Q | | | | 2.45E-03 | crit. | | | | 0.00401 | | | |
| K | | | | 2.87E-03 | crit. | | | | | | | |
| D | | | | | crit. | 0.00389 | 0.00503 | | | | | |
| E | | | | | crit. | | 0.00512 | | | | 4.88E-03 | 3.08E-03 |
| W | | | | | crit. | | | | | | | |
| R | | | | | crit. | | | | | | | |
| G | | 0.0048 | | | crit. | | | | | | | |

Table displays $k_{off}$ values (s−1) for every tolerable substitution within define CDR. In overall mutants present similar $k_{off}$ to parental molecule (4.94E-03±7.67E-04). Residues critical for IL-6 binding and did not tolerate replacements are indicated as 'crit'.

TABLE 16

| LIGHT CHAIN CDR1 | | | | | | | | | | |
|---|---|---|---|---|---|---|---|---|---|---|
| | S24 | A25 | S26 | I27 | S28 | Y29 | S30 | Y31 | M32 | Y33 |
| F | | | | 5.94E−03 | | | | 5.10E−03 | | 6.18E−03 |
| L | | | | 5.93E−03 | | 5.43E−03 | | | 4.92E−03 | |
| I | 4.12E−03 | | | | | | | | | |
| V | 4.16E−03 | | | | | | | | 4.55E−03 | |
| S | | 4.80E−03 | | | | | | | | |
| P | 3.97E−03 | | | | | | | | | |
| T | | 4.79E−03 | | | | | | | | |
| A | | | | | | | 6.54E−03 | | | |
| Y | | | | | | | | | | |
| H | | | 4.27E−03 | | | | | | | |
| Q | | | | | | | | | | |
| K | 4.16E−03 | | 4.41E−03 | | | | | | | |
| D | | | | | | | | | | |
| E | | | | | 4.51E−03 | | | | | |
| W | | | | 5.69E−03 | 3.98E−03 | | | | | |
| R | | | | | | | | | | |
| G | | | 3.94E−03 | | | | 6.77E−03 | 5.11E−03 | | |

Table displays $k_{off}$ values (s−1) for every tolerable substitution within define CDR. In overall mutants present similar $k_{off}$ to parental molecule (4.94E-03±7.67E-04). Residues critical for IL-6 binding and did not tolerate replacements are indicated as 'crit'.

TABLE 17

| LIGHT CHAIN CDR2 | | | | | | | | | | | |
|---|---|---|---|---|---|---|---|---|---|---|---|
| | L45 | L46 | I47 | Y48 | D49 | M50 | S51 | N52 | L53 | A54 | S55 |
| F | crit. | | | 5.37E−03 | | | | | | | |
| L | crit. | | | | | | | | | 4.89E−03 | 5.07E−03 |
| I | crit. | | | | | | | | | | 5.09E−03 |
| V | crit. | 5.03E−03 | 4.93E−03 | | | | | | | | 5.16E−03 |
| S | crit. | | | | | | | 5.55E−03 | | | |
| P | crit. | | | | | | | | | | |
| T | crit. | | | | | | | | | | 5.20E−03 |
| A | crit. | | | | | | | | | | |
| Y | crit. | | | | | | | | | 5.25E−03 | 5.08E−03 |
| H | crit. | | | | | | | | 4.98E−03 | | |
| Q | crit. | | | | | | | | | | |
| K | crit. | | | | | | 4.61E−03 | | | | |
| D | crit. | | | | | 4.58E−03 | 4.66E−03 | | | | |

TABLE 17-continued

LIGHT CHAIN CDR2

| | L45 | L46 | I47 | Y48 | D49 | M50 | S51 | N52 | L53 | A54 | S55 |
|---|---|---|---|---|---|---|---|---|---|---|---|
| E | crit. | | | | 6.19E−03 | 4.66E−03 | | | | | |
| W | crit. | | | 5.63E−03 | | | | | 5.01E−03 | | 5.10E−03 |
| R | crit. | | | | | | | 4.67E−03 | 5.00E−03 | | 5.26E−03 |
| G | crit. | | | | | | | | | 4.98E−03 | |

Table displays $k_{off}$ values (s−1) for every tolerable substitution within define CDR. In overall mutants present similar $k_{off}$ to parental molecule (4.94E−03±7.67E-04). Residues critical for IL-6 binding and did not tolerate replacements are indicated as 'crit'.

TABLE 18

| | LIGHT CHAIN CDR3 | | | | | | | | |
|---|---|---|---|---|---|---|---|---|---|
| | M88 | Q89 | W90 | S91 | G92 | Y93 | P94 | Y95 | T96 |
| F | | | crit. | | crit. | crit. | crit. | | |
| L | | | crit. | | crit. | crit. | crit. | | 4.78E−03 |
| I | | | crit. | | crit. | crit. | crit. | 6.08E−03 | 4.23E−03 |
| V | 4.95E−03 | | crit. | | crit. | crit. | crit. | | 5.04E−03 |
| S | | 6.01E−03 | crit. | | crit. | crit. | crit. | | |
| P | | | crit. | | crit. | crit. | crit. | | |
| T | | | crit. | | crit. | crit. | crit. | | |
| A | 4.79E−03 | 5.85E−03 | crit. | 5.59E−03 | crit. | crit. | crit. | | |
| Y | | | crit. | | crit. | crit. | crit. | | |
| H | | | crit. | | crit. | crit. | crit. | | |
| Q | | | crit. | | crit. | crit. | crit. | | |
| K | | | crit. | 5.49E−03 | crit. | crit. | crit. | | |
| D | | | crit. | | crit. | crit. | crit. | | |
| E | | | crit. | | crit. | crit. | crit. | | |
| W | | | crit. | | crit. | crit. | crit. | | |
| R | | | crit. | | crit. | crit. | crit. | | |
| G | | | crit. | | crit. | crit. | crit. | 4.62E−03 | |

Table displays $k_{off}$ values (s−1) for every tolerable substitution within define CDR. In overall mutants present similar $k_{off}$ to parental molecule (4.94E-03±7.67E-04). Residues critical for IL-6 binding and did not tolerate replacements are indicated as 'crit'.

Binding kinetics of these single mutant molecules to IL-6 were measured at 25° C. using a Biacore T200. Antibodies were captured on a Protein A chip (GE) by injecting 1:20 dilution of cell supernatant at 10 μL/min for 60 seconds. Five concentrations (0.56, 1.67, 5, 15 and 45 nM) of IL-6 were flowed over captured antibodies for 60 seconds at a flow rate of 30 μL/min and dissociated for 180 seconds in a single cycle kinetics Biacore assay format. The sensor chip was regenerated by a 60 seconds injection of 10 mM Glycine pH 1.7 at flow rate of 50 μL/min. A similar assay setup was used to monitor interactions between purified antibody samples and IL-6 at 37° C., when applicable. For this setup, 1 μg/mL of purified antibody was injected over a Protein A chip at 10 μL/min for 25-28 seconds. Data analysis for supernatant and purified samples were performed using BIAevaluation software (GE). All sensorgrams were double reference subtracted and fit using a 1:1 Langmuir binding model.

From all single point mutations tested (Table 19), the G66D mutation at the heavy chain CDR2 (sequential numbering of the antibody variable domain) resulted in a marked affinity boost (~2 fold decrease in $K_D$ relative to wild-type: $6.95\times10^{-11}$ M vs $1.58\times10^{-10}$ M respectively). G66D was retained, and the remaining heavy chain and light chain CDR residues that could have manufacturing related chemical liabilities (Cys, Met, Asn) were mutagenized. Based on this premise, two heavy chain variants were generated including triple mutations (Table 21): I) M341/G66D/I108V, II) M34W/G66D/I108V and three light chain variants including triple and quadruple mutations (Table 22): III) M32L/M50D/N52S/M88Q, IV) M32L/M50A/N52S/M88Q, V) M32L/M50D/M88Q (residue positions follow sequential numbering of the antibody variable heavy chain). We evaluated the IL-6 binding to all the possible combinations among these variants using the same Biacore assay setup described for the single point mutations. Our findings demonstrated these mutations countered the effect of the single point G66D mutation while keeping the affinity to IL-6 closer to the parent CDR sequence (Table 20). Based on these results, these modified CDRs were incorporated into the design of the anti-IL-6 and IL-6 Ab-VEGF Trap.

TABLE 19

| CDR | Heavy chain - mutation | Light chain - mutation | Sup/25° C. | | | | | |
|---|---|---|---|---|---|---|---|---|
| | | | Capture | ka (1/Ms) | kd (1/s) | KD (M) | Rmax (RU) | Chi² (RU²) |
| | WT | WT | 981.4 | 3.15E+05 | 1.26E−04 | 3.99E−10 | 223.2 | 1.108 |
| Heavy chain - CDR1 | G26S | WT | 437.8 | 5.51E+05 | 1.15E−04 | 2.09E−10 | 96.7 | 0.0358 |
| | G26R | WT | 638.4 | 4.02E+05 | 1.21E−04 | 3.02E−10 | 141.5 | 0.0304 |
| | F27G | WT | 764 | 8.56E+05 | 2.06E−04 | 2.40E−10 | 129.3 | 0.19 |
| | F27P | WT | 734.7 | 5.70E+05 | 1.96E−04 | 3.44E−10 | 125.9 | 0.0913 |
| | F27R | WT | 809.6 | 5.03E+05 | 2.09E−04 | 4.15E−10 | 137.7 | 0.0638 |
| | F27S | WT | 573.2 | 7.31E+05 | 2.03E−04 | 2.78E−10 | 93.5 | 0.12 |
| | F27V | WT | 699.4 | 4.70E+05 | 2.08E−04 | 4.42E−10 | 114 | 0.0548 |
| | T28Y | WT | 797.6 | 3.32E+05 | 1.37E−04 | 4.12E−10 | 165.6 | 0.229 |
| | T28K | WT | 773.6 | 3.86E+05 | 1.43E−04 | 3.70E−10 | 171 | 0.157 |
| | T28A | WT | 705.1 | 3.93E+05 | 13.9E−04 | 3.54E−10 | 157.5 | 0.0635 |
| | T28E | WT | 832.8 | 4.69E+05 | 1.63E−04 | 3.47E−10 | 192.9 | 0.112 |
| | F29G | WT | 653.3 | 4.95E+05 | 1.35E−04 | 2.73E−10 | 148.1 | 0.0271 |
| | F29 | WT | 623.6 | 4.99E+05 | 1.33E−04 | 2.66E−10 | 139.3 | 1.0423 |
| | S30W | WT | 619.7 | 4.17E+05 | 1.57E−04 | 3.76E−10 | 127.9 | 0.145 |
| | S30Y | WT | 545.2 | 3.65E+05 | 1.22E−04 | 3.34E−10 | 110.9 | 0.0853 |
| | S30G | WT | 686.2 | 3.98E+05 | 1.32E−04 | 3.33E−10 | 156 | 0.108 |
| | P31 | WT | | | | CRITICAL | | |
| | F32G | WT | 328.5 | 4.18E+05 | 1.33E−04 | 3.18E−10 | 68.3 | 0.0332 |
| | M34W | WT | 634.5 | 2.96E+05 | 1.15E−04 | 3.90E−10 | 119.6 | 0.0557 |
| | S35H | WT | 942.1 | 3.48E+05 | 1.32E−04 | 3.79E−10 | 202.8 | 0.0305 |
| | S35Q | WT | 587.6 | 3.75E+05 | 1.30E−04 | 3.46E−10 | 128.9 | 0.0834 |
| Heavy | V81I | WT | 128.6 | 4.60E+05 | 1.59E−04 | 3.46E−10 | 42.2 | 0.0224 |
| | V48Q | WT | 49.5 | 6.54E+05 | 1.38E−04 | 2.10E−10 | 12.8 | 0.0418 |
| | A49T | WT | 410.6 | 4.48E+05 | 1.51E−04 | 3.37E−10 | 96.2 | 0.0495 |
| | K50 | WT | | | | CRITICAL | | |
| | I51R | WT | 605.9 | 4.62E+05 | 7.60E−05 | 1.65E−10 | 132.1 | 0.168 |
| | S52 | WT | | | | CRITICAL | | |
| | P53 | WT | | | | CRITICAL | | |
| | G54 | WT | | | | CRITICAL | | |
| | G55 | WT | | | | CRITICAL | | |
| | S56R | WT | 521.8 | 2.73E+05 | 1.55E−04 | 5.67E−10 | 97.4 | 0.0349 |
| | S56H | WT | 582.3 | 3.56E+05 | 1.61E−04 | 4.52E−10 | 128.4 | 0.0384 |
| | W57F | WT | 335.5 | 5.77E+05 | 1.28E−04 | 2.22E−10 | 78.1 | 0.0213 |
| | T58K | WT | 553.5 | 4.60E+05 | 1.79E−04 | 3.90E−10 | 121 | 0.0168 |
| | T58R | WT | 606.4 | 3.57E+05 | 1.52E−04 | 4.26E−10 | 131.5 | 0.0529 |
| | T58V | WT | 621.7 | 8.03E+05 | 1.81E−04 | 2.26E−10 | 144 | 0.0386 |
| | Y59 | WT | | | | CRITICAL | | |
| | Y60 | WT | | | | CRITICAL | | |
| | S61R | WT | 510.6 | 3.48E+05 | 1.62E−04 | 4.67E−10 | 119.1 | 0.0401 |
| | S61A | WT | 546.2 | 3.79E+05 | 1.49E−04 | 3.94E−10 | 123.6 | 0.0376 |
| | D62Q | WT | 1055.5 | 4.03E+05 | 1.48E−04 | 3.66E−10 | 2.7.3 | 0.0974 |
| | D62F | WT | 279.2 | 4.20E+05 | 1.47E−04 | 3.50E−10 | 63.8 | 0.0214 |
| | T63D | WT | 547.4 | 4.10E+05 | 1.74E−04 | 4.23E−10 | 127.4 | 0.0677 |
| | T63E | WT | 622.5 | 3.80E+05 | 1.69E−04 | 4.45E−10 | 141.7 | 0.0419 |
| | T63K | WT | 882.7 | 5.46E+05 | 2.12E−04 | 3.88E−10 | 137.4 | 0.134 |
| | T63G | WT | 702.6 | 5.17E+05 | 2.09E−04 | 4.04E−10 | 134 | 0.0425 |
| | T63Q | WT | 900.9 | 3.09E+05 | 1.84E−04 | 5.94E−10 | 208.1 | 0.261 |
| | V64A | WT | 558.1 | 4.44E+05 | 1.78E−04 | 4.02E−10 | 130.3 | 0.0683 |
| | T65Y | WT | 559.1 | 749000 | 0.000206 | 2.75E−10 | 123.8 | 0.0642 |
| | T65G | WT | 3.2 | 597000 | 5.69E−05 | 9.54E−11 | 3 | 0.0498 |
| | G66E | WT | 743 | 1.02E+06 | 1.10E−04 | 1.07E−10 | 176.8 | 0.242 |
| | G66D | WT | 783.5 | 1.30E+06 | 1.17E−04 | 9.02E−11 | 184.9 | 0.254 |
| Heavy chain - CDR3 | A97V | WT | 547.3 | 3.11E+05 | 1.79E−04 | 5.74E−10 | 128.2 | 0.0654 |
| | R98G | WT | 693.2 | 1.76E+05 | 2.51E−04 | 1.42E−09 | 148.9 | 0.344 |
| | Q99A | WT | 879.2 | 3.68E+05 | 7.37E−04 | 2.00E−09 | 183.2 | 0.0575 |
| | Q99H | WT | 1004.6 | 5.39E+05 | 1.05E−03 | 1.94E−09 | 213.9 | 0.094 |
| | L100Q | WT | 1264.1 | 3.98E+05 | 1.53E−04 | 3.84E−10 | 2.81.2 | 0.0485 |
| | W101 | WT | | | | CRITICAL | | |
| | G102D | WT | 777.7 | 4.52E+05 | 6.00E−04 | 1.33E−09 | 136 | 0.0832 |
| | Y103D | WT | 774.6 | 7.37E+05 | 2.19E−04 | 2.97E−10 | 140 | 0.0826 |
| | Y103S | WT | 1016.6 | 5.46E+05 | 2.31E−04 | 4.23E−10 | 177.8 | 0.125 |
| | Y103E | WT | 794.4 | 7.18E+05 | 1.65E−04 | 2.29E−10 | 192.4 | 0.0289 |
| | Y104V | WT | 276.8 | 5.25E+05 | 7.03E−04 | 1.34E−09 | 41 | 0.0745 |
| | A105Q | WT | 524.4 | 474E+05 | 4.93E−04 | 1.04E−09 | 94.8 | 0.107 |
| | A105H | WT | 520.8 | 404E+05 | 7.23E−04 | 1.39E−09 | 108 | 0.0869 |
| | L106F | WT | 1138.8 | 5.91E+05 | 1.85E−04 | 3.14E−09 | 252.2 | 0.0955 |
| | L106I | WT | 268.1 | 4.79E+05 | 1.34E−04 | 1.79E−10 | 60 | 0.0889 |
| | D107E | WT | 900.1 | 5.09E+05 | 1.47E−04 | 2.90E−10 | 200.9 | 0.0643 |
| | I108F | WT | 1177.7 | 3.65E+05 | 1.46E−04 | 3.99E−10 | 251.7 | 0.0728 |
| | I108E | WT | 1135.7 | 5.71E+05 | 1.74E−04 | 3.05E−10 | 254.4 | 0.156 |
| | I108S | WT | 815.4 | 5.54E+05 | 1.41E−04 | 2.56E−10 | 177.3 | 0.0421 |
| Light chain - CDR1 | WT | S24P | 44.3 | 4.84E+05 | 2.67E−06 | 5.51E−12 | 11.2 | 0.0502 |
| | WT | S24K | 739 | 3.11E+05 | 1.32E−04 | 4.24E−10 | 167.3 | 0.025 |
| | WT | S24V | 787.2 | 3.40E+05 | 1.37E−04 | 4.03E−10 | 180.6 | 0.225 |

TABLE 19-continued

|  | | CDR mutation | Capture | ka (1/Ms) | kd (1/s) | KD (M) | Rmax (RU) | Chi² (RU²) |
|---|---|---|---|---|---|---|---|---|
|  | WT | S24I | 597.7 | 4.76E+05 | 1.35E-04 | 2.84E-10 | 129.6 | 0.0541 |
|  | WT | A25S | 386.6 | 5.35E+05 | 1.05E-04 | 1.97E-10 | 90.6 | 0.0195 |
|  | WT | A25T | 513 | 5.08E+05 | 1.19E-04 | 2.35E-10 | 118 | 0.0222 |
|  | WT | S26G | 5.9 | 7.93E+05 | 2.23E-04 | 2.81E-10 | 3.6 | 0.15 |
|  | WT | S26H | 525.5 | 4.15E+05 | 1.49E-04 | 3.60E-10 | 117.4 | 0.111 |
|  | WT | S26K | 696.4 | 3.79E+05 | 1.64E-04 | 4.33E-10 | 155.4 | 0.144 |
|  | WT | I27L | 878.5 | 4.37E+05 | 1.45E-04 | 3.32E-10 | 202 | 0.0356 |
|  | WT | I27W | 516.3 | 4.87E+05 | 1.61E-04 | 3.30E-10 | 113.3 | 0.129 |
|  | WT | I27F | 784.4 | 4.36E+05 | 1.93E-04 | 4.43E-10 | 168 | 0.0802 |
|  | WT | S28E | 673.8 | 4.20E+05 | 1.21E-04 | 2.89E-10 | 159.5 | 0.266 |
|  | WT | S28R | 468 | 3.69E+05 | 1.71E-04 | 4.64E-10 | 110.9 | 0.0196 |
|  | WT | V29L | 385.6 | 3.51E+05 | 1.71E-04 | 4.87E-10 | 83.4 | 0.171 |
|  | WT | S30G | 84.5 | 5.48E+05 | 1.73E-04 | 3.16E-10 | 19.3 | 0.0863 |
|  | WT | S30A | 760 | 2.55E+05 | 1.63E-04 | 6.39E-10 | 169 | 0.0653 |
|  | WT | Y31G | 405.9 | 3.05E+05 | 2.03E-04 | 6.66E-10 | 92.8 | 0.0183 |
|  | WT | Y31F | 745.1 | 2.92E+05 | 1.38E-04 | 4.72E-10 | 184.2 | 0.0274 |
|  | WT | M32L | 563.2 | 5.91E+05 | 1.18E-04 | 1.99E-10 | 130 | 0.0192 |
|  | WT | M32V | 426.5 | 5.05E+05 | 1.16E-04 | 2.30E-10 | 98.8 | 0.0226 |
|  | WT | Y33 | | | CRITICAL | | | |
| Light chain - CDR2 | WT | L45 | | | CRITICAL | | | |
|  | WT | L46V | 486.4 | 4.60E+05 | 2.03E-04 | 4.42E-10 | 96.3 | 0.0311 |
|  | WT | I47V | 490 | 4.71E+05 | 1.95E-04 | 4.14E-10 | 93.3 | 0.0258 |
|  | WT | Y48W | 500.3 | 3.45E+05 | 1.23E-04 | 3.56E-10 | 121.7 | 0.0146 |
|  | WT | D49E | 376.2 | 4.59E+05 | 1.11E-04 | 2.41E-10 | 79.7 | 0.0725 |
|  | WT | M50D | 544.3 | 8.06E+05 | 1.12E-04 | 1.38E-10 | 129.3 | 0.0328 |
|  | WT | S51K | 817 | 3.96E+05 | 2.12E-04 | 5.35E-10 | 137.3 | 0.0479 |
|  | WT | S51R | 419.5 | 4.99E+05 | 2.31E-04 | 4.63E-10 | 64.6 | 0.0410 |
|  | WT | S51D | 552.6 | 7.29E+05 | 2.16E-04 | 2.96E-10 | 77.5 | 0.0487 |
|  | WT | N52S | 671.2 | 4.30E+05 | 1.52E-04 | 3.55E-10 | 160.2 | 0.0246 |
|  | WT | L53H | 420.5 | 5.44E+05 | 2.18E-04 | 4.01E-10 | 64.9 | 0.0396 |
|  | WT | L53W | 10.2 | 1.19E+06 | 6.14E-04 | 5.18E-12 | 3.5 | 0.0526 |
|  | WT | L53R | 445.3 | 4.16E+05 | 1.85E-04 | 4.46E-10 | 87.7 | 0.0331 |
|  | WT | A54G | 302 | 4.75E+05 | 1.98E-04 | 4.16E-10 | 54.2 | 0.0241 |
|  | WT | A54Y | 104.2 | 6.52E+05 | 1.09E-04 | 1.68E-10 | 18 | 0.0725 |
|  | WT | A54L | 391.8 | 4.20E+05 | 2.10E-04 | 4.99E-10 | 68.2 | 0.0473 |
|  | WT | S55W | 472.5 | 5.63E+05 | 2.26E-04 | 4.01E-10 | 69.3 | 0.0716 |
|  | WT | S55Y | 615.7 | 4.36E+05 | 2.01E-04 | 4.61E-10 | 102.7 | 0.0384 |
|  | WT | S55R | 17.8 | 9.87E+05 | 1.07E-04 | 1.09E-10 | 5.2 | 0.0981 |
|  | WT | S55L | 661 | 6.68E+05 | 2.20E-04 | 3.29E-10 | 99.8 | 0.131 |
| Light chain - CDR3 | WT | M88V | 240.3 | 4.48E+05 | 1.07E-04 | 2.39E-10 | 49.4 | 0.0502 |
|  | WT | M88A | 328.8 | 4.51E+05 | 1.27E-04 | 2.82E-10 | 51.3 | 0.976 |
|  | WT | Q89S | 471.5 | 3.62E+05 | 2.72E-04 | 7.52E-10 | 61.2 | 0.0171 |
|  | WT | Q89A | 186.6 | 5.43E+05 | 2.27E-04 | 4.19E-10 | 32.2 | 0.085 |
|  | WT | W90 | | | CRITICAL | | | |
|  | WT | S91A | 345.3 | 3.41E+05 | 1.39E-04 | 4.07E-10 | 79 | 0.0325 |
|  | WT | G92 | | | CRITICAL | | | |
|  | WT | Y93 | | | CRITICAL | | | |
|  | WT | P94 | | | CRITICAL | | | |
|  | WT | Y95G | 503.8 | 8.82E+05 | 3.38E-04 | 3.83E-10 | 51 | 0.126 |
|  | WT | Y95I | 271.3 | 5.93E+05 | 4.44E-03 | 7.48E-09 | 42.2 | 0.107 |
|  | WT | T96L | 399 | 5.20E+05 | 1.35E-04 | 2.59E-10 | 83.8 | 1.01 |
|  | WT | T96V | 523 | 4.54E+05 | 1.92E-04 | 4.23E-10 | 110.6 | 0.169 |

|  | Heavy chain - mutation | Purified/37° C. | | | | | |
|---|---|---|---|---|---|---|---|
| CDR | | Capture | ka (1/Ms) | kd (1/s) | KD (M) | Rmax (RU) | Chi² (RU²) |
|  | WT | 138.1 | 8.80E+05 | 1.39E-04 | 1.58E-10 | 34.6 | 0.397 |
| Heavy chain - CDR1 | G26S | 172.4 | 8.42E+05 | 3.90E-04 | 4.63E-10 | 39.8 | 0.0688 |
|  | G26R | 183.3 | 7.02E+05 | 3.26E-04 | 4.65E-10 | 42.8 | 0.185 |
|  | F27G | | | | | | |
|  | F27P | | | | | | |
|  | F27R | | | | | | |
|  | F27S | | | | | | |
|  | F27V | | | | | | |
|  | T28Y | | | | | | |
|  | T28K | | | | | | |
|  | T28A | | | | | | |
|  | T28E | | | | | | |
|  | F29G | 156.2 | 8.50E+05 | 3.97E-04 | 4.66E-10 | 37.2 | 0.0579 |
|  | F29 | 174.1 | 8.42E+05 | 3.74E-04 | 4.44E-10 | 40.2 | 0.078 |
|  | S30W | | | | | | |
|  | S30Y | | | | | | |
|  | S30G | | | | | | |
|  | P31 | | | CRITICAL | | | |
|  | F32G | 155.1 | 6.50E+05 | 3.70E-05 | 5.69E-10 | 36.2 | 0.0601 |
|  | M34W | 118.3 | 5.99E+05 | 2.36E-04 | 3.94E-10 | 24.2 | 0.226 |
|  | S35H | | | | | | |
|  | S35Q | | | | | | |

TABLE 19-continued

| Region | Mutation | | | | | | |
|---|---|---|---|---|---|---|---|
| Heavy | V81I | | | | | | |
| | V48Q | | | | | | |
| | A49T | | | | | | |
| | K50 | | | | | | |
| | I51R | 126 | 6.79E+05 | 3.43E−04 | 5.05E−10 | 28.5 | 0.173 |
| | S52 | | | CRITICAL | | | |
| | P53 | | | CRITICAL | | | |
| | G54 | | | CRITICAL | | | |
| | G55 | | | CRITICAL | | | |
| | S56R | | | | | | |
| | S56H | | | | | | |
| | W57F | 146.5 | 8.64E+05 | 4.53E−04 | 5.24E−10 | 37.2 | 0.0527 |
| | T58K | | | | | | |
| | T58R | | | | | | |
| | T58V | | | | | | |
| | Y59 | | | CRITICAL | | | |
| | Y60 | | | CRITICAL | | | |
| | S61R | | | | | | |
| | S61A | | | | | | |
| | D62Q | 70.3 | 8.75E+05 | 6.01E−04 | 6.87E−10 | 17.5 | 0.156 |
| | D62F | | | | | | |
| | T63D | | | | | | |
| | T63E | | | | | | |
| | T63K | | | | | | |
| | T63G | | | | | | |
| | T63Q | | | | | | |
| | V64A | | | | | | |
| | T65Y | | | | | | |
| | T65G | | | | | | |
| | G66E | 105.5 | 1.91E+06 | 1.71E−04 | 8.95E−11 | 31.3 | 0.522 |
| | G66D | 142.8 | 1.96E+06 | 1.36E−04 | 6.95E−11 | 39.9 | 0.513 |
| Heavy chain - CDR3 | A97V | | | | | | |
| | R98G | | | | | | |
| | Q99A | | | | | | |
| | Q99H | | | | | | |
| | L100Q | 121.4 | 8.23E+05 | 4.10E−04 | 4.99E−10 | 28.4 | 0.155 |
| | W101 | | | CRITICAL | | | |
| | G102D | | | | | | |
| | Y103D | | | | | | |
| | Y103S | | | | | | |
| | Y103E | | | | | | |
| | Y104V | | | | | | |
| | A105Q | | | | | | |
| | A105H | | | | | | |
| | L106F | 444.9 | 8.52E+05 | 5.41E−04 | 6.34E−10 | 100.5 | 0.17 |
| | L106I | | | | | | |
| | D107E | 344.2 | 7.62E+05 | 4.02E−04 | 5.27E−10 | 78.7 | 0.145 |
| | I108F | 193.5 | 6.83E+05 | 4.01E−04 | 5.87E−10 | 42.7 | 0.216 |
| | I108E | 234.8 | 9.21E+05 | 3.72E−04 | 4.04E−10 | 53.8 | 0.255 |
| | I108S | 89.5 | 8.58E+05 | 3.36E−04 | 3.91E−10 | 20.8 | 0.362 |
| Light chain - CDR1 | WT | | | | | | |
| | WT | | | | | | |
| | WT | | | | | | |
| | WT | 351.4 | 7.82E+05 | 3.42E−04 | 4.38E−10 | 86.1 | 0.21 |
| | WT | 77.5 | 8.89E+05 | 3.78E−04 | 4.25E−10 | 19.8 | 0.163 |
| | WT | | | | | | |
| | WT | | | | | | |
| | WT | | | | | | |
| | WT | 166.2 | 8.11E+05 | 4.49E−04 | 5.53E−10 | 39.1 | 0.18 |
| | WT | 151.7 | 1.06E+06 | 7.64E−04 | 7.19E−10 | 30.6 | 0.221 |
| | WT | 165.3 | 1.01E+06 | 6.90E−04 | 6.85E−10 | 38.5 | 0.186 |
| | WT | | | | | | |
| | WT | | | | | | |
| | WT | | | | | | |
| | WT | | | | | | |
| | WT | | | | | | |
| | WT | | | | | | |
| | WT | 188.7 | 8.85E−05 | 3.50E−04 | 3.95E−10 | 44.6 | 0.216 |
| | WT | 175.6 | 8.61E+05 | 3.69E−04 | 4.29E−10 | 43.4 | 0.188 |
| | WT | | | CRITICAL | | | |
| Light chain - CDR2 | WT | | | CRITICAL | | | |
| | WT | | | | | | |
| | WT | | | | | | |
| | WT | | | | | | |
| | WT | 164.3 | 6.68E+05 | 4.17E−04 | 6.24E−10 | 36.5 | 0.081 |
| | WT | 48.4 | 1.49E+06 | 4.64E−04 | 3.11E−10 | 13.7 | 0.188 |
| | WT | | | | | | |
| | WT | | | | | | |

TABLE 19-continued

|  |  |  |  |  |  |  |  |
|---|---|---|---|---|---|---|---|
|  | WT |  |  |  |  |  |  |
|  | WT |  |  |  |  |  |  |
|  | WT |  |  |  |  |  |  |
|  | WT |  |  |  |  |  |  |
|  | WT |  |  |  |  |  |  |
|  | WT |  |  |  |  |  |  |
|  | WT |  |  |  |  |  |  |
|  | WT |  |  |  |  |  |  |
|  | WT |  |  |  |  |  |  |
|  | WT |  |  |  |  |  |  |
|  | WT |  |  |  |  |  |  |
|  | WT |  |  |  |  |  |  |
| Light | WT | 128.8 | 6.19E+05 | 4.41E−04 | 7.13E−10 | 29.8 | 0.176 |
| chain - | WT | 151.7 | 5.86E+05 | 1.32E−03 | 2.25E−09 | 27.5 | 0.141 |
| CDR3 | WT |  |  |  |  |  |  |
|  | WT |  |  | CRITICAL |  |  |  |
|  | WT |  |  |  |  |  |  |
|  | WT |  |  | CRITICAL |  |  |  |
|  | WT |  |  | CRITICAL |  |  |  |
|  | WT |  |  | CRITICAL |  |  |  |
|  | WT |  |  |  |  |  |  |
|  | WT |  |  |  |  |  |  |
|  | WT | 172.8 | 8.82E+05 | 7.95E−04 | 9.01E−10 | 37.1 | 0.234 |
|  | WT | 147.3 | 9.21E+05 | 6.39E−04 | 6.95E−10 | 34.8 | 0.202 |

Biacore kinetics for anti-IL-6 single point mutations. Data were obtained for samples prior (sup) at 25° C. and after purification at 37° C. Mutations selected to be at final CDR combinations (Table 19) are italicized. CDR positions that did not tolerate mutations in the bacterial screening are indicated as critical.

Biacore kinetics data for anti-IL-6 CDR variants. Kinetic data were obtained from cell culture supernatants (sup) at 25° C. and purified samples at 37° C. Heavy and light chain CDR mutations are indicated on the left and right side, respectively (heavy/light). Capture, kon (ka), koff (kd) rates and dissociation constants are listed in the table.

TABLE 20

|  | Sup/25° C. | | | | | |
|---|---|---|---|---|---|---|
|  | Capture | ka (1/Ms) | kd (1/s) | KD (M) | Rmax (RU) | Chi² (RU²) |
| Parent Sequence | 981.4 | 3.15E+05 | 1.26E−04 | 3.99E−10 | 223.2 | 0.108 |
| Heavy Chain CDR2 G66D | 783.5 | 1.30E+06 | 1.17E−04 | 9.02E−11 | 184.9 | 0.254 |
| M34I, G66D, I108V/M32L, M50D, N52S, M88Q | 949.4 | 3.62E+05 | 2.00E−04 | 5.52E−10 | 212.2 | 0.0546 |
| M34I, G66D, I108V/M32L, M50A, N52S, M88Q | 745.3 | 662000 | 0.000214 | 3.23E−10 | 155.7 | 0.0772 |
| M34I, G66D, I108V/M32L, M50D, M88Q | 106.8 | 3.67E+05 | 2.15E−04 | 5.86E−10 | 244.5 | 0.19 |
| M34W, G66D, I108V/M32L, M50D, N52S, M88Q | 603.5 | 4.67E+05 | 1.73E−04 | 3.70E−10 | 145.4 | 0.191 |
| M34W, G66D, I108V/M32L, M50A, N52S, M88Q | 429.9 | 555000 | 0.000165 | 2.97E−10 | 100.9 | 0.0366 |
| M34W, G66D, I108V/M32L, M50D, M88Q | 509.4 | 7.44E+05 | 1.72E−04 | 2.31E−10 | 123.4 | 0.171 |

|  | Purified/37° C. | | | | | |
|---|---|---|---|---|---|---|
|  | Capture | ka (1/Ms) | kd (1/s) | KD (M) | Rmax (RU) | Chi² (RU²) |
| Parent Sequence | 138.10 | 8.80E+05 | 1.39E−04 | 1.58E−10 | 34.6 | 0.397 |
| Heavy Chain CDR2 G66D | 142.80 | 1.96E+06| | 1.36E−04 | 6.95E−11 | 39.9 | 0.513 |
| M34I, G66D, I108V/M32L, M50D, N52S, M88Q | 116.20 | 1.12E+06 | 7.02E−04 | 6.25E−10 | 28.2 | 0.37 |
| M34I, G66D, I108V/M32L, M50A, N52S, M88Q | 120 | 1150000 | 0.000757 | 6.56E−10 | 29.5 | 0.273 |
| M34I, G66D, I108V/M32L, M50D, M88Q | 132.20 | 1.21E+06 | 7.30E−04 | 6.02E−10 | 31 | 0.656 |
| M34W, G66D, I108V/M32L, M50D, N52S, M88Q | 124.20 | 1.19E+06 | 5.91E−04 | 4.97E−10 | 30.1 | 0.625 |
| M34W, G66D, I108V/M32L, M50A, N52S, M88Q | 103.7 | 1080000 | 0.000662 | 6.15E−10 | 25.5 | 0.277 |
| M34W, G66D, I108V/M32L, M50D, M88Q | 115.50 | 1.34E+06 | 6.27E−04 | 4.69E−10 | 29.9 | 0.407 |

TABLE 21

ANTI-IL-6 HEAVY CHAIN VARIABLE REGION SEQUENCES. SOME EMBODIMENTS OF CDRS ARE UNDERLINED.

| ID | Sequence |
|---|---|
| I | EVQLVESGGGLVQPGGSLRLSCAASG<u>FTFSPFAIS</u>WVRQAPGKGLE WVAKI<u>SPGGSWTYYSDTVTDRFTFSLD</u>TSKSTAYLQMNSLRAEDTA VYYC<u>ARQLWGYYALDV</u>WGQGTLVTVSS (SEQ ID NO: 140) |
| II | EVQLVESGGGLVQPGGSLRLSCAASG<u>FTFSPFAW</u>SWVRQAPGKGLE WVAKI<u>SPGGSWTYYSDTVTDRFTFSLD</u>TSKSTAYLQMNSLRAEDTA VYYC<u>ARQLWGYYALDV</u>WGQGTLVTVSS (SEQ ID NO: 141) |

TABLE 22

ANTI-IL-6 LIGHT CHAIN VARIABLE REGION SEQUENCES. SOME EMBODIMENTS OF CDRS ARE UNDERLINED.

| ID | Sequence |
|---|---|
| III | DIQLTQSPSSLSASVGDRVTITC<u>SASISVSYLY</u>WYQQKPGKAPKL LIY<u>DDSSLAS</u>GVPSRFSGSGSGTDFTLTISSLQPEDFATYYC<u>QQW SGYPYT</u>FGQGTKVEIK (SEQ ID NO: 142) |
| IV | DIQLTQSPSSLSASVGDRVTITC<u>SASISVSYLY</u>WYQQKPGKAPKL LIY<u>DASSLAS</u>GVPSRFSGSGSGTDFTLTISSLQPEDFATYYC<u>QQW SGYPYT</u>FGQGTKVEIK (SEQ ID NO: 143) |
| V | DIQLTQSPSSLSASVGDRVTITC<u>SASISVSYLY</u>WYQQKPGKAPKL LIY<u>DDSNLAS</u>GVPSRFSGSGSGTDFTLTISSLQPEDFATYYC<u>QQW SGYPYT</u>FGQGTKVEIK (SEQ ID NO: 144) |

Example 2

Anti-IL-6 AB VEGF Trap Molecule Design and Construction

The VEGF binding moiety of the IL-6Ab-VEGF Trap consisted of a fusion between VEGFR1 domain 2 and VEGFR2 domain 3 (Table 23). This fusion works as a VEGF trap, preventing VEGF from binding to cellular VEGF receptors.

TABLE 23

VEGF TRAP SEQUENCE

SDTGRPFVEMYSEIPEIIHMTEGRELVIPCRVTSPNITVTLKKFPLDT
LIPDGKRIIWDSRKGFIISNATYKEIGLLTCEATVNGHLYKTNYLTHR
QTNTIIDVVLSPSHGIELSVGEKLVLNCTARTELNVGIDFNWEYPSSK
HQHKKLVNRDLKTQSGSEMKKFLSTLTIDGVTRSDQGLYTCAASSGLM
TKKNSTFVRVHEK
(SEQ ID NO: 145)

12 constructs were tested containing the VEGF trap in two distinct configurations (Table 24). In the first configuration, the VEGF trap was positioned at the beginning of the protein, followed by a duplicate series of a Gly-Gly-Gly-Gly-Ser linker (GS), which connects the VEGF trap to the N-terminus of the anti-IL-6 heavy chain (VEGF Trap-AntiIL-6; Table 24, molecules A-F). In the second configuration, the variable and constant domains of the heavy chain (Fab region) are connected to the VEGF Trap via the GS linker, and then the Fc domain is fused to the C-terminal end of the VEGF trap. Thus, in this configuration, the VEGF trap is sandwiched between the antibody Fab and Fc regions (AntiIL-6-VEGF Trap; Table 24, molecules G-L).

TABLE 24

HEAVY AND LIGHT CHAIN SEQUENCES FOR DUAL INHIBITOR MOLECULES. SOME EMBODIMENTS OF CDRS ARE UNDERLINED IN THE HEAVY AND LIGHT CHAINS, VEGF TRAP SEQUENCE IS BOLDED, GLY-SER LINKER IS ITALICIZED (AND BOLDED).

| ID | Heavy chain | Light chain |
|---|---|---|
| A | SDTGRPFVEMYSEIPEIIHMTEGRELVIPCRV TSPNITVTLKKFPLDTLIPDGKRIIWDSRKGF IISNATYKEIGLLTCEATVNGHLYKTNYLTHR QTNTIIDVVLSPSHGIELSVGEKLVLNCTART ELNVGIDFNWEYPSSKHQHKKLVNRDLKTQSG SEMKKFLSTLTIDGVTRSDQGLYTCAASSGLM TKKNSTFVRVHEK*GGGGSGGGGS*EVQLVESGG GLVQPGGSLRLSCAASGFTFSPFAISWVRQAP GKGLEWVAKISPGGSW<u>TYYSDTVTDRFTFSLD</u> TSKSTAYLQMNSLRAEDTAVYYC<u>ARQLWGYYA LDV</u>WGQGTLVTVSSASTKGPSVFPLAPSSKST SGGTAALGCLVKDYFPEPVTVSWNSGALTSGV HTFPAVLQSSGLYSLSSVVTVPSSSLGTQTYI CNVNHKPSNTKVDKKVEPKSCDKTHTCPPCPA PEAAGAPSVFLFPPKPKDTLMISRTPEVTCVV VDVSHEDPEVKFNWYVDGVEVHNAKTKPREEQ YNSTYRVVSVLTVLHQDWLNGKEYKCKVSNKA LPAPIEKTISKAKGQPREPQVYTLPPSREEMT KNQVSLTCLVKGFYPSDIAVEWESNGQPENNY KTTPPVLDSDGSFFLYSKLTVDKSRWQQGNVF SCSVMHEALHNHYTQKSLSCSPGK (SEQ ID NO: 269) | DIQLTQSPSSLSASVGDRVTITC<u>SASISVSYLY</u>WYQ QKPGKAPKL<u>LIYDDSSLAS</u>GVPSRFSGSGSGTDFTL TISSLQPEDFATYYC<u>QQWSGYPYT</u>FGQGTKVEIKRT VAAPSVFIFPPSDEQLKSGTASVVCLLNNFYPREAK VQWKVDNALQSGNSQESVTEQDSKDSTYSLSSTLTL SKADYEKHKVYACEVTHQGLSSPVTKSFNRGEC (SEQ ID NO: 146) |
| B | SDTGRPFVEMYSEIPEIIHMTEGRELVIPCRV TSPNITVTLKKFPLDTLIPDGKRIIWDSRKGF IISNATYKEIGLLTCEATVNGHLYKTNYLTHR QTNTIIDVVLSPSHGIELSVGEKLVLNCTART ELNVGIDFNWEYPSSKHQHKKLVNRDLKTQSG SEMKKFLSTLTIDGVTRSDQGLYTCAASSGLM TKKNSTFVRVHEK*GGGGSGGGGS*EVQLVESGG | DIQLTQSPSSLSASVGDRVTITC<u>SASISVSYLY</u>WYQ QKPGKAPKL<u>LIYDASSLAS</u>GVPSRFSGSGSGTDFTL TISSLQPEDFATYYC<u>QQWSGYPYT</u>FGQGTKVEIKRT VAAPSVFIFPPSDEQLKSGTASVVCLLNNFYPREAK VQWKVDNALQSGNSQESVTEQDSKDSTYSLSSTLTL SKADYEKHKVYACEVTHQGLSSPVTKSFNRGEC (SEQ ID NO: 148) |

TABLE 24-continued

HEAVY AND LIGHT CHAIN SEQUENCES FOR DUAL INHIBITOR MOLECULES. SOME
EMBODIMENTS OF CDRS ARE UNDERLINED IN THE HEAVY AND LIGHT CHAINS, VEGF
TRAP SEQUENCE IS BOLDED, GLY-SER LINKER IS ITALICIZED (AND BOLDED).

| ID | Heavy chain | Light chain |
|---|---|---|
|  | GLVQPGGSLRLSCAASGFTFSPFAISWVRQAP<br>GKGLEWVAKISPGGSWTYYSDTVTDRFTFSLD<br>TSKSTAYLQMNSLRAEDTAVYYCARQLWGYYA<br>LDVWGQGTLVTVSSASTKGPSVFPLAPSSKST<br>SGGTAALGCLVKDYFPEPVTVSWNSGALTSGV<br>HTFPAVLQSSGLYSLSSVVTVPSSSLGTQTYI<br>CNVNHKPSNTKVDKKVEPKSCDKTHTCPPCPA<br>PEAAGAPSVFLFPPKPKDTLMISRTPEVTCVV<br>VDVSHEDPEVKFNWYVDGVEVHNAKTKPREEQ<br>YNSTYRVVSVLTVLHQDWLNGKEYKCKVSNKA<br>LPAPIEKTISKAKGQPREPQVYTLPPSREEMT<br>KNQVSLTCLVKGFYPSDIAVEWESNGQPENNY<br>KTTPPVLDSDGSFFLYSKLTVDKSRWQQGNVF<br>SCSVMHEALHNHYTQKSLSCSPGK<br>(SEQ ID NO: 147) |  |
| C | SDTGRPFVEMYSEIPEIIHMTEGRELVIPCRV<br>TSPNITVTLKKFPLDTLIPDGKRIIWDSRKGF<br>IISNATYKEIGLLTCEATVNGHLYKTNYLTHR<br>QTNTIIDVVLSPSHGIELSVGEKLVLNCTART<br>ELNVGIDFNWEYPSSKHQHKKLVNRDLKTQSG<br>SEMKKFLSTLTIDGVTRSDQGLYTCAASSGLM<br>**TKKNSTFVRVHEK*GGGGSGGGGS*EVQLVESGG**<br>GLVQPGGSLRLSCAASGFTFSPFAISWVRQAP<br>GKGLEWVAKISPGGSWTYYSDTVTDRFTFSLD<br>TSKSTAYLQMNSLRAEDTAVYYCARQLWGYYA<br>LDVWGQGTLVTVSSASTKGPSVFPLAPSSKST<br>SGGTAALGCLVKDYFPEPVTVSWNSGALTSGV<br>HTFPAVLQSSGLYSLSSVVTVPSSSLGTQTYI<br>CNVNHKPSNTKVDKKVEPKSCDKTHTCPPCPA<br>PEAAGAPSVFLFPPKPKDTLMISRTPEVTCVV<br>VDVSHEDPEVKFNWYVDGVEVHNAKTKPREEQ<br>YNSTYRVVSVLTVLHQDWLNGKEYKCKVSNKA<br>LPAPIEKTISKAKGQPREPQVYTLPPSREEMT<br>KNQVSLTCLVKGFYPSDIAVEWESNGQPENNY<br>KTTPPVLDSDGSFFLYSKLTVDKSRWQQGNVF<br>SCSVMHEALHNHYTQKSLSCSPGK<br>(SEQ ID NO: 149) | DIQLTQSPSSLSASVGDRVTITCSASISVSYLYWYQ<br>QKPGKAPKLLIYDDSNLASGVPSRFSGSGSGTDFTL<br>TISSLQPEDFATYYCQQWSGYPYTFGQGTKVEIKRT<br>VAAPSVFIFPPSDEQLKSGTASVVCLLNNFYPREAK<br>VQWKVDNALQSGNSQESVTEQDSKDSTYSLSSTLTL<br>SKADYEKHKVYACEVTHQGLSSPVTKSFNRGEC<br>(SEQ ID NO: 150) |
| D | SDTGRPFVEMYSEIPEIIHMTEGRELVIPCRV<br>TSPNITVTLKKFPLDTLIPDGKRIIWDSRKGF<br>IISNATYKEIGLLTCEATVNGHLYKTNYLTHR<br>QTNTIIDVVLSPSHGIELSVGEKLVLNCTART<br>ELNVGIDFNWEYPSSKHQHKKLVNRDLKTQSG<br>SEMKKFLSTLTIDGVTRSDQGLYTCAASSGLM<br>**TKKNSTFVRVHEK*GGGGSGGGGS*EVQLVESGG**<br>GLVQPGGSLRLSCAASGFTFSPFAWSWVRQAP<br>GKGLEWVAKISPGGSWTYYSDTVTDRFTFSLD<br>TSKSTAYLQMNSLRAEDTAVYYCARQLWGYYA<br>LDVWGQGTLVTVSSASTKGPSVFPLAPSSKST<br>SGGTAALGCLVKDYFPEPVTVSWNSGALTSGV<br>HTFPAVLQSSGLYSLSSVVTVPSSSLGTQTYI<br>CNVNHKPSNTKVDKKVEPKSCDKTHTCPPCPA<br>PEAAGAPSVFLFPPKPKDTLMISRTPEVTCVV<br>VDVSHEDPEVKFNWYVDGVEVHNAKTKPREEQ<br>YNSTYRVVSVLTVLHQDWLNGKEYKCKVSNKA<br>LPAPIEKTISKAKGQPREPQVYTLPPSREEMT<br>KNQVSLTCLVKGFYPSDIAVEWESNGQPENNY<br>KTTPPVLDSDGSFFLYSKLTVDKSRWQQGNVF<br>SCSVMHEALHNHYTQKSLSCSPGK<br>(SEQ ID NO: 151) | DIQLTQSPSSLSASVGDRVTITCSASISVSYLYWYQ<br>QKPGKAPKLLIYDDSSLASGVPSRFSGSGSGTDFTL<br>TISSLQPEDFATYYCQQWSGYPYTFGQGTKVEIKRT<br>VAAPSVFIFPPSDEQLKSGTASVVCLLNNFYPREAK<br>VQWKVDNALQSGNSQESVTEQDSKDSTYSLSSTLTL<br>SKADYEKHKVYACEVTHQGLSSPVTKSFNRGEC<br>(SEQ ID NO: 152) |
| E | SDTGRPFVEMYSEIPEIIHMTEGRELVIPCRV<br>TSPNITVTLKKFPLDTLIPDGKRIIWDSRKGF<br>IISNATYKEIGLLTCEATVNGHLYKTNYLTHR<br>QTNTIIDVVLSPSHGIELSVGEKLVLNCTART<br>ELNVGIDFNWEYPSSKHQHKKLVNRDLKTQSG<br>SEMKKFLSTLTIDGVTRSDQGLYTCAASSGLM<br>**TKKNSTFVRVHEK*GGGGSGGGGS*EVQLVESGG**<br>GLVQPGGSLRLSCAASGFTFSPFAWSWVRQAP<br>GKGLEWVAKISPGGSWTYYSDTVTDRFTFSLD<br>TSKSTAYLQMNSLRAEDTAVYYCARQLWGYYA<br>LDVWGQGTLVTVSSASTKGPSVFPLAPSSKST<br>SGGTAALGCLVKDYFPEPVTVSWNSGALTSGV | DIQLTQSPSSLSASVGDRVTITCSASISVSYLYWYQ<br>QKPGKAPKLLIYDASSLASGVPSRFSGSGSGTDFTL<br>TISSLQPEDFATYYCQQWSGYPYTFGQGTKVEIKRT<br>VAAPSVFIFPPSDEQLKSGTASVVCLLNNFYPREAK<br>VQWKVDNALQSGNSQESVTEQDSKDSTYSLSSTLTL<br>SKADYEKHKVYACEVTHQGLSSPVTKSFNRGEC<br>(SEQ ID NO: 154) |

TABLE 24-continued

HEAVY AND LIGHT CHAIN SEQUENCES FOR DUAL INHIBITOR MOLECULES. SOME
EMBODIMENTS OF CDRS ARE UNDERLINED IN THE HEAVY AND LIGHT CHAINS, VEGF
TRAP SEQUENCE IS BOLDED, GLY-SER LINKER IS ITALICIZED (AND BOLDED).

| ID | Heavy chain | Light chain |
| --- | --- | --- |
|  | HTFPAVLQSSGLYSLSSVVTVPSSSLGTQTYI<br>CNVNHKPSNTKVDKKVEPKSCDKTHTCPPCPA<br>PEAAGAPSVFLFPPKPKDTLMISRTPEVTCVV<br>VDVSHEDPEVKFNWYVDGVEVHNAKTKPREEQ<br>YNSTYRVVSVLTVLHQDWLNGKEYKCKVSNKA<br>LPAPIEKTISKAKGQPREPQVYTLPPSREEMT<br>KNQVSLTCLVKGFYPSDIAVEWESNGQPENNY<br>KTTPPVLDSDGSFFLYSKLTVDKSRWQQGNVF<br>SCSVMHEALHNHYTQKSLSCSPGK<br>(SEQ ID NO: 153) |  |
| F | **SDTGRPFVEMYSEIPEIIHMTEGRELVIPCRV<br>TSPNITVTLKKFPLDTLIPDGKRIIWDSRKGF<br>IISNATYKEIGLLTCEATVNGHLYKTNYLTHR<br>QTNTIIDVVLSPSHGIELSVGEKLVLNCTART<br>ELNVGIDFNWEYPSSKHQHKKLVNRDLKTQSG<br>SEMKKFLSTLTIDGVTRSDQGLYTCAASSGLM<br>TKKNSTFVRVHEK*GGGGSGGGGS*EVQLVESGG**<br>GLVQPGGSLRLSCAASGFTFSPFAWSWVRQAP<br>GKGLEWVAKISPGGSW<u>TYYSDTVTDRFTFSLD</u><br>TSKSTAYLQMNSLRAEDTAVYYC<u>ARQLWGYYA</u><br><u>LDV</u>WGQGTLVTVSSASTKGPSVFPLAPSSKST<br>SGGTAALGCLVKDYFPEPVTVSWNSGALTSGV<br>HTFPAVLQSSGLYSLSSVVTVPSSSLGTQTYI<br>CNVNHKPSNTKVDKKVEPKSCDKTHTCPPCPA<br>PEAAGAPSVFLFPPKPKDTLMISRTPEVTCVV<br>VDVSHEDPEVKFNWYVDGVEVHNAKTKPREEQ<br>YNSTYRVVSVLTVLHQDWLNGKEYKCKVSNKA<br>LPAPIEKTISKAKGQPREPQVYTLPPSREEMT<br>KNQVSLTCLVKGFYPSDIAVEWESNGQPENNY<br>KTTPPVLDSDGSFFLYSKLTVDKSRWQQGNVF<br>SCSVMHEALHNHYTQKSLSCSPGK<br>(SEQ ID NO: 155) | DIQLTQSPSSLSASVGDRVTTTC<u>SASISVSYLY</u>WYQ<br>QKPGKAPKLLIY<u>DDSNLAS</u>GVPSRFSGSGSGTDFTL<br>TISSLQP<u>EDFATYYC</u><u>QQWSGYPYT</u>FGQGTKVEIKRT<br>VAAPSVFIFPPSDEQLKSGTASVVCLLNNFYPREAK<br>VQWKVDNALQSGNSQESVTEQDSKDSTYSLSSTLTL<br>SKADYEKHKVYACEVTHQGLSSPVTKSFNRGEC<br>(SEQ ID NO: 156) |
| G | EVQLVESGGGLVQPGGSLRLSCAASGFTFSPF<br>AISWVRQAPGKGLEWVAKISPGGSW<u>TYYSDTV</u><br><u>TDR</u>FTFSLDTSKSTAYLQMNSLRAEDTAVYYC<br><u>ARQLWGYYALDV</u>WGQGTLVTVSSASTKGPSVF<br>PLAPSSKSTSGGTAALGCLVKDYFPEPVTVSW<br>NSGALTSGVHTFPAVLQSSGLYSLSSVVTVPS<br>SSLGTQTYICNVNHKPSNTKVDKKVEPKSC*GG*<br>***GGSGGGGS*SDTGRPFVEMYSEIPEIIHMTEGR<br>ELVIPCRVTSPNITVTLKKFPLDTLIPDGKRI<br>IWDSRKGFIISNATYKEIGLLTCEATVNGHLY<br>KTNYLTHRQTNTIIDVVLSPSHGIELSVGEKL<br>VLNCTARTELNVGIDFNWEYPSSKHQHKKLVN<br>RDLKTQSGSEMKKFLSTLTIDGVTRSDQGLYT<br>CAASSGLMTKKNSTFVRVHEK**DKTHTCPPCPA<br>PEAAGAPSVFLFPPKPKDTLMISRTPEVTCVV<br>VDVSHEDPEVKFNWYVDGVEVHNAKTKPREEQ<br>YNSTYRVVSVLTVLHQDWLNGKEYKCKVSNKA<br>LPAPIEKTISKAKGQPREPQVYTLPPSREEMT<br>KNQVSLTCLVKGFYPSDIAVEWESNGQPENNY<br>KTTPPVLDSDGSFFLYSKLTVDKSRWQQGNVF<br>SCSVMHEALHNHYTQKSLSCSPGK<br>(SEQ ID NO: 157) | DIQLTQSPSSLSASVGDRVTITC<u>SASISVSYLY</u>WYQ<br>QKPGKAPKLLIY<u>DDSSLAS</u>GVPSRFSGSGSGTDFTL<br>TISSLQP<u>EDFATYYC</u><u>QQWSGYPYT</u>FGQGTKVEIKRT<br>VAAPSVFIFPPSDEQLKSGTASVVCLLNNFYPREAK<br>VQWKVDNALQSGNSQESVTEQDSKDSTYSLSSTLTL<br>SKADYEKHKVYACEVTHQGLSSPVTKSFNRGEC<br>(SEQ ID NO: 158) |
| H | EVQLVESGGGLVQPGGSLRLSCAASGFTFSPF<br>AISWVRQAPGKGLEWVAKISPGGSW<u>TYYSDTV</u><br><u>TDR</u>FTFSLDTSKSTAYLQMNSLRAEDTAVYYC<br><u>ARQLWGYYALDV</u>WGQGTLVTVSSASTKGPSVF<br>PLAPSSKSTSGGTAALGCLVKDYFPEPVTVSW<br>NSGALTSGVHTFPAVLQSSGLYSLSSVVTVPS<br>SSLGTQTYICNVNHKPSNTKVDKKVEPKSC*GG*<br>***GGSGGGGS*SDTGRPFVEMYSEIPEIIHMTEGR<br>ELVIPCRVTSPNITVTLKKFPLDTLIPDGKRI<br>IWDSRKGFIISNATYKEIGLLTCEATVNGHLY<br>KTNYLTHRQTNTIIDVVLSPSHGIELSVGEKL<br>VLNCTARTELNVGIDFNWEYPSSKHQHKKLVN<br>RDLKTQSGSEMKKFLSTLTIDGVTRSDQGLYT<br>CAASSGLMTKKNSTFVRVHEK**DKTHTCPPCPA<br>PEAAGAPSVFLFPPKPKDTLMISRTPEVTCVV<br>VDVSHEDPEVKFNWYVDGVEVHNAKTKPREEQ<br>YNSTYRVVSVLTVLHQDWLNGKEYKCKVSNKA | DIQLTQSPSSLSASVGDRVTITC<u>SASISVSYLY</u>WYQ<br>QKPGKAPKLLIY<u>DASSLAS</u>GVPSRFSGSGSGTDFTL<br>TISSLQP<u>EDFATYYC</u><u>QQWSGYPYT</u>FGQGTKVEIKRT<br>VAAPSVFIFPPSDEQLKSGTASVVCLLNNFYPREAK<br>VQWKVDNALQSGNSQESVTEQDSKDSTYSLSSTLTL<br>SKADYEKHKVYACEVTHQGLSSPVTKSFNRGEC<br>(SEQ ID NO: 160) |

TABLE 24-continued

HEAVY AND LIGHT CHAIN SEQUENCES FOR DUAL INHIBITOR MOLECULES. SOME EMBODIMENTS OF CDRS ARE UNDERLINED IN THE HEAVY AND LIGHT CHAINS, VEGF TRAP SEQUENCE IS BOLDED, GLY-SER LINKER IS ITALICIZED (AND BOLDED).

| ID | Heavy chain | Light chain |
|---|---|---|
|  | LPAPIEKTISKAKGQPREPQVYTLPPSREEMT<br>KNQVSLTCLVKGFYPSDIAVEWESNGQPENNY<br>KTTPPVLDSDGSFFLYSKLTVDKSRWQQGNVF<br>SCSVMHEALHNHYTQKSLSCSPGK<br>(SEQ ID NO: 159) |  |
| I | EVQLVESGGGLVQPGGSLRLSCAAS<u>GFTFSPF</u><br><u>AISW</u>VRQAPGKGLEWVAK<u>ISPGGSWTYYSDTV</u><br><u>TDRFT</u>FSLDTSKSTAYLQMNSLRAEDTAVYYC<br><u>ARQLWGYYALD</u>VWGQGTLVTVSSASTKGPSVF<br>PLAPSSKSTSGGTAALGCLVKDYFPEPVTVSW<br>NSGALTSGVHTFPAVLQSSGLYSLSSVVTVPS<br>SSLGTQTYICNVNHKPSNTKVDKKVEPKSC*GG*<br>***GGSGGGGS*DTGRPFVEMYSEIPEIIHMTEGR<br>ELVIPCRVTSPNITVTLKKFPLDTLIPDGKRI<br>IWDSRKGFIISNATYKEIGLLTCEATVNGHLY<br>KTNYLTHRQTNTIIDVVLSPSHGIELSVGEKL<br>VLNCTARTELNVGIDFNWEYPSSKHQHKKLVN<br>RDLKTQSGSEMKKFLSTLTIDGVTRSDQGLYT<br>CAASSGLMTKKNSTFVRVHEK**DKTHTCPPCPA<br>PEAAGAPSVFLFPPKPKDTLMISRTPEVTCVV<br>VDVSHEDPEVKFNWYVDGVEVHNAKTKPREEQ<br>YNSTYRVVSVLTVLHQDWLNGKEYKCKVSNKA<br>LPAPIEKTISKAKGQPREPQVYTLPPSREEMT<br>KNQVSLTCLVKGFYPSDIAVEWESNGQPENNY<br>KTTPPVLDSDGSFFLYSKLTVDKSRWQQGNVF<br>SCSVMHEALHNHYTQKSLSCSPGK<br>(SEQ ID NO: 161) | DIQLTQSPSSLSASVGDRVTITC<u>SASISVSYLY</u>WYQ<br>QKPGKAPKLLIY<u>DDSNLAS</u>GVPSRFSGSGSGTDFTL<br>TISSLQPEDFATYYC<u>QQWSGYPYT</u>FGQGTKVEIKRT<br>VAAPSVFIFPPSDEQLKSGTASVVCLLNNFYPREAK<br>VQWKVDNALQSGNSQESVTEQDSKDSTYSLSSTLTL<br>SKADYEKHKVYACEVTHQGLSSPVTKSFNRGEC<br>(SEQ ID NO: 162) |
| J | EVQLVESGGGLVQPGGSLRLSCAAS<u>GFTFSPF</u><br><u>AWSW</u>VRQAPGKGLEWVAK<u>ISPGGSWTYYSDTV</u><br><u>TDRFT</u>FSLDTSKSTAYLQMNSLRAEDTAVYYC<br><u>ARQLWGYYALD</u>VWGQGTLVTVSSASTKGPSVF<br>PLAPSSKSTSGGTAALGCLVKDYFPEPVTVSW<br>NSGALTSGVHTFPAVLQSSGLYSLSSVVTVPS<br>SSLGTQTYICNVNHKPSNTKVDKKVEPKSC*GG*<br>***GGSGGGGS*DTGRPFVEMYSEIPEIIHMTEGR<br>ELVIPCRVTSPNITVTLKKFPLDTLIPDGKRI<br>IWDSRKGFIISNATYKEIGLLTCEATVNGHLY<br>KTNYLTHRQTNTIIDVVLSPSHGIELSVGEKL<br>VLNCTARTELNVGIDFNWEYPSSKHQHKKLVN<br>RDLKTQSGSEMKKFLSTLTIDGVTRSDQGLYT<br>CAASSGLMTKKNSTFVRVHEK**DKTHTCPPCPA<br>PEAAGAPSVFLFPPKPKDTLMISRTPEVTCVV<br>VDVSHEDPEVKFNWYVDGVEVHNAKTKPREEQ<br>YNSTYRVVSVLTVLHQDWLNGKEYKCKVSNKA<br>LPAPIEKTISKAKGQPREPQVYTLPPSREEMT<br>KNQVSLTCLVKGFYPSDIAVEWESNGQPENNY<br>KTTPPVLDSDGSFFLYSKLTVDKSRWQQGNVF<br>SCSVMHEALHNHYTQKSLSCSPGK<br>(SEQ ID NO: 163) | DIQLTQSPSSLSASVGDRVTITC<u>SASISVSYLY</u>WYQ<br>QKPGKAPKLLIY<u>DDSSLAS</u>GVPSRFSGSGSGTDFTL<br>TISSLQPEDFATYYC<u>QQWSGYPYT</u>FGQGTKVEIKRT<br>VAAPSVFIFPPSDEQLKSGTASVVCLLNNFYPREAK<br>VQWKVDNALQSGNSQESVTEQDSKDSTYSLSSTLTL<br>SKADYEKHKVYACEVTHQGLSSPVTKSFNRGEC<br>(SEQ ID NO: 164) |
| K | EVQLVESGGGLVQPGGSLRLSCAAS<u>GFTFSPF</u><br><u>AWSW</u>VRQAPGKGLEWVAK<u>ISPGGSWTYYSDTV</u><br><u>TDRFT</u>FSLDTSKSTAYLQMNSLRAEDTAVYYC<br><u>ARQLWGYYALD</u>VWGQGTLVTVSSASTKGPSVF<br>PLAPSSKSTSGGTAALGCLVKDYFPEPVTVSW<br>NSGALTSGVHTFPAVLQSSGLYSLSSVVTVPS<br>SSLGTQTYICNVNHKPSNTKVDKKVEPKSC*GG*<br>***GGSGGGGS*DTGRPFVEMYSEIPEIIHMTEGR<br>ELVIPCRVTSPNITVTLKKFPLDTLIPDGKRI<br>IWDSRKGFIISNATYKEIGLLTCEATVNGHLY<br>KTNYLTHRQTNTIIDVVLSPSHGIELSVGEKL<br>VLNCTARTELNVGIDFNWEYPSSKHQHKKLVN<br>RDLKTQSGSEMKKFLSTLTIDGVTRSDQGLYT<br>CAASSGLMTKKNSTFVRVHEK**DKTHTCPPCPA<br>PEAAGAPSVFLFPPKPKDTLMISRTPEVTCVV<br>VDVSHEDPEVKFNWYVDGVEVHNAKTKPREEQ<br>YNSTYRVVSVLTVLHQDWLNGKEYKCKVSNKA<br>LPAPIEKTISKAKGQPREPQVYTLPPSREEMT<br>KNQVSLTCLVKGFYPSDIAVEWESNGQPENNY<br>KTTPPVLDSDGSFFLYSKLTVDKSRWQQGNVF<br>SCSVMHEALHNHYTQKSLSCSPGK<br>(SEQ ID NO: 165) | DIQLTQSPSSLSASVGDRVTITC<u>SASISVSYLY</u>WYQ<br>QKPGKAPKLLIY<u>DASSLAS</u>GVPSRFSGSGSGTDFTL<br>TISSLQPEDFATYYC<u>QQWSGYPYT</u>FGQGTKVEIKRT<br>VAAPSVFIFPPSDEQLKSGTASVVCLLNNFYPREAK<br>VQWKVDNALQSGNSQESVTEQDSKDSTYSLSSTLTL<br>SKADYEKHKVYACEVTHQGLSSPVTKSFNRGEC<br>(SEQ ID NO: 166) |

TABLE 24-continued

HEAVY AND LIGHT CHAIN SEQUENCES FOR DUAL INHIBITOR MOLECULES. SOME
EMBODIMENTS OF CDRS ARE UNDERLINED IN THE HEAVY AND LIGHT CHAINS, VEGF
TRAP SEQUENCE IS BOLDED, GLY-SER LINKER IS ITALICIZED (AND BOLDED).

| ID | Heavy chain | Light chain |
|---|---|---|
| L | EVQLVESGGGLVQPGGSLRLSCAASGFTFSPF AWSWVRQAPGKGLEWVAKISPGGSWTYYSDTV TDRFTFSLDTSKSTAYLQMNSLRAEDTAVYYC ARQLWGYYALDVWGQGTLVTVSSASTKGPSVF PLAPSSKSTSGGTAALGCLVKDYFPEPVTVSW NSGALTSGVHTFPAVLQSSGLYSLSSVVTVPS SSLGTQTYICNVNHKPSNTKVDKKVEPKSCGG ***GGSGGGGS*SDTGRPFVEMYSEIPEIIHMTEGR ELVIPCRVTSPNITVTLKKFPLDTLIPDGKRI IWDSRKGFIISNATYKEIGLLTCEATVNGHLY KTNYLTHRQTNTIIDVVLSPSHGIELSVGEKL VLNCTARTELNVGIDFNWEYPSSKHQHKKLVN RDLKTQSGSEMKKFLSTLTIDGVTRSDQGLYT CAASSGLMTKKNSTFVRVHEK**DKTHTCPPCPA PEAAGAPSVFLFPPKPKDTLMISRTPEVTCVV VDVSHEDPEVKFNWYVDGVEVHNAKTKPREEQ YNSTYRVVSVLTVLHQDWLNGKEYKCKVSNKA LPAPIEKTISKAKGQPREPQVYTLPPSREEMT KNQVSLTCLVKGFYPSDIAVEWESNGQPENNY KTTPPVLDSDGSFFLYSKLTVDKSRWQQGNVF SCSVMHEALHNHYTQKSLSCSPGK (SEQ ID NO: 167) | DIQLTQSPSSLSASVGDRVTITCSASISVSYLYWYQ QKPGKAPKLLIYDDSNLASGVPSRFSGSGSGTDFTL TISSLQPEDFATYYCQQWSGYPYTFGQGTKVEIKRT VAAPSVFIFPPSDEQLKSGTASVVCLLNNFYPREAK VQWKVDNALQSGNSQESVTEQDSKDSTYSLSSTLTL SKADYEKHKVYACEVTHQGLSSPVTKSFNRGEC (SEQ ID NO: 168) |

Biacore (setup as described in the previous session) kinetic data showed that although the $K_D$ values among all variants are comparable, there is a variation in the capture values for the supernatant samples (Table 25). This parameter is sensitive to the amount of antibody present in solution, which suggested a variation on the level protein expression among these molecules due to the different CDR compositions. On the other hand, the two VEGF Trap positions tested did not show marked influence on the kinetic data. Experiments monitoring expression levels (data not shown) showed the IL-6-VEGF Trap configuration has about 20% higher yield of expression in comparison to VEGF Trap-AntiIL-6 configuration. Preliminary Biacore data also indicates AntiIL-6-VEGF Trap configuration binds tighter to a VEGF homologue, the placental growth factor (PLGF) (data not shown).

Example 3

Dual Inhibitor Binding to VEGF Via Biacore

To evaluate the binding kinetics of the different dual inhibitors configurations to VEGF, a series of Biacore assays were performed to measure the affinity between these molecules. Binding kinetics were measured at 37° C. in buffer HBS-EP+ containing 1 mg/mL BSA. Anti-VEGF agents (VEGF Trap-AntiIL-6 (5 µg/mL), AntiIL-6-VEGF Trap (5 µg/mL), OG1950 (1 µg/mL) and Eylea (0.5 µg/mL)) were captured on a Protein A chip (GE) at 10 L/min for 25 seconds, five concentrations of VEGF-A165 (0.19, 0.56, 1.67, 5, 15 nM) were flowed over captured antibodies for 120 seconds at 30 L/min and dissociated for 30 min. The sensor chip surface was regenerated by 60 seconds injection of 10 mM Glycine, pH 1.7 at a flow rate of 50 µl/min. All

TABLE 25

Biacore kinetics data for dual inhibitor variants A-L binding to IL-6. Kinetic data were obtained from cell culture supernatants (sup) samples at 25° C. and purified samples at 37° C. Capture, kon (ka), koff (kd) rates and dissociation constants are listed.

| | Sup/25° C. | | | | Purified/37° C. | | | |
|---|---|---|---|---|---|---|---|---|
| ID | Capture | ka (1/Ms) | kd (1/s) | KD (M) | Capture | ka (1/Ms) | kd (1/s) | KD (M) |
| A | 521.4 | 3.09E+05 | 1.82E−04 | 5.89E−10 | 100 | 1.11E+06 | 5.38E−04 | 4.84E−10 |
| B | 144.3 | 6.05E+05 | 1.85E−04 | 3.05E−10 | 106.6 | 1.06E+06 | 5.36E−04 | 5.07E−10 |
| C | 474.6 | 3.79E+05 | 1.50E−04 | 3.94E−10 | 92 | 1.01E+06 | 4.81E−04 | 4.77E−10 |
| D | 356.2 | 4.33E+05 | 1.09E−04 | 2.53E−10 | 105.4 | 1.23E+06 | 4.47E−04 | 3.65E−10 |
| E | 228 | 5.04E+05 | 1.51E−04 | 2.99E−10 | 97.9 | 1.08E+06 | 4.59E−04 | 4.24E−10 |
| F | 272.1 | 6.11E+05 | 1.37E−04 | 2.25E−10 | 93.9 | 1.31E+06 | 4.46E−04 | 3.4E−10 |
| G | 519 | 2.52E+05 | 1.49E−04 | 5.89E−10 | 109 | 1.26E+06 | 5.67E−04 | 4.51E−10 |
| H | 424.7 | 4.54E+05 | 1.62E−04 | 3.56E−10 | 97.3 | 1.34E+06 | 5.29E−04 | 3.96E−10 |
| I | 552.8 | 2.17E+05 | 1.47E−04 | 6.79E−10 | 108.9 | 1.15E+06 | 4.99E−04 | 4.35E−10 |
| J | 335 | 5.34E+05 | 1.49E−04 | 2.80E−10 | 88.9 | 1.42E+06 | 6.64E−04 | 4.68E−10 |
| K | 279.8 | 6.29E+05 | 1.78E−04 | 2.82E−10 | 93.9 | 1.28E+06 | 5.79E−04 | 4.52E−10 |
| L | 312.4 | 7.05E+05 | 1.69E−04 | 2.39E−10 | 91.9 | 1.49E+06 | 6.50E−04 | 4.36E−10 | sensorgrams were double reference subtracted and fit using a 1:1 Langmuir binding model.

Figure 7:
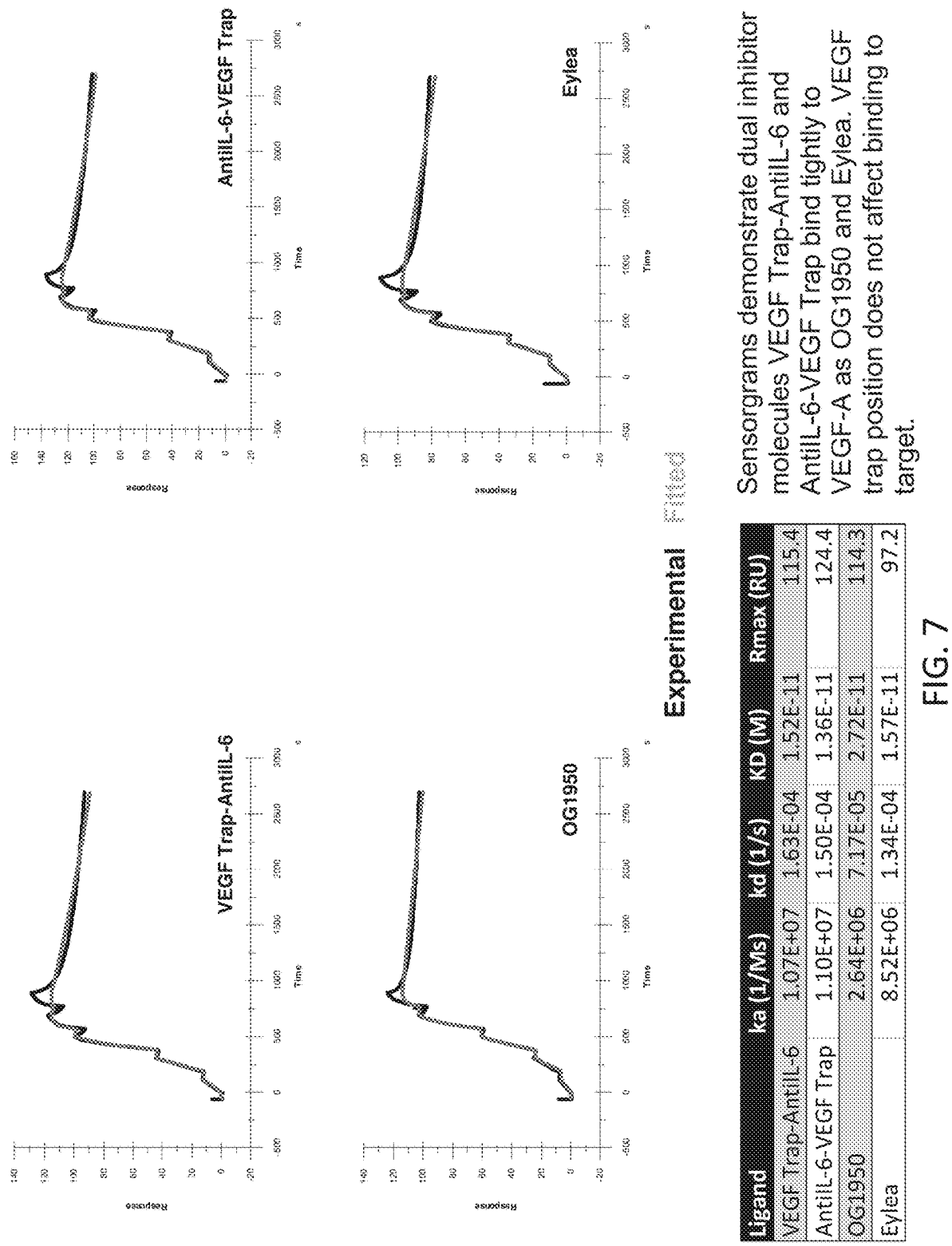
FIG. 7 depicts sensorgrams and table that demonstrate dual inhibitor molecules VEGFR-AntiIL-6 and AntiIL-6-VEGFR bind with similar affinity to VEGF-A as the anti-VEGF antibody OG1950 and Eylea. Thus, the position of the VEGF trap does not alter its affinity for its target.

Data show VEGF trap component in the dual inhibitor molecule binds tightly to VEGF-A independent of configuration. The anti-IL-6 molecule component did not seem to influence VEGF-A binding to the VEGF trap, since the dual inhibitor molecules show similar affinity to VEGF affinity as another VEGF trap-based molecule (Eylea). (FIG. 7)

IL-6 and VEGF-A Binding to Dual Inhibitor Molecules

A Biacore assay was implemented to directly monitor the dual binding of IL-6 and VEGF-A. Dual inhibitor molecules (2 µg/mL) were captured on a Protein A chip (GE) at 10 µL/min for 25 seconds, five concentrations of IL-6 and/or VEGF-A165 (0.19, 0.56, 1.67, 5, 15 nM) were flowed individually or mixed over captured antibodies for 120 seconds at 30 µL/min and dissociated for 30 min. The sensor chip surface was regenerated by 60 seconds injection of 10 mM Glycine, pH 1.7 at a flow rate of 50 µl/min. All data were double reference subtracted, and the sum of individual IL-6 and VEGF-A sensorgrams were used to create a theoretical curve, which was compared to the sensorgrams of mixed samples.

Figure 8:
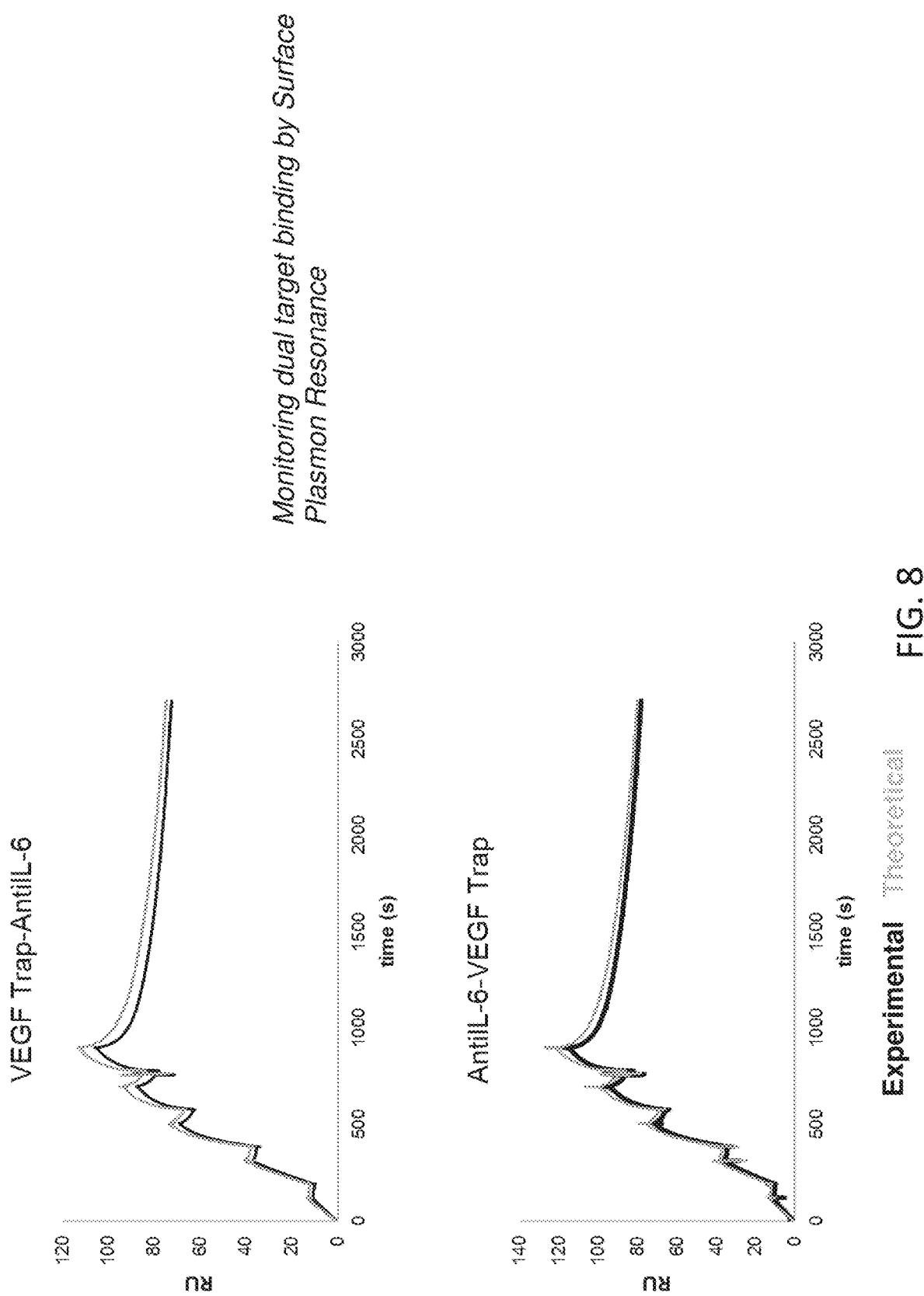
FIG. 8 depicts sensorgrams of independent or combined VEGF-A and IL-6 binding to dual inhibitors. IL-6Sensorgrams of mixed targets were compared to a theoretical curve (sum of individual IL-6 and VEGF-A sensorgrams). Results show theoretical and experimental curves superpose, which qualitatively indicates that both targets can bind to the dual inhibitor molecule without influencing each other's binding.

Results demonstrated that theoretical and experimental curves are nearly superimposed, which strongly supports a model where both targets bind to the dual inhibitor molecules without affecting their respective interactions. (FIG. 8)

Anti-IL-6 Binding to IL-6/IL-6-R Complex ELISA

IL-6/IL-6R complexes can bind to the membrane bound receptor, gp130, and this trimeric complex stimulates IL-6 signaling, such as proliferation and upregulation of VEGF. Inhibition of either IL-6 binding to IL-6R or IL-6/IL-6R binding to gp130 blocks IL-6 mediated downstream signaling pathways. To determine whether the anti-IL-6 antibodies block either of these binding events, an ELISA was first established to assess whether they can bind to IL-6 while it is complexed with IL-6 receptor.

A Nunc MaxiSorp ELISA was coated with 100 µl of 1 µg/ml of recombinant human IL-6R (R&D Systems) overnight. 10 nM IL-6 (R&D Systems) was mixed with a 3-fold dilution series of anti-IL-6 (final concentrations of 30 nM down to 10 µM). After blocking and washing, the mixture was added to the IL-6R coated plates. This assay was also performed by first incubating the IL-6R coated plate with 10 nM IL-6, washing, and then adding the anti-IL-6 antibody. For both methods, bound antibody/IL-6 complexes were detected with an anti-Human IgG HRP antibody and developed with TMB (KPL) for 10 minutes. Absorbance at 450 nM was measured on a SpectraMax Plus plate reader (Molecular Devices) and plotted against the concentration of antibody using GraphPad Prism software and fit with a non-linear regression curve.

A Nunc MaxiSorp ELISA was coated with 100 µl of 1 µg/ml of recombinant human IL-6 (R&D systems) overnight. A 3-fold dilution series of anti-IL-6 (R&D Systems; final concentrations of 30 nM down to 10 µM) was performed and solutions were added to the blocked IL-6 coated plates. Antibody/IL-6 complexes were detected with an anti-Human IgG HRP antibody and developed with TMB (KPL) for 10 minutes. Absorbance at 450 nM was measured on a SpectraMax Plus plate reader (Molecular Devices) and plotted against the concentration of antibody using GraphPad Prism software and fit with a non-linear regression curve.

Under the conditions tested, the anti-IL-6 antibody described here binds specifically to IL-6, but not when it is complexed with IL-6 receptor, suggesting that the antibody and IL-6R share a common epitope on IL-6. The results are shown in FIG. 4.

Competitive IL-6/IL-6R ELISA

An ELISA to determine whether the anti-IL-6 antibody and dual IL-6/VEGF inhibitors blocked IL-6 from binding to IL-6R was then performed A Nunc MaxiSorp ELISA was coated with 100 µl of 1 µg/ml of anti-IL-6/IL-6R complex antibody (R&D Systems; IL-6/IL-6R DuoSet) overnight. The plate was blocked in 2% bovine serum albumin (BSA) in PBS-Tween (PBST) for 2 hours. During blocking, 6 nM of IL-6 (R&D Systems), 1 nM of IL-6R (R&D Systems), and an 8-point, 3-fold dilution series of dual inhibitors or single arm controls (starting with 30 nM) were incubated at room temperature. This mixture was then added to the ELISA plate following a wash step. After 1 hour, the plate was washed and incubated with biotinylated anti-IL-6/IL-6R antibody (R&D Duoset). IL-6/IL-6R complexes were detected with steptravidin-HRP (1:2000 dilution; R&D Systems) and developed using TMB reagent (KPL) for 10 minutes. Absorbance at 450 nM was measured on a SpectraMax Plus plate reader (Molecular Devices) and plotted against the concentration of antibody using GraphPad Prism software and fit with a non-linear regression curve.

Figure 9:
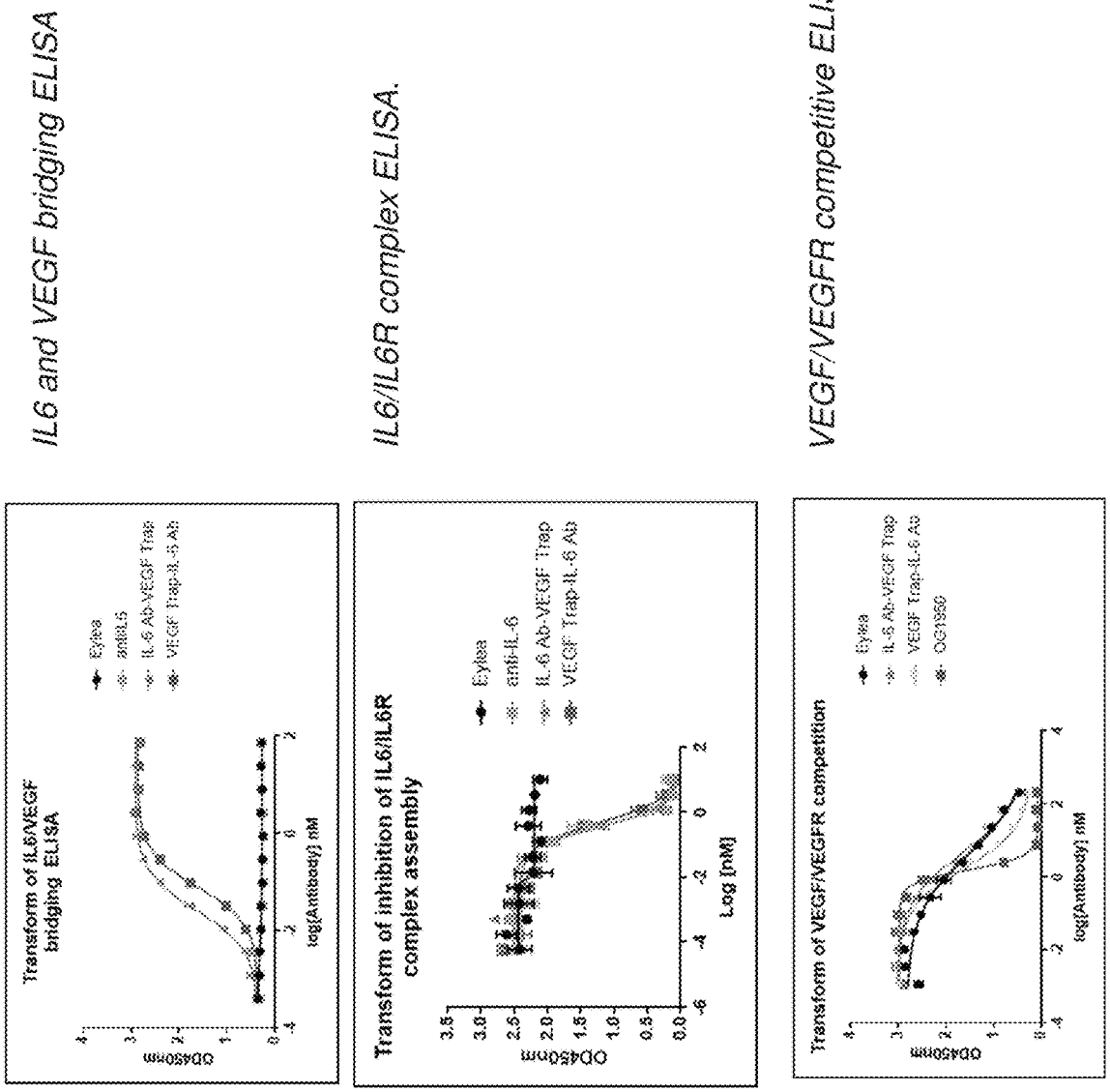
FIG. 9 depicts OD450 nm the results from various ELISA IL-6 assays. In the bridging ELISA (top), both dual inhibitors bridged btVEGF to IL-6, indicating both configurations can bind to both targets. EC50 VEGF Trap-antiIL-6=0.079 nM and antiIL-6-VEGF Trap=0.026 nM. Eylea and anti-IL-6 served as a negative controls.

Under these conditions, the anti-IL-6 antibody and dual IL-6/VEGF inhibitors effectively compete with IL-6R for binding to IL-6, and therefore inhibit the IL-6/IL-6R interaction. The IC50 values for dual inhibitor molecules are comparable (anti-IL-6=0.36 nM, VEGF Trap-anti-IL-6=0.47 nM, and anti-IL-6-VEGF Trap=0.32 nM), indicating that the configuration of the molecule does not influence IL-6 binding or inhibition. Eylea served as a negative control. (FIG. 9)

Competitive VEGF/VEGFR ELISA

To assess the function of the VEGF trap, the ability of the dual IL-6/VEGF inhibitors to block VEGF binding to its receptor (VEGFR) was tested by a competitive ELISA.

A Nunc MaxiSorp ELISA was coated with 100 µl of 1 µg/ml of recombinant, human VEGFR-Fc (R&D Systems) overnight. The plate was blocked in 2% bovine serum albumin (BSA) in PBS-Tween (PBST) for 2 hours. During blocking, 100 µM biotinylated VEGF (btVEGF; R&D Systems), was incubated with increasing concentrations of anti-IL-6-VEGF Trap, VEGF Trap-anti-IL-6, or the bivalent anti-VEGF antibody OG1950. Bound bt-VEGF was detected with steptravidin-HRP (1:2000 dilution; R&D Systems) and developed using TMB reagent (KPL) for 10 minutes. Absorbance at 450 nM was measured on a SpectraMax Plus plate reader (Molecular Devices) and plotted against the concentration of antibody using GraphPad Prism software and fit with a non-linear regression curve.

Under these conditions, the dual IL-6/VEGF inhibitors bind to VEGF and inhibits it from binding to its receptor. When the VEGF trap is situated at the N-terminal end of the anti-IL-6 antibody, VEGF inhibition is roughly 2.5-fold more potent than the molecule whose VEGF trap is positioned between the Fab and Fc domains of the anti-IL-6 antibody (IC50 1.74 nM vs. 4.53 nM, respectively), likely due to a change in valency from 2 binding sites to 1 binding site. The results are shown in FIG. 9.

Example 4

IL-6-VEGF Bridging ELISA

To ensure that the dual inhibitors can simultaneously bind to both IL-6 and VEGF, they were subjected to a bridging ELISA where they first interact with plate-bound IL-6, and then are incubated with biotinylated VEGF (btVEGF). Detection of btVEGF by streptavidin HRP indicates that IL-6 bound molecules are also able to bind btVEGF.

A Nunc MaxiSorp ELISA was coated with 100 μl of 1 μg/ml of recombinant, human IL-6 (Tonbo Sciences) overnight. The plate was blocked in 2% bovine serum albumin (BSA) in PBS-Tween (PBST) for 2 hours. During blocking, 100 μM btVEGF) was incubated with increasing concentrations of anti-IL-6-VEGF Trap, VEGF Trap-anti-IL-6, or the bivalent antiVEGF antibody OG1950 as a negative control. Bound btVEGF was detected with steptravidin-HRP (1:2000 dilution; R&D systems) and developed using TMB reagent (KPL) for 10 minutes. Absorbance at 450 nM was measured on a SpectraMax Plus plate reader (Molecular Devices) and plotted against the concentration of antibody using GraphPad Prism software and fit with a non-linear regression curve.

This assay confirmed that the dual IL-6/VEGF inhibitors simultaneously bind IL-6 and btVEGF. The orientation of the anti-IL-6 and VEGF Trap has slightly variable binding, with the anti-IL-6-VEGF Trap orientation being more favorable under these conditions (EC50 VEGF Trap-antiIL-6=0.079 nM and antiIL-6-VEGF Trap=0.026 nM). Eylea and anti-IL-6 served as negative controls. The results are shown in FIG. 9.

Example 5

Route 1 Synthesis of OG1802.

A first route for the synthesis of OG1802 is as follows. First, TFA/amine salt initiator (Compound L) having the structure shown in FIG. 2A was synthesized as follows.

First, Compound K, having the structure shown in FIG. 2B was synthesized as follows. Into a 200 mL round bottom flask under nitrogen was placed Compound J (OG1563) (1.9 g, 2.67 mmol, 3.3 equiv)

COMPOUND J

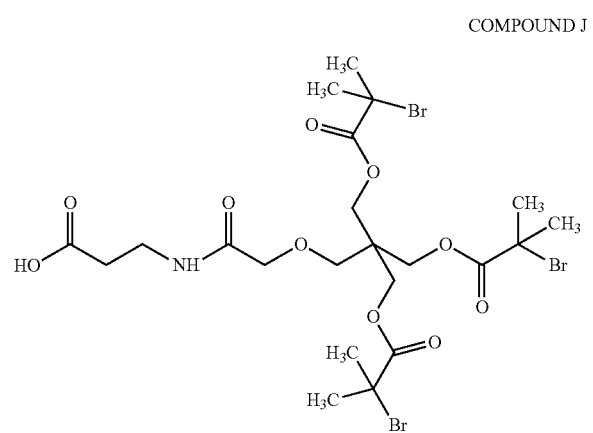 [SMILES: CC(C)(Br)C(=O)OCC(COCC(=O)NCCC(=O)O)(COC(=O)C(C)(C)Br)COC(=O)C(C)(C)Br]

and Compound E (0.525 g, 0.81 mmol, 1.0 equiv) (see FIG. 2L) followed by dimethylformamide (10 mL) then diisopropylethylamine (2.5 mL, 14.6 mmol, 18 equiv). The flask was cooled to 0° C. using an ice bath. To this was added propylphosphonic anhydride solution (50 wt. % in ethyl acetate, 2.5 mL, 4.04 mmol, 5 equiv) over ~6 minutes.

The reaction was warmed to room temperature and stirred for 15 minutes. The reaction was quenched by adding water (20 mL), saturated aqueous sodium bicarbonate (20 mL) and ethyl acetate (100 mL). The organic layer was separated and the aqueous layer extracted with ethyl acetate (75 mL). The combined organic layers were washed with saturated aqueous sodium bicarbonate (30 mL), 0.5 M aqueous citric acid (40 mL), water (25 mL), and saturated aqueous sodium chloride (40 mL), then dried (sodium sulfate), filtered and concentrated under vacuum. The residue which was used without further purification resulted in 2.0 g (0.80 mmol, 99%) of Compound K.

1H NMR (400 MHz DMSO-d6): δ=1.36 (s, 9H, OCCH3), 1.90 (s, 54H, CC(CH3)2Br), 2.31 (t, J=7.2 Hz, 6H, CCH2CH2NH), 2.98 (d, J=5.6 Hz, 6H, CCH2NH), 3.04 (q, J=6.0 Hz, 2H, OCH2CH2NH), 3.18 (s, 2H, OCH2C), 3.3-3.37 (m, 8H, CH2), 3.47-3.55 (m, 12H, CH$_2$), 3.58 (s, 6H, OCH2C), 3.87 (s, 6H, O=CCH2O), 4.27 (s, 18H, CCH2OC=O), 6.74 (br t, 1 H, CH2NHC=O), 7.69 (t, J=6.8 Hz, 3H, CH2NHC=O), 7.84 (t, J=6.0 Hz, 3H, CH2NHC=O). LC-MS (ES, m/z): [(M+2H-boc)/2]+Calcd for (C84H136Br9N7O33+2H-Boc)/2=1196.6; Found 1196.6.

Next Compound L (FIG. 2A) was synthesized as follows: into a 100 mL round bottom under nitrogen was added Compound K (2.0 g, 0.8 mmol), dichloromethane (10 mL) followed by trifluoroacetic acid (5 mL). The reaction was stirred at room temperature for 30 minutes. The reaction was concentrated under a vacuum. The reaction was diluted using dichloromethane (10 mL) and concentrated under a vacuum. The residue was dissolved using acetonitrile (10 mL), filtered through a syringe filter (Acrodisc CR25, PN 4225T) and loaded onto a preparatory HPLC column and eluted with 60% acetonitrile in water (with 0.1% trifluoroacetic acid) up to 98% acetonitrile (with 0.1% trifluoroacetic acid). The tubes containing product were pooled, concentrated under vacuum, frozen and placed on a lyophilizer. This resulted in 990 mgs (0.4 mmol, 50% over 2 steps) Compound L as a white powder. 1H NMR (400 MHz DMSO-d6): δ=1.90 (s, 54H, CC(CH3)2Br), 2.31 (t, J=7.2 Hz, 6H, CCH2CH2NH), 2.97-3.0 (m, 8H, CCH2NH and OCH2CH2NH), 3.17 (s, 2H, OCH2C), 3.3 (q, 6H, CH2CH2NHC=O), 3.4-3.59 (m, 20H, CH2), 3.87 (s, 6H, O=CCH2O), 4.27 (s, 18H, CCH2OC=O), 7.69-7.84 (m, 9H, both CH2NHC=O and NH3+). LC-MS (ES, m/z): [(M+2H)/2]+Calcd for (C$_{84}$H136Br9N7O33+2H)/2=1196.6; Found 1197.4.

Next, Compound L (FIG. 2A) was used as an initiator to synthesize MPC polymer. Initiator is typically prepared as a stock solution in DMF of about 100 mg/mL. The initiator and the ligand (2,2'-bipyridyl) were introduced into a Schlenk tube. The resultant solution was cooled to −78° C. using a dry ice/acetone mixture, and was degassed under vacuum for 10 min. The tube was refilled under Argon and the catalyst (CuBr unless otherwise indicated), kept under Argon, was introduced into the Schlenck tube (the Molar ratio of atom bromine on the initiator/catalyst (CuBr)/ligand was kept at 1/1/2). The solution became dark brown immediately. The Schlenk tube was sealed and immediately purged by applying a short cycle vacuum/Argon. A solution of HEMA-PC was prepared by mixing a defined quantity of monomer, prepared in a glovebox kept under nitrogen, with 200 proof degassed ethanol. The monomer solution was added drop wise into the Schlenk tube (via cannula) (and homogenized by light stirring). The temperature was maintained at −78° C. A thorough vacuum was applied to the reaction mixture for at least 10 to 15 min. until bubbling from the solution ceased. The tube was then refilled with Argon and warmed to room temperature. The solution was stirred, and as the polymerization proceeded, the solution became viscous. After 3 to 8 hours or just left overnight, the reaction was quenched by direct exposure to air in order to oxidize Cu (I) to Cu (II), the mixture became blue-green in color, and was passed through a silica column in order to remove the copper catalyst. The collected solution was concentrated by rotary evaporation and the resulting mixture was either precipitated with tetrahydrofuran or dialyzed against water followed by freeze drying to yield a free-flowing white powder. Table 26 below sets forth polymer data for polymer employing compound L as an initiator.

TABLE 26

| Theor. MW (kDa) | Polymer ID No. | Initiator | Mn(kDa) | Mp(kDa) | PDI |
|---|---|---|---|---|---|
| 500 | 130 | L | 490 | 530 | 1.1 |
| 750 | 150 | L | 645 | 750 | 1.1 |

Next, the maleimide Mal-PEG4-PFP ester was snapped on (as set forth in FIG. 2C) to the 750 kDa polymer referred to above to provide OG1802. Into a 20 mL vial was placed Polymer R3707 (750 kDa polymer made using L as initiator, 515 mg) and dissolved using ethanol (4.0 mL) after stirring for 40 minutes. To this was added a 1% solution of 4-methylmorpholine in acetonitrile (22 uL). In a separate vial was dissolved Mal-PEG4-PFP (1.97 mg) in acetonitrile (1.0 mL) and this solution was added to the polymer solution over ~2 minute at room temperature and the resulting solution was stirred for overnight. The reaction was diluted with 0.1% aqueous trifluoroacetic acid (2 mL) (pH ~5) followed by water (~12 mL), filtered through a syringe filter (Acrodisc Supor, PN 4612) and placed evenly into 3 Amicon centrifuge membrane dialysis tubes (30,000 mwco). The tubes were diluted and mixed with water (~5 mL each), placed into centrifuge (rpm 3200) for 25 minutes. The filtrate is removed for analysis while the retentate is diluted and mixed with water (~10 mL/tube). The centrifuge procedure repeated 5 more times, after which the retentate is removed and placed into a vial. The Amicon membrane tubes were rinsed with water (2×~2 mL each tube) and this combined with the retentate. The retentate solution was filtered through a syringe filter (Acrodisc Supor, PN 4612), frozen and placed on a lyophilizer. This resulted in 485 mgs as a white powder.

Example 6—Synthesis of Initiator OG1786

Figure 2E:
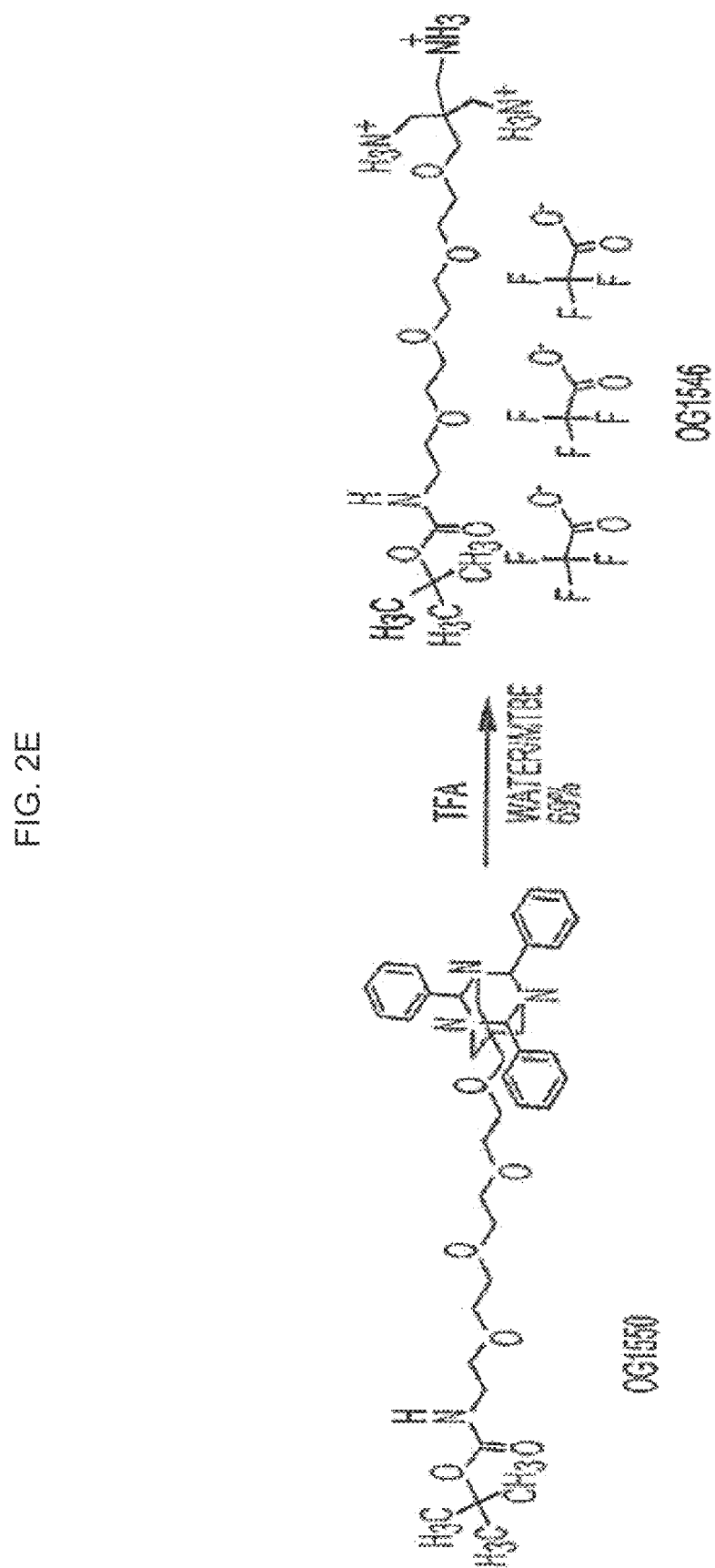
FIG. 2E shows the synthesis of OG1546 from OG1550.

OG1786 is the nine-arm initiator for polymer synthesis used as a precursor in the synthesis of OG1802. Each arm is terminated with a 2-bromoisobutyrate which is capable of initiating polymerization under ATRP. OG1786 is a salt of trifluoro acetic acid (TFA) as shown in FIG. 2D. OG1786 is prepared as follows. First, OG1550 is reacted with TFA (trifluoro acetic acid) to produce OG1546 as depicted in FIG. 2E.

In a 1L round bottom flask equipped with a magnetic stir bar and an addition funnel was added OG1550 (14.8 g), methyl tert-butyl ether (MTBE) (350 ml) and water (30 ml). The mixture was stirred to dissolve the OG1550, then cooled in an ice bath. To this mixture was added a solution of trifluoroacetic acid (4.9 ml) in water (90 ml) dropwise over 90 minutes. After addition is complete the mixture was stirred an additional 15 minutes then removed from the ice bath and allowed to warm to room temperature. The mixture was stirred (after removal from the ice bath) for a further 4-5 hours, until tlc showed ~5% starting material remaining, and the pH of the aqueous was between 3 and 4 (pH paper).

The mixture was partitioned. The MTBE layer was washed with water (30 ml). Combine aqueous layers then the aqueous extracted with MTBE (150 ml). This second MTBE phase was washed with water (30 ml). The combined aqueous layers were washed with a third portion of MTBE (100 ml). The third MBTE phase was washed with water (25 ml). The aqueous layers were again combined (~250 ml, pH ~4, by pH paper).

The product was collected by lyophilization. 11.5 g white solid was obtained. This material is extremely hygroscopic, so best handled under nitrogen. The product was confirmed by LCMS.

Figure 2F:
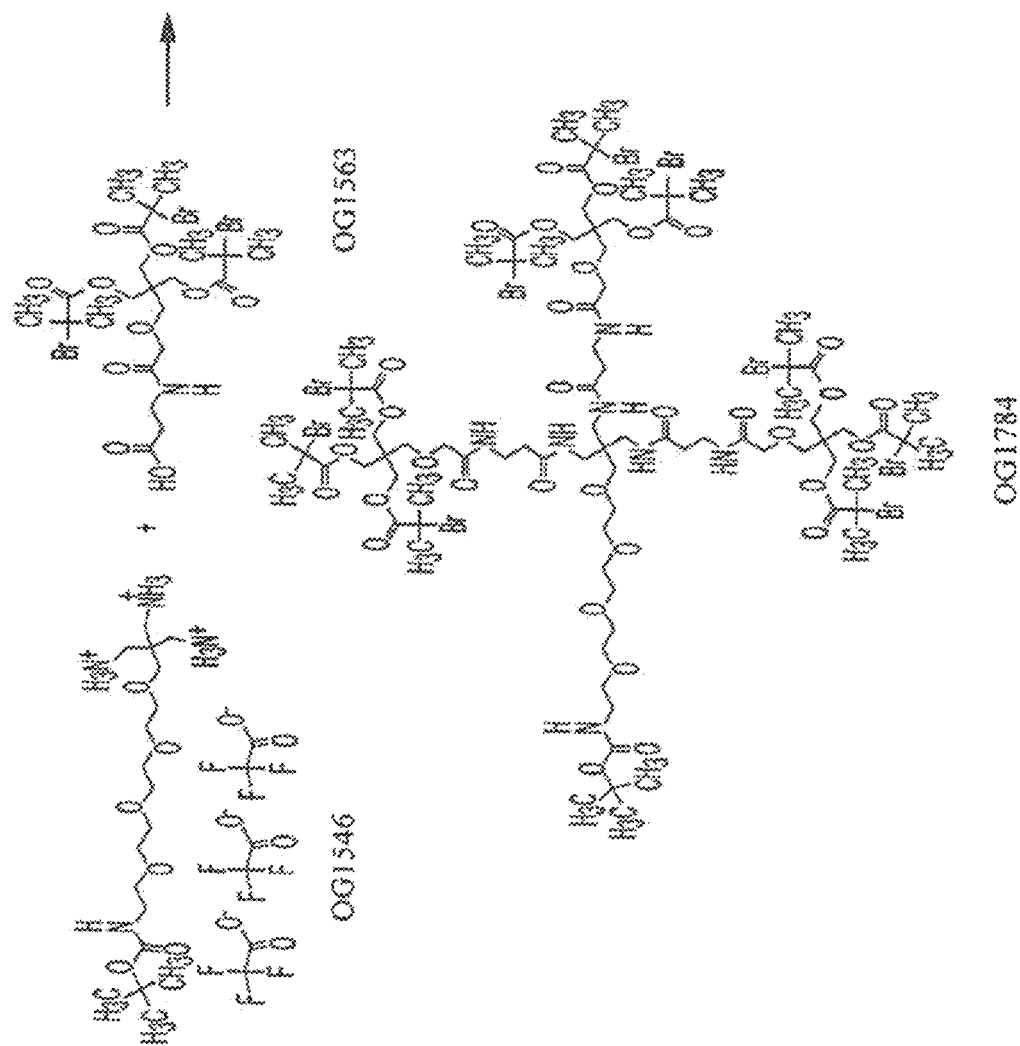
FIG. 2F shows the synthesis of OG1784 from OG1546 and OG1563.

The prepared OG1546 was then reacted with OG1563 to yield OG1784 (as depicted in FIG. 2F).

In a 250 ml flask under nitrogen equipped with a stir bar was added OG1546 (hygroscopic, 9.0 g), followed by N,N-dimethylformamide (110 ml). The mixture was stirred at room temperature until all OG1546 dissolved (about 15 minutes), then OG1563 (29.9 g) was added, and the mixture stirred a further 3 minutes until the OG1563 had also been dissolved. The resulting solution was cooled in an ice bath, and N,N-diisopropylethylamine (37.6 ml) was added over 3 minutes, followed by propylphosphonic anhydride (T3P), 50% in ethyl acetate (34.5 ml) dropwise over 5 minutes (T3P addition is exothermic). After T3P addition was complete, the flask was removed from the cooling bath and allowed to reach room temperature. Samples were then taken at 5 minute intervals for LCMS analysis. The reaction showed very light yellow/tan color.

After 20 minutes the reaction was cooled again in an ice bath and 5 ml water added. The mixture was then removed from the cooling bath and a further 50 ml water portion added, followed by 50 ml 0.5 M citric acid then isopropylacetate (300 ml). The mixture was partitioned. The aqueous phase (~300 ml) was extracted with additional isopropyl acetate (150 ml). The aqueous phase was AQ1 for HPLC test. The combined organics were washed with aqueous citric acid (115 ml, 65 mM, which was the mixture of 15 ml of 0.5 M citric acid plus 100 ml water), and the aqueous phase was AQ2 (pH~3). The organic phase was washed with water/saturated sodium chloride (100 ml/25 ml), and the aqueous phase was AQ3 (pH~3). The organic phase was finally washed with saturated sodium chloride (100 ml), and the aqueous phase was AQ4. None of the AQ fractions contained any significant product (data not provided). The organic phase confirmed the product via LCMS. The product was dried over sodium sulfate (80 g), filtered and rinsed with isopropyl acetate (75 ml), and concentrated on a rotary evaporator to a tan oil (33.2 g). The crude was stored overnight under nitrogen.

The next day the crude was allowed to come to room temperature, then dissolved in acetonitrile/water (46 ml/12 ml) and filtered using an HPLC filter disk (Cole-Parmer PTFE 0.2 μm, product number 02915-20). The filtrate was split into three equal portions and purified in three runs.

The filtrate was loaded onto a RediSep Rf Gold C18 column (275 g, SN 69-2203-339, Lot #24126-611Y) equilibrated with 50% acetonitrile/water. The material was eluted at 100 ml/min using the following gradient (solvent A: water, solvent B: acetonitrile). All the relevant fractions were checked by HPLC. The fractions adjudged to be pure enough were pooled (from all three runs) and concentrated (bath temperature kept at about 20° C.) on rotovap, then partitioned between dichloromethane (100 ml) and water (5 ml)/saturated sodium chloride (25 ml). The aqueous was extracted twice more with dichloromethane (2×30 ml). The combined organics were dried over sodium sulfate (35 g), filtered, rinsed with DCM (30 ml), and concentrated. The product and purity were confirmed by LCMS methods. The isolated yield and the purity of the R5172 and R5228 lots are shown in Table 27.

TABLE 27

| OG1784 lot | R5172 | R5228 |
|---|---|---|
| OG1546 used | 5.3 g | 9.0 g |
| OG1563 used | 17.6 g | 29.9 g |
| Isolated yield | 53% | 58% |
| Purity (a/a 210 nm) | 99.3% | 100.0% |

Figure 2G:
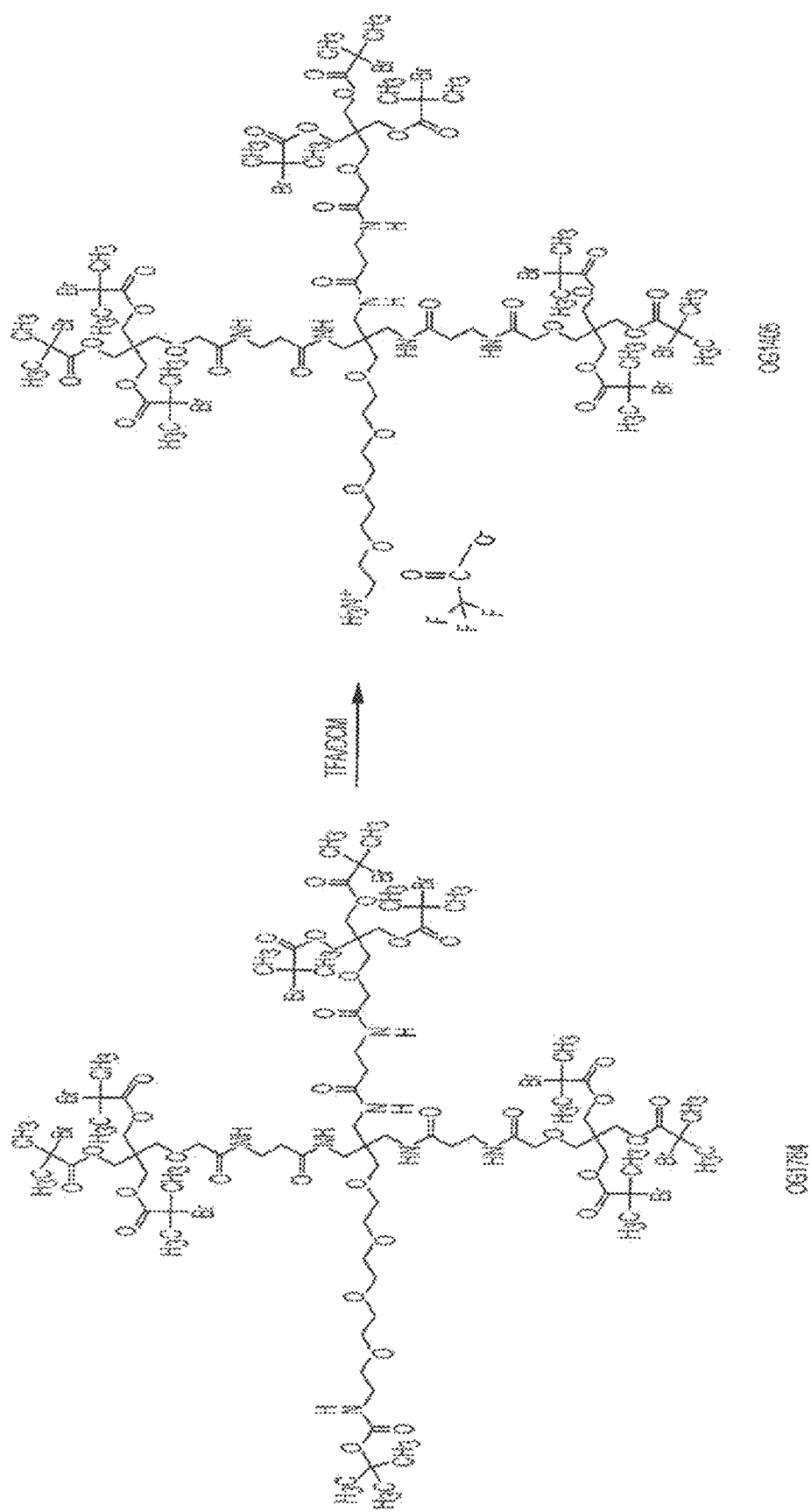
FIG. 2G shows the synthesis of OG1405 from OG1784.

Next OG1405 was prepared from OG1784 as depicted in FIG. 2G. In a 500 ml round bottom flask equipped with a magnetic stir bar was added OG1784 (20.9 g), followed by dichloromethane (50 ml) then trifluoroacetic acid (20 ml). The mixture was stirred at room temperature and HPLC analysis showed complete deprotection in 23 minutes. The mixture was concentrated on a rotary evaporator, redissolved in dichloromethane (25 ml) and re-concentrated, then redissolved in acetonitrile (25 ml) and re-concentrated. The product was confirmed by LCMS. The material from above (OG1405, 34.5 g, assume 21.0 g as quantitative yield) was used as a crude oil in the next step. No purification is needed.

Figure 2H:
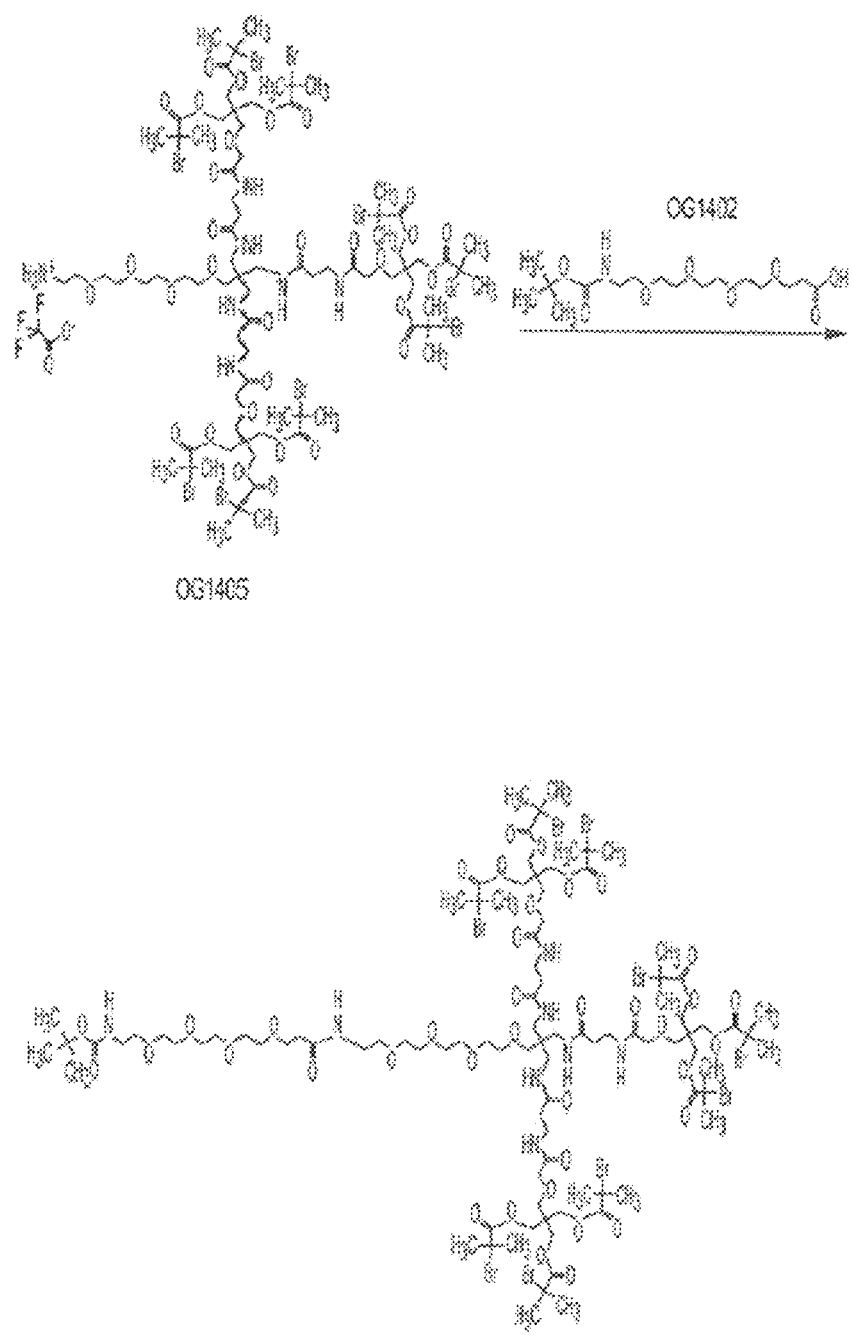
FIG. 2H shows the synthesis of OG 1785 from OG1405.
Figure 2L:
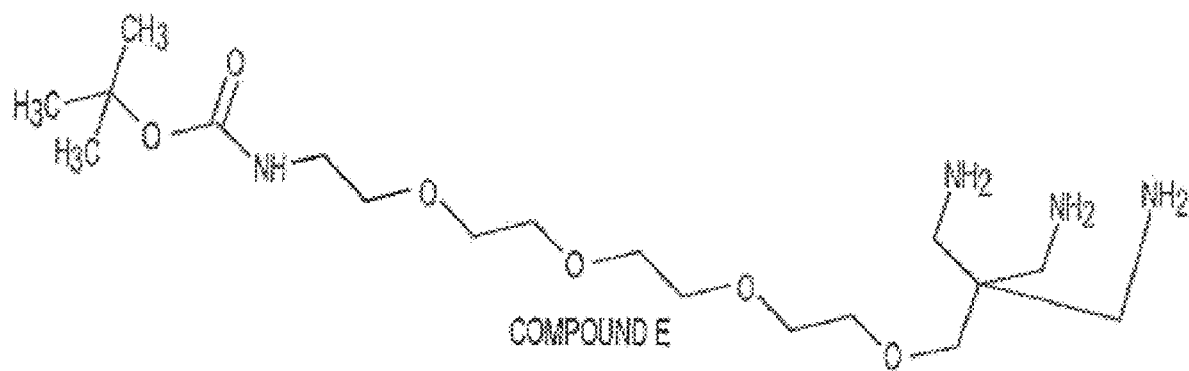
FIG. 2L shows Compound E.

Next, OG1405 was reacted with OG1402 to prepare OG1785 as set forth in FIG. 2H. In a 500 ml flask under nitrogen equipped with a stir bar was placed OG1402 (5.5 g), followed by acetonitrile (70 ml), then N,N-diisopropylethylamine (26.3 ml) and T3P solution (see above) (7.9 ml). The solution was stirred at room temperature for 30 minutes, then cooled in an ice water bath and a solution of OG1405 (crude oil from above, 34.5 g) in acetonitrile (70 ml) added. The mixture was warmed to room temperature. After 20 minutes the reaction was cooled in an ice water bath and quenched with water (5 ml). The mixture was then concentrated under vacuum using a rotary evaporator to half volume. Samples were taken for LCMS.

More water (50 ml), followed by 0.5 M citric acid (75 ml) and isopropyl acetate (175 ml) was added. The mixture was partitioned in 5 minutes. The aqueous was extracted with additional isopropyl acetate (50 mL). The combined organics were washed with aqueous citric acid (0.13 M, 30 ml, consist of 10 ml of 0.5 M citric acid and 20 ml water). The organics were then washed with the mixture of saturated sodium chloride (25 ml) and water (25 ml), then finally washed with the saturated sodium chloride (25 ml). They were then dried over sodium sulfate (124 g), filtered and rinsed with isopropyl acetate (30 ml), and concentrated under rotary evaporator to a tan oil (27.3 g). Samples were taken for LCMS analysis.

The oil was dissolved in acetonitrile/water (3:1, 15 ml/5 ml), filtered through an HPLC filter disk (Cole-Parmer PTFE membrane 0.2 m, product number 02915-20) and split into three equal portions, each of which were individually purified as follows.

Portions were loaded onto Redi-Sep Gold $C_{18}$ column (275 g, SN—69-2203-339, Lot 241234-611W) equilibrated at 50% solvent B (acetonitrile)/50% solvent A (water). The material was then purified by reverse phase HPLC with a solvent A: water/solvent B: acetonitrile gradient. Appropriate fractions were pooled and partitioned between dichloromethane (150 ml) and water (5 ml)/saturated sodium chloride (25 ml). The aqueous was extracted twice with dichloromethane (2×50 ml). Combined organics were dried over sodium sulfate (60 g), filtered and rinsed with dichloromethane (40 ml) and concentrated. Structure and purity were confirmed by various analytics including LCMS: OG1785 was isolated as a foamy solid (R5329, 19.0 g, 83% yield, 95.1% purity (a/a 210 nm), stored under nitrogen at 4° C.

Next, the tert-butyloxycarbonyl protecting group on OG1785 was removed using trifluoroacetic acid (TFA) to produce OG1786 as depicted in FIG. 21.

Example 7—Synthesis of Polymer OG1801

Polymer OG1801 is made first from the initiator OG1786. OG1801 has an amine functionality, which is more stable (than maleimide) during polymer synthesis. To synthesize polymer OG1801, a modified version of ATRP is used wherein the copper species (Cu(I)) is generated in situ by adding metallic copper to Cu (II). Starting materials and reagents needed in the reaction are calculated based on batch input of the monomer (HEMA-PC) OG47, as well as the targeted molecular weight (MW).

Weighed 50 g monomer OG47 in glove box and added 200 mL of degassed EtOH to dissolve the monomer at room temperature; sampled for monomer concentration test. Weighed Cu (II), Bpy, Cu(0) in a 500 mL flask; purged with Argon, while adding monomer solution to the flask; sealed the flask with stopper and vacuumed for 25 min until no bubbles. The reaction changed color gradually from light green to dark green, then to light brown; weighed ~200 mg of initiator OG1786 in glove box, and dissolved in ~2000 uL of DMF under room temperature to make 100 mg/mL stock solution; sampled for initiator concentration and purity test; added the initiator solution to the flask under Argon. The reaction solution became dark brown and started thickening over time; sealed the system and let the reaction occur over 2 days.

OG1801 was then prepared for addition of the maleimide and catalyst (copper) was removed as follows: A prepacked RediSep® Rf normal phase silica column is used to remove the catalyst. The size of the column is chosen based on the copper amount in the reaction mixture. For instance, a 330 g column (Cat. #69-2203-330, Column size 330 g, CV=443 mL) was used for a 50 g batch of OG1801. Teflon tubing is used for all the connection as EtOH is the elute solvent.

After copper removal, all the fractions were transferred to a round bottom flask in batches, and evaporated the EtOH by rotary evaporator at 45-50° C. at reduced pressure to dryness. In this step, EtOH volume collected from condensation was monitored to make sure EtOH removal was >90%. The polymer was dissolved in 250 mL of WFI and filtered using a 0.2 um filter. It resulted in a clear to light yellow polymer solution at ~150 mg/mL. The solution could be stored at 2-8° C. up to 3 month before use.

Example 8—Synthesis of Polymer OG1802

Starting materials and reagents needed in the reaction are calculated based on batch input of OG1801. The linker is 3-maleimidopropionic acid, NHS ester. Added 30 ml of 0.5 M sodium phosphate (in WFI, pH 8) to 50 g polymer solution (~150 mg/mL). Let stir for 1 min; pH was 8.0 by pH paper. Weighed 204.8 mg of linker and dissolved in DMF 4.1 mL to make 50 mg/mL stock sln. Added linker solution dropwise 815 uL per minute to the polymer sln with strong stirring. Took 5 min to added 4095 uL of linker solution. Reacted at room temperature for 30 min. Quenched reaction with 20 mL of 5% acetic acid to achieve a final pH of 5. Filtered the solution using 1L vacuum filter (0.2 um).

OG1802 (shown in FIG. 2K) is then purified as follows: Milipore cross flow cassettes are used for polymer purification in aqueous system. Started with concentrating the polymer solution to 250 mL (~200 mg/mL). Added the fresh WFI from reservoir, and adjusted the flow rate of the fresh WFI feed to the same as the permeate (~2 mL/min). The UF/DF was set up at 2-8° C. overnight. Typically 2.5 L of WFI was used (10× volume ratio to the polymer solution). A sample of retente was collected for purity test. The targeted purity was >98%. Filtered the polymer solution by 0.2 µM 1L filter bottle. The polymer solution could be stored at 2-8° C. for up to 3 month before conjugation.

Example 9—Alternative Phosphorylcholine Polymers

A HEA-PC polymer was synthesized as described below. HEA-PC (2-(acryloyloxy)ethyl-2-(trimethylammonium) ethyl phosphate), which is an acrylate as opposed to the methacrylate HEMA-PC described above, has the following structure:

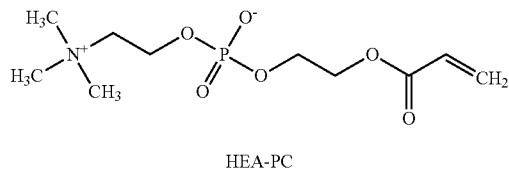 [SMILES: C=CC(=O)OCCOP(=O)([O-])OCC[N+](C)(C)C]

HEA-PC

HEA-PC was polymerized to the initiator shown in Example 5 as compound L.

TABLE 28

| Reactant | Name | Amount | MW |
|---|---|---|---|
| Initiator | Compound L (see above) | 1.65 mg | 2505.5 |
| Monomer | HEA-PC | 0.461 g | 281.24 |
| Catalyst | Cu (I) Bromide | 1.2 mg | 143.45 |
| Ligand | Tris [2-(dimethylamino)ethyl]amine (Me6TREN) | 2.73 mg | 230.39 |
| Solvent A | N,N-Dimethylformamide (DMF) | 21.85 µl | 73.09 |
| Solvent B | Water | 0.7 ml | 18.02 |
| Solvent C | Methanol | 0.7 ml | 32.04 |

Prepared a stock solution of initiator at 200 mg/mL by dissolving 2.2 mg of initiator in 11 µl of dry DMF and a 200 mg/ml solution of ligand by dissolving 4.6 mg of Me6TREN in 23 µL of dry DMF. Dispense 8.25 µl of the stock solution of initiator and 13.6 µl of the ligand into a tube. Degas at −78° C. for 5 mn then refill with Argon and add 1.2 mg of CuBr. Degas and refill with Argon. Add a stock solution of HEA-PC in methanol (weigh out 0.461 g of HEA-PC and dissolve it in 0.5 mL of methanol) to the solution inside the reactor at −78° C. Rinse the vial with 200 µl of methanol and add it inside the reactor at −78° C. and then 0.5 mL of distilled water then another 200 µl of water. Degas thoroughly until no bubbling is seen and all heterogeneity disappears (solid particulates dissolve or disappear). Refill with 4 psi of Argon and let the reaction to proceed at RT for an hour. The reaction was already viscous. The reaction was allowed to proceed for about one hour. A solution of bipyrindine in methanol (5 mg in 0.5 uL) was added. Another 2-3 ml of methanol was added and the catalyst was allowed to oxidize overnight at 4° C. Conversion determined by 1H NMR was estimated to be 94%.

The next day the polymer was dialyzed and subjected to SEC/MALS analysis using Shodex SB806M_HQ column (7.8×300 mm) in 1× PBS pH 7.4 at 1 ml/min, giving a PDI of 1.157, Mn of 723.5 kDa, Mp of 820.4 kDa and Mw of 837.2 kDa (before dialysis PDI is 1.12, Mn=695 kDa, Mp=778 kDa). Next a maleimide functionality was added to the polymer so that it could be conjugate to a protein.

Next, the maleimide Mal-PEG4-PFP (see Example 20 above) ester was snapped on to the HEA-PC polymer as shown in Example 20. The resulting maleimide functionalized HEA-PC polymer can then be conjugated to sulfhydryl groups as discussed herein for HEMA-PC polymers.

An acrylamide PC polymer was also made using the monomer 2-(acrylamyl)ethyl-2-(trimethylammonium)ethyl phosphate (Am—PC), having the following structure:

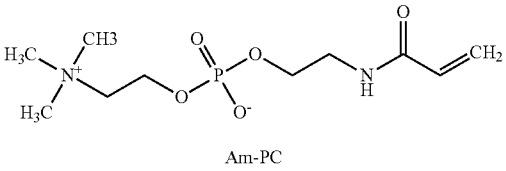 [SMILES: "Am-PC" ; C=CC(=O)NCCOP(=O)([O-])OCC[N+](C)(C)C]

Am-PC

The Am—PC was used for polymerization employing a 3 arm initiator (a TFA salt) having the structure:

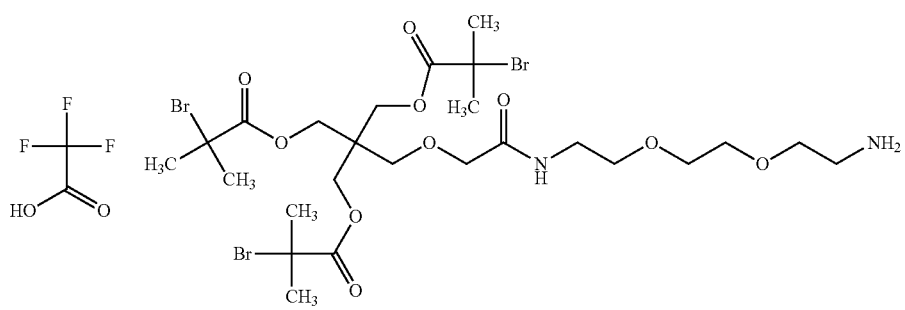 [SMILES: O=C(O)C(F)(F)F ; CC(C)(Br)C(=O)OCC(COCC(=O)NCCOCCOCCN)(COC(=O)C(C)(C)Br)COC(=O)C(C)(C)Br]

The synthesis of the Am—PC polymer was conducted as follows:

TABLE 29

| Reactant | Name/Identity | Amount | MW |
|---|---|---|---|
| Initiator | 3-arm initiator (see above) | 2.2 mg | 885.35 |
| Monomer | Am-PC | 0.5 g | 280.26 |
| Catalyst (I) | Copper (I) Bromide | 1 mg | 143.45 |
| Catalyst (II) | Copper (II) Bromide | 0.2 mg | 223.35 |
| Ligand | Tris[2-(dimethylamino)ethyl]amine (Me6TREN) | 3.94 mg | 230.39 |
| Solvent A | N,N-Dimethylformamide (DMF) | 31.7 µl | 73.09 |
| Solvent B | Water | 1 ml | 18.02 |
| Solvent C | Methanol | 1 ml | 32.04 |

A stock solution of ligand at 200 mg/mL was prepared by dissolving 9 mg of Me6TREN in 45 uL of dry DMF. Add 19.7 uL of the stock solution to a reaction vessel. Prepare a stock solution of initiator at 200 mg/mL by dissolving 6.5 mg of material in 32.5 uL of DMF. Add 11 uL of the initiator stock solution to the ligand from above. Degas for 5 min. Add 1 mg of CuBr. Prepared a stock solution of $CuBr_2$ at 200 mg/mL by dissolving 4 mg $CuBr_2$ in 20 µL of DMF. Add 0.5 g of monomer (AmPC) to 1 mL of methanol (slow dissolution/viscous solution), followed by 1 uL of the stock solution of $CuBr_2$. Add the monomer solution dropwise to the reaction mixture above. Rinse with 1 mL of water. Degas the reaction mixture thoroughly (freeze-thaw). Let the reaction proceed for 24 hours.

Afterwards the Am—PC polymer may be dialyzed. The molecular weight of the above polymer was determined by SEC/MALS: Mn is 215 kDa, Mp: 250 kDa, PDI is 1.17. Conversion was estimated by 1H NMR to be 94%. A maleimide functionality can be added to the Am—PC polymer as discussed above for HEMA-PC and HEA-PC. Maleimide functionalized Am—PC polymer can be conjugated to a protein as described above.

Example 10—Reverse Ellman's Assay for Calculating Free Maleimide in a Compound

After addition of the maleimide functionality to polymer OG1801 to form OG1802 (see above), an Ellman's assay was used to determine the amount of functional maleimide expressed as percent function (i.e. conjugatable) in a sample. Thiol converted Ellman's reagent (DTNB) to TNB- then to TNB2-in water at neutral and alkaline pH, which gave off a yellow color (measured at 412 nm). A standard curve was established with cysteine. Since the maleimide reacts with thiol, this assay actually measured the thiol (cysteine) left. The inhibition was calculated as the molarity ratios of (original thiol—thiol left after maleimide polymer addition)/(original thiol) and is expressed as a percentage where the higher the percent the higher the maleimide functionalization.

Reagents Employed in Assay: A standard curve was prepared using the cysteine from 62.5 µM to 2 µM. Polymer stock solutions were prepared by dissolving the powder in 1×PBS pH7.4 (reaction buffer) and mixing thoroughly. An equal molar of polymer and cysteine solutions were mixed and allowed to react at 27° C. for 30 minutes. The 150 µM of DTNB solution was added into the cysteine standards and polymer/cysteine reactions and the color was developed at 27° C. for 5 minutes. OD at 412 nm was read on the Spectramax plate reader and percent inhibition was calculated with the Softmax Pro software and the cysteine standard curve.

Example 11—Purification and Decapping of AntiIL-6-VEGF Trap Molecules

The heavy and light chains may be cloned into expression plasmids and transfected into CHO cells. Cells can be grown up in appropriate media and harvested. The antibody (or in the alternative the Ab-Trap) may be purified using Protein A affinity column capture and elution. The antibody (or in the alternative the Ab-Trap) cysteine at position 443 (L443C (EU numbering)) residue is typically "capped" or oxidized by chemicals in the cell culture media and is not available for conjugation. In this regard, purified antibody (or in the alternative the Ab-Trap) may be subjected to a decapping (i.e. reducing) procedure to remove the cap and enable the free (i.e. those not involved in Cys-Cys disulfide bonds) cysteine residue to be conjugated to the maleimide functionality of a polymer. Decapping may be done by mixing purified antibody (or in the alternative the Ab-Trap) protein with a 30× molar excess for 1 hour at ambient temperature of a reducing agent such as TCEP (3,3',3"-Phosphanetriyl-tripropanoic acid), Trisodium 3,3',3"-phosphinetriyltris(benzene-1-sulphonate) (TPPTS), or something similar. The reduction reaction may be monitored by SDS-PAGE. Following reduction, the antibody (or in the alternative the Ab-Trap) protein may be buffer exchanged using a Pellicon XL Ultrafiltration Cassette with 20 mM Tris pH7.5, 100 mM NaCl, 0.5 mM TCEP buffer to remove the cap. The TCEP reagent may then be removed in the same buffer exchange setup with 20 mM Tris pH7.5, 100 mM NaCl. Reduced antibody (or in the alternative the Ab-Trap) may then be allowed to reoxidized using 15× molar excess of the oxidation agent DHAA (DeHydroxy Ascorbic Acid) for 1 hr at ambient temperature which again is monitored by SDS-PAGE assay. The DHAA reagent may then be removed in the same buffer exchange setup with 20 mM Tris pH7.5, 100 mM NaCl.

Example 12A—Conjugation of Antibody (or in the Alternative the Ab-Trap) to MPC Polymer Decapped antibody (or in the alternative the Ab-Trap) may be conjugated to polymer OG1802 to yield the bioconjugate. An excess of OG1802 is used (3-20 fold molar excess). Conjugation can be monitored by cation-exchanger HPLC chromatography and driven to near completion. Antibody (or in the alternative the Ab-Trap) conjugate may be purified via cation exchanger chromatography and buffer exchanged into the formulation buffer by ultrafiltration/diafiltration (UF/DF). Antibody (or in the alternative the Ab-Trap) conjugate may be purified chromatographically as described above.

Example 12B—VEGFR-AntiIL6 Conjugation Reaction with OG1802

Figure 28:
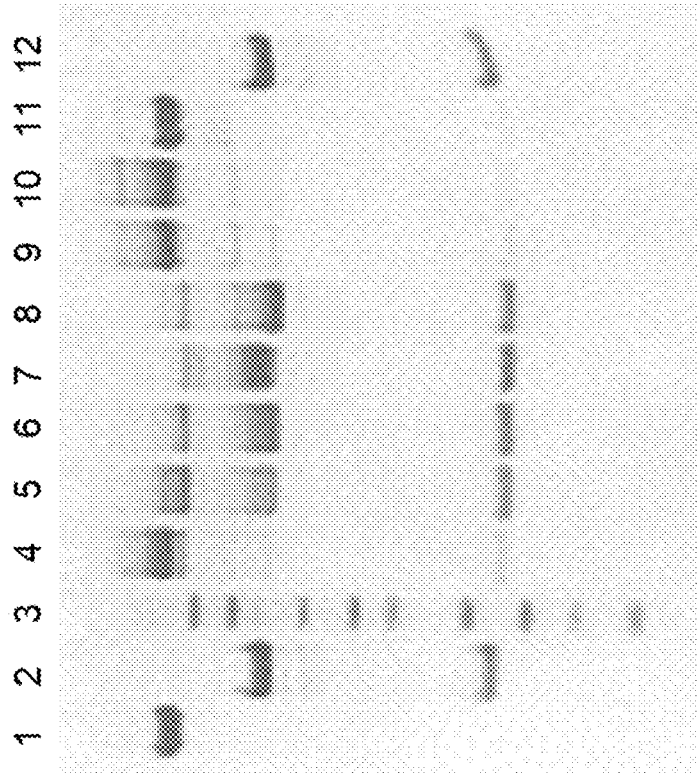
FIG. 28 depicts a SDS-PAGE of VEGFR-AntiIL6 reduction (Cys—decapping) reaction products. The lanes are as follows: 1. VEGFR-AntiIL6; 2. VEGFR-AntiIL6–fully reduced (TCEP); 3. Novex sharp pre-stained protein standard; 4. VEGFR-AntiIL6+30× TCEP, initial point; 5. VEGFR-AntiIL6+30× TCEP, after 30 min; 6. VEGFR-AntiIL6+30× TCEP, after 60 min; 7. VEGFR-AntiIL6 TCEP treated, buffer exchanged; 8. VEGFR-AntiIL6+15× dHAA, initial point; 9. VEGFR-AntiIL6+15× dHAA, after 30 min; 10. VEGFR-AntiIL6+15× dHAA, after 60 min; 11. VEGFR-AntiIL6 decapped; 12. VEGFR-AntiIL6 decapped, fully reduced (TCEP); Gel: NuPAGE Bis-Tris 4-12% Protein amount: 4 µg/lane; 30× TCEP=30 times molar excess TCEP 15× dHAA=15 times molar excess dHAA

VEGFR-AntiIL6 conjugation process with OG1802 involved two steps: an initial reduction reaction to remove the cysteine S protecting groups (decapping), which was followed by conjugation to the biopolymer OG1802 via maleimide-cysteine chemistry. The decapping was done by first reducing (30-60 min) VEGFR-AntiIL6 with 30× molar excess of 3,3',3"-Phosphanetriyltripropanoic acid (TCEP) followed by buffer exchange into 20 mM Tris-HCl pH 7.5, 100 mM NaCl to remove the cysteine cap and TCEP (FIG. 28). In the alternative, other reducing agents such as 3',3"-Phosphanetriyltris(benzenesulfonic acid) trisodium salt (TPPTS) could also be used for the decapping step.

Then, reduced VEGFR-AntiIL6 was oxidized (30-60 min) with 15× molar excess of dehydro-ascorbic acid (dHAA) followed by buffer exchange into 20 mM Tris pH 7.5, 100 mM NaCl to remove the oxidizing reagent (FIG. 28). Cumulative yield for the decapping procedure was 89% (TCEP reduction—94%, dHAA oxidation—95%).

Figure 29:
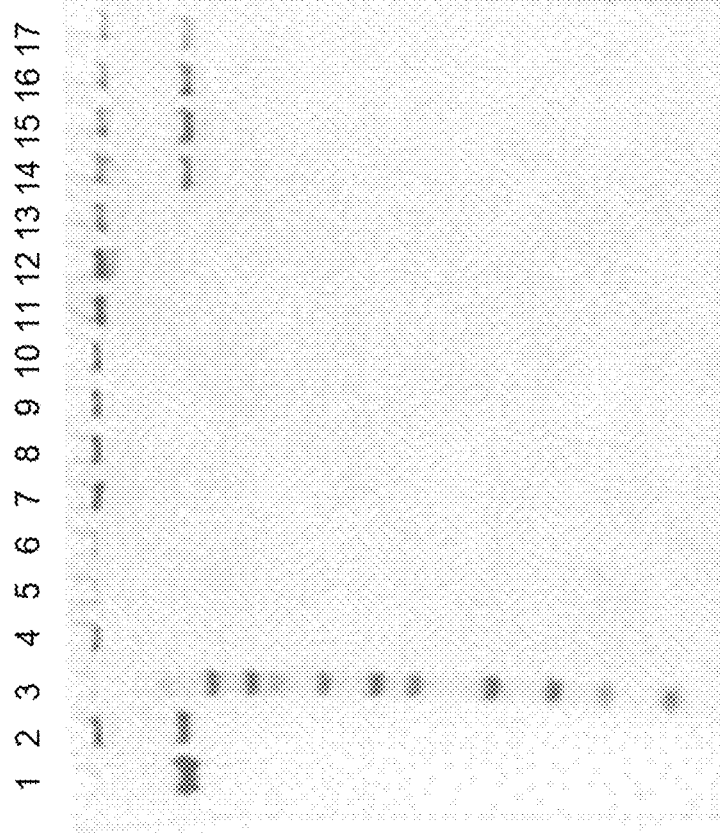
FIG. 29 depicts a SDS-PAGE of VEGFR-AntiIL6-OG1802 conjugate CEX chromatography. The Non-reducing gel: NuPAGE Bis-Tris 4-12%. Buffer A: 20 mM Sodium Acetate pH 5.5. Buffer B: 20 mM Sodium Acetate pH 5.5, 500 mM NaCl. The lanes are as follows: 1. VEGFR-AntiIL6; 2. VEGFR-AntiIL6-OG1802 (load); 3. Novex sharp pre-stained protein standard; 4. Flow-through; 5. Chase; 6. 30% buffer B—aliquot 1; 7. 30% buffer B—aliquot 2; 8. 30% buffer B—aliquot 3; 9. 30% buffer B—aliquot; 10. 40% buffer B—aliquot 1; 11. 40% buffer B—aliquot 2; 12. 40% buffer B—aliquot 3; 13. 40% buffer B—aliquot 4; 14. 60% buffer B—aliquot 1; 15. 60% buffer B—aliquot 2; 16. 60% buffer B—aliquot 3; 17. 100% buffer B—strip. Lanes 6-13 show protein conjugated material, conjugate cannot penetrate gel due to large size. Lanes 14-17 show protein mixture possibly containing aggregated, conjugated and non-conjugated protein material

The conjugation process was done by mixing VEGFR-AntiIL6 at a final concentration of 2.4 mg/mL (or 12.5 µM) with 5× molar excess of the biopolymer OG1802 at pH 8.0. The conjugation process took place at 2-8° C. for a period of 2 to 3 days. Conjugated VEGFR-Anti-IL6 was purified from unconjugated material by cation exchange chromatography (CEX) with Poros XS resin using a step gradient of increasing salt concentrations (0-500 mM NaCl) in buffer containing 20 mM sodium acetate pH 5.5 (FIG. 29). The fractions containing the bioconjugate VEGFR-AntiIL6-OG1802 were pooled and buffer exchanged into phosphate-buffered saline (PBS) pH 7.4 buffer. The conjugation efficiency was approximately 60% (determined by non-reducing SDS-PAGE and ImageJ analysis). The cumulative yield from initial protein material to bioconjugate was approximately 27%.

Figure 30:
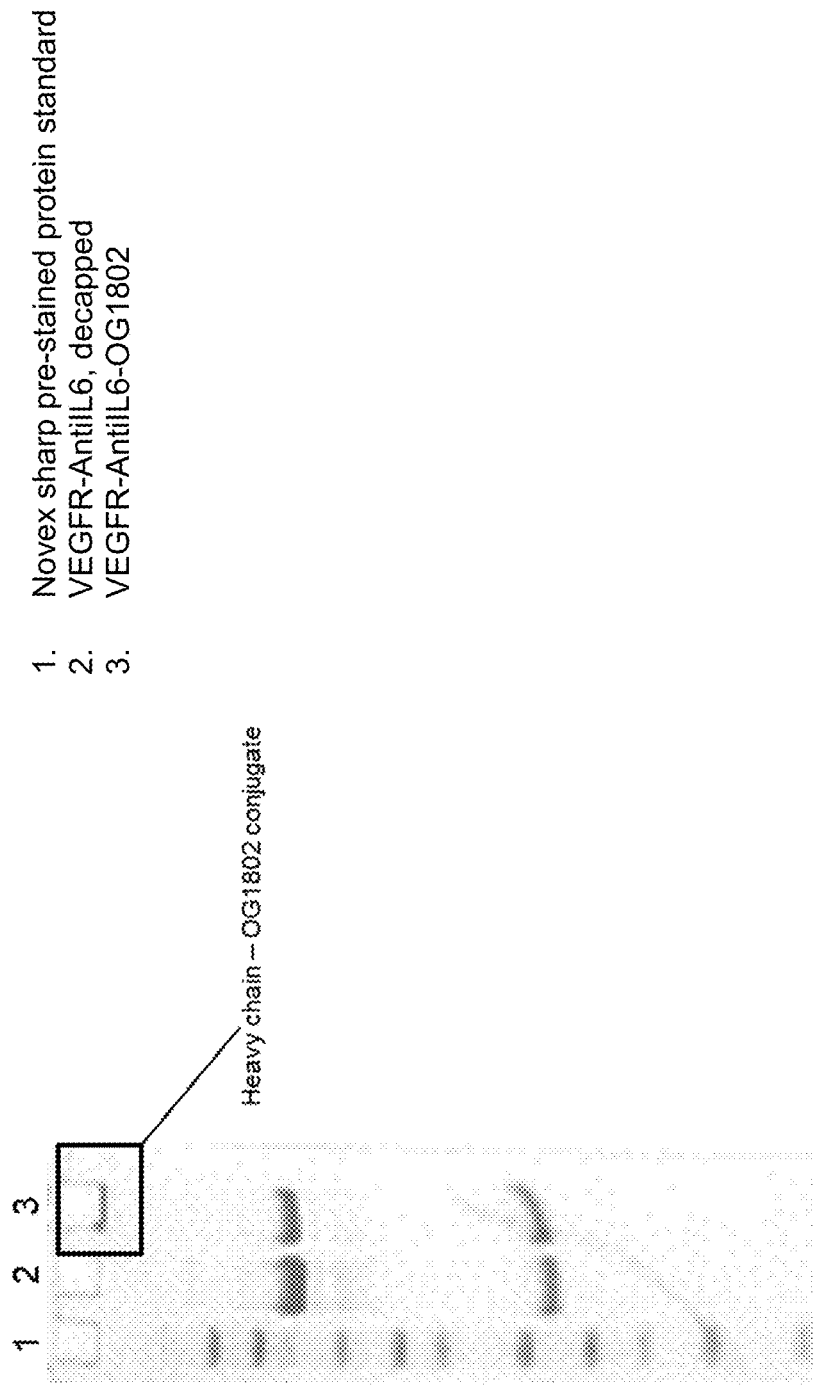
FIG. 30 depicts a SDS-PAGE of a protein-polymer conjugate vs non-conjugate protein material. Gel analysis demonstrates 57% heavy chain and 96% light chain band intensity ratios when bioconjugate (lane 3) is compared to VEGFR-AntiIL6 reference standard (lane 2), which indicates the presence of one OG1802 polymer per VEGFR-AntiIL6 molecule Reducing gel is: NuPAGE Bis-Tris 4-12% Reducing gel is: NuPAGE Bis-Tris 4-12%.
Figure 31:
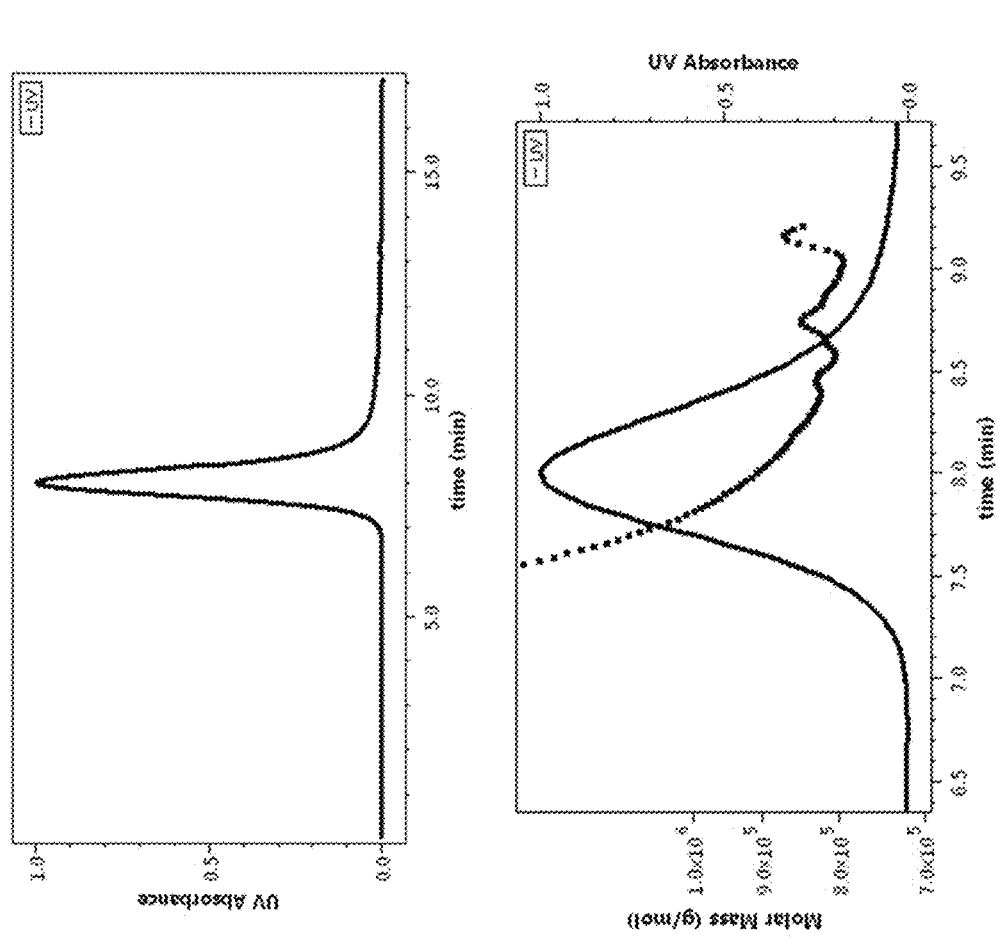
FIG. 31 depicts a SEC-MALS of VEGFR-AntiIL6-OG1802. The molecular weight of VEGFR-AntiIL6 conjugate was determined with integrated size exclusion chromatography (Shodex-SB806M-HQ) and light scattering (MALS). Top panel. Chromatogram shows the presence of a single eluting peak. Absence of additional peaks and shoulder suggest no aggregates and degraded material were present after conjugation and subsequent CEX separation steps. Bottom panel. Protein conjugate analysis of selected peak showed an experimentally measured average molecular weight (Mw) of 983 kDa for the VEGFR-AntiIL6-OG1802 bioconjugate. This value results from the conjugation of one VEGFR-AntiIL6 molecule (Mw ~189 kDa) and one OG1802 polymer (Mw~794 kDa).

SDS-PAGE (FIG. 30) and SEC-MALS (FIG. 31) analysis demonstrate one VEGFR-AntiIL6 molecule (~189 kDa) conjugated with one OG1802 polymer molecule (~794 kDa), which resulted in a bioconjugate of approximately ~983 kDa. SEC-MALS experiment was carried on by injecting 10 µg (protein mass) at flow rate 1 mL/min into a size exclusion chromatography column (Shodex-SB806M-HQ) pre-equilibrated with PBS buffer, in line with a light scattering (miniDAWN TREOS) and refractive index (Optilab T-rEX) detectors (Wyatt Technology). Data and protein conjugate analysis was done in ASTRA 7 (Wyatt Technology).

Example 13—VEGF Trap Cleavage Identification and Removal

As shown in FIGS. 11A and 11B, SDS-PAGE of protein A purified VEGFR-Anti-IL-6 and Anti-IL-6-VEGFR reduced products derived from ExpiCHO-S cells displayed unexpected bands with sizes dependent on the construct orientations. These bands indicated that a fraction of the dual inhibitor molecules underwent cleavage during production. In this example, VEGFR-AntiIL6 corresponds to a heavy chain molecule comprising of sequences 1A-2A-3H paired with a light chain containing sequence 4A. AntiIL-6 VEGFR corresponds to a heavy chain comprising of sequences 5H(Fab)-2A-1A-5H(Fc) paired with a light chain containing sequence 4A.

As illustrated in FIG. 12, these protein bands were transferred to a PVDF membrane and the first six residues of the protein bands were sequenced through Edman's N-terminal sequencing (Procise 494HT instrument). Results showed that cleaved products share the same N-terminal sequence (93LTHRQT), which is located within the VEGFR1 domain 2 at the VEGF trap region.

Figure 13A:
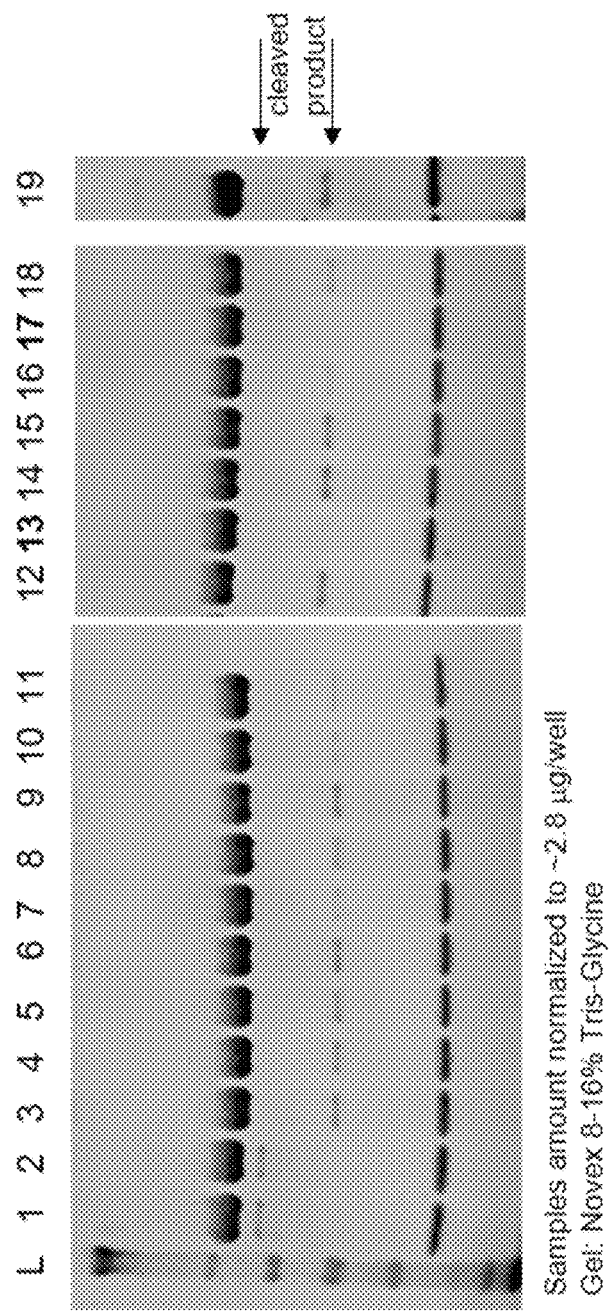

FIGS. 13A and 13B show the results of the mutations at the region flanking the cleavage site (K89TNY/LTHR96) that would disrupt protein cleave while maintaining the protein overall stability and binding to VEGF properties. Those mutations were chosen based on sequence conservation, for this purpose the Basic Local Alignment Search Tool (BLAST) was used to do a sequence similarity search and alignment between VEGFR1 domain 2 sequence and protein homologs within the Mammalia class. The 500 best hits were selected based on their BLAST E value score. From this initial cluster containing 500 sequences (cluster 1), the best scoring sequence for each individual species was selected reducing it to a set of 106 representative sequences (cluster_2). Based on sequence variations within the cleavage site flanking region observed in cluster_2, 16 Anti-IL-6-VEGFR single point mutants were generated and evaluated on the protein cleavage. These mutations were initially only introduced in the Anti-IL-6-VEGFR construct since it shows a better size separation between cleaved and intact products due to their molecular weight differences (~35 kDa).

Figure 13F:
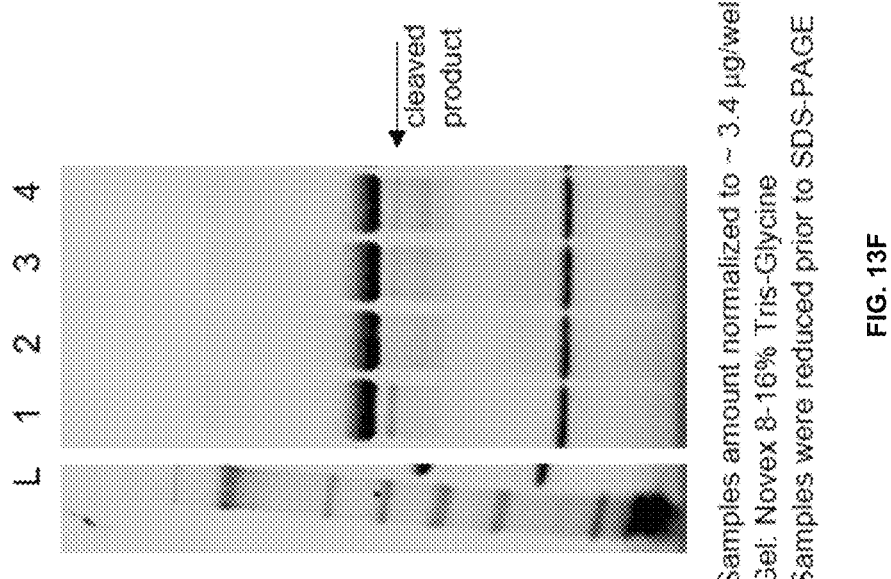

FIGS. 13A and 13B illustrate SDS-PAGE results of Anti-IL-6 VEGFR mutants demonstrating that modifications at the cleavage site tended to reduce the amount of cleaved product (indicated by arrows). Mutations T94I and H95I (residue numbering based on position at the VEGF trap sequence) markedly reduced the VEGF trap cleavage. Specifically, FIGS. 13A and 13B illustrate that most of the mutations reduced protein cleavage and mutations T94I (VEGFR_variant_1), illustrated in FIG. 13C, and H95I (VEGFR_variant_2), illustrated in FIG. 13D, had a more marked effect. Single point mutation (T94I, H95I) and double point mutation (T94I/H95I, VEGFR_variant_3), as illustrated by FIG. 13E, were subsequently introduced in the VEGFR-Anti-IL-6 construct. FIG. 13C indicates the position of T94I (underlined). FIG. 13D indicates the position of H95I (underlined). FIG. 13E indicates the position of T94I and H95I (underlined). As illustrated in FIGS. 13F and 13G, SDS-PAGE showed that similar reduction in protein cleavage was observed and this effect is further enhanced when double mutation is introduced.

Example 14—Dual Inhibitor VEGFR Variants Binding to VEGF Via Biacore

Figure 14A:
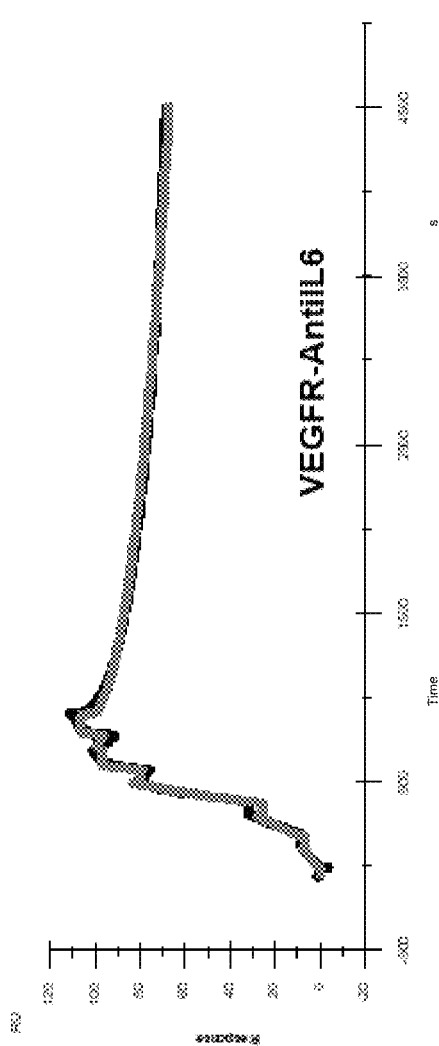
FIGS. 14A-14F depict Biacore assay results and measurements of affinity to VEGF-A.
Figure 14B:
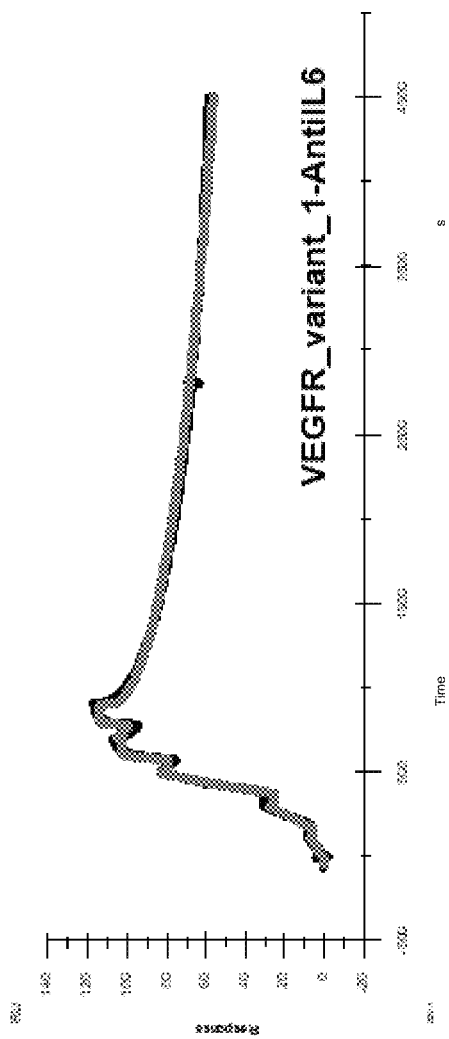
Figure 14C:
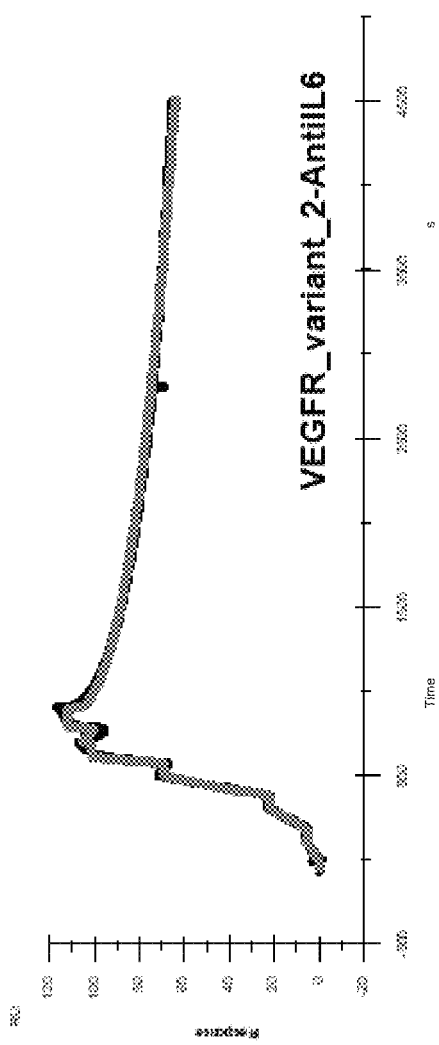
Figure 14D:
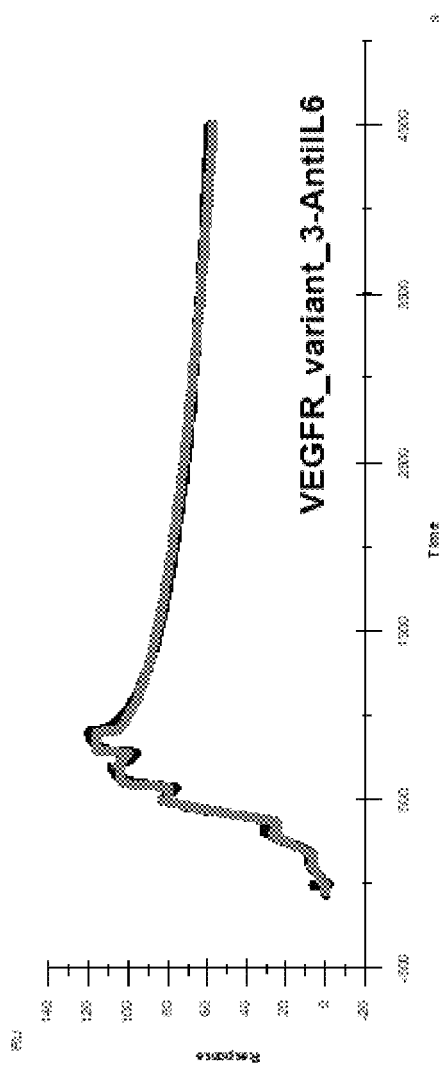
Figures 14E, 14F:
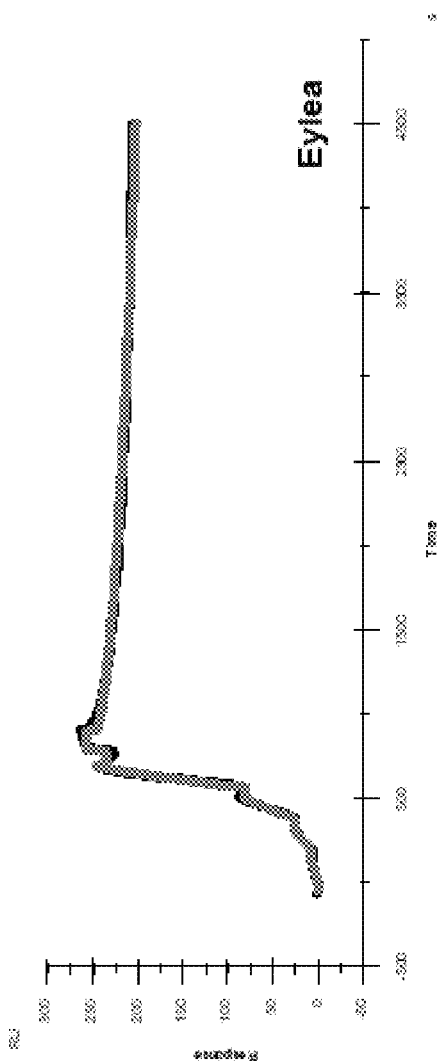

FIGS. 14A-14F illustrate the results for a series of Biacore assays used to determine the affinity between Anti-VEGF agents and VEGF. Binding kinetics between molecules were measured using a Biacore T200 (GE Healthcare) at 37° C. in buffer HBS-EP+ containing 1 mg/mL BSA. Anti-VEGF agents (VEGFR-Anti-IL-6 (5 µg/mL), VEGFR_variant_1-Anti-IL-6 (5 µg/mL), VEGFR_variant_2-Anti-IL-6 (5 µg/mL), VEGFR_variant_3-Anti-IL-6 (5 µg/mL) and Eylea (3 µg/mL)) were captured on a Protein A chip (GE) at 10 µL/min for 25 seconds, five concentrations of VEGF-A165 (0.19, 0.56, 1.67, 5, 15 nM) were flowed over captured antibodies for 120 seconds at 30 µL/min and dissociated for 60 min. The sensor chip surface was regenerated by 60 seconds injection of 10 mM Glycine, pH 1.7 at a flow rate of 50 µl/min. All sensorgrams were double reference subtracted and fit using a 1:1 Langmuir binding model. FIGS. 14A-14F show the introduction of single point mutations T94I (VEGFR_variant_1-Anti-IL-6), H95I (VEGFR_variant_2-Anti-IL-6) and double mutant T94I/H95I (VEGFR_variant_3-Anti-IL-6) minimally affects binding to VEGF. As can be seen in FIG. 14F, sensograms demonstrate dual inhibitor molecules VEGFR-Anti-IL-6 and variants bind tightly to VEGF-A as Eylea. In this example, the VEGFR-AntiIL6 molecules correspond to VEGFR variants (Sequences 1A-1D) fused to the AntiIL-6 moiety via the GS linker (sequences 2A-3H) paired with light chain containing sequence 4A.

Example 15—Cell Based VEGF Stimulated VEGFR Reporter Assay

Figure 15:
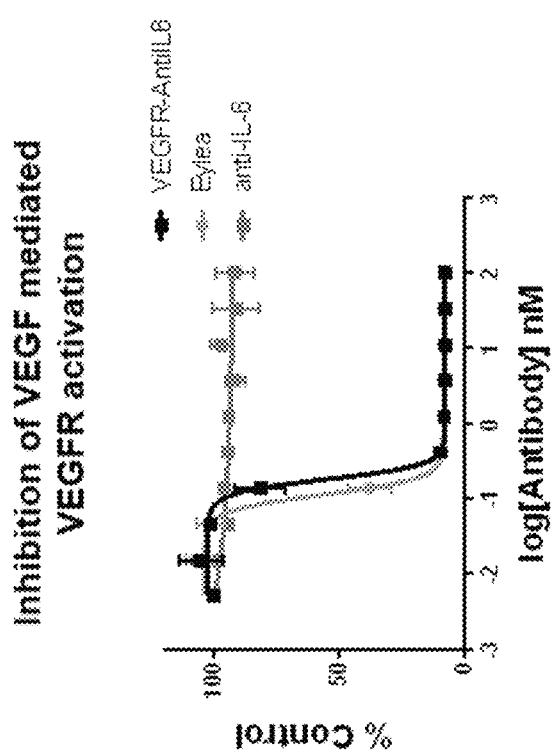
FIG. 15 depicts a cell-based VEGF stimulated VEGFR reporter assay.

The results of a cell-based VEGF stimulated VEGFR reporter assay are provided in FIG. 15. Dual inhibitor-VEGFR-AntiIL6, as noted above, blocks VEGF from binding VEGFR and stimulating downstream signaling to the same degree as Eylea (IC50 0.18 nM vs. 0.11 nM), while the anti-IL-6 antibody did not have any effect.

For the experiments, Promega KDR/VEGF HEK293 thaw-and-use cells (CS181405; Promega) were thawed and added to 4.6 mL of assay medium (10% FBS in DMEM). 25 µL of cells were transferred to each well of a 96-well plate. VEGF (500 µM final concentration) was mixed with a 10-point, 1:3 dilution series of inhibitors, starting at 100 nM (final concentration), and incubated for 30 minutes before adding 50 µL to the plated cells. After 6 hours, 75 µL of prepared Bio-Glo reagent (Promega) was added to the cells and incubated for 3-10 minutes at room temperature. Luminescence was measured on an iD3 plate reader (Molecular Devices). Relative luminescence units were normalized to the lowest inhibitor concentration for each curve and plotted as the average of replicates with standard error against the log of the concentration of antibody using GraphPad Prism software and fit with a non-linear regression curve. In this example, VEGFR-AntiIL6 corresponds to a heavy chain molecule comprising of sequences 1A-2A-3H paired with a light chain containing sequence 4A.

Example 16—HUVEC Tubule Formation Assay

Figure 16A:
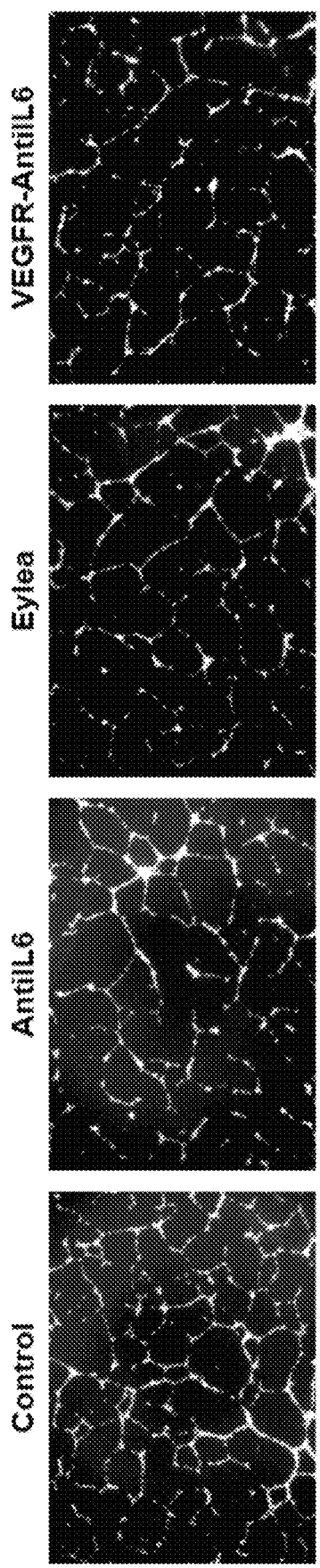
FIG. 16A depicts an assay of inhibition of VEGF/IL6 mediated human umbilical vein endothelial cells ("HUVEC") tubule formation.
Figure 16B:
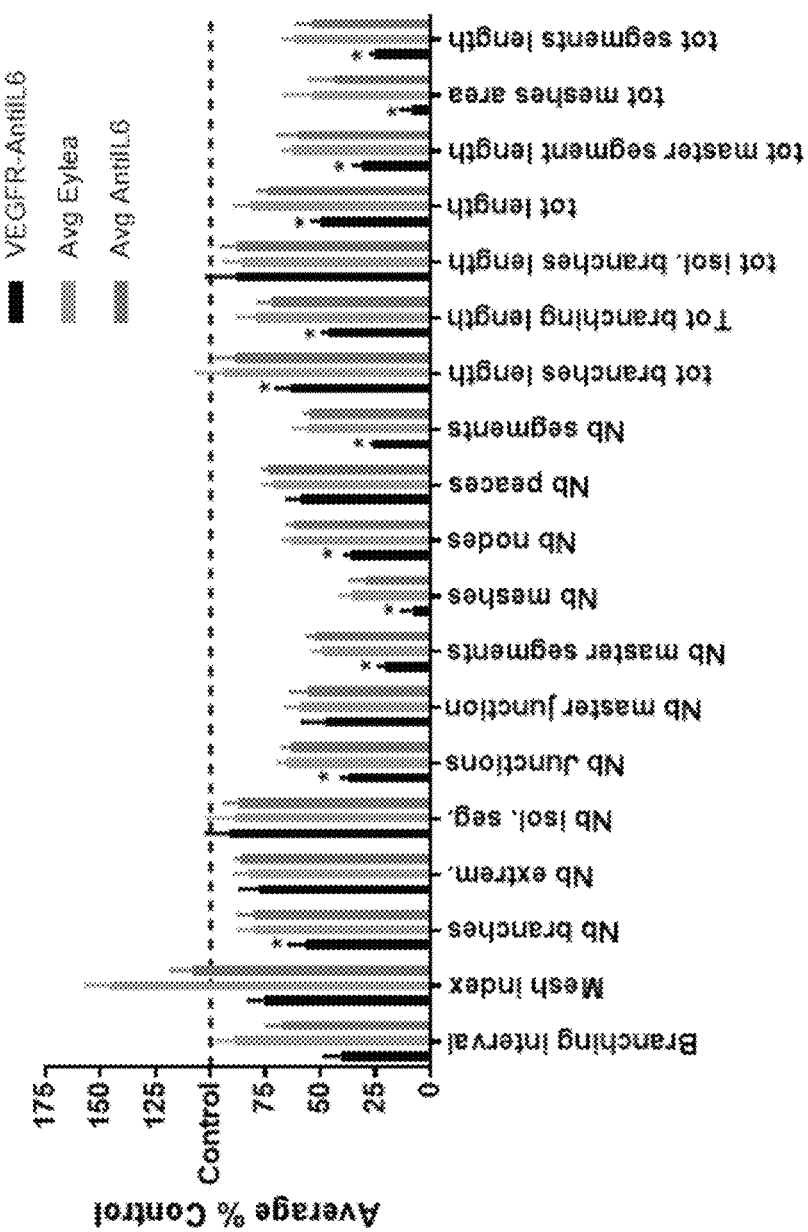

FIGS. 16A-16C illustrate the results of HUVEC tubule formulation assay.

Passage 2 or 3 HUVEC cells were cultured in Vascular Basal Media supplemented with 1× Bovine Brain Extract endothelial cell growth kit (ATCC; growth media) in 5% CO2 at 37° C. Once cells reached 70% confluency, cells were lifted from the plate using trypsin (0.05%; ATCC) and 0.75×10^6 cells plated in a T25 flask in growth media. Media was swapped for Assay Media (2% FBS in Vascular Basal Medium) the following day. After 6 hours, 5 µg/ml of Calcein AM was directly added to the media and incubatet for 30 minutes at 37° C. At the same time, 200 µL of pre-thawed Matrigel (growth factor reduced; Corning) were added to each well of an 8-well glass chamber slide and incubate at 37° C. for 30 minutes. During incubations, 25 nM of each inhibitor (final concentrations) was mixed with 3 nM VEGF (R&D), 12.5 nM IL6 (Tonbo), and 25 nM IL6R (Tonbo) (all final concentrations). Following the 30 minute Calcein AM incubation, the cells were washed 3× with PBS and then trypsinized. Harvested cells were centrifuged for 3 minutes at 1,500×g and resuspended in assay medium at a density of 500,000 cells/mL. 100 µL of cells were then mixed with 100 µL of prepared inhibitor/complex solutions, and then transferred to the Matrigel coated chamber slides and incubated overnight. The next day, tubules were imaged using a 10× objective lens and the GFP filter on a EVOS fluorescence microscope (Life Technologies). At least 2 representative images were taken for each condition and then analyzed using the Angiogenesis Analyzer Plugin for ImageJ (NIH), which evaluates and quantifies 20 tubule network formation parameters.

FIGS. 16A-16C show data as average with standard error from 4 independent experiments. Statistical significance was determined from all replicates from 4 independent experiments using an unpaired, two-tailed Students t-test. As illustrated in FIG. 16C, VEGFR-AntiIL6 significantly inhibited angiogenic parameters in 17/20 parameters as compared to the control. In contrast, Eylea inhibited in 4/20 parameters and anti-IL-6 inhibited in 7/20 parameters. VEGFR-AntiIL6 was significantly better than Eylea and Anti-IL-6 in 12/20 parameters, as indicated by asterisks in FIG. 16B. Furthermore, t-test statistics are presented in FIG. 16C. In this example, VEGFR-Anti-IL6 corresponds to a heavy chain molecule comprising of sequences 1A-2A-3H paired with a light chain containing sequence 4A.

In some embodiments, the VEGFR-Anti-IL6 construct allows for synergistic mechanisms to improve efficacy and durability in specific at-risk populations. At-risk populations include those with at-risk for or diagnosed with diabetic retinopathy or one or more inflammatory retinal disease.

Example 17—HUVEC Proliferation Assay

Figure 17:
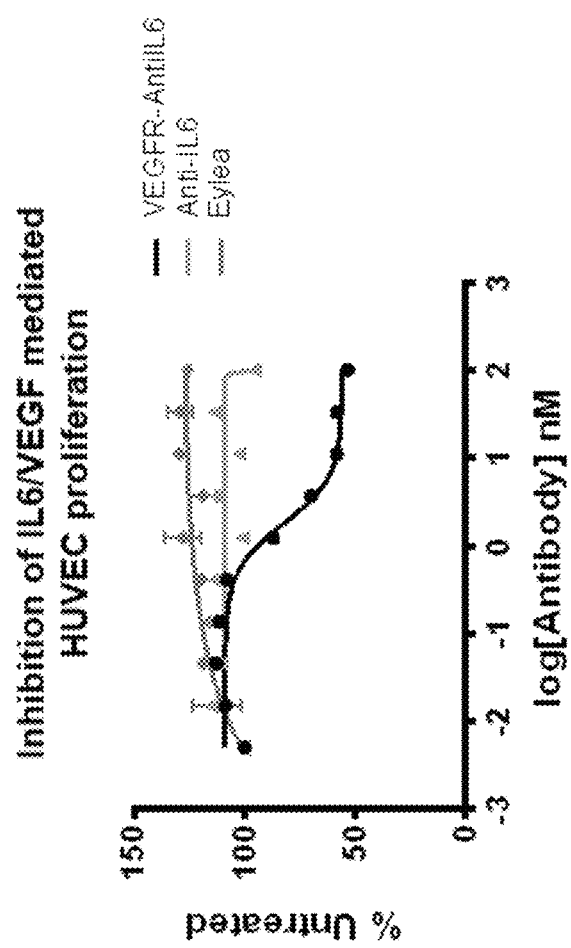
FIG. 17 depicts the results of an HUVEC proliferation assay.

FIG. 17 illustrates the results of an HUVEC proliferation assay. HUVEC cells (passages 2-5) were cultured in Vascular Basal Media supplemented with 1× Bovine Brain Extract endothelial cell growth kit (ATCC; growth media) in 5% CO2 at 37 degrees. Once cells reached 70% confluency, cells were lifted from the plate using trypsin (0.05%; ATCC) and 3,500 cells/well were seeded in the middle 60 wells of a 96-well gelatin coated plate in 100 uL of Assay Media (Vascular Basal Media supplemented with 1-glutamine, ascorbic acid, heparan sulfate, hydrocortisone, and 1% FBS) (Corning). After 24 hours of starvation, cells were stimulated with VEGF (1.5 nM), IL-6 (5 nM), and IL6R (10 nM) mixed with 10-point, 1:3 dilution series of inhibitors starting at 100 nM. These concentrations of VEGF and IL-6 induce proliferation at sub-maximal levels when added independently of each other, but demonstrated a synergistic growth curve when combined. 48 hours later, cell viability was measured using CellTiterBlue reagent (Promega) according to manufacturer's instructions on an iD3 plate reader (Molecular Devices). For absorbance measurements, the ratio of A570/A605 was determined and data were normalized to control (no inhibitor) cells for each replicate. Fluorescence measurements (555 ex/605 em) were normalized to control cells for each replicate.

As shown in FIG. 17, normalized values were plotted as the average of replicates with standard error against the concentration of antibody using GraphPad Prism software and fit with a non-linear regression curve.

As can be seen in FIG. 17, VEGFR-AntiIL6 dual inhibitor blocked synergistic stimulation of HUVEC proliferation by IL-6 and VEGF, while neither Eylea nor anti-Il-6Anti-IL-6 affected HUVEC growth under these conditions.

Example 18—Generation of Improved Anti-IL-6 Paratopes

The generation of improved Anti-IL-6 paratopes is described in the present example. Biacore kinetics results are shown in Tables 30, 31, 32, and 33.

To provide a superior anti-IL-6 paratope on the engineered human IgG1 framework, the G66D (CDR2) heavy chain mutant was affinity matured. Initially, G66D full heavy chain libraries containing random single point mutations at positions S35, I51, T63 and T65 were constructed, excluding substitutions for Cys, Met and Asn due to the chemical liabilities associated with these amino acids. Those four positions were selected based on their tolerance for mutations as observed in bacterial and mammalian screens. The mammalian expression vectors containing heavy chain mutations were co-transfected with light chain wild-type and variant M32L/M50D/N52S/M88Q into 3 mL cultures of Expi293 cells and incubated for five days. These cultures were centrifuged and supernatants containing secreted antibodies were harvested and diluted in HBS-EP+ running buffer (1:20 ratio).

The various constructs and resulting kinetic properties are provided below in Tables 30-33.

TABLE 30

Biacore Kinetics for Anti-IL-6 Heavy Chain Double Mutants

| Heavy chain - mutation | Light chain - mutation | Sup/37° C. | | | | | |
|---|---|---|---|---|---|---|---|
| | | Capture (RU) | ka (1/Ms) | kd (1/s) | KD (M) | Rmax (RU) | Chi$^2$ (RU$^2$) |
| WT | WT | 561.6 | 6.70E+05 | 2.55E−04 | 3.81E−10 | 125.50 | 0.0342 |
| G66D | WT | 878.9 | 1.83E+06 | 3.92E−04 | 2.15E−10 | 198.70 | 0.189 |
| S35H, G66D | WT | 1084.6 | 2.92E+06 | 3.97E−04 | 1.36E−10 | 231.60 | 0.839 |
| S35G, G66D | WT | 167 | 1.27E+06 | 3.605−04 | 2.84E−10 | 39.60 | 0.0144 |
| S35R, G66D | WT | 3.6 | 1.22E+02 | 2.95E−04 | 2.42E−06 | 0.00 | 0.0346 |
| S35Y, G66D | WT | 129.2 | 1.10E+06 | 5.516−04 | 5.03E−10 | 30.60 | 0.043 |
| S35P, G66D | WT | 48.4 | 1.03E+05 | 1.23E−03 | 1.19E−08 | 8.30 | 0.016 |
| S35W, G66D | WT | 161.5 | 9.23E+04 | 2.17E−03 | 2.35E−08 | 33.10 | 0.0784 |
| S35I, G66D | WT | 384.4 | 1.12E+06 | 3.76E−04 | 3.34E−10 | 87.40 | 0.0524 |
| S35V, G66D | WT | 856.3 | 1.13E+06 | 4.69E−04 | 4.14E−10 | 181.50 | 0.0742 |
| S35A, G66D | WT | 723.8 | 1.65E+06 | 4.94E−04 | 3.00E−10 | 168.80 | 0.076 |
| S35D, G66D | WT | 577.1 | 2.00E+06 | 6.41E−04 | 3.21E−10 | 147.80 | 0.0814 |
| S35L, G66D | WT | 257.5 | 1.11E+06 | 3.516−04 | 3.15E−10 | 57.70 | 0.0273 |
| S35T, G66D | WT | 674.3 | 1.38E+06 | 4.09E−04 | 2.97E−10 | 146.20 | 0.117 |
| S35K, G66D | WT | 16.4 | 1.70E+06 | 9.49E−04 | 5.57E−10 | 4.50 | 0.0309 |
| S35E, G66D | WT | 137.7 | 8.74E+05 | 5.09E−04 | 5.82E−10 | 31.00 | 0.0558 |
| S35F, G66D | WT | 143.6 | 1.59E+06 | 1.19E−03 | 7.49E−10 | 35.20 | 0.0522 |
| S35Q, G66D | WT | 390.6 | 1.31E+06 | 3.95E−04 | 3.02E−10 | 84.90 | 0.0382 |
| I51R, G66D | WT | 139.9 | 1.20E+06 | 2.02E−04 | 1.69E−10 | 31.60 | 0.0962 |
| I51V, G66D | WT | −10.4 | 1.81E+06 | 6.68E−06 | 3.69E−12 | 0.80 | 0.32 |
| I51W, G66D | WT | 559.1 | 1.91E+06 | 9.43E−03 | 4.93E−09 | 120.50 | 1.38 |
| I51Y, G66D | WT | 433 | 1.48E+06 | 5.10E−03 | 3.45E−09 | 100.60 | 0.449 |
| I51S, G66D | WT | 402.8 | 1.89E+06 | 3.62E−04 | 1.91E−10 | 94.90 | 0.186 |
| I51A, G66D | WT | 668.5 | 1.76E+06 | 5.76E−04 | 3.27E−10 | 149.70 | 0.203 |
| I51E, G66D | WT | 57.2 | 7.54E+05 | 7.60E−04 | 1.01E−09 | 10.70 | 0.056 |
| I51T, G66D | WT | 435.2 | 1.79E+06 | 4.15E−04 | 2.32E−10 | 102.10 | 0.107 |
| I51D, G66D | WT | 71.4 | 9.91E+05 | 2.67E−03 | 2.69E−09 | 12.40 | 0.0255 |
| I51F, G66D | WT | 367.9 | 1.36E+06 | 3.05E−03 | 2.246−09 | 82.90 | 0.13 |
| I51L, G66D | WT | 519.6 | 1.90E+06 | 7.33E−04 | 3.86E−10 | 118.50 | 0.1 |
| I51K, G66D | WT | 169.6 | 1.38E+06 | 4.026−04 | 2.91E−10 | 40.60 | 0.0621 |
| I51P, G66D | WT | 34 | 1.58E+04 | 6.12E−03 | 3.87E−07 | 9.80 | 0.0467 |
| I51H, G66D | WT | 249 | 1.52E+06 | 5.29E−04 | 3.48E−10 | 57.70 | 0.075 |
| I51Q, G66D | WT | 262 | 1.93E+06 | 6.48E−04 | 3.36E−10 | 61.40 | 0.1 |
| I51G, G66D | WT | 608 | 1.36E+06 | 5.81E−04 | 4.28E−10 | 135.50 | 0.0597 |
| T63S, G66D | WT | 723.7 | 2.52E+06 | 4.64E−04 | 1.84E−10 | 163.30 | 0.367 |
| T63I, G66D | WT | 682.7 | 1.77E+06 | 3.73E−04 | 2.11E−10 | 153.20 | 0.156 |
| T63H, G66D | WT | 811.6 | 1.98E+06 | 4.20E−04 | 2.13E−10 | 179.40 | 0.287 |
| T63E, G66D | WT | 630.3 | 2.61E+06 | 4.64E−04 | 1.78E−10 | 144.80 | 0.289 |
| T63V, G66D | WT | 708.8 | 1.84E+06 | 3.99E−04 | 2.176−10 | 158.80 | 0.249 |
| T63G, G66D | WT | 585.7 | 1.86E+06 | 3.97E−04 | 2.13E−10 | 131.30 | 0.166 |
| T63K, G66D | WT | 531.3 | 2.49E+06 | 4.61E−04 | 1.85E−10 | 120.50 | 0.333 |
| T63W, G66D | WT | 615.9 | 1.70E+06 | 4.27E−04 | 2.51E−10 | 136.30 | 0.143 |
| T63Q, G66D | WT | 673.7 | 2.01E+06 | 4.08E−04 | 2.03E−10 | 150.00 | 0.255 |
| T63R, G66D | WT | 729 | 2.66E+06 | 4.60E−04 | 1.73E−10 | 165.20 | 0.384 |
| T63L, G66D | WT | 698.9 | 1.73E+06 | 3.63E−04 | 2.10E−10 | 158.80 | 0.167 |
| T63D, G66D | WT | 684.8 | 1.92E+06 | 3.92E−04 | 2.04E−10 | 154.80 | 0.103 |
| T63A, G66D | WT | 632.4 | 2.80E+06 | 4.96E−04 | 1.77E−10 | 142.50 | 0.361 |
| T63Y, G66D | WT | 701.2 | 1.82E+06 | 3.83E−04 | 2.10E−10 | 157.00 | 0.169 |
| T63F, G66D | WT | 621.5 | 1.81E+06 | 4.01E−04 | 2.21E−10 | 137.80 | 0.169 |
| T63P, G66D | WT | 481.3 | 2.08E+06 | 4.36E−04 | 2.10E−10 | 110.50 | 0.203 |
| T65K, G66D | WT | 909.7 | 1.57E+06 | 4.12E−04 | 2.62E−10 | 199.50 | 0.226 |
| T65D, G66D | WT | 648.1 | 2.18E+06 | 4.426−04 | 2.03E−10 | 146.60 | 0.378 |
| T65L, G66D | WT | 662.8 | 1.77E+06 | 3.75E−04 | 2.12E−10 | 148.80 | 0.363 |
| T6SW, G66D | WT | 749 | 1.64E+06 | 3.70E−04 | 2.26E−10 | 154.50 | 0.508 |
| T65Q, G66D | WT | 863.8 | 3.28E+06 | 5.17E−04 | 1.58E−10 | 192.10 | 1.68 |
| T65E, G66D | WT | 937.2 | 2.20E+06 | 4.27E−04 | 1.94E−10 | 207.60 | 0.358 |
| T65V, G66D | WI | 872.5 | 2.88E+06 | 5.04E−04 | 1.75E−10 | 193.90 | 0.555 |
| T65S, G66D | WT | 935.4 | 1.82E+06 | 3.83E−04 | 2.10E−10 | 206.20 | 0.244 |
| T65Y, G66D | WT | 593.7 | 1.61E+06 | 3.61E−04 | 2.24E−10 | 128.00 | 0.0985 |
| T6SP, G66D | WT | 341.4 | 1.54E+06 | 5.68E−04 | 3.69E−10 | 80.80 | 0.0563 |
| T65A, G66D | WT | 690.4 | 1.64E+06 | 3.64E−04 | 2.22E−10 | 153.40 | 0.127 |
| T65H, G66D | WT | 659.8 | 1.63E+06 | 3.56E−04 | 2.19E−10 | 146.80 | 0.122 |
| T65R, G66D | WT | 730.4 | 2.00E+06 | 4.44E−04 | 2.22E−10 | 163.50 | 0.192 |
| T65G, G66D | WT | 56.1 | 1.77E+06 | 2.18E−04 | 1.23E−10 | 14.20 | 0.033 |
| T65F, G66D | WT | 587.6 | 1.56E+06 | 3.48E−04 | 2.23E−10 | 129.10 | 0.0947 |

TABLE 30-continued

Biacore Kinetics for Anti-IL-6 Heavy Chain Double Mutants

| | Purified/37° C. | | | | | |
|---|---|---|---|---|---|---|
| Heavy chain - mutation | Capture (RU) | ka (1/Ms) | kd (1/s) | KD (M) | Rmax (RU) | Chi² (RU²) |
| WT | 82.5 | 5.65E+05 | 1.28E−04 | 2.26E−10 | 17.4 | 0.171 |
| G66D | 90.5 | 1.57E+06 | 1.788−04 | 1.13E−10 | 20.4 | 0.166 |
| S35H, G66D | 78.1 | 1.77E+06 | 1.85E−04 | 1.05E−10 | 17.1 | 0.169 |
| S35G, G66D | | | | | | |
| S35R, G66D | | | | | | |
| S35Y, G66D | | | | | | |
| S35P, G66D | | | | | | |
| S35W, G66D | | | | | | |
| S35I, G66D | | | | | | |
| S35V, G66D | | | | | | |
| S35A, G66D | | | | | | |
| S35D, G66D | | | | | | |
| S35L, G66D | | | | | | |
| S35T, G66D | | | | | | |
| S35K, G66D | | | | | | |
| S35E, G66D | | | | | | |
| S35F, G66D | | | | | | |
| S35Q, G66D | | | | | | |
| I51R, G66D | | | | | | |
| I51V, G66D | | | | | | |
| I51W, G66D | | | | | | |
| I51Y, G66D | | | | | | |
| I51S, G66D | | | | | | |
| I51A, G66D | | | | | | |
| I51E, G66D | | | | | | |
| I51T, G66D | | | | | | |
| I51D, G66D | | | | | | |
| I51F, G66D | | | | | | |
| I51L, G66D | | | | | | |
| I51K, G66D | | | | | | |
| I51P, G66D | | | | | | |
| I51H, G66D | | | | | | |
| I51Q, G66D | | | | | | |
| I51G, G66D | | | | | | |
| T63S, G66D | | | | | | |
| T63I, G66D | | | | | | |
| T63H, G66D | | | | | | |
| T63E, G66D | 77.9 | 1.72E+06 | 2.52E−04 | 1.47E−10 | 17.1 | 0.151 |
| T63V, G66D | | | | | | |
| T63G, G66D | | | | | | |
| T63K, G66D | 77 | 1.46E+06 | 2.35E−04 | 1.61E−10 | 16.9 | 0.173 |
| T63W, G66D | | | | | | |
| T63Q, G66D | 70.9 | 1.30E+06 | 2.51E−04 | 1.93E−10 | 16.2 | 0.204 |
| T63R, G66D | | | | | | |
| T63L, G66D | | | | | | |
| T63D, G66D | | | | | | |
| T63A, G66D | | | | | | |
| T63Y, G66D | | | | | | |
| T63F, G66D | | | | | | |
| T63P, G66D | | | | | | |
| T65K, G66D | | | | | | |
| T65D, G66D | | | | | | |
| T65L, G66D | | | | | | |
| T65W, G66D | | | | | | |
| T65Q, G66D | 87.4 | 1.77E+06 | 2.62E−04 | 1.48E−10 | 19.1 | 0.135 |
| T65E, G66D | | | | | | |
| T65V, G66D | | | | | | |
| T65S, G66D | | | | | | |
| T65Y, G66D | | | | | | |
| T65P, G66D | | | | | | |
| T65A, G66D | | | | | | |
| T65H, G66D | | | | | | |
| T65R, G66D | | | | | | |
| T65G, G66D | | | | | | |
| T65F, G66D | | | | | | |

TABLE 31

| Biacore Kinetics for Anti-IL-6 Heavy Chain Double Mutants with Mutagenized Light Chain | | | | | | | |
|---|---|---|---|---|---|---|---|
| | | Sup/37° C. | | | | | |
| Heavy chain - mutatior | Light chain - mutation | Capture (RU) | ka (1/Ms) | kd (1/s) | KD (M) | Rmax (RU) | $Chi^2$ ($RU^2$) |
| WT | M32L, M50D, N52S, M88Q | 627.9 | 6.77E+05 | 4.14E−04 | 6.11E−10 | 133.3 | 0.0463 |
| G66D | M32L, M50D, NS2S, M88Q | 504.9 | 1.63E+06 | 4.83E−04 | 2.96E−10 | 110.5 | 0.0715 |
| S35H, G66D | M32L, M50D, N52S, M88Q | 1338.7 | 3.24E+06 | 5.39E−04 | 1.66E−10 | 270.1 | 1.6 |
| S35G, G66D | M32L, M50D, N52S, M88Q | 76.8 | 1.28E+06 | 7.81E−04 | 6.09E−10 | 17.1 | 0.0227 |
| S35R, G66D | M32L, M50D, N525, M88Q | 11.3 | 3.79E+03 | 1.21E−03 | 3.20E−07 | 0 | 0.0397 |
| S35Y, G66D | M32L, M50D, N52S, M88Q | 75.4 | 1.18E+06 | 4.04E−03 | 3.43E−09 | 16.6 | 0.121 |
| S35P, G66D | M32L, M50D, N52S, M88Q | 89.3 | 2.02E+05 | 5.48E−03 | 2.71E−08 | 13.4 | 0.0853 |
| S35W, G66D | M32L, M50D, N52S, M88Q | 384.2 | 1.71E+05 | 5.91E−03 | 3.46E−08 | 75.4 | 0.336 |
| S35I, G66D | M32L, M50D, N525, M88Q | 519.3 | 9.04E+05 | 1.47E−03 | 1.62E−09 | 108.3 | 0.221 |
| S35V, G66D | M32L, M50D, N52S, M88Q | 950.9 | 1.03E+06 | 1.37E−03 | 1.33E−09 | 194.4 | 0.0828 |
| 535A, G66D | M32L, M50D, NS25, M88Q | 326.2 | 1.93E+06 | 1.26E−03 | 6.57E−10 | 73.3 | 0.107 |
| S35D, G66D | M32L, M50D, N52S, M88Q | 251.8 | 2.35E+06 | 1.77E−03 | 7.53E−10 | 62.7 | 0.116 |
| S3SL, G66D | M32L, M50D, N52S, M88Q | 461.7 | 9.42E+05 | 2.43E−03 | 2.59E−09 | 100.2 | 0.0915 |
| S35T, G66D | M32L, M50D, N52S, M88Q | 265.5 | 1.43E+06 | 7.11E−04 | 4.98E−10 | 57.2 | 0.236 |
| S35K, G66D | M32L, M50D, NS2S, M88Q | −1.5 | 1.31E+06 | 3.46E−03 | 2.64E−09 | 1.80 | 0.0621 |
| S35E, G66D | M32L, M50D, N525, M88Q | 14.2 | 2.18E+06 | 1.89E−03 | 8.678-10 | 4.90 | 0.0255 |
| S35F, G66D | M32L, M50D, N52S, M88Q | 38.9 | 1.53E+06 | 4.84E−03 | 3.17E−09 | 8.10 | 0.0776 |
| S35Q, G66D | M32L, M50D, N52S, M88Q | 154.9 | 2.09E+06 | 6.26E−04 | 3.00E−10 | 35.30 | 0.104 |
| I51R, G66D | M32L, M50D, N525, M88Q | 34.4 | 1.63E+06 | 5.80E−05 | 3.57E−11 | 7.7 | 0.0516 |
| I51V, G66D | M32L, M50D, N525, M88Q | 72.6 | 1.76E+06 | 1.95E−03 | 1.11E−09 | 17.1 | 0.214 |
| IS1W, G66D | M32L, M50D, N52S, M88Q | 46.5 | 7.91E+05 | 3.83E−03 | 4.84E−09 | 8.2 | 0.134 |
| I51Y, G66D | M32L, M50D, N52S, M88Q | 48.2 | 6.10E+06 | 2.47E−02 | 4.04E−09 | 8.9 | 0.201 |
| I51S, G66D | M32L, M50D, N52S, M88Q | 118.4 | 1.85E+06 | 4.01E−04 | 2.17E−10 | 28.1 | 0.136 |
| I5IA, G66D | M32L, M50D, N52S, M88Q | 196.7 | 1.61E+06 | 8.99E−04 | 5.59E−10 | 44.8 | 0.0388 |
| I51E, G66D | M32L, M50D, NS2S, M88Q | 21.2 | 9.14E+05 | 1.96E−03 | 2.14E−09 | 3.5 | 0.129 |
| I51T, G66D | M32L, M50D, N52S, M88Q | 84.7 | 2.05E+06 | 4.78E−04 | 2.33E−10 | 20.4 | 0.131 |
| I51D, G66D | M32L, M50D, N52S, M88Q | 13.5 | 8.34E+05 | 7.99E−03 | 9.58E−09 | 2.9 | 0.0922 |
| I51F, G66D | M32L, M50D, N52S, M88Q | 32.3 | 1.37E+06 | 6.11E−03 | 4.45E−09 | 6.2 | 0.238 |
| I51L, G66D | M32L, M50D, N52S, M88Q | 69.4 | 1.64E+06 | 1.61E−03 | 9.80E−10 | 1.67E+01 | 0.053 |
| I51K, G66D | M32L, M50D, N52S, M88Q | 42.6 | 1.72E+06 | 6.01E−04 | 3.49E−10 | 9.00E+00 | 0.086 |
| I51P, G66D | M32L, M50D, N52S, M88Q | -4.4 | 1.25E+06 | 1.00E−02 | 8.04E−09 | 1.00E−01 | 0.154 |
| I51H, G66D | M32L, M50D, N52S, M88Q | 17.3 | 2.07E+06 | 1.04E−03 | 5.00E−10 | 5.60E+00 | 0.0639 |
| I51Q, G66D | M32L, M50D, N52S, M88Q | 43.5 | 1.96E+06 | 1.13E−03 | 5.75E−10 | 9.40E+00 | 0.123 |
| I51G, G66D | M32L, M50D, N525, M88Q | 152 | 1.40E+06 | 9.12E−04 | 6.52E−10 | 3.63E+01 | 0.208 |
| T63S, G66D | M32L, M50D, N52S, M88Q | 292.2 | 1.80E+06 | 4.99E−04 | 2.78E−10 | 66.8 | 0.298 |
| T63I, G66D | M32L, M50D, NS2S, M88Q | 287 | 1.55E+06 | 4.46E−04 | 2.88E−10 | 64.4 | 0.0411 |
| T63H, G66D | M32L, M50D, N52S, M88Q | 422.7 | 1.72E+06 | 4.81E−04 | 2.80E−10 | 93.5 | 0.138 |
| T63E, G66D | M32L, M50D, N52S, M88Q | 325.9 | 2.00€+06 | 4.85E−04 | 2.42E−10 | 75.2 | 0.13 |
| T63V, G66D | M32L, M50D, N52S, M88Q | 263.7 | 1.57E+06. | 4.30E−04 | 2.74E−10 | 59 | 0.0516 |
| T63G, G66D | M32L, M50D, N52S, M88Q | 136.6 | 1.73E+06 | 4.50E−04 | 2.61E−10 | 29.8 | 0.11 |
| T63K, G66D | M32L, M50D, N52S, M88Q | 626.9 | 2.15E+06 | 5.29E−04 | 2.46E−10 | 140.5 | 0.233 |
| T63W, G66D | M32L, M50D, N52S, M88Q | 153.7 | 1.57E+06 | 4.49E−04 | 2.86E−10 | 34.1 | 0.051 |
| T63Q, G66D | M32L, M50D, N52S, M88Q | 435.4 | 1.78E+06 | 4.61E−04 | 2.59E−10 | 96.6 | 0.164 |
| T63R, G66D | M32L, M50D, N52S, M88Q | 391.6 | 1.92E+06 | 5.26E−04 | 2.73E−10 | 88.7 | 0.184 |
| T63L, G66D | M32L, M50D, N52S, M88Q | 473.4 | 1.60E+06 | 4.54E−04 | 2.83E−10 | 105.1 | 0.0607 |
| T63D, G66D | M32L, M50D, N52S, M88Q | 294.9 | 1.66E+06 | 4.13E−04 | 2.49E−10 | 6.76E+01 | 0.0916 |
| T63A, G66D | M32L, M50D, N52S, M88Q | 415.5 | 1.70E+06 | 4.58E−04 | 2.68E−10 | 9.23E+01 | 0.155 |
| T63Y, G66D | M32L, M50D, N52S, M88Q | 198.4 | 1.91E+06 | 4.59E−04 | 2.41E−10 | 4.75E+01 | 0.266 |
| T63F, G66D | M32L, M50D, N52S, M88Q | 152,7 | 1.67E+06 | 4.59E−04 | 2.74E−10 | 3.53E+01 | 0.194 |
| T63P, G66D | M32L, M50D, N52S, M88Q | 144.9 | 1.70E+06 | 4.19E−04 | 2.46E−10 | 3.14E+01 | 0.257 |
| T65K, G66D | M32L, M50D, N52S, M88Q | 1236.8 | 1.63E+06 | 5.79E−04 | 3.56E−10 | 261 | 0.301 |
| T65D, G66D | M32L, M50D, N52S, M88Q | 391.9 | 1.03E+06 | 4.80E−04 | 4.65E−10 | 86.4 | 0.137 |
| T65L, G66D | M32L, M50D, N52S, M88Q | 490.4 | 1.53E+06 | 4.46E−04 | 2.93E−10 | 109.5 | 0.0578 |
| T65W, G66D | M32L, M50D, NS2S, M88Q | 324.9 | 1.19E+06 | 3.84E−04 | 3.22E−10 | 67.8 | 0.0812 |
| T65Q, G66D | M32L, M50D, N52S, M88Q | 631.4 | 2.186+06 | 5.62E−04 | 2.58E−10 | 144.7 | 0.191 |
| 165E, G66D | M32L, M50D, N52S, M88Q | 538.6 | 1.70E+06 | 4.74E−04 | 2.79E−10 | 118.8 | 0.268 |
| T65V, G66D | M32L, M50D, N52S, M88Q | 537.7 | 1.96E+06 | 5.51E−04 | 2.81E−10 | 118.6 | 0.303 |
| T65S, G66D | M32L, M50D, N52S, M88Q | 563.8 | 1.42E+06 | 4.416-04 | 3.10E−10 | 123.7 | 0.216 |
| T65Y, G66D | M32L, M50D, N52S, M88Q | 313.4 | 1.55E+06 | 3.67E−04 | 2.37E−10 | 16.5 | 0.54 |
| T65P, G66D | M32L, M50D, N52S, M88Q | 16.3 | 1.79E+06 | 1.08E−03 | 6.01E−10 | 4.7 | 0.673 |
| T65A, G66D | M32L, M50D, N52S, M88Q | 677.3 | 2.27E+06 | 5.42E−04 | 2.39E−10 | 1.51E+02 | 0.863 |
| T65H, G66D | M32L, M50D, N52S, M88Q | 385.7 | 1.43E+06 | 4.23E−04 | 2.97E−10 | 8.58E+01 | 0.0507 |
| T65R, G66D | M32L, M50D, N52S, M88Q | 986.3 | 1.63E+06 | 5.32E−04 | 3.27E−10 | 2.10E+02 | 0.321 |
| T65G, G66D | M32L, M50D, N52S, M88Q | 311.9 | 1.53E+06 | 4.77E−04 | 3.11E−10 | 7.20E+01 | 0.111 |
| T65F, G66D | M32L, M50D, N52S, M88Q | 300.9 | 1.34E+06 | 3.91E−04 | 2.91E−10 | 6.65E+01 | 0.131 |

TABLE 31-continued

Biacore Kinetics for Anti-IL-6 Heavy Chain Double Mutants with Mutagenized Light Chain

| Heavy chain - mutatior | Purified/37° C. | | | | | |
|---|---|---|---|---|---|---|
| | Capture (RU) | ka (1/Ms) | kd (1/s) | KD (M) | Rmax (RU) | Chi$^2$ (RU$^2$) |
| WT | 100.8 | 1.1ZE+06 | 3.19E−04 | 2.86E−10 | 19.5 | 0.133 |
| G66D | 72.2 | 1.69E+06 | 4.12E−04 | 2.44E−10 | 16.2 | 0.137 |
| S35H, G66D | 83.4 | 1.20E+06 | 2.54E−04 | 2.12E−10 | 17.6 | 0.151 |
| S35G, G66D | | | | | | |
| S35R, G66D | | | | | | |
| S35Y, G66D | | | | | | |
| S35P, G66D | | | | | | |
| S35W, G66D | | | | | | |
| S35I, G66D | | | | | | |
| S35V, G66D | | | | | | |
| 535A, G66D | | | | | | |
| S35D, G66D | | | | | | |
| S3SL, G66D | | | | | | |
| S35T, G66D | | | | | | |
| S35K, G66D | | | | | | |
| S35E, G66D | | | | | | |
| S35F, G66D | | | | | | |
| S35Q, G66D | | | | | | |
| I51R, G66D | | | | | | |
| I51V, G66D | | | | | | |
| IS1W, G66D | | | | | | |
| I51Y, G66D | | | | | | |
| I51S, G66D | | | | | | |
| I5IA, G66D | | | | | | |
| I51E, G66D | | | | | | |
| I51T, G66D | | | | | | |
| I51D, G66D | | | | | | |
| I51F, G66D | | | | | | |
| I51L, G66D | | | | | | |
| I51K, G66D | | | | | | |
| I51P, G66D | | | | | | |
| I51H, G66D | | | | | | |
| I51Q, G66D | | | | | | |
| I51G, G66D | | | | | | |
| T63S, G66D | | | | | | |
| T63I, G66D | | | | | | |
| T63H, G66D | | | | | | |
| T63E, G66D | 63.5 | 1.65E+06 | 3.27E−04 | 1.98E−10 | 14.2 | 0.154 |
| T63V, G66D | | | | | | |
| T63G, G66D | | | | | | |
| T63K, G66D | 63.5 | 1.59E+06 | 4.01E−04 | 2.526-10 | 14.4 | 0.165 |
| T63W, G66D | | | | | | |
| T63Q, G66D | 61.9 | 1.69E+06 | 3.41E−04 | 2.01E−10 | 14.1 | 0.108 |
| T63R, G66D | | | | | | |
| T63L, G66D | | | | | | |
| T63D, G66D | | | | | | |
| T63A, G66D | | | | | | |
| T63Y, G66D | | | | | | |
| T63F, G66D | | | | | | |
| T63P, G66D | | | | | | |
| T65K, G66D | | | | | | |
| T65D, G66D | | | | | | |
| T65L, G66D | | | | | | |
| T65W, G66D | | | | | | |
| T65Q, G66D | 80.2 | 1.82E+06 | 3.80E−04 | 2.09E−10 | 17.1 | 0.144 |
| 165E, G66D | | | | | | |
| T65V, G66D | | | | | | |
| T65S, G66D | | | | | | |
| T65Y, G66D | | | | | | |
| T65P, G66D | | | | | | |
| T65A, G66D | | | | | | |
| T65H, G66D | | | | | | |
| T65R, G66D | | | | | | |
| T65G, G66D | | | | | | |
| T65F, G66D | | | | | | |

TABLE 32

Biacore Kinetics for Anti-IL-6 Heavy Chain Triple mutants

| Heavy chain - mutation Light | Light chain - mutation | Sup/37° C. | | | | | |
|---|---|---|---|---|---|---|---|
| | | Capture (RU) | ka (1/Ms) | kd (1/s) | KD (M) | Rmax (RU | Chi$^2$ (RU$^2$) |
| WT | WT | 292.6 | 8.61E+05 | 5.59E−04 | 6.49E−10 | 60.7 | 0.141 |
| G66D | WT | 459.6 | 1.62E+06 | 4.80E−04 | 2.96E−10 | 98.7 | 0.176 |
| S35H, G66D | WT | 583.7 | 1.46E+06 | 5.48E−04 | 3.74E−10 | 118.3 | 0.212 |
| S35H, G66D, Q99V | WT | 233.5 | 8.98E+05 | 4.31E−03 | 4.80E−09 | 45.6 | 0.469 |
| S35H, G66D, Q99L | WT | 15.5 | 1.07E+06. | 2.62E−04 | 2.44E−10 | 3.9 | 0.101 |
| S35H, G66D, Q99F | WT | 17.9 | 4.89E+05 | 1.66E−03 | 3.39E−09 | 1.8 | 0.166 |
| S35H, G66D, Q99S | WT | 462.8 | 3.96E+06 | 2.57E−02 | 6.48E−09 | 69.4 | 0.905 |
| S35H, G66D, Q99E | WT | 456.3 | 4.93E+05 | 1.93E−03 | 3.91E−09 | 91.6 | 9.97 |
| S35H, G66D, Q99R | WT | 391.4 | 1.41E+05 | 1.61E−03 | 1.14E−08 | 49.5 | 0.331 |
| S35H, G66D, Q99H | WT | 237.2 | 8.02E+05 | 1.36E−03 | 1.70E−09 | 45 | 0.423 |
| S35H, G66D, Q99G | WT | 862.2 | 3.43E+06 | 3.30E−03 | 9.61E−10 | 190.1 | 0.879 |
| S35H, G66D, Q99I | WT | 56.9 | 8.68E+05 | 3.35E−03 | 3.86E−09 | 5.4 | 0.417 |
| S35H, G66D, Q99D | WT | 778 | 1.29E+06 | 3.02E−03 | 2.34E−09 | 128.6 | 0.815 |
| S35H, G66D, Q99A | WT | 328.3 | 1.85E+06 | 1.32E−03 | 7.17E−10 | 57 | 0.36 |
| S35H, G66D, Q99K | WT | 142.5 | 2.20E+05 | 3.33E−03 | 1.51E−08 | 21.8 | 0.719 |
| S35H, G66D, Q99Y | WT | 112.3 | 2.60E+06 | 2.15E−03 | 8.25E−10 | 12.6 | 0.191 |
| S35H, G66D, Q99T | WT | 845.8 | 1.69E+06 | 2.22E−03 | 1.31E−09 | 165.8 | 0.625 |
| S35H, G66D, L100I | WT | 525.4 | 9.31E+05 | 6.44E−04 | 6.92E−10 | 94.2 | 0.134 |
| S35H, G66D, L100Y | WT | 529.9 | 1.01E+06 | 6.42E−04 | 6.38E−10 | 101.3 | 0.0737 |
| S35H, G66D, L100H | WT | 523.5 | 7.23E+05 | 4.98E−04 | 6.88E−10 | 109.5 | 0.207 |
| S35H, G66D, L100R | WT | 562 | 9.51E+05 | 9.57E−04 | 1.01E−09 | 101.6 | 0.518 |
| S35H, G66D, L100E | WT | 438.7 | 1.13E+06 | 8.69E−04 | 7.66E−10 | 82.4 | 0.276 |
| S35H, G66D, L100O | WT | 510.6 | 1.79E+06 | 7.99E−04 | 4.47E−10 | 102.4 | 0.426 |
| S35H, G66D, L100A | WT | 870.7 | 4.52E+06 | 8.33E−04 | 1.84E−10 | 185.5 | 0.757 |
| S35H, G66D, L100S | WT | 970.4 | 3.28E+06 | 6.44E−04 | 1.96E−10 | 194.3 | 0.635 |
| S35H, G66D, L100G | WT | 1113.1 | 3.20E+06. | 9.60E−04 | 3.00E−10 | 228.6 | 0.655 |
| S35H, G66D, L100T | WT | 820.2 | 3.34E+06 | 7.24E−04 | 2.17E−10 | 168.7 | 0.635 |
| S35H, G66D, l100V | WT | 826.9 | 2.37E+06 | 5.79E−04 | 2.44E−10 | 151.4 | 0.515 |
| S35H, G66D, L100Q | WT | 903.7 | 3.56E+06 | 6.40E−04 | 1.80E−10 | 181.4 | 0.88 |
| S35H, G66D, L100K | WT | 882.8 | 5.88E+06 | 1.06E−03 | 1.80E−10 | 174.7 | 3.31 |
| S35H, G66D, L100F | WT | 1002.3 | 2.51E+06 | 6.12E−04 | 2.44E−10 | 194.6 | 0.752 |
| | Heavy chain - mutation Light | Purified/37° C. | | | | | |
| | | Capture (RU) | ka (1/Ms) | kd (1/s) | KD (M) | Rmax (RU) | Chi$^2$ (RU$^2$) |
| | WT | 71.1 | 6.15E+05 | 1.32E−04 | 2.14E−10 | 11.6 | 0.137 |
| | G66D | | | | | | |
| | S35H, G66D | | | | | | |
| | S35H, G66D, Q99V | | | | | | |
| | S35H, G66D, Q99L | | | | | | |
| | S35H, G66D, Q99F | | | | | | |
| | S35H, G66D, Q99S | | | | | | |
| | S35H, G66D, Q99E | | | | | | |
| | S35H, G66D, Q99R | | | | | | |
| | S35H, G66D, Q99H | | | | | | |
| | S35H, G66D, Q99G | | | | | | |
| | S35H, G66D, Q99I | | | | | | |
| | S35H, G66D, Q99D | | | | | | |
| | S35H, G66D, Q99A | | | | | | |
| | S35H, G66D, Q99K | | | | | | |
| | S35H, G66D, Q99Y | | | | | | |
| | S35H, G66D, Q99T | | | | | | |
| | S35H, G66D, L100I | | | | | | |
| | S35H, G66D, L100Y | | | | | | |
| | S35H, G66D, L100H | | | | | | |
| | S35H, G66D, L100R | | | | | | |
| | S35H, G66D, L100E | | | | | | |
| | S35H, G66D, L100O | | | | | | |
| | S35H, G66D, L100A | | | | | | |
| | S35H, G66D, L100S | | | | | | |
| | S35H, G66D, L100G | | | | | | |
| | S35H, G66D, L100T | | | | | | |
| | S35H, G66D, l100V | | | | | | |
| | S35H, G66D, L100Q | | | | | | |
| | S35H, G66D, L100K | | | | | | |
| | S35H, G66D, L100F | | | | | | |

TABLE 33

Biacore Kinetics for Anti-IL-6 Heavy Chain Triple Mutants Paired with Mutagenized Light Chain

| Heavy chain - mutation | Light chain - mutation | Sup/37° C. | | | | | |
|---|---|---|---|---|---|---|---|
| | | Capture (RU) | ka (1/Ms) | kd (1/s) | KD (M) | Rmax (RU) | Chi$^2$ (RU$^2$) |
| WT | M32L, M50D, N52S, M88Q | 239.2 | 9.20E+05 | 6.31E−04 | 6.86E−10 | 48.3 | 0.259 |
| G66D | M32L, M50D, N52S, M88Q | 149.1 | 1.66E+06 | 6.546-04 | 3.93E−10 | 32.2 | 0.401 |
| S35H, G66D | M32L, M50D, N52S, M88Q | 644 | 1.50E+06 | 6.07E−04 | 4.03E−10 | 128.2 | 0.329 |
| S3SH, G66D, Q99P | M32L, M50D, N52S, M88Q | 421.1 | 1.25E+06 | 1.69E−03 | 1.35E−09 | 81.4 | 0.893 |
| S35H, G66D, Q99V | M32L, M50D, N52S, M88Q | 9.7 | 7.94E+05 | 1.40E−03 | 1.76E−09 | 1.3 | 0.108 |
| S35H, G66D, Q99L | M32L, M50D, N52S, M88Q | 6.1 | 1.30E+06 | 7.75E−04 | 5.95E−10 | 1 | 0.19 |
| S35H, G66D, Q99F | M32L, M50D, N52S, M88Q | 56.4 | 1.14E+06 | 1.13E−04 | 9.97E−11 | 0.5 | 0.36 |
| S35H, G66D, Q99S | M32L, M50D, N52S, M88Q | 599.7 | 2.01E+05 | 1.546-03 | 7.66E−09 | 85.4 | 3 |
| S35H, G66D, Q99E | M32L, M50D, N52S, M88Q | 609.4 | 1.89E+05 | 8.90E−04 | 4.71E−09 | 148.2 | 0.726 |
| S35H, G66D, Q99W | M32L, M50D, N52S, M88Q | 5.6 | 1.12E+11 | 3.20E−03 | 2.85E−14 | 0.4 | 0.627 |
| S35H, G66D, Q99R | M32L, M50D, N52S, M88Q | 39.1 | 2.80E+05 | 6.57E−04 | 2.34E−09 | 1 | 0.094 |
| S35H, G66D, Q99H | M32L, M50D, N52S, M88Q | 31 | 7.98E+05 | 4.41E−03 | 5.52E−09 | 5.2 | 0.207 |
| S35H, G66D, Q99G | M32L, M50D, N52S, M88Q | 790.1 | 3.00E+06 | 7.74E−03 | 2.58E−09 | 174.8 | 1.22 |
| S35H, G66D, Q99I | M32L, M50D, N52S, M88Q | −1.8 | 5.416E+06 | 2.06E−04 | 3.81E−11 | 0.4 | 0.361 |
| S35H, G66D, Q99D | M32L, M50D, N52S, M88Q | 399.6 | 2.57E+10 | 9.26E+01 | 3.61E−09 | 50.8 | 2.88 |
| S35H, G66D, Q99A | M32L, M50D, N52S, M88Q | 574.6 | 1.47E+06 | 4.50E−03 | 3.07E−09 | 116.1 | 0.343 |
| S35H, G66D, Q99K | M32L, M50D, N52S, M88Q | 11.3 | 3.97E+06 | 1.46E−03 | 3.68E−10 | 0.4 | 0.111 |
| S35H, G66D, Q99Y | M32L, M50D, N52S, M88Q | 66.3 | 2.17E+06 | 5.47E−03 | 2.51E−09 | 4.5 | 0.0663 |
| S35H, G66D, Q99T | M32L, M50D, N52S, M88Q | 854.1 | 7.52E+06 | 4.90E−02 | 6.51E−09 | 152.2 | 4.72 |
| S35H, G66D, L100P | M32L, M50D, N52S, M88Q | 564.1 | 7.59€+05 | 3.54E−03 | 4.66E−09 | 100.6 | 14 |
| S35H, G66D, L100I | M32L, M50D, N52S, M88Q | 557.6 | 1.91E+06 | 7.12E−04 | 3.72E−10 | 108 | 0.361 |
| S35H, G66D, L100Y | M32L, M50D, N52S, M88Q | 491.9 | 8.58E+05 | 8.01E−04 | 9.34E−10 | 91.4 | 0.104 |
| S35H, G66D, L100H | M32L, M50D, N52S, M88Q | 618.7 | 1.55E+06 | 1.29E−03 | 8.30E−10 | 132.4 | 0.381 |
| S35H, G66D, L100W | M32L, M50D, N52S, M88Q | 456.4 | 6.25E+05 | 1.24E−03 | 1.98E−09 | 81.8 | 0.525 |
| S35H, G66D, L100R | M32L, M50D, N52S, M88Q | 732.6 | 1.32E+06 | 1.16E−03 | 8.78E−10 | 136.9 | 0.0885 |
| S35H, G66D, L100E | M32L, M50D, N52S, M88Q | 563.5 | 2.05E+06 | 1.45E−03 | 7.04E−10 | 112.8 | 0.197 |
| S35H, G66D, L100D | M32L, M50D, N52S, M88Q | 454.2 | 5.77E+06. | 2.02E−03 | 3.50E−10 | 97.1 | 0.22 |
| S35H, G66D, L100A | M32L, M50D, N52S, M88Q | 1033.5 | 5.82E+07 | 4.86E−03 | 8.34E−11 | 226.9 | 2.56 |
| S35H, G66D, L100S | M32L, M50D, N52S, M88Q | 1088.2 | 8.03E+06 | 9.13E−04 | 1.14E−10 | 229.1 | 1.17 |
| S35H, G66D, L100G | M32L, M50D, N52S, M88Q | 1193.9 | 6.87E+06 | 1.60E−03 | 2.33E−10 | 253.1 | 1.37 |
| S35H, G66D, L100T | M32L, M50D, N52S, M88Q | 939.8 | 1.36E+07 | 2.78E−03 | 2.04E−10 | 202.7 | 2.13 |
| S35H, G66D, L100V | M32L, M50D, N52S, M88Q | 985.4 | 5.01E+06 | 9.22E−04 | 1.84E−10 | 201 | 0.741 |
| S35H, G66D, L100Q | M32L, M50D, N52S, M88Q | 1087.6 | 4,97E+06 | 7.34E−04 | 1.48E−10 | 229.9 | 0.807 |
| S35H, G66D, L100K | M32L, M50D, N52S, M88Q | 1132.4 | 4.29E+06 | 8.22E−04 | 1.91E−10 | 233.6 | 1.71 |
| S35H, G66D, L100F | M32L, M50D, N52S, M88Q | 877.1 | 1.46E+06 | 6.14E−04 | 4.22E−10 | 168.2 | 0.231 |

| Heavy chain - mutation | Purified/37° C. | | | | | |
|---|---|---|---|---|---|---|
| | Capture (RU) | ka (1/Ms) | kd (1/s) | KD (M) | Rmax (RU) | Chi$^2$ (RU$^2$) |
| WT | | | | | | |
| G66D | | | | | | |
| S35H, G66D | 68.7 | 1.22E+06 | 2.38E−04 | 1.95E−10 | 12 | 0.172 |
| S3SH, G66D, Q99P | | | | | | |
| S35H, G66D, Q99V | | | | | | |
| S35H, G66D, Q99L | | | | | | |
| S35H, G66D, Q99F | | | | | | |
| S35H, G66D, Q99S | | | | | | |
| S35H, G66D, Q99E | | | | | | |
| S35H, G66D, Q99W | | | | | | |
| S35H, G66D, Q99R | | | | | | |
| S35H, G66D, Q99H | | | | | | |
| S35H, G66D, Q99G | | | | | | |
| S35H, G66D, Q99I | | | | | | |
| S35H, G66D, Q99D | | | | | | |
| S35H, G66D, Q99A | | | | | | |
| S35H, G66D, Q99K | | | | | | |
| S35H, G66D, Q99Y | | | | | | |
| S35H, G66D, Q99T | | | | | | |
| S35H, G66D, L100P | | | | | | |
| S35H, G66D, L100I | | | | | | |
| S35H, G66D, L100Y | | | | | | |
| S35H, G66D, L100H | | | | | | |
| S35H, G66D, L100W | | | | | | |
| S35H, G66D, L100R | | | | | | |
| S35H, G66D, L100E | | | | | | |
| S35H, G66D, L100D | | | | | | |
| S35H, G66D, L100A | 60.7 | 3.72E+06 | 4.06E−04 | 1.09E−10 | 11.3 | 0.139 |
| S35H, G66D, L100S | 86.7 | 3.61E+06 | 4.24E−04 | 1.17E−10 | 15.2 | 0.16 |
| S35H, G66D, L100G | 63.2 | 2.76E+06 | 6.94E−04 | 2.51E−10 | 12.6 | 0.153 |
| S35H, G66D, L100T | 62.1 | 1.83E+06 | 4.81E−04 | 2.63E−10 | 11.2 | 0.14 |
| S35H, G66D, L100V | 86.5 | 1.62E+06 | 3.85E−04 | 2.38E−10 | 14.2 | 0.16 |

TABLE 33-continued

Biacore Kinetics for Anti-IL-6 Heavy Chain Triple Mutants Paired with Mutagenized Light Chain

| | | | | | | |
|---|---|---|---|---|---|---|
| S35H, G66D, L100Q | 66.8 | 2.26E+06 | 3.36E-04 | 1.49E-10 | 12.9 | 0.152 |
| S35H, G66D, L100K | 88.8 | 1.49E+06 | 2.79E-04 | 1.88E-10 | 15.1 | 0.165 |
| S35H, G66D, L100F | | | | | | |

Binding kinetics of these mutant molecules to IL-6 were measured at 37° C. using a Biacore T200. Antibodies were captured on a Protein A chip (GE) by injecting 1:20 cell supernatant dilutions at 10 µL/min for 60 seconds. Five concentrations (0.56, 1.67, 5, 15 and 45 nM) of IL-6 were flowed over captured antibodies for 60 seconds at a flow rate of 30 µL/min and dissociated for 180 seconds in a single cycle kinetics Biacore assay format. The sensor chip was regenerated by a 60 seconds injection of 10 mM Glycine pH 1.7 at the flow rate of 50 µL/min. A similar assay setup was used to monitor interactions between purified antibody samples and IL-6 at 37° C., when applicable. For this setup, 1 µg/mL of purified antibody was injected over a Protein A chip at 10 L/min for 25 seconds. Five concentrations (0.56, 1.67, 5, 15 and 45 nM) of IL-6 were flowed over captured antibodies for 60 seconds at the flow rate of 30 L/min and dissociated for 1800 seconds in a single cycle kinetics Biacore assay format. The sensor chip was regenerated by a 60 seconds injection of 10 mM Glycine pH 1.7 at flow rate of 50 L/min. Data analysis for supernatant and purified samples were performed using BIAevaluation software (GE). All sensorgrams were double reference subtracted and fit using a 1:1 Langmuir binding model.

As shown by Tables 30 and 31, S35H G66D double mutant heavy chain presented a boost on protein expression, as indicated by the approximate two-fold increase in the capture level relative to the wild-type heavy chain. This mutant also presented a small increase in affinity depending on the paired light chain (wild-type: ~2 fold, M32L/M50D/N52S/M88Q: ~1.3 fold). Table 30 illustrates G66D optimization of LC wild type Biacore kinetics for Anti-IL-6 heavy chain double mutants. Data were obtained for samples prior (sup) and after purification, both at 37° C. Table 31 illustrates G66D optimization of LC mutant Biacore kinetics for Anti-IL-6 heavy chain double mutants paired with mutagenized light chain. Data were obtained for samples prior (sup) and after purification both at 37° C.

Therefore, this double mutant was selected as a starting point for another round where substitution-tolerant positions Q99 and L100 at CDR3 were randomly mutagenized, expressed, and evaluated for IL-6 binding as described for the G66D screening round. As shown in Tables 32 and 33, L100 substitutions for Ala, Ser, Gly, Thr, Gln, Lys presented superior expression when compared to wild-type as indicated by the capture levels. These mutants were therefore selected for purification and IL-6 binding evaluation. Affinity measurements with the purified material also showed superior IL-6 binding, as illustrated in Tables 32 and 33. Based on these results, these additional modified CDRs, as illustrated in FIG. 18, were incorporated into the design of the anti-IL-6 and anti-VEGF dual inhibitor molecules.

Table 32 illustrates G66D/S35H heavy chain modification paired with LC wild-type Biacore kinetics for Anti-IL-6 heavy chain triple mutants. Data were obtained for samples prior (sup) and after purification, both at 37° C. Table 33 illustrates G66D/S35H heavy chain modification paired with LC mutant Biacore kinetics for Anti-IL-6 heavy chain triple mutants paired with mutagenized light chain. Data were obtained for samples prior (sup) and after purification, both at 37° C.

Example 19—Anti-IL-6 Anti-VEGF Dual Inhibitor Variants

Based on the results with the VEGF trap variants and superior anti-IL-6 paratopes, 216 molecules in two different configurations were designed that were comprised of combinations of sequences as displayed in FIGS. 19, 20, 21, 22 and 23. For the first configuration (VEGFR-Anti-IL-6) the VEGF trap, as shown by sequences 1A-1D of FIG. 19 is positioned at the beginning of the protein, followed by a double repeat of a Gly-Gly-Gly-Gly-Ser linker (GS), as shown by sequence 2A of FIG. 20, which connects the trap to the N-terminus of the anti-IL-6 heavy chain, as shown by sequences 3A-3I of FIG. 21. These constructs can be paired with light chains listed as sequences 4A-4C of FIG. 22. In the second configuration (Anti-IL-6-VEGFR), the variable and constant domains of the heavy chain, illustrated by Heavy chain—Fab, sequences 5A-5I of FIG. 23, are connected to the VEGF trap, illustrated by sequences 1A-1D of FIG. 19, via the GS linker, illustrated by sequence 2A of FIG. 20, and then the Fc domain, illustrated by Heavy chain—Fc, sequences 5A-5I of FIG. 23, is fused to the C-terminal end of the VEGF trap. Thus, the VEGF trap is sandwiched between the antibody Fab and Fc regions.

FIG. 19 illustrates VEGF trap sequences. The variation in sequence is underlined and highlighted in bold. FIG. 20 illustrates double repeat Gly-Gly-Gly-Gly-Ser linker (GS) sequence. FIG. 21 illustrates heavy chain sequences for Anti-IL-6 molecules. CDRs are underlined. FIG. 22 illustrates light chain sequences for Anti-IL-6 molecules. CDRs are underlined. FIG. 23 illustrates heavy chain (separated into Fab and Fc) sequences for Anti-IL-6 molecules. CDRs are underlined.

In some embodiments, any of the options of the VEGF trap, wherein it is sandwiched between the antibody Fab and Fc regions, can be paired with light chains listed on sequences 4A-4C of FIG. 22. Thus, in some embodiments, the constructs outlined in FIG. 19 (the VEGFR sequences) can be used for any of the VEGF trap arrangements provided herein, or on their own.

Example 20—Binding Kinetics Between VEGFR-Trap Fc Fusion and VEGF

Anti-IL-6Anti-IL-6FIGS. 26A-26C illustrate the results for Biacore assays used to determine the affinity between Anti-VEGF agents and VEGF. Binding kinetics were measured using a Biacore T200 at 37° C. in buffer HBS-EP+ containing 1 mg/mL BSA. VEGFR-Fc (1 µg/mL) and Eylea (1 µg/mL) were captured on a Protein A chip-(GE) at 10 µL/min for 25 seconds, five concentrations of VEGF-A165 (0.19, 0.56, 1.67, 5, 15 nM) were flowed over captured anti-VEGF molecules for 120 seconds at 30 µL/min and dissociated for 30 min. The sensor chip surface was regenerated by 60 seconds injection of 10 mM Glycine, pH 1.7 at a flow rate of 50 μl/min. All sensorgrams were double reference subtracted and fit using a 1:1 Langmuir binding model. As shown in FIGS. 26A-26C, VEGFR-Fc and Eylea bind with similar affinity to VEGF. In this example, VEGFR-Fc contains sequence 6A.

Example 21—Removing Cleavage Product

As discussed in Example 13, VEGFR-AntiIL6 presents a minor degree of cleavage at the VEGFR1 domain 2 at the VEGF trap region. We developed two orthogonal chromatography methods to separate intact protein from cleaved material after the protein A purification step: i) cation exchange (CEX) and ii) hydrophobic interaction (HIC).

Figure 32:
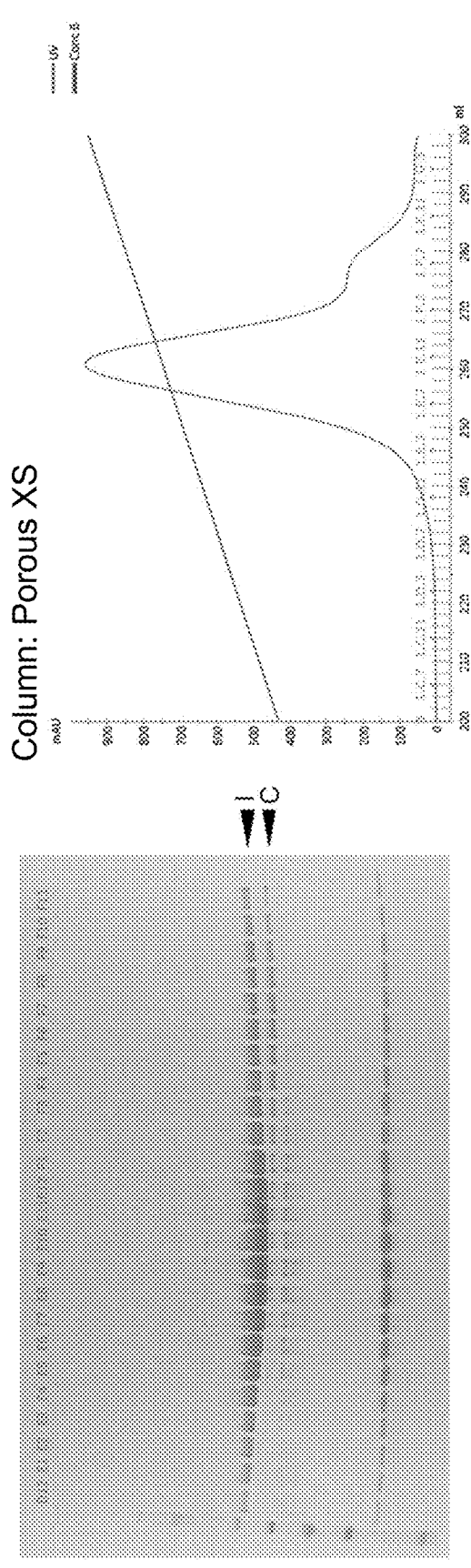
FIG. 32 depicts the results of a VEGFR-AntiIL6 CEX chromatography. Gel: is Novex 8-16% Tris-Glycine (reducing conditions), M=SeeBlue®Plus2 standard Lanes D12-F11 correspond to samples aliquoted at different buffer B concentrations as indicated on chromatogram Intact (I) and cleaved (C) heavy chains are indicated. In Column Porus XS Buffer A is 20 mM Sodium Phosphate pH 6 and buffer B is 20 mM Sodium Phosphate pH 6, 1 M NaCl.

For the CEX method, VEGFR-AntiIL6 protein A eluate pH solution is adjusted to 6, which is then injected into a Porous XS column pre-equilibrated with 20 mM sodium phosphate pH 6. Intact protein eluted at lower ionic strength than cleaved material and is almost entirely separated within a linear gradient of increasing ionic strength (0-1 M sodium chloride) (FIG. 32). Fractions enriched on intact protein were pooled and the overall recovery yield was approximately 57%.

For the HIC method, a mixture of VEGFR-AntiIL6 intact protein enriched with cleaved material was injected into a Butyl HP column pre-equilibrated with 20 mM sodium phosphate pH 6, 500 mM-1 M ammonium sulfate. Intact and cleaved proteins were separated within a linear gradient of decreasing ionic strength (1-0 M ammonium sulfate), where intact protein eluted at lower ionic strength than cleaved material and could be partially or completely separated depending on the fractions pooled (FIG. 33).

Example 22—VEGFR AntiIL6 Affinity to IL6 and VEGF-A Measured by KinExA

The Kinetic Exclusion Assay (KinExA®) 3200 system (Sapidyne Instruments Inc., Boise, ID) was used to measure the equilibrium binding affinity and kinetics between VEGFR-AntiIL6 or VEGFR-AntiIL6-OG1802 (the protein component of which is shown in FIG. 27) and VEGF or IL6 in solution. Azlactone beads coated with VEGF or IL6 were used to capture a fraction of free VEGFR-AntiIL6 or VEGFR-AntiIL6-OG1802 from an equilibrated sample of VEGFR-AntiIL6 or VEGFR-AntiIL6-OG1802 and VEGF or IL6. Captured dual inhibitor molecules were detected with a fluorescent labeled polyclonal anti-human antibody (Alexa 647 Goat, anti-human IgG).

Affinity between dual inhibitor molecules and VEGF were determined from 2-3 titration curves at increasing dual inhibitor concentrations and their corresponding VEGF titrating serial dilutions (indicated in parenthesis) listed as follow: I) VEGFR-AntiIL6: 1 nM (20 nM, 2-fold dilution, 12 dilutions) 3.5 hours incubation; 50 μM (500 μM, 2-fold dilution, 14 dilutions) 2.5 hours incubation; 10 μM (1 nM, 2-fold dilution, 13 dilutions) 23 hours incubation; II) VEGFR-AntiIL6-OG1802: 2 nM (30 nM, 2-fold dilution, 12 dilutions) 45 min incubation; 100 μM (15 nM, 2-fold dilution, 14 dilutions) 6 hours incubation; 7.5 μM (1 nM, 2-fold dilution, 14 dilutions) 48 hours incubation. Similar measurements were performed with IL6 under the following conditions: III) VEGFR-AntiIL6: 1 nM (20 nM, 2-fold dilution, 13 dilutions) 7 hours incubation; 10 μM (1 nM, 2-fold dilution, 13 dilutions) 42 hours incubation; 100 μM (1 nM, 2-fold dilution, 13 dilutions) 2.5 hours incubation; IV) VEGFR-AntiIL6-OG1802: 1 nM (22.5 nM, 2-fold dilution, 13 dilutions) 5.5 hours incubation; 100 μM (22.5 nM, 2-fold dilution, 14 dilutions) 12 hours incubation.

On rates ($k_{on}$, $M^{-1}s^{-1}$) between dual inhibitor molecules and VEGF or IL6 were directly determined from kinetic measurement experiments (1-2 curves for each analyzed pair), while off rates ($k_{off}$, $s^{-1}$) were calculated based on the following equation: $k_{off}=K_d \times k_{on}$. Measurements were conducted on four preparations containing i) 100 pM VEGFR-AntiIL6 and 86.4 pM VEGF, ii) 217 pM VEGFR-AntiIL6-OG1802 and 200 pM VEGF, iii) 100 pM VEGFR-AntiIL6 and 84.3 pM IL6, iv) 1000 pM VEGFR-AntiIL6 and 900 pM IL6.

All measurements were done at 37° C. using 1× PBS running buffer (pH 7.4) and samples prepared in 1×PBS (pH 7.4) with 1 mg/mL BSA. Data analyses were done using KinExA Pro software 4.3.11.

Under the conditions tested, VEGFR-AntiIL6-OG1802 binds to VEGF and IL6 in a comparable manner to VEGFR-AntiIL6 with Kd values of 2.10 pM to VEGFR-AntiIL6 and VEGF, 1.02 pM to VEGFR-AntiIL6-OG1802 and VEGF, 21.10 pM to VEGFR-AntiIL6 and IL6, 12.10 pM to VEGFR-AntiIL6-OG1802 and IL6 (see Tables 34 and 35).

TABLE 34

| | VEGF | |
|---|---|---|
| | VEGFR-AntiIL6 | VEGFR-AntiIL6-OG1802 |
| Kd (pM) | 2.10 | 1.02 |
| 95% confidence interval (pM) | 1.34-2.91 | 0.46-1.80 |
| On Rate ($M^{-1}s^{-1}$) | $4.04 \times 10^7$ | $3.75 \times 10^6$ |
| 95% confidence interval | $3.31 \times 10^7$-$4.92 \times 10^7$ | $2.90 \times 10^6$-$4.90 \times 10^6$ |
| Off Rate ($s^{-1}$) | $8.49 \times 10^{-5}$ | $3.83 \times 10^{-6}$ |

TABLE 35

| | IL-6 | |
|---|---|---|
| | VEGFR-AntiIL6 | VEGFR-AntiIL6-OG1802 |
| Kd (pM) | 21.10 | 12.10 |
| 95% confidence interval (pM) | 14.30-30.80 | 8.47-16.30 |
| On Rate ($M^{-1}s^{-1}$) | $1.15 \times 10^7$ | $8.00 \times 10^6$ |
| 95% confidence interval | $9.57 \times 10^6$-$1.37 \times 10^7$ | $6.44 \times 10^6$-$9.93 \times 10^6$ |
| Off Rate ($s^{-1}$) | $2.42 \times 10^{-4}$ | $9.66 \times 10^{-5}$ |

The measured affinities of VEGFR-AntiIL6 and VEGFR-AntiIL6-OG1802 were within error for both IL6 and VEGF, thus these results demonstrate that the biopolymer does not affect binding of dual inhibitors to its targets.

Example 23—VEGF/VEGFR Competitive ELISA

Figure 34:
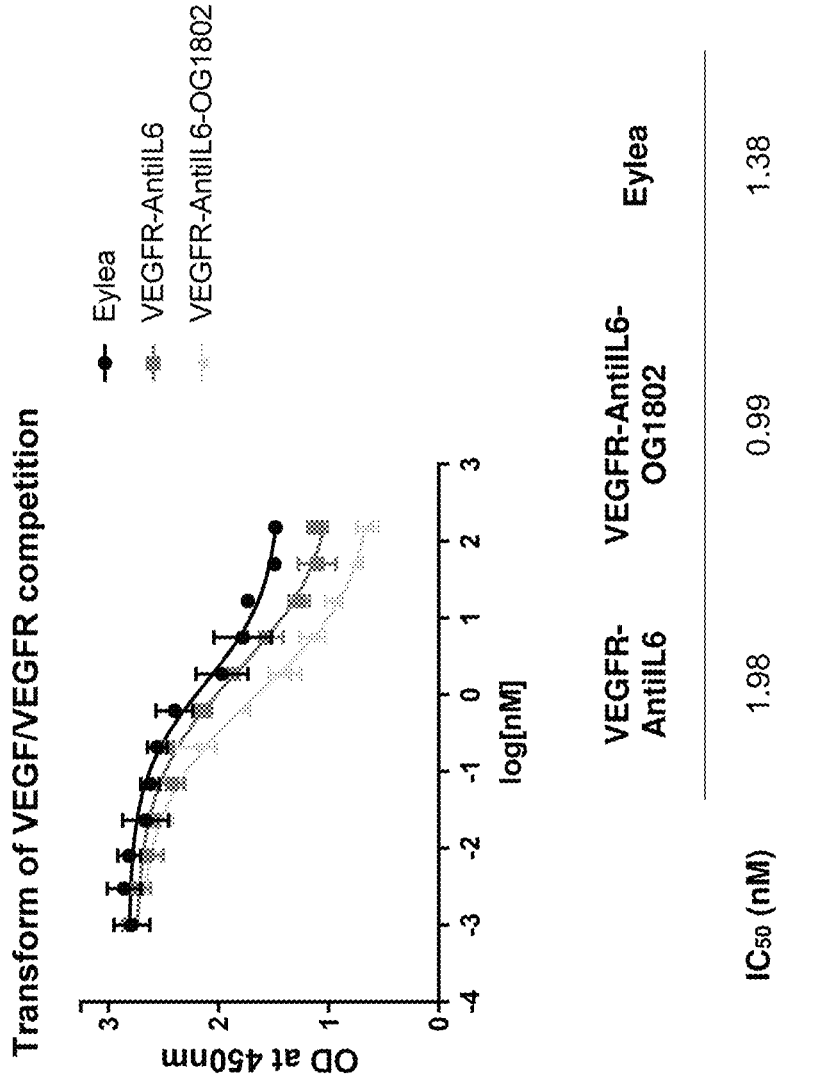
FIG. 34 depicts the results of a VEGF/VEGFR competitive ELISA.

This assay was performed as described in example 3. In this assay, VEGFR-AntiIL6, VEGFR-AntiIL6-OG1802 (as shown in FIG. 27), and Eylea all inhibited VEGF binding to VEGFR in varying degrees (FIG. 34). VEGFR-AntiIL6-OG1802 showed superior inhibition ($IC_{50}$=0.99 nM) when compared to VEGFR-Anti-IL6 ($IC_{50}$=1.98 nM) and Eylea ($IC_{50}$=1.38 nM). Additionally, VEGFR-AntiIL6 showed superior maximal inhibition over Eylea, while VEGFR-AntiIL6-OG1802 had an even more pronounced maximal inhibition (VEGFR-AntiIL6-OG1802=79.5%, VEGFR-Anti-IL6=67.0%, vs. Eylea=49.6%). These data indicate that the addition of the biopolymer OG1802 to VEGFR-AntiIL6 creates additional inhibitory abilities for VEGF binding to VEGFR. The biopolymer therefore adds to the function of the molecule.

Example 24-IL-6/IL-6R Competitive ELISA

This assay was performed as described in example 3.

Figure 35:
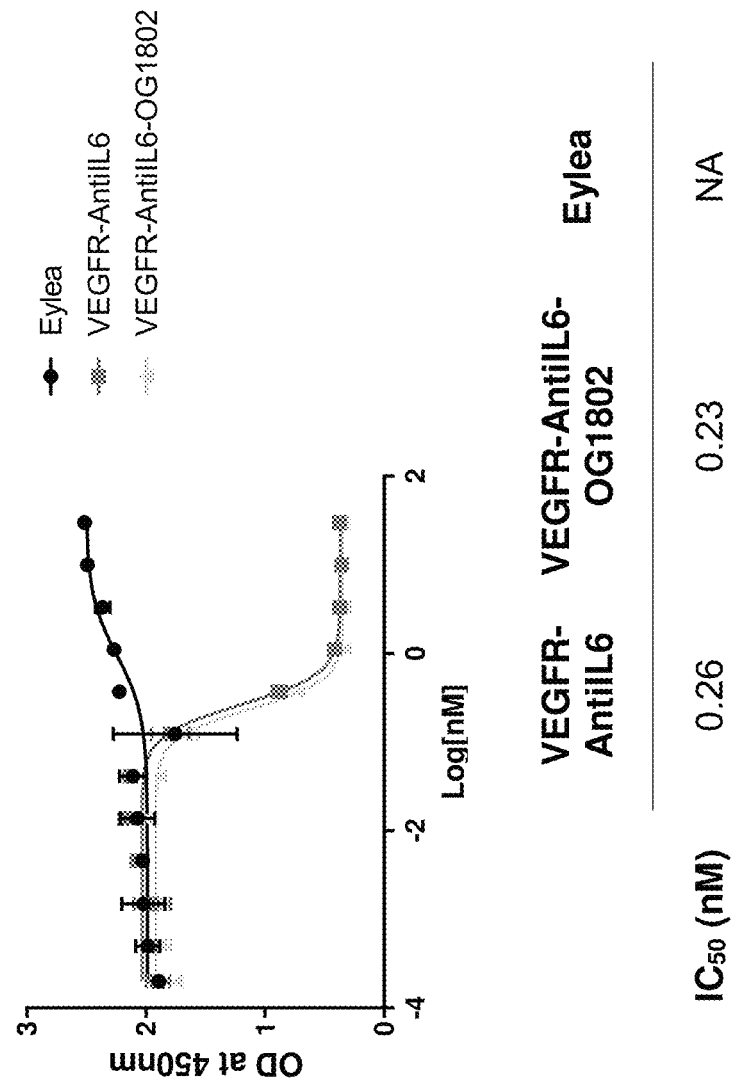
FIG. 35 depicts the results of a IL6/IL6R complex ELISA.

Under these conditions, the VEGFR-AntiIL6-OG1802 effectively blocked the IL-6/IL-6R interaction in a manner comparable to VEGFR-AntiIL6 with $IC_{50}$ values of 0.26 nM for VEGFR-AntiIL6 and 0.23 nM for VEGFR-AntiIL6-OG1802 (FIG. 35). These results indicate that the biopolymer does not alter the inhibitory effects of the dual inhibitor on IL6 binding to its receptor. Eylea served as a negative control.

Example 25—Cell Based VEGF Stimulated VEGFR Reporter Assay

This assay was performed as described in example 15.

Figure 36:
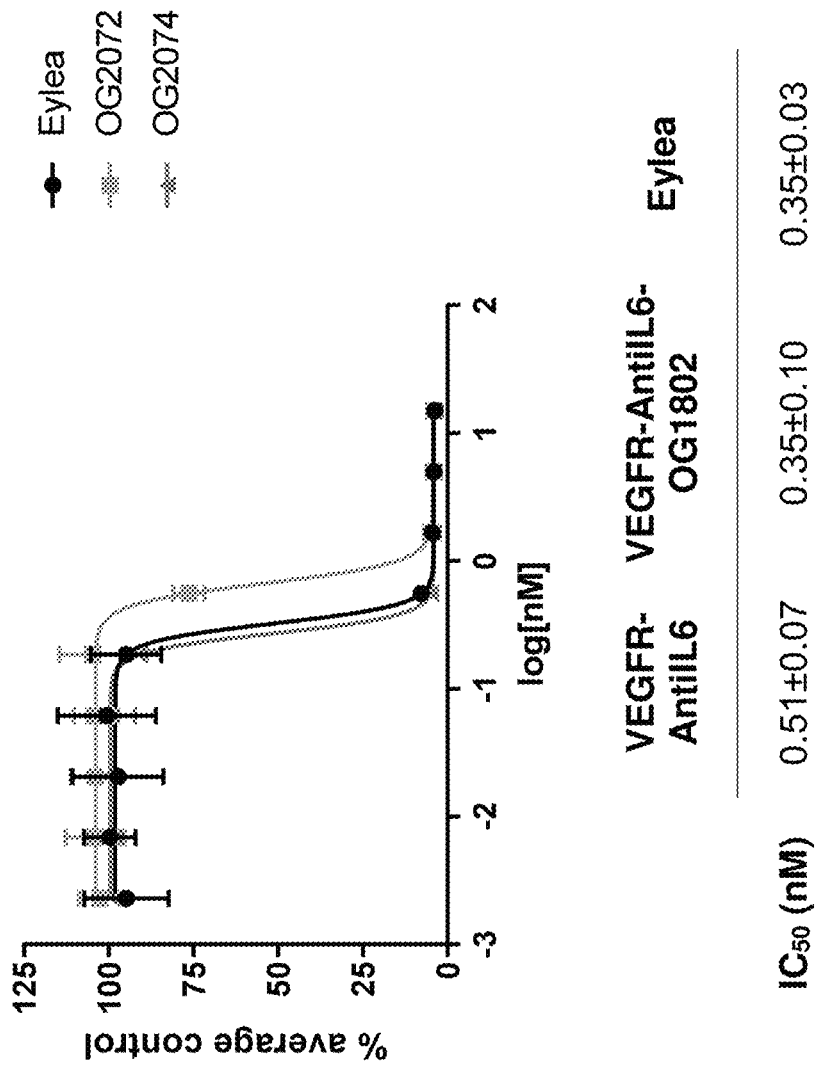
FIG. 36 depicts the results of a cell based VEGF stimulated VEGFR reporter assay.

Under the conditions tested, VEGFR-AntiIL6-OG1802 inhibited VEGF stimulated VEGFR reporter cells in a comparable manner to VEGFR-AntiIL6 and Eylea with average $IC_{50}$ values of 0.35±0.10 nM, 0.51±0.07 nM, and 0.35±0.03 nM, respectively (FIG. 36). There may be a trend that VEGR-AntiIL6-OG1802 (the protein component as shown in FIG. 27) and Eylea are moderately more efficacious than VEGFR-AntiIL6, but this is not a significant finding and falls within the error of the assay. We can conclude form these data that the bioconjugate inhibits VEGFR2 signaling similarly to its protein precursor.

Example 26—Lipopolysaccharide Stimulated Tubule Formation in HUVECs

Passage 2 HUVEC cells were cultured in Vascular Basal Media supplemented with 1× Bovine Brain Extract endothelial cell growth kit (ATCC; growth media) in 5% $CO_2$ at 37 degrees. Once cells reached 70% confluency, cells were lifted from the plate using trypsin (0.05%; ATCC) and 0.75×10^6 cells plated in a T25 flask in growth media.

The next day, media was swapped for Assay Media (2% FBS in Vascular Basal Medium). After 6 hours, 5 µg/ml of Calcein AM was added directly to the media and incubated for 30 minutes at 37 degrees.

At the same time, 200 µls of prethawed Matrigel (growth factor reduced; Corning) was added to each well of a 8-well glass chamber slide and incubated at 37 degrees for 30 minutes.

During incubations, inhibitors (37.5 nM final concentration) were mixed with lipopolysaccharide (LPS; Sigma; 1 ug/ml final concentration).

Following the 30 minute Calcein AM incubation, the cells were washed 3× with PBS and then trypsinized. Harvested cells were centrifuged for 3 minutes at 1,500×g and resuspended in assay medium at a density of 500,000 cells/ml. 150 µls of cells were then mixed with 100 µls of prepared inhibitor/complex solutions, and then transferred to the Matrigel coated chamber slides and incubated overnight.

The next day, tubules were imaged using a 10× objective lens and the GFP filter on a EVOS fluorescence microscope (Life Technologies). At least 2 representative images were taken for each condition and then analyzed using the Angiogenesis Analyzer Plugin for ImageJ (NIH), which evaluates and quantifies 20 tubule network formation parameters.

Statistical significance was determined from all replicates from independent experiments using a unpaired, two-tailed Students t-test.

Figure 37:
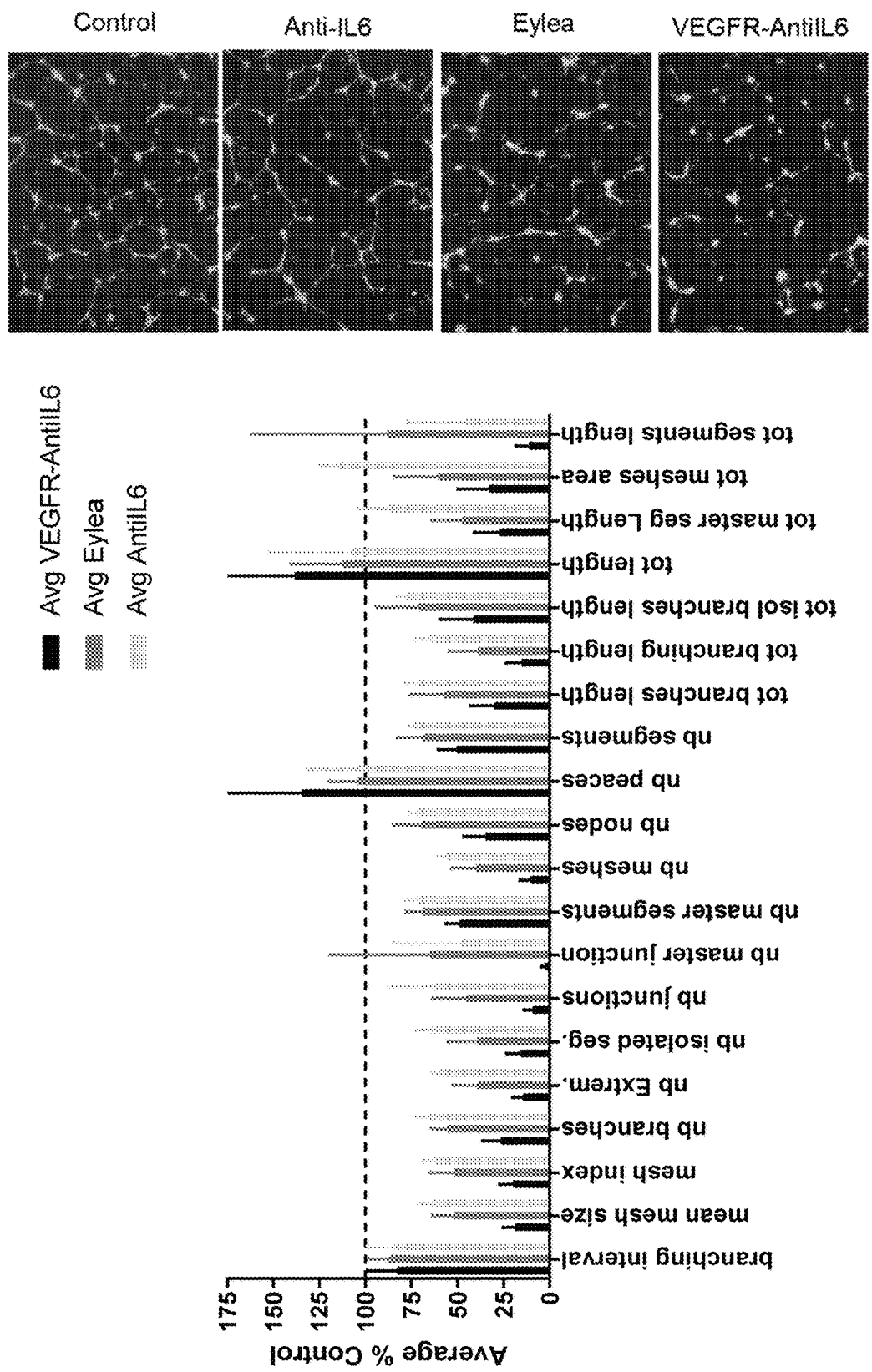
FIG. 37 depicts the lipopolysaccharide stimulated tubule formation in HUVECs.

Under these conditions, VEGFR-AntiIL6 showed statistically significant inhibition of 15/20 measured angiogenic parameters over control, while Eylea significantly inhibited 5/20 and anti-IL6 inhibited 3/20 relative to control treated cells. Altogether, all but one of the parameters that trended or were significantly affected by Eylea or anti-IL6 were significantly inhibited by VEGFR-AntiIL6. Additionally, there were several parameters where VEGFR-AntiIL6 displayed significantly better inhibition over Eylea (7/20) and anti-IL6 (10/20), 3 of which VEGFR-AntiIL6 was significantly better than both Eylea and anti-IL6. (FIG. 37 and FIGS. 38 and 11)

Figure 39:
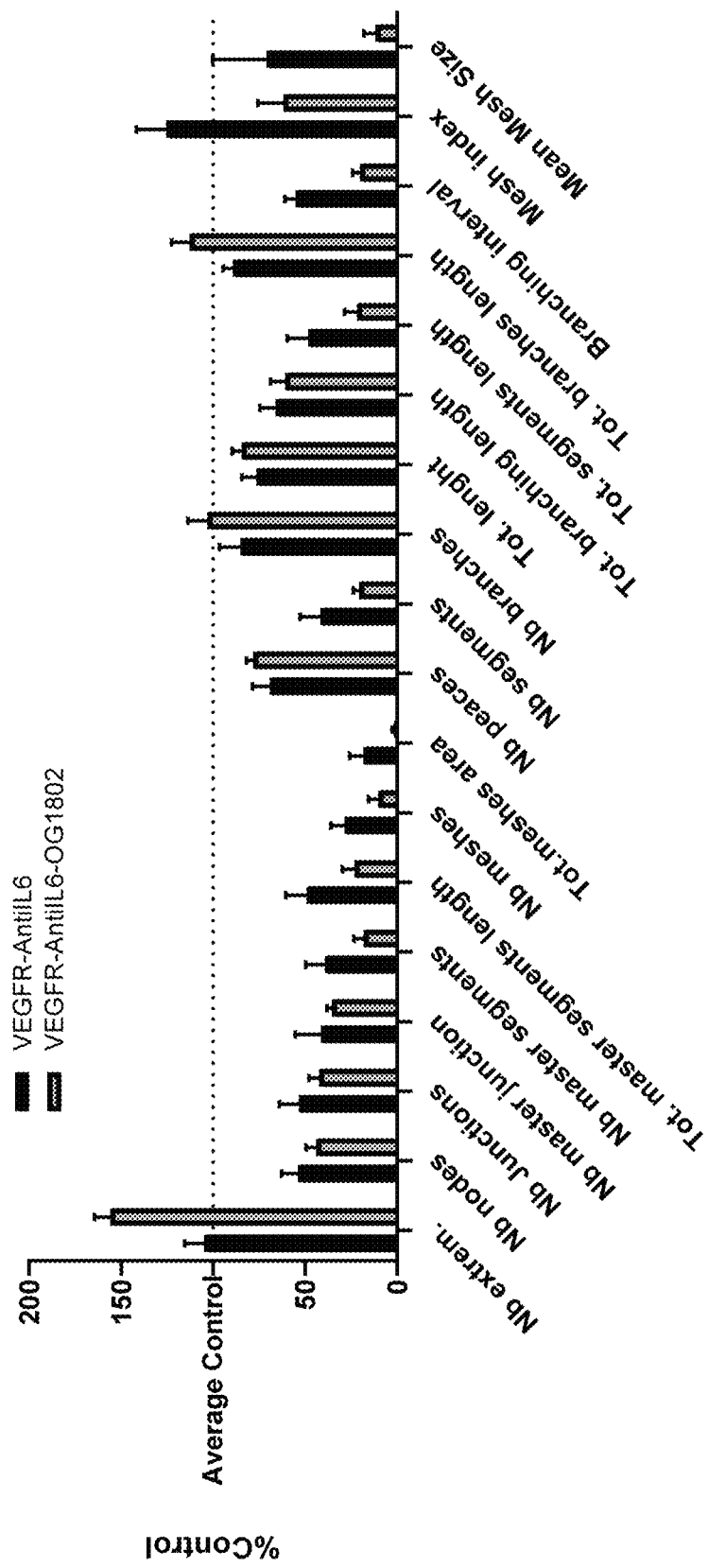
FIG. 39 depicts lipopolysaccharide stimulated tubule formation in HUVECs

VEGFR-AntiIL6-OG1802 effectively inhibited HUVEC tubule formation, and interestingly, VEGFR-AntiIL6-OG1802 showed a trend of increased inhibition in 9/20 parameters over VEGFR-AntiIL6. (FIG. 39). This implies that VEGFR-AntiIL6-OG1802 has added benefit over its unconjugated counterpart.

Example 27—HUVEC Proliferation Assay

This assay was performed as described in example 17.

Under the conditions tested, VEGFR-AntiIL6-OG1802 (the protein component as shown in FIG. 27) inhibited VEGF/IL6 stimulated HUVEC proliferation in a comparable manner to VEGFR-AntiIL6, while Eylea had no effect (FIG. 40A).

Interestingly, VEGFR-AntiIL6-OG1802 showed increased efficacy relative to VEGFR-AntiIL6 when different densities of cells were seeded per well at the beginning of the experiment. As shown in FIG. 40B, at 2,000 cells per well, VEGFR-AntiIL6 and VEGFR-AntiIL6-OG1802 showed nearly identical inhibition of HUVEC proliferation. At 4,000 cells per well, VEGFR-AntiIL6-OG1802 showed slightly better maximal inhibition than VEGFR-AntiIL6 (40% vs. 30%, respectively), and at 6,000 cells per well, VEGFR-AntiIL6-OG1802 inhibited proliferation by 25% relative to control, while VEGFR-AntiIL6 had no effect.

As shown in the examples above, without intending to be limited by theory, it appears that the biopolymer helps deliver its protein counterpart to the surface of the plate and cells. This allows the drug to primarily inhibit the pools of VEGF and IL6 that are most likely to activate cell signaling and avoid being saturated by VEGF and IL6 suspended higher in the fluid phase and less likely to affect cell signaling. As cell numbers increase, this effect would be more pronounced as more drug is needed to act on more cells. Thus, in some embodiments, the conjugate provides a superior product in that it can assist in distribution of the molecule.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

What is claimed is:

1. A protein construct comprising an antagonist IL-6 antibody fused to a VEGF trap, wherein the antibody comprises a heavy chain and a light chain, wherein
   (i) the heavy chain comprises the amino acid sequence of any one of SEQ ID NOs: 19-27, or comprises a heavy chain variable region (VH) comprising the amino acid sequence of any one of SEQ ID NOs: 7-13, 89, 90, 256-262; and the light chain that comprises the amino acid sequence of any one of SEQ ID NOs: 28-30, or comprises a light chain variable region (VL) comprising the amino acid sequence of any one of SEQ ID NOs: 91-93; or
   (ii) the heavy chain comprises a heavy chain variable region (VH) comprising 3 complementarity determining regions (CDRs): VH CDR1, VH CDR2, and VH CDR3 having the amino acid sequence from the CDR1, CDR2 and CDR3, respectively, in SEQ ID NO: 256; and the light chain comprises a light chain variable region (VL) comprising a VL CDR1, VL CDR2, and VL CDR3 having the amino acid sequence from the CDR1, CDR2, and CDR3, respectively, in one of SEQ ID NOs: 91-93; or
   (iii) the antibody comprises:
      a CDRH1 comprising the amino acid sequence in SEQ ID NO: 172;
      a CDRH2 comprising the amino acid sequence in SEQ ID NO: 173;
      a CDRH3 comprising the amino acid sequence in SEQ ID NO: 174:
      a CDRL1 comprising the amino acid sequence in SEQ ID NO: 199;
      a CDRL2 comprising the amino acid sequence in SEQ ID NO: 200;
      a CDRL3 comprising the amino acid sequence in SEQ ID NO: 201; and
      an Fc domain comprising:
         at least one of the following mutations (EU numbering): L234A, L235A, and G237A; and/or
         at least one of the following mutations (EU numbering): Q347C or L443C,
      wherein either:
         (a) the VEGF Trap is positioned at the N-terminal end of the heavy chain comprising IL-6 VH; or
         (b) the heavy chain comprises a hinge region and a CH1 domain, wherein the VEGF Trap is positioned between the hinge region and the CH1 domain of the heavy chain comprising IL-6 VH.

2. The protein construct of claim 1, wherein the VEGF Trap consists of the sequence of SEQ ID NO: 114.

3. A conjugate comprising:
   the protein construct of claim 1; and
   a polymer, wherein the polymer is covalently attached to the heavy chain of the protein construct, wherein the polymer comprises a phosphorylcholine containing polymer or a zwitterionic monomer.

4. The conjugate of claim 3, wherein the conjugate has a molecular weight between about 350,000 and 1,900,000 Daltons.
5. The conjugate of claim 3, which comprises the following structure:
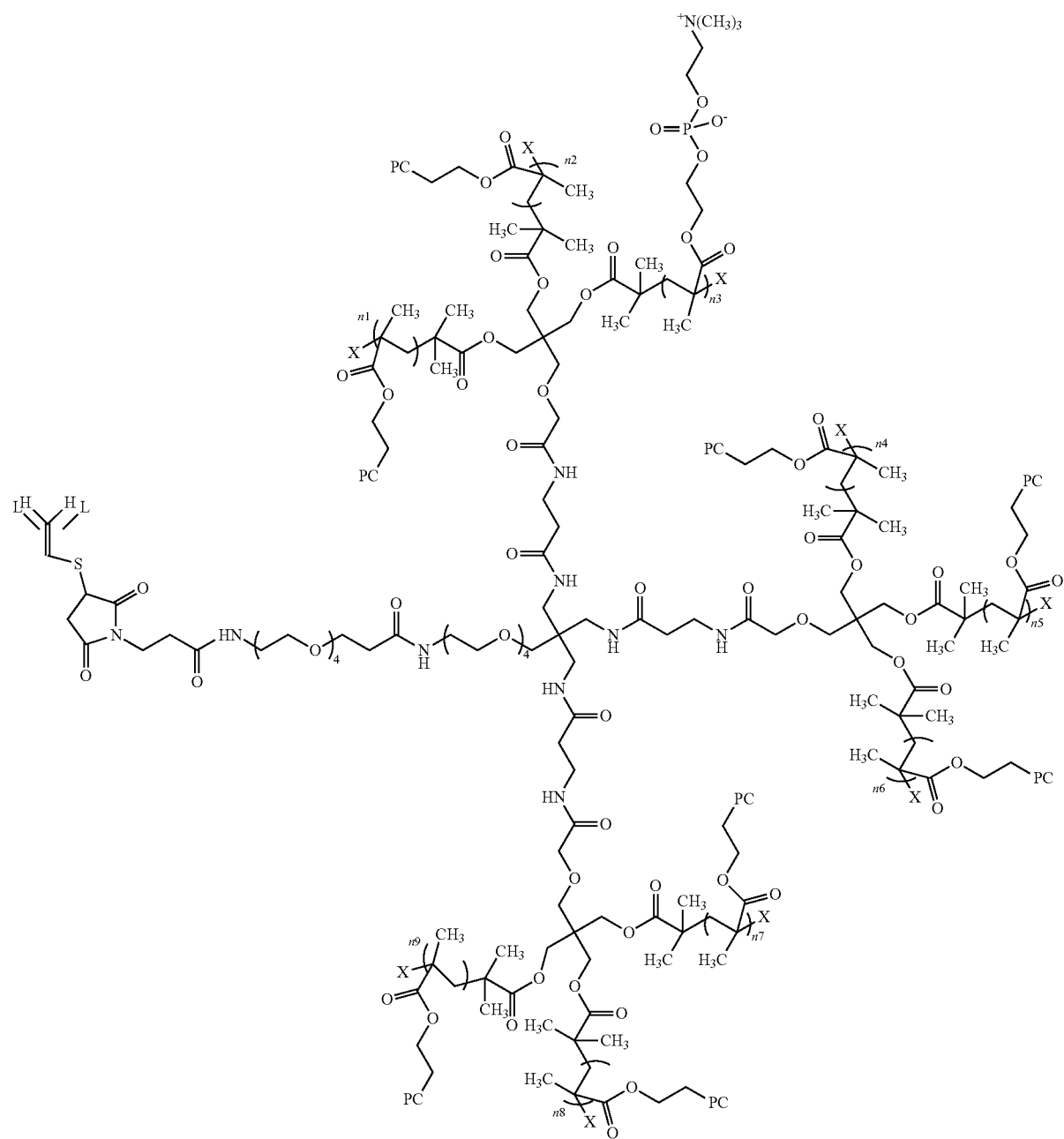
Formula (17)

wherein:

each heavy chain of the anti-TL-6 antibody and the VEGF Trap fused thereto is denoted by the letter H, and each light chain of the anti-IL-6 antibody is denoted by the letter L;

the polymer is bonded to the antibody through the sulfhydryl of C443 (EU numbering), which bond is depicted on one of the heavy chains;

PC is

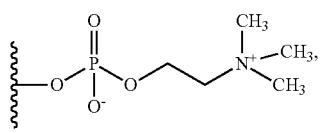 [SMILES: *OP(=O)([O-])OCC[N+](C)(C)C]

where the curvy line indicates the point of attachment to the rest of the polymer, where X=a) OR where R=H, methyl, ethyl, propyl, isopropyl, b) H, or c) any halide, including Br; and wherein n1, n2, n3, n4, n5, n6, n7, n8 and n9 each represents the number n of the following repeating units in Formula (17):

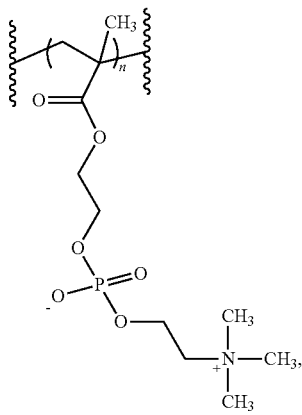

Formula (16)

where the wavy lines indicate the points of attachment between monomer units in the polymer, wherein n1, n2, n3, n4, n5, n6, n7, n8 and n9 are each an integer and are the same or different such that the sum of n1, n2, n3, n4, n5, n6, n7, n8 and n9 is 2500 plus or minus 15%, wherein the VEGF Trap is fused:
  to the N-terminal end of the heavy chain; or
  before the hinge region and after the CH1 domain of the heavy chain.

6. The conjugate of claim 5, wherein the VEGF trap comprises VEGFR1 domain 2 and VEGFR2 domain 3.

7. A method for the treatment of a neovascular retinal disease in a patient in need thereof, said method comprising:
  identifying a patient in need of treating a neovascular retinal disease; and
  administering to the patient the conjugate according to claim 3 to treat angiogenesis and/or inflammation associated with the neovascular retinal disease.

8. The method of claim 7, wherein the conjugate has a molecular weight between about 350,000 and 1,900,000 Daltons.

9. The method of claim 7, wherein the protein construct comprises two heavy chains and two light chains, wherein the conjugate comprises the following structure:

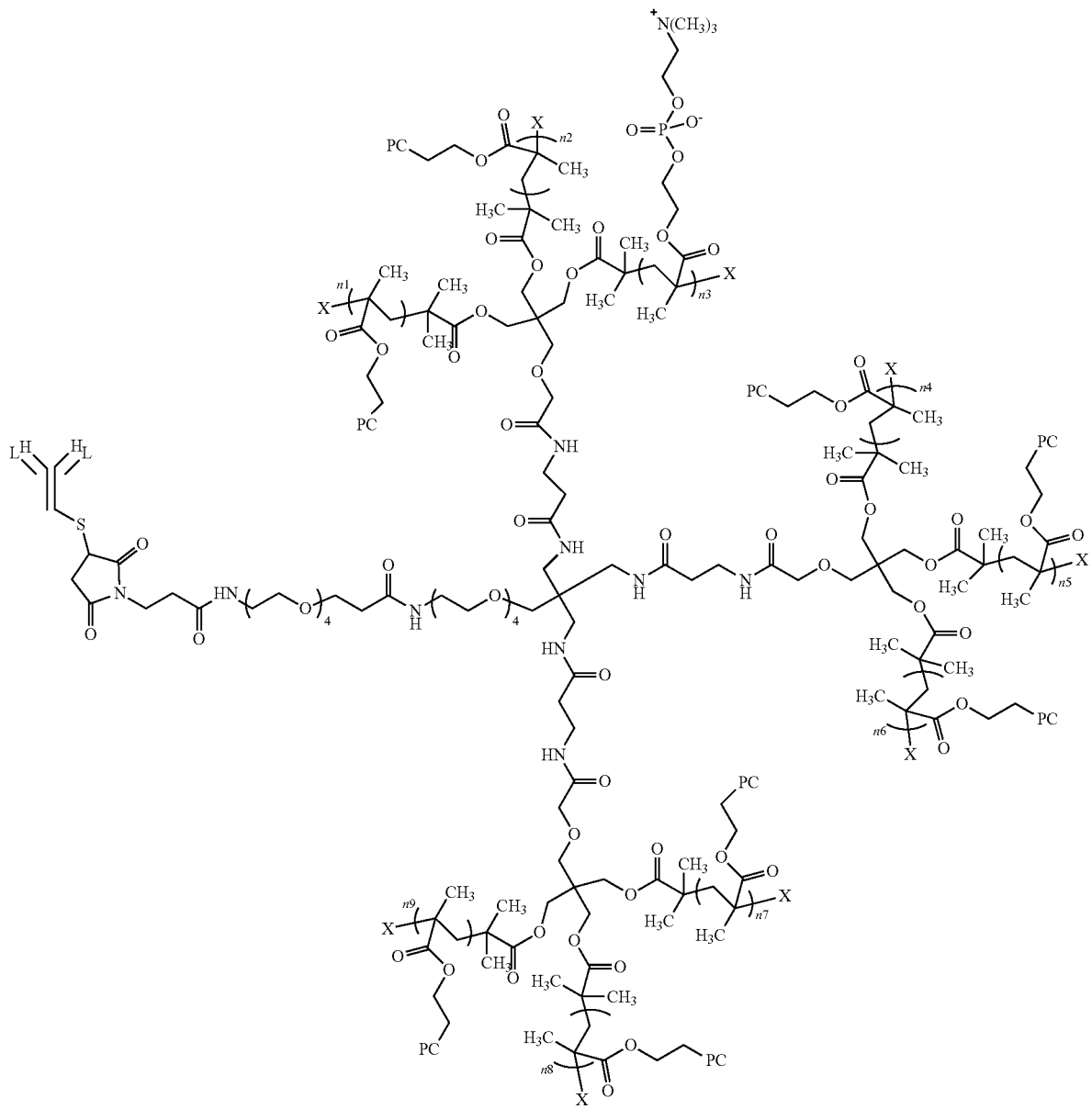

Formula (17)

wherein:
  each of the heavy chains of the protein construct is denoted by the letter H, and each of the light chains of the protein construct is denoted by the letter L;
  the polymer is bonded to one of the heavy chains through the sulfhydryl of C443 (EU numbering), which bond is depicted on the one of the heavy chains;

PC is

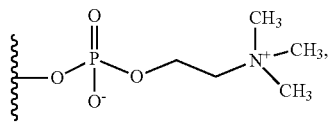 [SMILES: *OP(=O)([O-])OCC[N+](C)(C)C]

where the curvy line indicates the point of attachment to the rest of the polymer, where X=a) OR where R=H, methyl, ethyl, propyl, isopropyl, b) H, or c) any halide, including Br; and wherein n1, n2, n3, n4, n5, n6, n7, n8 and n9 each represents the number n of the following repeating units in Formula (17):

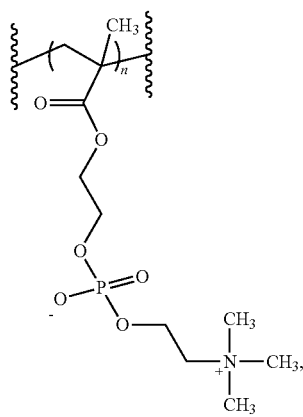

Formula (16)

where the wavy lines indicate the points of attachment between monomer units in the polymer,
wherein n1, n2, n3, n4, n5, n6, n7, n8 and n9 are each an integer and are the same or different such that the sum of n1, n2, n3, n4, n5, n6, n7, n8 and n9 is 2500 plus or minus 15%.

10. The method of claim 9, wherein both heavy chains comprise the amino acid sequence of SEQ ID NO:170, with or without the C-terminal lysine, and both light chains comprise the amino acid sequence of SEQ ID NO:169.

11. The conjugate of claim 3, wherein the VEGF trap comprises VEGFR1 domain 2 and VEGFR2 domain 3.

12. A method for the treatment of a neovascular retinal disease in a patient in need thereof, said method comprising:
identifying a patient in need of treating a neovascular retinal disease; and
administering to the patient the protein construct according to claim 1 to treat angiogenesis and/or inflammation associated with the neovascular retinal disease.

13. The method of claim 12, wherein the heavy chain comprises the amino acid sequence of SEQ ID NO: 170, with or without the C-terminal lysine, and the light chain comprises the amino acid sequence of SEQ ID NO:169.

14. The protein construct of claim 1, wherein the heavy chain comprises a heavy chain constant domain comprising a non-native cysteine residue at position 347 or 443 (EU numbering).

15. The protein construct of claim 1, wherein the VEGF trap comprises VEGFR1 domain 2 and VEGFR2 domain 3.

16. The protein construct of claim 1, wherein (ii) the heavy chain comprises a heavy chain variable region (VH) comprising 3 complementarity determining regions (CDRs): VH CDR1, VH CDR2, and VH CDR3 having the amino acid sequence from the CDR1, CDR2 and CDR3, respectively, in SEQ ID NO: 256; and the light chain comprises a light chain variable region (VL) comprising a VL CDR1, VL CDR2, and VL CDR3 having the amino acid sequence from the CDR1, CDR2, and CDR3, respectively, of SEQ ID NO: 91.

17. The protein construct of claim 16, wherein the heavy chain comprises a sequence at least 90% identical to SEQ ID NO:170, and the light chain comprises a sequence at least 90% identical to SEQ ID NO:169.

18. The protein construct of claim 17, wherein the heavy chain does not comprise the C-terminal lysine.

19. A protein construct that binds IL-6 and VEGF, comprising:
two light chains, each comprising an IL-6 VL; and
two heavy chains, each fused to a VEGF Trap and comprising an IL-6 VH and a Fc,
wherein either:
(a) the VEGF Trap is positioned at the N-terminal end of each heavy chain; or
(b) each heavy chain comprises a hinge region and a CH1 domain, wherein the VEGF Trap is positioned between the hinge region and the CH1 domain of each heavy chain,
wherein each VEGF Trap comprises the amino acid sequence of SEQ ID NO:114 and a mutation at position 94 or 95 as numbered according to SEQ ID NO: 114, wherein if the mutation occurs at position 94, the mutation is T94I and wherein if the mutation occurs at position 95, the mutation is H95I.

20. A VEGFR-Anti-IL-6 dual inhibitor, wherein the VEGFR-Anti-IL-6 dual inhibitor comprises a trap antibody fusion of an anti-IL 6 antibody and a VEGF trap, wherein the VEGF trap comprises an amino acid sequence selected from SEQ ID NOs: 15, 16, or 17,
wherein the antibody comprises:
a fragment antigen binding (Fab) region;
a hinge region; and
a fragment crystallizable (Fc) region, and
wherein the VEGF trap is positioned either:
at the N-terminal end of a heavy chain of the antibody, wherein the heavy chain comprises TL-6 VH; or
between the Fab and hinge regions.

21. The VEGFR-Anti-IL-6 dual inhibitor of claim 20, wherein the Fab region comprises:
a variable heavy region comprising an amino acid sequence selected from SEQ ID NO: 7-13, 89, 90, and 256-262; and
a variable light region comprising a CDRL1 having the amino acid sequence of SEQ ID NO:76, a CDRL2 having the amino acid sequence of any one of SEQ ID NOs:77, 80, and 83, and a CDRL3 having the amino acid sequence of SEQ ID NO:78.

22. The VEGFR-Anti-IL-6 dual inhibitor of claim 21, comprising a linker positioned between the anti-VEGF trap and either: (1) the IL-6 VH; or (2) a CH1 of the Fab region.

23. The VEGFR-Anti-IL-6 dual inhibitor of claim 22, wherein the linker comprises the sequence of SEQ ID NO: 18.

24. The VEGFR-Anti-IL-6 dual inhibitor of claim 20, wherein the VEGF trap is positioned between the Fab and hinge regions to form a VEGFR-Fc sequence, and wherein the VEGFR-Fc sequence comprises any one of SEQ ID NOs: 86-88.

25. A protein construct that binds IL-6 and VEGF, comprising:
two light chains, both light chains comprising:
(1) a CDRL1 having the amino acid sequence of SEQ ID NO: 76;
a CDRL2 having the amino acid sequence of any one of SEQ ID NOs: 77, 80, and 83; and
a CDRL3 having the amino acid sequence of SEQ ID NO: 78; or
(2) the CDRL1 of the light chain variable region having the amino acid sequence of SEQ ID NO: 28;
the CDRL2 of the light chain variable region having the amino acid sequence selected from SEQ ID NOs: 28-30; and the CDRL3 of the light chain variable region having the amino acid sequence of SEQ ID NO: 28;
two heavy chains, both heavy chains comprising:
(1)
a CDRH1 having the amino acid sequence of any one of SEQ ID NOs: 49, 70, 73;
a CDRH2 having the amino acid sequence of SEQ ID NO: 50; and
a CDRH3 having the amino acid sequence of any one of SEQ ID NOs: 51, 54, 57, 60, 63, 66, 69, and 72; or
(2)
the CDRH1 of a heavy chain variable region in the amino acid sequence selected from SEQ ID NOs: 7, 26, 27;
the CDRH2 of the heavy chain variable region in the amino acid sequence of SEQ ID NO:7; and
the CDRH3 of the heavy chain variable region in the amino acid sequence selected from SEQ ID NOs: 7-13, 26;
a VEGF trap sequence selected from SEQ ID NOs: 14-17 at the N-terminal end of the heavy chain, or the amino acid sequence selected from SEQ ID NOs: 85-88 positioned C-terminal to a CH1 domain of the heavy chain; and
a linker sequence of SEQ ID NO: 18 linking either the VEGF trap sequence selected from SEQ ID NOs: 14-17 and the heavy chain, or the CH1 domain of the heavy chain and the amino acid sequence selected from SEQ ID NOs: 85-88.

26. A conjugate comprising:
a protein construct comprising:
a first polypeptide comprising an amino acid sequence that is at least 90% identical to SEQ ID NO: 170, wherein the amino acid sequence of the first polypeptide comprises:
the 3 CDRs of SEQ ID NO: 170;
an Fc region; and
one of SEQ ID NOs: 14-17; and
a second polypeptide comprising an amino acid sequence at least 90% identical to SEQ ID NO: 169, wherein the amino acid sequence of the second polypeptide comprises the 3 CDRs of SEQ ID NO: 169,
wherein the first and second polypeptides are separate chains; and
a polymer covalently attached to a cysteine residue in the Fc region of the first polypeptide.

27. A protein construct that binds IL-6 and VEGF, comprising two heavy chains and two light chains,
wherein both heavy chains comprise either:
(1) a VEGF Trap protein fused at its C-terminus to the N-terminus of the heavy chain of an IL-6 antibody; or
(2) a heavy chain of an IL-6 antibody where a VEGF Trap protein has been inserted after the CH1 domain and before the hinge region to form a fusion protein,
wherein both light chains comprise the light chain of said IL-6 antibody,
wherein the IL-6 antibody has VH and VL domains selected from the group consisting of:
(A) the VH of SEQ ID NO:89 and the VL of SEQ ID NO:91;
(B) the VH of SEQ ID NO:89 and the VL of SEQ ID NO:92;
(C) the VH of SEQ ID NO:89 and the VL of SEQ ID NO:93;
(D) the VH of SEQ ID NO:90 and the VL of SEQ ID NO:91;
(E) the VH of SEQ ID NO:90 and the VL of SEQ ID NO:92;
(F) the VH of SEQ ID NO:90 and the VL of SEQ ID NO:93;
(G) the VH of SEQ ID NO:256 and the VL of SEQ ID NO:91;
(H) the VH of SEQ ID NO:256 and the VL of SEQ ID NO: 92; and
(I) the VH of SEQ ID NO:256 and the VL of SEQ ID NO:93.

28. The protein construct of claim 27, wherein the VEGF Trap protein is selected from SEQ ID NOs: 14-17.

29. The protein construct of claim 27, wherein the VEGF Trap protein consists of the sequence of:
SEQ ID NO: 114; or
SEQ ID NO: 114 comprising the mutation T94I or H95I.

30. The protein construct of claim 27 further comprising the linker of SEQ ID NO: 18 fused directly to the C-terminus of the VEGF Trap protein of part (1), or fused directly to the N-terminus of the VEGF Trap protein of part (2).

31. The protein construct of claim 27, wherein the IL-6 antibody comprises:
CDRH1 comprising SEQ ID NO: 172;
CDRH2 comprising SEQ ID NO: 173;
CDRH3 comprising SEQ ID NO: 174:
CDRL1 comprising SEQ ID NO: 199;
CDRL2 comprising SEQ ID NO: 200;
CDRL3 comprising SEQ ID NO: 201; and
wherein the Fe domain comprises at least one of the following mutations: L234A, L235A, and G237A (EU numbering).

32. The protein construct of claim 31, wherein the Fc domain comprises Q347C or L443C (EU numbering).

33. The protein construct of claim 27, wherein the heavy and light chains are selected from the group consisting of:
(A) the heavy chain of SEQ ID NO:116, and the light chain of SEQ ID NO:117;
(B) the heavy chain of SEQ ID NO:118, and the light chain of SEQ ID NO:119;
(C) the heavy chain of SEQ ID NO:120, and the light chain of SEQ ID NO:121;
(D) the heavy chain of SEQ ID NO:122, and the light chain of SEQ ID NO:123;
(E) the heavy chain of SEQ ID NO:124, and the light chain of SEQ ID NO:125;
(F) the heavy chain of SEQ ID NO:126, and the light chain of SEQ ID NO:127;
(G) the heavy chain of SEQ ID NO:263, and the light chain of SEQ ID NO:117;
(H) the heavy chain of SEQ ID NO:263, and the light chain of SEQ ID NO:119;
(I) the heavy chain of SEQ ID NO:263, and the light chain of SEQ ID NO:121;
(J) the heavy chain of SEQ ID NO:128, and the light chain of SEQ ID NO:129;
(K) the heavy chain of SEQ ID NO:130, and the light chain of SEQ ID NO:131;
(L) the heavy chain of SEQ ID NO:132, and the light chain of SEQ ID NO:133;
(M) the heavy chain of SEQ ID NO:134, and the light chain of SEQ ID NO:135;
(N) the heavy chain of SEQ ID NO:136, and the light chain of SEQ ID NO:137;
(O) the heavy chain of SEQ ID NO:138, and the light chain of SEQ ID NO:139;
(P) the heavy chain of SEQ ID NO:266, and the light chain of SEQ ID NO:117;
(Q) the heavy chain of SEQ ID NO:267, and the light chain of SEQ ID NO:119; and (R) the heavy chain of SEQ ID NO:268, and the light chain of SEQ ID NO:121.

34. A conjugate comprising: the protein construct of claim 27; and a polymer, wherein the polymer is covalently attached to a heavy chain, wherein the polymer comprises a phosphorylcholine containing polymer or a zwitterionic monomer.

35. The conjugate of claim 34, wherein the conjugate has a molecular weight between about 350,000 and 1,900,000 Daltons.

36. The protein construct of claim 27, wherein the VEGF trap comprises VEGFR1 domain 2 and VEGFR2 domain 3.

37. A protein construct that binds IL-6 and VEGF, comprising two heavy chains and two light chains,
wherein both heavy chains comprise a VEGF Trap protein fused at its C-terminus to the N-terminus of the heavy chain of an IL-6 antibody, and comprise the amino acid sequence of SEQ ID NO: 170, with or without the C-terminal lysine, and both light chains comprise the light chain of said IL-6 antibody, and comprise the amino acid sequence of SEQ ID NO:169.

38. A conjugate comprising the protein construct of claim 37 and a polymer, wherein the conjugate comprises the following structure:

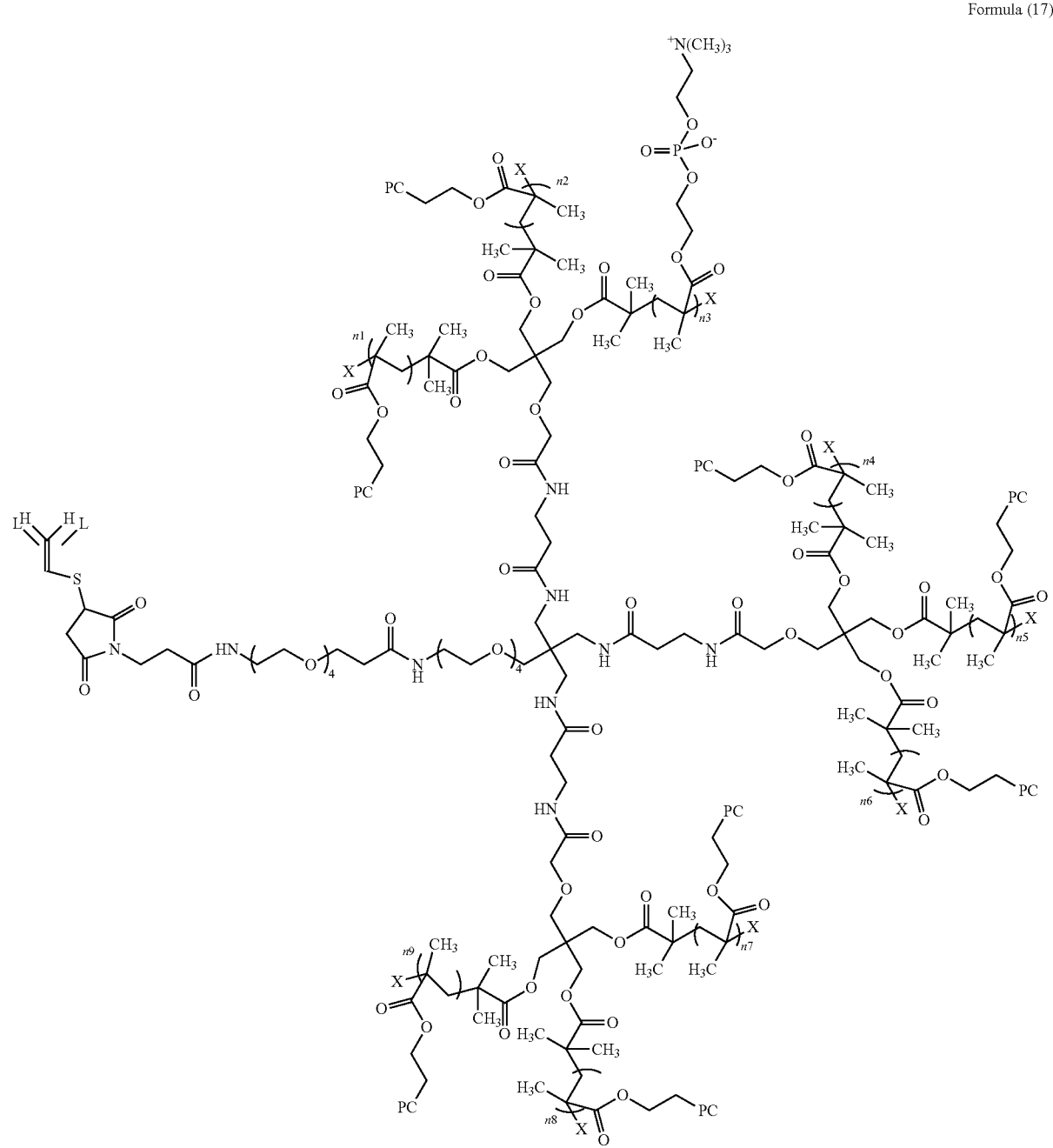

Formula (17)

wherein:

each heavy chain of the protein construct is denoted by the letter H, and each light chain of the protein construct is denoted by the letter L;

the polymer is bonded to one of the heavy chains through the sulfhydryl of C443 (EU numbering), which bond is depicted on the one of the heavy chains;

PC is

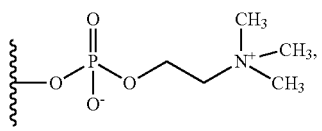

where the curvy line indicates the point of attachment to the rest of the polymer, where X=a) OR where R=H, methyl, ethyl, propyl, isopropyl, b) H, or c) and halide, including Br; and wherein n1, n2, n3, n4, n5, n6, n7, n8 and n9 each represents the number n of the following repeating units in Formula (17):

Formula (16)

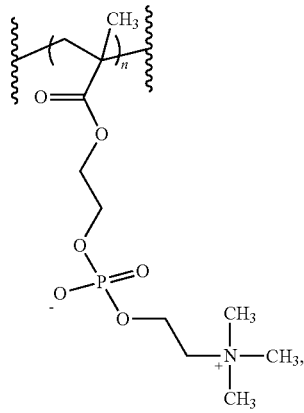

where the wavy lines indicate the points of attachment between monomer units in the polymer, wherein n1, n2, n3, n4, n5, n6, n7, n8 and n9 are each an integer and are the same or different such that the sum of n1, n2, n3, n4, n5, n6, n7, n8 and n9 is 2500 plus or minus 15%.

39. The conjugate of claim 38, wherein the heavy chain does not comprise the C-terminal lysine.

* * * * *

```
                       SEQUENCE LISTING

<160> NUMBER OF SEQ ID NOS: 269

<210> SEQ ID NO 1
<211> LENGTH: 183
<212> TYPE: PRT
<213> ORGANISM: Homo sapiens

<400> SEQUENCE: 1

Val Pro Pro Gly Glu Asp Ser Lys Asp Val Ala Ala Pro His Arg Gln
1               5                  10                  15

Pro Leu Thr Ser Ser Glu Arg Ile Asp Lys Gln Ile Arg Tyr Ile Leu
            20                  25                  30

Asp Gly Ile Ser Ala Leu Arg Lys Glu Thr Cys Asn Lys Ser Asn Met
        35                  40                  45

Cys Glu Ser Ser Lys Glu Ala Leu Ala Glu Asn Asn Leu Asn Leu Pro
    50                  55                  60

Lys Met Ala Glu Lys Asp Gly Cys Phe Gln Ser Gly Phe Asn Glu Glu
65                  70                  75                  80

Thr Cys Leu Val Lys Ile Ile Thr Gly Leu Leu Glu Phe Glu Val Tyr
                85                  90                  95

Leu Glu Tyr Leu Gln Asn Arg Phe Glu Ser Ser Glu Glu Gln Ala Arg
            100                 105                 110

Ala Val Gln Met Ser Thr Lys Val Leu Ile Gln Phe Leu Gln Lys Lys
        115                 120                 125

Ala Lys Asn Leu Asp Ala Ile Thr Thr Pro Asp Pro Thr Thr Asn Ala
    130                 135                 140

Ser Leu Leu Thr Lys Leu Gln Ala Gln Asn Gln Trp Leu Gln Asp Met
145                 150                 155                 160

Thr Thr His Leu Ile Leu Arg Ser Phe Lys Glu Phe Leu Gln Ser Ser
                165                 170                 175

Leu Arg Ala Leu Arg Gln Met
            180

<210> SEQ ID NO 2
<211> LENGTH: 119
<212> TYPE: PRT
<213> ORGANISM: Artificial Sequence
<220> FEATURE:
<223> OTHER INFORMATION: antibody

<400> SEQUENCE: 2

Glu Val Gln Leu Val Glu Ser Gly Gly Gly Leu Val Gln Pro Gly Gly
1               5                  10                  15

Ser Leu Arg Leu Ser Cys Ala Ala Ser Gly Phe Thr Phe Ser Pro Phe
            20                  25                  30

Ala Ile Ser Trp Val Arg Gln Ala Pro Gly Lys Gly Leu Glu Trp Val
        35                  40                  45

Ala Lys Ile Ser Pro Gly Gly Ser Trp Thr Tyr Tyr Ser Asp Thr Val
    50                  55                  60

Thr Asp Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95
```

Ala Arg Gln Leu Trp Gly Tyr Tyr Ala Leu Asp Val Trp Gly Gln Gly
            100                 105                 110

Thr Leu Val Thr Val Ser Ser
        115

<210> SEQ ID NO 3
<211> LENGTH: 106
<212> TYPE: PRT
<213> ORGANISM: Artificial Sequence
<220> FEATURE:
<223> OTHER INFORMATION: antibody

<400> SEQUENCE: 3

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ile Ser Val Ser Tyr Leu
            20                  25                  30

Tyr Trp Tyr Gln Gln Lys Pro Gly Lys Ala Pro Lys Leu Leu Ile Tyr
        35                  40                  45

Asp Asp Ser Ser Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Gly Tyr Pro Tyr Thr
                85                  90                  95

Phe Gly Gln Gly Thr Lys Val Glu Ile Lys
            100                 105

<210> SEQ ID NO 4
<211> LENGTH: 205
<212> TYPE: PRT
<213> ORGANISM: Artificial Sequence
<220> FEATURE:
<223> OTHER INFORMATION: trap

<400> SEQUENCE: 4

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Ile His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

```
Ser Glu Met Lys Lys Phe Leu Ser Thr Leu Thr Ile Asp Gly Val Thr
            165                 170                 175

Arg Ser Asp Gln Gly Leu Tyr Thr Cys Ala Ala Ser Ser Gly Leu Met
        180                 185                 190

Thr Lys Lys Asn Ser Thr Phe Val Arg Val His Glu Lys
        195                 200                 205

<210> SEQ ID NO 5
<211> LENGTH: 205
<212> TYPE: PRT
<213> ORGANISM: Artificial Sequence
<220> FEATURE:
<223> OTHER INFORMATION: trap

<400> SEQUENCE: 5

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr Ile Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
            165                 170                 175

Arg Ser Asp Gln Gly Leu Tyr Thr Cys Ala Ala Ser Ser Gly Leu Met
        180                 185                 190

Thr Lys Lys Asn Ser Thr Phe Val Arg Val His Glu Lys
        195                 200                 205

<210> SEQ ID NO 6
<211> LENGTH: 205
<212> TYPE: PRT
<213> ORGANISM: Artificial Sequence
<220> FEATURE:
<223> OTHER INFORMATION: trap

<400> SEQUENCE: 6

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45
```

Leu Ile Pro Asp Gly Lys Arg Ile Ile Trp Asp Ser Arg Lys Gly Phe
        50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Ile Ile Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys
        195                 200                 205

<210> SEQ ID NO 7
<211> LENGTH: 119
<212> TYPE: PRT
<213> ORGANISM: Artificial Sequence
<220> FEATURE:
<223> OTHER INFORMATION: antibody

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Pro Phe
            20                  25                  30

Ala Met His Trp Val Arg Gln Ala Pro Gly Lys Gly Leu Glu Trp Val
        35                  40                  45

Ala Lys Ile Ser Pro Gly Gly Ser Trp Thr Tyr Tyr Ser Asp Thr Val
    50                  55                  60

Thr Asp Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gln Ala Trp Gly Tyr Tyr Ala Leu Asp Ile Trp Gly Gln Gly
            100                 105                 110

Thr Leu Val Thr Val Ser Ser
        115

<210> SEQ ID NO 8
<211> LENGTH: 119
<212> TYPE: PRT
<213> ORGANISM: Artificial Sequence
<220> FEATURE:
<223> OTHER INFORMATION: antibody

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Pro Phe
            20                  25                  30

Ala Met His Trp Val Arg Gln Ala Pro Gly Lys Gly Leu Glu Trp Val
            35                  40                  45

Ala Lys Ile Ser Pro Gly Gly Ser Trp Thr Tyr Tyr Ser Asp Thr Val
 50                  55                  60

Thr Asp Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                 85                  90                  95

Ala Arg Gln Ser Trp Gly Tyr Tyr Ala Leu Asp Ile Trp Gly Gln Gly
            100                 105                 110

Thr Leu Val Thr Val Ser Ser
            115

<210> SEQ ID NO 9
<211> LENGTH: 119
<212> TYPE: PRT
<213> ORGANISM: Artificial Sequence
<220> FEATURE:
<223> OTHER INFORMATION: antibody

<400> SEQUENCE: 9

Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Ser Pro Phe
            20                  25                  30

Ala Met His Trp Val Arg Gln Ala Pro Gly Lys Gly Leu Glu Trp Val
            35                  40                  45

Ala Lys Ile Ser Pro Gly Gly Ser Trp Thr Tyr Tyr Ser Asp Thr Val
 50                  55                  60

Thr Asp Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                 85                  90                  95

Ala Arg Gln Gly Trp Gly Tyr Tyr Ala Leu Asp Ile Trp Gly Gln Gly
            100                 105                 110

Thr Leu Val Thr Val Ser Ser
            115

<210> SEQ ID NO 10
<211> LENGTH: 119
<212> TYPE: PRT
<213> ORGANISM: Artificial Sequence
<220> FEATURE:
<223> OTHER INFORMATION: antibody

<400> SEQUENCE: 10

Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Ser Pro Phe
            20                  25                  30

Ala Met His Trp Val Arg Gln Ala Pro Gly Lys Gly Leu Glu Trp Val
            35                  40                  45

Ala Lys Ile Ser Pro Gly Gly Ser Trp Thr Tyr Tyr Ser Asp Thr Val
 50                  55                  60

```
Thr Asp Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                 85                  90                  95

Ala Arg Gln Thr Trp Gly Tyr Tyr Ala Leu Asp Ile Trp Gly Gln Gly
            100                 105                 110

Thr Leu Val Thr Val Ser Ser
        115

<210> SEQ ID NO 11
<211> LENGTH: 119
<212> TYPE: PRT
<213> ORGANISM: Artificial Sequence
<220> FEATURE:
<223> OTHER INFORMATION: antibody

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Pro Phe
            20                  25                  30

Ala Met His Trp Val Arg Gln Ala Pro Gly Lys Gly Leu Glu Trp Val
        35                  40                  45

Ala Lys Ile Ser Pro Gly Gly Ser Trp Thr Tyr Tyr Ser Asp Thr Val
    50                  55                  60

Thr Asp Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                 85                  90                  95

Ala Arg Gln Val Trp Gly Tyr Tyr Ala Leu Asp Ile Trp Gly Gln Gly
            100                 105                 110

Thr Leu Val Thr Val Ser Ser
        115

<210> SEQ ID NO 12
<211> LENGTH: 119
<212> TYPE: PRT
<213> ORGANISM: Artificial Sequence
<220> FEATURE:
<223> OTHER INFORMATION: antibody

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Pro Phe
            20                  25                  30

Ala Met His Trp Val Arg Gln Ala Pro Gly Lys Gly Leu Glu Trp Val
        35                  40                  45

Ala Lys Ile Ser Pro Gly Gly Ser Trp Thr Tyr Tyr Ser Asp Thr Val
    50                  55                  60

Thr Asp Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                 85                  90                  95
```

Ala Arg Gln Gln Trp Gly Tyr Tyr Ala Leu Asp Ile Trp Gly Gln Gly
                100                 105                 110

Thr Leu Val Thr Val Ser Ser
        115

<210> SEQ ID NO 13
<211> LENGTH: 119
<212> TYPE: PRT
<213> ORGANISM: Artificial Sequence
<220> FEATURE:
<223> OTHER INFORMATION: antibody

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Pro Phe
            20                  25                  30

Ala Met His Trp Val Arg Gln Ala Pro Gly Lys Gly Leu Glu Trp Val
        35                  40                  45

Ala Lys Ile Ser Pro Gly Gly Ser Trp Thr Tyr Tyr Ser Asp Thr Val
    50                  55                  60

Thr Asp Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gln Lys Trp Gly Tyr Tyr Ala Leu Asp Ile Trp Gly Gln Gly
            100                 105                 110

Thr Leu Val Thr Val Ser Ser
        115

<210> SEQ ID NO 14
<211> LENGTH: 205
<212> TYPE: PRT
<213> ORGANISM: Artificial Sequence
<220> FEATURE:
<223> OTHER INFORMATION: trap

<400> SEQUENCE: 14

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
            35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys
        195                 200                 205

<210> SEQ ID NO 15
<211> LENGTH: 205
<212> TYPE: PRT
<213> ORGANISM: Artificial Sequence
<220> FEATURE:
<223> OTHER INFORMATION: trap

<400> SEQUENCE: 15

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
                20                  25                  30

Thr Ser Pro Asn Ile Thr Val Thr Leu Lys Lys Phe Pro Leu Asp Thr
            35                  40                  45

Leu Ile Pro Asp Gly Lys Arg Ile Ile Trp Asp Ser Arg Lys Gly Phe
        50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Ile His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys
        195                 200                 205

<210> SEQ ID NO 16
<211> LENGTH: 205
<212> TYPE: PRT
<213> ORGANISM: Artificial Sequence
<220> FEATURE:
<223> OTHER INFORMATION: trap

<400> SEQUENCE: 16

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
                20                  25                  30

```
Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
 50                  55                  60

Ile Ile Ser Asn Ala Thr Tyr Lys Glu Ile Gly Leu Leu Thr Cys Glu
 65                  70                  75                  80

Ala Thr Val Asn Gly His Leu Tyr Lys Thr Asn Tyr Leu Thr Ile Arg
                 85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys
        195                 200                 205

<210> SEQ ID NO 17
<211> LENGTH: 205
<212> TYPE: PRT
<213> ORGANISM: Artificial Sequence
<220> FEATURE:
<223> OTHER INFORMATION: trap

<400> SEQUENCE: 17

Ser Asp Thr Gly Arg Pro Phe Val Glu Met Tyr Ser Glu Ile Pro Glu
 1               5                  10                  15

Ile Ile His Met Thr Glu Gly Arg Glu Leu Val Ile Pro Cys Arg Val
                 20                  25                  30

Thr Ser Pro Asn Ile Thr Val Thr Leu Lys Lys Phe Pro Leu Asp Thr
            35                  40                  45

Leu Ile Pro Asp Gly Lys Arg Ile Ile Trp Asp Ser Arg Lys Gly Phe
 50                  55                  60

Ile Ile Ser Asn Ala Thr Tyr Lys Glu Ile Gly Leu Leu Thr Cys Glu
 65                  70                  75                  80

Ala Thr Val Asn Gly His Leu Tyr Lys Thr Asn Tyr Leu Ile Ile Arg
                 85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175
```

```
Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys
            195                 200                 205

<210> SEQ ID NO 18
<211> LENGTH: 10
<212> TYPE: PRT
<213> ORGANISM: Artificial Sequence
<220> FEATURE:
<223> OTHER INFORMATION: linker

<400> SEQUENCE: 18

Gly Gly Gly Gly Ser Gly Gly Gly Gly Ser
1               5                   10

<210> SEQ ID NO 19
<211> LENGTH: 449
<212> TYPE: PRT
<213> ORGANISM: Artificial Sequence
<220> FEATURE:
<223> OTHER INFORMATION: antibody

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Pro Phe
            20                  25                  30

Ala Met His Trp Val Arg Gln Ala Pro Gly Lys Gly Leu Glu Trp Val
            35                  40                  45

Ala Lys Ile Ser Pro Gly Gly Ser Trp Thr Tyr Tyr Ser Asp Thr Val
    50                  55                  60

Thr Asp Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gln Ala Trp Gly Tyr Tyr Ala Leu Asp Ile Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
                245                 250                 255
```

```
Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Cys Ser Pro Gly
            435                 440                 445

Lys

<210> SEQ ID NO 20
<211> LENGTH: 449
<212> TYPE: PRT
<213> ORGANISM: Artificial Sequence
<220> FEATURE:
<223> OTHER INFORMATION: antibody

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Pro Phe
            20                  25                  30

Ala Met His Trp Val Arg Gln Ala Pro Gly Lys Gly Leu Glu Trp Val
        35                  40                  45

Ala Lys Ile Ser Pro Gly Gly Ser Trp Thr Tyr Tyr Ser Asp Thr Val
50                  55                  60

Thr Asp Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gln Ser Trp Gly Tyr Tyr Ala Leu Asp Ile Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160
```

```
Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Cys Ser Pro Gly
            435                 440                 445

Lys

<210> SEQ ID NO 21
<211> LENGTH: 449
<212> TYPE: PRT
<213> ORGANISM: Artificial Sequence
<220> FEATURE:
<223> OTHER INFORMATION: antibody

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Pro Phe
            20                  25                  30

Ala Met His Trp Val Arg Gln Ala Pro Gly Lys Gly Leu Glu Trp Val
        35                  40                  45
```

```
Ala Lys Ile Ser Pro Gly Gly Ser Trp Thr Tyr Tyr Ser Asp Thr Val
     50                  55                  60

Thr Asp Arg Phe Thr Phe Ser Leu Asp Thr Ser Lys Ser Thr Ala Tyr
65                      70                  75                  80

Leu Gln Met Asn Ser Leu Arg Ala Glu Asp Thr Ala Val Tyr Tyr Cys
                 85                  90                  95

Ala Arg Gln Gly Trp Gly Tyr Tyr Ala Leu Asp Ile Trp Gly Gln Gly
                100                 105                 110

Thr Leu Val Thr Val Ser Ser Ala Ser Thr Lys Gly Pro Ser Val Phe
             115                 120                 125

Pro Leu Ala Pro Ser Ser Lys Ser Thr Ser Gly Gly Thr Ala Ala Leu
     130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                 165                 170                 175

Gln Ser Ser Gly Leu Tyr Ser Leu Ser Ser Val Val Thr Val Pro Ser
             180                 185                 190

Ser Ser Leu Gly Thr Gln Thr Tyr Ile Cys Asn Val Asn His Lys Pro
     195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
                 245                 250                 255

Arg Thr Pro Glu Val Thr Cys Val Val Val Asp Val Ser His Glu Asp
             260                 265                 270

Pro Glu Val Lys Phe Asn Trp Tyr Val Asp Gly Val Glu Val His Asn
         275                 280                 285

Ala Lys Thr Lys Pro Arg Glu Glu Gln Tyr Asn Ser Thr Tyr Arg Val
     290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                 325                 330                 335

Thr Ile Ser Lys Ala Lys Gly Gln Pro Arg Glu Pro Gln Val Tyr Thr
             340                 345                 350

Leu Pro Pro Ser Arg Glu Glu Met Thr Lys Asn Gln Val Ser Leu Thr
         355                 360                 365

Cys Leu Val Lys Gly Phe Tyr Pro Ser Asp Ile Ala Val Glu Trp Glu
     370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                 405                 410                 415

Ser Arg Trp Gln Gln Gly Asn Val Phe Ser Cys Ser Val Met His Glu
             420                 425                 430

Ala Leu His Asn His Tyr Thr Gln Lys Ser Leu Ser Cys Ser Pro Gly
         435                 440                 445

Lys
```

```
<210> SEQ ID NO 22
<211> LENGTH: 449
<212> TYPE: PRT
<213> ORGANISM: Artificial Sequence
<220> FEATURE:
<223> OTHER INFORMATION: antibody

<400> SEQUENCE: 22
```

| | | | | | | | | | | | | | | | |
|---|---|---|---|---|---|---|---|---|---|---|---|---|---|---|---|
| Glu | Val | Gln | Leu | Val | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Thr | Phe | Ser | Pro | Phe |
| | | | 20 | | | | | 25 | | | | | 30 | | |
| Ala | Met | His | Trp | Val | Arg | Gln | Ala | Pro | Gly | Lys | Gly | Leu | Glu | Trp | Val |
| | | 35 | | | | | 40 | | | | | 45 | | | |
| Ala | Lys | Ile | Ser | Pro | Gly | Gly | Ser | Trp | Thr | Tyr | Tyr | Ser | Asp | Thr | Val |
| | 50 | | | | | 55 | | | | | 60 | | | | |
| Thr | Asp | Arg | Phe | Thr | Phe | Ser | Leu | Asp | Thr | Ser | Lys | Ser | Thr | Ala | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ala | Arg | Gln | Thr | Trp | Gly | Tyr | Tyr | Ala | Leu | Asp | Ile | Trp | Gly | Gln | Gly |
| | | | 100 | | | | | 105 | | | | | 110 | | |
| Thr | Leu | Val | Thr | Val | Ser | Ser | Ala | Ser | Thr | Lys | Gly | Pro | Ser | Val | Phe |
| | | 115 | | | | | 120 | | | | | 125 | | | |
| Pro | Leu | Ala | Pro | Ser | Ser | Lys | Ser | Thr | Ser | Gly | Gly | Thr | Ala | Ala | Leu |
| | 130 | | | | | 135 | | | | | 140 | | | | |
| Gly | Cys | Leu | Val | Lys | Asp | Tyr | Phe | Pro | Glu | Pro | Val | Thr | Val | Ser | Trp |
| 145 | | | | | 150 | | | | | 155 | | | | | 160 |
| Asn | Ser | Gly | Ala | Leu | Thr | Ser | Gly | Val | His | Thr | Phe | Pro | Ala | Val | Leu |
| | | | | 165 | | | | | 170 | | | | | 175 | |
| Gln | Ser | Ser | Gly | Leu | Tyr | Ser | Leu | Ser | Ser | Val | Val | Thr | Val | Pro | Ser |
| | | | 180 | | | | | 185 | | | | | 190 | | |
| Ser | Ser | Leu | Gly | Thr | Gln | Thr | Tyr | Ile | Cys | Asn | Val | Asn | His | Lys | Pro |
| | | 195 | | | | | 200 | | | | | 205 | | | |
| Ser | Asn | Thr | Lys | Val | Asp | Lys | Lys | Val | Glu | Pro | Lys | Ser | Cys | Asp | Lys |
| | 210 | | | | | 215 | | | | | 220 | | | | |
| Thr | His | Thr | Cys | Pro | Pro | Cys | Pro | Ala | Pro | Glu | Ala | Ala | Gly | Ala | Pro |
| 225 | | | | | 230 | | | | | 235 | | | | | 240 |
| Ser | Val | Phe | Leu | Phe | Pro | Pro | Lys | Pro | Lys | Asp | Thr | Leu | Met | Ile | Ser |
| | | | | 245 | | | | | 250 | | | | | 255 | |
| Arg | Thr | Pro | Glu | Val | Thr | Cys | Val | Val | Val | Asp | Val | Ser | His | Glu | Asp |
| | | | 260 | | | | | 265 | | | | | 270 | | |
| Pro | Glu | Val | Lys | Phe | Asn | Trp | Tyr | Val | Asp | Gly | Val | Glu | Val | His | Asn |
| | | 275 | | | | | 280 | | | | | 285 | | | |
| Ala | Lys | Thr | Lys | Pro | Arg | Glu | Glu | Gln | Tyr | Asn | Ser | Thr | Tyr | Arg | Val |
| | 290 | | | | | 295 | | | | | 300 | | | | |
| Val | Ser | Val | Leu | Thr | Val | Leu | His | Gln | Asp | Trp | Leu | Asn | Gly | Lys | Glu |
| 305 | | | | | 310 | | | | | 315 | | | | | 320 |
| Tyr | Lys | Cys | Lys | Val | Ser | Asn | Lys | Ala | Leu | Pro | Ala | Pro | Ile | Glu | Lys |
| | | | | 325 | | | | | 330 | | | | | 335 | |
| Thr | Ile | Ser | Lys | Ala | Lys | Gly | Gln | Pro | Arg | Glu | Pro | Gln | Val | Tyr | Thr |
| | | | 340 | | | | | 345 | | | | | 350 | | |
| Leu | Pro | Pro | Ser | Arg | Glu | Glu | Met | Thr | Lys | Asn | Gln | Val | Ser | Leu | Thr |
| | | 355 | | | | | 360 | | | | | 365 | | | |

```
Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Cys Ser Pro Gly
        435                 440                 445

Lys

<210> SEQ ID NO 23
<211> LENGTH: 449
<212> TYPE: PRT
<213> ORGANISM: Artificial Sequence
<220> FEATURE:
<223> OTHER INFORMATION: antibody

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Pro Phe
            20                  25                  30

Ala Met His Trp Val Arg Gln Ala Pro Gly Lys Gly Leu Glu Trp Val
        35                  40                  45

Ala Lys Ile Ser Pro Gly Gly Ser Trp Thr Tyr Tyr Ser Asp Thr Val
    50                  55                  60

Thr Asp Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gln Val Trp Gly Tyr Tyr Ala Leu Asp Ile Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270
```

```
Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Cys Ser Pro Gly
            435                 440                 445

Lys

<210> SEQ ID NO 24
<211> LENGTH: 449
<212> TYPE: PRT
<213> ORGANISM: Artificial Sequence
<220> FEATURE:
<223> OTHER INFORMATION: antibody

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Pro Phe
            20                  25                  30

Ala Met His Trp Val Arg Gln Ala Pro Gly Lys Gly Leu Glu Trp Val
        35                  40                  45

Ala Lys Ile Ser Pro Gly Gly Ser Trp Thr Tyr Tyr Ser Asp Thr Val
    50                  55                  60

Thr Asp Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gln Gln Trp Gly Tyr Tyr Ala Leu Asp Ile Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

```
Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Cys Ser Pro Gly
        435                 440                 445

Lys

<210> SEQ ID NO 25
<211> LENGTH: 449
<212> TYPE: PRT
<213> ORGANISM: Artificial Sequence
<220> FEATURE:
<223> OTHER INFORMATION: antibody

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Pro Phe
            20                  25                  30

Ala Met His Trp Val Arg Gln Ala Pro Gly Lys Gly Leu Glu Trp Val
        35                  40                  45

Ala Lys Ile Ser Pro Gly Gly Ser Trp Thr Tyr Tyr Ser Asp Thr Val
    50                  55                  60

Thr Asp Arg Phe Thr Phe Ser Leu Asp Thr Ser Lys Ser Thr Ala Tyr
65                  70                  75                  80
```

```
Leu Gln Met Asn Ser Leu Arg Ala Glu Asp Thr Ala Val Tyr Tyr Cys
                85                  90                  95
Ala Arg Gln Lys Trp Gly Tyr Tyr Ala Leu Asp Ile Trp Gly Gln Gly
            100                 105                 110
Thr Leu Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
    210                 215                 220
Thr His Thr Cys Pro Pro Cys Pro Ala Pro Glu Ala Ala Gly Ala Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Glu Glu Met Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Cys Ser Pro Gly
        435                 440                 445
Lys

<210> SEQ ID NO 26
<211> LENGTH: 449
<212> TYPE: PRT
<213> ORGANISM: Artificial Sequence
<220> FEATURE:
<223> OTHER INFORMATION: antibody
```

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Pro Phe
            20                  25                  30

Ala Ile Ser Trp Val Arg Gln Ala Pro Gly Lys Gly Leu Glu Trp Val
        35                  40                  45

Ala Lys Ile Ser Pro Gly Gly Ser Trp Thr Tyr Tyr Ser Asp Thr Val
50                  55                  60

Thr Asp Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gln Leu Trp Gly Tyr Tyr Ala Leu Asp Val Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

```
Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Cys Ser Pro Gly
        435                 440                 445

Lys

<210> SEQ ID NO 27
<211> LENGTH: 449
<212> TYPE: PRT
<213> ORGANISM: Artificial Sequence
<220> FEATURE:
<223> OTHER INFORMATION: antibody

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Pro Phe
            20                  25                  30

Ala Trp Ser Trp Val Arg Gln Ala Pro Gly Lys Gly Leu Glu Trp Val
        35                  40                  45

Ala Lys Ile Ser Pro Gly Gly Ser Trp Thr Tyr Tyr Ser Asp Thr Val
    50                  55                  60

Thr Asp Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gln Leu Trp Gly Tyr Tyr Ala Leu Asp Val Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285
```

Ala Lys Thr Lys Pro Arg Glu Glu Gln Tyr Asn Ser Thr Tyr Arg Val
         290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                 325                 330                 335

Thr Ile Ser Lys Ala Lys Gly Gln Pro Arg Glu Pro Gln Val Tyr Thr
             340                 345                 350

Leu Pro Pro Ser Arg Glu Glu Met Thr Lys Asn Gln Val Ser Leu Thr
         355                 360                 365

Cys Leu Val Lys Gly Phe Tyr Pro Ser Asp Ile Ala Val Glu Trp Glu
         370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
             405                 410                 415

Ser Arg Trp Gln Gln Gly Asn Val Phe Ser Cys Ser Val Met His Glu
         420                 425                 430

Ala Leu His Asn His Tyr Thr Gln Lys Ser Leu Ser Cys Ser Pro Gly
         435                 440                 445

Lys

<210> SEQ ID NO 28
<211> LENGTH: 213
<212> TYPE: PRT
<213> ORGANISM: Artificial Sequence
<220> FEATURE:
<223> OTHER INFORMATION: antibody

<400> SEQUENCE: 28

Asp Ile Gln Leu Thr Gln Ser Pro Ser Leu Ser Ala Ser Val Gly
1               5                   10                  15

Asp Arg Val Thr Ile Thr Cys Ser Ala Ser Ile Ser Val Ser Tyr Leu
                 20                  25                  30

Tyr Trp Tyr Gln Gln Lys Pro Gly Lys Ala Pro Lys Leu Leu Ile Tyr
             35                  40                  45

Asp Asp Ser Ser Leu Ala Ser Gly Val Pro Ser Arg Phe Ser Gly Ser
         50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Gly Tyr Pro Tyr Thr
                 85                  90                  95

Phe Gly Gln Gly Thr Lys Val Glu Ile Lys Arg Thr Val Ala Ala Pro
             100                 105                 110

Ser Val Phe Ile Phe Pro Pro Ser Asp Glu Gln Leu Lys Ser Gly Thr
         115                 120                 125

Ala Ser Val Val Cys Leu Leu Asn Asn Phe Tyr Pro Arg Glu Ala Lys
     130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                 165                 170                 175

Thr Leu Thr Leu Ser Lys Ala Asp Tyr Glu Lys His Lys Val Tyr Ala
             180                 185                 190

Cys Glu Val Thr His Gln Gly Leu Ser Ser Pro Val Thr Lys Ser Phe
            195                 200                 205

Asn Arg Gly Glu Cys
    210

<210> SEQ ID NO 29
<211> LENGTH: 213
<212> TYPE: PRT
<213> ORGANISM: Artificial Sequence
<220> FEATURE:
<223> OTHER INFORMATION: antibody

<400> SEQUENCE: 29

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ile Ser Val Ser Tyr Leu
            20                  25                  30

Tyr Trp Tyr Gln Gln Lys Pro Gly Lys Ala Pro Lys Leu Leu Ile Tyr
        35                  40                  45

Asp Ala Ser Ser Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Gly Tyr Pro Tyr Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 30
<211> LENGTH: 213
<212> TYPE: PRT
<213> ORGANISM: Artificial Sequence
<220> FEATURE:
<223> OTHER INFORMATION: antibody

<400> SEQUENCE: 30

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ile Ser Val Ser Tyr Leu
            20                  25                  30

Tyr Trp Tyr Gln Gln Lys Pro Gly Lys Ala Pro Lys Leu Leu Ile Tyr
        35                  40                  45

Asp Asp Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Gly Tyr Pro Tyr Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 31
<211> LENGTH: 222
<212> TYPE: PRT
<213> ORGANISM: Artificial Sequence
<220> FEATURE:
<223> OTHER INFORMATION: antibody

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Pro Phe
            20                  25                  30

Ala Met His Trp Val Arg Gln Ala Pro Gly Lys Gly Leu Glu Trp Val
        35                  40                  45

Ala Lys Ile Ser Pro Gly Gly Ser Trp Thr Tyr Tyr Ser Asp Thr Val
    50                  55                  60

Thr Asp Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gln Ala Trp Gly Tyr Tyr Ala Leu Asp Ile Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

```
Ser Asn Thr Lys Val Asp Lys Lys Val Glu Pro Lys Ser Cys
210                 215                 220
```

<210> SEQ ID NO 32
<211> LENGTH: 222
<212> TYPE: PRT
<213> ORGANISM: Artificial Sequence
<220> FEATURE:
<223> OTHER INFORMATION: antibody

<400> SEQUENCE: 32

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Pro Phe
            20                  25                  30

Ala Met His Trp Val Arg Gln Ala Pro Gly Lys Gly Leu Glu Trp Val
        35                  40                  45

Ala Lys Ile Ser Pro Gly Gly Ser Trp Thr Tyr Tyr Ser Asp Thr Val
    50                  55                  60

Thr Asp Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gln Ser Trp Gly Tyr Tyr Ala Leu Asp Ile Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys
    210                 215                 220
```

<210> SEQ ID NO 33
<211> LENGTH: 222
<212> TYPE: PRT
<213> ORGANISM: Artificial Sequence
<220> FEATURE:
<223> OTHER INFORMATION: antibody

<400> SEQUENCE: 33

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Pro Phe
            20                  25                  30

Ala Met His Trp Val Arg Gln Ala Pro Gly Lys Gly Leu Glu Trp Val
        35                  40                  45

Ala Lys Ile Ser Pro Gly Gly Ser Trp Thr Tyr Tyr Ser Asp Thr Val
    50                  55                  60
```

```
Thr Asp Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                 85                  90                  95

Ala Arg Gln Gly Trp Gly Tyr Tyr Ala Leu Asp Ile Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys
    210                 215                 220

<210> SEQ ID NO 34
<211> LENGTH: 222
<212> TYPE: PRT
<213> ORGANISM: Artificial Sequence
<220> FEATURE:
<223> OTHER INFORMATION: antibody

<400> SEQUENCE: 34

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Pro Phe
             20                  25                  30

Ala Met His Trp Val Arg Gln Ala Pro Gly Lys Gly Leu Glu Trp Val
         35                  40                  45

Ala Lys Ile Ser Pro Gly Gly Ser Trp Thr Tyr Tyr Ser Asp Thr Val
     50                  55                  60

Thr Asp Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                 85                  90                  95

Ala Arg Gln Thr Trp Gly Tyr Tyr Ala Leu Asp Ile Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190
```

```
Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys
    210                 215                 220

<210> SEQ ID NO 35
<211> LENGTH: 222
<212> TYPE: PRT
<213> ORGANISM: Artificial Sequence
<220> FEATURE:
<223> OTHER INFORMATION: antibody

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Pro Phe
            20                  25                  30

Ala Met His Trp Val Arg Gln Ala Pro Gly Lys Gly Leu Glu Trp Val
        35                  40                  45

Ala Lys Ile Ser Pro Gly Gly Ser Trp Thr Tyr Tyr Ser Asp Thr Val
    50                  55                  60

Thr Asp Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gln Val Trp Gly Tyr Tyr Ala Leu Asp Ile Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys
    210                 215                 220

<210> SEQ ID NO 36
<211> LENGTH: 222
<212> TYPE: PRT
<213> ORGANISM: Artificial Sequence
<220> FEATURE:
<223> OTHER INFORMATION: antibody

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Pro Phe
            20                  25                  30

Ala Met His Trp Val Arg Gln Ala Pro Gly Lys Gly Leu Glu Trp Val
        35                  40                  45
```

```
Ala Lys Ile Ser Pro Gly Gly Ser Trp Thr Tyr Tyr Ser Asp Thr Val
 50                  55                  60

Thr Asp Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                 85                  90                  95

Ala Arg Gln Gln Trp Gly Tyr Tyr Ala Leu Asp Ile Trp Gly Gln Gly
                100                 105                 110

Thr Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys
210                 215                 220

<210> SEQ ID NO 37
<211> LENGTH: 222
<212> TYPE: PRT
<213> ORGANISM: Artificial Sequence
<220> FEATURE:
<223> OTHER INFORMATION: antibody

<400> SEQUENCE: 37

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Pro Phe
                 20                  25                  30

Ala Met His Trp Val Arg Gln Ala Pro Gly Lys Gly Leu Glu Trp Val
             35                  40                  45

Ala Lys Ile Ser Pro Gly Gly Ser Trp Thr Tyr Tyr Ser Asp Thr Val
 50                  55                  60

Thr Asp Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                 85                  90                  95

Ala Arg Gln Lys Trp Gly Tyr Tyr Ala Leu Asp Ile Trp Gly Gln Gly
                100                 105                 110

Thr Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190
```

-continued

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys
    210                 215                 220

<210> SEQ ID NO 38
<211> LENGTH: 222
<212> TYPE: PRT
<213> ORGANISM: Artificial Sequence
<220> FEATURE:
<223> OTHER INFORMATION: antibody

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Pro Phe
            20                  25                  30

Ala Ile Ser Trp Val Arg Gln Ala Pro Gly Lys Gly Leu Glu Trp Val
        35                  40                  45

Ala Lys Ile Ser Pro Gly Gly Ser Trp Thr Tyr Tyr Ser Asp Thr Val
    50                  55                  60

Thr Asp Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gln Leu Trp Gly Tyr Tyr Ala Leu Asp Val Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys
    210                 215                 220

<210> SEQ ID NO 39
<211> LENGTH: 222
<212> TYPE: PRT
<213> ORGANISM: Artificial Sequence
<220> FEATURE:
<223> OTHER INFORMATION: antibody

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Pro Phe
            20                  25                  30

Ala Trp Ser Trp Val Arg Gln Ala Pro Gly Lys Gly Leu Glu Trp Val
        35                  40                  45

```
Ala Lys Ile Ser Pro Gly Gly Ser Trp Thr Tyr Tyr Ser Asp Thr Val
     50                  55                  60

Thr Asp Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                 85                  90                  95

Ala Arg Gln Leu Trp Gly Tyr Tyr Ala Leu Asp Val Trp Gly Gln Gly
             100                 105                 110

Thr Leu Val Thr Val Ser Ser Ala Ser Thr Lys Gly Pro Ser Val Phe
         115                 120                 125

Pro Leu Ala Pro Ser Ser Lys Ser Thr Ser Gly Gly Thr Ala Ala Leu
     130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                 165                 170                 175

Gln Ser Ser Gly Leu Tyr Ser Leu Ser Ser Val Val Thr Val Pro Ser
             180                 185                 190

Ser Ser Leu Gly Thr Gln Thr Tyr Ile Cys Asn Val Asn His Lys Pro
         195                 200                 205

Ser Asn Thr Lys Val Asp Lys Lys Val Glu Pro Lys Ser Cys
     210                 215                 220

<210> SEQ ID NO 40
<211> LENGTH: 227
<212> TYPE: PRT
<213> ORGANISM: Artificial Sequence
<220> FEATURE:
<223> OTHER INFORMATION: antibody

<400> SEQUENCE: 40

Asp Lys Thr His Thr Cys Pro Pro Cys Pro Ala Pro Glu Ala Ala Gly
1               5                  10                  15

Ala Pro Ser Val Phe Leu Phe Pro Pro Lys Pro Lys Asp Thr Leu Met
             20                  25                  30

Ile Ser Arg Thr Pro Glu Val Thr Cys Val Val Val Asp Val Ser His
         35                  40                  45

Glu Asp Pro Glu Val Lys Phe Asn Trp Tyr Val Asp Gly Val Glu Val
     50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
             100                 105                 110

Glu Lys Thr Ile Ser Lys Ala Lys Gly Gln Pro Arg Glu Pro Gln Val
         115                 120                 125

Tyr Thr Leu Pro Pro Ser Arg Glu Glu Met Thr Lys Asn Gln Val Ser
     130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                 165                 170                 175
```

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Cys Ser
    210                 215                 220

Pro Gly Lys
225

<210> SEQ ID NO 41
<211> LENGTH: 227
<212> TYPE: PRT
<213> ORGANISM: Artificial Sequence
<220> FEATURE:
<223> OTHER INFORMATION: antibody

<400> SEQUENCE: 41

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Cys Ser
    210                 215                 220

Pro Gly Lys
225

<210> SEQ ID NO 42
<211> LENGTH: 227
<212> TYPE: PRT
<213> ORGANISM: Artificial Sequence
<220> FEATURE:
<223> OTHER INFORMATION: antobyd

<400> SEQUENCE: 42

```
Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Cys Ser
    210                 215                 220

Pro Gly Lys
225
```

<210> SEQ ID NO 43
<211> LENGTH: 227
<212> TYPE: PRT
<213> ORGANISM: Artificial Sequence
<220> FEATURE:
<223> OTHER INFORMATION: antibody

<400> SEQUENCE: 43

```
Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110
```

```
Glu Lys Thr Ile Ser Lys Ala Lys Gly Gln Pro Arg Glu Pro Gln Val
            115                 120                 125

Tyr Thr Leu Pro Pro Ser Arg Glu Glu Met Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Cys Ser
    210                 215                 220

Pro Gly Lys
225

<210> SEQ ID NO 44
<211> LENGTH: 227
<212> TYPE: PRT
<213> ORGANISM: Artificial Sequence
<220> FEATURE:
<223> OTHER INFORMATION: antibody

<400> SEQUENCE: 44

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Glu Glu Met Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Cys Ser
    210                 215                 220

Pro Gly Lys
225
```

```
<210> SEQ ID NO 45
<211> LENGTH: 227
<212> TYPE: PRT
<213> ORGANISM: Artificial Sequence
<220> FEATURE:
<223> OTHER INFORMATION: antibody

<400> SEQUENCE: 45

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Cys Ser
    210                 215                 220

Pro Gly Lys
225

<210> SEQ ID NO 46
<211> LENGTH: 227
<212> TYPE: PRT
<213> ORGANISM: Artificial Sequence
<220> FEATURE:
<223> OTHER INFORMATION: antibody

<400> SEQUENCE: 46

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80
```

```
Arg Val Val Ser Val Leu Thr Val Leu His Gln Asp Trp Leu Asn Gly
            85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Glu Glu Met Thr Lys Asn Gln Val Ser
        130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Cys Ser
    210                 215                 220

Pro Gly Lys
225

<210> SEQ ID NO 47
<211> LENGTH: 227
<212> TYPE: PRT
<213> ORGANISM: Artificial Sequence
<220> FEATURE:
<223> OTHER INFORMATION: antibody

<400> SEQUENCE: 47

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
            85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Glu Glu Met Thr Lys Asn Gln Val Ser
        130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205
```

His Glu Ala Leu His Asn His Tyr Thr Gln Lys Ser Leu Ser Cys Ser
    210                 215                 220

Pro Gly Lys
225

<210> SEQ ID NO 48
<211> LENGTH: 227
<212> TYPE: PRT
<213> ORGANISM: Artificial Sequence
<220> FEATURE:
<223> OTHER INFORMATION: antibody

<400> SEQUENCE: 48

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Cys Ser
    210                 215                 220

Pro Gly Lys
225

<210> SEQ ID NO 49
<211> LENGTH: 10
<212> TYPE: PRT
<213> ORGANISM: Artificial Sequence
<220> FEATURE:
<223> OTHER INFORMATION: antibody

<400> SEQUENCE: 49

Gly Phe Thr Phe Ser Pro Phe Ala Met His
1               5                   10

<210> SEQ ID NO 50
<211> LENGTH: 19
<212> TYPE: PRT

```
<213> ORGANISM: Artificial Sequence
<220> FEATURE:
<223> OTHER INFORMATION: antibody

<400> SEQUENCE: 50

Val Ala Lys Ile Ser Pro Gly Gly Ser Trp Thr Tyr Tyr Ser Asp Thr
1               5                   10                  15

Val Thr Asp

<210> SEQ ID NO 51
<211> LENGTH: 12
<212> TYPE: PRT
<213> ORGANISM: Artificial Sequence
<220> FEATURE:
<223> OTHER INFORMATION: antibody

<400> SEQUENCE: 51

Ala Arg Gln Ala Trp Gly Tyr Tyr Ala Leu Asp Ile
1               5                   10

<210> SEQ ID NO 52
<211> LENGTH: 10
<212> TYPE: PRT
<213> ORGANISM: Artificial Sequence
<220> FEATURE:
<223> OTHER INFORMATION: antibody

<400> SEQUENCE: 52

Gly Phe Thr Phe Ser Pro Phe Ala Met His
1               5                   10

<210> SEQ ID NO 53
<211> LENGTH: 19
<212> TYPE: PRT
<213> ORGANISM: Artificial Sequence
<220> FEATURE:
<223> OTHER INFORMATION: antibody

<400> SEQUENCE: 53

Val Ala Lys Ile Ser Pro Gly Gly Ser Trp Thr Tyr Tyr Ser Asp Thr
1               5                   10                  15

Val Thr Asp

<210> SEQ ID NO 54
<211> LENGTH: 12
<212> TYPE: PRT
<213> ORGANISM: Artificial Sequence
<220> FEATURE:
<223> OTHER INFORMATION: antibody

<400> SEQUENCE: 54

Ala Arg Gln Ser Trp Gly Tyr Tyr Ala Leu Asp Ile
1               5                   10

<210> SEQ ID NO 55
<211> LENGTH: 10
<212> TYPE: PRT
<213> ORGANISM: Artificial Sequence
<220> FEATURE:
<223> OTHER INFORMATION: antibody

<400> SEQUENCE: 55

Gly Phe Thr Phe Ser Pro Phe Ala Met His
1               5                   10
```

```
<210> SEQ ID NO 56
<211> LENGTH: 19
<212> TYPE: PRT
<213> ORGANISM: Artificial Sequence
<220> FEATURE:
<223> OTHER INFORMATION: antibody

<400> SEQUENCE: 56

Val Ala Lys Ile Ser Pro Gly Gly Ser Trp Thr Tyr Tyr Ser Asp Thr
1               5                   10                  15

Val Thr Asp

<210> SEQ ID NO 57
<211> LENGTH: 12
<212> TYPE: PRT
<213> ORGANISM: Artificial Sequence
<220> FEATURE:
<223> OTHER INFORMATION: antibody

<400> SEQUENCE: 57

Ala Arg Gln Gly Trp Gly Tyr Tyr Ala Leu Asp Ile
1               5                   10

<210> SEQ ID NO 58
<211> LENGTH: 10
<212> TYPE: PRT
<213> ORGANISM: Artificial Sequence
<220> FEATURE:
<223> OTHER INFORMATION: antibody

<400> SEQUENCE: 58

Gly Phe Thr Phe Ser Pro Phe Ala Met His
1               5                   10

<210> SEQ ID NO 59
<211> LENGTH: 19
<212> TYPE: PRT
<213> ORGANISM: Artificial Sequence
<220> FEATURE:
<223> OTHER INFORMATION: antibody

<400> SEQUENCE: 59

Val Ala Lys Ile Ser Pro Gly Gly Ser Trp Thr Tyr Tyr Ser Asp Thr
1               5                   10                  15

Val Thr Asp

<210> SEQ ID NO 60
<211> LENGTH: 12
<212> TYPE: PRT
<213> ORGANISM: Artificial Sequence
<220> FEATURE:
<223> OTHER INFORMATION: antibody

<400> SEQUENCE: 60

Ala Arg Gln Thr Trp Gly Tyr Tyr Ala Leu Asp Ile
1               5                   10

<210> SEQ ID NO 61
<211> LENGTH: 10
<212> TYPE: PRT
<213> ORGANISM: Artificial Sequence
<220> FEATURE:
<223> OTHER INFORMATION: antibody
```

-continued

```
<400> SEQUENCE: 61

Gly Phe Thr Phe Ser Pro Phe Ala Met His
1               5                   10

<210> SEQ ID NO 62
<211> LENGTH: 19
<212> TYPE: PRT
<213> ORGANISM: Artificial Sequence
<220> FEATURE:
<223> OTHER INFORMATION: antibody

<400> SEQUENCE: 62

Val Ala Lys Ile Ser Pro Gly Gly Ser Trp Thr Tyr Tyr Ser Asp Thr
1               5                   10                  15

Val Thr Asp

<210> SEQ ID NO 63
<211> LENGTH: 12
<212> TYPE: PRT
<213> ORGANISM: Artificial Sequence
<220> FEATURE:
<223> OTHER INFORMATION: antibody

<400> SEQUENCE: 63

Ala Arg Gln Val Trp Gly Tyr Tyr Ala Leu Asp Ile
1               5                   10

<210> SEQ ID NO 64
<211> LENGTH: 10
<212> TYPE: PRT
<213> ORGANISM: Artificial Sequence
<220> FEATURE:
<223> OTHER INFORMATION: antibody

<400> SEQUENCE: 64

Gly Phe Thr Phe Ser Pro Phe Ala Met His
1               5                   10

<210> SEQ ID NO 65
<211> LENGTH: 19
<212> TYPE: PRT
<213> ORGANISM: Artificial Sequence
<220> FEATURE:
<223> OTHER INFORMATION: antibody

<400> SEQUENCE: 65

Val Ala Lys Ile Ser Pro Gly Gly Ser Trp Thr Tyr Tyr Ser Asp Thr
1               5                   10                  15

Val Thr Asp

<210> SEQ ID NO 66
<211> LENGTH: 12
<212> TYPE: PRT
<213> ORGANISM: Artificial Sequence
<220> FEATURE:
<223> OTHER INFORMATION: antibody

<400> SEQUENCE: 66

Ala Arg Gln Gln Trp Gly Tyr Tyr Ala Leu Asp Ile
1               5                   10

<210> SEQ ID NO 67
<211> LENGTH: 10
<212> TYPE: PRT
```

<213> ORGANISM: Artificial Sequence
<220> FEATURE:
<223> OTHER INFORMATION: antibody

<400> SEQUENCE: 67

Gly Phe Thr Phe Ser Pro Phe Ala Met His
1               5                   10

<210> SEQ ID NO 68
<211> LENGTH: 19
<212> TYPE: PRT
<213> ORGANISM: Artificial Sequence
<220> FEATURE:
<223> OTHER INFORMATION: antibody

<400> SEQUENCE: 68

Val Ala Lys Ile Ser Pro Gly Gly Ser Trp Thr Tyr Tyr Ser Asp Thr
1               5                   10                  15

Val Thr Asp

<210> SEQ ID NO 69
<211> LENGTH: 12
<212> TYPE: PRT
<213> ORGANISM: Artificial Sequence
<220> FEATURE:
<223> OTHER INFORMATION: antibody

<400> SEQUENCE: 69

Ala Arg Gln Lys Trp Gly Tyr Tyr Ala Leu Asp Ile
1               5                   10

<210> SEQ ID NO 70
<211> LENGTH: 10
<212> TYPE: PRT
<213> ORGANISM: Artificial Sequence
<220> FEATURE:
<223> OTHER INFORMATION: antibody

<400> SEQUENCE: 70

Gly Phe Thr Phe Ser Pro Phe Ala Ile Ser
1               5                   10

<210> SEQ ID NO 71
<211> LENGTH: 19
<212> TYPE: PRT
<213> ORGANISM: Artificial Sequence
<220> FEATURE:
<223> OTHER INFORMATION: antibody

<400> SEQUENCE: 71

Val Ala Lys Ile Ser Pro Gly Gly Ser Trp Thr Tyr Tyr Ser Asp Thr
1               5                   10                  15

Val Thr Asp

<210> SEQ ID NO 72
<211> LENGTH: 12
<212> TYPE: PRT
<213> ORGANISM: Artificial Sequence
<220> FEATURE:
<223> OTHER INFORMATION: antibody

<400> SEQUENCE: 72

Ala Arg Gln Leu Trp Gly Tyr Tyr Ala Leu Asp Val
1               5                   10

```
<210> SEQ ID NO 73
<211> LENGTH: 10
<212> TYPE: PRT
<213> ORGANISM: Artificial Sequence
<220> FEATURE:
<223> OTHER INFORMATION: antibody

<400> SEQUENCE: 73

Gly Phe Thr Phe Ser Pro Phe Ala Trp Ser
1               5                   10

<210> SEQ ID NO 74
<211> LENGTH: 19
<212> TYPE: PRT
<213> ORGANISM: Artificial Sequence
<220> FEATURE:
<223> OTHER INFORMATION: antibody

<400> SEQUENCE: 74

Val Ala Lys Ile Ser Pro Gly Gly Ser Trp Thr Tyr Tyr Ser Asp Thr
1               5                   10                  15

Val Thr Asp

<210> SEQ ID NO 75
<211> LENGTH: 12
<212> TYPE: PRT
<213> ORGANISM: Artificial Sequence
<220> FEATURE:
<223> OTHER INFORMATION: antibody

<400> SEQUENCE: 75

Ala Arg Gln Leu Trp Gly Tyr Tyr Ala Leu Asp Val
1               5                   10

<210> SEQ ID NO 76
<211> LENGTH: 10
<212> TYPE: PRT
<213> ORGANISM: Artificial Sequence
<220> FEATURE:
<223> OTHER INFORMATION: antibody

<400> SEQUENCE: 76

Ser Ala Ser Ile Ser Val Ser Tyr Leu Tyr
1               5                   10

<210> SEQ ID NO 77
<211> LENGTH: 11
<212> TYPE: PRT
<213> ORGANISM: Artificial Sequence
<220> FEATURE:
<223> OTHER INFORMATION: antibody

<400> SEQUENCE: 77

Leu Leu Ile Tyr Asp Asp Ser Ser Leu Ala Ser
1               5                   10

<210> SEQ ID NO 78
<211> LENGTH: 9
<212> TYPE: PRT
<213> ORGANISM: Artificial Sequence
<220> FEATURE:
<223> OTHER INFORMATION: antibody

<400> SEQUENCE: 78

Gln Gln Trp Ser Gly Tyr Pro Tyr Thr
1               5
```

<210> SEQ ID NO 79
<211> LENGTH: 10
<212> TYPE: PRT
<213> ORGANISM: Artificial Sequence
<220> FEATURE:
<223> OTHER INFORMATION: antibody

<400> SEQUENCE: 79

Ser Ala Ser Ile Ser Val Ser Tyr Leu Tyr
1               5                   10

<210> SEQ ID NO 80
<211> LENGTH: 11
<212> TYPE: PRT
<213> ORGANISM: Artificial Sequence
<220> FEATURE:
<223> OTHER INFORMATION: antibody

<400> SEQUENCE: 80

Leu Leu Ile Tyr Asp Ala Ser Ser Leu Ala Ser
1               5                   10

<210> SEQ ID NO 81
<211> LENGTH: 9
<212> TYPE: PRT
<213> ORGANISM: Artificial Sequence
<220> FEATURE:
<223> OTHER INFORMATION: antibody

<400> SEQUENCE: 81

Gln Gln Trp Ser Gly Tyr Pro Tyr Thr
1               5

<210> SEQ ID NO 82
<211> LENGTH: 10
<212> TYPE: PRT
<213> ORGANISM: Artificial Sequence
<220> FEATURE:
<223> OTHER INFORMATION: antibody

<400> SEQUENCE: 82

Ser Ala Ser Ile Ser Val Ser Tyr Leu Tyr
1               5                   10

<210> SEQ ID NO 83
<211> LENGTH: 11
<212> TYPE: PRT
<213> ORGANISM: Artificial Sequence
<220> FEATURE:
<223> OTHER INFORMATION: antibody

<400> SEQUENCE: 83

Leu Leu Ile Tyr Asp Asp Ser Asn Leu Ala Ser
1               5                   10

<210> SEQ ID NO 84
<211> LENGTH: 9
<212> TYPE: PRT
<213> ORGANISM: Artificial Sequence
<220> FEATURE:
<223> OTHER INFORMATION: antibody

<400> SEQUENCE: 84

Gln Gln Trp Ser Gly Tyr Pro Tyr Thr
1               5

```
<210> SEQ ID NO 85
<211> LENGTH: 432
<212> TYPE: PRT
<213> ORGANISM: Artificial Sequence
<220> FEATURE:
<223> OTHER INFORMATION: antibody

<400> SEQUENCE: 85
```

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Asp Lys Thr
        195                 200                 205

His Thr Cys Pro Pro Cys Pro Ala Pro Glu Ala Ala Gly Ala Pro Ser
    210                 215                 220

Val Phe Leu Phe Pro Pro Lys Pro Lys Asp Thr Leu Met Ile Ser Arg
225                 230                 235                 240

Thr Pro Glu Val Thr Cys Val Val Val Asp Val Ser His Glu Asp Pro
                245                 250                 255

Glu Val Lys Phe Asn Trp Tyr Val Asp Gly Val Glu Val His Asn Ala
            260                 265                 270

Lys Thr Lys Pro Arg Glu Glu Gln Tyr Asn Ser Thr Tyr Arg Val Val
        275                 280                 285

Ser Val Leu Thr Val Leu His Gln Asp Trp Leu Asn Gly Lys Glu Tyr
    290                 295                 300

Lys Cys Lys Val Ser Asn Lys Ala Leu Pro Ala Pro Ile Glu Lys Thr
305                 310                 315                 320

Ile Ser Lys Ala Lys Gly Gln Pro Arg Glu Pro Gln Val Tyr Thr Leu
                325                 330                 335

Pro Pro Ser Arg Glu Glu Met Thr Lys Asn Gln Val Ser Leu Thr Cys
            340                 345                 350

Leu Val Lys Gly Phe Tyr Pro Ser Asp Ile Ala Val Glu Trp Glu Ser
        355                 360                 365

```
Asn Gly Gln Pro Glu Asn Asn Tyr Lys Thr Thr Pro Pro Val Leu Asp
        370                 375                 380

Ser Asp Gly Ser Phe Phe Leu Tyr Ser Lys Leu Thr Val Asp Lys Ser
385                 390                 395                 400

Arg Trp Gln Gln Gly Asn Val Phe Ser Cys Ser Val Met His Glu Ala
                405                 410                 415

Leu His Asn His Tyr Thr Gln Lys Ser Leu Ser Cys Ser Pro Gly Lys
                420                 425                 430

<210> SEQ ID NO 86
<211> LENGTH: 432
<212> TYPE: PRT
<213> ORGANISM: Artificial Sequence
<220> FEATURE:
<223> OTHER INFORMATION: antibody

<400> SEQUENCE: 86

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
                20                  25                  30

Thr Ser Pro Asn Ile Thr Val Thr Leu Lys Lys Phe Pro Leu Asp Thr
            35                  40                  45

Leu Ile Pro Asp Gly Lys Arg Ile Ile Trp Asp Ser Arg Lys Gly Phe
50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Ile His Arg
                85                  90                  95

Gln Thr Asn Thr Ile Ile Asp Val Val Leu Ser Pro Ser His Gly Ile
                100                 105                 110

Glu Leu Ser Val Gly Glu Lys Leu Val Leu Asn Cys Thr Ala Arg Thr
            115                 120                 125

Glu Leu Asn Val Gly Ile Asp Phe Asn Trp Glu Tyr Pro Ser Ser Lys
130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Asp Lys Thr
            195                 200                 205

His Thr Cys Pro Pro Cys Pro Ala Pro Glu Ala Ala Gly Ala Pro Ser
210                 215                 220

Val Phe Leu Phe Pro Pro Lys Pro Lys Asp Thr Leu Met Ile Ser Arg
225                 230                 235                 240

Thr Pro Glu Val Thr Cys Val Val Val Asp Val Ser His Glu Asp Pro
                245                 250                 255

Glu Val Lys Phe Asn Trp Tyr Val Asp Gly Val Glu Val His Asn Ala
                260                 265                 270

Lys Thr Lys Pro Arg Glu Glu Gln Tyr Asn Ser Thr Tyr Arg Val Val
            275                 280                 285

Ser Val Leu Thr Val Leu His Gln Asp Trp Leu Asn Gly Lys Glu Tyr
290                 295                 300
```

-continued

Lys Cys Lys Val Ser Asn Lys Ala Leu Pro Ala Pro Ile Glu Lys Thr
305                 310                 315                 320

Ile Ser Lys Ala Lys Gly Gln Pro Arg Glu Pro Gln Val Tyr Thr Leu
                325                 330                 335

Pro Pro Ser Arg Glu Glu Met Thr Lys Asn Gln Val Ser Leu Thr Cys
            340                 345                 350

Leu Val Lys Gly Phe Tyr Pro Ser Asp Ile Ala Val Glu Trp Glu Ser
                355                 360                 365

Asn Gly Gln Pro Glu Asn Asn Tyr Lys Thr Thr Pro Pro Val Leu Asp
            370                 375                 380

Ser Asp Gly Ser Phe Phe Leu Tyr Ser Lys Leu Thr Val Asp Lys Ser
385                 390                 395                 400

Arg Trp Gln Gln Gly Asn Val Phe Ser Cys Ser Val Met His Glu Ala
                405                 410                 415

Leu His Asn His Tyr Thr Gln Lys Ser Leu Ser Cys Ser Pro Gly Lys
            420                 425                 430

<210> SEQ ID NO 87
<211> LENGTH: 432
<212> TYPE: PRT
<213> ORGANISM: Artificial Sequence
<220> FEATURE:
<223> OTHER INFORMATION: antibody

<400> SEQUENCE: 87

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
                20                  25                  30

Thr Ser Pro Asn Ile Thr Val Thr Leu Lys Lys Phe Pro Leu Asp Thr
            35                  40                  45

Leu Ile Pro Asp Gly Lys Arg Ile Ile Trp Asp Ser Arg Lys Gly Phe
50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr Ile Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Asp Lys Thr
        195                 200                 205

His Thr Cys Pro Pro Cys Pro Ala Pro Glu Ala Ala Gly Ala Pro Ser
    210                 215                 220

Val Phe Leu Phe Pro Pro Lys Pro Lys Asp Thr Leu Met Ile Ser Arg
225                 230                 235                 240

```
Thr Pro Glu Val Thr Cys Val Val Asp Val Ser His Glu Asp Pro
            245                 250                 255

Glu Val Lys Phe Asn Trp Tyr Val Asp Gly Val Glu Val His Asn Ala
        260                 265                 270

Lys Thr Lys Pro Arg Glu Glu Gln Tyr Asn Ser Thr Tyr Arg Val Val
    275                 280                 285

Ser Val Leu Thr Val Leu His Gln Asp Trp Leu Asn Gly Lys Glu Tyr
290                 295                 300

Lys Cys Lys Val Ser Asn Lys Ala Leu Pro Ala Pro Ile Glu Lys Thr
305                 310                 315                 320

Ile Ser Lys Ala Lys Gly Gln Pro Arg Glu Pro Gln Val Tyr Thr Leu
            325                 330                 335

Pro Pro Ser Arg Glu Glu Met Thr Lys Asn Gln Val Ser Leu Thr Cys
        340                 345                 350

Leu Val Lys Gly Phe Tyr Pro Ser Asp Ile Ala Val Glu Trp Glu Ser
    355                 360                 365

Asn Gly Gln Pro Glu Asn Asn Tyr Lys Thr Thr Pro Pro Val Leu Asp
370                 375                 380

Ser Asp Gly Ser Phe Phe Leu Tyr Ser Lys Leu Thr Val Asp Lys Ser
385                 390                 395                 400

Arg Trp Gln Gln Gly Asn Val Phe Ser Cys Ser Val Met His Glu Ala
            405                 410                 415

Leu His Asn His Tyr Thr Gln Lys Ser Leu Ser Cys Ser Pro Gly Lys
        420                 425                 430

<210> SEQ ID NO 88
<211> LENGTH: 432
<212> TYPE: PRT
<213> ORGANISM: Artificial Sequence
<220> FEATURE:
<223> OTHER INFORMATION: antibody

<400> SEQUENCE: 88

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Ile Ile Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175
```

```
Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Asp Lys Thr
            195                 200                 205

His Thr Cys Pro Pro Cys Pro Ala Pro Glu Ala Ala Gly Ala Pro Ser
            210                 215                 220

Val Phe Leu Phe Pro Pro Lys Pro Lys Asp Thr Leu Met Ile Ser Arg
225                 230                 235                 240

Thr Pro Glu Val Thr Cys Val Val Val Asp Val Ser His Glu Asp Pro
                245                 250                 255

Glu Val Lys Phe Asn Trp Tyr Val Asp Gly Val Glu Val His Asn Ala
            260                 265                 270

Lys Thr Lys Pro Arg Glu Glu Gln Tyr Asn Ser Thr Tyr Arg Val Val
            275                 280                 285

Ser Val Leu Thr Val Leu His Gln Asp Trp Leu Asn Gly Lys Glu Tyr
            290                 295                 300

Lys Cys Lys Val Ser Asn Lys Ala Leu Pro Ala Pro Ile Glu Lys Thr
305                 310                 315                 320

Ile Ser Lys Ala Lys Gly Gln Pro Arg Glu Pro Gln Val Tyr Thr Leu
                325                 330                 335

Pro Pro Ser Arg Glu Glu Met Thr Lys Asn Gln Val Ser Leu Thr Cys
            340                 345                 350

Leu Val Lys Gly Phe Tyr Pro Ser Asp Ile Ala Val Glu Trp Glu Ser
            355                 360                 365

Asn Gly Gln Pro Glu Asn Asn Tyr Lys Thr Thr Pro Pro Val Leu Asp
            370                 375                 380

Ser Asp Gly Ser Phe Phe Leu Tyr Ser Lys Leu Thr Val Asp Lys Ser
385                 390                 395                 400

Arg Trp Gln Gln Gly Asn Val Phe Ser Cys Ser Val Met His Glu Ala
                405                 410                 415

Leu His Asn His Tyr Thr Gln Lys Ser Leu Ser Cys Ser Pro Gly Lys
            420                 425                 430

<210> SEQ ID NO 89
<211> LENGTH: 119
<212> TYPE: PRT
<213> ORGANISM: Artificial Sequence
<220> FEATURE:
<223> OTHER INFORMATION: antibody

<400> SEQUENCE: 89

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Pro Phe
            20                  25                  30

Ala Ile Ser Trp Val Arg Gln Ala Pro Gly Lys Gly Leu Glu Trp Val
            35                  40                  45

Ala Lys Ile Ser Pro Gly Gly Ser Trp Thr Tyr Tyr Ser Asp Thr Val
    50                  55                  60

Thr Asp Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gln Leu Trp Gly Tyr Tyr Ala Leu Asp Val Trp Gly Gln Gly
            100                 105                 110
```

Thr Leu Val Thr Val Ser Ser
        115

<210> SEQ ID NO 90
<211> LENGTH: 119
<212> TYPE: PRT
<213> ORGANISM: Artificial Sequence
<220> FEATURE:
<223> OTHER INFORMATION: antibody

<400> SEQUENCE: 90

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Pro Phe
            20                  25                  30

Ala Trp Ser Trp Val Arg Gln Ala Pro Gly Lys Gly Leu Glu Trp Val
        35                  40                  45

Ala Lys Ile Ser Pro Gly Gly Ser Trp Thr Tyr Tyr Ser Asp Thr Val
    50                  55                  60

Thr Asp Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gln Leu Trp Gly Tyr Tyr Ala Leu Asp Val Trp Gly Gln Gly
            100                 105                 110

Thr Leu Val Thr Val Ser Ser
        115

<210> SEQ ID NO 91
<211> LENGTH: 106
<212> TYPE: PRT
<213> ORGANISM: Artificial Sequence
<220> FEATURE:
<223> OTHER INFORMATION: antibody

<400> SEQUENCE: 91

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ile Ser Val Ser Tyr Leu
            20                  25                  30

Tyr Trp Tyr Gln Gln Lys Pro Gly Lys Ala Pro Lys Leu Leu Ile Tyr
        35                  40                  45

Asp Asp Ser Ser Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Gly Tyr Pro Tyr Thr
                85                  90                  95

Phe Gly Gln Gly Thr Lys Val Glu Ile Lys
            100                 105

<210> SEQ ID NO 92
<211> LENGTH: 106
<212> TYPE: PRT
<213> ORGANISM: Artificial Sequence
<220> FEATURE:
<223> OTHER INFORMATION: antibody

<400> SEQUENCE: 92

Asp Ile Gln Leu Thr Gln Ser Pro Ser Leu Ser Ala Ser Val Gly
1               5                   10                  15

Asp Arg Val Thr Ile Thr Cys Ser Ala Ser Ile Ser Val Ser Tyr Leu
            20                  25                  30

Tyr Trp Tyr Gln Gln Lys Pro Gly Lys Ala Pro Lys Leu Leu Ile Tyr
            35                  40                  45

Asp Ala Ser Ser Leu Ala Ser Gly Val Pro Ser Arg Phe Ser Gly Ser
50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Gly Tyr Pro Tyr Thr
                85                  90                  95

Phe Gly Gln Gly Thr Lys Val Glu Ile Lys
            100                 105

<210> SEQ ID NO 93
<211> LENGTH: 106
<212> TYPE: PRT
<213> ORGANISM: Artificial Sequence
<220> FEATURE:
<223> OTHER INFORMATION: antibody

<400> SEQUENCE: 93

Asp Ile Gln Leu Thr Gln Ser Pro Ser Leu Ser Ala Ser Val Gly
1               5                   10                  15

Asp Arg Val Thr Ile Thr Cys Ser Ala Ser Ile Ser Val Ser Tyr Leu
            20                  25                  30

Tyr Trp Tyr Gln Gln Lys Pro Gly Lys Ala Pro Lys Leu Leu Ile Tyr
            35                  40                  45

Asp Asp Ser Asn Leu Ala Ser Gly Val Pro Ser Arg Phe Ser Gly Ser
50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Gly Tyr Pro Tyr Thr
                85                  90                  95

Phe Gly Gln Gly Thr Lys Val Glu Ile Lys
            100                 105

<210> SEQ ID NO 94
<211> LENGTH: 10
<212> TYPE: PRT
<213> ORGANISM: Artificial Sequence
<220> FEATURE:
<223> OTHER INFORMATION: antibody

<400> SEQUENCE: 94

Gly Phe Thr Phe Ser Pro Phe Ala Met Ser
1               5                   10

<210> SEQ ID NO 95
<211> LENGTH: 17
<212> TYPE: PRT
<213> ORGANISM: Artificial Sequence
<220> FEATURE:
<223> OTHER INFORMATION: antibody

```
<400> SEQUENCE: 95

Lys Ile Ser Pro Gly Gly Ser Trp Thr Tyr Tyr Ser Asp Thr Val Thr
1               5                   10                  15

Gly

<210> SEQ ID NO 96
<211> LENGTH: 10
<212> TYPE: PRT
<213> ORGANISM: Artificial Sequence
<220> FEATURE:
<223> OTHER INFORMATION: antibody

<400> SEQUENCE: 96

Ser Ala Ser Ile Ser Val Ser Tyr Met Tyr
1               5                   10

<210> SEQ ID NO 97
<211> LENGTH: 7
<212> TYPE: PRT
<213> ORGANISM: Artificial Sequence
<220> FEATURE:
<223> OTHER INFORMATION: antibody

<400> SEQUENCE: 97

Asp Met Ser Asn Leu Ala Ser
1               5

<210> SEQ ID NO 98
<211> LENGTH: 9
<212> TYPE: PRT
<213> ORGANISM: Artificial Sequence
<220> FEATURE:
<223> OTHER INFORMATION: antibody

<400> SEQUENCE: 98

Met Gln Trp Ser Gly Tyr Pro Tyr Thr
1               5

<210> SEQ ID NO 99
<211> LENGTH: 10
<212> TYPE: PRT
<213> ORGANISM: Artificial Sequence
<220> FEATURE:
<223> OTHER INFORMATION: artifical

<400> SEQUENCE: 99

Gly Phe Thr Phe Ser Pro Phe Ala Ile Ser
1               5                   10

<210> SEQ ID NO 100
<211> LENGTH: 19
<212> TYPE: PRT
<213> ORGANISM: Artificial Sequence
<220> FEATURE:
<223> OTHER INFORMATION: antibody

<400> SEQUENCE: 100

Val Ala Lys Ile Ser Pro Gly Gly Ser Trp Thr Tyr Tyr Ser Asp Thr
1               5                   10                  15

Val Thr Asp

<210> SEQ ID NO 101
<211> LENGTH: 12
<212> TYPE: PRT
```

```
<213> ORGANISM: Artificial Sequence
<220> FEATURE:
<223> OTHER INFORMATION: antibody

<400> SEQUENCE: 101

Ala Arg Gln Leu Trp Gly Tyr Tyr Ala Leu Asp Val
1               5                   10

<210> SEQ ID NO 102
<211> LENGTH: 10
<212> TYPE: PRT
<213> ORGANISM: Artificial Sequence
<220> FEATURE:
<223> OTHER INFORMATION: antibody

<400> SEQUENCE: 102

Gly Phe Thr Phe Ser Pro Phe Ala Trp Ser
1               5                   10

<210> SEQ ID NO 103
<211> LENGTH: 19
<212> TYPE: PRT
<213> ORGANISM: Artificial Sequence
<220> FEATURE:
<223> OTHER INFORMATION: antibody

<400> SEQUENCE: 103

Val Ala Lys Ile Ser Pro Gly Gly Ser Trp Thr Tyr Tyr Ser Asp Thr
1               5                   10                  15

Val Thr Asp

<210> SEQ ID NO 104
<211> LENGTH: 12
<212> TYPE: PRT
<213> ORGANISM: Artificial Sequence
<220> FEATURE:
<223> OTHER INFORMATION: antibody

<400> SEQUENCE: 104

Ala Arg Gln Leu Trp Gly Tyr Tyr Ala Leu Asp Val
1               5                   10

<210> SEQ ID NO 105
<211> LENGTH: 10
<212> TYPE: PRT
<213> ORGANISM: Artificial Sequence
<220> FEATURE:
<223> OTHER INFORMATION: antibody

<400> SEQUENCE: 105

Ser Ala Ser Ile Ser Val Ser Tyr Leu Tyr
1               5                   10

<210> SEQ ID NO 106
<211> LENGTH: 11
<212> TYPE: PRT
<213> ORGANISM: Artificial Sequence
<220> FEATURE:
<223> OTHER INFORMATION: antibody

<400> SEQUENCE: 106

Leu Leu Ile Tyr Asp Asp Ser Ser Leu Ala Ser
1               5                   10

<210> SEQ ID NO 107
<211> LENGTH: 9
```

```
<212> TYPE: PRT
<213> ORGANISM: Artificial Sequence
<220> FEATURE:
<223> OTHER INFORMATION: antibody

<400> SEQUENCE: 107

Gln Gln Trp Ser Gly Tyr Pro Tyr Thr
1               5

<210> SEQ ID NO 108
<211> LENGTH: 10
<212> TYPE: PRT
<213> ORGANISM: Artificial Sequence
<220> FEATURE:
<223> OTHER INFORMATION: antibody

<400> SEQUENCE: 108

Ser Ala Ser Ile Ser Val Ser Tyr Leu Tyr
1               5                   10

<210> SEQ ID NO 109
<211> LENGTH: 11
<212> TYPE: PRT
<213> ORGANISM: Artificial Sequence
<220> FEATURE:
<223> OTHER INFORMATION: antibody

<400> SEQUENCE: 109

Leu Leu Ile Tyr Asp Ala Ser Ser Leu Ala Ser
1               5                   10

<210> SEQ ID NO 110
<211> LENGTH: 9
<212> TYPE: PRT
<213> ORGANISM: Artificial Sequence
<220> FEATURE:
<223> OTHER INFORMATION: antibody

<400> SEQUENCE: 110

Gln Gln Trp Ser Gly Tyr Pro Tyr Thr
1               5

<210> SEQ ID NO 111
<211> LENGTH: 10
<212> TYPE: PRT
<213> ORGANISM: Artificial Sequence
<220> FEATURE:
<223> OTHER INFORMATION: antibody

<400> SEQUENCE: 111

Ser Ala Ser Ile Ser Val Ser Tyr Leu Tyr
1               5                   10

<210> SEQ ID NO 112
<211> LENGTH: 11
<212> TYPE: PRT
<213> ORGANISM: Artificial Sequence
<220> FEATURE:
<223> OTHER INFORMATION: antibody

<400> SEQUENCE: 112

Leu Leu Ile Tyr Asp Asp Ser Asn Leu Ala Ser
1               5                   10

<210> SEQ ID NO 113
<211> LENGTH: 9
<212> TYPE: PRT
```

```
<213> ORGANISM: Artificial Sequence
<220> FEATURE:
<223> OTHER INFORMATION: antibody

<400> SEQUENCE: 113

Gln Gln Trp Ser Gly Tyr Pro Tyr Thr
1               5

<210> SEQ ID NO 114
<211> LENGTH: 205
<212> TYPE: PRT
<213> ORGANISM: Artificial Sequence
<220> FEATURE:
<223> OTHER INFORMATION: fusion

<400> SEQUENCE: 114

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys
        195                 200                 205

<210> SEQ ID NO 115
<211> LENGTH: 10
<212> TYPE: PRT
<213> ORGANISM: Artificial Sequence
<220> FEATURE:
<223> OTHER INFORMATION: antibody

<400> SEQUENCE: 115

Gly Gly Gly Gly Ser Gly Gly Gly Gly Ser
1               5                   10

<210> SEQ ID NO 116
<211> LENGTH: 664
<212> TYPE: PRT
<213> ORGANISM: Artificial Sequence
<220> FEATURE:
<223> OTHER INFORMATION: fuison
```

-continued

<400> SEQUENCE: 116

```
Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Gly Gly Gly
        195                 200                 205

Gly Ser Gly Gly Gly Gly Ser Glu Val Gln Leu Val Glu Ser Gly Gly
    210                 215                 220

Gly Leu Val Gln Pro Gly Gly Ser Leu Arg Leu Ser Cys Ala Ala Ser
225                 230                 235                 240

Gly Phe Thr Phe Ser Pro Phe Ala Ile Ser Trp Val Arg Gln Ala Pro
                245                 250                 255

Gly Lys Gly Leu Glu Trp Val Ala Lys Ile Ser Pro Gly Gly Ser Trp
            260                 265                 270

Thr Tyr Tyr Ser Asp Thr Val Thr Asp Arg Phe Thr Phe Ser Leu Asp
        275                 280                 285

Thr Ser Lys Ser Thr Ala Tyr Leu Gln Met Asn Ser Leu Arg Ala Glu
    290                 295                 300

Asp Thr Ala Val Tyr Tyr Cys Ala Arg Gln Leu Trp Gly Tyr Tyr Ala
305                 310                 315                 320

Leu Asp Val Trp Gly Gln Gly Thr Leu Val Thr Val Ser Ser Ala Ser
                325                 330                 335

Thr Lys Gly Pro Ser Val Phe Pro Leu Ala Pro Ser Ser Lys Ser Thr
            340                 345                 350

Ser Gly Gly Thr Ala Ala Leu Gly Cys Leu Val Lys Asp Tyr Phe Pro
        355                 360                 365

Glu Pro Val Thr Val Ser Trp Asn Ser Gly Ala Leu Thr Ser Gly Val
    370                 375                 380

His Thr Phe Pro Ala Val Leu Gln Ser Ser Gly Leu Tyr Ser Leu Ser
385                 390                 395                 400

Ser Val Val Thr Val Pro Ser Ser Ser Leu Gly Thr Gln Thr Tyr Ile
                405                 410                 415
```

```
Cys Asn Val Asn His Lys Pro Ser Asn Thr Lys Val Asp Lys Lys Val
                420                 425                 430

Glu Pro Lys Ser Cys Asp Lys Thr His Thr Cys Pro Pro Cys Pro Ala
            435                 440                 445

Pro Glu Ala Ala Gly Ala Pro Ser Val Phe Leu Phe Pro Pro Lys Pro
    450                 455                 460

Lys Asp Thr Leu Met Ile Ser Arg Thr Pro Glu Val Thr Cys Val Val
465                 470                 475                 480

Val Asp Val Ser His Glu Asp Pro Glu Val Lys Phe Asn Trp Tyr Val
                485                 490                 495

Asp Gly Val Glu Val His Asn Ala Lys Thr Lys Pro Arg Glu Glu Gln
                500                 505                 510

Tyr Asn Ser Thr Tyr Arg Val Val Ser Val Leu Thr Val Leu His Gln
            515                 520                 525

Asp Trp Leu Asn Gly Lys Glu Tyr Lys Cys Lys Val Ser Asn Lys Ala
530                 535                 540

Leu Pro Ala Pro Ile Glu Lys Thr Ile Ser Lys Ala Lys Gly Gln Pro
545                 550                 555                 560

Arg Glu Pro Gln Val Tyr Thr Leu Pro Pro Ser Arg Glu Glu Met Thr
                565                 570                 575

Lys Asn Gln Val Ser Leu Thr Cys Leu Val Lys Gly Phe Tyr Pro Ser
            580                 585                 590

Asp Ile Ala Val Glu Trp Glu Ser Asn Gly Gln Pro Glu Asn Asn Tyr
            595                 600                 605

Lys Thr Thr Pro Pro Val Leu Asp Ser Asp Gly Ser Phe Phe Leu Tyr
            610                 615                 620

Ser Lys Leu Thr Val Asp Lys Ser Arg Trp Gln Gln Gly Asn Val Phe
625                 630                 635                 640

Ser Cys Ser Val Met His Glu Ala Leu His Asn His Tyr Thr Gln Lys
                645                 650                 655

Ser Leu Ser Cys Ser Pro Gly Lys
                660

<210> SEQ ID NO 117
<211> LENGTH: 213
<212> TYPE: PRT
<213> ORGANISM: Artificial Sequence
<220> FEATURE:
<223> OTHER INFORMATION: light chain

<400> SEQUENCE: 117

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ile Ser Val Ser Tyr Leu
            20                  25                  30

Tyr Trp Tyr Gln Gln Lys Pro Gly Lys Ala Pro Lys Leu Leu Ile Tyr
        35                  40                  45

Asp Asp Ser Ser Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Gly Tyr Pro Tyr Thr
                85                  90                  95

Phe Gly Gln Gly Thr Lys Val Glu Ile Lys Arg Thr Val Ala Ala Pro
            100                 105                 110
```

```
Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
        210

<210> SEQ ID NO 118
<211> LENGTH: 664
<212> TYPE: PRT
<213> ORGANISM: Artificial Sequence
<220> FEATURE:
<223> OTHER INFORMATION: fusion

<400> SEQUENCE: 118

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Gly Gly Gly
        195                 200                 205

Gly Ser Gly Gly Gly Gly Ser Glu Val Gln Leu Val Glu Ser Gly Gly
    210                 215                 220

Gly Leu Val Gln Pro Gly Gly Ser Leu Arg Leu Ser Cys Ala Ala Ser
225                 230                 235                 240

Gly Phe Thr Phe Ser Pro Phe Ala Ile Ser Trp Val Arg Gln Ala Pro
                245                 250                 255
```

```
Gly Lys Gly Leu Glu Trp Val Ala Lys Ile Ser Pro Gly Gly Ser Trp
            260                 265                 270

Thr Tyr Tyr Ser Asp Thr Val Thr Asp Arg Phe Thr Phe Ser Leu Asp
            275                 280                 285

Thr Ser Lys Ser Thr Ala Tyr Leu Gln Met Asn Ser Leu Arg Ala Glu
            290                 295                 300

Asp Thr Ala Val Tyr Tyr Cys Ala Arg Gln Leu Trp Gly Tyr Ala
305                 310                 315                 320

Leu Asp Val Trp Gly Gln Gly Thr Leu Val Thr Val Ser Ser Ala Ser
                    325                 330                 335

Thr Lys Gly Pro Ser Val Phe Pro Leu Ala Pro Ser Ser Lys Ser Thr
            340                 345                 350

Ser Gly Gly Thr Ala Ala Leu Gly Cys Leu Val Lys Asp Tyr Phe Pro
            355                 360                 365

Glu Pro Val Thr Val Ser Trp Asn Ser Gly Ala Leu Thr Ser Gly Val
370                 375                 380

His Thr Phe Pro Ala Val Leu Gln Ser Ser Gly Leu Tyr Ser Leu Ser
385                 390                 395                 400

Ser Val Val Thr Val Pro Ser Ser Ser Leu Gly Thr Gln Thr Tyr Ile
            405                 410                 415

Cys Asn Val Asn His Lys Pro Ser Asn Thr Lys Val Asp Lys Lys Val
            420                 425                 430

Glu Pro Lys Ser Cys Asp Lys Thr His Thr Cys Pro Pro Cys Pro Ala
            435                 440                 445

Pro Glu Ala Ala Gly Ala Pro Ser Val Phe Leu Phe Pro Pro Lys Pro
450                 455                 460

Lys Asp Thr Leu Met Ile Ser Arg Thr Pro Glu Val Thr Cys Val Val
465                 470                 475                 480

Val Asp Val Ser His Glu Asp Pro Glu Val Lys Phe Asn Trp Tyr Val
                    485                 490                 495

Asp Gly Val Glu Val His Asn Ala Lys Thr Lys Pro Arg Glu Glu Gln
            500                 505                 510

Tyr Asn Ser Thr Tyr Arg Val Val Ser Val Leu Thr Val Leu His Gln
            515                 520                 525

Asp Trp Leu Asn Gly Lys Glu Tyr Lys Cys Lys Val Ser Asn Lys Ala
            530                 535                 540

Leu Pro Ala Pro Ile Glu Lys Thr Ile Ser Lys Ala Lys Gly Gln Pro
545                 550                 555                 560

Arg Glu Pro Gln Val Tyr Thr Leu Pro Pro Ser Arg Glu Glu Met Thr
                    565                 570                 575

Lys Asn Gln Val Ser Leu Thr Cys Leu Val Lys Gly Phe Tyr Pro Ser
            580                 585                 590

Asp Ile Ala Val Glu Trp Glu Ser Asn Gly Gln Pro Glu Asn Asn Tyr
            595                 600                 605

Lys Thr Thr Pro Pro Val Leu Asp Ser Asp Gly Ser Phe Phe Leu Tyr
            610                 615                 620

Ser Lys Leu Thr Val Asp Lys Ser Arg Trp Gln Gln Gly Asn Val Phe
625                 630                 635                 640

Ser Cys Ser Val Met His Glu Ala Leu His Asn His Tyr Thr Gln Lys
                    645                 650                 655

Ser Leu Ser Cys Ser Pro Gly Lys
                    660
```

```
<210> SEQ ID NO 119
<211> LENGTH: 213
<212> TYPE: PRT
<213> ORGANISM: Artificial Sequence
<220> FEATURE:
<223> OTHER INFORMATION: light chain

<400> SEQUENCE: 119

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ile Ser Val Ser Tyr Leu
            20                  25                  30

Tyr Trp Tyr Gln Gln Lys Pro Gly Lys Ala Pro Lys Leu Leu Ile Tyr
        35                  40                  45

Asp Ala Ser Ser Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Gly Tyr Pro Tyr Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 120
<211> LENGTH: 664
<212> TYPE: PRT
<213> ORGANISM: Artificial Sequence
<220> FEATURE:
<223> OTHER INFORMATION: fusion

<400> SEQUENCE: 120

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95
```

```
Gln Thr Asn Thr Ile Ile Asp Val Val Leu Ser Pro Ser His Gly Ile
                100                 105                 110

Glu Leu Ser Val Gly Glu Lys Leu Val Leu Asn Cys Thr Ala Arg Thr
            115                 120                 125

Glu Leu Asn Val Gly Ile Asp Phe Asn Trp Glu Tyr Pro Ser Ser Lys
        130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Gly Gly Gly
        195                 200                 205

Gly Ser Gly Gly Gly Gly Ser Glu Val Gln Leu Val Glu Ser Gly Gly
    210                 215                 220

Gly Leu Val Gln Pro Gly Gly Ser Leu Arg Leu Ser Cys Ala Ala Ser
225                 230                 235                 240

Gly Phe Thr Phe Ser Pro Phe Ala Ile Ser Trp Val Arg Gln Ala Pro
                245                 250                 255

Gly Lys Gly Leu Glu Trp Val Ala Lys Ile Ser Pro Gly Gly Ser Trp
            260                 265                 270

Thr Tyr Tyr Ser Asp Thr Val Thr Asp Arg Phe Thr Phe Ser Leu Asp
        275                 280                 285

Thr Ser Lys Ser Thr Ala Tyr Leu Gln Met Asn Ser Leu Arg Ala Glu
    290                 295                 300

Asp Thr Ala Val Tyr Tyr Cys Ala Arg Gln Leu Trp Gly Tyr Tyr Ala
305                 310                 315                 320

Leu Asp Val Trp Gly Gln Gly Thr Leu Val Thr Val Ser Ser Ala Ser
                325                 330                 335

Thr Lys Gly Pro Ser Val Phe Pro Leu Ala Pro Ser Ser Lys Ser Thr
            340                 345                 350

Ser Gly Gly Thr Ala Ala Leu Gly Cys Leu Val Lys Asp Tyr Phe Pro
        355                 360                 365

Glu Pro Val Thr Val Ser Trp Asn Ser Gly Ala Leu Thr Ser Gly Val
    370                 375                 380

His Thr Phe Pro Ala Val Leu Gln Ser Ser Gly Leu Tyr Ser Leu Ser
385                 390                 395                 400

Ser Val Val Thr Val Pro Ser Ser Ser Leu Gly Thr Gln Thr Tyr Ile
                405                 410                 415

Cys Asn Val Asn His Lys Pro Ser Asn Thr Lys Val Asp Lys Lys Val
            420                 425                 430

Glu Pro Lys Ser Cys Asp Lys Thr His Thr Cys Pro Pro Cys Pro Ala
        435                 440                 445

Pro Glu Ala Ala Gly Ala Pro Ser Val Phe Leu Phe Pro Pro Lys Pro
    450                 455                 460

Lys Asp Thr Leu Met Ile Ser Arg Thr Pro Glu Val Thr Cys Val Val
465                 470                 475                 480

Val Asp Val Ser His Glu Asp Pro Glu Val Lys Phe Asn Trp Tyr Val
                485                 490                 495

Asp Gly Val Glu Val His Asn Ala Lys Thr Lys Pro Arg Glu Glu Gln
            500                 505                 510
```

```
Tyr Asn Ser Thr Tyr Arg Val Val Ser Val Leu Thr Val Leu His Gln
            515                 520                 525
Asp Trp Leu Asn Gly Lys Glu Tyr Lys Cys Lys Val Ser Asn Lys Ala
        530                 535                 540
Leu Pro Ala Pro Ile Glu Lys Thr Ile Ser Lys Ala Lys Gly Gln Pro
545                 550                 555                 560
Arg Glu Pro Gln Val Tyr Thr Leu Pro Pro Ser Arg Glu Glu Met Thr
                565                 570                 575
Lys Asn Gln Val Ser Leu Thr Cys Leu Val Lys Gly Phe Tyr Pro Ser
            580                 585                 590
Asp Ile Ala Val Glu Trp Glu Ser Asn Gly Gln Pro Glu Asn Asn Tyr
        595                 600                 605
Lys Thr Thr Pro Pro Val Leu Asp Ser Asp Gly Ser Phe Phe Leu Tyr
            610                 615                 620
Ser Lys Leu Thr Val Asp Lys Ser Arg Trp Gln Gln Gly Asn Val Phe
625                 630                 635                 640
Ser Cys Ser Val Met His Glu Ala Leu His Asn His Tyr Thr Gln Lys
                645                 650                 655
Ser Leu Ser Cys Ser Pro Gly Lys
            660

<210> SEQ ID NO 121
<211> LENGTH: 213
<212> TYPE: PRT
<213> ORGANISM: Artificial Sequence
<220> FEATURE:
<223> OTHER INFORMATION: light chain

<400> SEQUENCE: 121

Asp Ile Gln Leu Thr Gln Ser Pro Ser Ser Leu Ser Ala Ser Val Gly
1               5                   10                  15
Asp Arg Val Thr Ile Thr Cys Ser Ala Ser Ile Ser Val Ser Tyr Leu
            20                  25                  30
Tyr Trp Tyr Gln Gln Lys Pro Gly Lys Ala Pro Lys Leu Leu Ile Tyr
        35                  40                  45
Asp Asp Ser Asn Leu Ala Ser Gly Val Pro Ser Arg Phe Ser Gly Ser
    50                  55                  60
Gly Ser Gly Thr Asp Phe Thr Leu Thr Ile Ser Ser Leu Gln Pro Glu
65                  70                  75                  80
Asp Phe Ala Thr Tyr Tyr Cys Gln Gln Trp Ser Gly Tyr Pro Tyr Thr
                85                  90                  95
Phe Gly Gln Gly Thr Lys Val Glu Ile Lys Arg Thr Val Ala Ala Pro
            100                 105                 110
Ser Val Phe Ile Phe Pro Pro Ser Asp Glu Gln Leu Lys Ser Gly Thr
        115                 120                 125
Ala Ser Val Val Cys Leu Leu Asn Asn Phe Tyr Pro Arg Glu Ala Lys
    130                 135                 140
Val Gln Trp Lys Val Asp Asn Ala Leu Gln Ser Gly Asn Ser Gln Glu
145                 150                 155                 160
Ser Val Thr Glu Gln Asp Ser Lys Asp Ser Thr Tyr Ser Leu Ser Ser
                165                 170                 175
Thr Leu Thr Leu Ser Lys Ala Asp Tyr Glu Lys His Lys Val Tyr Ala
            180                 185                 190
Cys Glu Val Thr His Gln Gly Leu Ser Ser Pro Val Thr Lys Ser Phe
        195                 200                 205
```

Asn Arg Gly Glu Cys
    210

<210> SEQ ID NO 122
<211> LENGTH: 664
<212> TYPE: PRT
<213> ORGANISM: Artificial Sequence
<220> FEATURE:
<223> OTHER INFORMATION: fusion

<400> SEQUENCE: 122

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Gly Gly Gly
        195                 200                 205

Gly Ser Gly Gly Gly Gly Ser Glu Val Gln Leu Val Glu Ser Gly Gly
    210                 215                 220

Gly Leu Val Gln Pro Gly Gly Ser Leu Arg Leu Ser Cys Ala Ala Ser
225                 230                 235                 240

Gly Phe Thr Phe Ser Pro Phe Ala Trp Ser Trp Val Arg Gln Ala Pro
                245                 250                 255

Gly Lys Gly Leu Glu Trp Val Ala Lys Ile Ser Pro Gly Gly Ser Trp
            260                 265                 270

Thr Tyr Tyr Ser Asp Thr Val Thr Asp Arg Phe Thr Phe Ser Leu Asp
        275                 280                 285

Thr Ser Lys Ser Thr Ala Tyr Leu Gln Met Asn Ser Leu Arg Ala Glu
    290                 295                 300

Asp Thr Ala Val Tyr Tyr Cys Ala Arg Gln Leu Trp Gly Tyr Tyr Ala
305                 310                 315                 320

Leu Asp Val Trp Gly Gln Gly Thr Leu Val Thr Val Ser Ser Ala Ser
                325                 330                 335

Thr Lys Gly Pro Ser Val Phe Pro Leu Ala Pro Ser Ser Lys Ser Thr
            340                 345                 350

```
Ser Gly Gly Thr Ala Ala Leu Gly Cys Leu Val Lys Asp Tyr Phe Pro
            355                 360                 365

Glu Pro Val Thr Val Ser Trp Asn Ser Gly Ala Leu Thr Ser Gly Val
    370                 375                 380

His Thr Phe Pro Ala Val Leu Gln Ser Ser Gly Leu Tyr Ser Leu Ser
385                 390                 395                 400

Ser Val Val Thr Val Pro Ser Ser Ser Leu Gly Thr Gln Thr Tyr Ile
                405                 410                 415

Cys Asn Val Asn His Lys Pro Ser Asn Thr Lys Val Asp Lys Lys Val
            420                 425                 430

Glu Pro Lys Ser Cys Asp Lys Thr His Thr Cys Pro Pro Cys Pro Ala
        435                 440                 445

Pro Glu Ala Ala Gly Ala Pro Ser Val Phe Leu Phe Pro Pro Lys Pro
    450                 455                 460

Lys Asp Thr Leu Met Ile Ser Arg Thr Pro Glu Val Thr Cys Val Val
465                 470                 475                 480

Val Asp Val Ser His Glu Asp Pro Glu Val Lys Phe Asn Trp Tyr Val
                485                 490                 495

Asp Gly Val Glu Val His Asn Ala Lys Thr Lys Pro Arg Glu Glu Gln
            500                 505                 510

Tyr Asn Ser Thr Tyr Arg Val Val Ser Val Leu Thr Val Leu His Gln
        515                 520                 525

Asp Trp Leu Asn Gly Lys Glu Tyr Lys Cys Lys Val Ser Asn Lys Ala
    530                 535                 540

Leu Pro Ala Pro Ile Glu Lys Thr Ile Ser Lys Ala Lys Gly Gln Pro
545                 550                 555                 560

Arg Glu Pro Gln Val Tyr Thr Leu Pro Pro Ser Arg Glu Glu Met Thr
                565                 570                 575

Lys Asn Gln Val Ser Leu Thr Cys Leu Val Lys Gly Phe Tyr Pro Ser
            580                 585                 590

Asp Ile Ala Val Glu Trp Glu Ser Asn Gly Gln Pro Glu Asn Asn Tyr
        595                 600                 605

Lys Thr Thr Pro Pro Val Leu Asp Ser Asp Gly Ser Phe Phe Leu Tyr
    610                 615                 620

Ser Lys Leu Thr Val Asp Lys Ser Arg Trp Gln Gln Gly Asn Val Phe
625                 630                 635                 640

Ser Cys Ser Val Met His Glu Ala Leu His Asn His Tyr Thr Gln Lys
                645                 650                 655

Ser Leu Ser Cys Ser Pro Gly Lys
            660

<210> SEQ ID NO 123
<211> LENGTH: 213
<212> TYPE: PRT
<213> ORGANISM: Artificial Sequence
<220> FEATURE:
<223> OTHER INFORMATION: light chain

<400> SEQUENCE: 123

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ile Ser Val Ser Tyr Leu
            20                  25                  30

Tyr Trp Tyr Gln Gln Lys Pro Gly Lys Ala Pro Lys Leu Leu Ile Tyr
        35                  40                  45
```

Asp Asp Ser Ser Leu Ala Ser Gly Val Pro Ser Arg Phe Ser Gly Ser
 50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Trp Ser Gly Tyr Pro Tyr Thr
                 85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
210

<210> SEQ ID NO 124
<211> LENGTH: 664
<212> TYPE: PRT
<213> ORGANISM: Artificial Sequence
<220> FEATURE:
<223> OTHER INFORMATION: fusion

<400> SEQUENCE: 124

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

```
Thr Lys Lys Asn Ser Thr Phe Val Arg Val His Glu Lys Gly Gly
            195                 200                 205
Gly Ser Gly Gly Gly Ser Glu Val Gln Leu Val Glu Ser Gly Gly
    210                 215                 220
Gly Leu Val Gln Pro Gly Gly Ser Leu Arg Leu Ser Cys Ala Ala Ser
225                 230                 235                 240
Gly Phe Thr Phe Ser Pro Phe Ala Trp Ser Trp Val Arg Gln Ala Pro
                245                 250                 255
Gly Lys Gly Leu Glu Trp Val Ala Lys Ile Ser Pro Gly Gly Ser Trp
            260                 265                 270
Thr Tyr Tyr Ser Asp Thr Val Thr Asp Arg Phe Thr Phe Ser Leu Asp
    275                 280                 285
Thr Ser Lys Ser Thr Ala Tyr Leu Gln Met Asn Ser Leu Arg Ala Glu
290                 295                 300
Asp Thr Ala Val Tyr Tyr Cys Ala Arg Gln Leu Trp Gly Tyr Tyr Ala
305                 310                 315                 320
Leu Asp Val Trp Gly Gln Gly Thr Leu Val Thr Val Ser Ser Ala Ser
                325                 330                 335
Thr Lys Gly Pro Ser Val Phe Pro Leu Ala Pro Ser Ser Lys Ser Thr
            340                 345                 350
Ser Gly Gly Thr Ala Ala Leu Gly Cys Leu Val Lys Asp Tyr Phe Pro
    355                 360                 365
Glu Pro Val Thr Val Ser Trp Asn Ser Gly Ala Leu Thr Ser Gly Val
370                 375                 380
His Thr Phe Pro Ala Val Leu Gln Ser Ser Gly Leu Tyr Ser Leu Ser
385                 390                 395                 400
Ser Val Val Thr Val Pro Ser Ser Ser Leu Gly Thr Gln Thr Tyr Ile
                405                 410                 415
Cys Asn Val Asn His Lys Pro Ser Asn Thr Lys Val Asp Lys Lys Val
            420                 425                 430
Glu Pro Lys Ser Cys Asp Lys Thr His Thr Cys Pro Pro Cys Pro Ala
    435                 440                 445
Pro Glu Ala Ala Gly Ala Pro Ser Val Phe Leu Phe Pro Pro Lys Pro
450                 455                 460
Lys Asp Thr Leu Met Ile Ser Arg Thr Pro Glu Val Thr Cys Val Val
465                 470                 475                 480
Val Asp Val Ser His Glu Asp Pro Glu Val Lys Phe Asn Trp Tyr Val
                485                 490                 495
Asp Gly Val Glu Val His Asn Ala Lys Thr Lys Pro Arg Glu Glu Gln
            500                 505                 510
Tyr Asn Ser Thr Tyr Arg Val Val Ser Val Leu Thr Val Leu His Gln
    515                 520                 525
Asp Trp Leu Asn Gly Lys Glu Tyr Lys Cys Lys Val Ser Asn Lys Ala
530                 535                 540
Leu Pro Ala Pro Ile Glu Lys Thr Ile Ser Lys Ala Lys Gly Gln Pro
545                 550                 555                 560
Arg Glu Pro Gln Val Tyr Thr Leu Pro Pro Ser Arg Glu Glu Met Thr
                565                 570                 575
Lys Asn Gln Val Ser Leu Thr Cys Leu Val Lys Gly Phe Tyr Pro Ser
            580                 585                 590
Asp Ile Ala Val Glu Trp Glu Ser Asn Gly Gln Pro Glu Asn Asn Tyr
    595                 600                 605
```

```
Lys Thr Thr Pro Pro Val Leu Asp Ser Asp Gly Ser Phe Phe Leu Tyr
            610                 615                 620

Ser Lys Leu Thr Val Asp Lys Ser Arg Trp Gln Gln Gly Asn Val Phe
625                 630                 635                 640

Ser Cys Ser Val Met His Glu Ala Leu His Asn His Tyr Thr Gln Lys
                645                 650                 655

Ser Leu Ser Cys Ser Pro Gly Lys
            660
```

<210> SEQ ID NO 125
<211> LENGTH: 213
<212> TYPE: PRT
<213> ORGANISM: Artificial Sequence
<220> FEATURE:
<223> OTHER INFORMATION: light chain

<400> SEQUENCE: 125

```
Asp Ile Gln Leu Thr Gln Ser Pro Ser Ser Leu Ser Ala Ser Val Gly
1               5                   10                  15

Asp Arg Val Thr Ile Thr Cys Ser Ala Ser Ile Ser Val Ser Tyr Leu
                20                  25                  30

Tyr Trp Tyr Gln Gln Lys Pro Gly Lys Ala Pro Lys Leu Leu Ile Tyr
            35                  40                  45

Asp Ala Ser Ser Leu Ala Ser Gly Val Pro Ser Arg Phe Ser Gly Ser
        50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Gly Tyr Pro Tyr Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 126
<211> LENGTH: 664
<212> TYPE: PRT
<213> ORGANISM: Artificial Sequence
<220> FEATURE:
<223> OTHER INFORMATION: fusion

<400> SEQUENCE: 126

```
Ser Asp Thr Gly Arg Pro Phe Val Glu Met Tyr Ser Glu Ile Pro Glu
1               5                   10                  15
```

```
Ile Ile His Met Thr Glu Gly Arg Glu Leu Val Ile Pro Cys Arg Val
            20              25              30

Thr Ser Pro Asn Ile Thr Val Thr Leu Lys Lys Phe Pro Leu Asp Thr
        35              40              45

Leu Ile Pro Asp Gly Lys Arg Ile Ile Trp Asp Ser Arg Lys Gly Phe
 50              55              60

Ile Ile Ser Asn Ala Thr Tyr Lys Glu Ile Gly Leu Leu Thr Cys Glu
65              70              75              80

Ala Thr Val Asn Gly His Leu Tyr Lys Thr Asn Tyr Leu Thr His Arg
            85              90              95

Gln Thr Asn Thr Ile Ile Asp Val Val Leu Ser Pro Ser His Gly Ile
            100             105             110

Glu Leu Ser Val Gly Glu Lys Leu Val Leu Asn Cys Thr Ala Arg Thr
        115             120             125

Glu Leu Asn Val Gly Ile Asp Phe Asn Trp Glu Tyr Pro Ser Ser Lys
    130             135             140

His Gln His Lys Lys Leu Val Asn Arg Asp Leu Lys Thr Gln Ser Gly
145             150             155             160

Ser Glu Met Lys Lys Phe Leu Ser Thr Leu Thr Ile Asp Gly Val Thr
            165             170             175

Arg Ser Asp Gln Gly Leu Tyr Thr Cys Ala Ala Ser Ser Gly Leu Met
        180             185             190

Thr Lys Lys Asn Ser Thr Phe Val Arg Val His Glu Lys Gly Gly Gly
        195             200             205

Gly Ser Gly Gly Gly Gly Ser Glu Val Gln Leu Val Glu Ser Gly Gly
    210             215             220

Gly Leu Val Gln Pro Gly Gly Ser Leu Arg Leu Ser Cys Ala Ala Ser
225             230             235             240

Gly Phe Thr Phe Ser Pro Phe Ala Trp Ser Trp Val Arg Gln Ala Pro
            245             250             255

Gly Lys Gly Leu Glu Trp Val Ala Lys Ile Ser Pro Gly Gly Ser Trp
            260             265             270

Thr Tyr Tyr Ser Asp Thr Val Thr Asp Arg Phe Thr Phe Ser Leu Asp
    275             280             285

Thr Ser Lys Ser Thr Ala Tyr Leu Gln Met Asn Ser Leu Arg Ala Glu
    290             295             300

Asp Thr Ala Val Tyr Tyr Cys Ala Arg Gln Leu Trp Gly Tyr Tyr Ala
305             310             315             320

Leu Asp Val Trp Gly Gln Gly Thr Leu Val Thr Val Ser Ser Ala Ser
            325             330             335

Thr Lys Gly Pro Ser Val Phe Pro Leu Ala Pro Ser Ser Lys Ser Thr
            340             345             350

Ser Gly Gly Thr Ala Ala Leu Gly Cys Leu Val Lys Asp Tyr Phe Pro
        355             360             365

Glu Pro Val Thr Val Ser Trp Asn Ser Gly Ala Leu Thr Ser Gly Val
    370             375             380

His Thr Phe Pro Ala Val Leu Gln Ser Ser Gly Leu Tyr Ser Leu Ser
385             390             395             400

Ser Val Val Thr Val Pro Ser Ser Leu Gly Thr Gln Thr Tyr Ile
            405             410             415

Cys Asn Val Asn His Lys Pro Ser Asn Thr Lys Val Asp Lys Lys Val
            420             425             430
```

```
Glu Pro Lys Ser Cys Asp Lys Thr His Thr Cys Pro Pro Cys Pro Ala
            435                 440                 445

Pro Glu Ala Ala Gly Ala Pro Ser Val Phe Leu Phe Pro Pro Lys Pro
    450                 455                 460

Lys Asp Thr Leu Met Ile Ser Arg Thr Pro Glu Val Thr Cys Val Val
465                 470                 475                 480

Val Asp Val Ser His Glu Asp Pro Glu Val Lys Phe Asn Trp Tyr Val
                485                 490                 495

Asp Gly Val Glu Val His Asn Ala Lys Thr Lys Pro Arg Glu Glu Gln
                500                 505                 510

Tyr Asn Ser Thr Tyr Arg Val Val Ser Val Leu Thr Val Leu His Gln
            515                 520                 525

Asp Trp Leu Asn Gly Lys Glu Tyr Lys Cys Lys Val Ser Asn Lys Ala
    530                 535                 540

Leu Pro Ala Pro Ile Glu Lys Thr Ile Ser Lys Ala Lys Gly Gln Pro
545                 550                 555                 560

Arg Glu Pro Gln Val Tyr Thr Leu Pro Pro Ser Arg Glu Glu Met Thr
                565                 570                 575

Lys Asn Gln Val Ser Leu Thr Cys Leu Val Lys Gly Phe Tyr Pro Ser
            580                 585                 590

Asp Ile Ala Val Glu Trp Glu Ser Asn Gly Gln Pro Glu Asn Asn Tyr
    595                 600                 605

Lys Thr Thr Pro Pro Val Leu Asp Ser Asp Gly Ser Phe Phe Leu Tyr
610                 615                 620

Ser Lys Leu Thr Val Asp Lys Ser Arg Trp Gln Gln Gly Asn Val Phe
625                 630                 635                 640

Ser Cys Ser Val Met His Glu Ala Leu His Asn His Tyr Thr Gln Lys
                645                 650                 655

Ser Leu Ser Cys Ser Pro Gly Lys
                660

<210> SEQ ID NO 127
<211> LENGTH: 213
<212> TYPE: PRT
<213> ORGANISM: Artificial Sequence
<220> FEATURE:
<223> OTHER INFORMATION: light chain

<400> SEQUENCE: 127

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ile Ser Val Ser Tyr Leu
            20                  25                  30

Tyr Trp Tyr Gln Gln Lys Pro Gly Lys Ala Pro Lys Leu Leu Ile Tyr
        35                  40                  45

Asp Asp Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Gly Tyr Pro Tyr Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125
```

```
Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
    210
```

<210> SEQ ID NO 128
<211> LENGTH: 664
<212> TYPE: PRT
<213> ORGANISM: Artificial Sequence
<220> FEATURE:
<223> OTHER INFORMATION: fusion

<400> SEQUENCE: 128

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Pro Phe
            20                  25                  30

Ala Ile Ser Trp Val Arg Gln Ala Pro Gly Lys Gly Leu Glu Trp Val
        35                  40                  45

Ala Lys Ile Ser Pro Gly Gly Ser Trp Thr Tyr Tyr Ser Asp Thr Val
50                  55                  60

Thr Asp Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gln Leu Trp Gly Tyr Tyr Ala Leu Asp Val Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Gly Gly
210                 215                 220

Gly Gly Ser Gly Gly Gly Gly Ser Ser Asp Thr Gly Arg Pro Phe Val
225                 230                 235                 240

Glu Met Tyr Ser Glu Ile Pro Glu Ile Ile His Met Thr Glu Gly Arg
                245                 250                 255

Glu Leu Val Ile Pro Cys Arg Val Thr Ser Pro Asn Ile Thr Val Thr
            260                 265                 270
```

```
Leu Lys Lys Phe Pro Leu Asp Thr Leu Ile Pro Asp Gly Lys Arg Ile
        275                 280                 285

Ile Trp Asp Ser Arg Lys Gly Phe Ile Ile Ser Asn Ala Thr Tyr Lys
290                 295                 300

Glu Ile Gly Leu Leu Thr Cys Glu Ala Thr Val Asn Gly His Leu Tyr
305                 310                 315                 320

Lys Thr Asn Tyr Leu Thr His Arg Gln Thr Asn Thr Ile Ile Asp Val
                325                 330                 335

Val Leu Ser Pro Ser His Gly Ile Glu Leu Ser Val Gly Glu Lys Leu
            340                 345                 350

Val Leu Asn Cys Thr Ala Arg Thr Glu Leu Asn Val Gly Ile Asp Phe
        355                 360                 365

Asn Trp Glu Tyr Pro Ser Ser Lys His Gln His Lys Lys Leu Val Asn
370                 375                 380

Arg Asp Leu Lys Thr Gln Ser Gly Ser Glu Met Lys Lys Phe Leu Ser
385                 390                 395                 400

Thr Leu Thr Ile Asp Gly Val Thr Arg Ser Asp Gln Gly Leu Tyr Thr
                405                 410                 415

Cys Ala Ala Ser Ser Gly Leu Met Thr Lys Lys Asn Ser Thr Phe Val
            420                 425                 430

Arg Val His Glu Lys Asp Lys Thr His Thr Cys Pro Pro Cys Pro Ala
        435                 440                 445

Pro Glu Ala Ala Gly Ala Pro Ser Val Phe Leu Phe Pro Pro Lys Pro
450                 455                 460

Lys Asp Thr Leu Met Ile Ser Arg Thr Pro Glu Val Thr Cys Val Val
465                 470                 475                 480

Val Asp Val Ser His Glu Asp Pro Glu Val Lys Phe Asn Trp Tyr Val
                485                 490                 495

Asp Gly Val Glu Val His Asn Ala Lys Thr Lys Pro Arg Glu Glu Gln
            500                 505                 510

Tyr Asn Ser Thr Tyr Arg Val Val Ser Val Leu Thr Val Leu His Gln
        515                 520                 525

Asp Trp Leu Asn Gly Lys Glu Tyr Lys Cys Lys Val Ser Asn Lys Ala
530                 535                 540

Leu Pro Ala Pro Ile Glu Lys Thr Ile Ser Lys Ala Lys Gly Gln Pro
545                 550                 555                 560

Arg Glu Pro Gln Val Tyr Thr Leu Pro Pro Ser Arg Glu Glu Met Thr
                565                 570                 575

Lys Asn Gln Val Ser Leu Thr Cys Leu Val Lys Gly Phe Tyr Pro Ser
            580                 585                 590

Asp Ile Ala Val Glu Trp Glu Ser Asn Gly Gln Pro Glu Asn Asn Tyr
        595                 600                 605

Lys Thr Thr Pro Pro Val Leu Asp Ser Asp Gly Ser Phe Phe Leu Tyr
610                 615                 620

Ser Lys Leu Thr Val Asp Lys Ser Arg Trp Gln Gln Gly Asn Val Phe
625                 630                 635                 640

Ser Cys Ser Val Met His Glu Ala Leu His Asn His Tyr Thr Gln Lys
                645                 650                 655

Ser Leu Ser Cys Ser Pro Gly Lys
            660

<210> SEQ ID NO 129
<211> LENGTH: 213
<212> TYPE: PRT
```

<213> ORGANISM: Artificial Sequence
<220> FEATURE:
<223> OTHER INFORMATION: light chain

<400> SEQUENCE: 129

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ile Ser Val Ser Tyr Leu
            20                  25                  30

Tyr Trp Tyr Gln Gln Lys Pro Gly Lys Ala Pro Lys Leu Leu Ile Tyr
        35                  40                  45

Asp Asp Ser Ser Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Gly Tyr Pro Tyr Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
        210

<210> SEQ ID NO 130
<211> LENGTH: 664
<212> TYPE: PRT
<213> ORGANISM: Artificial Sequence
<220> FEATURE:
<223> OTHER INFORMATION: fusion

<400> SEQUENCE: 130

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Pro Phe
            20                  25                  30

Ala Ile Ser Trp Val Arg Gln Ala Pro Gly Lys Gly Leu Glu Trp Val
        35                  40                  45

Ala Lys Ile Ser Pro Gly Gly Ser Trp Thr Tyr Tyr Ser Asp Thr Val
    50                  55                  60

Thr Asp Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gln Leu Trp Gly Tyr Tyr Ala Leu Asp Val Trp Gly Gln Gly
            100                 105                 110

```
Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Gly Gly
    210                 215                 220

Gly Gly Ser Gly Gly Gly Gly Ser Ser Asp Thr Gly Arg Pro Phe Val
225                 230                 235                 240

Glu Met Tyr Ser Glu Ile Pro Glu Ile Ile His Met Thr Glu Gly Arg
                245                 250                 255

Glu Leu Val Ile Pro Cys Arg Val Thr Ser Pro Asn Ile Thr Val Thr
            260                 265                 270

Leu Lys Lys Phe Pro Leu Asp Thr Leu Ile Pro Asp Gly Lys Arg Ile
        275                 280                 285

Ile Trp Asp Ser Arg Lys Gly Phe Ile Ile Ser Asn Ala Thr Tyr Lys
    290                 295                 300

Glu Ile Gly Leu Leu Thr Cys Glu Ala Thr Val Asn Gly His Leu Tyr
305                 310                 315                 320

Lys Thr Asn Tyr Leu Thr His Arg Gln Thr Asn Thr Ile Ile Asp Val
                325                 330                 335

Val Leu Ser Pro Ser His Gly Ile Glu Leu Ser Val Gly Glu Lys Leu
            340                 345                 350

Val Leu Asn Cys Thr Ala Arg Thr Glu Leu Asn Val Gly Ile Asp Phe
        355                 360                 365

Asn Trp Glu Tyr Pro Ser Ser Lys His Gln His Lys Lys Leu Val Asn
    370                 375                 380

Arg Asp Leu Lys Thr Gln Ser Gly Ser Glu Met Lys Lys Phe Leu Ser
385                 390                 395                 400

Thr Leu Thr Ile Asp Gly Val Thr Arg Ser Asp Gln Gly Leu Tyr Thr
                405                 410                 415

Cys Ala Ala Ser Ser Gly Leu Met Thr Lys Lys Asn Ser Thr Phe Val
            420                 425                 430

Arg Val His Glu Lys Asp Lys Thr His Thr Cys Pro Pro Cys Pro Ala
        435                 440                 445

Pro Glu Ala Ala Gly Ala Pro Ser Val Phe Leu Phe Pro Pro Lys Pro
    450                 455                 460

Lys Asp Thr Leu Met Ile Ser Arg Thr Pro Glu Val Thr Cys Val Val
465                 470                 475                 480

Val Asp Val Ser His Glu Asp Pro Glu Val Lys Phe Asn Trp Tyr Val
                485                 490                 495

Asp Gly Val Glu Val His Asn Ala Lys Thr Lys Pro Arg Glu Glu Gln
            500                 505                 510

Tyr Asn Ser Thr Tyr Arg Val Val Ser Val Leu Thr Val Leu His Gln
        515                 520                 525
```

Asp Trp Leu Asn Gly Lys Glu Tyr Lys Cys Lys Val Ser Asn Lys Ala
530                 535                 540

Leu Pro Ala Pro Ile Glu Lys Thr Ile Ser Lys Ala Lys Gly Gln Pro
545                 550                 555                 560

Arg Glu Pro Gln Val Tyr Thr Leu Pro Pro Ser Arg Glu Glu Met Thr
                565                 570                 575

Lys Asn Gln Val Ser Leu Thr Cys Leu Val Lys Gly Phe Tyr Pro Ser
                580                 585                 590

Asp Ile Ala Val Glu Trp Glu Ser Asn Gly Gln Pro Glu Asn Asn Tyr
            595                 600                 605

Lys Thr Thr Pro Pro Val Leu Asp Ser Asp Gly Ser Phe Phe Leu Tyr
            610                 615                 620

Ser Lys Leu Thr Val Asp Lys Ser Arg Trp Gln Gln Gly Asn Val Phe
625                 630                 635                 640

Ser Cys Ser Val Met His Glu Ala Leu His Asn His Tyr Thr Gln Lys
                645                 650                 655

Ser Leu Ser Cys Ser Pro Gly Lys
            660

<210> SEQ ID NO 131
<211> LENGTH: 213
<212> TYPE: PRT
<213> ORGANISM: Artificial Sequence
<220> FEATURE:
<223> OTHER INFORMATION: light chain

<400> SEQUENCE: 131

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ile Ser Val Ser Tyr Leu
                20                  25                  30

Tyr Trp Tyr Gln Gln Lys Pro Gly Lys Ala Pro Lys Leu Leu Ile Tyr
            35                  40                  45

Asp Ala Ser Ser Leu Ala Ser Gly Val Pro Ser Arg Phe Ser Gly Ser
50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Gly Tyr Pro Tyr Thr
                85                  90                  95

Phe Gly Gln Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
        210

<210> SEQ ID NO 132
<211> LENGTH: 664
<212> TYPE: PRT
<213> ORGANISM: Artificial Sequence
<220> FEATURE:
<223> OTHER INFORMATION: fusion

<400> SEQUENCE: 132

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Pro Phe
            20                  25                  30

Ala Ile Ser Trp Val Arg Gln Ala Pro Gly Lys Gly Leu Glu Trp Val
        35                  40                  45

Ala Lys Ile Ser Pro Gly Gly Ser Trp Thr Tyr Tyr Ser Asp Thr Val
    50                  55                  60

Thr Asp Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gln Leu Trp Gly Tyr Tyr Ala Leu Asp Val Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Gly Gly
    210                 215                 220

Gly Gly Ser Gly Gly Gly Ser Ser Asp Thr Gly Arg Pro Phe Val
225                 230                 235                 240

Glu Met Tyr Ser Glu Ile Pro Glu Ile Ile His Met Thr Glu Gly Arg
                245                 250                 255

Glu Leu Val Ile Pro Cys Arg Val Thr Ser Pro Asn Ile Thr Val Thr
            260                 265                 270

Leu Lys Lys Phe Pro Leu Asp Thr Leu Ile Pro Asp Gly Lys Arg Ile
        275                 280                 285

Ile Trp Asp Ser Arg Lys Gly Phe Ile Ile Ser Asn Ala Thr Tyr Lys
    290                 295                 300

Glu Ile Gly Leu Leu Thr Cys Glu Ala Thr Val Asn Gly His Leu Tyr
305                 310                 315                 320

Lys Thr Asn Tyr Leu Thr His Arg Gln Thr Asn Thr Ile Ile Asp Val
                325                 330                 335

Val Leu Ser Pro Ser His Gly Ile Glu Leu Ser Val Gly Glu Lys Leu
            340                 345                 350

Val Leu Asn Cys Thr Ala Arg Thr Glu Leu Asn Val Gly Ile Asp Phe
        355                 360                 365
```

Asn Trp Glu Tyr Pro Ser Ser Lys His Gln His Lys Leu Val Asn
            370                 375                 380

Arg Asp Leu Lys Thr Gln Ser Gly Ser Glu Met Lys Lys Phe Leu Ser
385                 390                 395                 400

Thr Leu Thr Ile Asp Gly Val Thr Arg Ser Asp Gln Gly Leu Tyr Thr
            405                 410                 415

Cys Ala Ala Ser Ser Gly Leu Met Thr Lys Lys Asn Ser Thr Phe Val
            420                 425                 430

Arg Val His Glu Lys Asp Lys Thr His Thr Cys Pro Pro Cys Pro Ala
            435                 440                 445

Pro Glu Ala Ala Gly Ala Pro Ser Val Phe Leu Phe Pro Pro Lys Pro
450                 455                 460

Lys Asp Thr Leu Met Ile Ser Arg Thr Pro Glu Val Thr Cys Val Val
465                 470                 475                 480

Val Asp Val Ser His Glu Asp Pro Glu Val Lys Phe Asn Trp Tyr Val
            485                 490                 495

Asp Gly Val Glu Val His Asn Ala Lys Thr Lys Pro Arg Glu Glu Gln
            500                 505                 510

Tyr Asn Ser Thr Tyr Arg Val Val Ser Val Leu Thr Val Leu His Gln
            515                 520                 525

Asp Trp Leu Asn Gly Lys Glu Tyr Lys Cys Lys Val Ser Asn Lys Ala
530                 535                 540

Leu Pro Ala Pro Ile Glu Lys Thr Ile Ser Lys Ala Lys Gly Gln Pro
545                 550                 555                 560

Arg Glu Pro Gln Val Tyr Thr Leu Pro Pro Ser Arg Glu Glu Met Thr
            565                 570                 575

Lys Asn Gln Val Ser Leu Thr Cys Leu Val Lys Gly Phe Tyr Pro Ser
            580                 585                 590

Asp Ile Ala Val Glu Trp Glu Ser Asn Gly Gln Pro Glu Asn Asn Tyr
            595                 600                 605

Lys Thr Thr Pro Pro Val Leu Asp Ser Asp Gly Ser Phe Phe Leu Tyr
610                 615                 620

Ser Lys Leu Thr Val Asp Lys Ser Arg Trp Gln Gln Gly Asn Val Phe
625                 630                 635                 640

Ser Cys Ser Val Met His Glu Ala Leu His Asn His Tyr Thr Gln Lys
            645                 650                 655

Ser Leu Ser Cys Ser Pro Gly Lys
            660

<210> SEQ ID NO 133
<211> LENGTH: 213
<212> TYPE: PRT
<213> ORGANISM: Artificial Sequence
<220> FEATURE:
<223> OTHER INFORMATION: fusion

<400> SEQUENCE: 133

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ile Ser Val Ser Tyr Leu
            20                  25                  30

Tyr Trp Tyr Gln Gln Lys Pro Gly Lys Ala Pro Lys Leu Leu Ile Tyr
        35                  40                  45

Asp Asp Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Gly Tyr Pro Tyr Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 134
<211> LENGTH: 664
<212> TYPE: PRT
<213> ORGANISM: Artificial Sequence
<220> FEATURE:
<223> OTHER INFORMATION: fusion

<400> SEQUENCE: 134

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Pro Phe
            20                  25                  30

Ala Trp Ser Trp Val Arg Gln Ala Pro Gly Lys Gly Leu Glu Trp Val
        35                  40                  45

Ala Lys Ile Ser Pro Gly Gly Ser Trp Thr Tyr Tyr Ser Asp Thr Val
    50                  55                  60

Thr Asp Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gln Leu Trp Gly Tyr Tyr Ala Leu Asp Val Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

```
Ser Asn Thr Lys Val Asp Lys Val Glu Pro Lys Ser Cys Gly Gly
    210                 215                 220

Gly Gly Ser Gly Gly Gly Ser Ser Asp Thr Gly Arg Pro Phe Val
225                 230                 235                 240

Glu Met Tyr Ser Glu Ile Pro Glu Ile Ile His Met Thr Glu Gly Arg
                245                 250                 255

Glu Leu Val Ile Pro Cys Arg Val Thr Ser Pro Asn Ile Thr Val Thr
            260                 265                 270

Leu Lys Lys Phe Pro Leu Asp Thr Leu Ile Pro Asp Gly Lys Arg Ile
        275                 280                 285

Ile Trp Asp Ser Arg Lys Gly Phe Ile Ile Ser Asn Ala Thr Tyr Lys
    290                 295                 300

Glu Ile Gly Leu Leu Thr Cys Glu Ala Thr Val Asn Gly His Leu Tyr
305                 310                 315                 320

Lys Thr Asn Tyr Leu Thr His Arg Gln Thr Asn Thr Ile Ile Asp Val
                325                 330                 335

Val Leu Ser Pro Ser His Gly Ile Glu Leu Ser Val Gly Glu Lys Leu
            340                 345                 350

Val Leu Asn Cys Thr Ala Arg Thr Glu Leu Asn Val Gly Ile Asp Phe
        355                 360                 365

Asn Trp Glu Tyr Pro Ser Ser Lys His Gln His Lys Lys Leu Val Asn
    370                 375                 380

Arg Asp Leu Lys Thr Gln Ser Gly Ser Glu Met Lys Lys Phe Leu Ser
385                 390                 395                 400

Thr Leu Thr Ile Asp Gly Val Thr Arg Ser Asp Gln Gly Leu Tyr Thr
                405                 410                 415

Cys Ala Ala Ser Ser Gly Leu Met Thr Lys Lys Asn Ser Thr Phe Val
            420                 425                 430

Arg Val His Glu Lys Asp Lys Thr His Thr Cys Pro Pro Cys Pro Ala
        435                 440                 445

Pro Glu Ala Ala Gly Ala Pro Ser Val Phe Leu Phe Pro Pro Lys Pro
    450                 455                 460

Lys Asp Thr Leu Met Ile Ser Arg Thr Pro Glu Val Thr Cys Val Val
465                 470                 475                 480

Val Asp Val Ser His Glu Asp Pro Glu Val Lys Phe Asn Trp Tyr Val
                485                 490                 495

Asp Gly Val Glu Val His Asn Ala Lys Thr Lys Pro Arg Glu Glu Gln
            500                 505                 510

Tyr Asn Ser Thr Tyr Arg Val Val Ser Val Leu Thr Val Leu His Gln
        515                 520                 525

Asp Trp Leu Asn Gly Lys Glu Tyr Lys Cys Lys Val Ser Asn Lys Ala
    530                 535                 540

Leu Pro Ala Pro Ile Glu Lys Thr Ile Ser Lys Ala Lys Gly Gln Pro
545                 550                 555                 560

Arg Glu Pro Gln Val Tyr Thr Leu Pro Pro Ser Arg Glu Glu Met Thr
                565                 570                 575

Lys Asn Gln Val Ser Leu Thr Cys Leu Val Lys Gly Phe Tyr Pro Ser
            580                 585                 590

Asp Ile Ala Val Glu Trp Glu Ser Asn Gly Gln Pro Glu Asn Asn Tyr
        595                 600                 605

Lys Thr Thr Pro Pro Val Leu Asp Ser Asp Gly Ser Phe Phe Leu Tyr
    610                 615                 620
```

```
Ser Lys Leu Thr Val Asp Lys Ser Arg Trp Gln Gln Gly Asn Val Phe
625                 630                 635                 640

Ser Cys Ser Val Met His Glu Ala Leu His Asn His Tyr Thr Gln Lys
                645                 650                 655

Ser Leu Ser Cys Ser Pro Gly Lys
            660
```

<210> SEQ ID NO 135
<211> LENGTH: 213
<212> TYPE: PRT
<213> ORGANISM: Artificial Sequence
<220> FEATURE:
<223> OTHER INFORMATION: light chain

<400> SEQUENCE: 135

```
Asp Ile Gln Leu Thr Gln Ser Pro Ser Ser Leu Ser Ala Ser Val Gly
1               5                   10                  15

Asp Arg Val Thr Ile Thr Cys Ser Ala Ser Ile Ser Val Ser Tyr Leu
                20                  25                  30

Tyr Trp Tyr Gln Gln Lys Pro Gly Lys Ala Pro Lys Leu Leu Ile Tyr
            35                  40                  45

Asp Asp Ser Ser Leu Ala Ser Gly Val Pro Ser Arg Phe Ser Gly Ser
50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Gly Tyr Pro Tyr Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
210
```

<210> SEQ ID NO 136
<211> LENGTH: 664
<212> TYPE: PRT
<213> ORGANISM: Artificial Sequence
<220> FEATURE:
<223> OTHER INFORMATION: light chain

<400> SEQUENCE: 136

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Pro Phe
                20                  25                  30

Ala Trp Ser Trp Val Arg Gln Ala Pro Gly Lys Gly Leu Glu Trp Val
            35                  40                  45
```

```
Ala Lys Ile Ser Pro Gly Gly Ser Trp Thr Tyr Tyr Ser Asp Thr Val
         50              55                  60

Thr Asp Arg Phe Thr Phe Ser Leu Asp Thr Ser Lys Ser Thr Ala Tyr
 65              70                  75                      80

Leu Gln Met Asn Ser Leu Arg Ala Glu Asp Thr Ala Val Tyr Tyr Cys
                 85                  90                  95

Ala Arg Gln Leu Trp Gly Tyr Tyr Ala Leu Asp Val Trp Gly Gln Gly
                100                 105                 110

Thr Leu Val Thr Val Ser Ser Ala Ser Thr Lys Gly Pro Ser Val Phe
             115                 120             125

Pro Leu Ala Pro Ser Ser Lys Ser Thr Ser Gly Gly Thr Ala Ala Leu
         130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                 165                 170                 175

Gln Ser Ser Gly Leu Tyr Ser Leu Ser Ser Val Val Thr Val Pro Ser
             180                 185                 190

Ser Ser Leu Gly Thr Gln Thr Tyr Ile Cys Asn Val Asn His Lys Pro
         195                 200                 205

Ser Asn Thr Lys Val Asp Lys Lys Val Glu Pro Lys Ser Cys Gly Gly
     210                 215                 220

Gly Gly Ser Gly Gly Gly Ser Ser Asp Thr Gly Arg Pro Phe Val
225             230                 235                 240

Glu Met Tyr Ser Glu Ile Pro Glu Ile Ile His Met Thr Glu Gly Arg
                 245                 250                 255

Glu Leu Val Ile Pro Cys Arg Val Thr Ser Pro Asn Ile Thr Val Thr
             260                 265                 270

Leu Lys Lys Phe Pro Leu Asp Thr Leu Ile Pro Asp Gly Lys Arg Ile
         275                 280                 285

Ile Trp Asp Ser Arg Lys Gly Phe Ile Ile Ser Asn Ala Thr Tyr Lys
     290                 295                 300

Glu Ile Gly Leu Leu Thr Cys Glu Ala Thr Val Asn Gly His Leu Tyr
305                 310                 315                 320

Lys Thr Asn Tyr Leu Thr His Arg Gln Thr Asn Thr Ile Ile Asp Val
                 325                 330                 335

Val Leu Ser Pro Ser His Gly Ile Glu Leu Ser Val Gly Glu Lys Leu
             340                 345                 350

Val Leu Asn Cys Thr Ala Arg Thr Glu Leu Asn Val Gly Ile Asp Phe
         355                 360                 365

Asn Trp Glu Tyr Pro Ser Ser Lys His Gln His Lys Lys Leu Val Asn
     370                 375                 380

Arg Asp Leu Lys Thr Gln Ser Gly Ser Glu Met Lys Lys Phe Leu Ser
385                 390                 395                 400

Thr Leu Thr Ile Asp Gly Val Thr Arg Ser Asp Gln Gly Leu Tyr Thr
                 405                 410                 415

Cys Ala Ala Ser Ser Gly Leu Met Thr Lys Lys Asn Ser Thr Phe Val
             420                 425                 430

Arg Val His Glu Lys Asp Lys Thr His Thr Cys Pro Pro Cys Pro Ala
         435                 440                 445

Pro Glu Ala Ala Gly Ala Pro Ser Val Phe Leu Phe Pro Pro Lys Pro
450                 455                 460
```

```
Lys Asp Thr Leu Met Ile Ser Arg Thr Pro Glu Val Thr Cys Val Val
465                 470                 475                 480

Val Asp Val Ser His Glu Asp Pro Glu Val Lys Phe Asn Trp Tyr Val
                485                 490                 495

Asp Gly Val Glu Val His Asn Ala Lys Thr Lys Pro Arg Glu Glu Gln
            500                 505                 510

Tyr Asn Ser Thr Tyr Arg Val Val Ser Val Leu Thr Val Leu His Gln
            515                 520                 525

Asp Trp Leu Asn Gly Lys Glu Tyr Lys Cys Lys Val Ser Asn Lys Ala
        530                 535                 540

Leu Pro Ala Pro Ile Glu Lys Thr Ile Ser Lys Ala Lys Gly Gln Pro
545                 550                 555                 560

Arg Glu Pro Gln Val Tyr Thr Leu Pro Pro Ser Arg Glu Glu Met Thr
                565                 570                 575

Lys Asn Gln Val Ser Leu Thr Cys Leu Val Lys Gly Phe Tyr Pro Ser
            580                 585                 590

Asp Ile Ala Val Glu Trp Glu Ser Asn Gly Gln Pro Glu Asn Asn Tyr
        595                 600                 605

Lys Thr Thr Pro Pro Val Leu Asp Ser Asp Gly Ser Phe Phe Leu Tyr
610                 615                 620

Ser Lys Leu Thr Val Asp Lys Ser Arg Trp Gln Gln Gly Asn Val Phe
625                 630                 635                 640

Ser Cys Ser Val Met His Glu Ala Leu His Asn His Tyr Thr Gln Lys
                645                 650                 655

Ser Leu Ser Cys Ser Pro Gly Lys
            660

<210> SEQ ID NO 137
<211> LENGTH: 213
<212> TYPE: PRT
<213> ORGANISM: Artificial Sequence
<220> FEATURE:
<223> OTHER INFORMATION: light chain

<400> SEQUENCE: 137

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ile Ser Val Ser Tyr Leu
                20                  25                  30

Tyr Trp Tyr Gln Gln Lys Pro Gly Lys Ala Pro Lys Leu Leu Ile Tyr
            35                  40                  45

Asp Ala Ser Ser Leu Ala Ser Gly Val Pro Ser Arg Phe Ser Gly Ser
        50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Gly Tyr Pro Tyr Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160
```

```
Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 138
<211> LENGTH: 664
<212> TYPE: PRT
<213> ORGANISM: Artificial Sequence
<220> FEATURE:
<223> OTHER INFORMATION: fusion

<400> SEQUENCE: 138

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Pro Phe
            20                  25                  30

Ala Trp Ser Trp Val Arg Gln Ala Pro Gly Lys Gly Leu Glu Trp Val
        35                  40                  45

Ala Lys Ile Ser Pro Gly Gly Ser Trp Thr Tyr Tyr Ser Asp Thr Val
50                  55                  60

Thr Asp Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gln Leu Trp Gly Tyr Tyr Ala Leu Asp Val Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Gly Gly
    210                 215                 220

Gly Gly Ser Gly Gly Gly Gly Ser Ser Asp Thr Gly Arg Pro Phe Val
225                 230                 235                 240

Glu Met Tyr Ser Glu Ile Pro Glu Ile Ile His Met Thr Glu Gly Arg
                245                 250                 255

Glu Leu Val Ile Pro Cys Arg Val Thr Ser Pro Asn Ile Thr Val Thr
            260                 265                 270

Leu Lys Lys Phe Pro Leu Asp Thr Leu Ile Pro Asp Gly Lys Arg Ile
        275                 280                 285

Ile Trp Asp Ser Arg Lys Gly Phe Ile Ile Ser Asn Ala Thr Tyr Lys
    290                 295                 300
```

-continued

```
Glu Ile Gly Leu Leu Thr Cys Glu Ala Thr Val Asn Gly His Leu Tyr
305                 310                 315                 320

Lys Thr Asn Tyr Leu Thr His Arg Gln Thr Asn Thr Ile Ile Asp Val
            325                 330                 335

Val Leu Ser Pro Ser His Gly Ile Glu Leu Ser Val Gly Lys Leu
        340                 345                 350

Val Leu Asn Cys Thr Ala Arg Thr Glu Leu Asn Val Gly Ile Asp Phe
            355                 360                 365

Asn Trp Glu Tyr Pro Ser Ser Lys His Gln His Lys Lys Leu Val Asn
370                 375                 380

Arg Asp Leu Lys Thr Gln Ser Gly Ser Glu Met Lys Lys Phe Leu Ser
385                 390                 395                 400

Thr Leu Thr Ile Asp Gly Val Thr Arg Ser Asp Gln Gly Leu Tyr Thr
                405                 410                 415

Cys Ala Ala Ser Ser Gly Leu Met Thr Lys Lys Asn Ser Thr Phe Val
            420                 425                 430

Arg Val His Glu Lys Asp Lys Thr His Thr Cys Pro Pro Cys Pro Ala
        435                 440                 445

Pro Glu Ala Ala Gly Ala Pro Ser Val Phe Leu Phe Pro Pro Lys Pro
    450                 455                 460

Lys Asp Thr Leu Met Ile Ser Arg Thr Pro Glu Val Thr Cys Val Val
465                 470                 475                 480

Val Asp Val Ser His Glu Asp Pro Glu Val Lys Phe Asn Trp Tyr Val
                485                 490                 495

Asp Gly Val Glu Val His Asn Ala Lys Thr Lys Pro Arg Glu Glu Gln
            500                 505                 510

Tyr Asn Ser Thr Tyr Arg Val Val Ser Val Leu Thr Val Leu His Gln
        515                 520                 525

Asp Trp Leu Asn Gly Lys Glu Tyr Lys Cys Lys Val Ser Asn Lys Ala
    530                 535                 540

Leu Pro Ala Pro Ile Glu Lys Thr Ile Ser Lys Ala Lys Gly Gln Pro
545                 550                 555                 560

Arg Glu Pro Gln Val Tyr Thr Leu Pro Pro Ser Arg Glu Glu Met Thr
                565                 570                 575

Lys Asn Gln Val Ser Leu Thr Cys Leu Val Lys Gly Phe Tyr Pro Ser
            580                 585                 590

Asp Ile Ala Val Glu Trp Glu Ser Asn Gly Gln Pro Glu Asn Asn Tyr
        595                 600                 605

Lys Thr Thr Pro Pro Val Leu Asp Ser Asp Gly Ser Phe Phe Leu Tyr
    610                 615                 620

Ser Lys Leu Thr Val Asp Lys Ser Arg Trp Gln Gln Gly Asn Val Phe
625                 630                 635                 640

Ser Cys Ser Val Met His Glu Ala Leu His Asn His Tyr Thr Gln Lys
                645                 650                 655

Ser Leu Ser Cys Ser Pro Gly Lys
            660
```

<210> SEQ ID NO 139
<211> LENGTH: 213
<212> TYPE: PRT
<213> ORGANISM: Artificial Sequence
<220> FEATURE:
<223> OTHER INFORMATION: light chain

```
<400> SEQUENCE: 139

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ile Ser Val Ser Tyr Leu
            20                  25                  30

Tyr Trp Tyr Gln Gln Lys Pro Gly Lys Ala Pro Lys Leu Leu Ile Tyr
        35                  40                  45

Asp Asp Ser Asn Leu Ala Ser Gly Val Pro Ser Arg Phe Ser Gly Ser
50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Gly Tyr Pro Tyr Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 140
<211> LENGTH: 119
<212> TYPE: PRT
<213> ORGANISM: Artificial Sequence
<220> FEATURE:
<223> OTHER INFORMATION: antibody

<400> SEQUENCE: 140

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Pro Phe
            20                  25                  30

Ala Ile Ser Trp Val Arg Gln Ala Pro Gly Lys Gly Leu Glu Trp Val
        35                  40                  45

Ala Lys Ile Ser Pro Gly Gly Ser Trp Thr Tyr Tyr Ser Asp Thr Val
50                  55                  60

Thr Asp Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gln Leu Trp Gly Tyr Tyr Ala Leu Asp Val Trp Gly Gln Gly
            100                 105                 110

Thr Leu Val Thr Val Ser Ser
        115
```

```
<210> SEQ ID NO 141
<211> LENGTH: 119
<212> TYPE: PRT
<213> ORGANISM: Artificial Sequence
<220> FEATURE:
<223> OTHER INFORMATION: antibody

<400> SEQUENCE: 141

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Pro Phe
            20                  25                  30

Ala Trp Ser Trp Val Arg Gln Ala Pro Gly Lys Gly Leu Glu Trp Val
        35                  40                  45

Ala Lys Ile Ser Pro Gly Gly Ser Trp Thr Tyr Tyr Ser Asp Thr Val
    50                  55                  60

Thr Asp Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gln Leu Trp Gly Tyr Tyr Ala Leu Asp Val Trp Gly Gln Gly
            100                 105                 110

Thr Leu Val Thr Val Ser Ser
        115

<210> SEQ ID NO 142
<211> LENGTH: 106
<212> TYPE: PRT
<213> ORGANISM: Artificial Sequence
<220> FEATURE:
<223> OTHER INFORMATION: antibody

<400> SEQUENCE: 142

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ile Ser Val Ser Tyr Leu
            20                  25                  30

Tyr Trp Tyr Gln Gln Lys Pro Gly Lys Ala Pro Lys Leu Leu Ile Tyr
        35                  40                  45

Asp Asp Ser Ser Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Gly Tyr Pro Tyr Thr
                85                  90                  95

Phe Gly Gln Gly Thr Lys Val Glu Ile Lys
            100                 105

<210> SEQ ID NO 143
<211> LENGTH: 106
<212> TYPE: PRT
<213> ORGANISM: Artificial Sequence
<220> FEATURE:
<223> OTHER INFORMATION: antibody

<400> SEQUENCE: 143

Asp Ile Gln Leu Thr Gln Ser Pro Ser Ser Leu Ser Ala Ser Val Gly
1               5                   10                  15
```

```
Asp Arg Val Thr Ile Thr Cys Ser Ala Ser Ile Ser Val Ser Tyr Leu
            20                  25                  30

Tyr Trp Tyr Gln Gln Lys Pro Gly Lys Ala Pro Lys Leu Leu Ile Tyr
        35                  40                  45

Asp Ala Ser Ser Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Gly Tyr Pro Tyr Thr
                85                  90                  95

Phe Gly Gln Gly Thr Lys Val Glu Ile Lys
            100                 105

<210> SEQ ID NO 144
<211> LENGTH: 106
<212> TYPE: PRT
<213> ORGANISM: Artificial Sequence
<220> FEATURE:
<223> OTHER INFORMATION: antibody

<400> SEQUENCE: 144

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ile Ser Val Ser Tyr Leu
            20                  25                  30

Tyr Trp Tyr Gln Gln Lys Pro Gly Lys Ala Pro Lys Leu Leu Ile Tyr
        35                  40                  45

Asp Asp Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Gly Tyr Pro Tyr Thr
                85                  90                  95

Phe Gly Gln Gly Thr Lys Val Glu Ile Lys
            100                 105

<210> SEQ ID NO 145
<211> LENGTH: 205
<212> TYPE: PRT
<213> ORGANISM: Artificial Sequence
<220> FEATURE:
<223> OTHER INFORMATION: trap

<400> SEQUENCE: 145

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
            35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95
```

```
Gln Thr Asn Thr Ile Ile Asp Val Val Leu Ser Pro Ser His Gly Ile
                100                 105                 110

Glu Leu Ser Val Gly Glu Lys Leu Val Leu Asn Cys Thr Ala Arg Thr
            115                 120                 125

Glu Leu Asn Val Gly Ile Asp Phe Asn Trp Glu Tyr Pro Ser Ser Lys
        130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys
        195                 200                 205

<210> SEQ ID NO 146
<211> LENGTH: 213
<212> TYPE: PRT
<213> ORGANISM: Artificial Sequence
<220> FEATURE:
<223> OTHER INFORMATION: light chain

<400> SEQUENCE: 146

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ile Ser Val Ser Tyr Leu
            20                  25                  30

Tyr Trp Tyr Gln Gln Lys Pro Gly Lys Ala Pro Lys Leu Leu Ile Tyr
        35                  40                  45

Asp Asp Ser Ser Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Gly Tyr Pro Tyr Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
        210

<210> SEQ ID NO 147
<211> LENGTH: 664
<212> TYPE: PRT
<213> ORGANISM: Artificial Sequence
```

<220> FEATURE:
<223> OTHER INFORMATION: fusion

<400> SEQUENCE: 147

```
Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Gly Gly Gly
        195                 200                 205

Gly Ser Gly Gly Gly Gly Ser Glu Val Gln Leu Val Glu Ser Gly Gly
    210                 215                 220

Gly Leu Val Gln Pro Gly Gly Ser Leu Arg Leu Ser Cys Ala Ala Ser
225                 230                 235                 240

Gly Phe Thr Phe Ser Pro Phe Ala Ile Ser Trp Val Arg Gln Ala Pro
                245                 250                 255

Gly Lys Gly Leu Glu Trp Val Ala Lys Ile Ser Pro Gly Gly Ser Trp
            260                 265                 270

Thr Tyr Tyr Ser Asp Thr Val Thr Asp Arg Phe Thr Phe Ser Leu Asp
        275                 280                 285

Thr Ser Lys Ser Thr Ala Tyr Leu Gln Met Asn Ser Leu Arg Ala Glu
    290                 295                 300

Asp Thr Ala Val Tyr Tyr Cys Ala Arg Gln Leu Trp Gly Tyr Tyr Ala
305                 310                 315                 320

Leu Asp Val Trp Gly Gln Gly Thr Leu Val Thr Val Ser Ser Ala Ser
                325                 330                 335

Thr Lys Gly Pro Ser Val Phe Pro Leu Ala Pro Ser Ser Lys Ser Thr
            340                 345                 350

Ser Gly Gly Thr Ala Ala Leu Gly Cys Leu Val Lys Asp Tyr Phe Pro
        355                 360                 365

Glu Pro Val Thr Val Ser Trp Asn Ser Gly Ala Leu Thr Ser Gly Val
    370                 375                 380

His Thr Phe Pro Ala Val Leu Gln Ser Ser Gly Leu Tyr Ser Leu Ser
385                 390                 395                 400
```

Ser Val Val Thr Val Pro Ser Ser Leu Gly Thr Gln Thr Tyr Ile
            405                 410                 415

Cys Asn Val Asn His Lys Pro Ser Asn Thr Lys Val Asp Lys Lys Val
            420                 425                 430

Glu Pro Lys Ser Cys Asp Lys Thr His Thr Cys Pro Pro Cys Pro Ala
        435                 440                 445

Pro Glu Ala Ala Gly Ala Pro Ser Val Phe Leu Phe Pro Pro Lys Pro
    450                 455                 460

Lys Asp Thr Leu Met Ile Ser Arg Thr Pro Glu Val Thr Cys Val Val
465                 470                 475                 480

Val Asp Val Ser His Glu Asp Pro Glu Val Lys Phe Asn Trp Tyr Val
                485                 490                 495

Asp Gly Val Glu Val His Asn Ala Lys Thr Lys Pro Arg Glu Glu Gln
            500                 505                 510

Tyr Asn Ser Thr Tyr Arg Val Val Ser Val Leu Thr Val Leu His Gln
        515                 520                 525

Asp Trp Leu Asn Gly Lys Glu Tyr Lys Cys Lys Val Ser Asn Lys Ala
    530                 535                 540

Leu Pro Ala Pro Ile Glu Lys Thr Ile Ser Lys Ala Lys Gly Gln Pro
545                 550                 555                 560

Arg Glu Pro Gln Val Tyr Thr Leu Pro Pro Ser Arg Glu Glu Met Thr
                565                 570                 575

Lys Asn Gln Val Ser Leu Thr Cys Leu Val Lys Gly Phe Tyr Pro Ser
            580                 585                 590

Asp Ile Ala Val Glu Trp Glu Ser Asn Gly Gln Pro Glu Asn Asn Tyr
        595                 600                 605

Lys Thr Thr Pro Pro Val Leu Asp Ser Asp Gly Ser Phe Phe Leu Tyr
    610                 615                 620

Ser Lys Leu Thr Val Asp Lys Ser Arg Trp Gln Gln Gly Asn Val Phe
625                 630                 635                 640

Ser Cys Ser Val Met His Glu Ala Leu His Asn His Tyr Thr Gln Lys
                645                 650                 655

Ser Leu Ser Cys Ser Pro Gly Lys
            660

<210> SEQ ID NO 148
<211> LENGTH: 213
<212> TYPE: PRT
<213> ORGANISM: Artificial Sequence
<220> FEATURE:
<223> OTHER INFORMATION: light chain

<400> SEQUENCE: 148

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ile Ser Val Ser Tyr Leu
            20                  25                  30

Tyr Trp Tyr Gln Gln Lys Pro Gly Lys Ala Pro Lys Leu Leu Ile Tyr
        35                  40                  45

Asp Ala Ser Ser Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Gly Tyr Pro Tyr Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
            130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
    210

<210> SEQ ID NO 149
<211> LENGTH: 664
<212> TYPE: PRT
<213> ORGANISM: Artificial Sequence
<220> FEATURE:
<223> OTHER INFORMATION: fusion

<400> SEQUENCE: 149

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
            115                 120                 125

Glu Leu Asn Val Gly Ile Asp Phe Asn Trp Glu Tyr Pro Ser Ser Lys
            130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Gly Gly Gly
            195                 200                 205

Gly Ser Gly Gly Gly Gly Ser Glu Val Gln Leu Val Glu Ser Gly Gly
    210                 215                 220

Gly Leu Val Gln Pro Gly Gly Ser Leu Arg Leu Ser Cys Ala Ala Ser
225                 230                 235                 240

```
Gly Phe Thr Phe Ser Pro Phe Ala Ile Ser Trp Val Arg Gln Ala Pro
                245                 250                 255
Gly Lys Gly Leu Glu Trp Val Ala Lys Ile Ser Pro Gly Gly Ser Trp
                260                 265                 270
Thr Tyr Tyr Ser Asp Thr Val Thr Asp Arg Phe Thr Phe Ser Leu Asp
                275                 280                 285
Thr Ser Lys Ser Thr Ala Tyr Leu Gln Met Asn Ser Leu Arg Ala Glu
        290                 295                 300
Asp Thr Ala Val Tyr Tyr Cys Ala Arg Gln Leu Trp Gly Tyr Tyr Ala
305                 310                 315                 320
Leu Asp Val Trp Gly Gln Gly Thr Leu Val Thr Val Ser Ser Ala Ser
                325                 330                 335
Thr Lys Gly Pro Ser Val Phe Pro Leu Ala Pro Ser Ser Lys Ser Thr
                340                 345                 350
Ser Gly Gly Thr Ala Ala Leu Gly Cys Leu Val Lys Asp Tyr Phe Pro
            355                 360                 365
Glu Pro Val Thr Val Ser Trp Asn Ser Gly Ala Leu Thr Ser Gly Val
            370                 375                 380
His Thr Phe Pro Ala Val Leu Gln Ser Ser Gly Leu Tyr Ser Leu Ser
385                 390                 395                 400
Ser Val Val Thr Val Pro Ser Ser Ser Leu Gly Thr Gln Thr Tyr Ile
                405                 410                 415
Cys Asn Val Asn His Lys Pro Ser Asn Thr Lys Val Asp Lys Lys Val
                420                 425                 430
Glu Pro Lys Ser Cys Asp Lys Thr His Thr Cys Pro Pro Cys Pro Ala
            435                 440                 445
Pro Glu Ala Ala Gly Ala Pro Ser Val Phe Leu Phe Pro Pro Lys Pro
450                 455                 460
Lys Asp Thr Leu Met Ile Ser Arg Thr Pro Glu Val Thr Cys Val Val
465                 470                 475                 480
Val Asp Val Ser His Glu Asp Pro Glu Val Lys Phe Asn Trp Tyr Val
                485                 490                 495
Asp Gly Val Glu Val His Asn Ala Lys Thr Lys Pro Arg Glu Glu Gln
            500                 505                 510
Tyr Asn Ser Thr Tyr Arg Val Val Ser Val Leu Thr Val Leu His Gln
        515                 520                 525
Asp Trp Leu Asn Gly Lys Glu Tyr Lys Cys Lys Val Ser Asn Lys Ala
530                 535                 540
Leu Pro Ala Pro Ile Glu Lys Thr Ile Ser Lys Ala Lys Gly Gln Pro
545                 550                 555                 560
Arg Glu Pro Gln Val Tyr Thr Leu Pro Pro Ser Arg Glu Glu Met Thr
                565                 570                 575
Lys Asn Gln Val Ser Leu Thr Cys Leu Val Lys Gly Phe Tyr Pro Ser
            580                 585                 590
Asp Ile Ala Val Glu Trp Glu Ser Asn Gly Gln Pro Glu Asn Asn Tyr
            595                 600                 605
Lys Thr Thr Pro Pro Val Leu Asp Ser Asp Gly Ser Phe Phe Leu Tyr
        610                 615                 620
Ser Lys Leu Thr Val Asp Lys Ser Arg Trp Gln Gln Gly Asn Val Phe
625                 630                 635                 640
Ser Cys Ser Val Met His Glu Ala Leu His Asn His Tyr Thr Gln Lys
                645                 650                 655
```

Ser Leu Ser Cys Ser Pro Gly Lys
            660

<210> SEQ ID NO 150
<211> LENGTH: 213
<212> TYPE: PRT
<213> ORGANISM: Artificial Sequence
<220> FEATURE:
<223> OTHER INFORMATION: light chain

<400> SEQUENCE: 150

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ile Ser Val Ser Tyr Leu
            20                  25                  30

Tyr Trp Tyr Gln Gln Lys Pro Gly Lys Ala Pro Lys Leu Leu Ile Tyr
        35                  40                  45

Asp Asp Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Gly Tyr Pro Tyr Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 151
<211> LENGTH: 664
<212> TYPE: PRT
<213> ORGANISM: Artificial Sequence
<220> FEATURE:
<223> OTHER INFORMATION: fusion

<400> SEQUENCE: 151

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

```
Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Gly Gly Gly
        195                 200                 205

Gly Ser Gly Gly Gly Gly Ser Glu Val Gln Leu Val Glu Ser Gly Gly
    210                 215                 220

Gly Leu Val Gln Pro Gly Gly Ser Leu Arg Leu Ser Cys Ala Ala Ser
225                 230                 235                 240

Gly Phe Thr Phe Ser Pro Phe Ala Trp Ser Trp Val Arg Gln Ala Pro
                245                 250                 255

Gly Lys Gly Leu Glu Trp Val Ala Lys Ile Ser Pro Gly Gly Ser Trp
            260                 265                 270

Thr Tyr Tyr Ser Asp Thr Val Thr Asp Arg Phe Thr Phe Ser Leu Asp
        275                 280                 285

Thr Ser Lys Ser Thr Ala Tyr Leu Gln Met Asn Ser Leu Arg Ala Glu
    290                 295                 300

Asp Thr Ala Val Tyr Tyr Cys Ala Arg Gln Leu Trp Gly Tyr Tyr Ala
305                 310                 315                 320

Leu Asp Val Trp Gly Gln Gly Thr Leu Val Thr Val Ser Ser Ala Ser
                325                 330                 335

Thr Lys Gly Pro Ser Val Phe Pro Leu Ala Pro Ser Ser Lys Ser Thr
            340                 345                 350

Ser Gly Gly Thr Ala Ala Leu Gly Cys Leu Val Lys Asp Tyr Phe Pro
        355                 360                 365

Glu Pro Val Thr Val Ser Trp Asn Ser Gly Ala Leu Thr Ser Gly Val
    370                 375                 380

His Thr Phe Pro Ala Val Leu Gln Ser Ser Gly Leu Tyr Ser Leu Ser
385                 390                 395                 400

Ser Val Val Thr Val Pro Ser Ser Ser Leu Gly Thr Gln Thr Tyr Ile
                405                 410                 415

Cys Asn Val Asn His Lys Pro Ser Asn Thr Lys Val Asp Lys Lys Val
            420                 425                 430

Glu Pro Lys Ser Cys Asp Lys Thr His Thr Cys Pro Pro Cys Pro Ala
        435                 440                 445

Pro Glu Ala Ala Gly Ala Pro Ser Val Phe Leu Phe Pro Pro Lys Pro
    450                 455                 460

Lys Asp Thr Leu Met Ile Ser Arg Thr Pro Glu Val Thr Cys Val Val
465                 470                 475                 480

Val Asp Val Ser His Glu Asp Pro Glu Val Lys Phe Asn Trp Tyr Val
                485                 490                 495
```

Asp Gly Val Glu Val His Asn Ala Lys Thr Lys Pro Arg Glu Glu Gln
            500                 505                 510

Tyr Asn Ser Thr Tyr Arg Val Val Ser Val Leu Thr Val Leu His Gln
            515                 520                 525

Asp Trp Leu Asn Gly Lys Glu Tyr Lys Cys Lys Val Ser Asn Lys Ala
        530                 535                 540

Leu Pro Ala Pro Ile Glu Lys Thr Ile Ser Lys Ala Lys Gly Gln Pro
545                 550                 555                 560

Arg Glu Pro Gln Val Tyr Thr Leu Pro Pro Ser Arg Glu Glu Met Thr
                565                 570                 575

Lys Asn Gln Val Ser Leu Thr Cys Leu Val Lys Gly Phe Tyr Pro Ser
            580                 585                 590

Asp Ile Ala Val Glu Trp Glu Ser Asn Gly Gln Pro Glu Asn Asn Tyr
        595                 600                 605

Lys Thr Thr Pro Pro Val Leu Asp Ser Asp Gly Ser Phe Phe Leu Tyr
610                 615                 620

Ser Lys Leu Thr Val Asp Lys Ser Arg Trp Gln Gln Gly Asn Val Phe
625                 630                 635                 640

Ser Cys Ser Val Met His Glu Ala Leu His Asn His Tyr Thr Gln Lys
                645                 650                 655

Ser Leu Ser Cys Ser Pro Gly Lys
                660

<210> SEQ ID NO 152
<211> LENGTH: 213
<212> TYPE: PRT
<213> ORGANISM: Artificial Sequence
<220> FEATURE:
<223> OTHER INFORMATION: light chain

<400> SEQUENCE: 152

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ile Ser Val Ser Tyr Leu
            20                  25                  30

Tyr Trp Tyr Gln Gln Lys Pro Gly Lys Ala Pro Lys Leu Leu Ile Tyr
        35                  40                  45

Asp Asp Ser Ser Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Gly Tyr Pro Tyr Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
    210

<210> SEQ ID NO 153
<211> LENGTH: 664
<212> TYPE: PRT
<213> ORGANISM: Artificial Sequence
<220> FEATURE:
<223> OTHER INFORMATION: fusion

<400> SEQUENCE: 153

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
                20                  25                  30

Thr Ser Pro Asn Ile Thr Val Thr Leu Lys Lys Phe Pro Leu Asp Thr
            35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
    115                 120                 125

Glu Leu Asn Val Gly Ile Asp Phe Asn Trp Glu Tyr Pro Ser Ser Lys
130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Gly Gly Gly
    195                 200                 205

Gly Ser Gly Gly Gly Gly Ser Glu Val Gln Leu Val Glu Ser Gly Gly
210                 215                 220

Gly Leu Val Gln Pro Gly Gly Ser Leu Arg Leu Ser Cys Ala Ala Ser
225                 230                 235                 240

Gly Phe Thr Phe Ser Pro Phe Ala Trp Ser Trp Val Arg Gln Ala Pro
                245                 250                 255

Gly Lys Gly Leu Glu Trp Val Ala Lys Ile Ser Pro Gly Gly Ser Trp
            260                 265                 270

Thr Tyr Tyr Ser Asp Thr Val Thr Asp Arg Phe Thr Phe Ser Leu Asp
    275                 280                 285

Thr Ser Lys Ser Thr Ala Tyr Leu Gln Met Asn Ser Leu Arg Ala Glu
290                 295                 300

Asp Thr Ala Val Tyr Tyr Cys Ala Arg Gln Leu Trp Gly Tyr Tyr Ala
305                 310                 315                 320

Leu Asp Val Trp Gly Gln Gly Thr Leu Val Thr Val Ser Ser Ala Ser
                325                 330                 335

-continued

Thr Lys Gly Pro Ser Val Phe Pro Leu Ala Pro Ser Ser Lys Ser Thr
                340                 345                 350

Ser Gly Gly Thr Ala Ala Leu Gly Cys Leu Val Lys Asp Tyr Phe Pro
            355                 360                 365

Glu Pro Val Thr Val Ser Trp Asn Ser Gly Ala Leu Thr Ser Gly Val
        370                 375                 380

His Thr Phe Pro Ala Val Leu Gln Ser Gly Leu Tyr Ser Leu Ser
385                 390                 395                 400

Ser Val Val Thr Val Pro Ser Ser Ser Leu Gly Thr Gln Thr Tyr Ile
                405                 410                 415

Cys Asn Val Asn His Lys Pro Ser Asn Thr Lys Val Asp Lys Lys Val
                420                 425                 430

Glu Pro Lys Ser Cys Asp Lys Thr His Thr Cys Pro Pro Cys Pro Ala
            435                 440                 445

Pro Glu Ala Ala Gly Ala Pro Ser Val Phe Leu Phe Pro Pro Lys Pro
        450                 455                 460

Lys Asp Thr Leu Met Ile Ser Arg Thr Pro Glu Val Thr Cys Val Val
465                 470                 475                 480

Val Asp Val Ser His Glu Asp Pro Glu Val Lys Phe Asn Trp Tyr Val
                485                 490                 495

Asp Gly Val Glu Val His Asn Ala Lys Thr Lys Pro Arg Glu Glu Gln
            500                 505                 510

Tyr Asn Ser Thr Tyr Arg Val Val Ser Val Leu Thr Val Leu His Gln
        515                 520                 525

Asp Trp Leu Asn Gly Lys Glu Tyr Lys Cys Lys Val Ser Asn Lys Ala
530                 535                 540

Leu Pro Ala Pro Ile Glu Lys Thr Ile Ser Lys Ala Lys Gly Gln Pro
545                 550                 555                 560

Arg Glu Pro Gln Val Tyr Thr Leu Pro Pro Ser Arg Glu Glu Met Thr
                565                 570                 575

Lys Asn Gln Val Ser Leu Thr Cys Leu Val Lys Gly Phe Tyr Pro Ser
            580                 585                 590

Asp Ile Ala Val Glu Trp Glu Ser Asn Gly Gln Pro Glu Asn Asn Tyr
        595                 600                 605

Lys Thr Thr Pro Pro Val Leu Asp Ser Asp Gly Ser Phe Phe Leu Tyr
610                 615                 620

Ser Lys Leu Thr Val Asp Lys Ser Arg Trp Gln Gln Gly Asn Val Phe
625                 630                 635                 640

Ser Cys Ser Val Met His Glu Ala Leu His Asn His Tyr Thr Gln Lys
                645                 650                 655

Ser Leu Ser Cys Ser Pro Gly Lys
            660

<210> SEQ ID NO 154
<211> LENGTH: 213
<212> TYPE: PRT
<213> ORGANISM: Artificial Sequence
<220> FEATURE:
<223> OTHER INFORMATION: light chain

<400> SEQUENCE: 154

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ile Ser Val Ser Tyr Leu
            20                  25                  30

```
Tyr Trp Tyr Gln Gln Lys Pro Gly Lys Ala Pro Lys Leu Leu Ile Tyr
             35                  40                  45

Asp Ala Ser Ser Leu Ala Ser Gly Val Pro Ser Arg Phe Ser Gly Ser
 50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Trp Ser Gly Tyr Pro Tyr Thr
                 85                  90                  95

Phe Gly Gln Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
    210

<210> SEQ ID NO 155
<211> LENGTH: 664
<212> TYPE: PRT
<213> ORGANISM: Artificial Sequence
<220> FEATURE:
<223> OTHER INFORMATION: fusion

<400> SEQUENCE: 155

Ser Asp Thr Gly Arg Pro Phe Val Glu Met Tyr Ser Glu Ile Pro Glu
 1               5                  10                  15

Ile Ile His Met Thr Glu Gly Arg Glu Leu Val Ile Pro Cys Arg Val
             20                  25                  30

Thr Ser Pro Asn Ile Thr Val Thr Leu Lys Lys Phe Pro Leu Asp Thr
         35                  40                  45

Leu Ile Pro Asp Gly Lys Arg Ile Ile Trp Asp Ser Arg Lys Gly Phe
 50                  55                  60

Ile Ile Ser Asn Ala Thr Tyr Lys Glu Ile Gly Leu Leu Thr Cys Glu
 65                  70                  75                  80

Ala Thr Val Asn Gly His Leu Tyr Lys Thr Asn Tyr Leu Thr His Arg
                 85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
            115                 120                 125

Glu Leu Asn Val Gly Ile Asp Phe Asn Trp Glu Tyr Pro Ser Ser Lys
130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175
```

```
Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Gly Gly
        195                 200                 205

Gly Ser Gly Gly Gly Gly Ser Glu Val Gln Leu Val Glu Ser Gly Gly
        210                 215                 220

Gly Leu Val Gln Pro Gly Gly Ser Leu Arg Leu Ser Cys Ala Ala Ser
225                 230                 235                 240

Gly Phe Thr Phe Ser Pro Phe Ala Trp Ser Trp Val Arg Gln Ala Pro
                245                 250                 255

Gly Lys Gly Leu Glu Trp Val Ala Lys Ile Ser Pro Gly Gly Ser Trp
            260                 265                 270

Thr Tyr Tyr Ser Asp Thr Val Thr Asp Arg Phe Thr Phe Ser Leu Asp
        275                 280                 285

Thr Ser Lys Ser Thr Ala Tyr Leu Gln Met Asn Ser Leu Arg Ala Glu
        290                 295                 300

Asp Thr Ala Val Tyr Tyr Cys Ala Arg Gln Leu Trp Gly Tyr Tyr Ala
305                 310                 315                 320

Leu Asp Val Trp Gly Gln Gly Thr Leu Val Thr Val Ser Ser Ala Ser
                325                 330                 335

Thr Lys Gly Pro Ser Val Phe Pro Leu Ala Pro Ser Ser Lys Ser Thr
            340                 345                 350

Ser Gly Gly Thr Ala Ala Leu Gly Cys Leu Val Lys Asp Tyr Phe Pro
        355                 360                 365

Glu Pro Val Thr Val Ser Trp Asn Ser Gly Ala Leu Thr Ser Gly Val
        370                 375                 380

His Thr Phe Pro Ala Val Leu Gln Ser Ser Gly Leu Tyr Ser Leu Ser
385                 390                 395                 400

Ser Val Val Thr Val Pro Ser Ser Ser Leu Gly Thr Gln Thr Tyr Ile
                405                 410                 415

Cys Asn Val Asn His Lys Pro Ser Asn Thr Lys Val Asp Lys Lys Val
            420                 425                 430

Glu Pro Lys Ser Cys Asp Lys Thr His Thr Cys Pro Pro Cys Pro Ala
        435                 440                 445

Pro Glu Ala Ala Gly Ala Pro Ser Val Phe Leu Phe Pro Pro Lys Pro
450                 455                 460

Lys Asp Thr Leu Met Ile Ser Arg Thr Pro Glu Val Thr Cys Val Val
465                 470                 475                 480

Val Asp Val Ser His Glu Asp Pro Glu Val Lys Phe Asn Trp Tyr Val
                485                 490                 495

Asp Gly Val Glu Val His Asn Ala Lys Thr Lys Pro Arg Glu Glu Gln
            500                 505                 510

Tyr Asn Ser Thr Tyr Arg Val Val Ser Val Leu Thr Val Leu His Gln
        515                 520                 525

Asp Trp Leu Asn Gly Lys Glu Tyr Lys Cys Lys Val Ser Asn Lys Ala
        530                 535                 540

Leu Pro Ala Pro Ile Glu Lys Thr Ile Ser Lys Ala Lys Gly Gln Pro
545                 550                 555                 560

Arg Glu Pro Gln Val Tyr Thr Leu Pro Pro Ser Arg Glu Glu Met Thr
                565                 570                 575

Lys Asn Gln Val Ser Leu Thr Cys Leu Val Lys Gly Phe Tyr Pro Ser
            580                 585                 590
```

```
Asp Ile Ala Val Glu Trp Glu Ser Asn Gly Gln Pro Glu Asn Asn Tyr
            595                 600                 605

Lys Thr Thr Pro Pro Val Leu Asp Ser Asp Gly Ser Phe Phe Leu Tyr
        610                 615                 620

Ser Lys Leu Thr Val Asp Lys Ser Arg Trp Gln Gln Gly Asn Val Phe
625                 630                 635                 640

Ser Cys Ser Val Met His Glu Ala Leu His Asn His Tyr Thr Gln Lys
                645                 650                 655

Ser Leu Ser Cys Ser Pro Gly Lys
            660

<210> SEQ ID NO 156
<211> LENGTH: 213
<212> TYPE: PRT
<213> ORGANISM: Artificial Sequence
<220> FEATURE:
<223> OTHER INFORMATION: light chain

<400> SEQUENCE: 156

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ile Ser Val Ser Tyr Leu
            20                  25                  30

Tyr Trp Tyr Gln Gln Lys Pro Gly Lys Ala Pro Lys Leu Leu Ile Tyr
        35                  40                  45

Asp Asp Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Gly Tyr Pro Tyr Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 157
<211> LENGTH: 664
<212> TYPE: PRT
<213> ORGANISM: Artificial Sequence
<220> FEATURE:
<223> OTHER INFORMATION: fusion
```

<400> SEQUENCE: 157

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Pro Phe
            20                  25                  30

Ala Ile Ser Trp Val Arg Gln Ala Pro Gly Lys Gly Leu Glu Trp Val
        35                  40                  45

Ala Lys Ile Ser Pro Gly Gly Ser Trp Thr Tyr Tyr Ser Asp Thr Val
    50                  55                  60

Thr Asp Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gln Leu Trp Gly Tyr Tyr Ala Leu Asp Val Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Gly Gly
    210                 215                 220

Gly Gly Ser Gly Gly Gly Gly Ser Ser Asp Thr Gly Arg Pro Phe Val
225                 230                 235                 240

Glu Met Tyr Ser Glu Ile Pro Glu Ile Ile His Met Thr Glu Gly Arg
                245                 250                 255

Glu Leu Val Ile Pro Cys Arg Val Thr Ser Pro Asn Ile Thr Val Thr
            260                 265                 270

Leu Lys Lys Phe Pro Leu Asp Thr Leu Ile Pro Asp Gly Lys Arg Ile
        275                 280                 285

Ile Trp Asp Ser Arg Lys Gly Phe Ile Ile Ser Asn Ala Thr Tyr Lys
    290                 295                 300

Glu Ile Gly Leu Leu Thr Cys Glu Ala Thr Val Asn Gly His Leu Tyr
305                 310                 315                 320

Lys Thr Asn Tyr Leu Thr His Arg Gln Thr Asn Thr Ile Ile Asp Val
                325                 330                 335

Val Leu Ser Pro Ser His Gly Ile Glu Leu Ser Val Gly Glu Lys Leu
            340                 345                 350

Val Leu Asn Cys Thr Ala Arg Thr Glu Leu Asn Val Gly Ile Asp Phe
        355                 360                 365

Asn Trp Glu Tyr Pro Ser Ser Lys His Gln His Lys Lys Leu Val Asn
    370                 375                 380

Arg Asp Leu Lys Thr Gln Ser Gly Ser Glu Met Lys Lys Phe Leu Ser
385                 390                 395                 400
```

```
Thr Leu Thr Ile Asp Gly Val Thr Arg Ser Asp Gln Gly Leu Tyr Thr
                405                 410                 415

Cys Ala Ala Ser Ser Gly Leu Met Thr Lys Lys Asn Ser Thr Phe Val
            420                 425                 430

Arg Val His Glu Lys Asp Lys Thr His Thr Cys Pro Pro Cys Pro Ala
        435                 440                 445

Pro Glu Ala Ala Gly Ala Pro Ser Val Phe Leu Phe Pro Pro Lys Pro
    450                 455                 460

Lys Asp Thr Leu Met Ile Ser Arg Thr Pro Glu Val Thr Cys Val Val
465                 470                 475                 480

Val Asp Val Ser His Glu Asp Pro Glu Val Lys Phe Asn Trp Tyr Val
                485                 490                 495

Asp Gly Val Glu Val His Asn Ala Lys Thr Lys Pro Arg Glu Glu Gln
            500                 505                 510

Tyr Asn Ser Thr Tyr Arg Val Val Ser Val Leu Thr Val Leu His Gln
        515                 520                 525

Asp Trp Leu Asn Gly Lys Glu Tyr Lys Cys Lys Val Ser Asn Lys Ala
    530                 535                 540

Leu Pro Ala Pro Ile Glu Lys Thr Ile Ser Lys Ala Lys Gly Gln Pro
545                 550                 555                 560

Arg Glu Pro Gln Val Tyr Thr Leu Pro Pro Ser Arg Glu Glu Met Thr
                565                 570                 575

Lys Asn Gln Val Ser Leu Thr Cys Leu Val Lys Gly Phe Tyr Pro Ser
            580                 585                 590

Asp Ile Ala Val Glu Trp Glu Ser Asn Gly Gln Pro Glu Asn Asn Tyr
        595                 600                 605

Lys Thr Thr Pro Pro Val Leu Asp Ser Asp Gly Ser Phe Phe Leu Tyr
    610                 615                 620

Ser Lys Leu Thr Val Asp Lys Ser Arg Trp Gln Gln Gly Asn Val Phe
625                 630                 635                 640

Ser Cys Ser Val Met His Glu Ala Leu His Asn His Tyr Thr Gln Lys
                645                 650                 655

Ser Leu Ser Cys Ser Pro Gly Lys
            660

<210> SEQ ID NO 158
<211> LENGTH: 213
<212> TYPE: PRT
<213> ORGANISM: Artificial Sequence
<220> FEATURE:
<223> OTHER INFORMATION: light chain

<400> SEQUENCE: 158

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ile Ser Val Ser Tyr Leu
            20                  25                  30

Tyr Trp Tyr Gln Gln Lys Pro Gly Lys Ala Pro Lys Leu Leu Ile Tyr
        35                  40                  45

Asp Asp Ser Ser Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Gly Tyr Pro Tyr Thr
                85                  90                  95
```

```
Phe Gly Gln Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 159
<211> LENGTH: 664
<212> TYPE: PRT
<213> ORGANISM: Artificial Sequence
<220> FEATURE:
<223> OTHER INFORMATION: fusion

<400> SEQUENCE: 159

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Pro Phe
            20                  25                  30

Ala Ile Ser Trp Val Arg Gln Ala Pro Gly Lys Gly Leu Glu Trp Val
        35                  40                  45

Ala Lys Ile Ser Pro Gly Gly Ser Trp Thr Tyr Tyr Ser Asp Thr Val
    50                  55                  60

Thr Asp Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gln Leu Trp Gly Tyr Tyr Ala Leu Asp Val Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Gly Gly
    210                 215                 220

Gly Gly Ser Gly Gly Gly Gly Ser Ser Asp Thr Gly Arg Pro Phe Val
225                 230                 235                 240
```

-continued

Glu Met Tyr Ser Glu Ile Pro Glu Ile Ile His Met Thr Glu Gly Arg
             245                 250                 255

Glu Leu Val Ile Pro Cys Arg Val Thr Ser Pro Asn Ile Thr Val Thr
             260                 265                 270

Leu Lys Lys Phe Pro Leu Asp Thr Leu Ile Pro Asp Gly Lys Arg Ile
             275                 280                 285

Ile Trp Asp Ser Arg Lys Gly Phe Ile Ile Ser Asn Ala Thr Tyr Lys
         290                 295                 300

Glu Ile Gly Leu Leu Thr Cys Glu Ala Thr Val Asn Gly His Leu Tyr
305                 310                 315                 320

Lys Thr Asn Tyr Leu Thr His Arg Gln Thr Asn Thr Ile Ile Asp Val
             325                 330                 335

Val Leu Ser Pro Ser His Gly Ile Glu Leu Ser Val Gly Glu Lys Leu
             340                 345                 350

Val Leu Asn Cys Thr Ala Arg Thr Glu Leu Asn Val Gly Ile Asp Phe
             355                 360                 365

Asn Trp Glu Tyr Pro Ser Ser Lys His Gln His Lys Lys Leu Val Asn
         370                 375                 380

Arg Asp Leu Lys Thr Gln Ser Gly Ser Glu Met Lys Lys Phe Leu Ser
385                 390                 395                 400

Thr Leu Thr Ile Asp Gly Val Thr Arg Ser Asp Gln Gly Leu Tyr Thr
             405                 410                 415

Cys Ala Ala Ser Ser Gly Leu Met Thr Lys Lys Asn Ser Thr Phe Val
             420                 425                 430

Arg Val His Glu Lys Asp Lys Thr His Thr Cys Pro Pro Cys Pro Ala
             435                 440                 445

Pro Glu Ala Ala Gly Ala Pro Ser Val Phe Leu Phe Pro Pro Lys Pro
             450                 455                 460

Lys Asp Thr Leu Met Ile Ser Arg Thr Pro Glu Val Thr Cys Val Val
465                 470                 475                 480

Val Asp Val Ser His Glu Asp Pro Glu Val Lys Phe Asn Trp Tyr Val
             485                 490                 495

Asp Gly Val Glu Val His Asn Ala Lys Thr Lys Pro Arg Glu Glu Gln
             500                 505                 510

Tyr Asn Ser Thr Tyr Arg Val Val Ser Val Leu Thr Val Leu His Gln
             515                 520                 525

Asp Trp Leu Asn Gly Lys Glu Tyr Lys Cys Lys Val Ser Asn Lys Ala
         530                 535                 540

Leu Pro Ala Pro Ile Glu Lys Thr Ile Ser Lys Ala Lys Gly Gln Pro
545                 550                 555                 560

Arg Glu Pro Gln Val Tyr Thr Leu Pro Pro Ser Arg Glu Glu Met Thr
             565                 570                 575

Lys Asn Gln Val Ser Leu Thr Cys Leu Val Lys Gly Phe Tyr Pro Ser
             580                 585                 590

Asp Ile Ala Val Glu Trp Glu Ser Asn Gly Gln Pro Glu Asn Asn Tyr
             595                 600                 605

Lys Thr Thr Pro Pro Val Leu Asp Ser Asp Gly Ser Phe Phe Leu Tyr
             610                 615                 620

Ser Lys Leu Thr Val Asp Lys Ser Arg Trp Gln Gln Gly Asn Val Phe
625                 630                 635                 640

Ser Cys Ser Val Met His Glu Ala Leu His Asn His Tyr Thr Gln Lys
             645                 650                 655

```
Ser Leu Ser Cys Ser Pro Gly Lys
            660
```

<210> SEQ ID NO 160
<211> LENGTH: 213
<212> TYPE: PRT
<213> ORGANISM: Artificial Sequence
<220> FEATURE:
<223> OTHER INFORMATION: light chain

<400> SEQUENCE: 160

```
Asp Ile Gln Leu Thr Gln Ser Pro Ser Ser Leu Ser Ala Ser Val Gly
1               5                   10                  15

Asp Arg Val Thr Ile Thr Cys Ser Ala Ser Ile Ser Val Ser Tyr Leu
            20                  25                  30

Tyr Trp Tyr Gln Gln Lys Pro Gly Lys Ala Pro Lys Leu Leu Ile Tyr
        35                  40                  45

Asp Ala Ser Ser Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Gly Tyr Pro Tyr Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 161
<211> LENGTH: 664
<212> TYPE: PRT
<213> ORGANISM: Artificial Sequence
<220> FEATURE:
<223> OTHER INFORMATION: fusion

<400> SEQUENCE: 161

```
Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Pro Phe
            20                  25                  30

Ala Ile Ser Trp Val Arg Gln Ala Pro Gly Lys Gly Leu Glu Trp Val
        35                  40                  45

Ala Lys Ile Ser Pro Gly Gly Ser Trp Thr Tyr Tyr Ser Asp Thr Val
    50                  55                  60

Thr Asp Arg Phe Thr Phe Ser Leu Asp Thr Ser Lys Ser Thr Ala Tyr
65                  70                  75                  80
```

```
Leu Gln Met Asn Ser Leu Arg Ala Glu Asp Thr Ala Val Tyr Tyr Cys
                85                  90                  95

Ala Arg Gln Leu Trp Gly Tyr Tyr Ala Leu Asp Val Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Gly Gly
        210                 215                 220

Gly Gly Ser Gly Gly Gly Ser Ser Asp Thr Gly Arg Pro Phe Val
225                 230                 235                 240

Glu Met Tyr Ser Glu Ile Pro Glu Ile Ile His Met Thr Glu Gly Arg
                245                 250                 255

Glu Leu Val Ile Pro Cys Arg Val Thr Ser Pro Asn Ile Thr Val Thr
            260                 265                 270

Leu Lys Lys Phe Pro Leu Asp Thr Leu Ile Pro Asp Gly Lys Arg Ile
        275                 280                 285

Ile Trp Asp Ser Arg Lys Gly Phe Ile Ile Ser Asn Ala Thr Tyr Lys
    290                 295                 300

Glu Ile Gly Leu Leu Thr Cys Glu Ala Thr Val Asn Gly His Leu Tyr
305                 310                 315                 320

Lys Thr Asn Tyr Leu Thr His Arg Gln Thr Asn Thr Ile Ile Asp Val
                325                 330                 335

Val Leu Ser Pro Ser His Gly Ile Glu Leu Ser Val Gly Glu Lys Leu
            340                 345                 350

Val Leu Asn Cys Thr Ala Arg Thr Glu Leu Asn Val Gly Ile Asp Phe
            355                 360                 365

Asn Trp Glu Tyr Pro Ser Ser Lys His Gln His Lys Lys Leu Val Asn
370                 375                 380

Arg Asp Leu Lys Thr Gln Ser Gly Ser Glu Met Lys Lys Phe Leu Ser
385                 390                 395                 400

Thr Leu Thr Ile Asp Gly Val Thr Arg Ser Asp Gln Gly Leu Tyr Thr
                405                 410                 415

Cys Ala Ala Ser Ser Gly Leu Met Thr Lys Lys Asn Ser Thr Phe Val
            420                 425                 430

Arg Val His Glu Lys Asp Lys Thr His Thr Cys Pro Pro Cys Pro Ala
            435                 440                 445

Pro Glu Ala Ala Gly Ala Pro Ser Val Phe Leu Phe Pro Pro Lys Pro
450                 455                 460

Lys Asp Thr Leu Met Ile Ser Arg Thr Pro Glu Val Thr Cys Val Val
465                 470                 475                 480

Val Asp Val Ser His Glu Asp Pro Glu Val Lys Phe Asn Trp Tyr Val
                485                 490                 495
```

Asp Gly Val Glu Val His Asn Ala Lys Thr Lys Pro Arg Glu Gln
            500                 505                 510

Tyr Asn Ser Thr Tyr Arg Val Ser Val Leu Thr Val Leu His Gln
            515                 520                 525

Asp Trp Leu Asn Gly Lys Glu Tyr Lys Cys Lys Val Ser Asn Lys Ala
530                 535                 540

Leu Pro Ala Pro Ile Glu Lys Thr Ile Ser Lys Ala Lys Gly Gln Pro
545                 550                 555                 560

Arg Glu Pro Gln Val Tyr Thr Leu Pro Pro Ser Arg Glu Glu Met Thr
                565                 570                 575

Lys Asn Gln Val Ser Leu Thr Cys Leu Val Lys Gly Phe Tyr Pro Ser
            580                 585                 590

Asp Ile Ala Val Glu Trp Glu Ser Asn Gly Gln Pro Glu Asn Asn Tyr
            595                 600                 605

Lys Thr Thr Pro Pro Val Leu Asp Ser Asp Gly Ser Phe Phe Leu Tyr
610                 615                 620

Ser Lys Leu Thr Val Asp Lys Ser Arg Trp Gln Gln Gly Asn Val Phe
625                 630                 635                 640

Ser Cys Ser Val Met His Glu Ala Leu His Asn His Tyr Thr Gln Lys
                645                 650                 655

Ser Leu Ser Cys Ser Pro Gly Lys
                660

<210> SEQ ID NO 162
<211> LENGTH: 213
<212> TYPE: PRT
<213> ORGANISM: Artificial Sequence
<220> FEATURE:
<223> OTHER INFORMATION: light chain

<400> SEQUENCE: 162

Asp Ile Gln Leu Thr Gln Ser Pro Ser Leu Ser Ala Ser Val Gly
1               5                   10                  15

Asp Arg Val Thr Ile Thr Cys Ser Ala Ser Ile Ser Val Ser Tyr Leu
            20                  25                  30

Tyr Trp Tyr Gln Gln Lys Pro Gly Lys Ala Pro Lys Leu Leu Ile Tyr
            35                  40                  45

Asp Asp Ser Asn Leu Ala Ser Gly Val Pro Ser Arg Phe Ser Gly Ser
50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Gly Tyr Pro Tyr Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

```
Cys Glu Val Thr His Gln Gly Leu Ser Ser Pro Val Thr Lys Ser Phe
            195                 200                 205

Asn Arg Gly Glu Cys
    210
```

<210> SEQ ID NO 163
<211> LENGTH: 664
<212> TYPE: PRT
<213> ORGANISM: Artificial Sequence
<220> FEATURE:
<223> OTHER INFORMATION: fusion

<400> SEQUENCE: 163

```
Glu Val Gln Leu Val Glu Ser Gly Gly Gly Leu Val Gln Pro Gly Gly
1               5                  10                  15

Ser Leu Arg Leu Ser Cys Ala Ala Ser Gly Phe Thr Phe Ser Pro Phe
            20                  25                  30

Ala Trp Ser Trp Val Arg Gln Ala Pro Gly Lys Gly Leu Glu Trp Val
        35                  40                  45

Ala Lys Ile Ser Pro Gly Gly Ser Trp Thr Tyr Tyr Ser Asp Thr Val
    50                  55                  60

Thr Asp Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gln Leu Trp Gly Tyr Tyr Ala Leu Asp Val Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Gly Gly
    210                 215                 220

Gly Gly Ser Gly Gly Gly Gly Ser Ser Asp Thr Gly Arg Pro Phe Val
225                 230                 235                 240

Glu Met Tyr Ser Glu Ile Pro Glu Ile Ile His Met Thr Glu Gly Arg
                245                 250                 255

Glu Leu Val Ile Pro Cys Arg Val Thr Ser Pro Asn Ile Thr Val Thr
            260                 265                 270

Leu Lys Lys Phe Pro Leu Asp Thr Leu Ile Pro Asp Gly Lys Arg Ile
        275                 280                 285

Ile Trp Asp Ser Arg Lys Gly Phe Ile Ile Ser Asn Ala Thr Tyr Lys
    290                 295                 300

Glu Ile Gly Leu Leu Thr Cys Glu Ala Thr Val Asn Gly His Leu Tyr
305                 310                 315                 320

Lys Thr Asn Tyr Leu Thr His Arg Gln Thr Asn Thr Ile Ile Asp Val
                325                 330                 335
```

```
Val Leu Ser Pro Ser His Gly Ile Glu Leu Ser Val Gly Glu Lys Leu
            340                 345                 350

Val Leu Asn Cys Thr Ala Arg Thr Glu Leu Asn Val Gly Ile Asp Phe
            355                 360                 365

Asn Trp Glu Tyr Pro Ser Ser Lys His Gln His Lys Lys Leu Val Asn
370                 375                 380

Arg Asp Leu Lys Thr Gln Ser Gly Ser Glu Met Lys Lys Phe Leu Ser
385                 390                 395                 400

Thr Leu Thr Ile Asp Gly Val Thr Arg Ser Asp Gln Gly Leu Tyr Thr
            405                 410                 415

Cys Ala Ala Ser Ser Gly Leu Met Thr Lys Lys Asn Ser Thr Phe Val
            420                 425                 430

Arg Val His Glu Lys Asp Lys Thr His Thr Cys Pro Pro Cys Pro Ala
            435                 440                 445

Pro Glu Ala Ala Gly Ala Pro Ser Val Phe Leu Phe Pro Pro Lys Pro
            450                 455                 460

Lys Asp Thr Leu Met Ile Ser Arg Thr Pro Glu Val Thr Cys Val Val
465                 470                 475                 480

Val Asp Val Ser His Glu Asp Pro Glu Val Lys Phe Asn Trp Tyr Val
            485                 490                 495

Asp Gly Val Glu Val His Asn Ala Lys Thr Lys Pro Arg Glu Glu Gln
            500                 505                 510

Tyr Asn Ser Thr Tyr Arg Val Val Ser Val Leu Thr Val Leu His Gln
            515                 520                 525

Asp Trp Leu Asn Gly Lys Glu Tyr Lys Cys Lys Val Ser Asn Lys Ala
530                 535                 540

Leu Pro Ala Pro Ile Glu Lys Thr Ile Ser Lys Ala Lys Gly Gln Pro
545                 550                 555                 560

Arg Glu Pro Gln Val Tyr Thr Leu Pro Pro Ser Arg Glu Glu Met Thr
            565                 570                 575

Lys Asn Gln Val Ser Leu Thr Cys Leu Val Lys Gly Phe Tyr Pro Ser
            580                 585                 590

Asp Ile Ala Val Glu Trp Glu Ser Asn Gly Gln Pro Glu Asn Asn Tyr
            595                 600                 605

Lys Thr Thr Pro Pro Val Leu Asp Ser Asp Gly Ser Phe Phe Leu Tyr
610                 615                 620

Ser Lys Leu Thr Val Asp Lys Ser Arg Trp Gln Gln Gly Asn Val Phe
625                 630                 635                 640

Ser Cys Ser Val Met His Glu Ala Leu His Asn His Tyr Thr Gln Lys
            645                 650                 655

Ser Leu Ser Cys Ser Pro Gly Lys
            660

<210> SEQ ID NO 164
<211> LENGTH: 213
<212> TYPE: PRT
<213> ORGANISM: Artificial Sequence
<220> FEATURE:
<223> OTHER INFORMATION: light chain

<400> SEQUENCE: 164

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ile Ser Val Ser Tyr Leu
            20                  25                  30
```

```
Tyr Trp Tyr Gln Gln Lys Pro Gly Lys Ala Pro Lys Leu Leu Ile Tyr
        35                  40                  45

Asp Asp Ser Ser Leu Ala Ser Gly Val Pro Ser Arg Phe Ser Gly Ser
 50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Trp Ser Gly Tyr Pro Tyr Thr
                 85                  90                  95

Phe Gly Gln Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 165
<211> LENGTH: 664
<212> TYPE: PRT
<213> ORGANISM: Artificial Sequence
<220> FEATURE:
<223> OTHER INFORMATION: fusion

<400> SEQUENCE: 165

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Pro Phe
            20                  25                  30

Ala Trp Ser Trp Val Arg Gln Ala Pro Gly Lys Gly Leu Glu Trp Val
        35                  40                  45

Ala Lys Ile Ser Pro Gly Gly Ser Trp Thr Tyr Tyr Ser Asp Thr Val
 50                  55                  60

Thr Asp Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                 85                  90                  95

Ala Arg Gln Leu Trp Gly Tyr Tyr Ala Leu Asp Val Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

```
Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Gly Gly
    210                 215                 220

Gly Gly Ser Gly Gly Gly Ser Ser Asp Thr Gly Arg Pro Phe Val
225                 230                 235                 240

Glu Met Tyr Ser Glu Ile Pro Glu Ile Ile His Met Thr Glu Gly Arg
                245                 250                 255

Glu Leu Val Ile Pro Cys Arg Val Thr Ser Pro Asn Ile Thr Val Thr
            260                 265                 270

Leu Lys Lys Phe Pro Leu Asp Thr Leu Ile Pro Asp Gly Lys Arg Ile
        275                 280                 285

Ile Trp Asp Ser Arg Lys Gly Phe Ile Ile Ser Asn Ala Thr Tyr Lys
    290                 295                 300

Glu Ile Gly Leu Leu Thr Cys Glu Ala Thr Val Asn Gly His Leu Tyr
305                 310                 315                 320

Lys Thr Asn Tyr Leu Thr His Arg Gln Thr Asn Thr Ile Ile Asp Val
                325                 330                 335

Val Leu Ser Pro Ser His Gly Ile Glu Leu Ser Val Gly Glu Lys Leu
            340                 345                 350

Val Leu Asn Cys Thr Ala Arg Thr Glu Leu Asn Val Gly Ile Asp Phe
        355                 360                 365

Asn Trp Glu Tyr Pro Ser Ser Lys His Gln His Lys Lys Leu Val Asn
    370                 375                 380

Arg Asp Leu Lys Thr Gln Ser Gly Ser Glu Met Lys Lys Phe Leu Ser
385                 390                 395                 400

Thr Leu Thr Ile Asp Gly Val Thr Arg Ser Asp Gln Gly Leu Tyr Thr
                405                 410                 415

Cys Ala Ala Ser Ser Gly Leu Met Thr Lys Lys Asn Ser Thr Phe Val
            420                 425                 430

Arg Val His Glu Lys Asp Lys Thr His Thr Cys Pro Pro Cys Pro Ala
        435                 440                 445

Pro Glu Ala Ala Gly Ala Pro Ser Val Phe Leu Phe Pro Pro Lys Pro
450                 455                 460

Lys Asp Thr Leu Met Ile Ser Arg Thr Pro Glu Val Thr Cys Val Val
465                 470                 475                 480

Val Asp Val Ser His Glu Asp Pro Glu Val Lys Phe Asn Trp Tyr Val
                485                 490                 495

Asp Gly Val Glu Val His Asn Ala Lys Thr Lys Pro Arg Glu Glu Gln
            500                 505                 510

Tyr Asn Ser Thr Tyr Arg Val Val Ser Val Leu Thr Val Leu His Gln
        515                 520                 525

Asp Trp Leu Asn Gly Lys Glu Tyr Lys Cys Lys Val Ser Asn Lys Ala
    530                 535                 540

Leu Pro Ala Pro Ile Glu Lys Thr Ile Ser Lys Ala Lys Gly Gln Pro
545                 550                 555                 560

Arg Glu Pro Gln Val Tyr Thr Leu Pro Pro Ser Arg Glu Glu Met Thr
                565                 570                 575

Lys Asn Gln Val Ser Leu Thr Cys Leu Val Lys Gly Phe Tyr Pro Ser
            580                 585                 590
```

```
Asp Ile Ala Val Glu Trp Glu Ser Asn Gly Gln Pro Glu Asn Asn Tyr
            595                 600                 605

Lys Thr Thr Pro Pro Val Leu Asp Ser Asp Gly Ser Phe Phe Leu Tyr
610                 615                 620

Ser Lys Leu Thr Val Asp Lys Ser Arg Trp Gln Gln Gly Asn Val Phe
625                 630                 635                 640

Ser Cys Ser Val Met His Glu Ala Leu His Asn His Tyr Thr Gln Lys
                645                 650                 655

Ser Leu Ser Cys Ser Pro Gly Lys
            660

<210> SEQ ID NO 166
<211> LENGTH: 213
<212> TYPE: PRT
<213> ORGANISM: Artificial Sequence
<220> FEATURE:
<223> OTHER INFORMATION: light chain

<400> SEQUENCE: 166

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ile Ser Val Ser Tyr Leu
            20                  25                  30

Tyr Trp Tyr Gln Gln Lys Pro Gly Lys Ala Pro Lys Leu Leu Ile Tyr
        35                  40                  45

Asp Ala Ser Ser Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Gly Tyr Pro Tyr Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 167
<211> LENGTH: 664
<212> TYPE: PRT
<213> ORGANISM: Artificial Sequence
<220> FEATURE:
<223> OTHER INFORMATION: fusion
```

<400> SEQUENCE: 167

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Pro Phe
            20                  25                  30

Ala Trp Ser Trp Val Arg Gln Ala Pro Gly Lys Gly Leu Glu Trp Val
        35                  40                  45

Ala Lys Ile Ser Pro Gly Gly Ser Trp Thr Tyr Tyr Ser Asp Thr Val
    50                  55                  60

Thr Asp Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gln Leu Trp Gly Tyr Tyr Ala Leu Asp Val Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Gly Gly
    210                 215                 220

Gly Gly Ser Gly Gly Gly Gly Ser Ser Asp Thr Gly Arg Pro Phe Val
225                 230                 235                 240

Glu Met Tyr Ser Glu Ile Pro Glu Ile Ile His Met Thr Glu Gly Arg
                245                 250                 255

Glu Leu Val Ile Pro Cys Arg Val Thr Ser Pro Asn Ile Thr Val Thr
            260                 265                 270

Leu Lys Lys Phe Pro Leu Asp Thr Leu Ile Pro Asp Gly Lys Arg Ile
        275                 280                 285

Ile Trp Asp Ser Arg Lys Gly Phe Ile Ile Ser Asn Ala Thr Tyr Lys
    290                 295                 300

Glu Ile Gly Leu Leu Thr Cys Glu Ala Thr Val Asn Gly His Leu Tyr
305                 310                 315                 320

Lys Thr Asn Tyr Leu Thr His Arg Gln Thr Asn Thr Ile Ile Asp Val
                325                 330                 335

Val Leu Ser Pro Ser His Gly Ile Glu Leu Ser Val Gly Glu Lys Leu
            340                 345                 350

Val Leu Asn Cys Thr Ala Arg Thr Glu Leu Asn Val Gly Ile Asp Phe
        355                 360                 365

Asn Trp Glu Tyr Pro Ser Ser Lys His Gln His Lys Lys Leu Val Asn
    370                 375                 380

Arg Asp Leu Lys Thr Gln Ser Gly Ser Glu Met Lys Lys Phe Leu Ser
385                 390                 395                 400

Thr Leu Thr Ile Asp Gly Val Thr Arg Ser Asp Gln Gly Leu Tyr Thr
            405                 410                 415

Cys Ala Ala Ser Ser Gly Leu Met Thr Lys Lys Asn Ser Thr Phe Val
            420                 425                 430

Arg Val His Glu Lys Asp Lys Thr His Thr Cys Pro Pro Cys Pro Ala
            435                 440                 445

Pro Glu Ala Ala Gly Ala Pro Ser Val Phe Leu Phe Pro Pro Lys Pro
450                 455                 460

Lys Asp Thr Leu Met Ile Ser Arg Thr Pro Glu Val Thr Cys Val Val
465                 470                 475                 480

Val Asp Val Ser His Glu Asp Pro Glu Val Lys Phe Asn Trp Tyr Val
            485                 490                 495

Asp Gly Val Glu Val His Asn Ala Lys Thr Lys Pro Arg Glu Glu Gln
            500                 505                 510

Tyr Asn Ser Thr Tyr Arg Val Val Ser Val Leu Thr Val Leu His Gln
            515                 520                 525

Asp Trp Leu Asn Gly Lys Glu Tyr Lys Cys Lys Val Ser Asn Lys Ala
530                 535                 540

Leu Pro Ala Pro Ile Glu Lys Thr Ile Ser Lys Ala Lys Gly Gln Pro
545                 550                 555                 560

Arg Glu Pro Gln Val Tyr Thr Leu Pro Pro Ser Arg Glu Glu Met Thr
            565                 570                 575

Lys Asn Gln Val Ser Leu Thr Cys Leu Val Lys Gly Phe Tyr Pro Ser
            580                 585                 590

Asp Ile Ala Val Glu Trp Glu Ser Asn Gly Gln Pro Glu Asn Asn Tyr
            595                 600                 605

Lys Thr Thr Pro Pro Val Leu Asp Ser Asp Gly Ser Phe Phe Leu Tyr
610                 615                 620

Ser Lys Leu Thr Val Asp Lys Ser Arg Trp Gln Gln Gly Asn Val Phe
625                 630                 635                 640

Ser Cys Ser Val Met His Glu Ala Leu His Asn His Tyr Thr Gln Lys
            645                 650                 655

Ser Leu Ser Cys Ser Pro Gly Lys
            660

<210> SEQ ID NO 168
<211> LENGTH: 213
<212> TYPE: PRT
<213> ORGANISM: Artificial Sequence
<220> FEATURE:
<223> OTHER INFORMATION: light chain

<400> SEQUENCE: 168

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ile Ser Val Ser Tyr Leu
            20                  25                  30

Tyr Trp Tyr Gln Gln Lys Pro Gly Lys Ala Pro Lys Leu Leu Ile Tyr
            35                  40                  45

Asp Asp Ser Asn Leu Ala Ser Gly Val Pro Ser Arg Phe Ser Gly Ser
        50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Gly Tyr Pro Tyr Thr
            85                  90                  95

```
Phe Gly Gln Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
                115                 120                 125

Ala Ser Val Val Cys Leu Leu Asn Asn Phe Tyr Pro Arg Glu Ala Lys
            130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
            210

<210> SEQ ID NO 169
<211> LENGTH: 213
<212> TYPE: PRT
<213> ORGANISM: Artificial Sequence
<220> FEATURE:
<223> OTHER INFORMATION: antibody

<400> SEQUENCE: 169

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ile Ser Val Ser Tyr Leu
                20                  25                  30

Tyr Trp Tyr Gln Gln Lys Pro Gly Lys Ala Pro Lys Leu Leu Ile Tyr
            35                  40                  45

Asp Asp Ser Ser Leu Ala Ser Gly Val Pro Ser Arg Phe Ser Gly Ser
50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Gly Tyr Pro Tyr Thr
                85                  90                  95

Phe Gly Gln Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
                115                 120                 125

Ala Ser Val Val Cys Leu Leu Asn Asn Phe Tyr Pro Arg Glu Ala Lys
            130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
            210

<210> SEQ ID NO 170
```

<211> LENGTH: 664
<212> TYPE: PRT
<213> ORGANISM: Artificial Sequence
<220> FEATURE:
<223> OTHER INFORMATION: antibody

<400> SEQUENCE: 170

```
Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Gly Gly Gly
        195                 200                 205

Gly Ser Gly Gly Gly Gly Ser Glu Val Gln Leu Val Glu Ser Gly Gly
    210                 215                 220

Gly Leu Val Gln Pro Gly Gly Ser Leu Arg Leu Ser Cys Ala Ala Ser
225                 230                 235                 240

Gly Phe Thr Phe Ser Pro Phe Ala Met His Trp Val Arg Gln Ala Pro
                245                 250                 255

Gly Lys Gly Leu Glu Trp Val Ala Lys Ile Ser Pro Gly Gly Ser Trp
            260                 265                 270

Thr Tyr Tyr Ser Asp Thr Val Thr Asp Arg Phe Thr Phe Ser Leu Asp
        275                 280                 285

Thr Ser Lys Ser Thr Ala Tyr Leu Gln Met Asn Ser Leu Arg Ala Glu
    290                 295                 300

Asp Thr Ala Val Tyr Tyr Cys Ala Arg Gln Ala Trp Gly Tyr Tyr Ala
305                 310                 315                 320

Leu Asp Ile Trp Gly Gln Gly Thr Leu Val Thr Val Ser Ser Ala Ser
                325                 330                 335

Thr Lys Gly Pro Ser Val Phe Pro Leu Ala Pro Ser Ser Lys Ser Thr
            340                 345                 350

Ser Gly Gly Thr Ala Ala Leu Gly Cys Leu Val Lys Asp Tyr Phe Pro
        355                 360                 365

Glu Pro Val Thr Val Ser Trp Asn Ser Gly Ala Leu Thr Ser Gly Val
    370                 375                 380
```

His Thr Phe Pro Ala Val Leu Gln Ser Ser Gly Leu Tyr Ser Leu Ser
385                 390                 395                 400

Ser Val Val Thr Val Pro Ser Ser Leu Gly Thr Gln Thr Tyr Ile
            405                 410                 415

Cys Asn Val Asn His Lys Pro Ser Asn Thr Lys Val Asp Lys Lys Val
            420                 425                 430

Glu Pro Lys Ser Cys Asp Lys Thr His Thr Cys Pro Pro Cys Pro Ala
            435                 440                 445

Pro Glu Ala Ala Gly Ala Pro Ser Val Phe Leu Phe Pro Pro Lys Pro
    450                 455                 460

Lys Asp Thr Leu Met Ile Ser Arg Thr Pro Glu Val Thr Cys Val Val
465                 470                 475                 480

Val Asp Val Ser His Glu Asp Pro Glu Val Lys Phe Asn Trp Tyr Val
            485                 490                 495

Asp Gly Val Glu Val His Asn Ala Lys Thr Lys Pro Arg Glu Glu Gln
            500                 505                 510

Tyr Asn Ser Thr Tyr Arg Val Val Ser Val Leu Thr Val Leu His Gln
            515                 520                 525

Asp Trp Leu Asn Gly Lys Glu Tyr Lys Cys Lys Val Ser Asn Lys Ala
530                 535                 540

Leu Pro Ala Pro Ile Glu Lys Thr Ile Ser Lys Ala Lys Gly Gln Pro
545                 550                 555                 560

Arg Glu Pro Gln Val Tyr Thr Leu Pro Pro Ser Arg Glu Glu Met Thr
            565                 570                 575

Lys Asn Gln Val Ser Leu Thr Cys Leu Val Lys Gly Phe Tyr Pro Ser
            580                 585                 590

Asp Ile Ala Val Glu Trp Glu Ser Asn Gly Gln Pro Glu Asn Asn Tyr
            595                 600                 605

Lys Thr Thr Pro Pro Val Leu Asp Ser Asp Gly Ser Phe Phe Leu Tyr
610                 615                 620

Ser Lys Leu Thr Val Asp Lys Ser Arg Trp Gln Gln Gly Asn Val Phe
625                 630                 635                 640

Ser Cys Ser Val Met His Glu Ala Leu His Asn His Tyr Thr Gln Lys
            645                 650                 655

Ser Leu Ser Cys Ser Pro Gly Lys
            660

<210> SEQ ID NO 171
<211> LENGTH: 10
<212> TYPE: PRT
<213> ORGANISM: Artificial Sequence
<220> FEATURE:
<223> OTHER INFORMATION: antibody

<400> SEQUENCE: 171

Gln Leu Trp Gly Tyr Tyr Ala Leu Asp Ile
1               5                   10

<210> SEQ ID NO 172
<211> LENGTH: 5
<212> TYPE: PRT
<213> ORGANISM: Artificial Sequence
<220> FEATURE:
<223> OTHER INFORMATION: antibody

```
<400> SEQUENCE: 172

Pro Phe Ala Met His
1               5

<210> SEQ ID NO 173
<211> LENGTH: 17
<212> TYPE: PRT
<213> ORGANISM: Artificial Sequence
<220> FEATURE:
<223> OTHER INFORMATION: antibody

<400> SEQUENCE: 173

Lys Ile Ser Pro Gly Gly Ser Trp Thr Tyr Tyr Ser Asp Thr Val Thr
1               5                   10                  15

Asp

<210> SEQ ID NO 174
<211> LENGTH: 10
<212> TYPE: PRT
<213> ORGANISM: Artificial Sequence
<220> FEATURE:
<223> OTHER INFORMATION: antibody

<400> SEQUENCE: 174

Gln Ala Trp Gly Tyr Tyr Ala Leu Asp Ile
1               5                   10

<210> SEQ ID NO 175
<211> LENGTH: 5
<212> TYPE: PRT
<213> ORGANISM: Artificial Sequence
<220> FEATURE:
<223> OTHER INFORMATION: antibody

<400> SEQUENCE: 175

Pro Phe Ala Met His
1               5

<210> SEQ ID NO 176
<211> LENGTH: 17
<212> TYPE: PRT
<213> ORGANISM: Artificial Sequence
<220> FEATURE:
<223> OTHER INFORMATION: antibody

<400> SEQUENCE: 176

Lys Ile Ser Pro Gly Gly Ser Trp Thr Tyr Tyr Ser Asp Thr Val Thr
1               5                   10                  15

Asp

<210> SEQ ID NO 177
<211> LENGTH: 10
<212> TYPE: PRT
<213> ORGANISM: Artificial Sequence
<220> FEATURE:
<223> OTHER INFORMATION: antibody

<400> SEQUENCE: 177

Gln Ser Trp Gly Tyr Tyr Ala Leu Asp Ile
1               5                   10

<210> SEQ ID NO 178
<211> LENGTH: 5
<212> TYPE: PRT
```

```
<213> ORGANISM: Artificial Sequence
<220> FEATURE:
<223> OTHER INFORMATION: antibody

<400> SEQUENCE: 178

Pro Phe Ala Met His
1               5

<210> SEQ ID NO 179
<211> LENGTH: 17
<212> TYPE: PRT
<213> ORGANISM: Artificial Sequence
<220> FEATURE:
<223> OTHER INFORMATION: antibody

<400> SEQUENCE: 179

Lys Ile Ser Pro Gly Gly Ser Trp Thr Tyr Tyr Ser Asp Thr Val Thr
1               5                   10                  15
Asp

<210> SEQ ID NO 180
<211> LENGTH: 10
<212> TYPE: PRT
<213> ORGANISM: Artificial Sequence
<220> FEATURE:
<223> OTHER INFORMATION: antibody

<400> SEQUENCE: 180

Gln Gly Trp Gly Tyr Tyr Ala Leu Asp Ile
1               5                   10

<210> SEQ ID NO 181
<211> LENGTH: 5
<212> TYPE: PRT
<213> ORGANISM: Artificial Sequence
<220> FEATURE:
<223> OTHER INFORMATION: antibody

<400> SEQUENCE: 181

Pro Phe Ala Met His
1               5

<210> SEQ ID NO 182
<211> LENGTH: 17
<212> TYPE: PRT
<213> ORGANISM: Artificial Sequence
<220> FEATURE:
<223> OTHER INFORMATION: antibody

<400> SEQUENCE: 182

Lys Ile Ser Pro Gly Gly Ser Trp Thr Tyr Tyr Ser Asp Thr Val Thr
1               5                   10                  15
Asp

<210> SEQ ID NO 183
<211> LENGTH: 10
<212> TYPE: PRT
<213> ORGANISM: Artificial Sequence
<220> FEATURE:
<223> OTHER INFORMATION: antibody

<400> SEQUENCE: 183

Gln Thr Trp Gly Tyr Tyr Ala Leu Asp Ile
1               5                   10
```

<210> SEQ ID NO 184
<211> LENGTH: 5
<212> TYPE: PRT
<213> ORGANISM: Artificial Sequence
<220> FEATURE:
<223> OTHER INFORMATION: antibody

<400> SEQUENCE: 184

Pro Phe Ala Met His
1               5

<210> SEQ ID NO 185
<211> LENGTH: 17
<212> TYPE: PRT
<213> ORGANISM: Artificial Sequence
<220> FEATURE:
<223> OTHER INFORMATION: antibody

<400> SEQUENCE: 185

Lys Ile Ser Pro Gly Gly Ser Trp Thr Tyr Tyr Ser Asp Thr Val Thr
1               5                   10                  15

Asp

<210> SEQ ID NO 186
<211> LENGTH: 10
<212> TYPE: PRT
<213> ORGANISM: Artificial Sequence
<220> FEATURE:
<223> OTHER INFORMATION: antibody

<400> SEQUENCE: 186

Gln Val Trp Gly Tyr Tyr Ala Leu Asp Ile
1               5                   10

<210> SEQ ID NO 187
<211> LENGTH: 5
<212> TYPE: PRT
<213> ORGANISM: Artificial Sequence
<220> FEATURE:
<223> OTHER INFORMATION: antibody

<400> SEQUENCE: 187

Pro Phe Ala Met His
1               5

<210> SEQ ID NO 188
<211> LENGTH: 17
<212> TYPE: PRT
<213> ORGANISM: Artificial Sequence
<220> FEATURE:
<223> OTHER INFORMATION: antibody

<400> SEQUENCE: 188

Lys Ile Ser Pro Gly Gly Ser Trp Thr Tyr Tyr Ser Asp Thr Val Thr
1               5                   10                  15

Asp

<210> SEQ ID NO 189
<211> LENGTH: 10
<212> TYPE: PRT
<213> ORGANISM: Artificial Sequence
<220> FEATURE:
<223> OTHER INFORMATION: antibody

```
<400> SEQUENCE: 189

Gln Gln Trp Gly Tyr Tyr Ala Leu Asp Ile
1               5                   10

<210> SEQ ID NO 190
<211> LENGTH: 5
<212> TYPE: PRT
<213> ORGANISM: Artificial Sequence
<220> FEATURE:
<223> OTHER INFORMATION: antibody

<400> SEQUENCE: 190

Pro Phe Ala Met His
1               5

<210> SEQ ID NO 191
<211> LENGTH: 17
<212> TYPE: PRT
<213> ORGANISM: Artificial Sequence
<220> FEATURE:
<223> OTHER INFORMATION: antibody

<400> SEQUENCE: 191

Lys Ile Ser Pro Gly Gly Ser Trp Thr Tyr Tyr Ser Asp Thr Val Thr
1               5                   10                  15

Asp

<210> SEQ ID NO 192
<211> LENGTH: 10
<212> TYPE: PRT
<213> ORGANISM: Artificial Sequence
<220> FEATURE:
<223> OTHER INFORMATION: antibody

<400> SEQUENCE: 192

Gln Lys Trp Gly Tyr Tyr Ala Leu Asp Ile
1               5                   10

<210> SEQ ID NO 193
<211> LENGTH: 5
<212> TYPE: PRT
<213> ORGANISM: Artificial Sequence
<220> FEATURE:
<223> OTHER INFORMATION: antibody

<400> SEQUENCE: 193

Pro Phe Ala Ile Ser
1               5

<210> SEQ ID NO 194
<211> LENGTH: 17
<212> TYPE: PRT
<213> ORGANISM: Artificial Sequence
<220> FEATURE:
<223> OTHER INFORMATION: antibody

<400> SEQUENCE: 194

Lys Ile Ser Pro Gly Gly Ser Trp Thr Tyr Tyr Ser Asp Thr Val Thr
1               5                   10                  15

Asp

<210> SEQ ID NO 195
<211> LENGTH: 10
<212> TYPE: PRT
```

```
<213> ORGANISM: Artificial Sequence
<220> FEATURE:
<223> OTHER INFORMATION: antibody

<400> SEQUENCE: 195

Gln Leu Trp Gly Tyr Tyr Ala Leu Asp Val
1               5                   10

<210> SEQ ID NO 196
<211> LENGTH: 5
<212> TYPE: PRT
<213> ORGANISM: Artificial Sequence
<220> FEATURE:
<223> OTHER INFORMATION: antibody

<400> SEQUENCE: 196

Pro Phe Ala Trp Ser
1               5

<210> SEQ ID NO 197
<211> LENGTH: 17
<212> TYPE: PRT
<213> ORGANISM: Artificial Sequence
<220> FEATURE:
<223> OTHER INFORMATION: antibody

<400> SEQUENCE: 197

Lys Ile Ser Pro Gly Gly Ser Trp Thr Tyr Tyr Ser Asp Thr Val Thr
1               5                   10                  15

Asp

<210> SEQ ID NO 198
<211> LENGTH: 10
<212> TYPE: PRT
<213> ORGANISM: Artificial Sequence
<220> FEATURE:
<223> OTHER INFORMATION: antibody

<400> SEQUENCE: 198

Gln Leu Trp Gly Tyr Tyr Ala Leu Asp Val
1               5                   10

<210> SEQ ID NO 199
<211> LENGTH: 10
<212> TYPE: PRT
<213> ORGANISM: Artificial Sequence
<220> FEATURE:
<223> OTHER INFORMATION: antibody

<400> SEQUENCE: 199

Ser Ala Ser Ile Ser Val Ser Tyr Leu Tyr
1               5                   10

<210> SEQ ID NO 200
<211> LENGTH: 7
<212> TYPE: PRT
<213> ORGANISM: Artificial Sequence
<220> FEATURE:
<223> OTHER INFORMATION: antibody

<400> SEQUENCE: 200

Asp Asp Ser Ser Leu Ala Ser
1               5

<210> SEQ ID NO 201
<211> LENGTH: 9
```

```
<212> TYPE: PRT
<213> ORGANISM: Artificial Sequence
<220> FEATURE:
<223> OTHER INFORMATION: antibody

<400> SEQUENCE: 201

Gln Gln Trp Ser Gly Tyr Pro Tyr Thr
1               5

<210> SEQ ID NO 202
<211> LENGTH: 10
<212> TYPE: PRT
<213> ORGANISM: Artificial Sequence
<220> FEATURE:
<223> OTHER INFORMATION: antibody

<400> SEQUENCE: 202

Ser Ala Ser Ile Ser Val Ser Tyr Leu Tyr
1               5                   10

<210> SEQ ID NO 203
<211> LENGTH: 7
<212> TYPE: PRT
<213> ORGANISM: Artificial Sequence
<220> FEATURE:
<223> OTHER INFORMATION: antibody

<400> SEQUENCE: 203

Asp Ala Ser Ser Leu Ala Ser
1               5

<210> SEQ ID NO 204
<211> LENGTH: 9
<212> TYPE: PRT
<213> ORGANISM: Artificial Sequence
<220> FEATURE:
<223> OTHER INFORMATION: antibody

<400> SEQUENCE: 204

Gln Gln Trp Ser Gly Tyr Pro Tyr Thr
1               5

<210> SEQ ID NO 205
<211> LENGTH: 10
<212> TYPE: PRT
<213> ORGANISM: Artificial Sequence
<220> FEATURE:
<223> OTHER INFORMATION: antibody

<400> SEQUENCE: 205

Ser Ala Ser Ile Ser Val Ser Tyr Leu Tyr
1               5                   10

<210> SEQ ID NO 206
<211> LENGTH: 7
<212> TYPE: PRT
<213> ORGANISM: Artificial Sequence
<220> FEATURE:
<223> OTHER INFORMATION: antibody

<400> SEQUENCE: 206

Asp Asp Ser Asn Leu Ala Ser
1               5

<210> SEQ ID NO 207
<211> LENGTH: 9
<212> TYPE: PRT
```

```
<213> ORGANISM: Artificial Sequence
<220> FEATURE:
<223> OTHER INFORMATION: antibody

<400> SEQUENCE: 207

Gln Gln Trp Ser Gly Tyr Pro Tyr Thr
1               5

<210> SEQ ID NO 208
<211> LENGTH: 10
<212> TYPE: PRT
<213> ORGANISM: Artificial Sequence
<220> FEATURE:
<223> OTHER INFORMATION: antibody

<400> SEQUENCE: 208

Gly Phe Thr Phe Ser Pro Phe Ala Met His
1               5                   10

<210> SEQ ID NO 209
<211> LENGTH: 19
<212> TYPE: PRT
<213> ORGANISM: Artificial Sequence
<220> FEATURE:
<223> OTHER INFORMATION: antibody

<400> SEQUENCE: 209

Val Ala Lys Ile Ser Pro Gly Gly Ser Trp Thr Tyr Tyr Ser Asp Thr
1               5                   10                  15

Val Thr Asp

<210> SEQ ID NO 210
<211> LENGTH: 12
<212> TYPE: PRT
<213> ORGANISM: Artificial Sequence
<220> FEATURE:
<223> OTHER INFORMATION: antibody

<400> SEQUENCE: 210

Ala Arg Gln Ala Trp Gly Tyr Tyr Ala Leu Asp Ile
1               5                   10

<210> SEQ ID NO 211
<211> LENGTH: 10
<212> TYPE: PRT
<213> ORGANISM: Artificial Sequence
<220> FEATURE:
<223> OTHER INFORMATION: antibody

<400> SEQUENCE: 211

Gly Phe Thr Phe Ser Pro Phe Ala Met His
1               5                   10

<210> SEQ ID NO 212
<211> LENGTH: 19
<212> TYPE: PRT
<213> ORGANISM: Artificial Sequence
<220> FEATURE:
<223> OTHER INFORMATION: antibody

<400> SEQUENCE: 212

Val Ala Lys Ile Ser Pro Gly Gly Ser Trp Thr Tyr Tyr Ser Asp Thr
1               5                   10                  15

Val Thr Asp
```

```
<210> SEQ ID NO 213
<211> LENGTH: 12
<212> TYPE: PRT
<213> ORGANISM: Artificial Sequence
<220> FEATURE:
<223> OTHER INFORMATION: antibody

<400> SEQUENCE: 213

Ala Arg Gln Ser Trp Gly Tyr Tyr Ala Leu Asp Ile
1               5                   10

<210> SEQ ID NO 214
<211> LENGTH: 10
<212> TYPE: PRT
<213> ORGANISM: Artificial Sequence
<220> FEATURE:
<223> OTHER INFORMATION: antibody

<400> SEQUENCE: 214

Gly Phe Thr Phe Ser Pro Phe Ala Met His
1               5                   10

<210> SEQ ID NO 215
<211> LENGTH: 19
<212> TYPE: PRT
<213> ORGANISM: Artificial Sequence
<220> FEATURE:
<223> OTHER INFORMATION: antibody

<400> SEQUENCE: 215

Val Ala Lys Ile Ser Pro Gly Gly Ser Trp Thr Tyr Tyr Ser Asp Thr
1               5                   10                  15

Val Thr Asp

<210> SEQ ID NO 216
<211> LENGTH: 12
<212> TYPE: PRT
<213> ORGANISM: Artificial Sequence
<220> FEATURE:
<223> OTHER INFORMATION: antibody

<400> SEQUENCE: 216

Ala Arg Gln Gly Trp Gly Tyr Tyr Ala Leu Asp Ile
1               5                   10

<210> SEQ ID NO 217
<211> LENGTH: 10
<212> TYPE: PRT
<213> ORGANISM: Artificial Sequence
<220> FEATURE:
<223> OTHER INFORMATION: antibody

<400> SEQUENCE: 217

Gly Phe Thr Phe Ser Pro Phe Ala Met His
1               5                   10

<210> SEQ ID NO 218
<211> LENGTH: 19
<212> TYPE: PRT
<213> ORGANISM: Artificial Sequence
<220> FEATURE:
<223> OTHER INFORMATION: antibody

<400> SEQUENCE: 218

Val Ala Lys Ile Ser Pro Gly Gly Ser Trp Thr Tyr Tyr Ser Asp Thr
1               5                   10                  15
```

Val Thr Asp

<210> SEQ ID NO 219
<211> LENGTH: 12
<212> TYPE: PRT
<213> ORGANISM: Artificial Sequence
<220> FEATURE:
<223> OTHER INFORMATION: antibody

<400> SEQUENCE: 219

Ala Arg Gln Thr Trp Gly Tyr Tyr Ala Leu Asp Ile
1               5                   10

<210> SEQ ID NO 220
<211> LENGTH: 10
<212> TYPE: PRT
<213> ORGANISM: Artificial Sequence
<220> FEATURE:
<223> OTHER INFORMATION: antibody

<400> SEQUENCE: 220

Gly Phe Thr Phe Ser Pro Phe Ala Met His
1               5                   10

<210> SEQ ID NO 221
<211> LENGTH: 19
<212> TYPE: PRT
<213> ORGANISM: Artificial Sequence
<220> FEATURE:
<223> OTHER INFORMATION: antibody

<400> SEQUENCE: 221

Val Ala Lys Ile Ser Pro Gly Gly Ser Trp Thr Tyr Tyr Ser Asp Thr
1               5                   10                  15

Val Thr Asp

<210> SEQ ID NO 222
<211> LENGTH: 12
<212> TYPE: PRT
<213> ORGANISM: Artificial Sequence
<220> FEATURE:
<223> OTHER INFORMATION: antibody

<400> SEQUENCE: 222

Ala Arg Gln Val Trp Gly Tyr Tyr Ala Leu Asp Ile
1               5                   10

<210> SEQ ID NO 223
<211> LENGTH: 10
<212> TYPE: PRT
<213> ORGANISM: Artificial Sequence
<220> FEATURE:
<223> OTHER INFORMATION: antibody

<400> SEQUENCE: 223

Gly Phe Thr Phe Ser Pro Phe Ala Met His
1               5                   10

<210> SEQ ID NO 224
<211> LENGTH: 19
<212> TYPE: PRT
<213> ORGANISM: Artificial Sequence
<220> FEATURE:
<223> OTHER INFORMATION: antibody -continued

```
<400> SEQUENCE: 224

Val Ala Lys Ile Ser Pro Gly Gly Ser Trp Thr Tyr Tyr Ser Asp Thr
1               5                   10                  15

Val Thr Asp

<210> SEQ ID NO 225
<211> LENGTH: 12
<212> TYPE: PRT
<213> ORGANISM: Artificial Sequence
<220> FEATURE:
<223> OTHER INFORMATION: antibody

<400> SEQUENCE: 225

Ala Arg Gln Gln Trp Gly Tyr Tyr Ala Leu Asp Ile
1               5                   10

<210> SEQ ID NO 226
<211> LENGTH: 10
<212> TYPE: PRT
<213> ORGANISM: Artificial Sequence
<220> FEATURE:
<223> OTHER INFORMATION: antibody

<400> SEQUENCE: 226

Gly Phe Thr Phe Ser Pro Phe Ala Met His
1               5                   10

<210> SEQ ID NO 227
<211> LENGTH: 19
<212> TYPE: PRT
<213> ORGANISM: Artificial Sequence
<220> FEATURE:
<223> OTHER INFORMATION: antibody

<400> SEQUENCE: 227

Val Ala Lys Ile Ser Pro Gly Gly Ser Trp Thr Tyr Tyr Ser Asp Thr
1               5                   10                  15

Val Thr Asp

<210> SEQ ID NO 228
<211> LENGTH: 12
<212> TYPE: PRT
<213> ORGANISM: Artificial Sequence
<220> FEATURE:
<223> OTHER INFORMATION: antibody

<400> SEQUENCE: 228

Ala Arg Gln Lys Trp Gly Tyr Tyr Ala Leu Asp Ile
1               5                   10

<210> SEQ ID NO 229
<211> LENGTH: 10
<212> TYPE: PRT
<213> ORGANISM: Artificial Sequence
<220> FEATURE:
<223> OTHER INFORMATION: antibody

<400> SEQUENCE: 229

Gly Phe Thr Phe Ser Pro Phe Ala Ile Ser
1               5                   10

<210> SEQ ID NO 230
<211> LENGTH: 19
<212> TYPE: PRT
```

```
<213> ORGANISM: Artificial Sequence
<220> FEATURE:
<223> OTHER INFORMATION: antibody

<400> SEQUENCE: 230

Val Ala Lys Ile Ser Pro Gly Gly Ser Trp Thr Tyr Tyr Ser Asp Thr
1               5                   10                  15

Val Thr Asp

<210> SEQ ID NO 231
<211> LENGTH: 12
<212> TYPE: PRT
<213> ORGANISM: Artificial Sequence
<220> FEATURE:
<223> OTHER INFORMATION: antibody

<400> SEQUENCE: 231

Ala Arg Gln Leu Trp Gly Tyr Tyr Ala Leu Asp Val
1               5                   10

<210> SEQ ID NO 232
<211> LENGTH: 10
<212> TYPE: PRT
<213> ORGANISM: Artificial Sequence
<220> FEATURE:
<223> OTHER INFORMATION: antibody

<400> SEQUENCE: 232

Gly Phe Thr Phe Ser Pro Phe Ala Trp Ser
1               5                   10

<210> SEQ ID NO 233
<211> LENGTH: 20
<212> TYPE: PRT
<213> ORGANISM: Artificial Sequence
<220> FEATURE:
<223> OTHER INFORMATION: antibody

<400> SEQUENCE: 233

Trp Val Ala Lys Ile Ser Pro Gly Gly Ser Trp Thr Tyr Tyr Ser Asp
1               5                   10                  15

Thr Val Thr Asp
                20

<210> SEQ ID NO 234
<211> LENGTH: 12
<212> TYPE: PRT
<213> ORGANISM: Artificial Sequence
<220> FEATURE:
<223> OTHER INFORMATION: antibody

<400> SEQUENCE: 234

Ala Arg Gln Leu Trp Gly Tyr Tyr Ala Leu Asp Val
1               5                   10

<210> SEQ ID NO 235
<211> LENGTH: 10
<212> TYPE: PRT
<213> ORGANISM: Artificial Sequence
<220> FEATURE:
<223> OTHER INFORMATION: antibody

<400> SEQUENCE: 235

Ser Ala Ser Ile Ser Val Ser Tyr Leu Tyr
1               5                   10
```

<210> SEQ ID NO 236
<211> LENGTH: 11
<212> TYPE: PRT
<213> ORGANISM: Artificial Sequence
<220> FEATURE:
<223> OTHER INFORMATION: antibody

<400> SEQUENCE: 236

Leu Leu Ile Tyr Asp Asp Ser Ser Leu Ala Ser
1               5                   10

<210> SEQ ID NO 237
<211> LENGTH: 9
<212> TYPE: PRT
<213> ORGANISM: Artificial Sequence
<220> FEATURE:
<223> OTHER INFORMATION: antibody

<400> SEQUENCE: 237

Gln Gln Trp Ser Gly Tyr Pro Tyr Thr
1               5

<210> SEQ ID NO 238
<211> LENGTH: 10
<212> TYPE: PRT
<213> ORGANISM: Artificial Sequence
<220> FEATURE:
<223> OTHER INFORMATION: antibody

<400> SEQUENCE: 238

Ser Ala Ser Ile Ser Val Ser Tyr Leu Tyr
1               5                   10

<210> SEQ ID NO 239
<211> LENGTH: 11
<212> TYPE: PRT
<213> ORGANISM: Artificial Sequence
<220> FEATURE:
<223> OTHER INFORMATION: antibody

<400> SEQUENCE: 239

Leu Leu Ile Tyr Asp Ala Ser Ser Leu Ala Ser
1               5                   10

<210> SEQ ID NO 240
<211> LENGTH: 9
<212> TYPE: PRT
<213> ORGANISM: Artificial Sequence
<220> FEATURE:
<223> OTHER INFORMATION: antibody

<400> SEQUENCE: 240

Gln Gln Trp Ser Gly Tyr Pro Tyr Thr
1               5

<210> SEQ ID NO 241
<211> LENGTH: 10
<212> TYPE: PRT
<213> ORGANISM: Artificial Sequence
<220> FEATURE:
<223> OTHER INFORMATION: antibody

<400> SEQUENCE: 241

Ser Ala Ser Ile Ser Val Ser Tyr Leu Tyr
1               5                   10

```
<210> SEQ ID NO 242
<211> LENGTH: 11
<212> TYPE: PRT
<213> ORGANISM: Artificial Sequence
<220> FEATURE:
<223> OTHER INFORMATION: antibody

<400> SEQUENCE: 242

Leu Leu Ile Tyr Asp Asp Ser Asn Leu Ala Ser
1               5                   10

<210> SEQ ID NO 243
<211> LENGTH: 9
<212> TYPE: PRT
<213> ORGANISM: Artificial Sequence
<220> FEATURE:
<223> OTHER INFORMATION: antibody

<400> SEQUENCE: 243

Gln Gln Trp Ser Gly Tyr Pro Tyr Thr
1               5

<210> SEQ ID NO 244
<211> LENGTH: 5
<212> TYPE: PRT
<213> ORGANISM: Artificial Sequence
<220> FEATURE:
<223> OTHER INFORMATION: antibody

<400> SEQUENCE: 244

Pro Phe Ala Met Ser
1               5

<210> SEQ ID NO 245
<211> LENGTH: 17
<212> TYPE: PRT
<213> ORGANISM: Artificial Sequence
<220> FEATURE:
<223> OTHER INFORMATION: antibody

<400> SEQUENCE: 245

Lys Ile Ser Pro Gly Gly Ser Trp Thr Tyr Tyr Ser Asp Thr Val Thr
1               5                   10                  15

Gly

<210> SEQ ID NO 246
<211> LENGTH: 10
<212> TYPE: PRT
<213> ORGANISM: Artificial Sequence
<220> FEATURE:
<223> OTHER INFORMATION: antibody

<400> SEQUENCE: 246

Gln Leu Trp Gly Tyr Tyr Ala Leu Asp Ile
1               5                   10

<210> SEQ ID NO 247
<211> LENGTH: 10
<212> TYPE: PRT
<213> ORGANISM: Artificial Sequence
<220> FEATURE:
<223> OTHER INFORMATION: antibody

<400> SEQUENCE: 247

Ser Ala Ser Ile Ser Val Ser Tyr Met Tyr
1               5                   10
```

<210> SEQ ID NO 248
<211> LENGTH: 7
<212> TYPE: PRT
<213> ORGANISM: Artificial Sequence
<220> FEATURE:
<223> OTHER INFORMATION: antibody

<400> SEQUENCE: 248

Asp Met Ser Asn Leu Ala Ser
1               5

<210> SEQ ID NO 249
<211> LENGTH: 9
<212> TYPE: PRT
<213> ORGANISM: Artificial Sequence
<220> FEATURE:
<223> OTHER INFORMATION: antibody

<400> SEQUENCE: 249

Met Gln Trp Ser Gly Tyr Pro Tyr Thr
1               5

<210> SEQ ID NO 250
<211> LENGTH: 10
<212> TYPE: PRT
<213> ORGANISM: Artificial Sequence
<220> FEATURE:
<223> OTHER INFORMATION: antibody

<400> SEQUENCE: 250

Gly Phe Thr Phe Ser Pro Phe Ala Met Ser
1               5                   10

<210> SEQ ID NO 251
<211> LENGTH: 20
<212> TYPE: PRT
<213> ORGANISM: Artificial Sequence
<220> FEATURE:
<223> OTHER INFORMATION: antibody

<400> SEQUENCE: 251

Trp Val Ala Lys Ile Ser Pro Gly Gly Ser Trp Thr Tyr Tyr Ser Asp
1               5                   10                  15

Thr Val Thr Gly
            20

<210> SEQ ID NO 252
<211> LENGTH: 12
<212> TYPE: PRT
<213> ORGANISM: Artificial Sequence
<220> FEATURE:
<223> OTHER INFORMATION: antibody

<400> SEQUENCE: 252

Ala Arg Gln Leu Trp Gly Tyr Tyr Ala Leu Asp Ile
1               5                   10

<210> SEQ ID NO 253
<211> LENGTH: 10
<212> TYPE: PRT
<213> ORGANISM: Artificial Sequence
<220> FEATURE:
<223> OTHER INFORMATION: antibody

```
<400> SEQUENCE: 253

Ser Ala Ser Ile Ser Val Ser Tyr Met Tyr
1               5                   10

<210> SEQ ID NO 254
<211> LENGTH: 11
<212> TYPE: PRT
<213> ORGANISM: Artificial Sequence
<220> FEATURE:
<223> OTHER INFORMATION: antibody

<400> SEQUENCE: 254

Leu Leu Ile Tyr Asp Met Ser Asn Leu Ala Ser
1               5                   10

<210> SEQ ID NO 255
<211> LENGTH: 9
<212> TYPE: PRT
<213> ORGANISM: Artificial Sequence
<220> FEATURE:
<223> OTHER INFORMATION: antibody

<400> SEQUENCE: 255

Met Gln Trp Ser Gly Tyr Pro Tyr Thr
1               5

<210> SEQ ID NO 256
<211> LENGTH: 119
<212> TYPE: PRT
<213> ORGANISM: Artificial Sequence
<220> FEATURE:
<223> OTHER INFORMATION: antibody

<400> SEQUENCE: 256

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Pro Phe
            20                  25                  30

Ala Met His Trp Val Arg Gln Ala Pro Gly Lys Gly Leu Glu Trp Val
        35                  40                  45

Ala Lys Ile Ser Pro Gly Gly Ser Trp Thr Tyr Tyr Ser Asp Thr Val
    50                  55                  60

Thr Asp Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gln Ala Trp Gly Tyr Tyr Ala Leu Asp Ile Trp Gly Gln Gly
            100                 105                 110

Thr Leu Val Thr Val Ser Ser
        115

<210> SEQ ID NO 257
<211> LENGTH: 119
<212> TYPE: PRT
<213> ORGANISM: Artificial Sequence
<220> FEATURE:
<223> OTHER INFORMATION: antibody

<400> SEQUENCE: 257

Glu Val Gln Leu Val Glu Ser Gly Gly Gly Leu Val Gln Pro Gly Gly
1               5                   10                  15
```

Ser Leu Arg Leu Ser Cys Ala Ala Ser Gly Phe Thr Phe Ser Pro Phe
            20                  25                  30

Ala Met His Trp Val Arg Gln Ala Pro Gly Lys Gly Leu Glu Trp Val
        35                  40                  45

Ala Lys Ile Ser Pro Gly Gly Ser Trp Thr Tyr Tyr Ser Asp Thr Val
 50                  55                  60

Thr Asp Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gln Ser Trp Gly Tyr Tyr Ala Leu Asp Ile Trp Gly Gln Gly
            100                 105                 110

Thr Leu Val Thr Val Ser Ser
            115

<210> SEQ ID NO 258
<211> LENGTH: 119
<212> TYPE: PRT
<213> ORGANISM: Artificial Sequence
<220> FEATURE:
<223> OTHER INFORMATION: antibody

<400> SEQUENCE: 258

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Pro Phe
            20                  25                  30

Ala Met His Trp Val Arg Gln Ala Pro Gly Lys Gly Leu Glu Trp Val
        35                  40                  45

Ala Lys Ile Ser Pro Gly Gly Ser Trp Thr Tyr Tyr Ser Asp Thr Val
 50                  55                  60

Thr Asp Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gln Gly Trp Gly Tyr Tyr Ala Leu Asp Ile Trp Gly Gln Gly
            100                 105                 110

Thr Leu Val Thr Val Ser Ser
            115

<210> SEQ ID NO 259
<211> LENGTH: 119
<212> TYPE: PRT
<213> ORGANISM: Artificial Sequence
<220> FEATURE:
<223> OTHER INFORMATION: antibody

<400> SEQUENCE: 259

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Pro Phe
            20                  25                  30

Ala Met His Trp Val Arg Gln Ala Pro Gly Lys Gly Leu Glu Trp Val
        35                  40                  45

Ala Lys Ile Ser Pro Gly Gly Ser Trp Thr Tyr Tyr Ser Asp Thr Val
 50                  55                  60

Thr Asp Arg Phe Thr Phe Ser Leu Asp Thr Ser Lys Ser Thr Ala Tyr
65                  70                  75                  80

```
Leu Gln Met Asn Ser Leu Arg Ala Glu Asp Thr Ala Val Tyr Tyr Cys
                85                  90                  95

Ala Arg Gln Thr Trp Gly Tyr Tyr Ala Leu Asp Ile Trp Gly Gln Gly
            100                 105                 110

Thr Leu Val Thr Val Ser Ser
        115

<210> SEQ ID NO 260
<211> LENGTH: 119
<212> TYPE: PRT
<213> ORGANISM: Artificial Sequence
<220> FEATURE:
<223> OTHER INFORMATION: antibody

<400> SEQUENCE: 260

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Pro Phe
            20                  25                  30

Ala Met His Trp Val Arg Gln Ala Pro Gly Lys Gly Leu Glu Trp Val
            35                  40                  45

Ala Lys Ile Ser Pro Gly Gly Ser Trp Thr Tyr Tyr Ser Asp Thr Val
        50                  55                  60

Thr Asp Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gln Val Trp Gly Tyr Tyr Ala Leu Asp Ile Trp Gly Gln Gly
            100                 105                 110

Thr Leu Val Thr Val Ser Ser
        115

<210> SEQ ID NO 261
<211> LENGTH: 119
<212> TYPE: PRT
<213> ORGANISM: Artificial Sequence
<220> FEATURE:
<223> OTHER INFORMATION: antibody

<400> SEQUENCE: 261

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Pro Phe
            20                  25                  30

Ala Met His Trp Val Arg Gln Ala Pro Gly Lys Gly Leu Glu Trp Val
            35                  40                  45

Ala Lys Ile Ser Pro Gly Gly Ser Trp Thr Tyr Tyr Ser Asp Thr Val
        50                  55                  60

Thr Asp Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gln Gln Trp Gly Tyr Tyr Ala Leu Asp Ile Trp Gly Gln Gly
            100                 105                 110

Thr Leu Val Thr Val Ser Ser
        115
```

-continued

```
<210> SEQ ID NO 262
<211> LENGTH: 119
<212> TYPE: PRT
<213> ORGANISM: Artificial Sequence
<220> FEATURE:
<223> OTHER INFORMATION: antibody

<400> SEQUENCE: 262

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Pro Phe
            20                  25                  30

Ala Met His Trp Val Arg Gln Ala Pro Gly Lys Gly Leu Glu Trp Val
        35                  40                  45

Ala Lys Ile Ser Pro Gly Gly Ser Trp Thr Tyr Tyr Ser Asp Thr Val
    50                  55                  60

Thr Asp Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gln Lys Trp Gly Tyr Tyr Ala Leu Asp Ile Trp Gly Gln Gly
            100                 105                 110

Thr Leu Val Thr Val Ser Ser
        115

<210> SEQ ID NO 263
<211> LENGTH: 664
<212> TYPE: PRT
<213> ORGANISM: Artificial Sequence
<220> FEATURE:
<223> OTHER INFORMATION: fusion

<400> SEQUENCE: 263

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190
```

```
Thr Lys Lys Asn Ser Thr Phe Val Arg Val His Glu Lys Gly Gly
            195                 200                 205
Gly Ser Gly Gly Gly Ser Glu Val Gln Leu Val Glu Ser Gly Gly
            210                 215                 220
Gly Leu Val Gln Pro Gly Gly Ser Leu Arg Leu Ser Cys Ala Ala Ser
225                 230                 235                 240
Gly Phe Thr Phe Ser Pro Phe Ala Met His Trp Val Arg Gln Ala Pro
            245                 250                 255
Gly Lys Gly Leu Glu Trp Val Ala Lys Ile Ser Pro Gly Gly Ser Trp
            260                 265                 270
Thr Tyr Tyr Ser Asp Thr Val Thr Asp Arg Phe Thr Phe Ser Leu Asp
            275                 280                 285
Thr Ser Lys Ser Thr Ala Tyr Leu Gln Met Asn Ser Leu Arg Ala Glu
            290                 295                 300
Asp Thr Ala Val Tyr Tyr Cys Ala Arg Gln Ala Trp Gly Tyr Tyr Ala
305                 310                 315                 320
Leu Asp Ile Trp Gly Gln Gly Thr Leu Val Thr Val Ser Ser Ala Ser
            325                 330                 335
Thr Lys Gly Pro Ser Val Phe Pro Leu Ala Pro Ser Ser Lys Ser Thr
            340                 345                 350
Ser Gly Gly Thr Ala Ala Leu Gly Cys Leu Val Lys Asp Tyr Phe Pro
            355                 360                 365
Glu Pro Val Thr Val Ser Trp Asn Ser Gly Ala Leu Thr Ser Gly Val
            370                 375                 380
His Thr Phe Pro Ala Val Leu Gln Ser Ser Gly Leu Tyr Ser Leu Ser
385                 390                 395                 400
Ser Val Val Thr Val Pro Ser Ser Ser Leu Gly Thr Gln Thr Tyr Ile
                405                 410                 415
Cys Asn Val Asn His Lys Pro Ser Asn Thr Lys Val Asp Lys Lys Val
                420                 425                 430
Glu Pro Lys Ser Cys Asp Lys Thr His Thr Cys Pro Pro Cys Pro Ala
            435                 440                 445
Pro Glu Ala Ala Gly Ala Pro Ser Val Phe Leu Phe Pro Pro Lys Pro
            450                 455                 460
Lys Asp Thr Leu Met Ile Ser Arg Thr Pro Glu Val Thr Cys Val Val
465                 470                 475                 480
Val Asp Val Ser His Glu Asp Pro Glu Val Lys Phe Asn Trp Tyr Val
                485                 490                 495
Asp Gly Val Glu Val His Asn Ala Lys Thr Lys Pro Arg Glu Glu Gln
            500                 505                 510
Tyr Asn Ser Thr Tyr Arg Val Val Ser Val Leu Thr Val Leu His Gln
            515                 520                 525
Asp Trp Leu Asn Gly Lys Glu Tyr Lys Cys Lys Val Ser Asn Lys Ala
            530                 535                 540
Leu Pro Ala Pro Ile Glu Lys Thr Ile Ser Lys Ala Lys Gly Gln Pro
545                 550                 555                 560
Arg Glu Pro Gln Val Tyr Thr Leu Pro Pro Ser Arg Glu Glu Met Thr
                565                 570                 575
Lys Asn Gln Val Ser Leu Thr Cys Leu Val Lys Gly Phe Tyr Pro Ser
            580                 585                 590
Asp Ile Ala Val Glu Trp Glu Ser Asn Gly Gln Pro Glu Asn Asn Tyr
            595                 600                 605
```

```
Lys Thr Thr Pro Pro Val Leu Asp Ser Asp Gly Ser Phe Phe Leu Tyr
        610                 615                 620

Ser Lys Leu Thr Val Asp Lys Ser Arg Trp Gln Gln Gly Asn Val Phe
625                 630                 635                 640

Ser Cys Ser Val Met His Glu Ala Leu His Asn His Tyr Thr Gln Lys
                645                 650                 655

Ser Leu Ser Cys Ser Pro Gly Lys
            660

<210> SEQ ID NO 264
<211> LENGTH: 664
<212> TYPE: PRT
<213> ORGANISM: Artificial Sequence
<220> FEATURE:
<223> OTHER INFORMATION: fusion

<400> SEQUENCE: 264

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
                20                  25                  30

Thr Ser Pro Asn Ile Thr Val Thr Leu Lys Lys Phe Pro Leu Asp Thr
            35                  40                  45

Leu Ile Pro Asp Gly Lys Arg Ile Ile Trp Asp Ser Arg Lys Gly Phe
        50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Gly Gly Gly
        195                 200                 205

Gly Ser Gly Gly Gly Gly Ser Glu Val Gln Leu Val Glu Ser Gly Gly
210                 215                 220

Gly Leu Val Gln Pro Gly Gly Ser Leu Arg Leu Ser Cys Ala Ala Ser
225                 230                 235                 240

Gly Phe Thr Phe Ser Pro Phe Ala Met His Trp Val Arg Gln Ala Pro
                245                 250                 255

Gly Lys Gly Leu Glu Trp Val Ala Lys Ile Ser Pro Gly Gly Ser Trp
            260                 265                 270

Thr Tyr Tyr Ser Asp Thr Val Thr Asp Arg Phe Thr Phe Ser Leu Asp
        275                 280                 285

Thr Ser Lys Ser Thr Ala Tyr Leu Gln Met Asn Ser Leu Arg Ala Glu
290                 295                 300
```

Asp Thr Ala Val Tyr Tyr Cys Ala Arg Gln Ala Trp Gly Tyr Tyr Ala
305                 310                 315                 320

Leu Asp Ile Trp Gly Gln Gly Thr Leu Val Thr Val Ser Ser Ala Ser
            325                 330                 335

Thr Lys Gly Pro Ser Val Phe Pro Leu Ala Pro Ser Ser Lys Ser Thr
        340                 345                 350

Ser Gly Gly Thr Ala Ala Leu Gly Cys Leu Val Lys Asp Tyr Phe Pro
    355                 360                 365

Glu Pro Val Thr Val Ser Trp Asn Ser Gly Ala Leu Thr Ser Gly Val
370                 375                 380

His Thr Phe Pro Ala Val Leu Gln Ser Ser Gly Leu Tyr Ser Leu Ser
385                 390                 395                 400

Ser Val Val Thr Val Pro Ser Ser Ser Leu Gly Thr Gln Thr Tyr Ile
            405                 410                 415

Cys Asn Val Asn His Lys Pro Ser Asn Thr Lys Val Asp Lys Lys Val
        420                 425                 430

Glu Pro Lys Ser Cys Asp Lys Thr His Thr Cys Pro Pro Cys Pro Ala
    435                 440                 445

Pro Glu Ala Ala Gly Ala Pro Ser Val Phe Leu Phe Pro Pro Lys Pro
450                 455                 460

Lys Asp Thr Leu Met Ile Ser Arg Thr Pro Glu Val Thr Cys Val Val
465                 470                 475                 480

Val Asp Val Ser His Glu Asp Pro Glu Val Lys Phe Asn Trp Tyr Val
            485                 490                 495

Asp Gly Val Glu Val His Asn Ala Lys Thr Lys Pro Arg Glu Glu Gln
        500                 505                 510

Tyr Asn Ser Thr Tyr Arg Val Val Ser Val Leu Thr Val Leu His Gln
    515                 520                 525

Asp Trp Leu Asn Gly Lys Glu Tyr Lys Cys Lys Val Ser Asn Lys Ala
530                 535                 540

Leu Pro Ala Pro Ile Glu Lys Thr Ile Ser Lys Ala Lys Gly Gln Pro
545                 550                 555                 560

Arg Glu Pro Gln Val Tyr Thr Leu Pro Pro Ser Arg Glu Glu Met Thr
            565                 570                 575

Lys Asn Gln Val Ser Leu Thr Cys Leu Val Lys Gly Phe Tyr Pro Ser
        580                 585                 590

Asp Ile Ala Val Glu Trp Glu Ser Asn Gly Gln Pro Glu Asn Asn Tyr
    595                 600                 605

Lys Thr Thr Pro Pro Val Leu Asp Ser Asp Gly Ser Phe Phe Leu Tyr
610                 615                 620

Ser Lys Leu Thr Val Asp Lys Ser Arg Trp Gln Gln Gly Asn Val Phe
625                 630                 635                 640

Ser Cys Ser Val Met His Glu Ala Leu His Asn His Tyr Thr Gln Lys
            645                 650                 655

Ser Leu Ser Cys Ser Pro Gly Lys
        660

<210> SEQ ID NO 265
<211> LENGTH: 664
<212> TYPE: PRT
<213> ORGANISM: Artificial Sequence
<220> FEATURE:
<223> OTHER INFORMATION: trap

<400> SEQUENCE: 265

```
Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Gly Gly Gly
        195                 200                 205

Gly Ser Gly Gly Gly Gly Ser Glu Val Gln Leu Val Glu Ser Gly Gly
    210                 215                 220

Gly Leu Val Gln Pro Gly Gly Ser Leu Arg Leu Ser Cys Ala Ala Ser
225                 230                 235                 240

Gly Phe Thr Phe Ser Pro Phe Ala Met His Trp Val Arg Gln Ala Pro
                245                 250                 255

Gly Lys Gly Leu Glu Trp Val Ala Lys Ile Ser Pro Gly Gly Ser Trp
            260                 265                 270

Thr Tyr Tyr Ser Asp Thr Val Thr Asp Arg Phe Thr Phe Ser Leu Asp
        275                 280                 285

Thr Ser Lys Ser Thr Ala Tyr Leu Gln Met Asn Ser Leu Arg Ala Glu
    290                 295                 300

Asp Thr Ala Val Tyr Tyr Cys Ala Arg Gln Ala Trp Gly Tyr Tyr Ala
305                 310                 315                 320

Leu Asp Ile Trp Gly Gln Gly Thr Leu Val Thr Val Ser Ser Ala Ser
                325                 330                 335

Thr Lys Gly Pro Ser Val Phe Pro Leu Ala Pro Ser Ser Lys Ser Thr
            340                 345                 350

Ser Gly Gly Thr Ala Ala Leu Gly Cys Leu Val Lys Asp Tyr Phe Pro
        355                 360                 365

Glu Pro Val Thr Val Ser Trp Asn Ser Gly Ala Leu Thr Ser Gly Val
    370                 375                 380

His Thr Phe Pro Ala Val Leu Gln Ser Ser Gly Leu Tyr Ser Leu Ser
385                 390                 395                 400
```

Ser Val Val Thr Val Pro Ser Ser Leu Gly Thr Gln Thr Tyr Ile
            405                 410                 415

Cys Asn Val Asn His Lys Pro Ser Asn Thr Lys Val Asp Lys Lys Val
            420                 425                 430

Glu Pro Lys Ser Cys Asp Lys Thr His Thr Cys Pro Pro Cys Pro Ala
            435                 440                 445

Pro Glu Ala Ala Gly Ala Pro Ser Val Phe Leu Phe Pro Pro Lys Pro
450                 455                 460

Lys Asp Thr Leu Met Ile Ser Arg Thr Pro Glu Val Thr Cys Val Val
465                 470                 475                 480

Val Asp Val Ser His Glu Asp Pro Glu Val Lys Phe Asn Trp Tyr Val
            485                 490                 495

Asp Gly Val Glu Val His Asn Ala Lys Thr Lys Pro Arg Glu Glu Gln
            500                 505                 510

Tyr Asn Ser Thr Tyr Arg Val Val Ser Val Leu Thr Val Leu His Gln
            515                 520                 525

Asp Trp Leu Asn Gly Lys Glu Tyr Lys Cys Lys Val Ser Asn Lys Ala
530                 535                 540

Leu Pro Ala Pro Ile Glu Lys Thr Ile Ser Lys Ala Lys Gly Gln Pro
545                 550                 555                 560

Arg Glu Pro Gln Val Tyr Thr Leu Pro Pro Ser Arg Glu Glu Met Thr
            565                 570                 575

Lys Asn Gln Val Ser Leu Thr Cys Leu Val Lys Gly Phe Tyr Pro Ser
            580                 585                 590

Asp Ile Ala Val Glu Trp Glu Ser Asn Gly Gln Pro Glu Asn Asn Tyr
            595                 600                 605

Lys Thr Thr Pro Pro Val Leu Asp Ser Asp Gly Ser Phe Phe Leu Tyr
610                 615                 620

Ser Lys Leu Thr Val Asp Lys Ser Arg Trp Gln Gln Gly Asn Val Phe
625                 630                 635                 640

Ser Cys Ser Val Met His Glu Ala Leu His Asn His Tyr Thr Gln Lys
            645                 650                 655

Ser Leu Ser Cys Ser Pro Gly Lys
            660

<210> SEQ ID NO 266
<211> LENGTH: 664
<212> TYPE: PRT
<213> ORGANISM: Artificial Sequence
<220> FEATURE:
<223> OTHER INFORMATION: fusion

<400> SEQUENCE: 266

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Pro Phe
            20                  25                  30

Ala Met His Trp Val Arg Gln Ala Pro Gly Lys Gly Leu Glu Trp Val
            35                  40                  45

Ala Lys Ile Ser Pro Gly Gly Ser Trp Thr Tyr Tyr Ser Asp Thr Val
            50                  55                  60

Thr Asp Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
            85                  90                  95

-continued

```
Ala Arg Gln Ala Trp Gly Tyr Tyr Ala Leu Asp Ile Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Gly Gly
            210                 215                 220

Gly Gly Ser Gly Gly Gly Gly Ser Ser Asp Thr Gly Arg Pro Phe Val
225                 230                 235                 240

Glu Met Tyr Ser Glu Ile Pro Glu Ile Ile His Met Thr Glu Gly Arg
                245                 250                 255

Glu Leu Val Ile Pro Cys Arg Val Thr Ser Pro Asn Ile Thr Val Thr
            260                 265                 270

Leu Lys Lys Phe Pro Leu Asp Thr Leu Ile Pro Asp Gly Lys Arg Ile
            275                 280                 285

Ile Trp Asp Ser Arg Lys Gly Phe Ile Ile Ser Asn Ala Thr Tyr Lys
            290                 295                 300

Glu Ile Gly Leu Leu Thr Cys Glu Ala Thr Val Asn Gly His Leu Tyr
305                 310                 315                 320

Lys Thr Asn Tyr Leu Thr His Arg Gln Thr Asn Thr Ile Ile Asp Val
                325                 330                 335

Val Leu Ser Pro Ser His Gly Ile Glu Leu Ser Val Gly Glu Lys Leu
            340                 345                 350

Val Leu Asn Cys Thr Ala Arg Thr Glu Leu Asn Val Gly Ile Asp Phe
            355                 360                 365

Asn Trp Glu Tyr Pro Ser Ser Lys His Gln His Lys Lys Leu Val Asn
            370                 375                 380

Arg Asp Leu Lys Thr Gln Ser Gly Ser Glu Met Lys Lys Phe Leu Ser
385                 390                 395                 400

Thr Leu Thr Ile Asp Gly Val Thr Arg Ser Asp Gln Gly Leu Tyr Thr
                405                 410                 415

Cys Ala Ala Ser Ser Gly Leu Met Thr Lys Lys Asn Ser Thr Phe Val
            420                 425                 430

Arg Val His Glu Lys Asp Lys Thr His Thr Cys Pro Pro Cys Pro Ala
            435                 440                 445

Pro Glu Ala Ala Gly Ala Pro Ser Val Phe Leu Phe Pro Pro Lys Pro
            450                 455                 460

Lys Asp Thr Leu Met Ile Ser Arg Thr Pro Glu Val Thr Cys Val Val
465                 470                 475                 480

Val Asp Val Ser His Glu Asp Pro Glu Val Lys Phe Asn Trp Tyr Val
                485                 490                 495

Asp Gly Val Glu Val His Asn Ala Lys Thr Lys Pro Arg Glu Glu Gln
            500                 505                 510
```

```
Tyr Asn Ser Thr Tyr Arg Val Val Ser Val Leu Thr Val Leu His Gln
            515                 520                 525

Asp Trp Leu Asn Gly Lys Glu Tyr Lys Cys Lys Val Ser Asn Lys Ala
530                 535                 540

Leu Pro Ala Pro Ile Glu Lys Thr Ile Ser Lys Ala Lys Gly Gln Pro
545                 550                 555                 560

Arg Glu Pro Gln Val Tyr Thr Leu Pro Pro Ser Arg Glu Glu Met Thr
                565                 570                 575

Lys Asn Gln Val Ser Leu Thr Cys Leu Val Lys Gly Phe Tyr Pro Ser
                580                 585                 590

Asp Ile Ala Val Glu Trp Glu Ser Asn Gly Gln Pro Glu Asn Asn Tyr
            595                 600                 605

Lys Thr Thr Pro Pro Val Leu Asp Ser Asp Gly Ser Phe Phe Leu Tyr
            610                 615                 620

Ser Lys Leu Thr Val Asp Lys Ser Arg Trp Gln Gln Gly Asn Val Phe
625                 630                 635                 640

Ser Cys Ser Val Met His Glu Ala Leu His Asn His Tyr Thr Gln Lys
                645                 650                 655

Ser Leu Ser Cys Ser Pro Gly Lys
                660

<210> SEQ ID NO 267
<211> LENGTH: 664
<212> TYPE: PRT
<213> ORGANISM: Artificial Sequence
<220> FEATURE:
<223> OTHER INFORMATION: fusion

<400> SEQUENCE: 267

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Pro Phe
                20                  25                  30

Ala Met His Trp Val Arg Gln Ala Pro Gly Lys Gly Leu Glu Trp Val
            35                  40                  45

Ala Lys Ile Ser Pro Gly Gly Ser Trp Thr Tyr Tyr Ser Asp Thr Val
        50                  55                  60

Thr Asp Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gln Ala Trp Gly Tyr Tyr Ala Leu Asp Ile Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205
```

```
Ser Asn Thr Lys Val Asp Lys Lys Val Glu Pro Lys Ser Cys Gly Gly
210                 215                 220

Gly Gly Ser Gly Gly Gly Ser Ser Asp Thr Gly Arg Pro Phe Val
225                 230             235                 240

Glu Met Tyr Ser Glu Ile Pro Glu Ile Ile His Met Thr Gly Arg
            245                 250                 255

Glu Leu Val Ile Pro Cys Arg Val Thr Ser Pro Asn Ile Thr Val Thr
260                 265                 270

Leu Lys Lys Phe Pro Leu Asp Thr Leu Ile Pro Asp Gly Lys Arg Ile
            275                 280                 285

Ile Trp Asp Ser Arg Lys Gly Phe Ile Ile Ser Asn Ala Thr Tyr Lys
290                 295                 300

Glu Ile Gly Leu Leu Thr Cys Glu Ala Thr Val Asn Gly His Leu Tyr
305                 310                 315                 320

Lys Thr Asn Tyr Leu Thr His Arg Gln Thr Asn Thr Ile Ile Asp Val
            325                 330                 335

Val Leu Ser Pro Ser His Gly Ile Glu Leu Ser Val Gly Glu Lys Leu
            340                 345                 350

Val Leu Asn Cys Thr Ala Arg Thr Glu Leu Asn Val Gly Ile Asp Phe
            355                 360                 365

Asn Trp Glu Tyr Pro Ser Ser Lys His Gln His Lys Lys Leu Val Asn
370                 375                 380

Arg Asp Leu Lys Thr Gln Ser Gly Ser Glu Met Lys Lys Phe Leu Ser
385                 390                 395                 400

Thr Leu Thr Ile Asp Gly Val Thr Arg Ser Asp Gln Gly Leu Tyr Thr
            405                 410                 415

Cys Ala Ala Ser Ser Gly Leu Met Thr Lys Lys Asn Ser Thr Phe Val
            420                 425                 430

Arg Val His Glu Lys Asp Lys Thr His Thr Cys Pro Pro Cys Pro Ala
            435                 440                 445

Pro Glu Ala Ala Gly Ala Pro Ser Val Phe Leu Phe Pro Pro Lys Pro
450                 455                 460

Lys Asp Thr Leu Met Ile Ser Arg Thr Pro Glu Val Thr Cys Val Val
465                 470                 475                 480

Val Asp Val Ser His Glu Asp Pro Glu Val Lys Phe Asn Trp Tyr Val
            485                 490                 495

Asp Gly Val Glu Val His Asn Ala Lys Thr Lys Pro Arg Glu Glu Gln
            500                 505                 510

Tyr Asn Ser Thr Tyr Arg Val Val Ser Val Leu Thr Val Leu His Gln
            515                 520                 525

Asp Trp Leu Asn Gly Lys Glu Tyr Lys Cys Lys Val Ser Asn Lys Ala
530                 535                 540

Leu Pro Ala Pro Ile Glu Lys Thr Ile Ser Lys Ala Lys Gly Gln Pro
545                 550                 555                 560

Arg Glu Pro Gln Val Tyr Thr Leu Pro Pro Ser Arg Glu Glu Met Thr
            565                 570                 575

Lys Asn Gln Val Ser Leu Thr Cys Leu Val Lys Gly Phe Tyr Pro Ser
            580                 585                 590

Asp Ile Ala Val Glu Trp Glu Ser Asn Gly Gln Pro Glu Asn Asn Tyr
            595                 600                 605

Lys Thr Thr Pro Pro Val Leu Asp Ser Asp Gly Ser Phe Phe Leu Tyr
610                 615                 620
```

```
Ser Lys Leu Thr Val Asp Lys Ser Arg Trp Gln Gln Gly Asn Val Phe
625                 630                 635                 640

Ser Cys Ser Val Met His Glu Ala Leu His Asn His Tyr Thr Gln Lys
                645                 650                 655

Ser Leu Ser Cys Ser Pro Gly Lys
            660

<210> SEQ ID NO 268
<211> LENGTH: 664
<212> TYPE: PRT
<213> ORGANISM: Artificial Sequence
<220> FEATURE:
<223> OTHER INFORMATION: fusion

<400> SEQUENCE: 268

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Pro Phe
            20                  25                  30

Ala Met His Trp Val Arg Gln Ala Pro Gly Lys Gly Leu Glu Trp Val
        35                  40                  45

Ala Lys Ile Ser Pro Gly Gly Ser Trp Thr Tyr Tyr Ser Asp Thr Val
    50                  55                  60

Thr Asp Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gln Ala Trp Gly Tyr Tyr Ala Leu Asp Ile Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Gly Gly
    210                 215                 220

Gly Gly Ser Gly Gly Gly Gly Ser Ser Asp Thr Gly Arg Pro Phe Val
225                 230                 235                 240

Glu Met Tyr Ser Glu Ile Pro Glu Ile Ile His Met Thr Glu Gly Arg
                245                 250                 255

Glu Leu Val Ile Pro Cys Arg Val Thr Ser Pro Asn Ile Thr Val Thr
            260                 265                 270

Leu Lys Lys Phe Pro Leu Asp Thr Leu Ile Pro Asp Gly Lys Arg Ile
        275                 280                 285

Ile Trp Asp Ser Arg Lys Gly Phe Ile Ile Ser Asn Ala Thr Tyr Lys
    290                 295                 300

Glu Ile Gly Leu Leu Thr Cys Glu Ala Thr Val Asn Gly His Leu Tyr
305                 310                 315                 320
```

```
Lys Thr Asn Tyr Leu Thr His Arg Gln Thr Asn Thr Ile Ile Asp Val
            325                 330                 335

Val Leu Ser Pro Ser His Gly Ile Glu Leu Ser Val Gly Glu Lys Leu
            340                 345                 350

Val Leu Asn Cys Thr Ala Arg Thr Glu Leu Asn Val Gly Ile Asp Phe
            355                 360                 365

Asn Trp Glu Tyr Pro Ser Ser Lys His Gln His Lys Lys Leu Val Asn
        370                 375                 380

Arg Asp Leu Lys Thr Gln Ser Gly Ser Glu Met Lys Lys Phe Leu Ser
385                 390                 395                 400

Thr Leu Thr Ile Asp Gly Val Thr Arg Ser Asp Gln Gly Leu Tyr Thr
                405                 410                 415

Cys Ala Ala Ser Ser Gly Leu Met Thr Lys Lys Asn Ser Thr Phe Val
                420                 425                 430

Arg Val His Glu Lys Asp Lys Thr His Thr Cys Pro Pro Cys Pro Ala
            435                 440                 445

Pro Glu Ala Ala Gly Ala Pro Ser Val Phe Leu Phe Pro Pro Lys Pro
        450                 455                 460

Lys Asp Thr Leu Met Ile Ser Arg Thr Pro Glu Val Thr Cys Val Val
465                 470                 475                 480

Val Asp Val Ser His Glu Asp Pro Glu Val Lys Phe Asn Trp Tyr Val
                485                 490                 495

Asp Gly Val Glu Val His Asn Ala Lys Thr Lys Pro Arg Glu Glu Gln
            500                 505                 510

Tyr Asn Ser Thr Tyr Arg Val Val Ser Val Leu Thr Val Leu His Gln
        515                 520                 525

Asp Trp Leu Asn Gly Lys Glu Tyr Lys Cys Lys Val Ser Asn Lys Ala
    530                 535                 540

Leu Pro Ala Pro Ile Glu Lys Thr Ile Ser Lys Ala Lys Gly Gln Pro
545                 550                 555                 560

Arg Glu Pro Gln Val Tyr Thr Leu Pro Pro Ser Arg Glu Glu Met Thr
                565                 570                 575

Lys Asn Gln Val Ser Leu Thr Cys Leu Val Lys Gly Phe Tyr Pro Ser
            580                 585                 590

Asp Ile Ala Val Glu Trp Glu Ser Asn Gly Gln Pro Glu Asn Asn Tyr
        595                 600                 605

Lys Thr Thr Pro Pro Val Leu Asp Ser Asp Gly Ser Phe Phe Leu Tyr
    610                 615                 620

Ser Lys Leu Thr Val Asp Lys Ser Arg Trp Gln Gln Gly Asn Val Phe
625                 630                 635                 640

Ser Cys Ser Val Met His Glu Ala Leu His Asn His Tyr Thr Gln Lys
                645                 650                 655

Ser Leu Ser Cys Ser Pro Gly Lys
            660

<210> SEQ ID NO 269
<211> LENGTH: 664
<212> TYPE: PRT
<213> ORGANISM: Artificial Sequence
<220> FEATURE:
<223> OTHER INFORMATION: fusion

<400> SEQUENCE: 269

Ser Asp Thr Gly Arg Pro Phe Val Glu Met Tyr Ser Glu Ile Pro Glu
1               5                   10                  15
```

-continued

Ile Ile His Met Thr Glu Gly Arg Glu Leu Val Ile Pro Cys Arg Val
            20                  25                  30
Thr Ser Pro Asn Ile Thr Val Thr Leu Lys Lys Phe Pro Leu Asp Thr
        35                  40                  45
Leu Ile Pro Asp Gly Lys Arg Ile Ile Trp Asp Ser Arg Lys Gly Phe
 50                  55                  60
Ile Ile Ser Asn Ala Thr Tyr Lys Glu Ile Gly Leu Leu Thr Cys Glu
 65                  70                  75                  80
Ala Thr Val Asn Gly His Leu Tyr Lys Thr Asn Tyr Leu Thr His Arg
                 85                  90                  95
Gln Thr Asn Thr Ile Ile Asp Val Val Leu Ser Pro Ser His Gly Ile
            100                 105                 110
Glu Leu Ser Val Gly Glu Lys Leu Val Leu Asn Cys Thr Ala Arg Thr
        115                 120                 125
Glu Leu Asn Val Gly Ile Asp Phe Asn Trp Glu Tyr Pro Ser Ser Lys
130                 135                 140
His Gln His Lys Lys Leu Val Asn Arg Asp Leu Lys Thr Gln Ser Gly
145                 150                 155                 160
Ser Glu Met Lys Lys Phe Leu Ser Thr Leu Thr Ile Asp Gly Val Thr
                165                 170                 175
Arg Ser Asp Gln Gly Leu Tyr Thr Cys Ala Ala Ser Ser Gly Leu Met
            180                 185                 190
Thr Lys Lys Asn Ser Thr Phe Val Arg Val His Glu Lys Gly Gly Gly
        195                 200                 205
Gly Ser Gly Gly Gly Gly Ser Glu Val Gln Leu Val Glu Ser Gly Gly
    210                 215                 220
Gly Leu Val Gln Pro Gly Gly Ser Leu Arg Leu Ser Cys Ala Ala Ser
225                 230                 235                 240
Gly Phe Thr Phe Ser Pro Phe Ala Ile Ser Trp Val Arg Gln Ala Pro
                245                 250                 255
Gly Lys Gly Leu Glu Trp Val Ala Lys Ile Ser Pro Gly Gly Ser Trp
            260                 265                 270
Thr Tyr Tyr Ser Asp Thr Val Thr Asp Arg Phe Thr Phe Ser Leu Asp
        275                 280                 285
Thr Ser Lys Ser Thr Ala Tyr Leu Gln Met Asn Ser Leu Arg Ala Glu
    290                 295                 300
Asp Thr Ala Val Tyr Tyr Cys Ala Arg Gln Leu Trp Gly Tyr Tyr Ala
305                 310                 315                 320
Leu Asp Val Trp Gly Gln Gly Thr Leu Val Thr Val Ser Ser Ala Ser
                325                 330                 335
Thr Lys Gly Pro Ser Val Phe Pro Leu Ala Pro Ser Ser Lys Ser Thr
            340                 345                 350
Ser Gly Gly Thr Ala Ala Leu Gly Cys Leu Val Lys Asp Tyr Phe Pro
        355                 360                 365
Glu Pro Val Thr Val Ser Trp Asn Ser Gly Ala Leu Thr Ser Gly Val
    370                 375                 380
His Thr Phe Pro Ala Val Leu Gln Ser Ser Gly Leu Tyr Ser Leu Ser
385                 390                 395                 400
Ser Val Val Thr Val Pro Ser Ser Ser Leu Gly Thr Gln Thr Tyr Ile
                405                 410                 415
Cys Asn Val Asn His Lys Pro Ser Asn Thr Lys Val Asp Lys Lys Val
            420                 425                 430

```
Glu Pro Lys Ser Cys Asp Lys Thr His Thr Cys Pro Pro Cys Pro Ala
    435                 440                 445

Pro Glu Ala Ala Gly Ala Pro Ser Val Phe Leu Phe Pro Pro Lys Pro
    450                 455                 460

Lys Asp Thr Leu Met Ile Ser Arg Thr Pro Glu Val Thr Cys Val Val
465                 470                 475                 480

Val Asp Val Ser His Glu Asp Pro Glu Val Lys Phe Asn Trp Tyr Val
                485                 490                 495

Asp Gly Val Glu Val His Asn Ala Lys Thr Lys Pro Arg Glu Glu Gln
                500                 505                 510

Tyr Asn Ser Thr Tyr Arg Val Val Ser Val Leu Thr Val Leu His Gln
        515                 520                 525

Asp Trp Leu Asn Gly Lys Glu Tyr Lys Cys Lys Val Ser Asn Lys Ala
    530                 535                 540

Leu Pro Ala Pro Ile Glu Lys Thr Ile Ser Lys Ala Lys Gly Gln Pro
545                 550                 555                 560

Arg Glu Pro Gln Val Tyr Thr Leu Pro Pro Ser Arg Glu Glu Met Thr
                565                 570                 575

Lys Asn Gln Val Ser Leu Thr Cys Leu Val Lys Gly Phe Tyr Pro Ser
                580                 585                 590

Asp Ile Ala Val Glu Trp Glu Ser Asn Gly Gln Pro Glu Asn Asn Tyr
        595                 600                 605

Lys Thr Thr Pro Pro Val Leu Asp Ser Asp Gly Ser Phe Phe Leu Tyr
    610                 615                 620

Ser Lys Leu Thr Val Asp Lys Ser Arg Trp Gln Gln Gly Asn Val Phe
625                 630                 635                 640

Ser Cys Ser Val Met His Glu Ala Leu His Asn His Tyr Thr Gln Lys
                645                 650                 655

Ser Leu Ser Cys Ser Pro Gly Lys
                660
```